US009133168B2

(12) United States Patent
Brollo et al.

(10) Patent No.: US 9,133,168 B2
(45) Date of Patent: Sep. 15, 2015

(54) PYRIMIDINE DERIVATIVES, PREPARATION THEREOF, AND PHARMACEUTICAL USE THEREOF AS AKT(PKB) PHOSPHORYLATION INHIBITORS

(75) Inventors: Maurice Brollo, Paris (FR); Jean-Christophe Carry, Paris (FR); Victor Certal, Paris (FR); Eric Didier, Paris (FR); Gilles Doerflinger, Paris (FR); Youssef El Ahmad, Paris (FR); Frank Halley, Paris (FR); Karl Andreas Karlsson, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/977,396

(22) PCT Filed: Dec. 22, 2011

(86) PCT No.: PCT/EP2011/073875
§ 371 (c)(1),
(2), (4) Date: Jun. 28, 2013

(87) PCT Pub. No.: WO2012/089633
PCT Pub. Date: Jul. 5, 2012

(65) Prior Publication Data
US 2013/0274253 A1   Oct. 17, 2013

(30) Foreign Application Priority Data

| Dec. 28, 2010 | (FR) | 10 61297 |
| Dec. 28, 2010 | (FR) | 10 61298 |
| Dec. 28, 2010 | (FR) | 10 61300 |
| Dec. 28, 2010 | (FR) | 10 61301 |
| Dec. 28, 2010 | (FR) | 10 61303 |
| Oct. 14, 2011 | (FR) | 11 59313 |
| Oct. 14, 2011 | (FR) | 11 59315 |
| Oct. 14, 2011 | (FR) | 11 59316 |
| Oct. 14, 2011 | (FR) | 11 59317 |

(51) Int. Cl.
*C07D 413/14* (2006.01)
*C07D 413/04* (2006.01)
*C07D 401/04* (2006.01)
*C07D 403/06* (2006.01)
*C07D 209/30* (2006.01)
*C07D 403/04* (2006.01)
*C07D 471/10* (2006.01)
*C07D 403/14* (2006.01)

(52) U.S. Cl.
CPC ............ *C07D 403/06* (2013.01); *C07D 209/30* (2013.01); *C07D 401/04* (2013.01); *C07D 403/04* (2013.01); *C07D 403/14* (2013.01); *C07D 413/04* (2013.01); *C07D 413/14* (2013.01); *C07D 471/10* (2013.01)

(58) Field of Classification Search
CPC ... C07D 413/14; C07D 413/04; C07D 401/04
USPC .................. 544/122, 319; 514/235.5, 269
See application file for complete search history.

(56) References Cited

U.S. PATENT DOCUMENTS

2007/0083053 A1   4/2007   Sakurai et al.

FOREIGN PATENT DOCUMENTS

| WO | WO 2008/013322 A1 | 1/2008 |
| WO | WO 2008/148074 A2 | 12/2008 |
| WO | WO 2010/056631 A1 | 5/2010 |
| WO | WO 2011/001114 A1 | 1/2011 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Carry, et al. Document No. 154:133358, retrieved from CAPLUS; Jan 7, 2011.*
Qun Li, et al., Recent progress in the discovery of Akt inhibitors as anticancer agents, Expert Opinion on Therapeutic Patents, Informa Healthcare, (Jan. 1, 2007) vol. 17, No. 9, pp. 107-1130.
An T. Vu, et al., 1-(Indolin-1-yl)-1-phenyl-3-propan-2-olamines as Potent and Selective Norepinephrine Reuptake Inhibitors, Journal of Medicinal Chemistry, American Chemical Society, (Mar. 1, 2010) vol. 53, No. 5, pp. 2051-2062.
He Zhao, et al., Indoline and Piperazine Containing Derivatives as a Novel Class of Mixed D2/D4 Receptor Antagonists. Part 1: Indentification and Structure-Activity Relationships, Bioorganic and Medicinal Chemistry Letters, (Jan. 1, 2012) vol. 12, No. 21, pp. 3105-3109.
Douglas G. Batt, et al., Heteroatom- and Carbon-Linked Biphenyl Analogs of Brequinar As Immunosuppressive Agents, & Medicinal Chemistry Letters, Pergamon, Elsevier Science (Jul. 7, 1998) vol. 8, No. 13, pp. 1745-1750.
Corinne Pasquier, et al., Synthesis and application in enantioselective hydrogenation of new free and chromium complexed aminophosphine-phosphinite ligands, Tetrahedron Asymmetry, Pergamon Press Ltd., (Jan. 30, 1998) vol. 9, No. 2, pp. 193-196.
International Search Report dated Feb. 23, 2012 issued in PCT/EP2011/073875.
Samuels, et al., "High Frequency of Mutations of the PIK3CA Gene in Human Cancers"; Science, vol. 304, Apr. 23, 2004, p. 554.
Cheng, et al., "AKT2, a Putative Oncogene Encoding a Member of a Subfamily of Protein-Serine/Threonine Kinases, Is Amplifed in Human Ovarian Cancer"; Proc. Natl. Acad. Sci. USA, vol. 89, Oct. 1992, p. 9267-9271.
Cheng, et al., "Amplification of AKT2 in Human Pancreatic Cancer Cells and Inhibition of AKT2 Expression and Tumorigenicity by Antisense RNA"; Proc. Natl. Acad. Sci. USA, vol. 93, Apr. 1996, pp. 3636-3641.

(Continued)

*Primary Examiner* — Shawquia Jackson
(74) *Attorney, Agent, or Firm* — Morrison & Foerster LLP

(57) ABSTRACT

The present invention relates to novel chemical compounds derived from pyrimidines, to the method for preparing same, to the novel intermediates obtained, to the use thereof as drugs, to the pharmaceutical compositions containing same, and to the therapeutic use thereof as AKT inhibitors.

12 Claims, No Drawings

(56) References Cited

OTHER PUBLICATIONS

Levine, et al., "Frequent Mutation of the PIK3CA Gene in Ovarian and Breast Cancers"; Clin. Cander Res 2005; 11: pp. 2875-2878.
Endersby, et al.; "PTEN Signaling in Brain; Neuropathology and Tumorigenesis"; Oncogene (2008) 27, pp. 5416-5430.
Gurrieri, et al., "Loss of the Tumor Suppressor Pml in Human Cancers of Multiple Histologic Origins"; Journal of the National Cancer Institute, Col. 96, No. 4, Feb. 18, 2004 pp. 269-279.
Hartmann, et al., "PIK3CA Mutations in Glioblastoma Multiforme"; aCTA nEUROPATHOL (2005) 109: pp. 639-642.
Li, et al., "PTEN, a Putative Protein Tyrosine Phosphate Gene Mutated in Human Brain, Breast, and Prostate Cancer"; Science 275, 1943 (1997); pp. 1943-1947.
Maxwell, et al., "Mutation of the Pten Tumor Suppressor Gene in Endometrial Hyperplasias"; Cancer Res 1998; 58: pp. 2500-2503.
Shah, et al., "LKB1 and Lung Cancer: More Than the Usual Suspects"; Cancer Res 2008;68: pp. 3562-3565.
Steck, et al., "Identification of a Candidate Tumour Suppressor Gene, MMAC1, At Chromosome 10q23.3 That Is Mutated in Mulitple Advanced Cancers"; Nature Genetics, vol. 15, Apr. 15, 1997, pp. 356-362.
Testa, et al., "AKT Plays a Central Role in Tumorigenesis"; PNAS, Sep. 25, 2001; vol. 98, No. 20, pp. 10983-10985.
Yuan, et al., "Pl3K Pathway Alterations in Cancer: Variations on a Theme", Oncogene (2008) 27, pp. 5497-5510.
Yuan, et al., "Frequent Activation of AKT2 and Induction of Apoptosis by Inhibition of Phosphoinositide-3-OH Kinase/Akt Pathway in Human Ovarian Cancer"; Oncogene (2000) 19, pp. 2324-2330.
Zhou, et al., "PTEN Mutational Spectra, Expression Levels, and Subcellular Localization in Microsatellite Stable and Unstable Colorectal Cancers"; American Journal of Pathology, vol. 161, No. 2, Aug. 2002, pp. 439-447.

* cited by examiner

PYRIMIDINE DERIVATIVES, PREPARATION THEREOF, AND PHARMACEUTICAL USE THEREOF AS AKT(PKB) PHOSPHORYLATION INHIBITORS

The present invention relates to novel chemical compounds derived from pyrimidines, to the process for preparing same, to the novel intermediates obtained, to the use thereof as medicines, to the pharmaceutical compositions containing same and to the novel use of such derivatives.

The present invention thus also relates to the use of said derivatives for preparing a medicine intended for treating human beings.

More particularly, the invention relates to novel pyrimidine derivatives and to the pharmaceutical use thereof for preventing and treating affections capable of being modulated by inhibiting the PI3K/AKT/mTOR pathway. AKT is a key participant in this signaling pathway. A high level of AKT phosphorylation is the marker for activation of the pathway which is found in numerous human cancers.

The products of the present invention can thus in particular be used for preventing or treating affections capable of being modulated by inhibition of the AKT phosphorylation (P-AKT). The inhibition of P-AKT can in particular be obtained by inhibition of the PI3K/AKT/mTOR pathway, and in particular by inhibition of kinases belonging to this pathway, for instance receptor tyrosine kinases, such as EGFR, IGFR, ErbB2,3'-phosphoinositide-dependent protein kinase-1 (PDK1), phosphoinositide kinase PI3K, serine-threonine kinase AKT or the mTOR kinase.

The inhibition and regulation of the PI3K/AKT/mTOR pathway constitutes in particular a new and powerful mechanism of action for treating a large number of cancer diseases, including solid and liquid tumors.

Such affections that the products of the present application can treat are solid or liquid human tumors.

Role of the PI3K/AKT/mTOR Pathway

The PI3K/AKT/mTOR signaling pathway is a complex network which regulates many cell functions, such as cell growth, survival, proliferation and motility, which are key processes of tumorigenesis.

This signaling pathway is an important target in the treatment of cancer since most of its effectors are modified in human tumors. The main effectors which contribute to the activation of the pathway are i) oncogenes such as ErbB1 (EGFR), ErbB2 (HER2), PIK3CA and AKT which are activated by mutation, amplification or overexpression; ii) deficiency of tumor suppressor genes such as PTEN, TSC1/2, LKB and PML which are inactivated following mutations or deletions (Jiang L-Z & Liu L-Z, Biochim Biophys Acta, 2008, 1784: 150; Vivanco I & Sawyers C L, 2002, Nat Rev Cancer, 2: 489; Cully M et al., Nature Rev. Cancer, 2006, 6:184).

The activation of the oncogenes of this signaling pathway is found in many human cancer diseases:
 PIK3CA-activating mutations are present in 15-30% of colon, breast, endometrial, liver, ovarian and prostate cancers (T L Yuan and L C Cantley, Oncogene, 2008, 27: 5497; Y. Samuels et al. Science, 2004, 304: 554; K E. Bachman et al. Cancer Biol Ther, 2004, 3: 772; D A Levine et al. Clin Canc Res. 2005, 11: 2875; C. Hartmann et al. Acta Neuropathol. 2005, 109: 639);
 amplifications, activating mutations and overexpressions of RTKs such as EGFR and HER2 in brain, breast and lung (NSCLC) cancers;
 the amplification and activating overexpression of AKT in brain, lung (NSCLC), breast, kidney, ovarian and pancreatic cancers (Testa J R. and Bellacosa A., Proct. Natl. Acad. Sci. USA 2001, 98: 10983; Cheng et al., Proct. Natl. Acad. Sci. USA 1992, 89: 9267; Bellacosa et al., Int. J. Cancer, 1995, 64: 280; Cheng et al., Proct. Natl. Acad. Sci. USA 1996, 93: 3636; Yuan et al., Oncogene, 2000, 19: 2324).

Deficiency of the tumor suppressor genes of this signaling pathway is also found in many human cancer diseases:
 the deletion of PTEN in 50% of lung (NSCLC), liver, kidney, prostate, breast, brain, pancreatic, endometrial and colon cancers (Maxwell G L et al. Canc. Res. 1998, 58: 2500; Zhou X-P et al. Amer. J. Pathol., 2002, 161: 439; Endersby R & Baker S J, Oncogene, 2008, 27: 5416; Li et al. Science, 1997, 275: 1943; Steack P A et al., Nat. Genet., 1997, 15: 356);
 mutations of TSC1/2 in more than 50% of tuberous scleroses; mutations or deletions of LKB1 (or STK11) which predispose to cancers of the gastrointestinal tract and to pancreatic cancer and which are found in particular in 10-38% of lung adenocarcinomas (Shah U. et al. Cancer Res. 2008, 68: 3562);
 modifications of PML in particular by translocation in the human tumors (Gurrieri C et al, J. NAtl Cancer Inst. 2004, 96: 269).

Furthermore, this signaling pathway is a major factor in resistance to chemotherapy, to radiotherapy and to targeted therapies, such as inhibitors of EGFR and HER2, for example (C. Sawyers et al. Nat Rev 2002).

Role of AKT

AKT (protein kinase B; PKB) is a serine-threonine kinase which occupies a central place in one of the major cell signaling pathways, the PI3K/AKT pathway. AKT is in particular involved in the growth, proliferation and survival of tumor cells. AKT is activated in two steps (1) by phosphorylation of threonine 308 (P-T308) by PDK1 and (2) by phosphorylation of serine 473 (P-S473) by mTORC2 (or mTOR-Rictor complex), resulting in total activation. AKT in turn regulates a large number of proteins, including mTOR (mammalian target of Rapamycin), BAD, GSK3, p21, p27, FOXO or FKHRL1 (Manning B D & Cantley L C, Cell, 2007 129: 1261). The activation of AKT promotes the internalization of nutrients, thereby triggering an anabolic metabolization process which supports cell growth and proliferation. In particular, AKT controls the initiation of protein synthesis through a cascade of interactions which takes place by means of TSC1/2 (tuberous sclerosis complex), Rheb, and TOR so as to result in two critical targets of the signaling pathway, p70S6K and 4EBP. AKT also induces inhibitory phosphorylation of the Forkhead transcription factor and the inactivation of GSK313, which result in the inhibition of apoptosis and in progression of the cell cycle (Franke T F, Oncogene, 2008, 27: 6473). AKT is therefore a target for anticancer therapy, and the inhibition of AKT activation by inhibition of its phosphorylation can induce apoptosis in malignant cells and thereby provide a treatment for cancer.

Receptor Tyrosine Kinases Such as IGF1R

Abnormally high levels of protein kinase activity have been implicated in many diseases resulting from abnormal cell functions. This can originate either directly or indirectly from a dysfunction in the mechanisms of control of the kinase activity, linked for example to a mutation, an overexpression or an inappropriate activation of the enzyme, or via an overproduction or underproduction of cytokines or growth factors, also involved in signal transduction upstream or downstream of the kinases. In all these cases, a selective inhibition of the action of the kinases leads to the hope of a beneficial effect.

The insulin-like growth factor receptor type 1 (IGF-1-R) is a transmembrane receptor tyrosine kinase which binds first and foremost to IGFI, but also to IGFII and to insulin with a lower affinity. The binding of IGF1 to its receptor leads to oligomerization of the receptor, activation of the tyrosine kinase, intermolecular autophosphorylation and the phosphorylation of cell substrates (main substrates: IRS1 and Shc). The receptor activated by its ligand induces a mitogenic activity in normal cells. However, IGF-1-R plays an important role in "abnormal" growth.

Several clinical reports underline the important role of the IGF-I pathway in the development of human cancers:

IGF-1-R is often found overexpressed in many tumor types (breast, colon, lung, sarcoma, prostate, multiple myeloma) and its presence is often associated with a more aggressive phenotype.

High concentrations of circulating IGF1 are strongly correlated with a risk of prostate, lung and breast cancer.

Furthermore, it has been widely documented that IGF-1-R is necessary for the establishment and maintenance of the transformed phenotype both in vitro and in vivo (Baserga R, Exp. Cell. Res., 1999, 253, pages 1-6). The kinase activity of IGF-1-R is essential to the activity of transformation of several oncogenes: EGFR, PDGFR, SV40 virus large T antigen, activated Ras, Raf, and v-Src. The expression of IGF-1-R in normal fibroblasts induces a neoplastic phenotype, which can subsequently lead to tumor formation in vivo. The expression of IGF-1-R plays an important role in substrate-independent growth. IGF-1-R has also been shown to be a protector in apoptosis induced by chemotherapy, by radiation, and apoptosis induced by cytokines. Furthermore, the inhibition of endogenous IGF-1-R by a dominant negative, the formation of a triple helix or the expression of an antisense causes a suppression of the transforming activity in vitro and a decrease in tumor growth in animal models.

PDK1

3'-Phosphoinositide-dependent protein kinase-1 (PDK1) is one of the essential components of the PI3K-AKT signaling pathway. It is a serine-threonine (Ser/Thr) kinase, the role of which is to phosphorylate and activate other Ser/Thr kinases of the AGC family involved in the control of cell growth, proliferation and survival and in the regulation of the metabolism. These kinases include protein kinase B (PKB or AKT), SGK (or serum and glucocorticoid regulated kinase), RSK (or p90 ribosomal S6 kinase), p70S6K (or p70 ribosomal S6 kinase) and also various isoforms of protein kinase C (PKC) (Vanhaesebroeck B. & Alessi D R., Biochem J, 2000, 346: 561). One of the key roles of PDK1 is therefore the activation of AKT: in the presence of PIP3, the second messenger generated by PI3K, PDK-1 is recruited to the plasma membrane via its PH (pleckstrin homology) domain and phosphorylates AKT on threonine 308 located in the activation loop, which is an essential modification in AKT activation. PDK1 is expressed ubiquitously and is a constitutively active kinase. PDK1 is a key element in the PI3K/AKT signaling pathway for regulating key processes in tumor genesis, such as cell proliferation and survival. Since this pathway is activated in more than 50% of human cancers, PDK1 represents a target for anticancer therapy. The inhibition of PDK1 should result in an effective inhibition of the proliferation and survival of cancer cells and therefore provide a therapeutic benefit for human cancers (Bayascas J R, Cell cycle, 2008, 7: 2978; Peifer C. & Alessi D R, ChemMedChem, 2008, 3: 1810).

Phosphoinositide-3 Kinases (PI3Ks)

The PI3K lipid kinase is an important target in this signaling pathway for oncology. The class-I PI3Ks are divided up into class Ia (PI3Kα,β,δ) activated by receptor tyrosine kinases (RTKs), G protein-coupled receptors (GPCRs), GTPases of the family Rho, p21-Ras and into class Ib (PI3Kγ) activated by GPCRs and by p21-Ras. The class-Ia PI3Ks are heterodimers which consist of a catalytic subunit p110α, β or δ and a regulatory subunit p85 or p55. Class Ib (p110γ) is monomeric. The class-I PI3Ks are lipid/protein kinases which are activated by RTKs, GPCRs or Ras after recruitment to the membrane. These class-I PI3Ks phosphorylate phosphatidylinositol 4,5-biphosphate (PIP2) on position 3 of the inositol to give phosphatidylinositol 3,4,5-triphosphate (PIP3), a key second messenger of this signaling pathway. In turn, PIP3 recruits AKT and PDK1 to the membrane, where they bind via their pleckstrin homology domain (PH domain), resulting in the activation of AKT via phosphorylation by PDK1 on threonine 308. AKT phosphorylates many substrates, thus playing a key role in many processes resulting in cell transformation, such as cell proliferation, growth and survival and also angiogenesis.

The class-I PI3Ks are implicated in human cancers: somatic mutations of the PIK3CA gene which encodes PI3Kαβ are found in 15-35% of human tumors, with in particular two main oncogenic mutations H1047R (in the kinase domain) and E545K/E542K (in the helical domain) (Y. Samuels et al. Science, 2004, 304: 554; T L Yuan and L C Cantley, Oncogene, 2008, 27: 5497). PI3K inhibitors are expected to be effective in treating numerous human cancers which exhibit genetic modifications resulting in the activation of the PI3K/AKT/mTOR pathway (Vogt P. et al., Virology, 2006, 344: 131; Zhao L & Vogt P K, Oncogene, 2008, 27: 5486).

Kinase-inhibiting morpholinopyrimidinone derivatives are known to those skilled in the art.

Application WO2008/148074 describes products which have an mTOR-inhibiting activity. These products are pyrido [1,2-a]pyrimidin-4-ones which differ from the products of the present invention owing to their entirely aromatic nature and to their substitutions.

Application WO2008/064244 describes the use of PI3Kβ-inhibiting products TGX-221 and TGX-155 which are of use in the treatment of cancer and in particular in breast cancer. These products are pyrido[1,2-a]pyrimidin-4-ones previously described in applications WO2004/016607 and WO2001/053266, which differ from the products of the present invention owing to their entirely aromatic nature and to their substitutions.

Applications WO2006/109081, WO2006/109084 and WO2006/126010 describe DNA-PK-inhibiting products which are of use in the treatment of ATM-deficient cancers. These products are pyrido[1,2-a]pyrimidin-4-ones which differ from the products of the present invention owing to their entirely aromatic nature and to their substitutions.

Application WO2003/024949 describes DNA-PK-inhibiting products which are of use in the treatment of ATM-deficient cancers. These products are pyrido[1,2-a]pyrimidin-4-ones which differ from the products of the present invention owing to their entirely aromatic nature and to their substitutions.

Kinase-inhibiting morpholinopyrimidine derivatives are also known to those skilled in the art.

Applications WO2009/007748, WO2009/007749, WO2009/007750 and WO2009/007751 describe products which have an mTOR-inhibiting and/or PI3K-inhibiting activity for the treatment of cancers. These products are pyrimidines substituted in the 2, 4 and 6 positions and the products of the present invention differ therefrom owing to the presence of the carbonyl or thiocarbonyl group on the pyrimidine and also by virtue of the various substituents.

General Formulae of the Compounds According to the Invention:

A subject of the present invention is compounds of formulae (Ia), (Ib), (Ic), (Id) and (Ie).

A subject of the present invention is the products of formula (Ia):

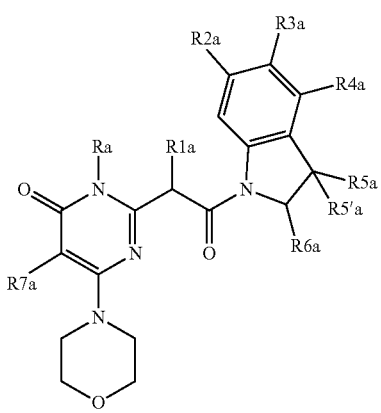

(Ia)

wherein:
Ra is a hydrogen atom or an alkyl radical;
R1a is a hydrogen atom or a methyl radical;
R2a is a hydrogen atom or a fluorine atom;
R3a is a hydrogen atom or a halogen atom;
R4a is a hydrogen atom, a halogen atom or a hydroxyl, alkyl or alkoxy radical, the alkyl radicals being optionally substituted with one or more radicals, which may be identical or different, selected from halogen atoms and the hydroxyl radical, the alkoxy radicals being optionally substituted with one or more halogen atoms;
R5a and R'5a, which may be identical or different, are a hydrogen atom or an alkyl radical;
R6a is a hydrogen atom or an alkyl radical optionally substituted with one or more radicals, which may be identical or different, selected from halogen atoms and the hydroxyl radical;
R7a is a halogen atom;
said products of formula (Ia) being in any of the possible racemic, enantiomeric and diastereoisomeric isomer forms, and also the addition salts with inorganic and organic acids or with inorganic and organic bases of said products of formula (Ia).

A subject of the present invention is thus the products of formula (Ia) such that:
Ra is a hydrogen atom or a methyl radical;
R1a is a hydrogen atom or a methyl radical;
R2a is a hydrogen atom or a fluorine atom;
R3a is a hydrogen atom or a fluorine atom;
R4a is a hydrogen atom, a halogen atom or an alkyl radical optionally substituted with one or more radicals, which may be identical or different, selected from halogen atoms;
R5a and R'5a are a hydrogen atom;
R6a is a hydrogen atom or an alkyl radical optionally substituted with one or more radicals, which may be identical or different, selected from fluorine atoms and the hydroxyl radical;
R7a is a fluorine, bromine or chlorine atom;
said products of formula (Ia) being in any of the possible racemic, enantiomeric and diastereoisomeric isomer forms, and also the addition salts with inorganic and organic acids or with inorganic and organic bases of said products of formula (Ia).

In the products of formula (Ia) as defined above, R4a is, for example, a hydrogen atom or a halogen atom, such as fluorine, chlorine or bromine, or else the $CF_3$ radical, the other substituents Ra, R1a, R2a, R3a, R5a, R'5a and R6a having any one of their meanings indicated above for said products of formula (Ia).

In the products of formula (Ia), R6a is, for example, a hydrogen atom or a methyl radical optionally substituted with a fluorine atom or the hydroxyl radical, the other substituents Ra, R1a, R2a, R3a, R4a, R5a and R'5a having any one of their meanings indicated above for said products of formula (Ia).

A subject of the present invention is also the products of formula (Ib):

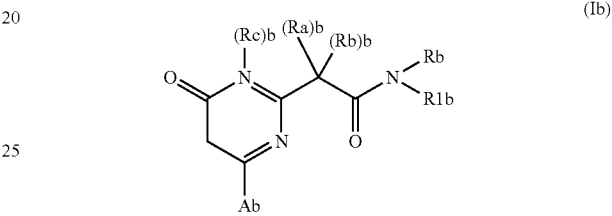

(Ib)

wherein:
Ab is a morpholine radical or a pyridyl radical, defined as follows:
the morpholine radical, that Ab may represent, being substituted with one or more radicals selected from a deuterium atom, and alkyl radicals which are themselves optionally substituted with one or more radicals selected from halogen atoms and the hydroxyl radical, it being understood that two adjacent substituents of the morpholine can together form a cyclic radical with the carbon atoms to which they are bonded;
the pyridyl radical, that Ab may represent, being optionally substituted with a halogen atom or an alkyl or alkoxy radical;
R1b is an aryl or heteroaryl radical optionally substituted with one or more radicals, which may be identical or different, selected from halogen atoms and hydroxyl, CN, nitro, —COOH, —COOalk, —N(Rx)b, (Ry)b, —CON(Rx)b(Ry)b, —N(Rx)bCO(Ry)b, —CO(Ry)b, —N(Rx)bCO$_2$(Rz)b, alkoxy, phenoxy, alkylthio, alkyl, alkenyl, alkynyl, cycloalkyl, O-cycloalkyl, heterocycloalkyl, aryl and heteroaryl radicals;
the latter alkoxy, phenoxy, alkylthio, alkyl, alkenyl, alkynyl, heterocycloalkyl, aryl and heteroaryl radicals being themselves optionally substituted with one or more radicals, which may be identical or different, selected from halogen atoms and hydroxyl, alkoxy and N(Rv)b(Rw)b radicals;
the aryl and heteroaryl radicals being, in addition, optionally substituted with one or more alkyl and alkoxy radicals which are themselves optionally substituted with one or more halogen atoms;
it being possible for the heterocycloalkyl and heteroaryl radicals to, in addition, contain an oxo radical;
Rb is a hydrogen atom or else forms, with R1b, a saturated or partially or totally unsaturated 5- or 6-membered ring fused to an aryl or heteroaryl residue and optionally containing one or more other heteroatoms selected from O, S, N, NH and Nalk, this bicyclic radical being optionally substituted with one or more radicals, which may be identical or different, selected from halogen atoms and hydroxyl, alkyl and alkoxy radicals;

(Ra)b and (Rb)b, which may be identical or different, are independently a hydrogen atom, a halogen atom or an alkyl radical optionally substituted with one or more halogen atoms;

(Rc)b is a hydrogen atom or an alkyl radical optionally substituted with one or more halogen atoms;

N(Rx)b(Ry)b being such that (Rx)b is a hydrogen atom or an alkyl radical and (Ry)b is a hydrogen atom, a cycloalkyl radical or an alkyl radical optionally substituted with one or more radicals, which may be identical or different, selected from hydroxyl, alkoxy, N(Rv)b(Rw)b and heterocycloalkyl radicals; or (Rx)b and (Ry)b form, with the nitrogen atom to which they are bonded, a cyclic radical containing from 3 to 10 ring members and optionally one or more other heteroatoms selected from O, S, NH and N-alkyl, this cyclic radical being optionally substituted;

N(Rv)b(Rw)b being such that (Rv)b is a hydrogen atom or an alkyl radical and (Rw)b is a hydrogen atom, a cycloalkyl radical or an alkyl radical optionally substituted with one or more radicals, which may be identical or different, selected from hydroxyl, alkoxy and heterocycloalkyl radicals; or (Rv)b and (Rw)b form, with the nitrogen atom to which they are bonded, a cyclic radical containing from 3 to 10 ring members and optionally one or more other heteroatoms selected from O, S, NH and N-alkyl, this cyclic radical being optionally substituted;

the cyclic radicals that (Rx)b and (Ry)b or (Rv)b and (Rw)b can respectively form with the nitrogen atom to which they are bonded being optionally substituted with one or more radicals, which may be identical or different, selected from halogen atoms, and alkyl, hydroxyl, oxo, alkoxy, $NH_2$, NHalk and $N(alk)_2$ radicals;

(Rz)b is the values for (Ry)b with the exception of hydrogen;

(Rx)b, (Ry)b and (Rz)b in the N(Rx)bCO(Ry)b, —CO(Ry)b and N(Rx)bCO$_2$(Rz)b radicals being selected from the meanings indicated above for (Rx)b, (Ry)b, and (Rz)b;

all the alkyl (alk), alkoxy and alkylthio radicals above being linear or branched and containing from 1 to 6 carbon atoms, said products of formula (Ib) being in any of the possible racemic, enantiomeric and diastereoisomeric isomer forms, and also the addition salts with inorganic and organic acids or with inorganic and organic bases of said products of formula (Ib).

Particular note is made of the products of formula (Ib) as defined above wherein, when R1b is a phenyl radical and Ab is a morpholine radical, then R1b does not bear a pyrrole radical as substituent.

Particular note is also made of the products of formula (Ib) as defined above wherein, when R1b is a phenyl radical and Ab is a pyridyl radical, then R1b is necessarily substituted with at least one substituent as defined above (i.e. R1b is not unsubstituted phenyl) and when R1b has only one substituent in the meta position, then this substituent is not a fluorine atom.

A subject of the present invention is also the products of formula (Ic):

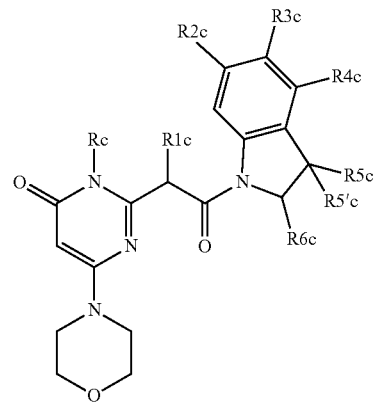

wherein:
Rc is a hydrogen atom or an alkyl radical;
R1c is a hydrogen atom or a methyl radical;
R2c is a hydrogen atom or a fluorine atom;
R3c is a hydrogen atom or a halogen atom;
R4c is a hydrogen atom, a halogen atom or a hydroxyl, alkyl or alkoxy radical, the alkyl radicals being optionally substituted with one or more radicals, which may be identical or different, selected from halogen atoms and the hydroxyl radical, the alkoxy radicals being optionally substituted with one or more halogen atoms;
R5c and R5'c, which may be identical or different, are a hydrogen atom or an alkyl radical;
R6c is a hydrogen atom or an alkyl radical optionally substituted with one or more radicals, which may be identical or different, selected from halogen atoms (F) and hydroxyl and alkoxy radicals;

said products of formula (Ic) being in any of the possible racemic, enantiomeric and diastereoisomeric isomer forms, and also the addition salts with inorganic and organic acids or with inorganic and organic bases of said products of formula (Ic).

A subject of the present invention is the products of formula (Ic) as defined above, wherein:
Rc is a hydrogen atom or a methyl radical;
R1c is a hydrogen atom;
R2c is a hydrogen atom or a fluorine atom;
R3c is a hydrogen atom or a fluorine atom;
R4c is a hydrogen atom, a fluorine, chlorine or bromine atom or a hydroxyl radical;
R5c and R5'c, which may be identical or different, are a hydrogen atom or a methyl radical;
R6c is a hydrogen atom or a methyl, ethyl or isopropyl radical;
said products of formula (Ic) being in any of the possible racemic, enantiomeric and diastereoisomeric isomer forms, and also the addition salts with inorganic and organic acids or with inorganic and organic bases of said products of formula (Ic).

The products of formula (Ic) according to the present invention are such that:
either R4c is not F, Cl or Br when R2c, R3c, R5c and R6c are a hydrogen atom,
or R6c is not methyl when R2c, R3c, R4c and R5c are a hydrogen atom.

A subject of the present invention is also the products of formula (Id):

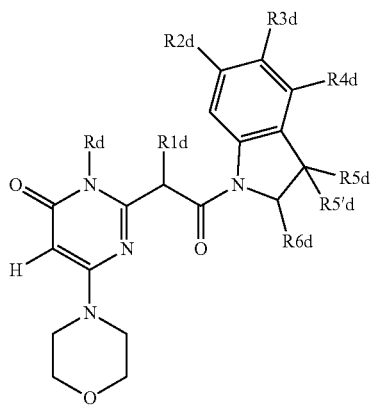

(Id)

wherein:

Rd is a hydrogen atom or an alkyl, cycloalkyl, aryl, heteroaryl, $NH_2$ or CN radical;

R1d is a hydrogen atom or a methyl radical;

R2d is a hydrogen atom or a fluorine atom;

R3d is a hydrogen atom or a halogen atom;

R4d is a hydrogen atom, halogen atoms and hydroxyl, alkyl, alkoxy, heterocycloalkyl, aryl, heteroaryl and N(Rx)d (Ry)d radicals; all these alkyl, alkoxy, heterocycloalkyl, aryl and heteroaryl radicals being themselves optionally substituted with one or more radicals, which may be identical or different, selected from halogen atoms and hydroxyl, oxo, alkyl, heterocycloalkyl, alkoxy, N(Rv)d(Rw)d and —$SO_2$Alk radicals;

R5d and R5'd, which may be identical or different, are a hydrogen atom or an alkyl radical or form, together with the carbon atom to which they are bonded, a cyclic radical containing from 3 to 10 ring members (spirocycloalkyl) optionally containing one or more heteroatoms (spiroheterocycloalkyl) selected from O, S and NH, these cyclic radicals being optionally substituted with one or more radicals, which may be identical or different, selected from halogen atoms and alkyl, cycloalkyl, hydroxyl, oxo, alkoxy, $NH_2$, NHalk and N(alk)$_2$ radicals;

R6d is a hydrogen atom; an alkyl radical which is itself optionally substituted with one or more radicals, which may be identical or different, selected from halogen atoms, deuterium atoms and hydroxyl and alkoxy radicals; a cycloalkyl radical or a phenyl radical which is itself optionally substituted with one or more radicals, which may be identical or different, selected from halogen atoms or alkoxy radicals;

it being possible for R5d and R6d to optionally form, with the carbon atoms to which they are bonded, a cyclic radical containing from 3 to 10 ring members (cycloalkyl) optionally containing one or more heteroatoms (heterocycloalkyl) selected from O, S and NH, these cyclic radicals being optionally substituted with one or more radicals, which may be identical or different, selected from halogen atoms and alkyl, hydroxyl, oxo, alkoxy, $NH_2$; NHalk and N(alk)$_2$ radicals;

N(Rx)d(Ry)d being such that (Rx)d is a hydrogen atom or an alkyl radical and (Ry)d is a hydrogen atom, a cycloalkyl radical or an alkyl radical optionally substituted with one or more radicals, which may be identical or different, selected from hydroxyl, alkoxy, N(Rv)d(Rw)d and heterocycloalkyl radicals; or (Rx)d and (Ry)d form, with the nitrogen atom to which they are bonded, a cyclic radical containing from 3 to 10 ring members and optionally one or more other heteroatoms selected from O, S, NH and N-alkyl, this cyclic radical being optionally substituted with one or more radicals, which may be identical or different, selected from halogen atoms and hydroxyl, oxo, alkyl, heterocycloalkyl, alkoxy, N(Rv)d (Rw)d and —$SO_2$Alk radicals;

N(Rv)d(Rw)d being such that (Rv)d is a hydrogen atom or an alkyl radical and (Rw)d is a hydrogen atom, a cycloalkyl radical or an alkyl radical optionally substituted with one or more radicals, which may be identical or different, selected from hydroxyl, alkoxy and heterocycloalkyl radicals; or (Rv)d and (Rw)d form, with the nitrogen atom to which they are bonded, a cyclic radical containing from 3 to 10 ring members and optionally one or more other heteroatoms selected from O, S, NH and N-alkyl, this cyclic radical being optionally substituted with one or more radicals, which may be identical or different, selected from halogen atoms and hydroxyl, oxo, alkyl, heterocycloalkyl, alkoxy, $NH_2$, NHalk and N(alk)$_2$ and —$SO_2$Alk radicals;

said products of formula (Id) being in any of the possible racemic, enantiomeric and diastereoisomeric isomer forms, and also the addition salts with inorganic and organic acids or with inorganic and organic bases of said products of formula (Id).

A subject of the present invention is thus the products of formula (Id) as defined above.

A subject of the present invention is thus the products of formula (Id) as defined above, wherein Rd is a hydrogen atom or an alkyl, cycloalkyl, aryl or heteroaryl radical, and the other substituents R1d, R2d, R3d, R4d, R5d, R5'd and R6d have any one of the definitions indicated above or hereinafter for said products of formula (Id).

The products of formula (Id) according to the present invention are such that:
  either at least one of R2d, R3d, R4d, R5d, R5'd and R6d is other than halogen, hydroxyl, alkyl and alkoxy; the other substituents Rd and R1d of said products of formula (Id) having any one of the definitions indicated above or hereinafter;
  or Rd is not a hydrogen atom or an alkyl radical optionally substituted with one or more halogen atoms, the other substituents R1d, R2d, R3d, R4d, R5d, R5'd and R6d of said products of formula (Id) having any one of the definitions indicated above or hereinafter.

A subject of the present invention is also the products of formula (Ie):

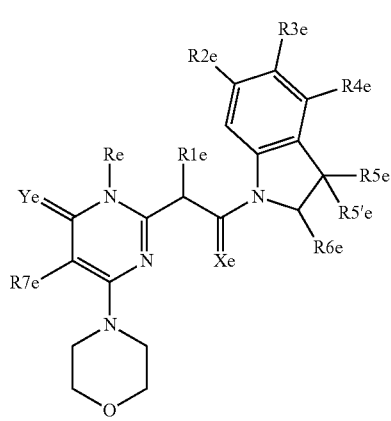

(Ie)

wherein:

Xe and Ye, which may be identical or different, are such that:
  Xe is O or S and Ye is S;
  Re is a hydrogen atom or an alkyl radical;
  R1e is a hydrogen atom or a methyl radical;
  R2e is a hydrogen atom or a fluorine atom;

R3e is a hydrogen atom or a halogen atom;

R4e is a hydrogen atom, a halogen atom or a hydroxyl, alkyl or alkoxy radical, the alkyl radicals being optionally substituted with one or more radicals, which may be identical or different, selected from halogen atoms and the hydroxyl radical, the alkoxy radicals being optionally substituted with one or more halogen atoms;

R5e and R5'e, which may be identical or different, are a hydrogen atom or an alkyl radical;

R6e is a hydrogen atom or an alkyl radical optionally substituted with one or more radicals, which may be identical or different, selected from halogen atoms and the hydroxyl radical;

R7e is a hydrogen atom or a halogen atom;

said products of formula (Ie) being in any of the possible racemic, enantiomeric and diastereoisomeric isomer forms, and also the addition salts with inorganic and organic acids or with inorganic and organic bases of said products of formula (Ie).

The present invention thus relates to the products of formula (Ie) as defined above, wherein:

Xe and Ye, which may be identical or different, are such that:

Xe is O or S and Y is S;

Re is a hydrogen atom;

R1e is a hydrogen atom or a methyl radical;

R2e is a hydrogen atom or a fluorine atom;

R3e is a hydrogen atom or a halogen atom;

R4e is a hydrogen atom, a halogen atom or a hydroxyl, alkyl or alkoxy radical, the alkyl radicals being optionally substituted with one or more radicals, which may be identical or different, selected from halogen atoms and the hydroxyl radical, the alkoxy radicals being optionally substituted with one or more halogen atoms;

R5e and R5'e, which may be identical or different, are a hydrogen atom or an alkyl radical;

R6e is a hydrogen atom or an alkyl radical optionally substituted with one or more radicals, which may be identical or different, selected from halogen atoms and the hydroxyl radicals;

R7e is a hydrogen atom;

said products of formula (Ie) being in any of the possible racemic, enantiomeric and diastereoisomeric isomer forms, and also the addition salts with inorganic and organic acids or with inorganic and organic bases of said products of formula (Ie).

In formulae (Ia), (Ib), (Ic), (Id) and (Ie):

the term alkyl radical (or alk) denotes linear or branched radicals containing from 1 to 10 carbon atoms, such as methyl, ethyl, propyl, isopropyl, butyl, isobutyl, sec-butyl, tert-butyl, pentyl, isopentyl, hexyl, isohexyl and equally heptyl, octyl, nonyl and decyl and also the linear or branched positional isomers thereof; preference is given to the alkyl radicals containing from 1 to 6 carbon atoms and more particularly the alkyl radicals containing from 1 to 4 carbon atoms of the above list;

the term alkoxy radical denotes linear and branched radicals containing from 1 to 10 carbon atoms, such as methoxy, ethoxy, propoxy, isopropoxy, linear secondary or tertiary butoxy, pentoxy or hexoxy and also the linear or branched positional isomers thereof; preference is given to the alkoxy radicals containing from 1 to 4 carbon atoms of the above list;

the term halogen atom denotes chlorine, bromine, iodine or fluorine atoms and preferably the chlorine, bromine or fluorine atom;

the term cycloalkyl radical denotes a saturated carbocyclic radical containing 3 to 10 carbon atoms and thus denotes in particular cyclopropyl, cyclobutyl, cyclopentyl and cyclohexyl radicals and most particularly cyclopropyl, cyclopentyl and cyclohexyl radicals;

the term alkylthio radical denotes the linear, and where appropriate branched, radicals methylthio, ethylthio, propylthio, isopropylthio, linear secondary or tertiary butylthio, pentylthio or hexylthio and also the linear or branched positional isomers thereof; preference is given to the alkylthio radicals containing from 1 to 4 carbon atoms of the above list;

in the —O-cycloalkyl radical, cycloalkyl is as defined above;

the term heterocycloalkyl radical thus denotes a monocyclic or bicyclic carbocyclic radical containing from 3 to 10 ring members, interrupted with one or more heteroatoms, which may be identical or different, selected from oxygen, nitrogen or sulfur atoms; mention may, for example, be made of morpholinyl, thiomorpholinyl, homomorpholinyl, aziridyl, azetidyl, piperazinyl, piperidyl, homopiperazinyl, pyrrolidinyl, imidazolidinyl, pyrazolidinyl, tetrahydrofuryl, tetrahydrothienyl, tetrahydropyran, oxodihydropyridazinyl, or else oxetanyl radicals, all these radicals being optionally substituted; mention may in particular be made of morpholinyl, thiomorpholinyl, homomorpholinyl, piperazinyl, piperidyl, homopiperazinyl or else pyrrolidinyl radicals;

the terms aryl and heteroaryl denote monocyclic or bicyclic, respectively carbocyclic and heterocyclic, unsaturated or partially unsaturated radicals containing at most 12 ring members, which can optionally contain a —C(O) ring member, the heterocyclic radicals containing one or more heteroatoms, which may be identical or different, selected from O, N or S, with N, where appropriate, being optionally substituted;

the term aryl radical thus denotes monocyclic or bicyclic radicals containing 6 to 12 ring members, such as, for example, phenyl, naphthyl, biphenyl, indenyl, fluorenyl and anthracenyl radicals, more particularly phenyl and naphthyl radicals and even more particularly the phenyl radical. It may be noted that a carbocyclic radical containing a —C(O) ring member is, for example, the tetralone radical;

the term heteroaryl radical thus denotes monocyclic or bicyclic radicals containing 5 to 12 ring members: monocyclic heteroaryl radicals such as, for example, the following radicals: thienyl such as 2-thienyl and 3-thienyl, furyl such as 2-furyl and 3-furyl, pyranyl, pyrrolyl, pyrrolinyl, pyrazolinyl, imidazolyl, pyrazolyl, pyridyl such as 2-pyridyl, 3-pyridyl and 4-pyridyl, pyrazinyl, pyrimidinyl, pyridazinyl, oxazolyl, thiazolyl, isothiazolyl, diazolyl, thiadiazolyl, thiatriazolyl, oxadiazolyl, isoxazolyl such as 3- or 4-isoxazolyl, furazanyl, tetrazolyl which is free or salified, all these radicals being optionally substituted, among which more particularly thienyl such as 2-thienyl and 3-thienyl, furyl such as 2-furyl, pyrrolyl, pyrrolinyl, pyrazolinyl, imidazolyl, pyrazolyl, oxazolyl, isoxazolyl, pyridyl and pyridazinyl radicals, these radicals being optionally substituted; bicyclic heteroaryl radicals such as, for example, benzothienyl such as 3-benzothienyl, benzothiazolyl, quinolyl, isoquinolyl, dihydroquinolyl, quinolone, tetralone, adamentyl, benzofuryl, isobenzofuryl, dihydrobenzofuran, ethylenedioxyphenyl, thianthrenyl, benzopyrrolyl, benzimidazolyl, benzoxazolyl, thionaphthyl, indolyl, azaindolyl, indazolyl, purinyl, thienopyrazolyl, tetrahydroindazolyl, tetrahydrocyclopentapyrazolyl, dihydrofuropyrazolyl, tetrahydropyrrolopyrazolyl, oxotetrahydropyrrolopyrazolyl, tetrahydropyranopyrazolyl, tetrahydropyridinopyrazolyl or oxodihydropyridinopyrazolyl radicals, all these radicals being optionally substituted.

As examples of heteroaryl or bicyclic radicals, mention may more particularly be made of pyrimidinyl, pyridyl, pyrrolyl, azaindolyl, indazolyl or pyrazolyl, benzothiazolyl or benzimidazolyl radicals which are optionally substituted with one or more identical or different substituents, as indicated above.

The carboxy radical(s) of the products of formulae (Ia) to (Ie) may be salified or esterified with various groups known to those skilled in the art, among which mention may, for example, be made of:

among the salification compounds, inorganic bases such as, for example, an equivalent of sodium, of potassium, of lithium, of calcium, of magnesium or of ammonium, or organic bases such as, for example, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine or N-methylglucamine, among the esterification compounds, alkyl radicals so as to form alkoxycarbonyl groups, such as, for example, methoxycarbonyl, ethoxycarbonyl, tert-butoxycarbonyl or benzyloxycarbonyl, it being possible for these alkyl radicals to be substituted with radicals selected, for example, from halogen atoms and hydroxyl, alkoxy, acyl, acyloxy, alkylthio, amino or aryl radicals, for instance in chloromethyl, hydroxypropyl, methoxymethyl, propionyloxymethyl, methylthiomethyl, dimethylaminoethyl, benzyl or phenethyl groups.

The addition salts with inorganic or organic acids of the products of formulae (Ia) to (Ie) can, for example, be the salts formed with hydrochloric acid, hydrobromic acid, hydroiodic acid, nitric acid, sulfuric acid, phosphoric acid, propionic acid, acetic acid, trifluoroacetic acid, formic acid, benzoic acid, maleic acid, fumaric acid, succinic acid, tartaric acid, citric acid, oxalic acid, glyoxylic acid, aspartic acid, ascorbic acid, alkylmonosulfonic acids such as, for example, methanesulfonic acid, ethanesulfonic acid or propanesulfonic acid, alkyldisulfonic acids such as, for example, methanedisulfonic acid or alpha, beta-ethanedisulfonic acid, arylmonosulfonic acids such as benzenesulfonic acid and aryldisulfonic acids.

It may be recalled that stereoisomerism can be defined in its broad sense as the isomerism of compounds having the same structural formulae, but the various groups of which are arranged differently in space, such as, in particular, in monosubstituted cyclohexanes, the substituent of which can be in the axial or equatorial position, and the various possible rotational conformations of ethane derivatives. However, there is another type of stereoisomerism, which is due to the different spatial arrangements of substituents bonded either on double bonds or on rings, which is commonly referred to as geometric isomerism or cis-trans isomerism. The term stereoisomers is used in the present application in its broadest sense and therefore relates to all the compounds indicated above.

According to Certain Preferred Embodiments of the Invention:

For the Products of Formula (Ib):

In the products of formula (Ib) as defined above, R1b can thus, for example, be a phenyl radical optionally substituted with one or more radicals, which may be identical or different, selected from halogen atoms and CN, nitro, —COOH, —COOalk, —N(Rx)b(Ry)b, alkoxy, alkyl, alkynyl and cycloalkyl radicals;

the latter alkoxy, alkyl and alkynyl radicals being themselves optionally substituted with one or more radicals, which may be identical or different, selected from halogen atoms and hydroxyl, alkoxy and N(Rv)b(Rw)b radicals, with (Rx)b, (Ry)b, (Rv)b and (Rw)b as defined above or hereinafter.

In the products of formula (Ib) as defined above, N(Rx)b(Ry)b may be such that either (Rx)b is a hydrogen atom or an alkyl radical and (Ry)b is a hydrogen atom or an alkyl radical; or (Rx)b and (Ry)b form, with the nitrogen atom to which they are bonded, a cyclic radical containing from 3 to 10 ring members and optionally one or more other heteroatoms selected from O, S, NH and N-alkyl, this cyclic radical being optionally substituted;

and N(Rv)b(Rw)b can be such that (Rv)b is a hydrogen atom or an alkyl radical and (Rw)b is a hydrogen atom or an alkyl radical;

said products of formula (Ib) being in any of the possible racemic, enantiomeric and diastereoisomeric isomer forms, and also the addition salts with inorganic and organic acids or with inorganic and organic bases of said products of formula (Ib).

In particular, when N(Rx)b(Ry)b or N(Rv)b(Rw)b forms a ring as defined above, such an aminated ring may be selected in particular from pyrrolidinyl, pyrazolidinyl, pyrazolinyl, piperidyl, azepinyl, morpholinyl, homomorpholinyl, piperazinyl or homopiperazinyl radicals, these radicals being themselves optionally substituted as indicated above or hereinafter.

The N(Rx)b(Ry)b or N(Rv)b(Rw)b ring may more particularly be selected from the radicals pyrrolidinyl and morpholinyl optionally substituted with one or two alkyl radicals or piperazinyl radicals optionally substituted on the second nitrogen atom with an alkyl, phenyl and/or $CH_2$-phenyl radical, which are themselves optionally substituted with one or more radicals, which may be identical or different, selected from halogen atoms and alkyl, hydroxyl and alkoxy radicals.

A subject of the present invention is thus the products of formula (Ib) as defined above, wherein:

Ab is a pyridyl radical or a morpholine radical, as defined hereinafter:

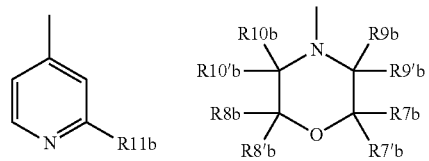

wherein:

R11b is a hydrogen atom, a halogen atom, an alkoxy radical or an alkyl radical;

R7b, R7'b, R8b and R8'b, which may be identical or different, are a hydrogen atom or a deuterium atom D, or an alkyl radical optionally substituted with one or more radicals selected from a fluorine atom and the hydroxyl radical, R9b, R9'b, R10b and R10'b, which may be identical or different, are a hydrogen atom or a deuterium atom D, it being understood that at least one of R7b, R7'b, R8b, R8'b, R9b, R9'b, R10b and R10'b is other than a hydrogen atom, it being understood that R7b with R9b or else R8b with R10b can together form a cyclic radical with the carbon atoms to which they are bonded;

R1b is a phenyl radical, optionally substituted with one or more radicals, which may be identical or different, selected from halogen atoms and CN, $NH_2$, NHalk, $N(alk)_2$, alkoxy and alkyl radicals, the latter alkoxy and alkyl radicals being themselves optionally substituted with one or more radicals, which may be identical or different, selected from halogen atoms and hydroxyl and alkoxy radicals;

Rb is a hydrogen atom or else forms, with R1b, a 2,3-dihydroindol-1-yl ring defined as follows:

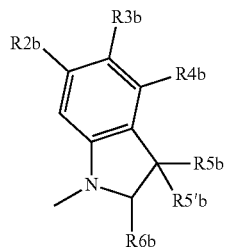

wherein:
R2b is a hydrogen atom or a fluorine atom;
R3b is a hydrogen atom or a halogen atom;
R4b is a hydrogen atom, a halogen atom or a hydroxyl, alkyl or alkoxy radical, the alkyl radicals being optionally substituted with one or more radicals, which may be identical or different, selected from halogen atoms and the hydroxyl radical, the alkoxy radicals being optionally substituted with one or more halogen atoms;
R5b and R5'b, which may be identical or different, are a hydrogen atom or an alkyl radical;
R6b is a hydrogen atom or an alkyl radical optionally substituted with one or more radicals, which may be identical or different, selected from halogen (F) atoms and hydroxyl and alkoxy radicals;
(Ra)b and (Rb)b, which may be identical or different, are independently a hydrogen atom or an alkyl radical;
(Rc)b is a hydrogen atom or an alkyl radical;
said products of formula (Ib) being in any of the possible racemic, enantiomeric and diastereoisomeric isomer forms, and also the addition salts with inorganic and organic acids or with inorganic and organic bases of said products of formula (Ib).

A subject of the present invention is particularly the products of formula (Ib) as defined above, wherein:

Ab is a morpholine radical or a pyridyl radical, as defined hereinafter:

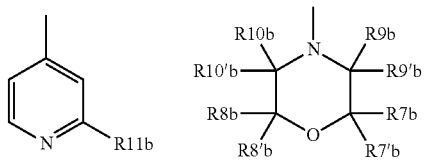

wherein:
R11b is a hydrogen atom, a fluorine atom, an alkoxy radical or an alkyl radical;
and R7b, R7'b, R8b, R8'b, R9b, R9'b, R10b and R10'b are such that:
either R7b, R7'b, R8b, R8'b, R9b, R9'b, R10b and R10'b are all a deuterium atom D;

or R7b, R7'b, R8b and R8'b are all a hydrogen atom and R9b, R9'b, R10b and R10'b are all a deuterium atom D;

or R7b is an alkyl radical optionally substituted with one or more radicals selected from a fluorine atom and the hydroxyl radical, and R7'b, R8b, R8'b, R9b, R9'b, R10b and R10'b are all a hydrogen atom;

or R7b with R9b or else R8b with R10b together form a cyclic radical with the carbon atoms to which they are bonded;

R1b is a phenyl radical optionally substituted with one or more radicals selected from fluorine and chlorine atoms;

Rb is a hydrogen atom or else forms, with R1b, the bicycle defined hereinafter:

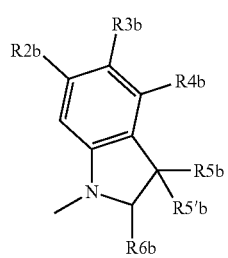

wherein:
R2b is a hydrogen atom or a fluorine atom;
R3b is a hydrogen atom or a fluorine atom;
R4b is a hydrogen atom or a fluorine or chlorine atom;
R5b and R5'b are a hydrogen atom;
R6b is a hydrogen atom or a methyl radical;
(Ra)b and (Rb)b are a hydrogen atom;
(Rc)b is a hydrogen atom;
said products of formula (Ib) being in any of the possible racemic, enantiomeric and diastereoisomeric isomer forms, and also the addition salts with inorganic and organic acids or with inorganic and organic bases of said products of formula (Ib).

For the Compounds of Formula (Id):
In the products of formula (Id) as defined above, N(Rx)d (Ry)d can, for example, be such that either (Rx)d is a hydrogen atom or an alkyl radical and (Ry)d is a hydrogen atom or an alkyl radical; or (Rx)d and (Ry)d form, with the nitrogen atom to which they are bonded, a cyclic radical containing from 3 to 7 ring members and optionally one or more other heteroatoms selected from O, S and NH, this cyclic radical being optionally substituted as indicated above or hereinafter;

and N(Rv)d(Rw)d can be such that (Rv)d is a hydrogen atom or an alkyl radical and (Rw)d is a hydrogen atom or an alkyl radical; or (Rv)d and (Rw)d form, with the nitrogen atom to which they are bonded, a cyclic radical containing from 3 to 7 ring members and optionally one or more other heteroatoms selected from O, S and NH, this cyclic radical being optionally substituted as indicated above or hereinafter;

said products of formula (Id) being in any of the possible racemic, enantiomeric and diastereoisomeric isomer forms, and also the addition salts with inorganic and organic acids or with inorganic and organic bases of said products of formula (Id).

In particular, when N(Rx)d(Ry)d or N(Rv)d(Rw)d forms a ring respectively with the atom to which it is bonded as defined above, such an aminated ring can be selected in particular from pyrrolidinyl, pyrazolidinyl, pyrazolinyl, piperidyl, azepinyl, morpholinyl, homomorpholinyl, piperazinyl or homopiperazinyl radicals, these radicals being themselves optionally substituted as indicated above or hereinafter.

The N(Rx)d(Ry)d or N(Rv)d(Rw)d ring can more particularly be selected from the pyrrolidinyl radical or the morpholinyl radical itself optionally substituted with one or two alkyl radical(s) or piperazinyl radical(s) itself(themselves) optionally substituted on the second nitrogen atom with an alkyl, phenyl, —CH$_2$-phenyl or —SO$_2$-Alk radical, all these latter alkyl, Alk and phenyl radicals being themselves optionally substituted with one or more radicals, which may be identical or different, selected from halogen atoms and alkyl, hydroxyl and alkoxy radicals.

A subject of the present invention is thus the products of formula (Id) as defined above, wherein:

Rd is a hydrogen atom or an alkyl, cycloalkyl, phenyl, NH$_2$ or CN radical;

R1d is a hydrogen atom or a methyl radical;

R2d is a hydrogen atom or a fluorine atom;

R3d is a hydrogen atom or a fluorine atom;

R4d is a hydrogen atom; a halogen atom; or a hydroxyl, alkyl, alkoxy, heterocycloalkyl, N(Rx)d(Ry)d, phenyl or heteroaryl radical; the alkyl radicals being optionally substituted with one or more radicals, which may be identical or different, selected from halogen atoms and hydroxyl, heterocycloalkyl and N(Rv)d(Rw)d radicals; the alkoxy radicals being optionally substituted with one or more halogen atoms;

R5d and R5'd, which may be identical or different, are a hydrogen atom or an alkyl radical or form, together with the carbon atom to which they are bonded, a cyclic radical having from 3 to 6 ring members optionally containing one or more heteroatoms selected from O, S and NH, optionally substituted with an alkyl or cycloalkyl radical;

R6d is a hydrogen atom; or an alkyl radical (itself optionally substituted with one or more radicals, which may be identical or different, selected from fluorine atoms, deuterium atoms and hydroxyl and alkoxy radicals; a cycloalkyl radical or a phenyl radical itself optionally substituted with one or more radicals, which may be identical or different, selected from fluorine atoms or alkoxy radicals;

it being possible for R5d and R6d to optionally form, with the carbon atoms to which they are bonded, a cyclic radical containing from 3 to 7 ring members;

said products of formula (Id) being in any of the possible racemic, enantiomeric and diastereoisomeric isomer forms, and also the addition salts with inorganic and organic acids or with inorganic and organic bases of said products of formula (Id).

A subject of the present invention is particularly the products of formula (Id) as defined above, wherein:

R2d is a hydrogen atom or a fluorine atom;

R3d is a hydrogen atom or a fluorine, chlorine or bromine atom;

R4d is a hydrogen atom; a halogen atom selected from chlorine, fluorine and bromine; or a hydroxyl or alkyl radical; an alkoxy radical; a pyrrolidinyl radical or a piperidyl radical optionally substituted with an alkyl radical; a morpholinyl radical; a piperazinyl radical optionally substituted with Alk on N; a phenyl radical optionally substituted with one or more radicals selected from Cl or F atoms or OCH$_3$; and a pyridyl radical; it being understood that the alkyl radicals are optionally substituted with one or more radicals, which may be identical or different, selected from fluorine atoms, the hydroxyl radical, and the piperazinyl radical itself optionally substituted on N with an alkyl or SO$_2$-alk radical; it being understood that the alkoxy radicals are optionally substituted with one or more fluorine atoms;

R5d and R5'd, which may be identical or different, are a hydrogen atom or an alkyl radical or form, together with the carbon atom to which they are bonded, a spirocyclopropyl, spirotetrahydropyran or spiropiperidyl radical optionally substituted with an alkyl or cycloalkyl radical on N;

R6d is a hydrogen atom; or an alkyl radical itself optionally substituted with one or more radicals, which may be identical or different, selected from fluorine atoms; a cyclopropyl radical; or a phenyl radical itself optionally substituted with one or more radicals, which may be identical or different, selected from fluorine atoms;

it being possible for R5d and R6d to optionally form, with the carbon atoms to which they are bonded, a cyclopentyl radical;

said products of formula (Id) being in any of the possible racemic, enantiomeric and diastereoisomeric isomer forms, and also the addition salts with inorganic and organic acids or with inorganic and organic bases of said products of formula (Id).

In the products of formula (Id) as defined above, when R4d is an alkyl or alkoxy radical optionally substituted with one or more halogen atoms, R4d can in particular be a —CF$_3$, —OCF$_3$ or else —OCHF$_2$ radical.

For the Compounds of Formula (Ie):

A subject of the present invention is thus the products of formula (Ie) as defined above, wherein:

Xe and Ye, which may be identical or different, are such that:

Xe is O or S and Ye is S;

Re is a hydrogen atom or a methyl radical;

R1e is a hydrogen atom or a methyl radical;

R2e is a hydrogen atom or a fluorine atom;

R3e is a hydrogen atom or a fluorine atom;

R4e is a hydrogen atom, a halogen atom or an alkyl radical optionally substituted with one or more radicals, which may be identical or different, selected from halogen atoms;

R5e and R5'e are a hydrogen atom;

R6e is a hydrogen atom or an alkyl radical optionally substituted with one or more radicals, which may be identical or different, selected from fluorine atoms and the hydroxyl radical;

R7e is a hydrogen atom or a fluorine atom;

said products of formula (Ie) being in any of the possible racemic, enantiomeric and diastereoisomeric isomer forms, and also the addition salts with inorganic and organic acids or with inorganic and organic bases of said products of formula (Ie).

A subject of the present invention is thus the products of formula (Ie) as defined above, wherein:

Xe and Ye, which may be identical or different, are such that:

Xe is O or S and Ye is S;

Re is a hydrogen atom;

R1e is a hydrogen atom or a methyl radical;

R2e is a hydrogen atom or a fluorine atom;

R3e is a hydrogen atom or a fluorine atom;

R4e is a hydrogen atom, a halogen atom or an alkyl radical optionally substituted with one or more radicals, which may be identical or different, selected from halogen atoms;

R5e and R5'e are a hydrogen atom;

R6e is a hydrogen atom or an alkyl radical optionally substituted with one or more radicals, which may be identical or different, selected from fluorine atoms and the hydroxyl radical;

R7e is a hydrogen atom;

said products of formula (Ie) being in any of the possible racemic, enantiomeric and diastereoisomeric isomer forms, and also the addition salts with inorganic and organic acids or with inorganic and organic bases of said products of formula (Ie).

In the products of formula (Ie) as defined above, R4e is, for example, a hydrogen atom or a halogen atom such as fluorine, chlorine or bromine or else the CF$_3$ radical, the other substituents Re, R1e, R2e, R3e, R5e, R5'e and R6e having any one of their meanings indicated above for said products of formula (Ie).

In the products of formula (Ie), R6e is, for example, a hydrogen atom or a methyl radical optionally substituted with a fluorine atom or the hydroxyl radical. The other substituents Re, R1e, R2e, R3e, R4e, R5e and R5'e having any one of their meanings indicated above for said products of formula (Ie).

Preparation Processes:

A subject of the present invention is also any process for preparing the products of formulae (Ia), (Ib), (Ic), (Id) and (Ie) as defined above.

The products according to the invention can be prepared using conventional organic chemistry methods.

General Preparation:

Preparation of Compounds of Formula (Ia):

The products of general formula (Ia) according to the present invention can in particular be prepared as indicated in general schemes (1A)a-(1E)a below. In this respect, the methods described cannot constitute a limitation of the scope of the invention, with regard to the methods for preparing the claimed compounds.

The preparations of the examples of the present invention give illustrations of the schemes below.

Such synthesis schemes form part of the present invention: a subject of the present invention is thus also the processes for preparing the products of formula Ca to (Ia) as defined in general schemes (1A)a-(1E)a below.

Schemes (1A)a-(1E)a below illustrate the methods used to prepare the products of formula (Ia). In this respect, they cannot constitute a limitation of the scope of the invention, with regard to the methods for preparing the claimed compounds.

The products of formula (Ia) as defined above according to the present invention can thus in particular be prepared according to the processes described in schemes (1A)a-(1E)a.

A subject of the present invention is thus also the process for preparing products of formula (Ia) according to scheme (1A)a as defined hereinafter.

A subject of the present invention is thus also the process for preparing products of formula (Ia) according to scheme (1B)a as defined hereinafter.

A subject of the present invention is thus also the process for preparing products of formula (Ia) according to scheme (1C)a as defined hereinafter.

A subject of the present invention is thus also the process for preparing products of formula (Ia) according to scheme (1D)a as defined hereinafter.

A subject of the present invention is thus also the process for preparing products of formula (Ia) according to scheme (1E)a as defined hereinafter.

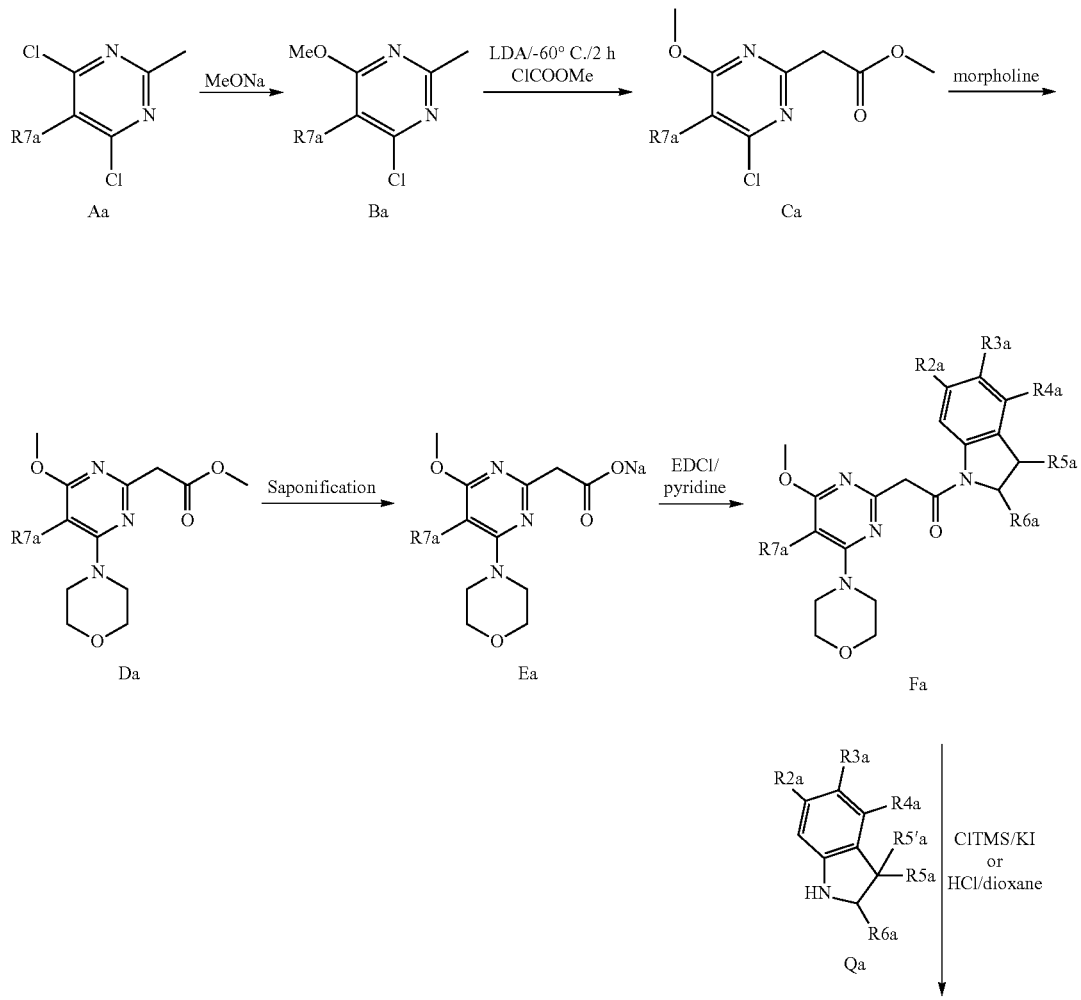

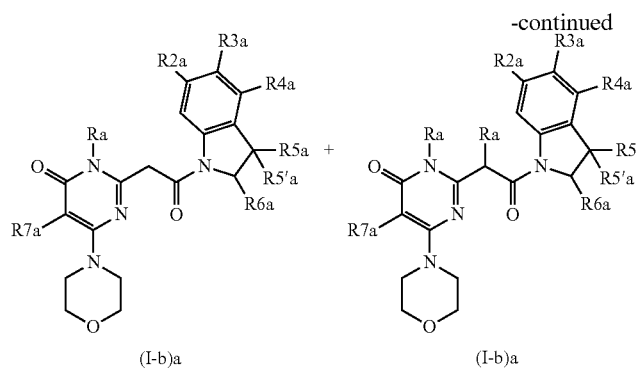

(I-b)a  (I-b)a  (I-a)a wherein the substituents Ra, R1a, R2a, R3a, R4a, R5a, R5'a, R6a and R7a have the meanings indicated above.

In general scheme (1A)a:

The methoxypyrimidine derivatives Ba can be prepared from the compounds Aa by reaction with sodium methoxide in a solvent such as THF or methanol, at a temperature of between 0° C. and 25° C., according to, for example, the conditions described by Ioannidis, S. et al. (Bioorganic and Medicinal Chemistry Letters, (2010), 20(5), 1669-1673).

The compounds Ca can be obtained by treatment of the compounds Ba in the presence of methyl chloroformate with LDA (lithium diisopropylamide) in a solvent such as THF, at a temperature of between −78° C. and 25° C., according to, for example, the conditions described by Tomioka K. et al. (Tetrahedron, (1988), 44(14), 4351-4356).

The compounds Da can be obtained from a compound Ca by reaction with morpholine, in the absence of solvent, at a temperature of between 0° C. and 25° C., as described, for example, by Aliabiev S. B. (Lett. Org. Chem. (2007), 4(4), 273-280).

The carboxylate Ea can be obtained by hydrolysis of the ester Da in the presence of a base such as sodium hydroxide or lithium hydroxide, in a solvent such as tetrahydrofuran or methanol, at a temperature of between 0° C. and 30° C.

The amides Fa can be obtained from the carboxylate Ea by coupling reaction of an indoline Qa in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)-phosphonium hexafluorophosphate], PyBOP [(benzotriazol-1-yloxy)trispyrrolidino-phosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron (2001), 57, 1551-1558.

The pyrimidones (I-a)a can be obtained from the compounds Fa by reaction with hydrochloric dioxane, at a temperature of between 22° C. and the boiling point of the solvent, for instance under the conditions described by Harnden M. R. et al. (J. Med. Chem. (1993), 36(10), 1343-1355).

When R7a=F, the pyrimidones (I-a)a can also be obtained from the compounds Fa, by reaction with chlorotrimethylsilane and potassium iodide or iodotrimethylsilane, in a solvent such as acetonitrile, at a temperature of between 22° C. and the boiling point of the solvent, for instance under the conditions described by Shiao M. J. (J. Org. Chem. (1993), 58(17), 4742-4744).

The products (I-b)a and (I-c)a can be obtained from the products (I-a)a by reaction with a compound Ra-Xa (Xa=Cl, Br, I or triflate), in the presence of a base such as sodium hydroxide, potassium tert-butoxide or cesium carbonate, in a solvent such as methanol, ethanol or dioxane, at a temperature of between 0° C. and 50° C., according to, for example, the process described by Noël D. D'Angelo et al. in J. Med. Chem. (2008), 51, 5766-5779.

Alternatively, the compounds (Ia) can be obtained according to general scheme (1B)a.

General scheme (1B)a:

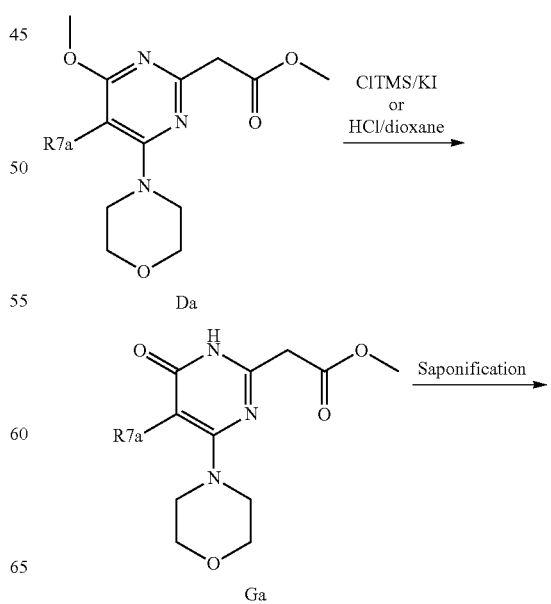

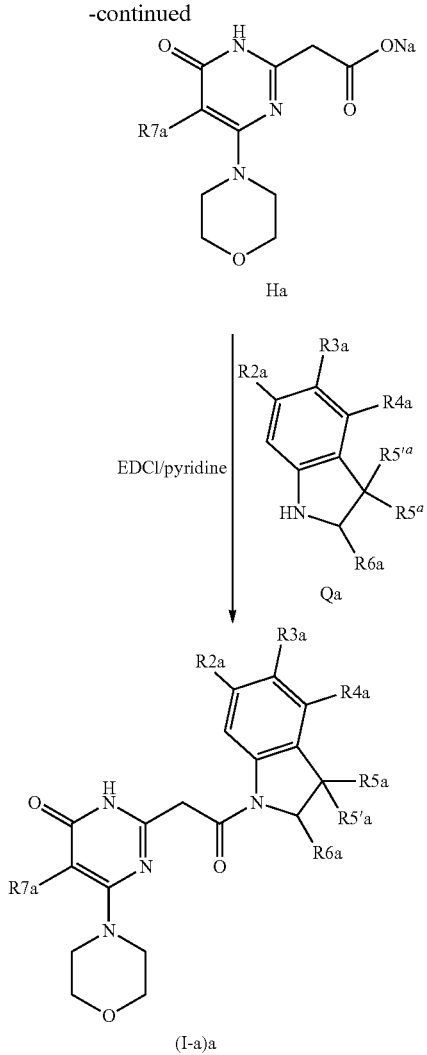

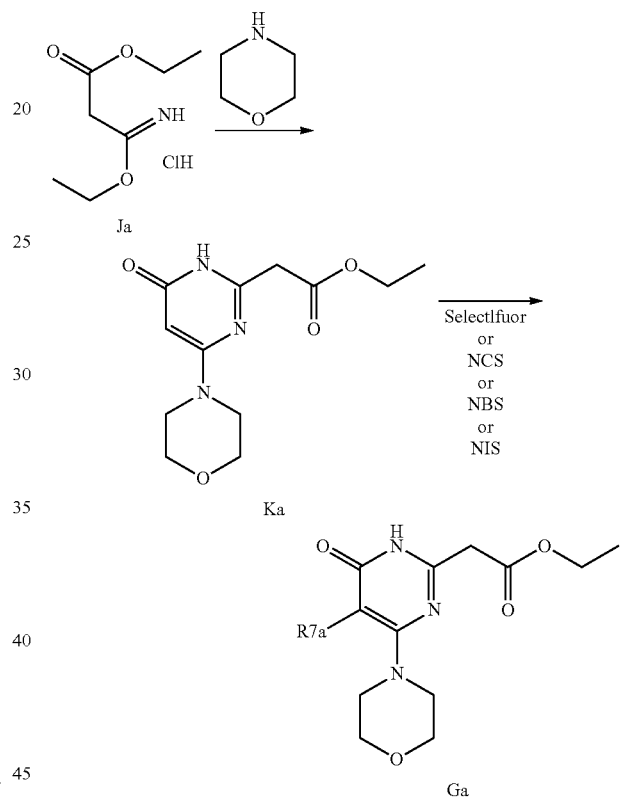

wherein the substituents R2a, R3a, R4a, R5a, R5'a, R6a and R7a have the meanings indicated above.

The pyrimidones Ga can be obtained from the compounds Da by reaction with hydrochloric dioxane, at a temperature of between 22° C. and the boiling point of the solvent, for instance under the conditions described by Harnden M. R. et al. (J. Med. Chem. (1993), 36(10), 1343-1355).

When R7a=F, the pyrimidones Ga can also be obtained from the compounds Da, by reaction with chlorotrimethylsilane and potassium iodide or iodotrimethylsilane, in a solvent such as acetonitrile, at a temperature of between 22° C. and the boiling point of the solvent, for instance under the conditions described by Shiao M. J. (J. Org. Chem. (1993), 58(17), 4742-4744).

The carboxylate Ha can be obtained by hydrolysis of the ester Ga in the presence of a base such as sodium hydroxide or lithium hydroxide, in a solvent such as tetrahydrofuran or methanol, at a temperature of between 0° C. and 30° C.

The amides (I-a)a can be obtained from the carboxylate Ha by a coupling reaction of an indoline Qa in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron (2001), 57, 1551-1558.

Alternatively, the compounds Ga can be obtained according to general scheme (1C)a.

General scheme (1C)a:

wherein the substituent R7a has the meanings indicated above.

The ester Ka can be obtained by one-pot reaction between morpholine and an excess (for example 3 equivalents) of malonic imino ether Ja (or of its aminoacrylate tautomer), in a solvent such as ethanol, at a temperature of between 20° C. and the boiling point of the solvent.

The pyrimidones Ga can be obtained from the compounds Ka, when R7a=F, with a fluorinating reagent such as Selectfluor, in a solvent such as acetonitrile, at a temperature of between 22° C. and the boiling point of the solvent, for instance under the conditions described by Banks R. E. (Journal of Fluorine Chemistry (1998), 87, 1-17).

When R7a=Cl, Br or I, the pyrimidones Ga can be obtained from the compounds Ka by reaction with N-chlorosuccinimide, N-bromosuccinimide or N-iodosuccinimide, in a solvent such as chloroform, at a temperature of between 22° C. and the boiling point of the solvent, for instance under the conditions described by Kanojia R. M. et al. (J. Med. Chem. (1988), 31(7), 1363-1368).

Alternatively, the compounds (I-a)a can be obtained according to general scheme (1D)a.

General scheme (1D)a:

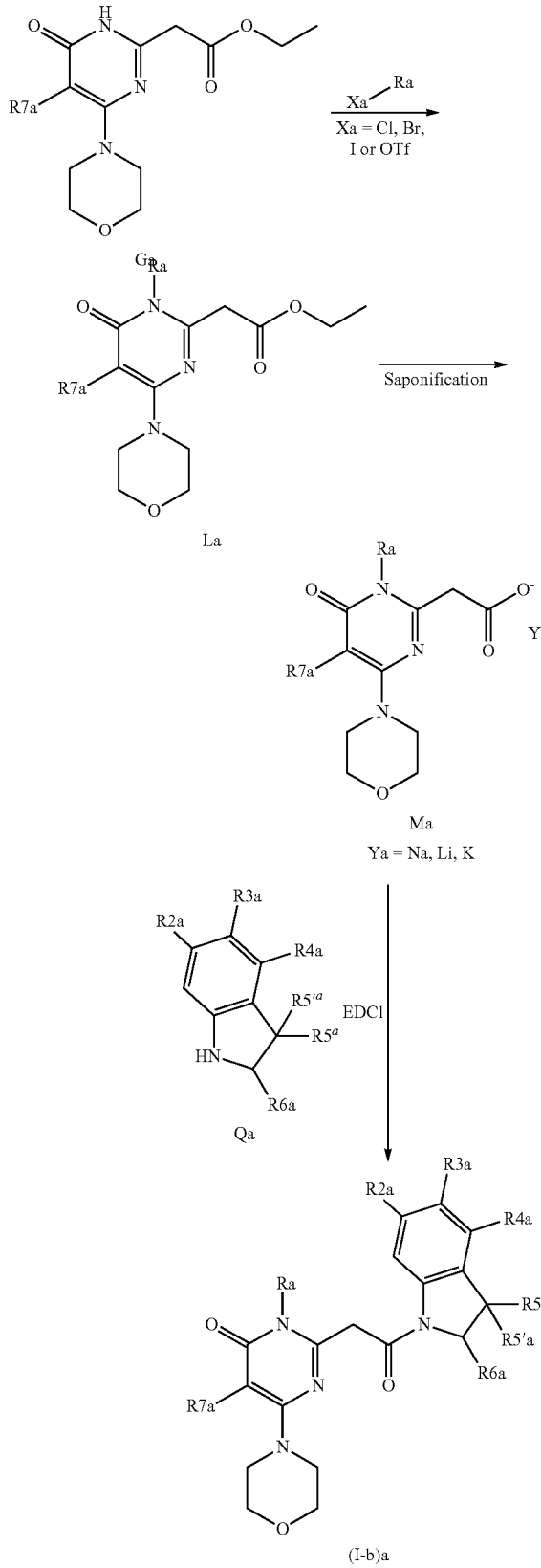

Ya = Na, Li, K (I-b)a wherein the substituents Ra, R2a, R3a, R4a, R5a, R5'a, R6a and R7a have the meanings indicated above.

In general scheme (1D)a:

The esters La can be obtained from the esters Ga by reaction with a compound Ra-Xa (Xa=Cl, Br, I or triflate), in the presence of a base such as sodium hydroxide, potassium tert-butoxide or cesium carbonate, in a solvent such as methanol, ethanol or dioxane, at a temperature of between 0° C. and 50° C., according to, for example, the process described by Noël D. D'Angelo et al. in J. Med. Chem. (2008), 51, 5766-5779.

The carboxylates Ma can be obtained by hydrolysis of the esters La, in the presence of a base such as sodium hydroxide or lithium hydroxide, in a solvent such as tetrahydrofuran or methanol, at a temperature of between 0° C. and 30° C.

The amides (I-b)a can be obtained from the carboxylates Ma by a coupling reaction of an indoline Qa in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron (2001), 57, 1551-1558.

Alternatively, the compounds (I-a)a can be obtained according to general scheme (1E)a.

General scheme (1E)a:

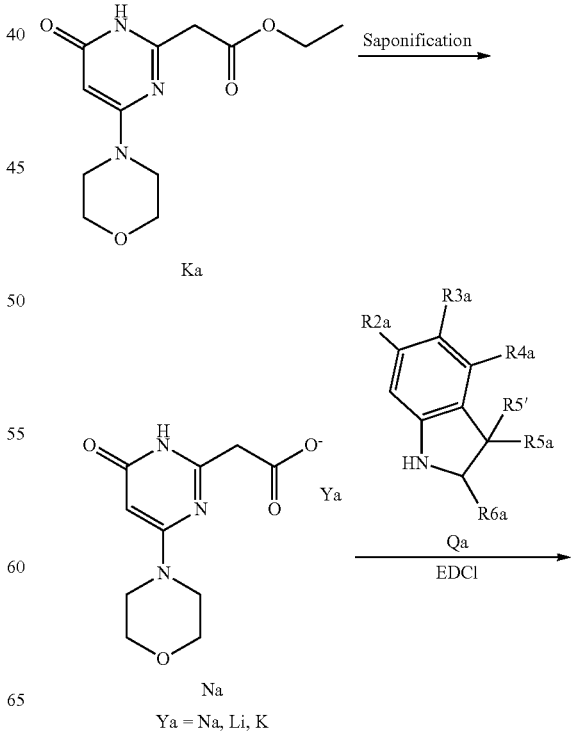

Ya = Na, Li, K

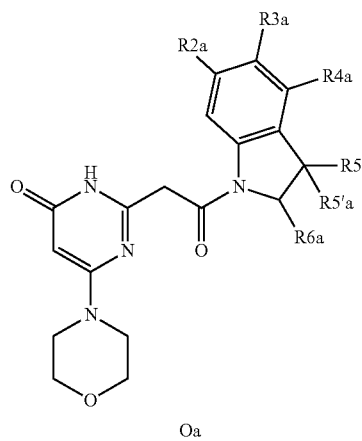

Oa

↓ Selectfluor or NCS or NBS or NIS

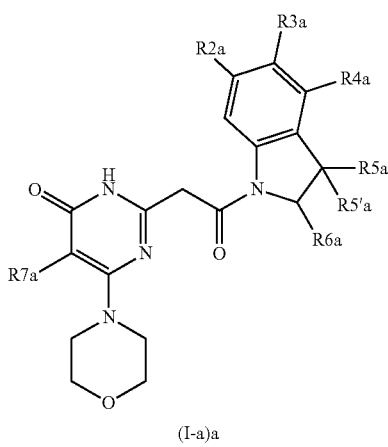

(I-a)a wherein the substituents R2a, R3a, R4a, R5a, R5'a, R6a and R7a have the meanings indicated above.

The carboxylates Na can be obtained by hydrolysis of the esters Ka, in the presence of a base such as sodium hydroxide or lithium hydroxide, in a solvent such as tetrahydrofuran or methanol, at a temperature of between 0° C. and 30° C.

The amides Oa can be obtained from the carboxylates Na by condensation of an indoline Qa in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron (2001), 57, 1551-1558.

The pyrimidones (I-a)a can be obtained from the compounds Oa, when R7a=F, with a fluorinating reagent such as Selectfluor, in a solvent such as acetonitrile, at a temperature of between 22° C. and the boiling point of the solvent, for instance under the conditions described by Banks R. E. (Journal of Fluorine Chemistry (1998), 87, 1-17).

When R7a=Cl, Br or I, the pyrimidones (I-a)a can be obtained from the compounds Oa by reaction with N-chlorosuccinimide, N-bromosuccinimide or N-iodosuccinimide, in a solvent such as chloroform, at a temperature of between 22° C. and the boiling point of the solvent, for instance under the conditions described by Kanojia R. M. et al. (J. Med. Chem. (1988), 31(7), 1363-1368).

The indolines Qa, which are reference examples, can be obtained according to general scheme (1F)a.

General scheme (1F)a:

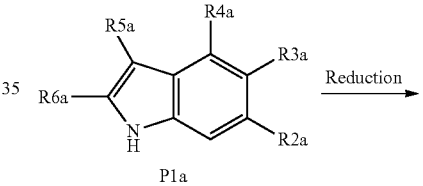

wherein the substituents R2a, R3a, R4a, R5a and R6a have the meanings indicated above.

The indolines, which are reference examples, of general formula Qa, when they are not commercially available, can be generally obtained from the corresponding indoles P1a by reduction in the presence of a reducing agent such as a hydride (sodium cyanoborohydride, for example) in a solvent such as acetic acid or trifluoroacetic acid, at a temperature of between −5° C. and 25° C., as described, for example, by Kumar, Y. (Synth. Commun., 1983, 13(6), 489-494).

The enantiomerically enriched indolines can be obtained, for example, by chemical resolution of the enantiomers using an enantiomerically pure chiral moiety, as described in general scheme (1G)a.

General scheme (1G)a:

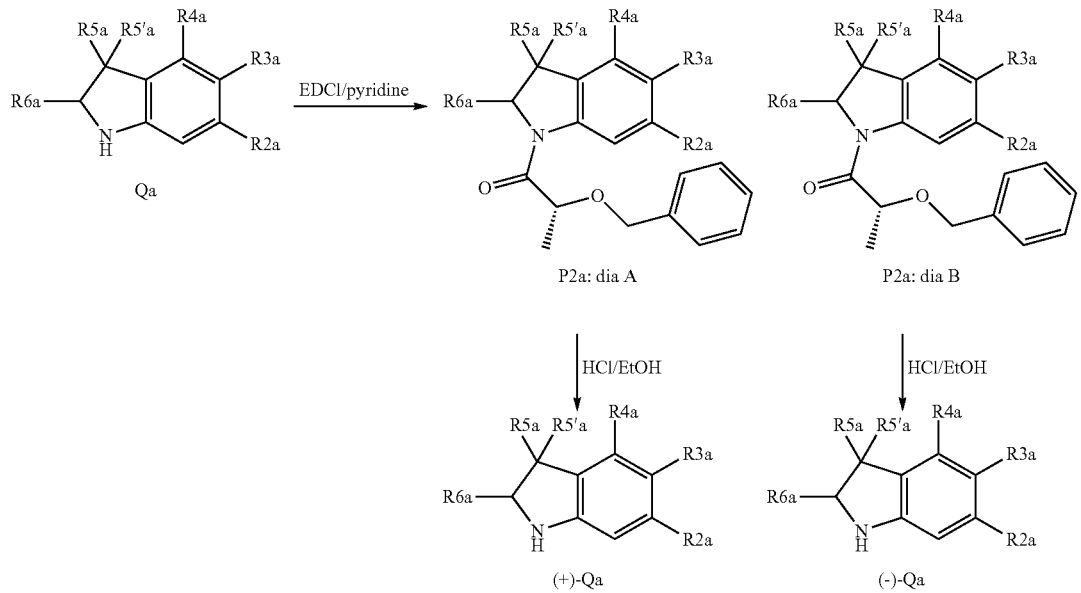

wherein the substituents R2a, R3a, R4a, R5a, R5'a and R6a have the meanings indicated above.

For example, the resolution of the enantiomers of the indoline Qa can be carried out by chromatographic separation of the two diastereoisomers formed by peptide-type coupling with O-benzyl-D-lactic acid in the presence of a peptide coupling agent such as, for example, EDCI (N-[3-(dimethylamino)propyl]-N'-ethylcarbodiimide), DMT-MM [4-(4,6-dimethoxy-1,2,3-triazin-2-yl)-4-methylmorpholinium chloride], BOP [benzotriazol-1-yloxytris(dimethylamino) phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 100° C., for instance under the conditions described by Kunishima, M. et al. (Tetrahedron, 2001, 57, 1551-1558). The (+)-Qa and (−)-Qa enantiomers can be respectively obtained from the compounds P2a: dia A and P2a: dia B by reaction in the presence of an acid such as concentrated hydrochloric acid, in a solvent such as an alcohol (ethanol for example), at a temperature of between 20° C. and the boiling point of the solvent, for instance under the conditions described by Krasnov, V. P. et al. (Mendeleev Commun. 2002, 12(1), 27-28).

The indoles of general formula (P1-a)a can in particular be prepared as indicated in general scheme (1H)a below.

General scheme (1H)a:

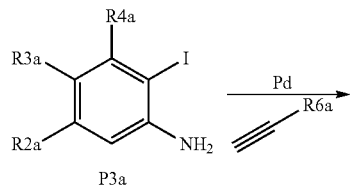

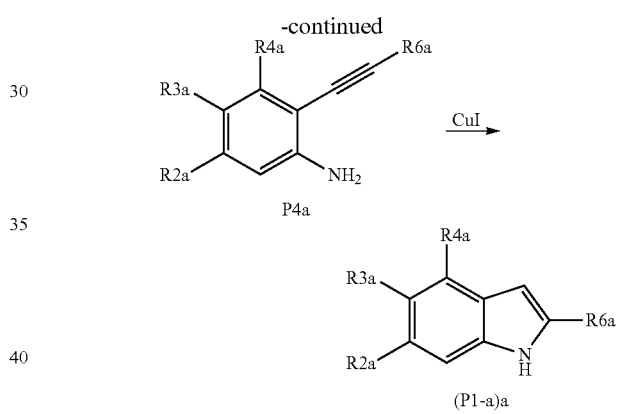

wherein the substituents R2a, R3a, R4a, and R6a have the meanings indicated above.

In general scheme (1H)a:

The derivatives P4a can be prepared from the compounds P3a by Sonogashira-type coupling with an alkyne in the presence of a catalyst based on palladium and copper iodide in a solvent such as triethylamine, at a temperature of between 0° C. and the boiling point of the solvent according to, for example, the conditions described by Kuyper, F. et al. (J. Med. Chem., 1996, 39(4), 892-903).

The indoles (P1-a)a can be obtained by cyclization of the compounds P4a in the presence of copper iodide in a solvent such as DMF, at a temperature of between 22° C. and the boiling point of the solvent, according to, for example, the conditions described by Kuyper, F. et al. (J. Med. Chem., 1996, 39(4), 892-903).

Alternatively, the derivatives of general formula (P1-b)a can be obtained according to general scheme (1J)a below, by analogy with the conditions described in patent US 2004/0224973 A1.

General scheme (1J)a:

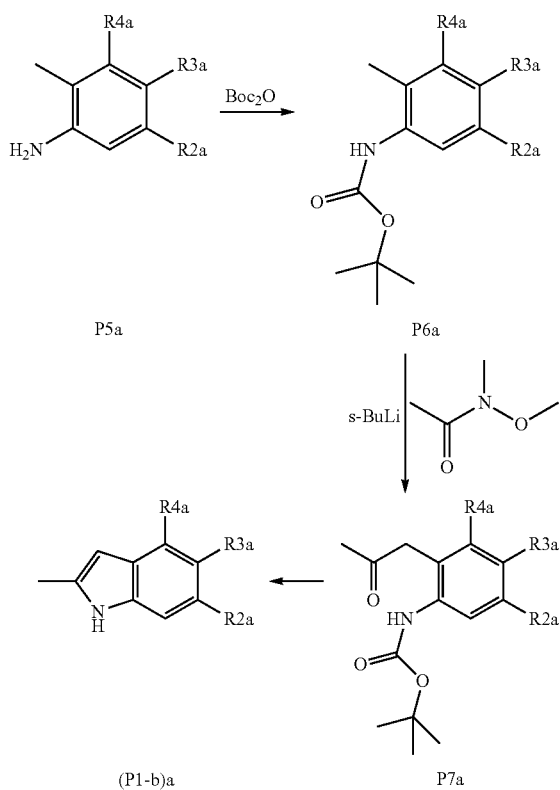

wherein the substituents R2a, R3a and R4a have the meanings indicated above.

In general scheme (1J)a:

The derivatives P6a can be prepared from the corresponding commercial aniline derivatives P5a by acylation reaction with di-tert-butyl dicarbonate, in a solvent such as tetrahydrofuran at a temperature of between 20° C. and the boiling point of the solvent.

The derivatives P7a can be prepared from the carbamate derivatives P6a, by reaction in the presence of a base such as sec-butyllithium, and then of N-methoxy-N-methylacetamide, in a solvent such as tetrahydrofuran at a temperature of between −50° C. and −10° C.

The derivatives (P1-b)a can be prepared from the derivatives P7a, by reaction in the presence of an acid such as trifluoroacetic acid, in a solvent such as dichloromethane, at a temperature of between 0° C. and 20° C.

Among the starting products of formulae Aa, Ja and Qa, some are known and can be obtained either commercially or according to the usual methods known to those skilled in the art, for example from commercial products.

Preparation of Compounds of Formula (Ib):

The products of general formula (Ib) according to the present invention can in particular be prepared as indicated in general schemes (1A)b-(1C)b below. In this respect, the methods described cannot constitute a limitation of the scope of the invention, with regards to the methods for preparing the claimed compounds.

The preparations of the examples of the present invention give illustrations of the schemes below.

Such synthesis schemes form part of the present invention: a subject of the present invention is thus also the processes for preparing the products of formula Jb to (Ib) or as defined in general schemes (1A)b-(1C)b below.

General scheme (1A)b:

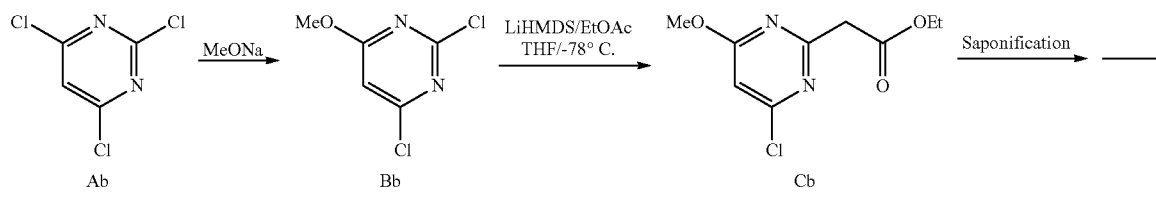

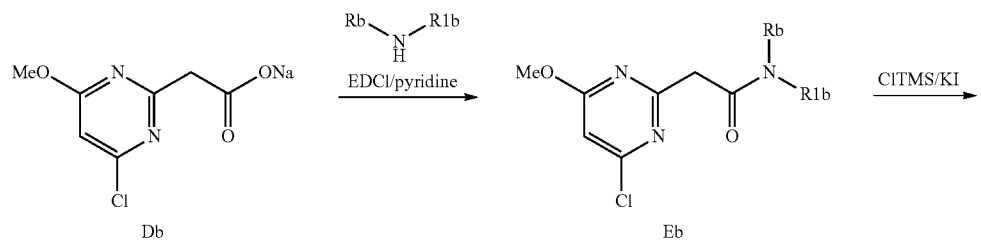

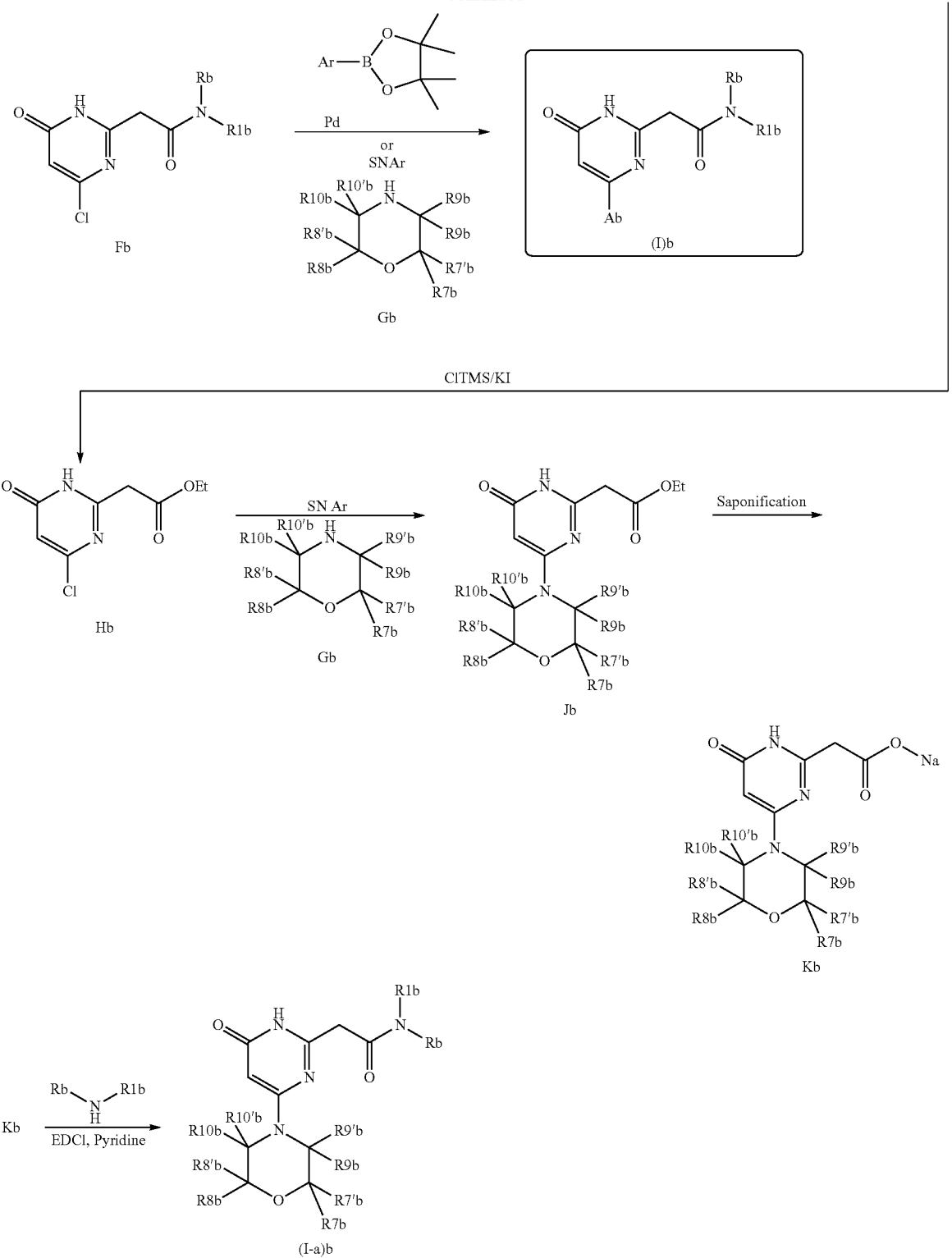

wherein the substituents Rb, R1b, R7b, R7'b, R8b, R8'b, R9b, R9'b, R10b and R10'b have the meanings indicated above.

In general scheme (1A)b:

The methoxypyrimidine derivatives Bb are prepared from the compounds Ab by reaction with sodium methoxide in a solvent such as THF or methanol, at a temperature of between 0° C. and 25° C., according to, for example, the conditions as described by Ioannidis, S. et al. (Bioorganic and Medicinal Chemistry Letters, (2010), 20(5), 1669-1673).

The compounds Cb can be obtained by treatment of the compounds Bb in the presence of ethyl acetate with LiHMDS (lithium bis(trimethylsilyl)amide) in a solvent such as THF, at a temperature of between −78° C. and 25° C., according to, for example, the conditions described by Chekmarev D. S. et al. (Tetrahedron, (2006), 62(42), 9919-9930).

The carboxylate Db can be obtained by hydrolysis of the ester Cb in the presence of a base such as sodium hydroxide or lithium hydroxide, in a solvent such as tetrahydrofuran or methanol, at a temperature of between 0° C. and 30° C.

The amides Eb can be obtained from the carboxylate Db by coupling reaction of an amine NHRbR1b in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron (2001), 57, 1551-1558.

The pyrimidones Fb can be obtained from the compounds Eb by reaction with chlorotrimethylsilane and potassium iodide or iodotrimethylsilane, in a solvent such as acetonitrile, at a temperature of between 22° C. and the boiling point of the solvent, for instance the conditions described by Shiao M. J. (J. Org. Chem. (1993), 58(17), 4742-4744).

The compounds (Ib), when the group Ab is a substituted morpholine, can be obtained from a compound Fb by reaction with a substituted morpholine Gb, in the absence of solvent, or in the presence of a solvent at a temperature of between 25° C. and the boiling point of the solvent, as described, for example, by Aliabiev S. B. (Lett. Org. Chem. (2007), 4(4), 273-280). When the group Ab is a heterocycle, these compounds (Ib) can be obtained from a compound Fb by coupling to with a boronic acid or a boronate in the presence of a palladium catalyst, such as tetrakis(triphenylphosphine)palladium, and of a base, such as cesium carbonate, in a solvent such as dioxane and at a temperature of between 25° C. and the boiling point of the solvent or under microwave irradiation at a temperature of between 60° C. and 150° C. as described, for example, by Diemer V. (European Journal of Organic Chemistry (2006), 12, 2727-2738).

The pyrimidones Hb can be obtained from the compounds Cb by reaction with chlorotrimethylsilane and potassium iodide or iodotrimethylsilane, in a solvent such as acetonitrile, at a temperature of between 22° C. and the boiling point of the solvent, for instance the conditions described by Shiao M. J. (J. Org. Chem. (1993), 58(17), 4742-4744).

The compounds Jb can be obtained from a compound Hb by reaction with a substituted morpholine Gb, in the absence of solvent, or in the presence of a solvent, at a temperature of between 25° C. and the boiling point of the solvent, as described, for example, by Aliabiev S. B. (Lett. Org. Chem. (2007), 4(4), 273-280).

The carboxylate Kb can be obtained by hydrolysis of the ester Jb in the presence of a base such as sodium hydroxide or lithium hydroxide, in a solvent such as tetrahydrofuran or methanol, at a temperature of between 0° C. and 30° C.

The amides (I-a)b can be obtained from the carboxylate Kb by a coupling reaction of an amine NHRbR1b in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron (2001), 57, 1551-1558.

Alternatively, the compounds (Ib), when the group Ab is a substituted morpholine, can be obtained according to general scheme (1B)b.

General Scheme (1B)b:

wherein the substituents Rb, R1b, R7b, R7'b, R8b, R8'b, R9b, R9'b, R10b and R10'b have the meanings indicated above.

General scheme (1B)b:

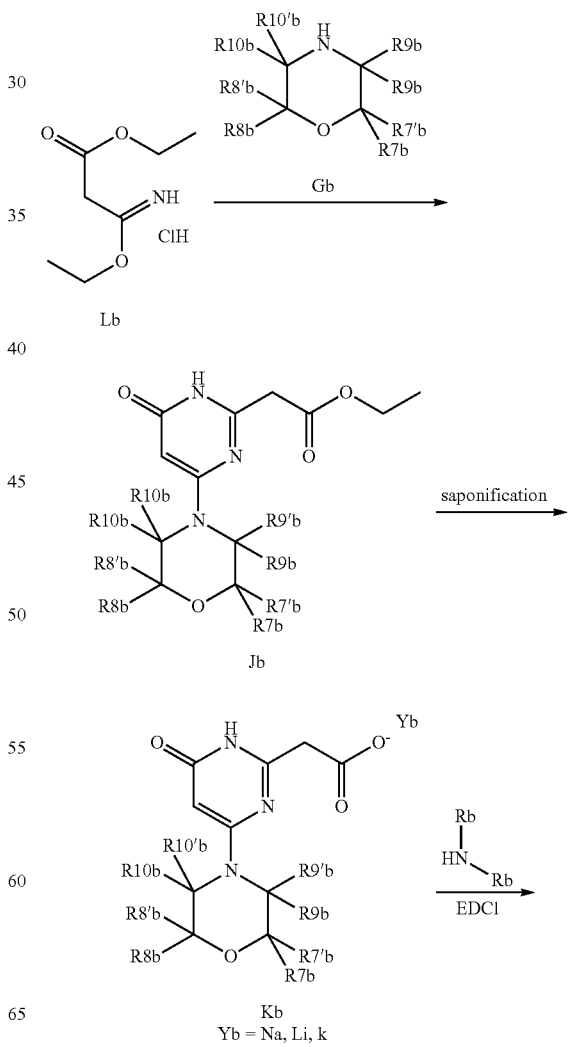

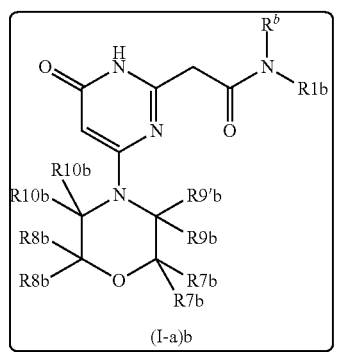

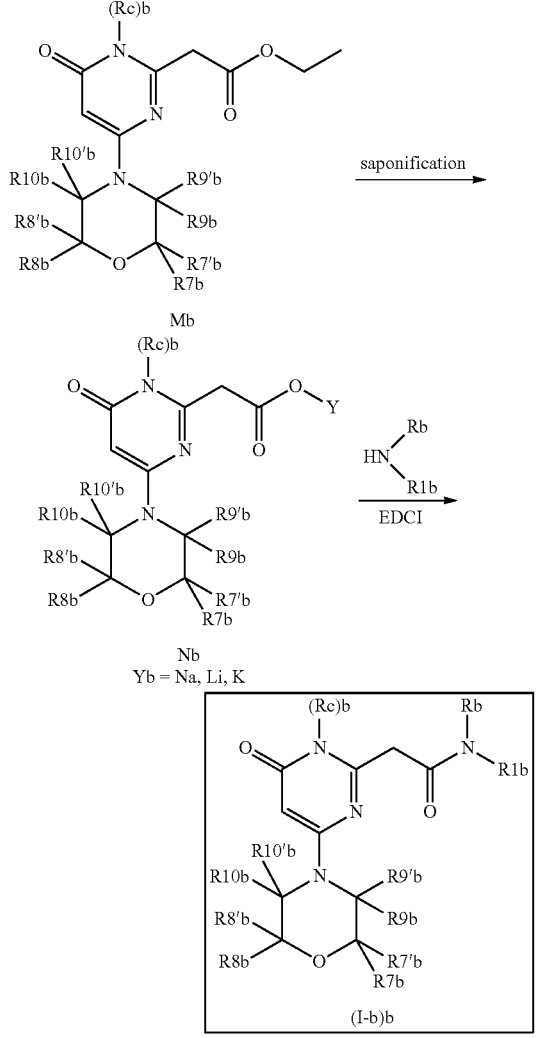

The ester Jb can be obtained by one-pot reaction between the substituted morpholine Gb and an excess (for example 3 equivalents) of imino ether Lb (or of its aminoacrylate tautomer), in a solvent such as ethanol, at a temperature of between 20° C. and the boiling point of the solvent.

The carboxylate Kb can be obtained by hydrolysis of the ester Jb in the presence of a base such as sodium hydroxide or lithium hydroxide, in a solvent such as tetrahydrofuran or methanol, at a temperature of between 0° C. and 30° C.

The amides (I-a)b can be obtained from the carboxylate Kb by a coupling reaction of an amine NHRbR1b in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron (2001), 57, 1551-1558.

Alternatively, the compounds (Ib) can be obtained according to general scheme (1C)b.

General scheme (1C)b:

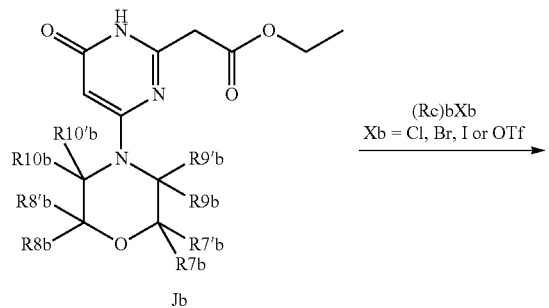

wherein the substituents (Rc)b, Rb, R1b, R7b, R7'b, R8b, R8'b, R9b, R9'b, R10b and R10'b have the meanings indicated above.

In general scheme (1C)b:

The esters Mb can be obtained from the ester Jb by reaction with a compound (Rc)b-Xb (Xb=Cl, Br, I or triflate), in the presence of a base such as sodium hydroxide, potassium tert-butoxide or cesium carbonate, in a solvent such as methanol, ethanol or dioxane, at a temperature of between 0° C. and 50° C., according to, for example, the process described by Noël D. D'Angelo et al. in J. Med. Chem. (2008), 51, 5766-5779.

The carboxylates Nb can be obtained by hydrolysis of the esters Mb, in the presence of a base such as sodium hydroxide or lithium hydroxide, in a solvent such as tetrahydrofuran or methanol, at a temperature of between 0° C. and 30° C.

The amides (I-b)b can be obtained from the carboxylates Nb by a coupling reaction of an amine NHbRbR1b in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron (2001), 57, 1551-1558.

Among the products, some are known and can be obtained either commercially, or according to the usual methods known to those skilled in the art, for example from commercial products.

When Rb and R1b together form an indoline ring of general formula (Pb), these indolines, when they are not commercial, can be generally obtained from the corresponding indoles O1b by reduction in the presence of a reducing agent such as a hydride (sodium cyanoborohydride, for example) in a solvent such as acetic acid or trifluoroacetic acid, at a temperature of between −5° C. and 25° C., as described, for example, by Kumar, Y. (Synth. Commun., 1983, 13(6), 489).

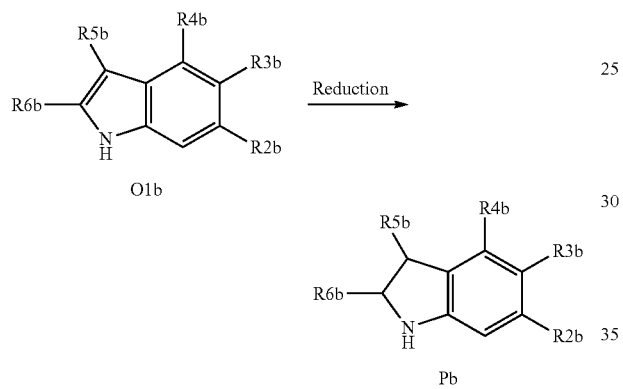

wherein the substituents R2b, R3b, R4b, R5b and R6b have the meanings indicated above.

The enantiomerically enriched indolines can be obtained, for example, by chemical resolution of the enantiomers using an enantiomerically pure chiral moiety, as described in general scheme (1D)b. For example, the resolution of the enantiomers of the indoline Pb can be carried out by chromatographic separation of the two diastereoisomers formed by peptide-type coupling with o-benzyl-D-lactic acid in the presence of a peptide coupling agent such as, for example, EDCI (N-[3-(dimethylamino)propyl]-N'-ethylcarbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 100° C., for instance under the conditions described by Kunishima, M. et al. (Tetrahedron, 2001, 57, 1551). The (+)-Pb and (−)-Pb enantiomers can be respectively obtained from the compounds O2b: dia A and O2b: dia B by reaction in the presence of an acid such as concentrated hydrochloric acid, in a solvent such as an alcohol (ethanol, for example), at a temperature of between 20° C. and the boiling point of the solvent, for instance under the conditions described by Krasnov, V. P. et al. (*Mendeleev Commun.* 2002, 12(1), 27).

General scheme (1D)b:

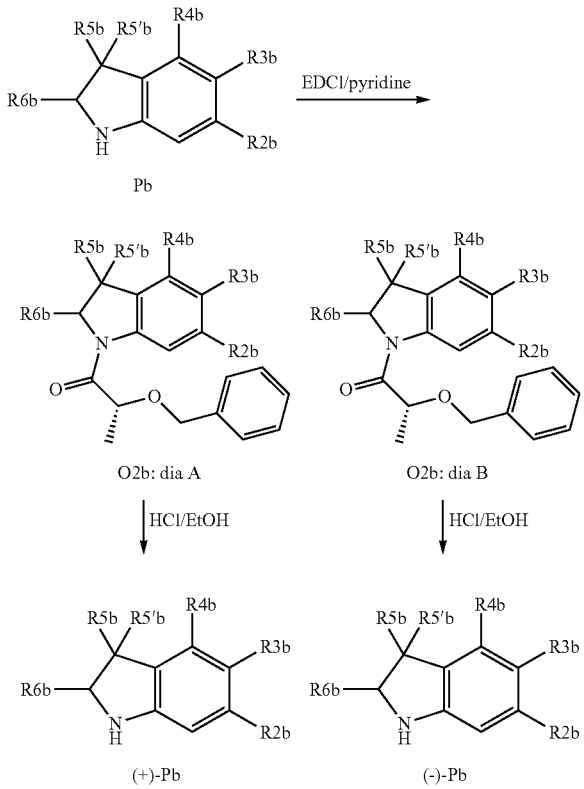

wherein the substituents R2b, R3b, R4b, R5b, R5'b and R6b have the meanings indicated above.

The products of general formula (P1b) can in particular be prepared as indicated in general scheme (1E)b below.

General scheme (1E)b:

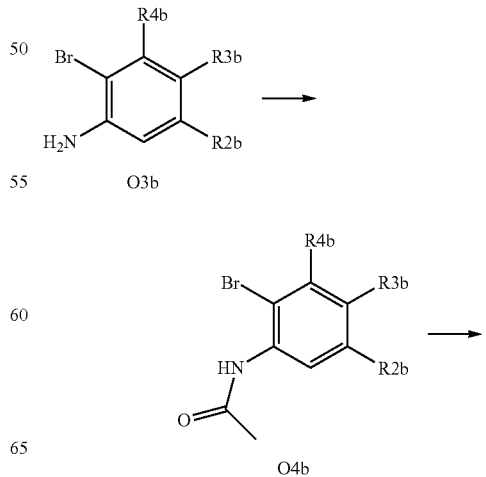

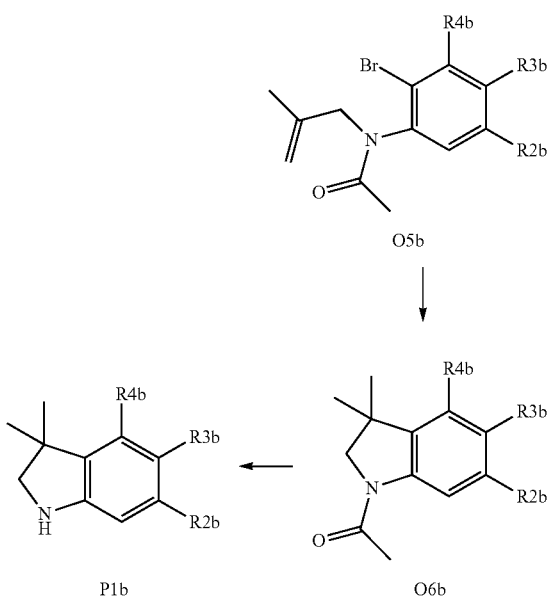

wherein the substituents R2b, R3b and R4b have the meanings indicated above.

In general scheme (1E)b:

The derivatives O4b can be prepared from the corresponding commercial aniline derivatives O3b, by acetylation reaction with acetyl chloride, in the presence of a base such as an amine (preferably triethylamine), in a solvent such as dichloromethane, at a temperature of between 0° C. and the boiling point of the solvent.

The derivatives O5b can be prepared from the anilide derivatives O4b, by reaction with 3-bromo-2-methylpropene, in the presence of a base such as potassium carbonate and of a hydride such as sodium hydride, in a solvent such as toluene, at a temperature of between 20° C. and the boiling point of the solvent, by analogy with the conditions described by Edwards, J. P. et al. (*Bioorg. Med. Chem., Lett.,* 1998, 8, 745).

The derivatives O6b can be prepared by cyclization reaction of the derivatives O5b, for example in the presence of a catalyst such as a palladium derivative (preferably palladium diacetate), of tetrabutylammonium chloride, in the presence of a base such as triethylamine, in a solvent such as N,N-dimethylformamide, at a temperature of between 20° C. and the boiling point of the solvent, by analogy with the conditions described by Larock, R. C. et al. (*Tetrahedron Lett.,* 1987, 28, 5291).

The derivatives P1b can be prepared from the derivatives O6b, by reaction in the presence of an acid such as concentrated hydrochloric acid, at a temperature of between 20° C. and the boiling point of the solvent, under the conditions known to those skilled in the art.

Preparation of Compounds of Formula (Ic)

The products of general formula (Ic) according to the present invention can in particular be prepared as indicated in general schemes (1A)c-(1D)c below. In this respect, the methods described cannot constitute a limitation of the scope of the invention, with regard to the methods for preparing the claimed compounds.

The preparations of the examples of the present invention give illustrations of the schemes below.

Such synthesis schemes form part of the present invention: a subject of the present invention is thus also the processes for preparing the products of formulae Cc to (I-d)c as defined in general schemes (1A)c-(1D)c below.

Such synthesis schemes form part of the present invention: a subject of the present invention is thus also the processes for preparing the products of formulae Cc, Dc, Ec and Fc, as defined in general schemes (1A)c-(1D)c below.

General scheme (1A)c:

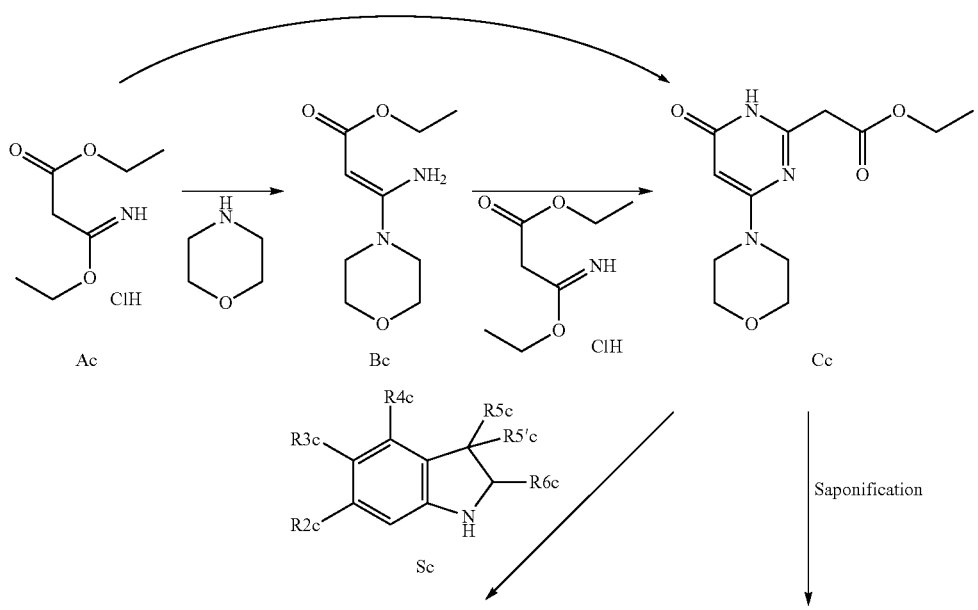

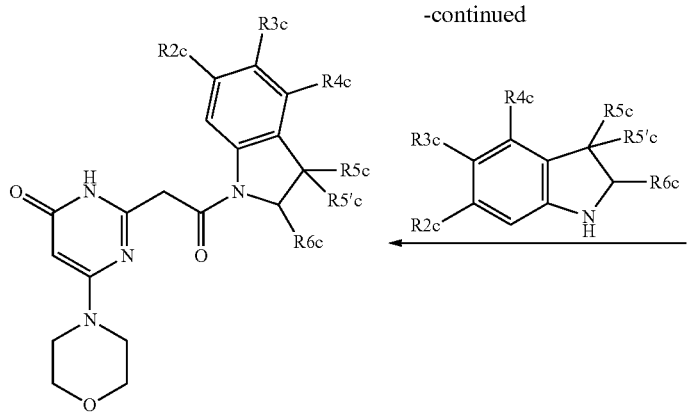

(I-a)c

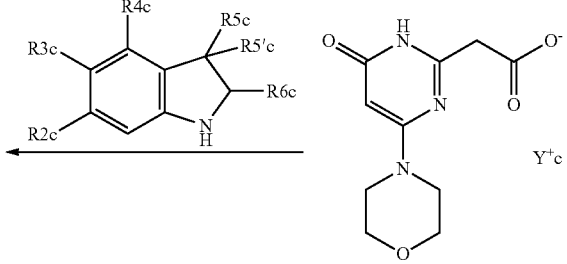

Dc
Yc = Na, Li, K wherein the substituents R2c, R3c, R4c, R5c, R5'c and R6c have the meanings indicated above.

In general scheme (1A)c:

The ketene aminal Bc can be obtained from the imino ether Ac or from its commercial aminoacrylate tautomer, by reaction with morpholine in a solvent such as ethanol, at a temperature of between 0° C. and the boiling point of the solvent, according to the process described by Landwehr J. et al. in J. Med. Chem. 2006, 49, 4327-4332.

The ester Cc can be obtained by reaction of the ketene aminal Bc with the imino ether Ac, or its aminoacrylate tautomer, in a solvent such as ethanol, at a temperature of between 20° C. and the boiling point of the solvent.

Alternatively, the ester Cc can be obtained by one-pot reaction between morpholine and an excess (for example 3 equivalents) of imino ether Ac (or of its aminoacrylate tautomer), in a solvent such as ethanol, at a temperature of between 20° C. and the boiling point of the solvent.

The carboxylate Dc can be obtained by hydrolysis of the ester Cc in the presence of a base such as sodium hydroxide or lithium hydroxide, in a solvent such as tetrahydrofuran or methanol, at a temperature of between 0° C. and 30° C.

The amides (I-a)c can be obtained from the carboxylate Dc by a coupling reaction of an indoline Sc in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron (2001), 57, 1551-1558.

The amides (I-a)c can also be obtained from the ester Cc by reaction of an indoline Sc in the presence of an agent such as trimethyl aluminum or potassium tert-butoxide, in a solvent such as toluene, tetrahydrofuran or N,N-dimethylformamide, at a temperature of between 20° C. and 150° C., for instance under the conditions described by Perreux L. et al. in Tetrahedron 2003 (59) 2185-2189 and by Auzeloux, P et al. in J. Med. Chem. 2000, 43 (2), 190-197.

General scheme (1B)c:

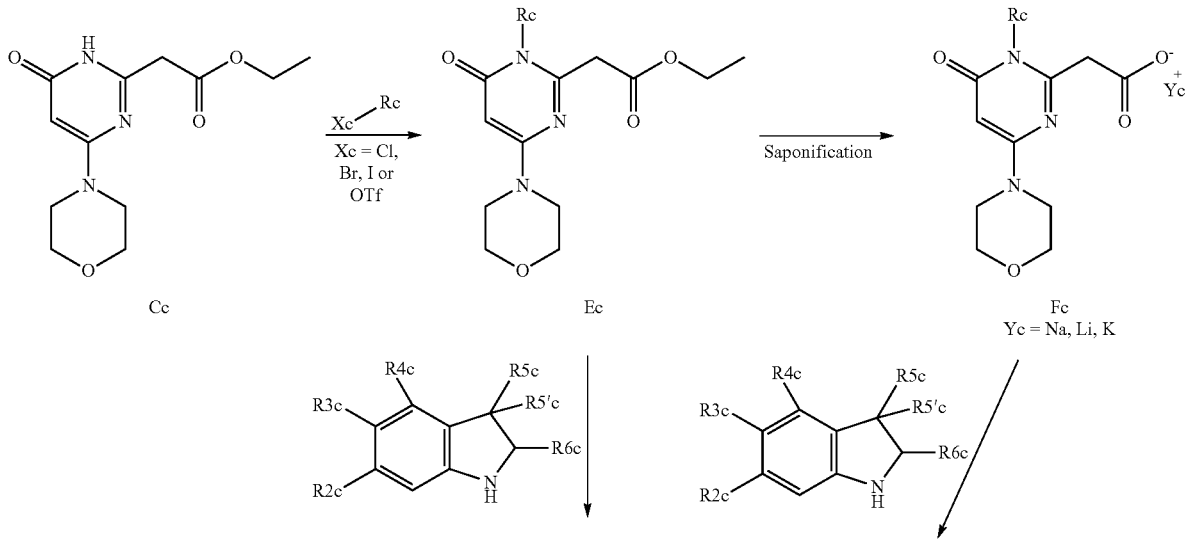

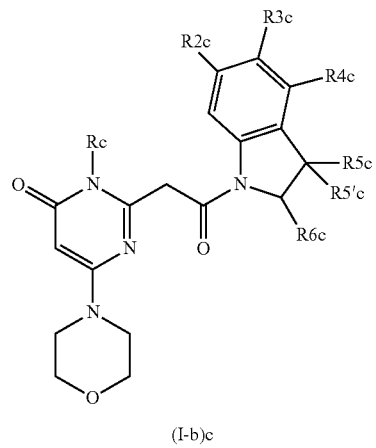

(I-b)c wherein the substituents Rc, R2c, R3c, R4c, R5c, R5'c and R6c have the meanings indicated above.

In general scheme (1B)c:

The esters Ec can be obtained from the ester Cc by reaction with a compound Rc-Xc (Xc=Cl, Br, I or triflate), in the presence of a base such as sodium hydroxide, potassium tert-butoxide or cesium carbonate, in a solvent such as methanol, ethanol or dioxane, at a temperature of between 0° C. and 50° C., according to, for example, the process described by Noël D. D'Angelo et al. in J. Med. Chem. 2008, 51, 5766-5779.

The carboxylates Fc can be obtained by hydrolysis of the esters Ec, in the presence of a base such as sodium hydroxide or lithium hydroxide, in a solvent such as tetrahydrofuran or methanol, at a temperature of between 0° C. and 30° C.

The amides (I-b)c can be obtained from the carboxylates Fc by a coupling reaction of an indoline Sc in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron (2001), 57, 1551-1558.

The amides (I-b)c can also be obtained from the esters Ec by reaction of an indoline Sc, in the presence of an agent such as trimethyl aluminum, in a solvent such as toluene, at a temperature of between 20° C. and the boiling point of the solvent, for instance under the conditions described by Auzeloux, P et al. in J. Med. Chem. 2000, 43 (2), 190-197.

General scheme (1C)c:

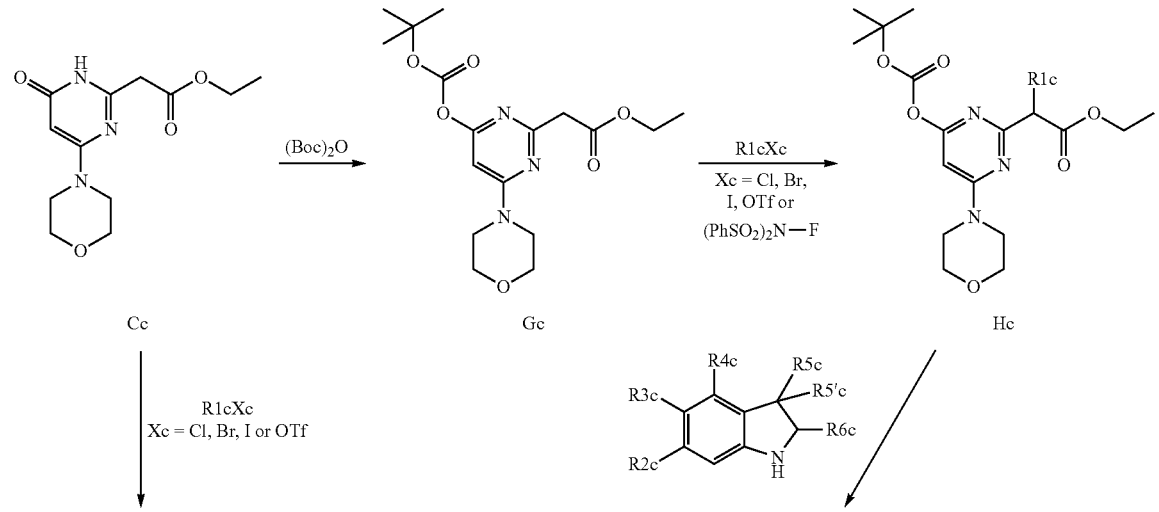

-continued

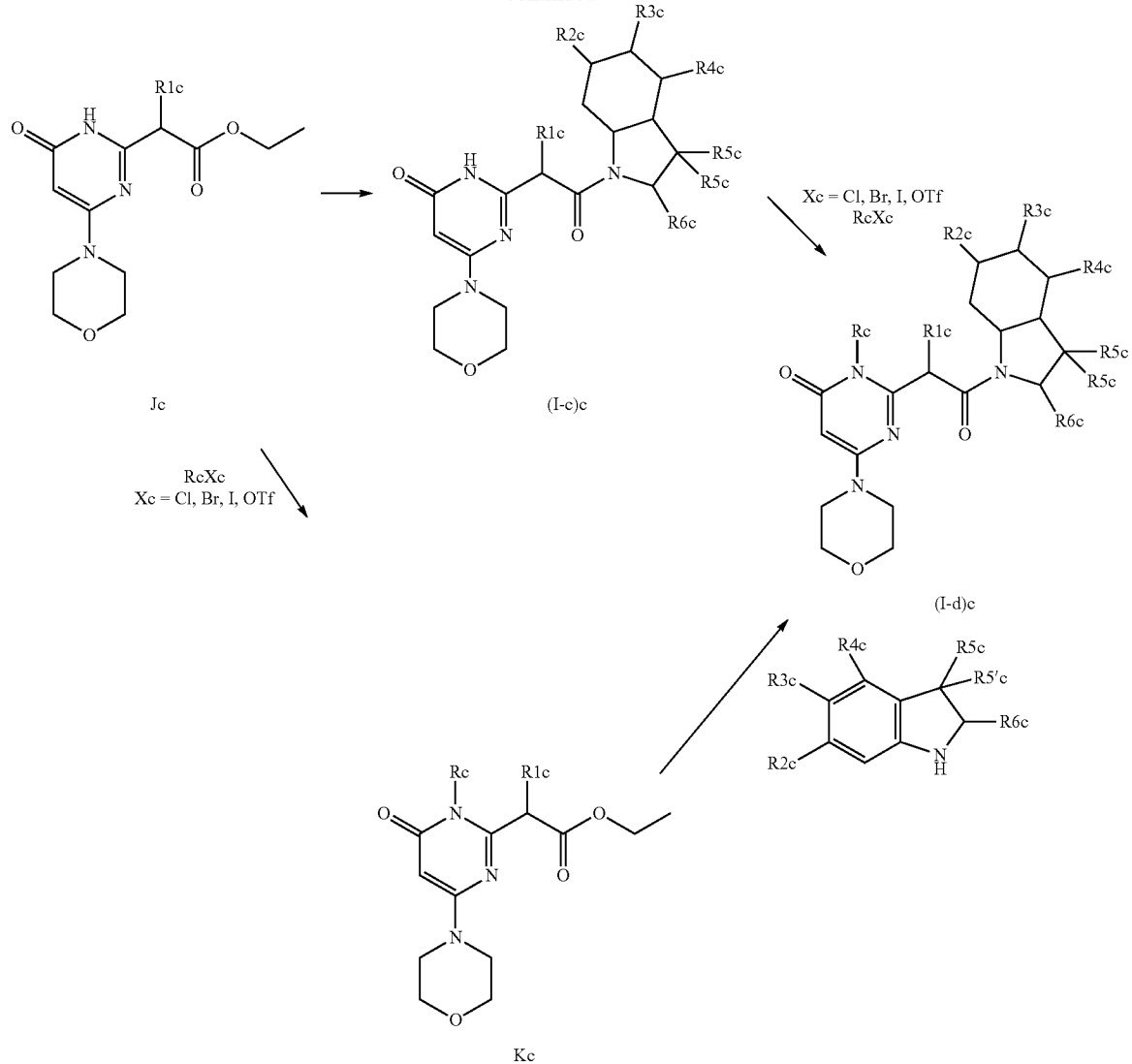

wherein the substituents Rc, R1c, R2c, R3c, R4c, R5c, R5'c and R6c have the meanings indicated above.

In general scheme (1C)c:

The ester Gc can be obtained from the ester Cc by reaction with (Boc)$_2$O (tert-butyl dicarbonate), in a solvent such as N,N-dimethylformamide, dioxane, acetonitrile or dichloromethane, in the presence of a base, for instance sodium hydride, triethylamine, N,N-diisopropylethylamine or pyridine, at a temperature of between 0° C. and 60° C., according to, for example, the process described by Hioki K. et al. Synthesis 2006, 12, 1931-1933.

The products Hc can be obtained from the ester Gc by reaction with R1c-Xc (Xc=Cl, Br, I or OTf and R2c and R3c are alkyl groups), in the presence of a base such as sodium hydroxide, potassium tert-butoxide or cesium carbonate, in a solvent such as methanol, ethanol or dioxane, at a temperature of between 0° C. and 100° C., according to, for example, the process described by Noël D. D'Angelo et al. in J. Med. Chem. 2008, 51, 5766-5779.

The product Hc wherein R1c=F can be obtained by reaction of the product Gc with N-fluorobenzenesulfonimide, in the presence of a base such as the potassium salt of hexamethyldisilylazane, in a solvent such as tetrahydrofuran, at a temperature of between –78° C. and 20° C., according to, for example, the process described by Christopher S. Burgey et al. in J. Med. Chem. 2003, 46, 461-473.

The esters Jc wherein the group R1c is an alkyl radical can be obtained from the ester Cc in the same way as the products Hc, in the presence of a base such as butyllithium, sodium hydride, potassium tert-butoxide or cesium carbonate, in a solvent such as methanol, ethanol, tetrahydrofuran, N,N-dimethylformamide or dioxane, at a temperature of between 0° C. and 50° C.

The amides (I-c)c can be obtained from the esters Hc or Jc by reaction of an indoline Sc, in the presence of an agent such as trimethyl aluminum, in a solvent such as toluene, at a temperature of between 20° C. and the boiling point of the solvent, for instance under the conditions described by Auzeloux, P et al. in J. Med. Chem. 2000, 43 (2), 190-197.

The amides (I-d)c can be obtained from the amides (I-c)c by reaction with a compound Rc-Xc (Xc=Cl, Br, I or triflate), in the presence of a base such as sodium hydroxide, potassium tert-butoxide or cesium carbonate, in a solvent such as methanol, ethanol or dioxane, at a temperature of between 0°

C. and 50° C., according to, for example, the process described by Noel D. D'Angelo et al. in J. Med. Chem. 2008, 51, 5766-5779.

Alternatively, the amides (I-d)c can be obtained from the esters Kc by reaction of an indoline Sc, in the presence of an agent such as trimethyl aluminum, in a solvent such as toluene, at a temperature of between 20° C. and the boiling point of the solvent, for instance under the conditions described by Auzeloux, P et al. in J. Med. Chem. 2000, 43 (2), 190-197.

The esters Kc can be obtained from the esters Jc by reaction with a compound Rc-Xc (Xc=Cl, Br, I or triflate), in the presence of a base such as sodium hydroxide, potassium tert-butoxide or cesium carbonate, in a solvent such as methanol, ethanol or dioxane, at a temperature of between 0° C. and 50° C., according to, for example, the process described by Noël D. D'Angelo et al. in J. Med. Chem. 2008, 51, 5766-5779.

General scheme (1D)c:

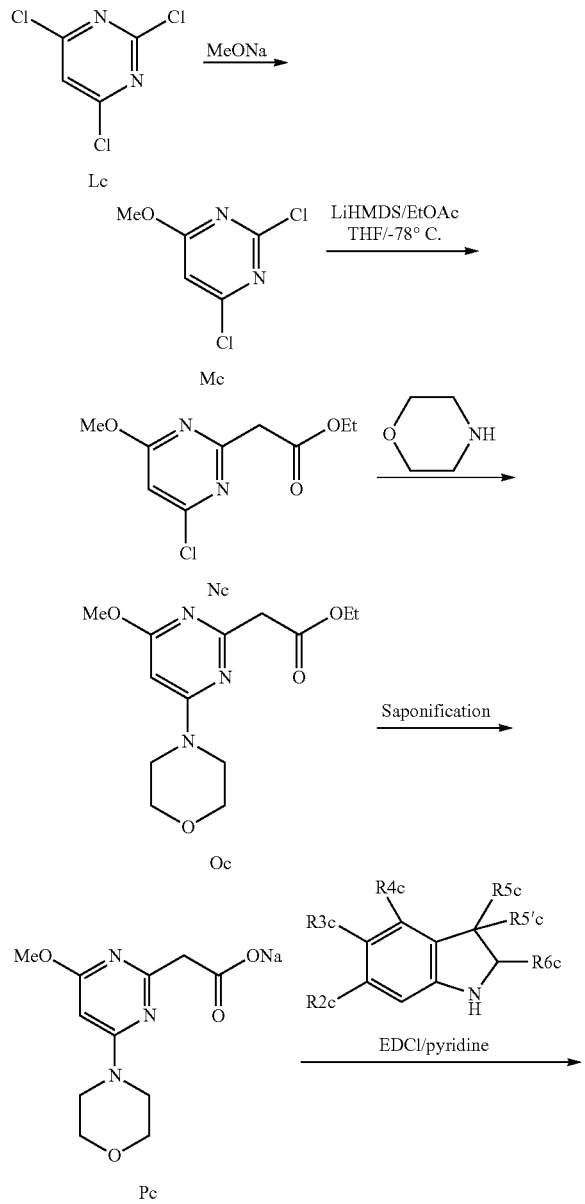

wherein the substituents R2c, R3c, R4c, R5c, R5'c and R6c have the meanings indicated above.

In general scheme (1D)c:

The methoxypyrimidine derivative Mc is prepared from the compound Lc by reaction with sodium methoxide in a solvent such as THF or methanol, at a temperature of between 0° C. and 25° C., according to, for example, the conditions described by Ioannidis, S. et al. (Bioorganic and Medicinal Chemistry Letters, (2010), 20(5), 1669-1673).

The compound Nc can be obtained by treatment of the compound Mc in the presence of ethyl acetate with LiHMDS (lithium bis(trimethylsilyl)amide) in a solvent such as THF, at a temperature of between −78° C. and 25° C., according to, for example, the conditions described by Chekmarev D. S. et al. Tetrahedron, (2006), 62(42), 9919-9930.

The compound Oc can be obtained from the compound Nc by reaction with morpholine, in the absence of solvent, or in the presence of a solvent, at a temperature of between 25° C. and the boiling point of the solvent, as described, for example, by Aliabiev S. B. (Lett. Org. Chem. (2007), 4(4), 273-280).

The carboxylate Pc can be obtained by hydrolysis of the ester Oc in the presence of a base such as sodium hydroxide or lithium hydroxide, in a solvent such as tetrahydrofuran or methanol, at a temperature of between 0° C. and 30° C.

The amide Qc can be obtained from the carboxylate Ec by a coupling reaction of an indoline Sc in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron (2001), 57, 1551-1558.

The compound Rc can be obtained from Qc using a base such as sodium hydride in tetrahydrofuran between 0° C. and 40° C.

The amides (I-c)c can be obtained from the compound Rc by reaction with chlorotrimethylsilane and potassium iodide or iodotrimethylsilane, in a solvent such as acetonitrile, at a temperature of between 22° C. and the boiling point of the solvent, for instance the conditions described by Shiao M. J. (J. Org. Chem. (1993), 58(17), 4742-4744.

Among the starting products of formula Lc or Mc, some are known and can be obtained either commercially or according to the usual methods known to those skilled in the art, for example from commercial products.

The indolines of general formula Sc, when they are not commercially available, can be generally obtained from the corresponding indoles T1c by reduction in the presence of a reducing agent such as a hydride (sodium cyanoborohydride, for example) in a solvent such as acetic acid or trifluoroacetic acid, at a temperature of between −5° C. and 25° C., as described, for example, by Kumar, Y. (*Synth. Commun.*, 1983, 13(6), 489).

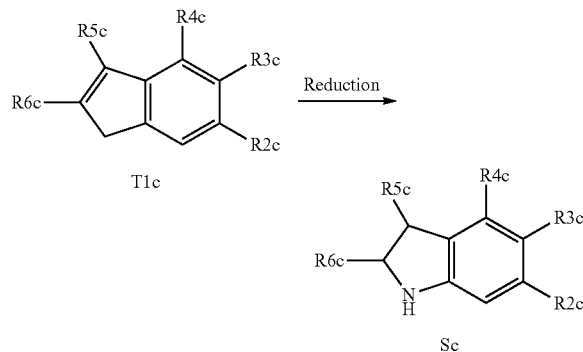

wherein the substituents R2c, R3c, R4c, R5c and R6c have the meanings indicated above.

The enantiomerically enriched indolines can be obtained, for example, by chemical resolution of the enantiomers using an enantiomerically pure chiral moiety, as described in general scheme (1E)c. For example, the resolution of the enantiomers of the indoline Sc can be carried out by chromatographic separation of the two diastereoisomers formed by peptide-type coupling with o-benzyl-D-lactic acid in the presence of a peptide coupling agent such as, for example, EDCI (N-[3-(dimethylamino)propyl]-N'-ethylcarbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 100° C., for instance under the conditions described by Kunishima, M. et al. (Tetrahedron, 2001, 57, 1551). The (+)-Sc and (−)-Sc enantiomers can be respectively obtained from the compounds T2c: dia A and T2: dia Bc by reaction in the presence of an acid such as concentrated hydrochloric acid, in a solvent such as an alcohol (ethanol, for example), at a temperature of between 20° C. and the boiling point of the solvent, for instance under the conditions described by Krasnov, V. P. et al. (*Mendeleev Commun.* 2002, 12(1), 27).

General scheme (1E)c:

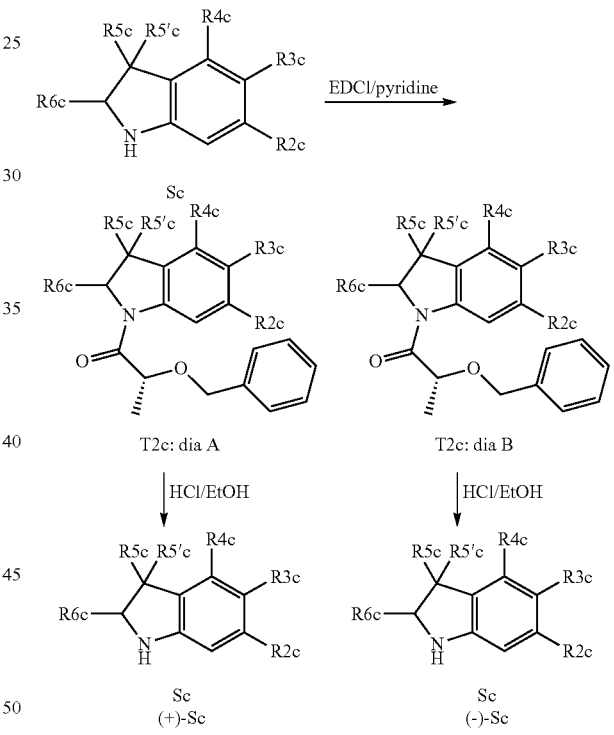

wherein the substituents R2c, R3c, R4c, R5c, R5'c and R6c have the meanings indicated above.

The products of general formula (T1-a)c can in particular be prepared as indicated in general scheme (1F)c below.

General scheme (1F)c:

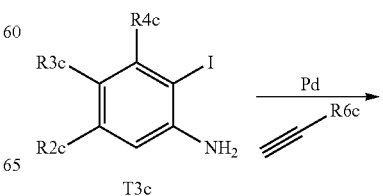

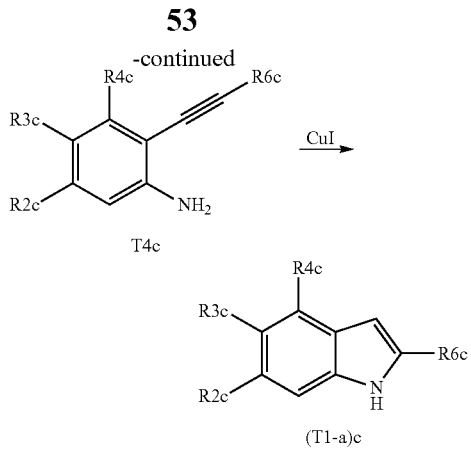

wherein the substituents R2c, R3c, R4c and R6c have the meanings indicated above.

In general scheme (1F)c:

The derivatives T4c can be prepared from the compounds T3c by Sonogashira-type coupling with a true alkyne in the presence of a catalyst based on palladium and copper iodide, in a solvent such as triethylamine, at a temperature of between 0° C. and the boiling point of the solvent, according to, for example, the conditions described by Kuyper, F. et al. (*J. Med. Chem.*, 1996, 39(4), 892).

The indoles (T1-a)c can be obtained by cyclization of the compounds T4c in the presence of copper iodide in a solvent such as DMF, at a temperature of between 22° C. and the boiling point of the solvent, according to, for example, the conditions described by Kuyper, F. et al. (*J. Med. Chem.*, 1996, 39(4), 892).

Alternatively, the derivatives of general formula (T1-b)c can be obtained according to general scheme (1G)c below, from the corresponding commercial indole-2-carboxylic acids T5c, via a decarboxylation reaction. This reaction is preferentially carried out at a temperature of between 200° C. and 240° C., in the presence of copper(0) and quinoline according to, for example, the conditions described by Tapia, R. A. et al. (*Bioorg. Med. Chem.*, 2003, 11, 3407).

General scheme (1G)c:

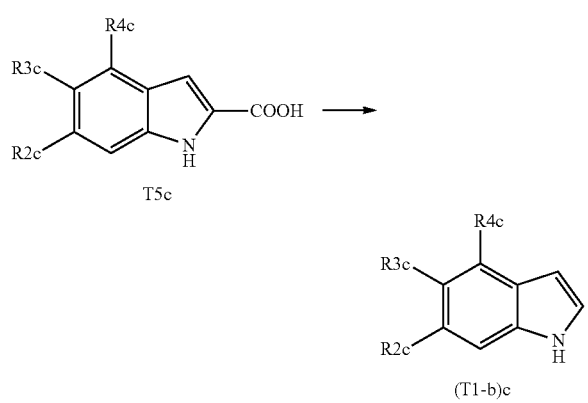

wherein the substituents R2c, R3c and R4c have the meanings indicated above.

Alternatively, the derivatives of general formula (T1-c)c can be obtained according to general scheme (1H)c below, by analogy with the conditions described in patent US 2004/0224973 A1.

General scheme (1H)c:

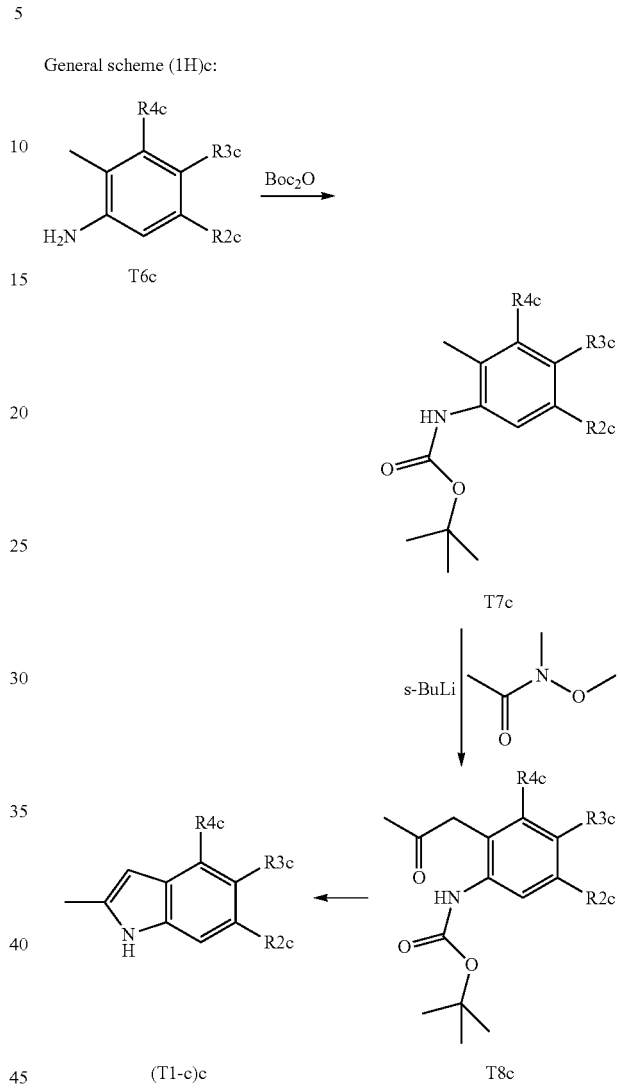

wherein the substituents R2c, R3c and R4c have the meanings indicated above.

In general scheme (1H)c:

The derivatives T7c can be prepared from the corresponding commercial aniline derivatives T6c, by acylation reaction with di-tert-butyl dicarbonate, in a solvent such as tetrahydrofuran, at a temperature of between 20° C. and the boiling point of the solvent.

The derivatives T8c can be prepared from the carbamate derivatives T7c, by reaction in the presence of a base such as sec-butyllithium, and then of N-methoxy-N-methylacetamide, in a solvent such as tetrahydrofuran at a temperature of between −50° C. and −10° C.

The derivatives (T1-c)c can be prepared from the derivatives T8c, by reaction in the presence of an acid such as trifluoroacetic acid, in a solvent such as dichloromethane, at a temperature of between 0° C. and 20° C.

Alternatively, the derivatives of general formula S1c can be obtained according to general scheme (1I)c below.

General scheme (1I)c:

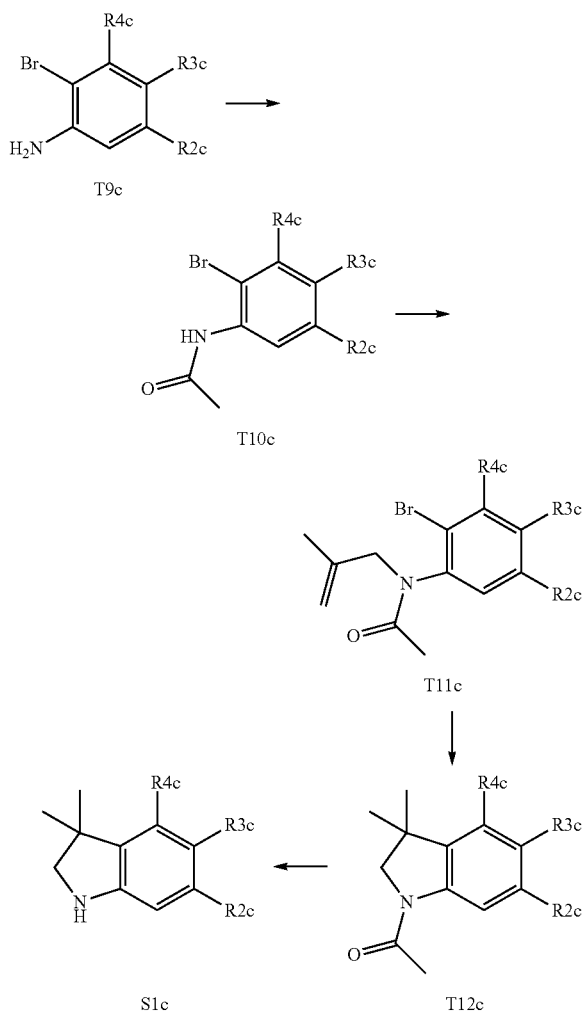

wherein the substituents R2c, R3c and R4c have the meanings indicated above.

In general scheme (1I)c:

The derivatives T10c can be prepared from the corresponding commercial aniline derivatives T9c, by acetylation reaction with acetyl chloride, in the presence of a base such as an amine (preferably triethylamine), in a solvent such as dichloromethane, at a temperature of between 0° C. and the boiling point of the solvent.

The derivatives T11c can be prepared from the anilide derivatives T10c, by reaction with 3-bromo-2-methylpropene, in the presence of a base such as potassium carbonate and of a hydride such as sodium hydride, in a solvent such as toluene at a temperature of between 20° C. and the boiling point of the solvent, by analogy with the conditions described by Edwards, J. P. et al. (*Bioorg. Med. Chem. Lett.*, 1998, 8, 745).

The derivatives T12c can be prepared by cyclization reaction of the derivatives T11c, for example in the presence of a catalyst such as a palladium derivative (preferably palladium diacetate), of tetrabutylammonium chloride, in the presence of a base such as triethylamine, in a solvent such as N,N-dimethylformamide, at a temperature of between 20° C. and the boiling point of the solvent, by analogy with the conditions described by Larock, R. C. et al. (*Tetrahedron Lett.*, 1987, 28, 5291).

The derivatives S1c can be prepared from the derivatives T12c, by reaction in the presence of an acid such as concentrated hydrochloric acid, at a temperature of between 20° C. and the boiling point of the solvent, under conditions known to those skilled in the art.

Preparation of Compounds of Formula (Id)

The products of general formula (Id) according to the present invention can in particular be prepared as indicated in general schemes (1A)d-(1C)d below. In this respect, the methods described cannot constitute a limitation of the scope of the invention, with regard to the methods for preparing the claimed compounds.

The preparations of the examples of the present invention give illustrations of the schemes below.

Such synthesis schemes form part of the present invention: a subject of the present invention is thus also the processes for preparing the products of formulae Cd to (I-d)d, as defined in general schemes (1A)d, (1B)d, (1C)d and (1K)d below.

General scheme (1A)d:

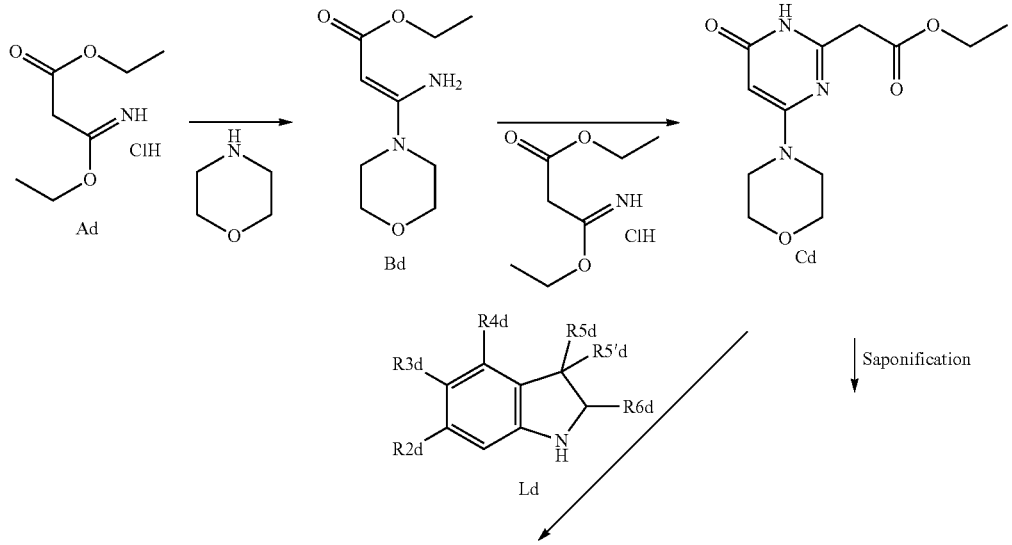

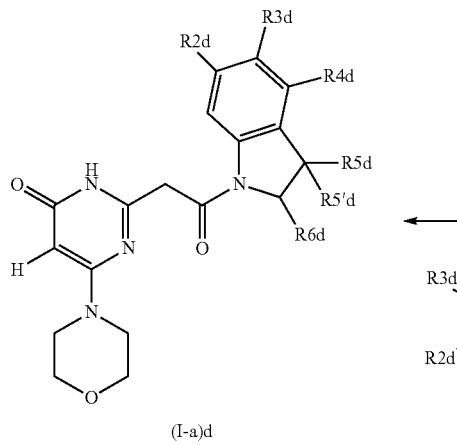

(I-a)d

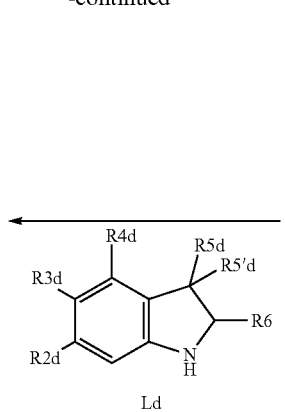

Ld

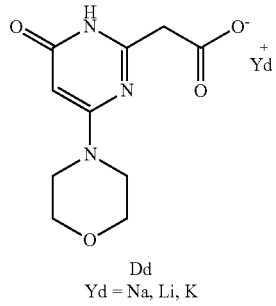

Dd
Yd = Na, Li, K wherein the substituents R2d, R3d, R4d, R5d, R5'd and R6d have the meanings indicated above.

In general scheme (1A)d:

The ketene aminal Bd can be obtained from the imino ether Ad or from its commercial aminoacrylate tautomer, by reaction with morpholine in a solvent such as ethanol, at a temperature of between 0° C. and the boiling point of the solvent, according to the process described by Landwehr J. et al. in J. Med. Chem. 2006, 49, 4327-4332.

The ester Cd can be obtained by reaction of the ketene aminal Bd with the imino ether Ad, or its aminoacrylate tautomer, in a solvent such as ethanol, at a temperature of between 20° C. and the boiling point of the solvent.

Alternatively, the ester Cd can be obtained by one-pot reaction between morpholine and an excess (for example 3 equivalents) of imino ether Ad (or of its aminoacrylate tautomer), in a solvent such as ethanol, at a temperature of between 20° C. and the boiling point of the solvent.

The carboxylate Dd can be obtained by hydrolysis of the ester Cd in the presence of a base such as sodium hydroxide or lithium hydroxide, in a solvent such as tetrahydrofuran or methanol, at a temperature of between 0° C. and 30° C.

The amides (I-a)d can be obtained from the carboxylate Dd by a coupling reaction of an indoline Ld in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron 2001, 57, 1551-1558.

The amides (I-a)d can also be obtained from the ester Cd by reaction of an indoline Ld in the presence of an agent such as trimethyl aluminum or potassium tert-butoxide, in a solvent such as toluene, tetrahydrofuran or N,N-dimethylformamide, at a temperature of between 20° C. and 150° C., for instance under the conditions described by Perreux L. et al. in Tetrahedron 2003 (59) 2185-2189 and by Auzeloux, P et al. in J. Med. Chem. 2000, 43 (2), 190-197.

General scheme (1B)d:

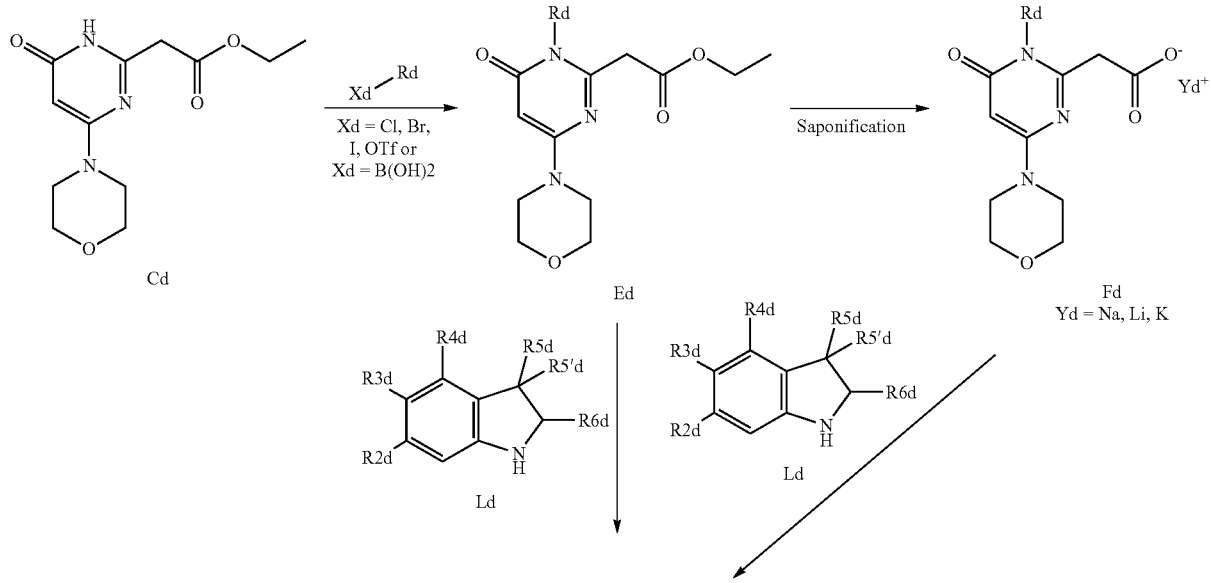

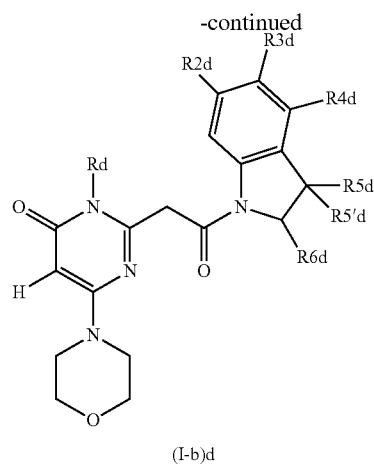

(I-b)d wherein the substituents Rd, R2d, R3d, R4d, R5d, R5'd and R6d have the meanings indicated above.

In general scheme (1B)d:

The esters Ed can be obtained from the ester Cd by reaction with a compound Rd-Xd (Xd=Cl, Br, I or triflate), in the presence of a base such as sodium hydroxide, potassium tert-butoxide or cesium carbonate, in a solvent such as methanol, ethanol or dioxane, at a temperature of between 0° C. and 50° C., according to, for example, the process described by Noël D. D'Angelo et al. in J. Med. Chem. 2008, 51, 5766-5779.

The esters Ed can also be obtained from the ester Cd by reaction with a compound R5d-Xd (Xd=B(OH)$_2$), in the presence of a base such as DMAP (dimethylpyridin-4-ylamine) and NaHMDS (sodium salt of 1,1,1,3,3,3-hexamethyldisilazane), and of a copper(II) salt such as copper acetate (Cu(OAc)$_2$) in a solvent such as toluene, dioxane or tetrahydrofuran, at a temperature of between 0° C. and the boiling point of the solvent, according to, for example, the process described by Takayuki Tsuritani et al. (Organic Letters 2008, 10(8), 1653-1655).

The carboxylates Fd can be obtained by hydrolysis of the esters Ed, in the presence of a base such as sodium hydroxide or lithium hydroxide, in a solvent such as tetrahydrofuran or methanol, at a temperature of between 0° C. and 30° C.

The amides (I-b)d can be obtained from the carboxylates Fd by a coupling reaction of an indoline Ld in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium)hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron 2001, 57, 1551-1558.

The amides (I-b)d can also be obtained from the esters Ed by reaction of an indoline Ld, in the presence of an agent such as trimethyl aluminum, in a solvent such as toluene, at a temperature of between 20° C. and the boiling point of the solvent, for instance under the conditions described by Auzeloux, P et al. in J. Med. Chem. 2000, 43 (2), 190-197.

General scheme (1C)d:

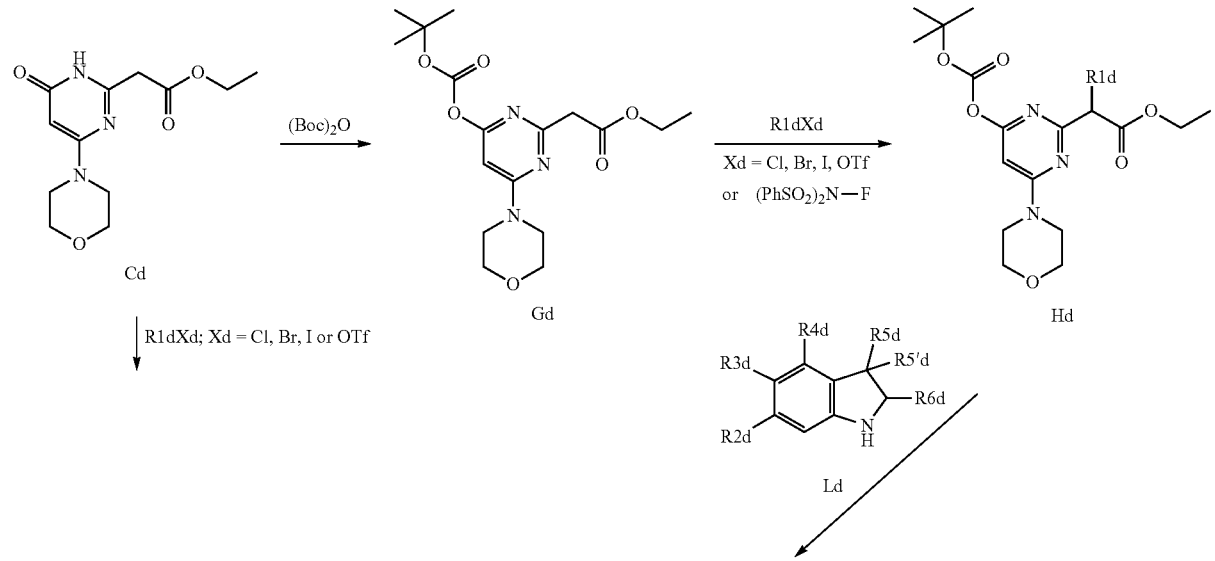

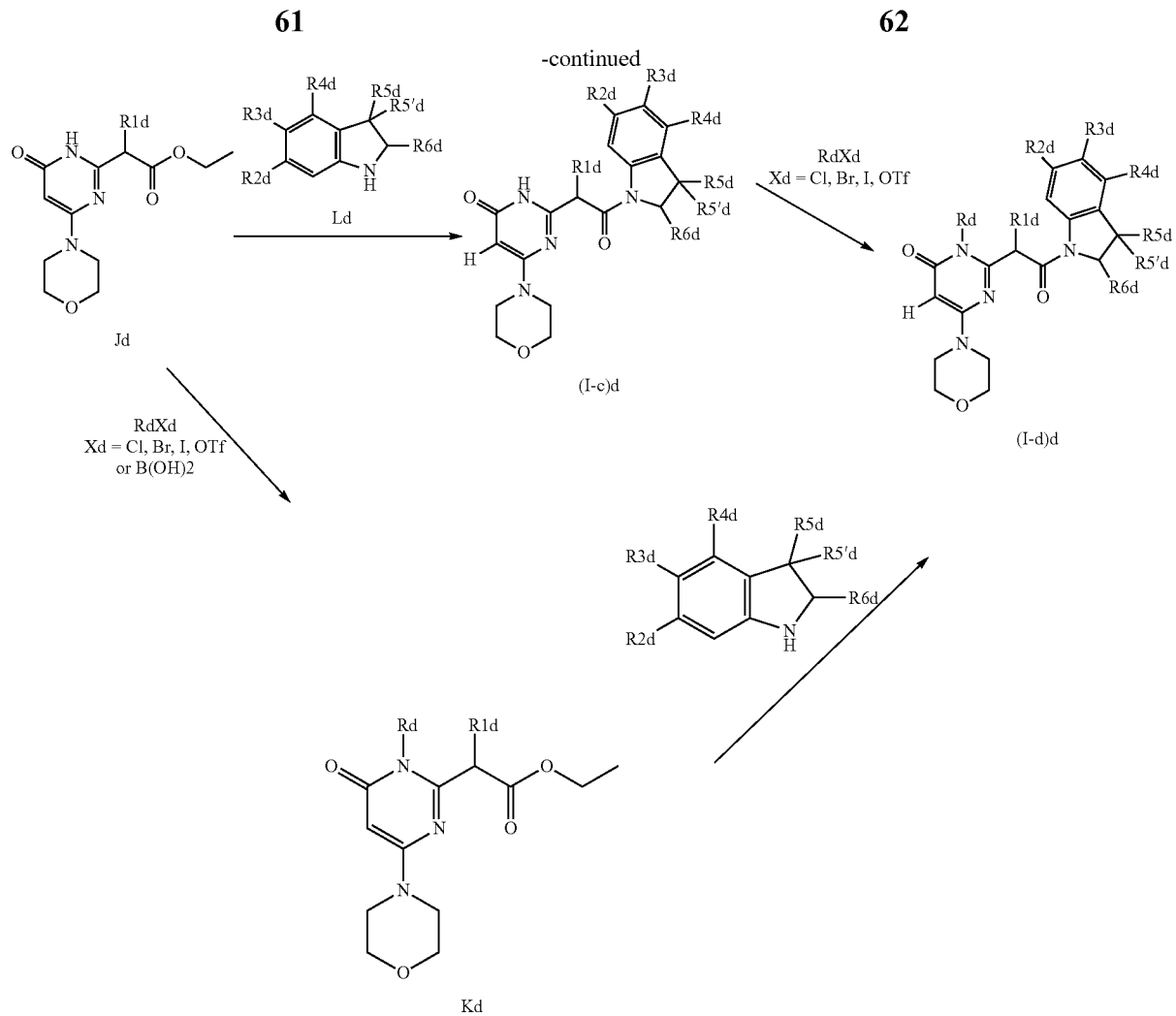

wherein the substituents Rd, R1d, R2d, R3d, R4d, R5d, R5'd and R6d have the meanings indicated above.

In general scheme (1C)d:

The ester Gd can be obtained from the ester Cd by reaction with (Boc)₂O (tert-butyl dicarbonate), in a solvent such as N,N-dimethylformamide, dioxane, acetonitrile or dichloromethane, in the presence of a base, for instance sodium hydride, triethylamine, N,N-diisopropylethylamine or pyridine, at a temperature of between 0° C. and 60° C., according to, for example, the process described by Hioki K. et al. Synthesis 2006, 12, 1931-1933.

The products Hd can be obtained from the ester Gd by reaction with R1d-Xd (Xd=Cl, Br, I or OTf and R1d is an alkyl group), in the presence of a base such as sodium hydroxide, potassium tert-butoxide or cesium carbonate, in a solvent such as methanol, ethanol or dioxane, at a temperature of between 0° C. and 100° C., according to, for example, the process described by Noël D. D'Angelo et al. in J. Med. Chem. 2008, 51, 5766-5779.

The product Hd wherein R1d=F can be obtained by reaction of the product Gd with N-fluorobenzenesulfonimide, in the presence of a base such as the potassium salt of hexamethyldisilylazane, in a solvent such as tetrahydrofuran, at a temperature of between −78° C. and 20° C., according to, for example, the process described by Christopher S. Burgey et al. in J. Med. Chem. 2003, 46, 461-473.

The esters Jd wherein the R1d group is an alkyl radical can be obtained from the ester Cd in the same way as the products Hd, in the presence of a base such as butyllithium, sodium hydride, potassium tert-butoxide or cesium carbonate, in a solvent such as methanol, ethanol, tetrahydrofuran, N,N-dimethylformamide or dioxane, at a temperature of between 0° C. and 50° C.

The amides (I-c)d can be obtained from the esters Hd or Jd by reaction of an indoline Ld, in the presence of an agent such as trimethyl aluminum, in a solvent such as toluene, at a temperature of between 20° C. and the boiling point of the solvent, for instance under the conditions described by Auzeloux, P et al. in J. Med. Chem. 2000, 43 (2), 190-197.

The amides (I-d)d can be obtained from the amides (I-c)d by reaction with a compound Rd-Xd (Xd=Cl, Br, I or triflate), in the presence of a base such as sodium hydroxide, potassium tert-butoxide or cesium carbonate, in a solvent such as methanol, ethanol or dioxane, at a temperature of between 0° C. and 50° C., according to, for example, the process described by Noel D. D'Angelo et al. in J. Med. Chem. 2008, 51, 5766-5779.

Alternatively, the amides (I-d)d can be obtained from the esters Kd by reaction of an indoline Ld, in the presence of an agent such as trimethyl aluminum, in a solvent such as toluene, at a temperature of between 20° C. and the boiling point of the solvent, for instance under the conditions described by Auzeloux, P et al. in J. Med. Chem. 2000, 43 (2), 190-197.

The esters Kd can be obtained from the esters Jd by reaction with a compound Rd-Xd (Xd=Cl, Br, I, triflate or boronate B(OH)$_2$), in the presence of a base such as sodium hydroxide, potassium tert-butoxide or cesium carbonate, in a solvent such as methanol, ethanol or dioxane, at a temperature of between 0° C. and 50° C., according to, for example, the process described by Noël D. D'Angelo et al. in J. Med. Chem. 2008, 51, 5766-5779.

Among the starting products of formula Ad or Bd, some are known and can be obtained either commercially or according to the usual methods known to those skilled in the art, for example from commercial products.

The indolines of general formula (Ld), when they are not commercially available, can be generally obtained from the corresponding indoles M1d by reduction in the presence of a reducing agent such as a hydride (sodium cyanoborohydride, for example), in a solvent such as acetic acid or trifluoroacetic acid, at a temperature of between −5° C. and 25° C., as described, for example, by Kumar, Y. (*Synth. Commun.*, 1983, 13(6), 489).

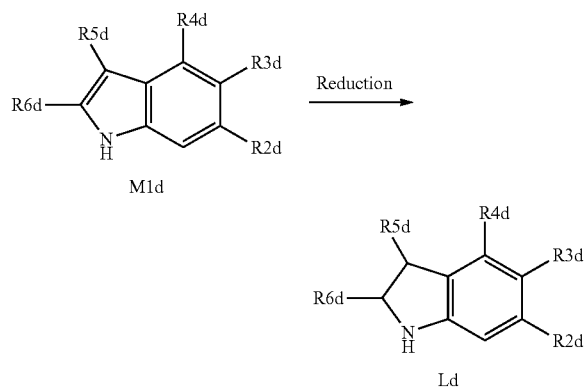

wherein the substituents R2d, R3d, R4d, R5d and R6d have the meanings indicated above.

The enantiomerically enriched indolines can be obtained, for example, by chemical resolution of the enantiomers using an enantiomerically pure chiral moiety, as described in general scheme (1D)d. For example, the resolution of the enantiomers of the indoline Ld can be carried out by chromatographic separation of the two diastereoisomers formed by peptide-type coupling with o-benzyl-D-lactic acid in the presence of a peptide coupling agent such as, for example, EDCI (N-[3-(dimethylamino)propyl]-N'-ethylcarbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 100° C., for instance under the conditions described by Kunishima, M. et al. (*Tetrahedron*, 2001, 57, 1551). The (+)-Ld and (−)-Ld enantiomers can be respectively obtained from the compounds M2d: dia A and M2d: dia B by reaction in the presence of an acid such as concentrated hydrochloric acid, in a solvent such as an alcohol (ethanol, for example), at a temperature of between 20° C. and the boiling point of the solvent, for instance under the conditions described by Krasnov, V. P. et al. (*Mendeleev Commun.* 2002, 12(1), 27).

General scheme (1D)d:

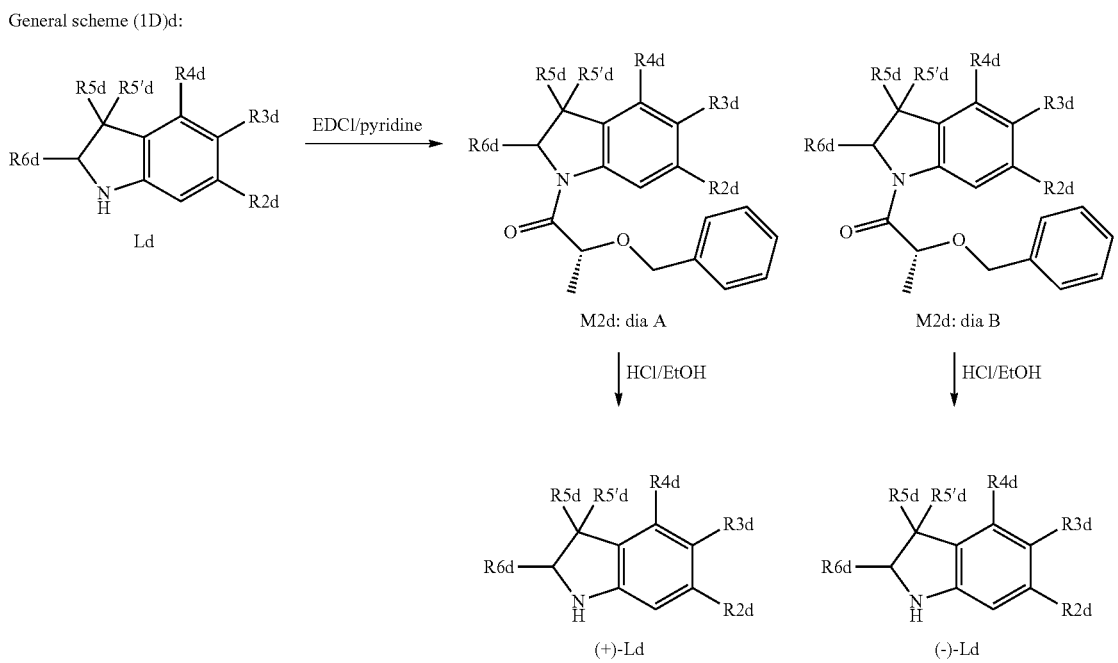

wherein the substituents R2d, R3d, R4d, R5d, R5'd and R6d have the meanings indicated above.

The products of general formula (M1-a)d can in particular be prepared as indicated in general scheme (1E)d below, from the compounds M3d by Suzuki-type coupling with an arylboronic acid or an arylboronate in the presence of a palladium-based catalyst (dichlorobis(tri-o-tolylphosphine)palladium(II), for example), and of a base such as potassium carbonate in a solvent such as a mixture of dioxane and water at a temperature of between 20° C. and the boiling point of the solvent, or alternatively with an arylboronic acid or an arylboronate in the presence of a catalyst such as [1,1'-bis(diphenylphosphino)ferrocene]dichloropalladium(II), of copper(I) chloride and of a base such as cesium carbonate in a solvent such as N,N-dimethylformamide, at a temperature of between 20° C. and the boiling point of the solvent (optionally under microwave irradiation), according to, for example, the conditions described in patent US 2007/0072897 A1.

General scheme (1E)d:

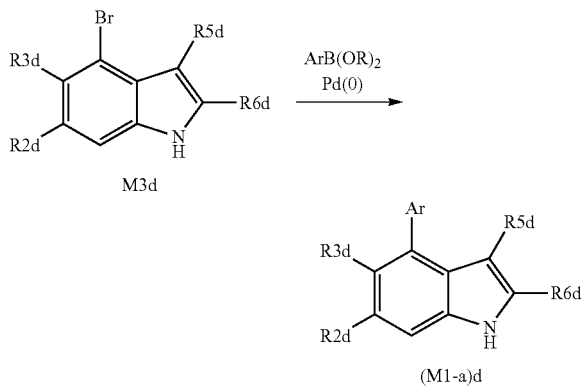

wherein the substituents R2d, R3d, R5d and R6d have the meanings indicated above.

Alternatively, the derivatives of general formula (M1-b)d can be obtained according to general scheme (1F)d below, from the corresponding commercial indole-2-carboxylic acids M4d, via a decarboxylation reaction. This reaction is preferentially carried out at a temperature of between 200° C. and 240° C., in the presence of copper(0) and quinoline according to, for example, the conditions described by Tapia, R. A. et al. (*Bioorg. Med. Chem.*, 2003, 11, 3407).

General scheme (1F)d:

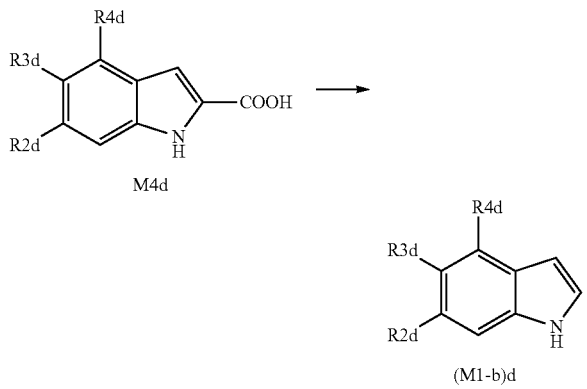

wherein the substituents R2d, R3d and R4d have the meanings indicated above.

Alternatively, the derivatives of general formula (M1-c)d can be obtained according to general scheme (1G)d below, by analogy with the conditions described by Katayama, M. et al. (*Biosci. Biotechnol. Biochem.*, 2008, 72(8), 2025).

General scheme (1G)d:

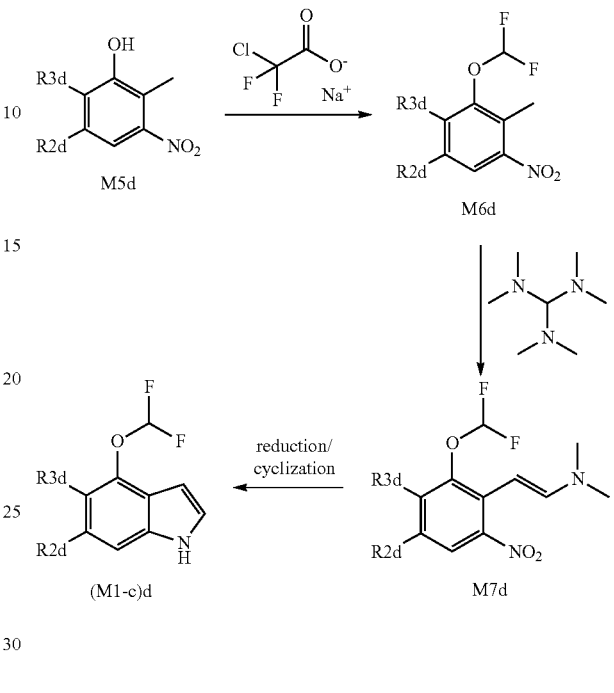

wherein the substituents R2d and R3d have the meanings indicated above.

In general scheme (1G)d:

The derivatives M6d can be prepared from the corresponding commercial derivatives M5d, by reaction with sodium chlorodifluoroacetate, in the presence of a base such as potassium carbonate, in a solvent such as a mixture of N,N-dimethylformamide and water, at a temperature of between 20° C. and the boiling point of the solvent, by analogy with the conditions described in patent WO2009/92590.

The derivatives M7d can be prepared from the derivatives M6d, by reaction with tris(dimethylamino)methane, in a solvent such as N,N-dimethylformamide, at a temperature of between 20° C. and the boiling point of the solvent, by analogy with the conditions described by Hume, W. E. et al. (*Tetrahedron*, 2002, 58, 3605).

The derivatives (M1-c)d can be prepared from the derivatives M7d, by reduction and cyclization in the presence of hydrazine hydrate, and of a catalyst such as Raney nickel, in a solvent such as a mixture of methanol and tetrahydrofuran, at a temperature of between 20° C. and the boiling point of the solvent, by analogy with the conditions described by Hume, W. E. et al. (*Tetrahedron*, 2002, 58, 3605).

Alternatively, the derivatives of general formula (M1-d)d, wherein Xd is an $SO_2Alk$ or Alk group, can be obtained according to general scheme (1H)d below, from the corresponding commercial aldehydes M8d, by reductive amination reaction in the presence of the corresponding commercial piperazines and of a reducing agent such as sodium triacetoxyborohydride, in a solvent such as tetrahydrofuran, at a temperature of between 20° C. and the boiling point of the solvent, according to, for example, the conditions described in patent WO2007/113249 A2.

General scheme (1H)d:

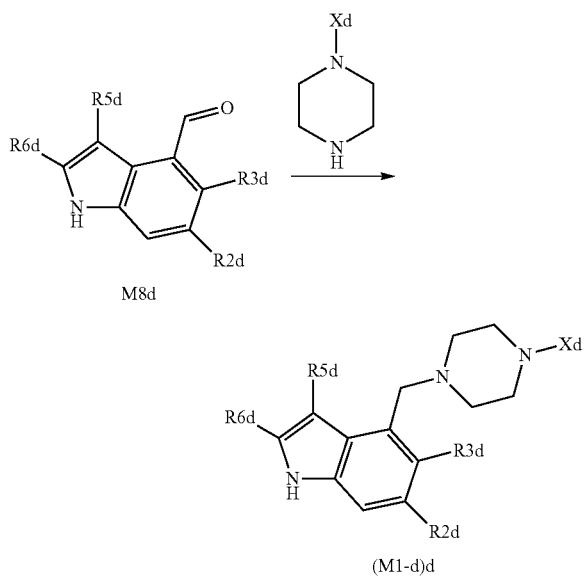

wherein the substituents R2d, R3d, R5d and R6d have the meanings indicated above.

Alternatively, the derivatives of general formula (M1-e)d can be obtained according to general scheme (1I)d below, from the corresponding commercial 4-hydroxy-2-methylindole derivatives M9d, by reaction with freon-22, in the presence of a phase-transfer agent such as tetrabutylammonium bromide and of a base such as sodium hydroxide, in a solvent such as dichloromethane, at a temperature of between 0° C. and ambient temperature, according to, for example, the conditions described in patent WO2006/019831.

General scheme (1I)d:

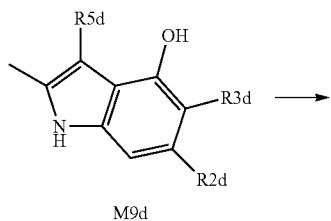

wherein the substituents R2d, R3d and R5d have the meanings indicated above.

The products of general formula (M1-f)d can in particular be prepared as indicated in general scheme (1J)d below.

General scheme (1J)d:

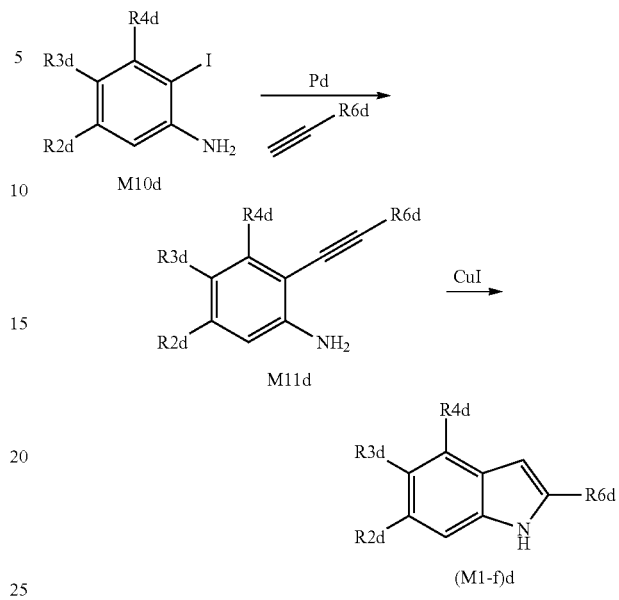

wherein the substituents R2d, R3d, R4d and R6d have the meanings indicated above.

In general scheme (1J)d:

The derivatives M11d can be prepared from the compounds M10d by Sonogashira-type coupling with a true alkyne in the presence of a palladium-based catalyst such as bis(triphenylphosphine)palladium(II) dichloride and of copper iodide, in a solvent such as triethylamine and optionally in the presence of a cosolvent such as N,N-dimethylformamide, at a temperature of between 0° C. and the boiling point of the solvent, according to, for example, the conditions described by Kuyper, F. et al. (*J. Med. Chem.*, 1996, 39(4), 892).

The indoles (M1-f)d can be obtained by cyclization of the compounds M1ld in the presence of copper iodide in a solvent such as DMF, at a temperature of between 22° C. and the boiling point of the solvent, according to, for example, the conditions described by Kuyper, F. et al. (*J. Med. Chem.*, 1996, 39(4), 892).

General scheme (1K)d:

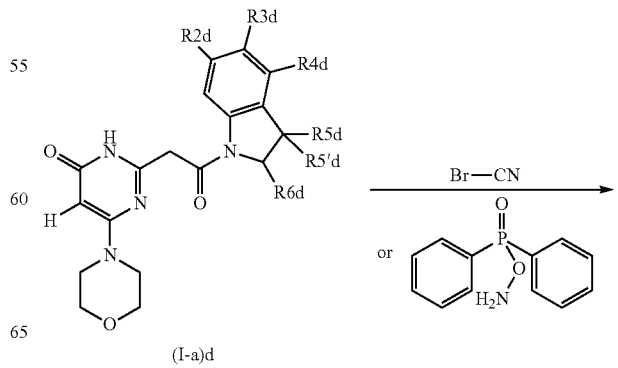

-continued

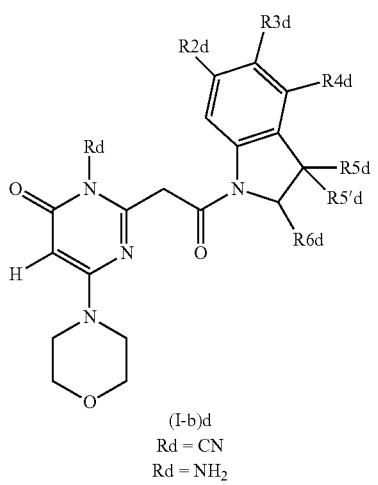

(I-b)d
Rd = CN
Rd = NH$_2$ wherein the substituents Rd, R2d, R3d, R4d, R5d, R5'd and R6d have the meanings indicated above.

In general scheme (1K)d:

The amides (I-b)d can be obtained from the amides (I-a)d by reaction with cyanogen bromide (CNBr) in the presence of a base such as sodium hydroxide, potassium tert-butoxide or cesium carbonate, in a solvent such as methanol, ethanol or dioxane, at a temperature of between 0° C. and 50° C., using as a basis the process described by Noël D. D'Angelo et al. in J. Med. Chem. 2008, 51, 5766-5779 and replacing the alkylating agents with cyanogen bromide.

The amides (I-b)d can also be obtained from the amides (I-a)d by reaction with o-diphenylphosphinylhydroxylamine in the presence of a base such as cesium carbonate, in a solvent such as dimethylformamide, at a temperature of between 0° C. and 50° C., according to, for example, the process described by S. Hanessian et al. in Bioorg. Med. Chem. Lett. 2008, 18, 1972-1976.

Preparation of Compounds of Formula (Ie)

The products of general formula (Ie) according to the present invention can in particular be prepared as indicated in general schemes (1A)e, (1B)e and (1C)e below. In this respect, the methods described cannot constitute a limitation of the scope of the invention, with regard to the methods for preparing the claimed compounds.

The preparations of the examples of the present invention give illustrations of the schemes below.

Such synthesis schemes form part of the present invention: a subject of the present invention is thus also the processes for preparing the products of formulae Be to (Ie), as defined in general schemes (1A)e, (1B)e and (1C)e below.

Schemes (1A)e, (1B)e and (1C)e below illustrate the methods used for preparing the products of formula (Ie). In this respect, they cannot constitute a limitation of the scope of the invention, with regard to the methods for preparing the claimed compounds.

The products of formula (Ie) as defined above according to the present invention can thus in particular be prepared according to the processes described in schemes (1A)e, (1B)e and (1C)e.

A subject of the present invention is thus also the process for preparing products of formula (Ie) according to scheme (1A)e as defined hereinafter.

A subject of the present invention is thus also the process for preparing products of formula (Ie) according to scheme (1B)e as defined hereinafter.

A subject of the present invention is thus also the process for preparing products of formula (Ie) according to scheme (1C)e as defined hereinafter.

General scheme (1A)e:

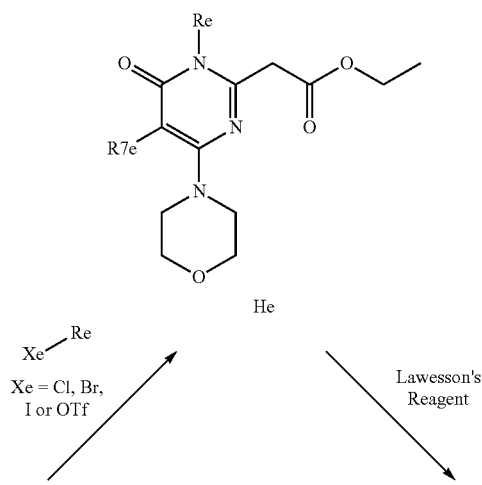

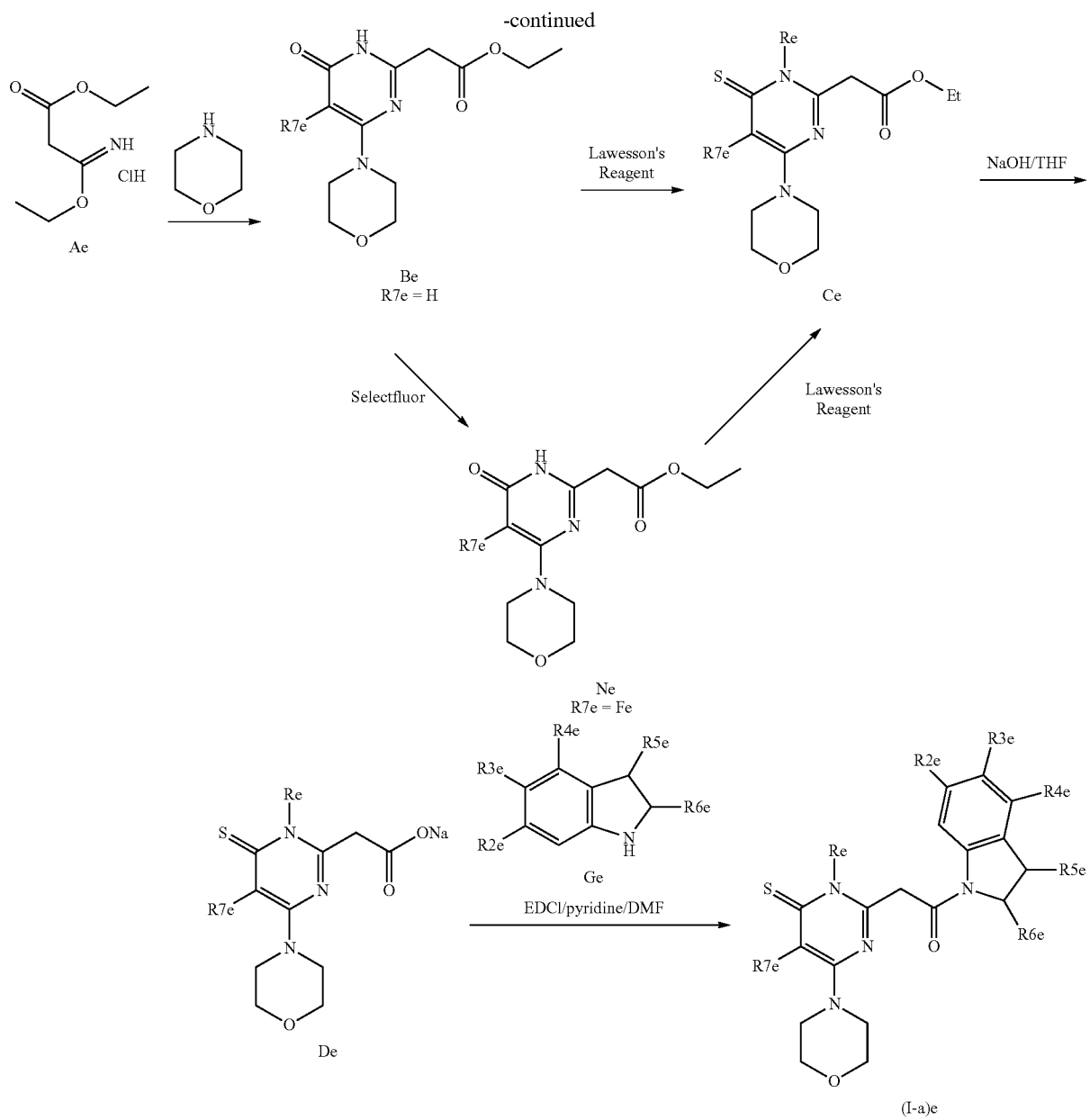

wherein the substituents Re, R2e, R3e, R4e, R5e, R6e and R7e have the meanings indicated above.

The ester Be can be obtained by one-pot reaction between morpholine and an excess (for example 3 equivalents) of imino ether Ae (or of its aminoacrylate tautomer), in a solvent such as ethanol, at a temperature of between 20° C. and the boiling point of the solvent.

The esters He can be obtained from the ester Be by reaction with a compound Re—Xe (Xe=Cl, Br, I or triflate), in the presence of a base such as sodium hydroxide, potassium tert-butoxide or cesium carbonate, in a solvent such as methanol, ethanol or dioxane, at a temperature of between 0° C. and 50° C., according to, for example, the process described by Noël D. D'Angelo et al. in J. Med. Chem. (2008), 51, 5766-5779.

The pyrimidones Ne can be obtained from the compounds Be, with a fluorinating reagent such as Selectfluor, in a solvent such as acetonitrile, at a temperature of between 22° C. and the boiling point of the solvent, for instance under the conditions described by Banks R. E. (Journal of Fluorine Chemistry (1998), 87, 1-17).

The thiopyrimidones Ce can be obtained from the pyrimidones Be, He or Ne by reaction with a sulfurization reagent such as Lawesson's reagent, in a solvent such as toluene, at a temperature of between 22° C. and the boiling point of the solvent, for instance under the conditions described by Jones G. (Journal of the Chemical Society, Perkin Transactions 1: Organic and Bio-Organic Chemistry (1972-1999), (1983), 11, 2645-2648).

The carboxylates De can be obtained by hydrolysis of the esters Ce, in the presence of a base such as sodium hydroxide or lithium hydroxide, in a solvent such as tetrahydrofuran or methanol, at a temperature of between 0° C. and 30° C.

The amides (I)e can be obtained from the carboxylates De by a coupling reaction of an indoline Ge in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron (2001), 57, 1551-1558.

Alternatively, the compounds (Ie) can be obtained according to general scheme (1B)e.

PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron (2001), 57, 1551-1558.

The thiopyrimidones (I-a)e and the thiopyrimidone-thioamides (I-b)e can be obtained from the compounds Fe by reaction with a sulfurization reagent such as Lawesson's reagent, in a solvent such as toluene, at a temperature of between 22° C. and the boiling point of the solvent, for instance under the conditions described by Jones G. (Journal

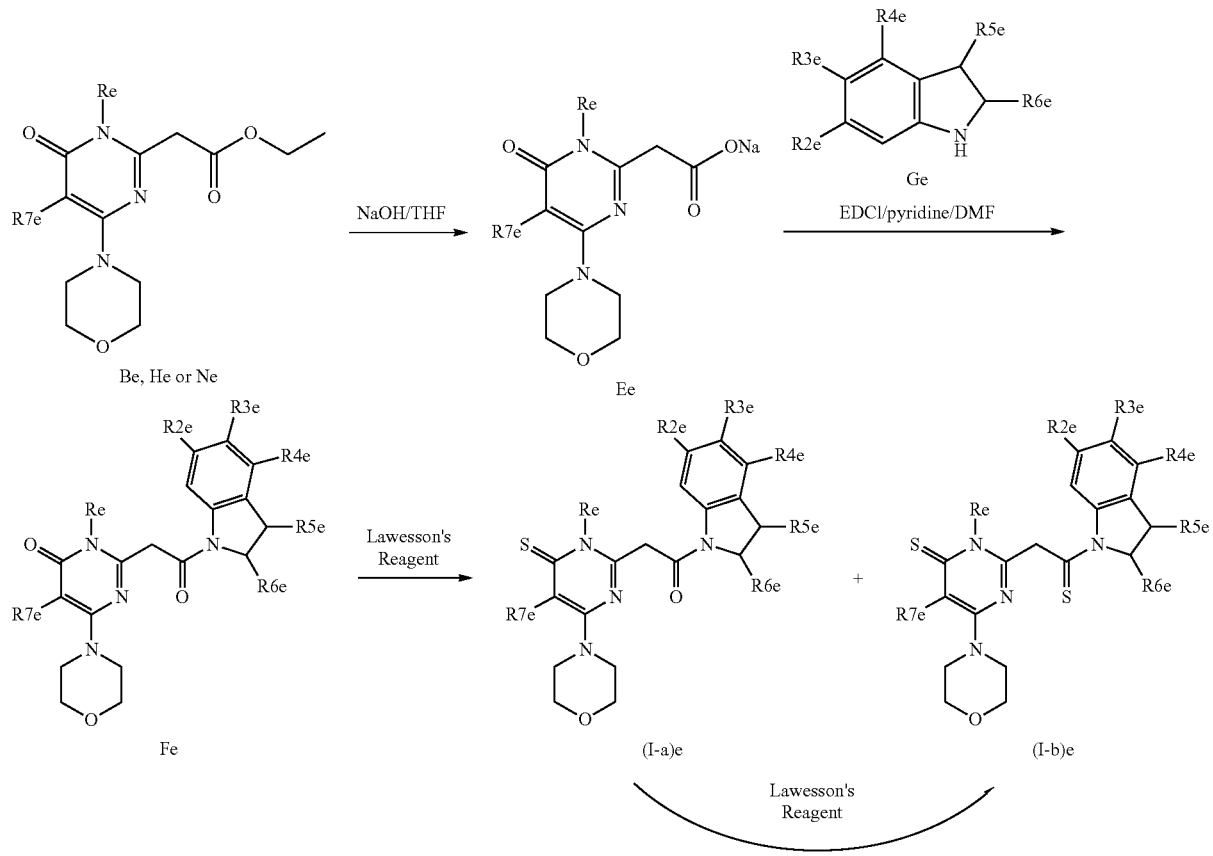

wherein the substituents Re, R2e, R3e, R4e, R5e, R6e and R7e have the meanings indicated above.

The carboxylates Ee can be obtained by hydrolysis of the esters Be, He or Ne in the presence of a base such as sodium hydroxide or lithium hydroxide, in a solvent such as tetrahydrofuran or methanol, at a temperature of between 0° C. and 30° C.

The amides Fe can be obtained from the carboxylates Ee by a coupling reaction of an indoline Ge in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], of the Chemical Society, Perkin Transactions 1: Organic and Bio-Organic Chemistry (1972-1999), (1983), 11, 2645-2648).

The thiopyrimidone-thioamides (I-b)e can be obtained from the thiopyrimidones (I-a)e by reaction with a sulfurization reagent such as Lawesson's reagent, in a solvent such as toluene, at a temperature of between 22° C. and the boiling point of the solvent, for instance under the conditions described by Jones G. (Journal of the Chemical Society, Perkin Transactions 1: Organic and Bio-Organic Chemistry (1972-1999), (1983), 11, 2645-2648).

Alternatively, the compounds (Ie) can be obtained according to general scheme (1C)e.

General scheme (1C)e:

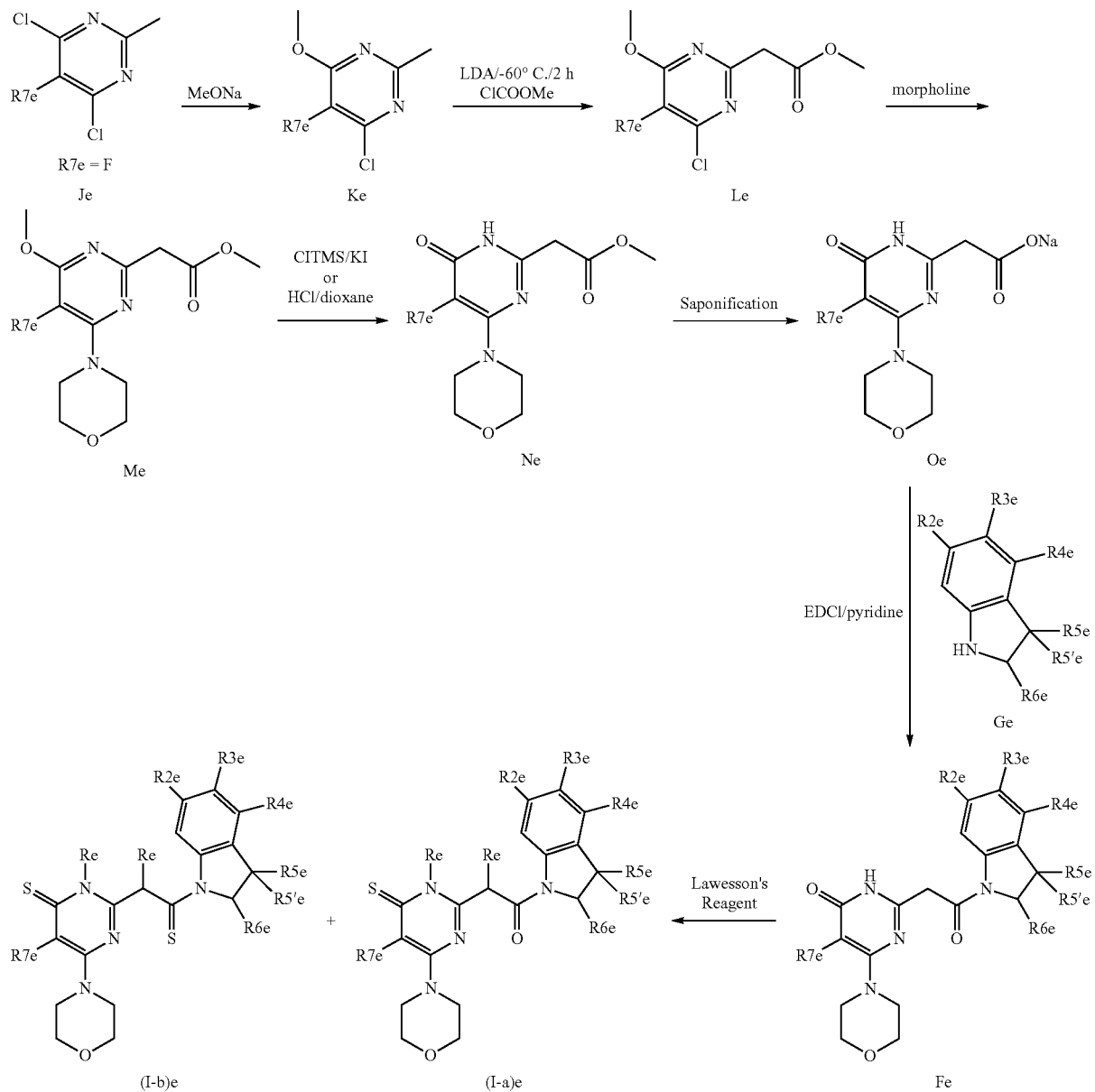

wherein the substituents Re, R1e, R2e, R3e, R4e, R5e, R5'e, R6e and R7e have the meanings indicated above.

In general scheme (1C)e:

The methoxypyrimidine derivatives Ke can be prepared from the compounds Je by reaction with sodium methoxide in a solvent such as THF or methanol, at a temperature of between 0° C. and 25° C., according to, for example, the conditions described by Ioannidis, S. et al. (Bioorganic and Medicinal Chemistry Letters, (2010), 20(5), 1669-1673).

The compounds Le can be obtained by treatment of the compounds Ke in the presence of methyl chloroformate with LDA (lithium diisopropylamide) in a solvent such as THF, at a temperature of between −78° C. and 25° C., according to, for example, the conditions described by Tomioka K. et al. (Tetrahedron, (1988), 44(14), 4351-4356).

The compounds Me can be obtained from a compound Le by reaction with morpholine, in the absence of solvent, at a temperature of between 0° C. and 25° C., as described, for example, by Aliabiev S. B. (Lett. Org. Chem. (2007), 4(4), 273-280).

The compounds Ne can be obtained from the compounds Me by reaction with chlorotrimethylsilane and potassium iodide or iodotrimethylsilane, in a solvent such as acetonitrile, at a temperature of between 22° C. and the boiling point of the solvent, for instance under the conditions described by Shiao M. J. (J. Org. Chem. (1993), 58(17), 4742-4744).

The carboxylate Oe can be obtained by hydrolysis of the ester Ne in the presence of a base such as sodium hydroxide or lithium hydroxide, in a solvent such as tetrahydrofuran or methanol, at a temperature of between 0° C. and 30° C.

The amides Fe can be obtained from the carboxylate Oe by a coupling reaction of an indoline Ge in the presence of a peptide coupling agent such as, for example, EDCI (ethyl dimethylaminopropyl carbodiimide), DMT-MM [4-(4,6-dimethoxy-1,2,3-triazin-2-yl)-4-methylmorpholinium chloride], BOP [benzotriazol-1-yloxytris(dimethylamino)phosphonium hexafluorophosphate], PyBOP [(benzotriazol-1-yloxy)trispyrrolidinophosphonium hexafluorophosphate], PyBROP [bromotrispyrrolidinophosphonium hexafluorophosphate], HATU [O-(7-azabenzotriazol-1-yl)-1,1,3,3-tetramethyluronium hexafluorophosphate] or an HOBT/EDCI [hydroxybenzotriazole/ethyldimethylaminopropyl carbodiimide] mixture, in a solvent such as N,N-dimethylformamide, pyridine, ethanol, water or methanol, at a temperature of between 20° C. and 50° C., for instance under the conditions described by Kunishima M. et al. in Tetrahedron (2001), 57, 1551-1558.

The thiopyrimidones (I-a)e and the thiopyrimidone-thioamides (I-b)e can be obtained from the compounds Pe by reaction with a sulfurization reagent such as Lawesson's reagent, in a solvent such as toluene, at a temperature of between 22° C. and the boiling point of the solvent, for instance under the conditions described by Jones G. (Journal of the Chemical Society, Perkin Transactions 1: Organic and Bio-Organic Chemistry (1972-1999), (1983), 11, 2645-2648).

It is understood for those skilled in the art that, in order to carry out the processes according to the invention described above, it may be necessary to introduce protective groups for the amino, carboxyl and alcohol groups in order to avoid side reactions.

The following nonexhaustive list of examples of protection of reactive groups may be mentioned:
 hydroxyl groups can be protected, for example, with alkyl radicals, such as tert-butyl, trimethylsilyl, tert-butyldimethylsilyl, methoxymethyl, tetrahydropyranyl, benzyl or acetyl,
 amino groups can be protected, for example, with acetyl, trityl, benzyl, tert-butoxycarbonyl, BOC, benzyloxycarbonyl or phthalimido radicals or other radicals known in peptide chemistry,
 acid groups can be protected, for example, in the form of esters formed with readily cleavable esters, such as benzyl or tert-butyl esters or esters known in peptide chemistry.

A list of various usable protective groups will be found in the manuals known to those skilled in the art, and for example in patent BF 2 499 995.

It may be noted that it is possible, if desired and if necessary, to subject intermediate products or products of formulae (Ia) to (Ie) thus obtained by means of the processes indicated above, in order to obtain other intermediates or other products of formulae (Ia) to (Ie), to one or more conversion reactions known to those skilled in the art, such as, for example:
 a) a reaction for esterification of an acid group,
 b) a reaction for saponification of an ester group to an acid group,
 c) a reaction for reduction of a free or esterified carboxy group to an alcohol group,
 d) a reaction for conversion of an alkoxy group to a hydroxyl group, or else from a hydroxyl group to an alkoxy group,
 e) a reaction for removal of the protective groups that the protected reactive groups may bear,
 f) a reaction for salification with an inorganic or organic acid or with a base so as to obtain the corresponding salt,
 g) a reaction for resolving racemic forms into resolved products,
said products of formulae (Ia) to (Ie) thus obtained being in any of the possible racemic, enantiomeric and diastereoisomeric isomer forms.

The reactions a) to g) can be carried out under the usual conditions known to those skilled in the art, such as, for example, those indicated hereinafter.

a) The products described above can, if desired, be subjected, on the possible carboxy groups, to esterification reactions which can be carried out according to the usual methods known to those skilled in the art.

b) The possible conversions of ester groups into acid groups of the products described above can, if desired, be carried out under the usual conditions known to those skilled in the art, in particular by acid or alkaline hydrolysis, for example with sodium hydroxide or potassium hydroxide in an alcoholic medium such as, for example, in methanol, or else with hydrochloric or sulfuric acid.

The saponification reaction can be carried out under the usual methods known to those skilled in the art, such as, for example, in a solvent such as methanol or ethanol, dioxane or dimethoxyethane, in the presence of sodium hydroxide or of potassium hydroxide.

c) The possible free or esterified carboxy groups of the products described above can, if desired, be reduced to alcohol groups by methods known to those skilled in the art: the possible esterified carboxy groups can, if desired, be reduced to alcohol groups by methods known to those skilled in the art, and in particular with lithium aluminum hydride in a solvent such as, for example, tetrahydrofuran or else dioxane or ethyl ether.

The possible free carboxy groups of the products described above can, if desired, be reduced to alcohol groups in particular with boron hydride.

d) The possible alkoxy groups, such as, in particular, methoxy groups, of the products described above can, if desired, be converted into hydroxyl groups under the usual conditions known to those skilled in the art, for example with boron tribromide in a solvent such as, for example, methylene chloride, with pyridine hydrobromide or hydrochloride, or else with hydrobromic or hydrochloric acid in water or trifluoroacetic acid at reflux.

e) The removal of protective groups such as, for example, those indicated above can be carried out under the usual conditions known to those skilled in the art, in particular by acid hydrolysis carried out with an acid such as hydrochloric acid, benzenesulfonic or para-toluenesulfonic acid, formic acid or trifluoroacetic acid, or else by catalytic hydrogenation.

The phthalimido group can be removed with hydrazine.

f) The products described above can, if desired, be subjected to salification reactions, for example with an inorganic or organic acid or with an inorganic or organic base according to the usual methods known to those skilled in the art: such a salification reaction can be carried out, for example, in the presence of hydrochloric acid or else of tartaric, citric or methanesulfonic acid, in an alcohol such as, for example, ethanol or methanol.

g) The possible optically active forms of the products described above can be prepared by resolution of the racemic mixtures according to the usual methods known to those skilled in the art.

The products of formulae (Ia), (Ib), (Ic), (Id) or (Ie) as defined above and also the addition salts thereof with acids have interesting pharmacological properties, in particular owing to their kinase-inhibiting properties as indicated above.

The products of the present invention are in particular of use for tumor therapy.

The products of the invention can also thus increase the therapeutic effects of commonly used antitumor agents.

These properties justify the therapeutic use thereof, and a subject of the invention is particularly, as medicines, the products of formula (Ia), (Ib), (Ic), (Id) or (Ie) as defined above, said products of formula (Ia), (Ib), (Ic), (Id) or (Ie) being in any of the possible racemic, enantiomeric and diastereoisomeric isomer forms, and also the pharmaceutically acceptable addition salts with inorganic and organic acids or with inorganic and organic bases and said products of formula (Ia), (Ib), (Ic), (Id) or (Ie).

A Subject of the Invention is Most Particularly the Products Corresponding to the Following Formulae, and More Particularly the Products Corresponding to the Following Formulae as Medicines:

Compounds of Formula (Ia):
- -5-fluoro-2-[2-(4-fluoro-2,3-dihydro-1H-indol-1-yl)-2-oxoethyl]-6-(morpholin-4-yl)pyrimidin-4(3H)-one
- -5-fluoro-2-[2-(4-fluoro-2,3-dihydro-1H-indol-1-yl)-2-oxoethyl]-3-methyl-6-(morpholin-4-yl)pyrimidin-4(3H)-one
- -5-fluoro-2-[1-(4-fluoro-2,3-dihydro-1H-indol-1-yl)-1-oxopropan-2-yl]-3-methyl-6-(morpholin-4-yl)pyrimidin-4(3H)-one
- -5-fluoro-2-{2-[(2R)-2-methyl-2,3-dihydro-1H-indol-1-yl]-2-oxoethyl}-6-(morpholin-4-yl)pyrimidin-4(3H)-one
- -5-fluoro-2-{2-[(2S)-2-methyl-2,3-dihydro-1H-indol-1-yl]-2-oxoethyl}-6-(morpholin-4-yl)pyrimidin-4(3H)-one
- -5-fluoro-2-{2-[(2R)-5-fluoro-2-methyl-2,3-dihydro-1H-indol-1-yl]-2-oxoethyl}-6-(morpholin-4-yl)pyrimidin-4(3H)-one
- -5-fluoro-2-{2-[(2S)-5-fluoro-2-methyl-2,3-dihydro-1H-indol-1-yl]-2-oxoethyl}-6-(morpholin-4-yl)pyrimidin-4(3H)-one
- -5-fluoro-3-methyl-2-{2-[(2S)-2-methyl-2,3-dihydro-1H-indol-1-yl]-2-oxoethyl}-6-(morpholin-4-yl)pyrimidin-4(3H)-one
- -5-fluoro-3-methyl-2-{2-[(2R)-2-methyl-2,3-dihydro-1H-indol-1-yl]-2-oxoethyl}-6-(morpholin-4-yl)pyrimidin-4(3H)-one
- -5-fluoro-2-{2-[(2R)-4-fluoro-2-methyl-2,3-dihydro-1H-indol-1-yl]-2-oxoethyl}-6-(morpholin-4-yl)pyrimidin-4(3H)-one
- -5-fluoro-2-{2-[(2S)-4-fluoro-2-methyl-2,3-dihydro-1H-indol-1-yl]-2-oxoethyl}-6-(morpholin-4-yl)pyrimidin-4(3H)-one
- -2-{2-[(2S)-5,6-difluoro-2-methyl-2,3-dihydro-1H-indol-1-yl]-2-oxoethyl}-5-fluoro-6-(morpholin-4-yl)pyrimidin-4(3H)-one
- -2-{2-[(2R)-5,6-difluoro-2-methyl-2,3-dihydro-1H-indol-1-yl]-2-oxoethyl}-5-fluoro-6-(morpholin-4-yl)pyrimidin-4(3H)-one
- -5-fluoro-2-{2-[(2S)-5-fluoro-2-methyl-2,3-dihydro-1H-indol-1-yl]-2-oxoethyl}-3-methyl-6-(morpholin-4-yl)pyrimidin-4(3H)-one
- -5-fluoro-2-{2-[(2R)-5-fluoro-2-methyl-2,3-dihydro-1H-indol-1-yl]-2-oxoethyl}-3-methyl-6-(morpholin-4-yl)pyrimidin-4(3H)-one
- -2-{2-[(2R)-4-bromo-2-methyl-2,3-dihydro-1H-indol-1-yl]-2-oxoethyl}-5-fluoro-6-(morpholin-4-yl)pyrimidin-4(3H)-one
- -2-{2-[(2S)-4-bromo-2-methyl-2,3-dihydro-1H-indol-1-yl]-2-oxoethyl}-5-fluoro-6-(morpholin-4-yl)pyrimidin-4(3H)-one
- -2-{2-[(2R)-4-chloro-2-methyl-2,3-dihydro-1H-indol-1-yl]-2-oxoethyl}-5-fluoro-6-(morpholin-4-yl)pyrimidin-4(3H)-one
- -2-{2-[(2S)-4-chloro-2-methyl-2,3-dihydro-1H-indol-1-yl]-2-oxoethyl}-5-fluoro-6-(morpholin-4-yl)pyrimidin-4(3H)-one
- -2-{2-[(2R)-4,5-difluoro-2-methyl-2,3-dihydro-1H-indol-1-yl]-2-oxoethyl}-5-fluoro-6-(morpholin-4-yl)pyrimidin-4(3H)-one
- -2-{2-[(2S)-4,5-difluoro-2-methyl-2,3-dihydro-1H-indol-1-yl]-2-oxoethyl}-5-fluoro-6-(morpholin-4-yl)pyrimidin-4(3H)-one
- -5-fluoro-2-{2-[(2S)-4-fluoro-2-methyl-2,3-dihydro-1H-indol-1-yl]-2-oxoethyl}-3-methyl-6-(morpholin-4-yl)pyrimidin-4(3H)-one
- -5-fluoro-2-{2-[(2R)-4-fluoro-2-methyl-2,3-dihydro-1H-indol-1-yl]-2-oxoethyl}-3-methyl-6-(morpholin-4-yl)pyrimidin-4(3H)-one
- -2-{2-[(2R)-4,5-difluoro-2-methyl-2,3-dihydro-1H-indol-1-yl]-2-oxoethyl}-5-fluoro-3-methyl-6-(morpholin-4-yl)pyrimidin-4(3H)-one
- -2-{2-[(2S)-4,5-difluoro-2-methyl-2,3-dihydro-1H-indol-1-yl]-2-oxoethyl}-5-fluoro-3-methyl-6-(morpholin-4-yl)pyrimidin-4(3H)-one
- -2-{2-[(2R)-5,6-difluoro-2-methyl-2,3-dihydro-1H-indol-1-yl]-2-oxoethyl}-5-fluoro-3-methyl-6-(morpholin-4-yl)pyrimidin-4(3H)-one
- -2-{2-[(2S)-5,6-difluoro-2-methyl-2,3-dihydro-1H-indol-1-yl]-2-oxoethyl}-5-fluoro-3-methyl-6-(morpholin-4-yl)pyrimidin-4(3H)-one
- -2-{2-[(2R)-4-chloro-2-methyl-2,3-dihydro-1H-indol-1-yl]-2-oxoethyl}-5-fluoro-3-methyl-6-(morpholin-4-yl)pyrimidin-4(3H)-one
- -2-{2-[(2S)-4-chloro-2-methyl-2,3-dihydro-1H-indol-1-yl]-2-oxoethyl}-5-fluoro-3-methyl-6-(morpholin-4-yl)pyrimidin-4(3H)-one
- -2-{2-[(2R)-4-bromo-2-methyl-2,3-dihydro-1H-indol-1-yl]-2-oxoethyl}-5-fluoro-3-methyl-6-(morpholin-4-yl)pyrimidin-4(3H)-one
- -2-{2-[(2S)-4-bromo-2-methyl-2,3-dihydro-1H-indol-1-yl]-2-oxoethyl}-5-fluoro-3-methyl-6-(morpholin-4-yl)pyrimidin-4(3H)-one
- -5-fluoro-2-{2-[(2S)-6-fluoro-2-methyl-2,3-dihydro-1H-indol-1-yl]-2-oxoethyl}-6-(morpholin-4-yl)pyrimidin-4(3H)-one
- -5-fluoro-2-{2-[(2R)-6-fluoro-2-methyl-2,3-dihydro-1H-indol-1-yl]-2-oxoethyl}-6-(morpholin-4-yl)pyrimidin-4(3H)-one
- -5-chloro-2-{2-[(2R)-2-methyl-2,3-dihydro-1H-indol-1-yl]-2-oxoethyl}-6-(morpholin-4-yl)pyrimidin-4(3H)-one
- -5-chloro-2-{2-[(2S)-2-methyl-2,3-dihydro-1H-indol-1-yl]-2-oxoethyl}-6-(morpholin-4-yl)pyrimidin-4(3H)-one
- -2-{2-[4-chloro-5-fluoro-2-methyl-2,3-dihydro-1H-indol-1-yl]-2-oxoethyl}-5-fluoro-3-methyl-6-(morpholin-4-yl)pyrimidin-4(3H)-one
- -5-bromo-2-[2-((S)-2-methyl-2,3-dihydroindol-1-yl)-2-oxoethyl]-6-morpholin-4-yl-3H-pyrimidin-4-one
- -5-fluoro-2-[2-((+)-2-hydroxymethyl-2,3-dihydroindol-1-yl)-2-oxoethyl]-6-morpholin-4-yl-3H-pyrimidin-4-one
- -5-fluoro-2-[2-((−)-2-hydroxymethyl-2,3-dihydroindol-1-yl)-2-oxoethyl]-6-morpholin-4-yl-3H-pyrimidin-4-one and also the addition salts with inorganic and organic acids or with inorganic and organic bases of said products of formula (Ia).

Compounds of Formula (Ib):
N-(4-fluorophenyl)-2-[4-(2-methylmorpholin-4-yl)-6-oxo-1,6-dihydropyrimidin-2-yl]acetamide N-(4-fluorophenyl)-2-[4-((S)-2-methylmorpholin-4-yl)-6-oxo-1,6-dihydropyrimidin-2-yl]acetamide 2-[4-(2-fluoromethylmorpholin-4-yl)-6-oxo-1,6-dihydropyrimidin-2-yl]-N-(4-fluorophenyl)acetamide (+)-2-[4-(2-fluoromethylmorpholin-4-yl)-6-oxo-1,6-dihydropyrimidin-2-yl]-N-(4-fluorophenyl)acetamide (+)-N-(3-chloro-4-fluorophenyl)-2-[4-(2-fluoromethylmorpholin-4-yl)-1-methyl-6-oxo-1,6-dihydropyrimidin-2-yl]acetamide 2-[2-(4-fluoro-2,3-dihydroindol-1-yl)-2-oxoethyl]-6-(2-fluoromethylmorpholin-4-yl)-3H-pyrimidin-4-one (+)-2-[2-(4-fluoro-2,3-dihydroindol-1-yl)-2-oxoethyl]-6-(2-fluoromethylmorpholin-4-yl)-3H-pyrimidin-4-one 2-[2-(4-fluoro-2,3-dihydroindol-1-yl)-2-oxoethyl]-6-(2-methylmorpholin-4-yl)-3H-pyrimidin-4-one (−)-2-[2-(4-fluoro-2,3-dihydroindol-1-yl)-2-oxoethyl]-6-(2-methylmorpholin-4-yl)-3H-pyrimidin-4-one (+)-2-[2-(4-fluoro-2,3-dihydroindol-1-yl)-2-oxoethyl]-6-(2-methylmorpholin-4-yl)-3H-pyrimidin-4-one 2-[2-(4-fluoro-2,3-dihydroindol-1-yl)-2-oxoethyl]-6-(hexahydro-cyclopenta[1,4]oxazin-4-yl)-3H-pyrimidin-4-one 2-[2-(4-fluoro-2,3-dihydroindol-1-yl)-2-oxoethyl]-6-pyridin-4-yl-3H-pyrimidin-4-one 2-[2-(4-fluoro-2,3-dihydroindol-1-yl)-2-oxoethyl]-6-(2-methoxypyridin-4-yl)-3H-pyrimidin-4-one (±)-2-[4-(2-ethylmorpholin-4-yl)-6-oxo-1,6-dihydropyrimidin-2-yl]-N-(4-fluorophenyl)acetamide (+)-2-[4-(2-ethylmorpholin-4-yl)-6-oxo-1,6-dihydropyrimidin-2-yl]-N-(4-fluorophenyl)acetamide 2-[2-(4-fluoro-2,3-dihydroindol-1-yl)-2-oxoethyl]-6-(2,2,3,3,5,5,6,6-D8-morpholin)-4-yl-3h-pyrimidin-4-one 2-[2-(4-fluoro-2,3-dihydroindol-1-yl)-2-oxoethyl]-6-(3,3,5,5-D4-morpholin)-4-yl-3H-pyrimidin-4-one 2-(4-chloro-6-methoxypyrimidin-2-yl)-1-(3,3-dimethyl-2,3-dihydroindol-1-yl)ethanone (+)-2-[2-(2-methyl-2,3-dihydroindol-1-yl)-2-oxoethyl]-6-(3,3,5,5-D4-morpholin)-4-yl-3H-pyrimidin-4-one (−)-2-[2-(2-methyl-2,3-dihydroindol-1-yl)-2-oxoethyl]-6-(3,3,5,5-D4-morpholin)-4-yl-3H-pyrimidin-4-one (+)-2-[2-(2-methyl-2,3-dihydroindol-1-yl)-2-oxoethyl]-6-(2,2,3,3,5,5,6,6-D8-morpholin)-4-yl-3H-pyrimidin-4-one (−)-2-[2-(2-methyl-2,3-dihydroindol-1-yl)-2-oxoethyl]-6-(2,2,3,3,5,5,6,6-D8-morpholin)-4-yl-3H-pyrimidin-4-one 2-[2-(4-fluoro-2,3-dihydroindol-1-yl)-2-oxoethyl]-6-(2-methylpyridin-4-yl)-3H-pyrimidin-4-one 2-[2-(4-fluoro-2,3-dihydroindol-1-yl)-2-oxoethyl]-6-(2-fluoropyridin-4-yl)-3H-pyrimidin-4-one (−)-2-[2-(4-chloro-2,3-dihydroindol-1-yl)-2-oxoethyl]-6-(2-hydroxymethyl-morpholin-4-yl)-3H-pyrimidin-4-one (+)-2-[2-(4-chloro-2,3-dihydroindol-1-yl)-2-oxoethyl]-6-(2-hydroxymethyl-morpholin-4-yl)-3H-pyrimidin-4-one (±)-2-[2-(4-fluoro-2,3-dihydroindol-1-yl)-2-oxoethyl]-6-(2-hydroxymethyl-morpholin-4-yl)-3H-pyrimidin-4-one (±)-2-[2-(4-chloro-2,3-dihydroindol-1-yl)-2-oxoethyl]-6-(2-methylmorpholin-4-yl)-3H-pyrimidin-4-one (+)-2-[2-((S)-2-methyl-2,3-dihydroindol-1-yl)-2-oxoethyl]-6-(2-methylmorpholin-4-yl)-3H-pyrimidin-4-one (+)-6-(2-fluoromethylmorpholin-4-yl)-2-[2-((S)-2-methyl-2,3-dihydroindol-1-yl)-2-oxoethyl]-3H-pyrimidin-4-one (+)-6-(2-hydroxymethylmorpholin-4-yl)-2-[2-((S)-2-methyl-2,3-dihydroindol-1-yl)-2-oxoethyl]-3H-pyrimidin-4-one and also the addition salts with inorganic and organic acids or with inorganic and organic bases of said products of formula (Ib).

Compounds of Formula (Ic):

-2-[2-(4-chloro-2-methyl-2,3-dihydro-1H-indol-1-yl)-2-oxoethyl]-6-(morpholin-4-yl)pyrimidin-4(3H)-one -2-{2-[(2S)-4-chloro-2-methyl-2,3-dihydro-1H-indol-1-yl]-2-oxoethyl}-6-(morpholin-4-yl)pyrimidin-4(3H)-one -2-{2-[(2R)-4-chloro-2-methyl-2,3-dihydro-1H-indol-1-yl]-2-oxoethyl}-6-(morpholin-4-yl)pyrimidin-4(3H)-one -2-[2-(4-chloro-3,3-dimethyl-2,3-dihydro-1H-indol-1-yl)-2-oxoethyl]-3-methyl-6-(morpholin-4-yl)pyrimidin-4(3H)-one -2-[2-(4-chloro-3,3-dimethyl-2,3-dihydro-1H-indol-1-yl)-2-oxoethyl]-6-(morpholin-4-yl)pyrimidin-4(3H)-one -2-[2-(4-hydroxy-2-methyl-2,3-dihydro-1H-indol-1-yl)-2-oxoethyl]-6-(morpholin-4-yl)pyrimidin-4(3H)-one -2-[2-(4-fluoro-3,3-dimethyl-2,3-dihydro-1H-indol-1-yl)-2-oxoethyl]-3-methyl-6-(morpholin-4-yl)pyrimidin-4(3H)-one -2-[2-(4-fluoro-3,3-dimethyl-2,3-dihydro-1H-indol-1-yl)-2-oxoethyl]-6-(morpholin-4-yl)pyrimidin-4(3H)-one -2-{2-[(2S)-4-hydroxy-2-methyl-2,3-dihydro-1H-indol-1-yl]-2-oxoethyl}-6-(morpholin-4-yl)pyrimidin-4(3H)-one -2-{2-[(2R)-4-hydroxy-2-methyl-2,3-dihydro-1H-indol-1-yl]-2-oxoethyl}-6-(morpholin-4-yl)pyrimidin-4(3H)-one -2-{2-[(3R)-4-hydroxy-3-methyl-2,3-dihydro-1H-indol-1-yl]-2-oxoethyl}-6-(morpholin-4-yl)pyrimidin-4(3H)-one -2-{2-[(3S)-4-hydroxy-3-methyl-2,3-dihydro-1H-indol-1-yl]-2-oxoethyl}-6-(morpholin-4-yl)pyrimidin-4(3H)-one -2-{2-[(2S)-5-fluoro-2-methyl-2,3-dihydro-1H-indol-1-yl]-2-oxoethyl}-6-(morpholin-4-yl)pyrimidin-4(3H)-one -2-{2-[(2R)-5-fluoro-2-methyl-2,3-dihydro-1H-indol-1-yl]-2-oxoethyl}-6-(morpholin-4-yl)pyrimidin-4(3H)-one -2-{2-[(2S)-5-fluoro-2-methyl-2,3-dihydro-1H-indol-1-yl]-2-oxoethyl}-3-methyl-6-(morpholin-4-yl)pyrimidin-4(3H)-one -2-{2-[(2R)-5-fluoro-2-methyl-2,3-dihydro-1H-indol-1-yl]-2-oxoethyl}-3-methyl-6-(morpholin-4-yl)pyrimidin-4(3H)-one -2-{2-[(2S)-4,5-difluoro-2-methyl-2,3-dihydro-1H-indol-1-yl]-2-oxoethyl}-6-(morpholin-4-yl)pyrimidin-4(3H)-one -2-{2-[(2R)-4,5-difluoro-2-methyl-2,3-dihydro-1H-indol-1-yl]-2-oxoethyl}-6-(morpholin-4-yl)pyrimidin-4(3H)-one -2-{2-[(2S)-4,5-difluoro-2-methyl-2,3-dihydro-1H-indol-1-yl]-2-oxoethyl}-3-methyl-6-(morpholin-4-yl)pyrimidin-4(3H)-one -2-{2-[(2R)-4,5-difluoro-2-methyl-2,3-dihydro-1H-indol-1-yl]-2-oxoethyl}-3-methyl-6-(morpholin-4-yl)pyrimidin-4(3H)-one -2-{2-[(2R)-5,6-difluoro-2-methyl-2,3-dihydro-1H-indol-1-yl]-2-oxoethyl}-6-(morpholin-4-yl)pyrimidin-4(3H)-one -2-{2-[(2S)-5,6-difluoro-2-methyl-2,3-dihydro-1H-indol-1-yl]-2-oxoethyl}-6-(morpholin-4-yl)pyrimidin-4(3H)-one -2-{2-[(2S)-5,6-difluoro-2-methyl-2,3-dihydro-1H-indol-1-yl]-2-oxoethyl}-3-methyl-6-(morpholin-4-yl)pyrimidin-4(3H)-one -2-{2-[(2R)-5,6-difluoro-2-methyl-2,3-dihydro-1H-indol-1-yl]-2-oxoethyl}-3-methyl-6-(morpholin-4-yl)pyrimidin-4(3H)-one -2-{2-[(2R)-4-bromo-2-methyl-2,3-dihydro-1H-indol-1-yl]-2-oxoethyl}-6-(morpholin-4-yl)pyrimidin-4(3H)-one -2-{2-[(2S)-4-bromo-2-methyl-2,3-dihydro-1H-indol-1-yl]-2-oxoethyl}-6-(morpholin-4-yl)pyrimidin-4(3H)-one -2-{2-[(2R)-4-fluoro-2-methyl-2,3-dihydro-1H-indol-1-yl]-2-oxoethyl}-6-(morpholin-4-yl)pyrimidin-4(3H)-one -2-{2-[(2S)-4-fluoro-2-methyl-2,3-dihydro-1H-indol-1-yl]-2-oxoethyl}-6-(morpholin-4-yl)pyrimidin-4(3H)-one

- -2-{2-[(2R)-4-fluoro-2-methyl-2,3-dihydro-1H-indol-1-yl]-2-oxoethyl}-3-methyl-6-(morpholin-4-yl)pyrimidin-4(3H)-one
- -2-{2-[(2S)-4-fluoro-2-methyl-2,3-dihydro-1H-indol-1-yl]-2-oxoethyl}-3-methyl-6-(morpholin-4-yl)pyrimidin-4(3H)-one
- -2-{2-[(2R)-4-bromo-2-methyl-2,3-dihydro-1H-indol-1-yl]-2-oxoethyl}-3-methyl-6-(morpholin-4-yl)pyrimidin-4(3H)-one
- -2-{2-[(2S)-4-bromo-2-methyl-2,3-dihydro-1H-indol-1-yl]-2-oxoethyl}-3-methyl-6-(morpholin-4-yl)pyrimidin-4(3H)-one
- -2-{2-[(2R)-4-chloro-2-methyl-2,3-dihydro-1H-indol-1-yl]-2-oxoethyl}-3-methyl-6-(morpholin-4-yl)pyrimidin-4(3H)-one
- -2-{2-[(2S)-4-chloro-2-methyl-2,3-dihydro-1H-indol-1-yl]-2-oxoethyl}-3-methyl-6-(morpholin-4-yl)pyrimidin-4(3H)-one
- -2-{2-[(2R)-6-fluoro-2-methyl-2,3-dihydro-1H-indol-1-yl]-2-oxoethyl}-6-(morpholin-4-yl)pyrimidin-4(3H)-one
- -2-{2-[(2S)-6-fluoro-2-methyl-2,3-dihydro-1H-indol-1-yl]-2-oxoethyl}-6-(morpholin-4-yl)pyrimidin-4(3H)-one
- -2-{2-[(2R)-4-chloro-5-fluoro-2-methyl-2,3-dihydro-1H-indol-1-yl]-2-oxoethyl}-6-(morpholin-4-yl)pyrimidin-4(3H)-one
- -2-{2-[(2S)-4-chloro-5-fluoro-2-methyl-2,3-dihydro-1H-indol-1-yl]-2-oxoethyl}-6-(morpholin-4-yl)pyrimidin-4(3H)-one
- -2-{2-[(2R)-2-isopropyl-2,3-dihydroindol-1-yl]-2-oxoethyl}-6-morpholin-4-yl-3H-pyrimidin-4-one
- -2-{2-[(2S)-2-isopropyl-2,3-dihydroindol-1-yl]-2-oxoethyl}-6-morpholin-4-yl-3H-pyrimidin-4-one
- -2-[1-(4-fluoro-2,3-dihydro-1H-indol-1-yl)-1-oxopropan-2-yl]-6-(morpholin-4-yl)pyrimidin-4(3H)-one
- -2-[2-((R)-2-ethyl-2,3-dihydroindol-1-yl)-2-oxoethyl]-6-morpholin-4-yl-3H-pyrimidin-4-one
- -2-[2-((S)-2-ethyl-2,3-dihydroindol-1-yl)-2-oxoethyl]-6-morpholin-4-yl-3H-pyrimidin-4-one
- -2-[(2R)-2-fluoro-1-(4-fluoro-2,3-dihydro-1H-indol-1-yl)-1-oxopropan-2-yl]-6-(morpholin-4-yl)pyrimidin-4(3H)-one
- -2-[(2S)-2-fluoro-1-(4-fluoro-2,3-dihydro-1H-indol-1-yl)-1-oxopropan-2-yl]-6-(morpholin-4-yl)pyrimidin-4(3H)-one
- -1-{[4-(morpholin-4-yl)-6-oxo-1,6-dihydropyrimidin-2-yl]acetyl}-2,3-dihydro-1H-indole-4-carbonitrile and also the addition salts with inorganic and organic acids or with inorganic and organic bases of said products of formula (Ic).

Compounds of Formula (Id):
- -6-(morpholin-4-yl)-2-[2-oxo-2-(spiro[cyclopropane-1,3'-indol]-1'(2'H)-yl)ethyl]pyrimidin-4(3H)-one
- -6-(morpholin-4-yl)-2-[2-oxo-2-(4-phenyl-2,3-dihydro-1H-indol-1-yl)ethyl]pyrimidin-4(3H)-one
- -6-(morpholin-4-yl)-2-{2-oxo-2-[4-(trifluoromethoxy)-2,3-dihydro-1H-indol-1-yl]ethyl}pyrimidin-4(3H)-one
- -3-methyl-6-(morpholin-4-yl)-2-{2-oxo-2-[4-(trifluoromethyl)-2,3-dihydro-1H-indol-1-yl]ethyl}pyrimidin-4(3H)-one
- -6-(morpholin-4-yl)-2-{2-oxo-2-[4-(trifluoromethyl)-2,3-dihydro-1H-indol-1-yl]ethyl}pyrimidin-4(3H)-one
- -2-{2-[4-(2-methoxyphenyl)-2,3-dihydro-1H-indol-1-yl]-2-oxoethyl}-6-(morpholin-4-yl)pyrimidin-4(3H)-one
- -6-(morpholin-4-yl)-2-{2-oxo-2-[4-(1-propylpiperidin-3-yl)-2,3-dihydro-1H-indol-1-yl]ethyl}pyrimidin-4(3H)-one
- -2-{2-[4-(difluoromethoxy)-2,3-dihydro-1H-indol-1-yl]-2-oxoethyl}-3-methyl-6-(morpholin-4-yl)pyrimidin-4(3H)-one
- -2-{2-[4-(difluoromethoxy)-2,3-dihydro-1H-indol-1-yl]-2-oxoethyl}-6-(morpholin-4-yl)pyrimidin-4(3H)-one
- -6-(morpholin-4-yl)-2-{2-oxo-2-[4-(pyridin-4-yl)-2,3-dihydro-1H-indol-1-yl]ethyl}pyrimidin-4(3H)-one
- -2-[2-(1-methylspiro[indole-3,4'-piperidin]-1(2H)-yl)-2-oxoethyl]-6-(morpholin-4-yl)pyrimidin-4(3H)-one
- -6-(morpholin-4-yl)-2-{2-oxo-2-[4-(pyridin-2-yl)-2,3-dihydro-1H-indol-1-yl]ethyl}pyrimidin-4(3H)-one
- -6-(morpholin-4-yl)-2-{2-oxo-2-[4-(pyridin-3-yl)-2,3-dihydro-1H-indol-1-yl]ethyl}pyrimidin-4(3H)-one
- -2-{2-[4-(2-chlorophenyl)-2,3-dihydro-1H-indol-1-yl]-2-oxoethyl}-6-(morpholin-4-yl)pyrimidin-4(3H)-one
- -2-[2-(4-chloro-2,3-dihydro-1H-indol-1-yl)-2-oxoethyl]-3-cyclopropyl-6-(morpholin-4-yl)pyrimidin-4(3H)-one
- -6-(morpholin-4-yl)-2-[2-oxo-2-(2,3,3a,8b-tetrahydrocyclopenta[b]indol-4(1H)-yl)ethyl]pyrimidin-4(3H)-one
- -2-[2-(4-{[4-(methylsulfonyl)piperazin-1-yl]methyl}-2,3-dihydro-1H-indol-1-yl)-2-oxoethyl]-6-(morpholin-4-yl)pyrimidin-4(3H)-one
- -2-(2-{4-[(4-methylpiperazin-1-yl)methyl]-2,3-dihydro-1H-indol-1-yl}-2-oxoethyl)-6-(morpholin-4-yl)pyrimidin-4(3H)-one
- -2-{2-[4-(2-fluorophenyl)-2,3-dihydro-1H-indol-1-yl]-2-oxoethyl}-6-(morpholin-4-yl)pyrimidin-4(3H)-one
- -3-methyl-2-(2-{4-[(4-methylpiperazin-1-yl)methyl]-2,3-dihydro-1H-indole-1-yl}-2-oxoethyl)-6-(morpholin-4-yl)pyrimidin-4(3H)-one
- -6-(morpholin-4-yl)-2-[2-oxo-2-(2',3',5',6'-tetrahydrospiro[indole-3,4'-pyran]-1(2H)-yl)ethyl]pyrimidin-4(3H)-one
- -3-methyl-6-(morpholin-4-yl)-2-[2-oxo-2-(2',3',5',6'-tetrahydrospiro[indole-3,4'-pyran]-1(2H)-yl)ethyl]pyrimidin-4(3H)-one
- -3-methyl-6-(morpholin-4-yl)-2-[2-oxo-2-(spiro[indole-3,4'-piperidin]-1(2H)-yl)ethyl]pyrimidin-4(3H)-one
- -6-(morpholin-4-yl)-2-{2-oxo-2-[(2R)-2-phenyl-2,3-dihydro-1H-indol-1-yl]ethyl}pyrimidin-4(3H)-one
- -6-(morpholin-4-yl)-2-{2-oxo-2-[(2S)-2-phenyl-2,3-dihydro-1H-indol-1-yl]ethyl}pyrimidin-4(3H)-one
- -2-{2-[4-(4-methylpiperazin-1-yl)-2,3-dihydro-1H-indol-1-yl]-2-oxoethyl}-6-(morpholin-4-yl)pyrimidin-4(3H)-one
- -2-{2-[(2R)-2-(4-fluorophenyl)-2,3-dihydro-1H-indol-1-yl]-2-oxoethyl}-6-(morpholin-4-yl)pyrimidin-4(3H)-one
- -2-{2-[(2S)-2-(4-fluorophenyl)-2,3-dihydro-1H-indol-1-yl]-2-oxoethyl}-6-(morpholin-4-yl)pyrimidin-4(3H)-one
- -2-{2-[(2R)-4-(difluoromethoxy)-2-methyl-2,3-dihydro-1H-indol-1-yl]-2-oxoethyl}-6-(morpholin-4-yl)pyrimidin-4(3H)-one
- -2-{2-[(2S)-4-(difluoromethoxy)-2-methyl-2,3-dihydro-1H-indol-1-yl]-2-oxoethyl}-6-(morpholin-4-yl)pyrimidin-4(3H)-one
- -2-{2-[(2R)-4-(difluoromethoxy)-2-methyl-2,3-dihydro-1H-indol-1-yl]-2-oxoethyl}-3-methyl-6-(morpholin-4-yl)pyrimidin-4(3H)-one
- -2-{2-[(2S)-4-(difluoromethoxy)-2-methyl-2,3-dihydro-1H-indol-1-yl]-2-oxoethyl}-3-methyl-6-(morpholin-4-yl)pyrimidin-4(3H)-one
- -6-(morpholin-4-yl)-2-{2-[4-(morpholin-4-yl)-2,3-dihydro-1H-indol-1-yl]-2-oxoethyl}pyrimidin-4(3H)-one
- -2-{2-[(2R)-2-cyclopropyl-2,3-dihydro-1H-indol-1-yl]-2-oxoethyl}-6-(morpholin-4-yl)pyrimidin-4(3H)-one
- -2-{2-[(2S)-2-cyclopropyl-2,3-dihydro-1H-indol-1-yl]-2-oxoethyl}-6-(morpholin-4-yl)pyrimidin-4(3H)-one -2-{2-[(2R)-2-methyl-4-(trifluoromethyl)-2,3-dihydro-1H-indol-1-yl]-2-oxoethyl}-6-(morpholin-4-yl)pyrimidin-4(3H)-one -2-{2-[(2S)-2-methyl-4-(trifluoromethyl)-2,3-dihydro-1H-indol-1-yl]-2-oxoethyl}-6-(morpholin-4-yl)pyrimidin-4(3H)-one -2-[2-((+)-2-fluoromethyl-2,3-dihydroindol-1-yl)-2-oxoethyl]-6-morpholin-4-yl-3H-pyrimidin-4-one -2-[2-(2,3-dihydroindol-1-yl)-2-oxoethyl]-6-morpholin-4-yl-3-phenyl-3H-pyrimidin-4-one -2-[2-((−)-2-fluoromethyl-2,3-dihydroindol-1-yl)-2-oxoethyl]-6-morpholin-4-yl-3H-pyrimidin-4-one -3-amino-2-[2-(2,3-dihydro-1H-indol-1-yl)-2-oxoethyl]-6-(morpholin-4-yl)pyrimidin-4(3H)-one 2-[2-(2,3-dihydro-1H-indol-1-yl)-2-oxoethyl]-4-(morpholin-4-yl)-6-oxopyrimidine-1(6H)-carbonitrile and also the addition salts with inorganic and organic acids or with inorganic and organic bases of said products of formula (Id).

Compounds of Formula (Ie):

-1-((S)-2-methyl-2,3-dihydroindol-1-yl)-2-(4-morpholin-4-yl-6-thioxo-1,6-dihydropyrimidin-2-yl)ethanone -1-((R)-2-methyl-2,3-dihydroindol-1-yl)-2-(4-morpholin-4-yl-6-thioxo-1,6-dihydropyrimidin-2-yl) ethanone -2-[2-((S)-2-methyl-2,3-dihydroindol-1-yl)-2-thioxoethyl]-6-morpholin-4-yl-3H-pyrimidine-4-thione -1-((S)-2-methyl-2,3-dihydroindol-1-yl)-2-(1-methyl-4-morpholin-4-yl-6-thioxo-1,6-dihydropyrimidin-2-yl) ethanone -1-((R)-2-methyl-2,3-dihydroindol-1-yl)-2-(1-methyl-4-morpholin-4-yl-6-thioxo-1,6-dihydropyrimidin-2-yl) ethanone -1-(4-fluoro-2,3-dihydroindol-1-yl)-2-(1-methyl-4-morpholin-4-yl-6-thioxo-1,6-dihydropyrimidin-2-yl)ethanone -1-(4-chloro-2,3-dihydroindol-1-yl)-2-(1-methyl-4-morpholin-4-yl-6-thioxo-1,6-dihydropyrimidin-2-yl) ethanone -1-((+)-4,5-difluoro-2-methyl-2,3-dihydroindol-1-yl)-2-(5-fluoro-4-morpholin-4-yl-6-thioxo-1,6-dihydropyrimidin-2-yl)ethanone -2-[2-((+)-4,5-difluoro-2-methyl-2,3-dihydroindol-1-yl)-2-thioxoethyl]-5-fluoro-6-morpholin-4-yl-3H-pyrimidine-4-thione -2-(5-fluoro-4-morpholin-4-yl-6-thioxo-1,6-dihydropyrimidin-2-yl)-1-((S)-2-methyl-2,3-dihydroindol-1-yl)ethanone -2-(5-fluoro-4-morpholin-4-yl-6-thioxo-1,6-dihydropyrimidin-2-yl)-1-((R)-2-methyl-2,3-dihydroindol-1-yl)ethanone and also the addition salts with inorganic and organic acids or with inorganic and organic bases of said products of formula (Ie).

A subject of the present invention is also the compounds listed above, as medicines.

A subject of the present invention is also any process for preparing the products of formulae (Ia) to (Ie) as defined above.

The products according to the invention can be prepared using conventional organic chemistry methods.

The invention also relates to pharmaceutical compositions containing, as active ingredients, at least one of the products of formulae (Ia), (Ib), (Ic), (Id) or (Ie) as defined above or a pharmaceutically acceptable salt of this product or a prodrug of this product and, where appropriate, a pharmaceutically acceptable support.

The invention thus extends to the pharmaceutical compositions containing, as active ingredient, at least one of the medicines as defined above.

Such pharmaceutical compositions of the present invention can also, where appropriate, contain active ingredients of other antimitotic medicines, such as, in particular, those based on taxol, cisplatin, DNA-intercalating agents, and the like.

These pharmaceutical compositions can be administered orally, parenterally or locally by topical application to the skin or the mucous membranes or by intravenous or intramuscular injection.

These compositions may be solid or liquid and be in any of the pharmaceutical forms commonly used in human medicine, for instance simple or sugar-coated tablets, pills, lozenges, capsules, drops, granules, injectable preparations, ointments, creams or gels; they are prepared according to the usual methods. The active ingredient may be incorporated therein with excipients normally used in these pharmaceutical compositions, such as talc, gum arabic, lactose, starch, magnesium stearate, cocoa butter, aqueous or nonaqueous carriers, fatty substances of animal or vegetable origin, paraffin derivatives, glycols, the various wetting agents, dispersants or emulsifiers, or preservatives.

The usual dosage, which is variable depending on the product used, the subject treated and the affection in question, can be, for example, from 0.05 to 5 g per day in adults, or preferably from 0.1 to 2 g per day.

Such a medicine can in particular be intended for the treatment or prevention of a disease in a mammal.

A subject of the present invention is in particular the use of a product of formula (Ia), (Ib), (Ic), (Id) or (Ie) as defined above, for preparing a medicine intended for the prevention or treatment of diseases related to an uncontrolled proliferation.

A subject of the present invention is thus most particularly the use of a product of formula (Ia), (Ib), (Ic), (Id) or (Ie) as defined above, for preparing a medicine intended for the treatment or prevention of diseases in oncology and in particular intended for the treatment of cancers.

Among these cancers, the treatment of solid or liquid tumors and the treatment of cancers resistant to cytotoxic agents are of interest.

The products of the present invention that are mentioned can in particular be used for the treatment of primary tumors and/or of metastases, in particular in gastric, hepatic, renal, ovarian, colon, prostate, endometrial and lung (NSCLC and SCLC) cancers, glioblastomas, thyroid, bladder and breast cancers, in melanoma, in lymphoid or myeloid hematopoietic tumors, in sarcomas, in brain, larynx and lymphatic system cancers, bone and pancreatic cancers, and in hamartomas.

A subject of the present invention is also the use of the products of formula (Ia), (Ib), (Ic), (Id) or (Ie) as defined above, for preparing medicines intended for cancer chemotherapies.

Such medicines intended for cancer chemotherapy can be used alone or in combination.

The products of the present application can in particular be administered alone or in combination with chemotherapy or radiotherapy or else in combination, for example, with other therapeutic agents.

Such therapeutic agents may be commonly used antitumor agents.

As kinase inhibitors, mention may be made of butyrolactone, flavopiridol and 2-(2-hydroxyethylamino)-6-benzylamino-9-methylpurine, also known as olomucine.

Thus, the present application relates in particular to the products of formula (Ia), (Ib), (Ic), (Id) or (Ie) as defined above, for use thereof in the treatment of cancers.

Thus, the present application relates in particular to the products of formula (Ia), (Ib), (Ic), (Id) or (Ie) as defined above, for use thereof in the treatment of solid or liquid tumors.

Thus, the present application relates in particular to the products of formula (Ia), (Ib), (Ic), (Id) or (Ie) as defined above, for use thereof in the treatment of cancers resistant to cytotoxic agents.

Thus, the present application relates in particular to the products of formula (Ia), (Ib), (Ic), (Id) or (Ie) as defined above, for use thereof in the treatment of primary tumors and/or of metastases, in particular in gastric, hepatic, renal, ovarian, colon, prostate and lung (NSCLC and SCLC) cancers, glioblastomas, thyroid, bladder and breast cancers, in melanoma, in lymphoid or myeloid hematopoietic tumors, in sarcomas, in brain, larynx and lymphatic system cancers, bone and pancreatic cancers, and in hamartomas.

Thus, the present application relates in particular to the products of formula (Ia), (Ib), (Ic), (Id) or (Ie) as defined above, for use thereof in cancer chemotherapy.

Thus, the present application relates in particular to the products of formula (Ia), (Ib), (Ic), (Id) or (Ie) as defined above, for use thereof in cancer chemotherapy, alone or in combination.

The products of the present application can in particular be administered alone or in combination with chemotherapy or radiotherapy or else in combination, for example, with other therapeutic agents.

Such therapeutic agents may be commonly used antitumor agents.

As kinase inhibitors, mention may be made of butyrolactone, flavopiridol and 2-(2-hydroxyethylamino)-6-benzylamino-9-methylpurine, also known as olomucine.

Thus, the present application relates in particular to the products of formula (Ia), (Ib), (Ic), (Id) or (Ie) as defined above, for use thereof in the treatment of cancers.

Thus, the present application relates in particular to the products of formula (Ia), (Ib), (Ic), (Id) or (Ie) as defined above, for use thereof in the treatment of solid or liquid tumors.

Thus, the present application relates in particular to the products of formula (Ia), (Ib), (Ic), (Id) or (Ie) as defined above, for use thereof in the treatment of cancers resistant to cytotoxic agents.

Thus, the present application relates in particular to the products of formula (Ia), (Ib), (Ic), (Id) or (Ie) as defined above, for use thereof in the treatment of primary tumors and/or of metastases, in particular in gastric, hepatic, renal, ovarian, colon, prostate and lung (NSCLC and SCLC) cancers, glioblastomas, thyroid, bladder and breast cancers, in melanoma, in lymphoid or myeloid hematopoietic tumors, in sarcomas, in brain, larynx and lymphatic system cancers, bone and pancreatic cancers, and in hamartomas.

Thus, the present application relates in particular to the products of formula (Ia), (Ib), (Ic), (Id) or (Ie) as defined above, for use thereof in cancer chemotherapy.

Thus, the present application relates in particular to the products of formula (Ia), (Ib), (Ic), (Id) or (Ie) as defined above, for use thereof in cancer chemotherapy, alone or in combination.

Intermediate Products:

Intermediate Products in the Preparation of the Compounds of Formula (Ia):

A subject of the present invention is also, as novel industrial products, the synthesis intermediates of formulae Ga, La, Ha, Ma and Qa as defined above and recalled hereinafter:

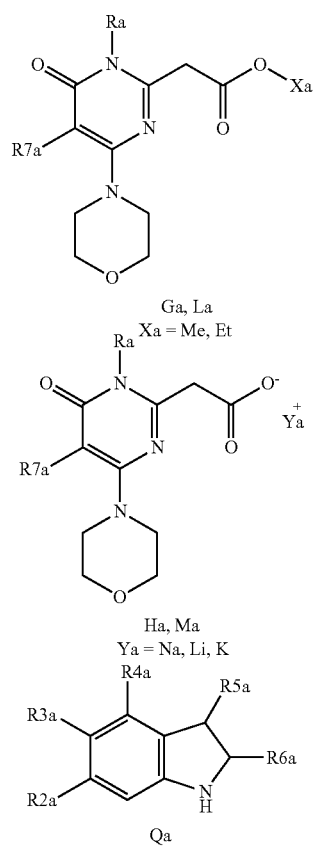

wherein R7a has the definition indicated above, and Ra is hydrogen in the products Ga and Ha, and Ra is alkyl in the products La and Ma, these products being in any of the possible racemic, enantiomeric and diastereoisomeric isomer forms.

Intermediate Products in the Preparation of the Compounds of Formula (Ib):

A subject of the present invention is also, as novel industrial products, the synthesis intermediates of formulae Jb, Mb, Kb and Nb and certain indolines Pb as defined above and recalled hereinafter:

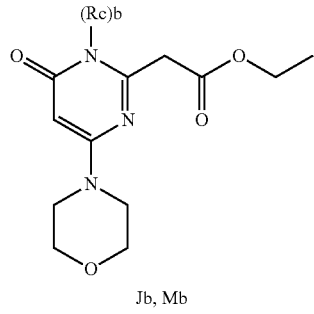

-continued

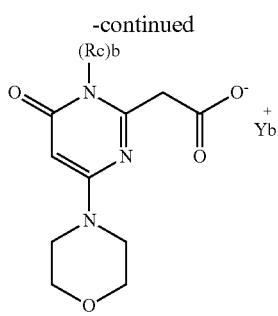

Kb, Nb
Yb = Na, Li, K

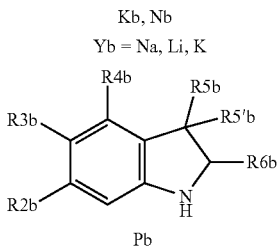

Pb wherein (Rc)b, R2b, R3b, R4b, R5b, R5'b and R6b have any one of the definitions indicated above, these products being in any of the possible racemic, enantiomeric and diastereoisomeric isomer forms.

Intermediate Products in the Preparation of the Compounds of Formula (Ic):

A subject of the present invention is also, as novel industrial products, the synthesis intermediates of formulae Cc, Dc, Ec and Fc and certain indolines Sc as defined above and recalled hereinafter:

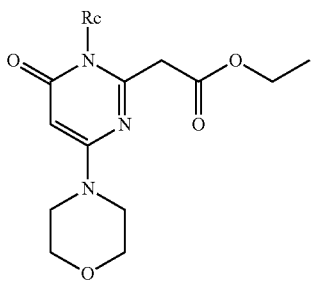

Cc, Ec

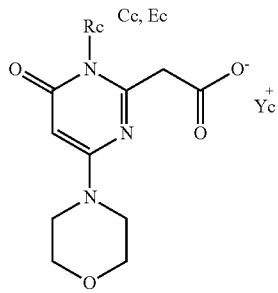

Dc, Fc
Yc = Na, Li, K

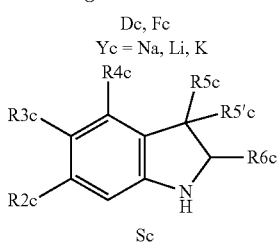

Sc wherein Rc, R2c, R3c, R4c, R5c, R5'c and R6c have any one of the definitions indicated above, these products being in any of the possible racemic, enantiomeric and diastereoisomeric isomer forms.

Intermediate Products in the Preparation of the Compounds of Formula (Id):

Thus, the present application relates in particular to the products of formula (Id) as defined above, for use thereof in cancer chemotherapy, alone or in combination.

A subject of the present invention is also, as novel industrial products, the synthesis intermediates of formulae Cd, Dd, Ed and Fd and also certain indolines Ld as defined above and recalled hereinafter:

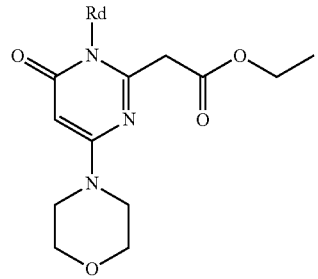

Cd, Ed

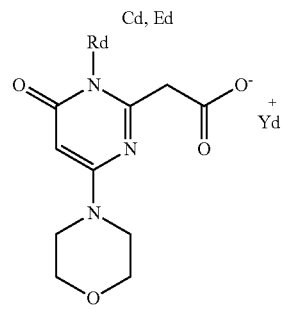

Dd, Fd
Yd = Na, Li, K

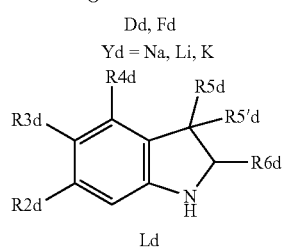

Ld wherein Rd, R2d, R3d, R4d, R5d, R5'd and R6d have any one of the definitions above, these products being in any of the possible racemic, enantiomeric and diastereoisomeric isomer forms.

Intermediate Products in the Preparation of the Compounds of Formula (Ie):

A subject of the present invention is also, as novel industrial products, the synthesis intermediates of formulae Ce and De as defined above and recalled hereinafter:

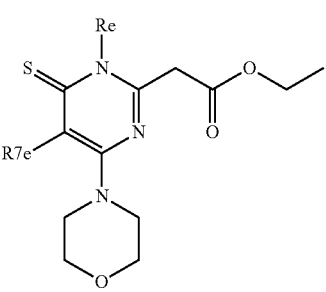

Ce

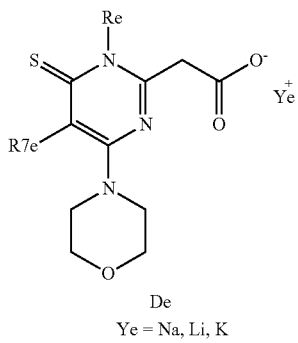

De

Ye = Na, Li, K wherein Re is a hydrogen atom in the products of formulae Ce and De.

A subject of the present invention is also any process for preparing the products of formulae (Ia) to (Ie) as defined above.

The products according to the invention can be prepared using conventional organic chemistry methods.

EXPERIMENTAL SECTION

The nomenclature of the compounds of this present invention was performed with the ACDLABS version 10.0 software.

The microwave oven used is a Biotage, Initiator™ 2.0, 400 W max, 2450 MHz apparatus.

The $^1$H NMR spectra at 400 MHz and $^1$H NMR spectra at 500 MHz were carried out on a Bruker Avance DRX-400 or Bruker Avance DPX-500 spectrometer with the chemical shifts (δ in ppm) in the solvent dimethyl sulfoxide-$d_6$ (DMSO-d6) referenced at 2.5 ppm at the temperature of 303K, except when another solvent is specified (chloroform-d: referenced at 7.26 ppm).

The mass spectra (MS) were obtained either by method A or by method B.

Method A:

Waters UPLC-SQD apparatus; ionization: positive and/or negative mode electrospray (ES+/−); chromatographic conditions: column: Acquity BEH $C_{18}$ 1.7 μm-2.1×50 mm; solvents: A: $H_2O$ (0.1% formic acid) B: $CH_3CN$ (0.1% formic acid); column temperature: 50° C.; flow rate: 1 ml/min; gradient (2 min): from 5 to 50% of B in 0.8 min; 1.2 min: 100% of B; 1.85 min: 100% of B; 1.95: 5% of B; retention time=Tr (min).

Method B:

Waters ZQ apparatus; ionization: positive and/or negative mode electrospray (ES+/−); chromatographic conditions: column: XBridge $C_{18}$ 2.5 μm-3×50 mm; solvents: A: $H_2O$ (0.1% formic acid) B: $CH_3CN$ (0.1% formic acid); column temperature: 70° C.; flow rate: 0.9 ml/min; gradient (7 min): from 5 to 100% of B in 5.3 min; 5.5 min: 100% of B; 6.3 min: 5% of B; retention time=Tr (min).

The optical rotations (OR) were performed on a polarimeter, model 341, from Perkin Elmer. Wavelength: sodium α line (589 nanometers).

Synthesis of the Compounds of Formula (Ia)

Example 1a

Synthesis of 5-fluoro-2-[2-(4-fluoro-2,3-dihydro-1H-indol-1-yl)-2-oxoethyl]-6-(morpholin-4-yl)pyrimidin-4(3H)-one Step 1a 4-Chloro-5-fluoro-6-methoxy-2-methylpyrimidine

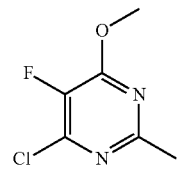

3.21 g of sodium methoxide are added to a solution of 9.8 g of 2-methyl-4,6-dichloro-5-fluoropyrimidine in 80 ml of THF cooled to 5° C. in an ice bath. The ice bath is removed. The suspension is stirred at ambient temperature for 3 hours. The reaction medium is cooled to 5° C. in an ice bath. 20 ml of water and 100 ml of ethyl acetate are added. After settling out, the organic phase is dried over magnesium sulfate, filtered, and concentrated under reduced pressure to give 9 g of 4-chloro-5-fluoro-6-methoxy-2-methylpyrimidine in the form of a colorless oil which crystallizes, the characteristics of which are the following:

Mass spectrometry: method A

Retention time Tr (min)=0.82; [M+H]+: m/z 177

Step 2a (4-Chloro-5-fluoro-6-methoxypyrimidin-2-yl)acetic acid methyl ester

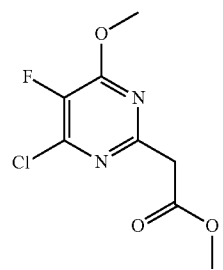

95 ml of 2M LDA (THF) are added dropwise to a solution of 6.7 g of 4-chloro-5-fluoro-6-methoxy-2-methylpyrimidine and 4.83 ml of methyl chloroformate in 100 ml of anhydrous THF cooled to −60° C. in a dry ice/MeOH bath.

The reaction medium is stirred at −60° C. for one hour.

The cooling bath is lowered so as to allow the temperature to rise to 22° C. The reaction medium is stirred at 22° C. for two hours.

20 ml of water and 150 ml of ethyl acetate are added. After settling out, the organic phase is dried over magnesium sulfate, filtered, and then concentrated under reduced pressure. The residue obtained is purified on a silica cartridge: eluent: DCM so as to give 8.36 g of (4-chloro-5-fluoro-6-methoxypyrimidin-2-yl)acetic acid methyl ester in the form of a bright yellow oil, the characteristics of which are the following:
Mass spectrometry: method A
Retention time Tr (min)=0.84; [M+H]+: m/z 235

Step 3a (5-Fluoro-4-methoxy-6-morpholin-4-ylpyrimidin-2-yl)acetic acid methyl ester

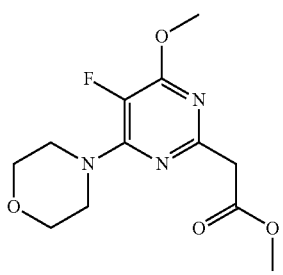

A solution of 8.36 g of (4-chloro-5-fluoro-6-methoxypyrimidin-2-yl)acetic acid methyl ester in 76 ml of morpholine is stirred at ambient temperature for one and a half hours. The reaction medium is concentrated under reduced pressure. The residue obtained is taken up with 50 ml of water and 200 ml of ethyl acetate. After settling out, the organic phase is dried over magnesium sulfate, filtered, and then concentrated under reduced pressure so as to give 8.86 g of (5-fluoro-4-methoxy-6-morpholin-4-ylpyrimidin-2-yl)acetic acid methyl ester in the form of a beige solid, the characteristics of which are the following:
Mass spectrometry: method A
Retention time Tr (min)=0.84; [M+H]+: m/z 286

Step 4a

Sodium (5-fluoro-4-methoxy-6-morpholin-4-ylpyrimidin-2-yl)acetate

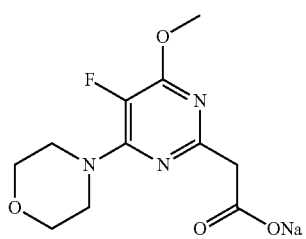

7.9 ml of 2N sodium hydroxide are added to a solution of 3.46 g of (5-fluoro-4-methoxy-6-morpholin-4-ylpyrimidin-2-yl)acetic acid methyl ester in 36 ml of THF. The reaction medium is stirred at ambient temperature for 24 hours. The reaction medium is concentrated under reduced pressure. The residue obtained is oven-dried under vacuum in the presence of $P_2O_5$ so as to give 3.7 g of sodium (5-fluoro-4-methoxy-6-morpholin-4-ylpyrimidin-2-yl)acetate, the characteristics of which are the following:
Mass spectrometry: method A
Retention time Tr (min)=0.66; [M+H]+: m/z 272; [M−H]−: m/z 270; base peak: m/z 226

Step 5a 1-(4-Fluoro-2,3-dihydroindol-1-yl)-2-(5-fluoro-4-methoxy-6-morpholin-4-ylpyrimidin-2-yl)ethanone

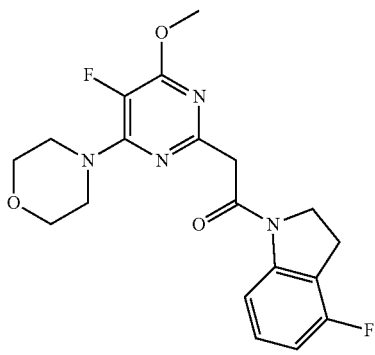 [SMILES: COc1nc(CC(=O)N2CCc3c(F)cccc32)nc(N2CCOCC2)c1F]

59 mg of 4-fluoro-2,3-dihydro-1H-indole and 78 mg of N-[3-(dimethylamino)propyl]-N'-ethylcarbodiimide hydrochloride are added to a solution of 100 mg of sodium (5-fluoro-4-methoxy-6-morpholin-4-ylpyrimidin-2-yl)acetate in 0.7 ml of DMF and 0.06 ml of pyridine.
The reaction medium is stirred at ambient temperature for 18 hours.
10 ml of ethyl acetate and 5 ml of water are added. After settling out, the organic phase is dried over magnesium sulfate, filtered, and then concentrated under reduced pressure. The solid obtained is taken up with ethyl ether and then filtered so as to give 70 mg of 1-(4-fluoro-2,3-dihydroindol-1-yl)-2-(5-fluoro-4-methoxy-6-morpholin-4-ylpyrimidin-2-yl)ethanone in the form of a white solid, the characteristics of which are the following:
Mass spectrometry: method A
Retention time Tr (min)=1.01; [M+H]+: m/z 391

Step 6a

5-Fluoro-2-[2-(4-fluoro-2,3-dihydroindol-1-yl)-2-oxoethyl]-6-morpholin-4-yl-3H-pyrimidin-4-one

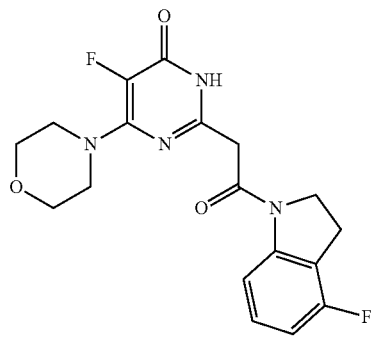 [SMILES: O=C(Cc1nc(N2CCOCC2)c(F)c(=O)[nH]1)N1CCc2c(F)cccc21]

70 mg of 1-(4-fluoro-2,3-dihydroindol-1-yl)-2-(5-fluoro-4-methoxy-6-morpholin-4-ylpyrimidin-2-yl)ethanone are placed in a round-bottomed flask with 0.9 ml of acetonitrile.
89 mg of KI and 0.07 ml of trimethylchlorosilane are added. The suspension is stirred at ambient temperature overnight.
The reaction medium is concentrated under reduced pressure.
The residue obtained is taken up with water and ethyl ether. The solid formed is filtered off, washed with water and ethyl ether and then dried under vacuum so as to give 53 mg of 5-fluoro-2-[2-(4-fluoro-2,3-dihydroindol-1-yl)-2-oxoethyl]-6-morpholin-4-yl-3H-pyrimidin-4-one in the form of a white solid.

$^1$H NMR spectrum (400 MHz, d in ppm, DMSO-d6): 3.19 (t, J=8.3 Hz, 2H); 3.55 (m, 4H); 3.63 (m, 4H); 3.77 (s, 2H); 4.19 (t, J=8.3 Hz, 2H); 6.87 (t, J=8.6 Hz, 1H); 7.22 (m, 1H); 7.83 (d, J=8.1 Hz, 1H); 12.29 (broad m, 1H)

Mass spectrometry: method A
Retention time Tr (min)=0.72; [M+H]+: m/z 377; [M−H]−: m/z 375

Example 2a and Example 3a

Synthesis of 5-fluoro-2-[1-(4-fluoro-2,3-dihydro-1H-indol-1-yl)-1-oxopropan-2-yl]-3-methyl-6-(morpholin-4-yl)pyrimidin-4(3H)-one and of 5-fluoro-2-[2-(4-fluoro-2,3-dihydro-1H-indol-1-yl)-2-oxoethyl]-3-methyl-6-(morpholin-4-yl)pyrimidin-4(3H)-one

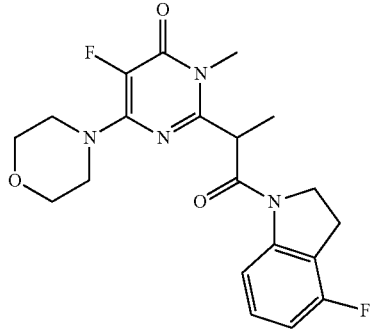 [SMILES: CC(C(=O)N1CCc2c(F)cccc21)c1nc(N2CCOCC2)c(F)c(=O)n1C]

70 mg of 5-fluoro-2-[2-(4-fluoro-2,3-dihydroindol-1-yl)-2-oxoethyl]-6-morpholin-4-yl-3H-pyrimidin-4-one are placed in a round-bottomed flask with 5 ml of DMF.

180 mg of cesium carbonate and 0.015 ml of iodomethane are added. The suspension is stirred at ambient temperature for one hour.

20 ml of water and 30 ml of ethyl acetate are added. After settling out, the organic phase is dried over magnesium sulfate, filtered, and then concentrated under reduced pressure. The residue obtained is purified on a silica column: eluent 98/02 dichloromethane/methanol, so as to give 6 mg of 5-fluoro-2-[1-(4-fluoro-2,3-dihydro-1H-indol-1-yl)-1-oxopropan-2-yl]-3-methyl-6-(morpholin-4-yl)pyrimidin-4(3H)-one, the characteristics of which are the following:

$^1$H NMR spectrum (400 MHz, d in ppm, DMSO-d6) for this batch, a 50%-50% mixture of the conformers is observed with: 1.44 (d, J=6.8 Hz, 3H); 3.18 (t, J=8.6 Hz, 2H); 3.39 (s, 3H); 3.55 (m, 8H); 3.98 (m, 1H); 4.30 (m, 1H); 4.39 (q, J=6.8 Hz, 1H); 6.87 (t, J=8.3 Hz, 1H); 7.22 (dt, J=5.9 and 8.3 Hz, 1H); 7.87 (d, J=8.3 Hz, 1H)

Mass spectrometry: method A
Retention time Tr (min)=0.80; [M+H]+: m/z 405; [M−H]−: m/z 403

And 24 mg of 5-fluoro-2-[2-(4-fluoro-2,3-dihydroindol-1-yl)-2-oxoethyl]-3-methyl-6-morpholin-4-yl-3H-pyrimidin-4-one, the characteristics of which are the following:

$^1$H NMR spectrum (400 MHz, d in ppm, DMSO-d6): 3.19 (t, J=8.6 Hz, 2H); 3.36 (s, 3H); 3.51 to 3.63 (m, 8H); 4.11 (s, 2H); 4.24 (t, J=8.6 Hz, 2H); 6.88 (t, J=8.3 Hz, 1H); 7.22 (dt, J=5.9 and 8.3 Hz, 1H); 7.83 (d, J=8.3 Hz, 1H)

Mass spectrometry: method A
Retention time Tr (min)=0.77; [M+H]+: m/z 391; [M−H]−: m/z 389

Example 4a and Example 5a

Synthesis of 5-fluoro-2-{2-[(2R)-2-methyl-2,3-dihydro-1H-indol-1-yl]-2-oxoethyl}-6-(morpholin-4-yl)pyrimidin-4(3H)-one and 5-fluoro-2-{2-[(2S)-2-methyl-2,3-dihydro-1H-indol-1-yl]-2-oxoethyl}-6-(morpholin-4-yl)pyrimidin-4(3H)-one Step 1a 2-(5-Fluoro-4-methoxy-6-morpholin-4-ylpyrimidin-2-yl)-1-(2-methyl-2,3-dihydroindol-1-yl)ethanone

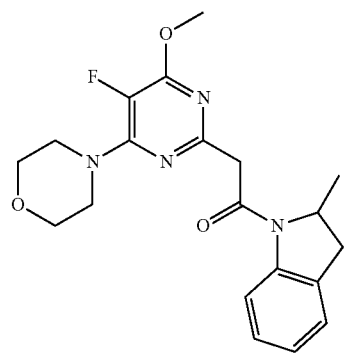 [SMILES: COc1nc(CC(=O)N2c3ccccc3CC2C)nc(N2CCOCC2)c1F]

The product is prepared by following the procedure described in example 1a (step 5a) using 600 mg of sodium (5-fluoro-4-methoxy-6-morpholin-4-ylpyrimidin-2-yl)acetate obtained in example 1a (step 4a) and 272 mg of 2-methyl-2,3-dihydro-1H-indole. After purification by silica column chromatography (eluent: 97/03 dichloromethane/ethyl acetate), 366 mg of 2-(5-fluoro-4-methoxy-6-morpholin-4-ylpyrimidin-2-yl)-1-(2-methyl-2,3-dihydroindol-1-yl) ethanone are obtained in the form of a white powder, the characteristics of which are the following:

Mass spectrometry: method A
Retention time Tr (min)=1.02; [M+H]+: m/z 387

Step 2a

5-Fluoro-2-{2-[(2R)-2-methyl-2,3-dihydro-1H-indol-1-yl]-2-oxoethyl}-6-(morpholin-4-yl)pyrimidin-4(3H)-one and 5-fluoro-2-{2-[(2S)-2-methyl-2,3-dihydro-1H-indol-1-yl]-2-oxoethyl}-6-(morpholin-4-yl)pyrimidin-4(3H)-one

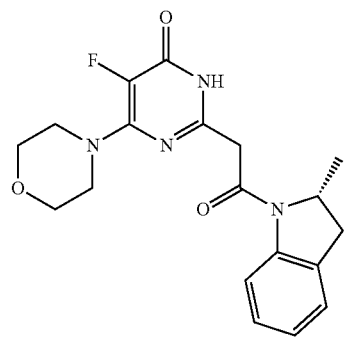

-continued

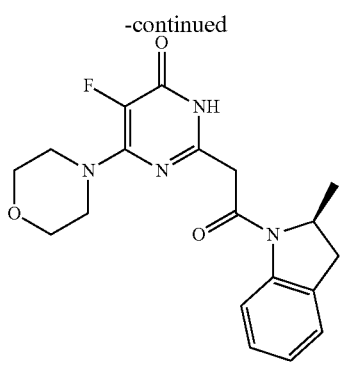

5-Fluoro-2-[2-(2-methyl-2,3-dihydroindol-1-yl)-2-oxoethyl]-6-morpholin-4-yl-3H-pyrimidin-4-one is prepared by following the procedure described in example 1a (step 6a) using 366 mg of 2-(5-fluoro-4-methoxy-6-morpholin-4-ylpyrimidin-2-yl)-1-(2-methyl-2,3-dihydroindol-1-yl)ethanone, 472 mg of potassium iodide and 0.36 of trimethylchlorosilane. After purification by silica column chromatography (eluent: 98/02 dichloromethane/methanol), 75 mg of 5-fluoro-2-[2-(2-methyl-2,3-dihydroindol-1-yl)-2-oxoethyl]-6-morpholin-4-yl-3H-pyrimidin-4-one are obtained in the form of a solid, the characteristics of which are the following:

Mass spectrometry: method A
Retention time Tr (min)=0.73; [M+H]+: m/z 373; [M−H]−: m/z 371

The enantiomers are separated by chiral column chromatography:

Stationary phase: Chiralpak T304 20 μm; mobile phase: EtOH (40%)/MeOH (25%)/heptane (35%)/triethylamine (0.1%); flow rate: 250 ml/min.

The dextrorotatory enantiomer is concentrated so as to obtain 102 mg of 5-fluoro-2-[2-((R)-2-methyl-2,3-dihydroindol-1-yl)-2-oxoethyl]-6-morpholin-4-yl-3H-pyrimidin-4-one in the form of a white solid, the characteristics of which are the following:

$^1$H NMR spectrum (400 MHz, d in ppm, DMSO-d6): 1.25 (broad d, J=6.3 Hz, 3H); 2.69 (d, J=16.3 Hz, 1H); 3.20 to 3.42 (partially masked m, 1H); 3.48 to 3.65 (m, 8H); 3.71 (d, J=15.8 Hz, 1H); 3.91 (d, J=15.8 Hz, 1H); 4.70 (m, 1H); 7.04 (t, J=8.1 Hz, 1H); 7.18 (t, J=8.1 Hz, 1H); 7.29 (d, J=8.1 Hz, 1H); 7.96 (d, J=8.1 Hz, 1H); 12.28 (broad m, 1H)

Mass spectrometry: method A
Retention time Tr (min)=0.73; [M+H]+: m/z 373; [M−H]−: m/z 371

Optical rotation: $\alpha_D$=+90; C=0.845 mg/0.5 ml DMSO

The levorotatory enantiomer is concentrated so as to obtain 88 mg of 5-fluoro-2-[2-((S)-2-methyl-2,3-dihydroindol-1-yl)-2-oxoethyl]-6-morpholin-4-yl-3H-pyrimidin-4-one in the form of a white solid, the characteristics of which are the following:

$^1$H NMR spectrum (400 MHz, d in ppm, DMSO-d6): 1.25 (d, J=6.3 Hz, 3H); 2.69 (d, J=16.3 Hz, 1H); 3.22 to 3.43 (partially masked m, 1H); 3.52 to 3.66 (m, 8H); 3.72 (d, J=15.8 Hz, 1H); 3.93 (d, J=15.8 Hz, 1H); 4.69 (m, 1H); 7.05 (t, J=8.1 Hz, 1H); 7.18 (t, J=8.1 Hz, 1H); 7.29 (d, J=8.1 Hz, 1H); 7.96 (d, J=8.1 Hz, 1H); 12.25 (broad m, 1H)

Mass spectrometry: method A
Retention time Tr (min)=0.73; [M+H]+: m/z 373; [M−H]−: m/z 371

Optical rotation: $\alpha_D$=−35; C=0.910 mg/0.5 ml DMSO

Example 6a and Example 7a

Synthesis of 5-fluoro-2-[2-((+)-5-fluoro-2-methyl-2,3-dihydroindol-1-yl)-2-oxoethyl]-6-morpholin-4-yl-3H-pyrimidin-4-one and 5-fluoro-2-[2-((−)-5-fluoro-2-methyl-2,3-dihydroindol-1-yl)-2-oxoethyl]-6-morpholin-4-yl-3H-pyrimidin-4-one Step 1a (5-Fluoro-4-morpholin-4-yl-6-oxo-1,6-dihydropyrimidin-2-yl)acetic acid methyl ester

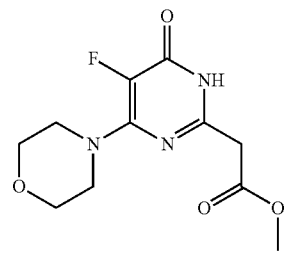 [SMILES: COC(=O)Cc1nc(N2CCOCC2)c(F)c(=O)[nH]1]

In a round-bottomed flask, 722 mg of KI and 0.56 ml of trimethylchlorosilane are added to a solution of 386 mg of (5-fluoro-4-methoxy-6-morpholin-4-ylpyrimidin-2-yl)acetic acid methyl ester obtained in example 1a (step 3a) in 4.7 ml of acetonitrile. The suspension is stirred at ambient temperature for 24 hours.

The reaction medium is concentrated under reduced pressure.

The residue obtained is taken up with water and ethyl acetate. After settling out, the organic phase is dried over magnesium sulfate, filtered, and then concentrated under reduced pressure. The residue obtained is purified by silica column chromatography (eluent: 98/02 dichloromethane/methanol) so as to give 155 mg of (5-fluoro-4-morpholin-4-yl-6-oxo-1,6-dihydropyrimidin-2-yl)acetic acid methyl ester in the form of a beige solid, the characteristics of which are the following:

Mass spectrometry: method A
Retention time Tr (min)=0.43; [M+H]+: m/z 272; [M−H]−: m/z 270; base peak 238

Step 2a

Sodium (5-fluoro-4-morpholin-4-yl-6-oxo-1,6-dihydropyrimidin-2-yl)acetate

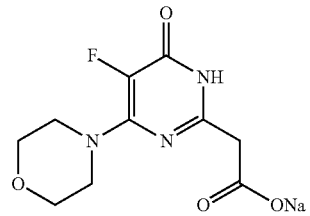

0.43 ml of 2N sodium hydroxide is added to a solution of 116 mg of (5-fluoro-4-morpholin-4-yl-6-oxo-1,6-dihydropyrimidin-2-yl)acetic acid methyl ester in 1.2 ml of THF. The reaction medium is stirred at ambient temperature for 24 hours. The reaction medium is concentrated under reduced pressure. The residue obtained is oven-dried under vacuum in the presence of $P_2O_5$ so as to give 110 mg of sodium (5-fluoro-4-morpholin-4-yl-6-oxo-1,6-dihydropyrimidin-2-yl)acetate, the characteristics of which are the following:

Mass spectrometry: method A
Retention time Tr (min)=0.32; [M+H]+: m/z 258; [M−H]−: m/z 256; base peak: m/z 212

Step 2'a

Alternatively, the sodium (5-fluoro-4-morpholin-4-yl-6-oxo-1,6-dihydropyrimidin-2-yl)acetate compound can be obtained in three steps:

Step (2'a)a

Ethyl [4-(morpholin-4-yl)-6-oxo-1,6-dihydropyrimidin-2-yl]acetate

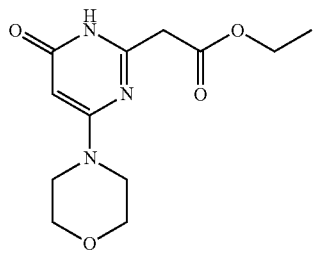 [SMILES: CCOC(=O)Cc1nc(N2CCOCC2)cc(=O)[nH]1]

168.5 ml of ethyl 3-ethoxy-3-iminopropanoate hydrochloride and then 155 ml of N,N-diisopropylethylamine in 200 ml of ethanol are added to a solution of 25 g of morpholine in 400 ml of ethanol, heated to 95° C. The reaction mixture is heated at 95° C. for 30 hours and then allowed to return to ambient temperature. The precipitate formed is filtered off through sintered glass and then washed with 100 ml of ethanol, 2 times 500 ml of water and, finally, 500 ml of ethyl ether. The solid is dried under vacuum so as to give 35 g of ethyl [4-(morpholin-4-yl)-6-oxo-1,6-dihydropyrimidin-2-yl]acetate in the form of a white solid, the characteristics of which are the following:

$^1$H NMR spectrum (400 MHz): 1.19 (t, J=7.1 Hz, 3H); 3.38 to 3.44 (m, 4H); 3.56 (s, 2H); 3.61 (dd, J=4.0 and 5.7 Hz, 4H); 4.12 (q, J=7.1 Hz, 2H); 5.20 (s, 1H); 11.69 (broad s, 1H)
Mass spectrometry: method A
Retention time Tr (min)=0.48;
[M+H]+: m/z 268; [M−H]−: m/z 266

Step (2'b)a (5-Fluoro-4-morpholin-4-yl-6-oxo-1,6-dihydropyrimidin-2-yl)acetic acid ethyl ester

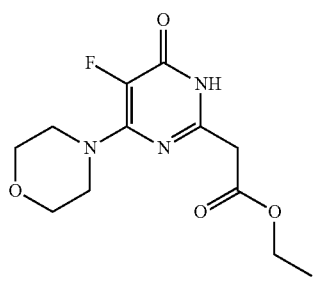 [SMILES: CCOC(=O)Cc1nc(N2CCOCC2)c(F)c(=O)[nH]1]

In a round-bottomed flask, 5 g of ethyl [4-(morpholin-4-yl)-6-oxo-1,6-dihydropyrimidin-2-yl]acetate obtained in the previous step with 50 ml of acetonitrile are heated to 74° C. A solution of 7.67 g of Selectfluor solubilized in a mixture of 25 ml of water and 25 ml of acetonitrile is added, dropwise, and at 74° C., to this solution.
The reaction medium is heated at 75° C. for 90 minutes.
After cooling, 200 ml of ethyl acetate and then 100 ml of a saturated sodium bicarbonate solution are added. After settling out, the organic phase is dried over magnesium sulfate, filtered, and then concentrated under reduced pressure. The residue obtained is purified by silica column chromatography (eluent: dichloromethane/methanol gradient of 100/0 to 95/05) so as to give 0.8 g of (5-fluoro-4-morpholin-4-yl-6-oxo-1,6-dihydropyrimidin-2-yl)acetic acid ethyl ester in the form of a beige solid, the characteristics of which are the following:

$^1$H NMR spectrum (400 MHz, d in ppm, DMSO-d6): 1.19 (t, J=7.1 Hz, 3H); 3.56 (m, 6H); 3.63 (m, 4H); 4.12 (q, J=7.1 Hz, 2H); 12.32 (broad m, 1H)

Step (2'c)a

Sodium (5-fluoro-4-morpholin-4-yl-6-oxo-1,6-dihydropyrimidin-2-yl)acetate

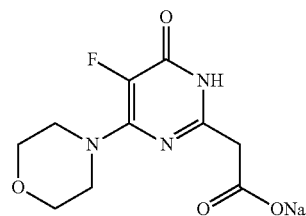

2.9 ml of 2N sodium hydroxide are added to a solution of 800 mg of (5-fluoro-4-morpholin-4-yl-6-oxo-1,6-dihydropyrimidin-2-yl)acetic acid ethyl ester in 10 ml of THF. The reaction medium is stirred at ambient temperature for 24 hours. The reaction medium is concentrated under reduced pressure. The residue obtained is oven-dried under vacuum in the presence of $P_2O_5$, so as to give 780 mg of sodium (5-fluoro-4-morpholin-4-yl-6-oxo-1,6-dihydropyrimidin-2-yl)acetate, the characteristics of which are the following:

Mass spectrometry: method A
Retention time Tr (min)=0.32; [M+H]+: m/z 258;
m/z 256; base peak: m/z 212

Step 3a

5-Fluoro-2-[2-((+)-5-fluoro-2-methyl-2,3-dihydroindol-1-yl)-2-oxoethyl]-6-morpholin-4-yl-3H-pyrimidin-4-one and 5-fluoro-2-[2-((−)-5-fluoro-2-methyl-2,3-dihydroindol-1-yl)-2-oxoethyl]-6-morpholin-4-yl-3H-pyrimidin-4-one

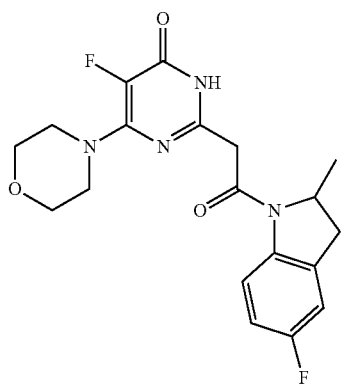

-continued

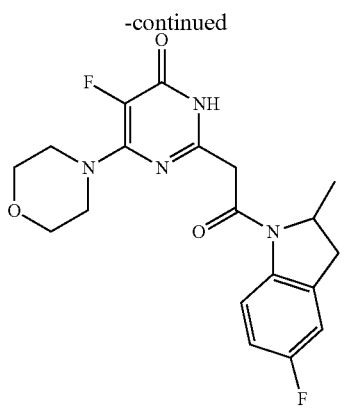

5-Fluoro-2-[2-(5-fluoro-2-methyl-2,3-dihydroindol-1-yl)-2-oxoethyl]-6-morpholin-4-yl)-3H-pyrimidin-4-one is prepared by following the procedure described in example 1a (step 5a) using 182 mg of sodium (5-fluoro-4-morpholin-4-yl-6-oxo-1,6-dihydropyrimidin-2-yl)acetate (obtained in step 2a) and 197 mg of 5-fluoro-2-methyl-2,3-dihydro-1H-indole (reference example 1a). After silica column purification, eluent: 98/02 dichloromethane/methanol, 85 mg of 5-fluoro-2-[2-(5-fluoro-2-methyl-2,3-dihydroindol-1-yl)-2-oxoethyl]-6-morpholin-4-yl-3H-pyrimidin-4-one are obtained in the form of a white solid, the characteristics of which are the following:

Mass spectrometry: method A
Retention time Tr (min)=0.75; [M+H]+: m/z 391; [M−H]−: m/z 389

The enantiomers are separated by chiral column chromatography:

Stationary phase: Chiralpak AY 20 μm batch KLB001; mobile phase: acetonitrile (98%)/isopropanol (02%); flow rate: 180 ml/min.

The dextrorotatory enantiomer is concentrated so as to obtain 66 mg of 5-fluoro-2-[2-((+)-5-fluoro-2-methyl-2,3-dihydroindol-1-yl)-2-oxoethyl]-6-morpholin-4-yl-3H-pyrimidin-4-one in the form of a white solid, the characteristics of which are the following:

$^1$H NMR spectrum (400 MHz, d in ppm, DMSO-d6): 1.25 (d, J=6.4 Hz, 3H); 2.68 (d, J=16.3 Hz, 1H); 3.37 (m, 1H); 3.51 (m, 4H); 3.58 to 3.70 (m, 5H); 3.89 (m, 1H); 4.73 (m, 1H); 7.00 (dt, J=3.0 and 8.4 Hz, 1H); 7.15 (broad d, J=9.5 Hz, 1H); 7.94 (dd, J=5.0 and 8.4 Hz, 1H); 12.32 (broad m, 1H)

Mass spectrometry: method A
Retention time Tr (min)=0.75; [M+H]+: m/z 391; [M−H]−: m/z 389

Optical rotation: $\alpha_D$=+70.8+/−1.3; C=1.773 mg/0.5 ml DMSO

The levorotatory enantiomer is concentrated so as to obtain 58 mg of 5-fluoro-2-[2-((−)-5-fluoro-2-methyl-2,3-dihydroindol-1-yl)-2-oxoethyl]-6-morpholin-4-yl-3H-pyrimidin-4-one in the form of a white solid, the characteristics of which are the following:

$^1$H NMR spectrum (400 MHz, d in ppm, DMSO-d6) for this batch, all the signals are broad with: 1.25 (d, J=6.3 Hz, 3H); 2.69 (d, J=16.3 Hz, 1H); 3.36 (m, 1H); 3.52 (m, 4H); 3.58 to 3.70 (m, 5H); 3.86 (m, 1H); 4.74 (m, 1H); 7.00 (m, 1H); 7.15 (d, J=9.5 Hz, 1H); 7.93 (m, 1H); 12.28 (broad m, 1H)

Mass spectrometry: method A
Retention time Tr (min)=0.76; [M+H]+: m/z 391; [M−H]−: m/z 389

Optical rotation: $\alpha_D$=−72.4+/−1.4; C=1.662 mg/0.5 ml DMSO

Example 8a

Synthesis of 5-fluoro-3-methyl-2-{2-[(2S)-2-methyl-2,3-dihydro-1H-indol-1-yl]-2-oxoethyl}-6-(morpholin-4-yl)pyrimidin-4(3H)-one Step 1a (5-Fluoro-1-methyl-4-morpholin-4-yl-6-oxo-1,6-dihydropyrimidin-2-yl)acetic acid methyl ester

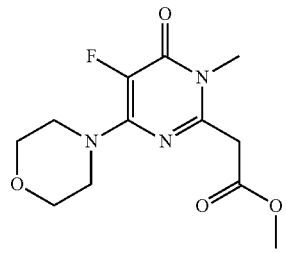 [SMILES: COC(=O)Cc1nc(N2CCOCC2)c(F)c(=O)n1C]

2 g of (5-fluoro-4-morpholin-4-yl-6-oxo-1,6-dihydropyrimidin-2-yl)acetic acid methyl ester are placed in a round-bottomed flask with 50 ml of acetonitrile.

3.12 g of cesium carbonate and 0.6 ml of iodomethane are added. The suspension is stirred at ambient temperature for 18 hours.

The reaction medium is filtered. The filtrate is concentrated under reduced pressure. The residue obtained is purified on a silica column: eluent 98/02 dichloromethane/methanol, so as to give 759 mg of (5-fluoro-1-methyl-4-morpholin-4-yl-6-oxo-1,6-dihydropyrimidin-2-yl)acetic acid methyl ester, the characteristics of which are the following:

Mass spectrometry: method A
Retention time Tr (min)=0.47; [M+H]+: m/z 286; [M−H]−: m/z 284

Step 2a

Sodium (5-fluoro-1-methyl-4-morpholin-4-yl-6-oxo-1,6-dihydropyrimidin-2-yl)acetate

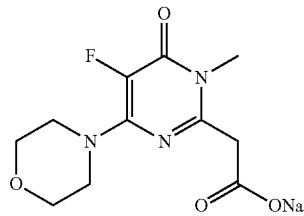

2 ml of 2N sodium hydroxide are added to a solution of 759 mg of (5-fluoro-1-methyl-4-morpholin-4-yl-6-oxo-1,6-dihydropyrimidin-2-yl)acetic acid methyl ester in 8 ml of THF. The reaction medium is stirred at ambient temperature for 24 hours. The reaction medium is concentrated under reduced pressure. The residue obtained is oven-dried under vacuum in the presence of $P_2O_5$, so as to give 695 mg of sodium (5-fluoro-1-methyl-4-morpholin-4-yl-6-oxo-1,6-dihydropyrimidin-2-yl)acetate in the form of a white solid which is used as it is in the next step.

Mass spectrometry: method A
[M+H]+: m/z 272; [M−H]−: m/z 270; base peak: m/z 226

Step 3a

Synthesis of 5-fluoro-3-methyl-2-{2-[(2S)-2-methyl-2,3-dihydro-1H-indol-1-yl]-2-oxoethyl}-6-(morpholin-4-yl)pyrimidin-4(3H)-one

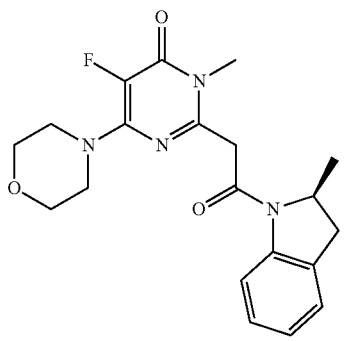 [SMILES: C[C@H]1Cc2ccccc2N1C(=O)Cc1nc(N2CCOCC2)c(F)c(=O)n1C]

The product is prepared by following the procedure described in example 1a (step 5a) using 88 mg of sodium (5-fluoro-1-methyl-4-morpholin-4-yl-6-oxo-1,6-dihydropyrimidin-2-yl)acetate described in step 2a and 40 mg of (S)-2-methyl-2,3-dihydro-1H-indole (which can be prepared according to Krasnov, V. P. et al. (Mendeleev Commun. (2002), 12(1), 27-28). After silica column purification: eluent 98/02 dichloromethane/methanol, 60 mg of 5-fluoro-3-methyl-2-[2-((S)-2-methyl-2,3-dihydroindol-1-yl)-2-oxoethyl]-6-morpholin-4-yl-3H-pyrimidin-4-one are obtained in the form of a solid, the characteristics of which are the following:

$^1$H NMR spectrum (400 MHz, d in ppm, DMSO-d6): 1.27 (d, J=6.4 Hz, 3H); 2.69 (d, J=16.3 Hz, 1H); 3.38 (s, 3H); 3.39 (partially masked m, 1H); 3.50 to 3./1 H); 7.06 (t, J=8.1 Hz, 1H); 7.18 (t, J=8.1 Hz, 1H); 7.29 (d, J=8.1 Hz, 1H); 7.94 (d, J=8.1 Hz, 1H)

Mass spectrometry: method A

Retention time Tr (min)=0.77; [M+H]+: m/z 387; [M−H]−: m/z 385

Optical rotation: α$_D$=−36.0+/−1.0. C=1.608 mg/0.5 ml DMSO

Example 9a

Synthesis of 5-fluoro-3-methyl-2-{2-[(2R)-2-methyl-2,3-dihydro-1H-indol-1-yl]-2-oxoethyl}-6-(morpholin-4-yl)pyrimidin-4(3H)-one

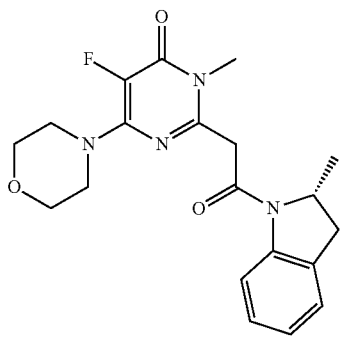 [SMILES: C[C@@H]1Cc2ccccc2N1C(=O)Cc1nc(N2CCOCC2)c(F)c(=O)n1C]

The product is prepared by following the procedure described in example 1a (step 5a) using 88 mg of sodium (5-fluoro-1-methyl-4-morpholin-4-yl-6-oxo-1,6-dihydropyrimidin-2-yl)acetate obtained in step 2a of example 8a and 40 mg of (R)-2-methyl-2,3-dihydro-1H-indole (which can be prepared according to Krasnov, V. P. et al. (Mendeleev Commun. (2002), 12(1), 27-28)). After silica column purification: eluent 98/02 dichloromethane/methanol, 62 mg of 5-fluoro-3-methyl-2-[2-((R)-2-methyl-2,3-dihydroindol-1-yl)-2-oxoethyl]-6-morpholin-4-yl-3H-pyrimidin-4-one are obtained in the form of a solid, the characteristics of which are the following:

$^1$H NMR spectrum (400 MHz, d in ppm, DMSO-d6): 1.27 (d, J=6.4 Hz, 3H); 2.69 (d, J=16.3 Hz, 1H); 3.38 (s, 3H); 3.40 (m, 1H); 3.51 to 3.62 (m, 8H); 4.01 (d, J=16.9 Hz, 1H); 4.28 (d, J=16.9 Hz, 1H); 4.69 (m, 1H); 7.05 (t, J=8.1 Hz, 1H); 7.18 (t, J=8.1 Hz, 1H); 7.29 (d, J=8.1 Hz, 1H); 7.94 (d, J=8.1 Hz, 1H)

Mass spectrometry: method A

Retention time Tr (min)=0.77; [M+H]+: m/z 387; [M−H]−: m/z 385

Optical rotation: α$_D$=+57. C=1.469 mg/0.5 ml DMSO

Example 10a

Synthesis of 5-fluoro-2-[2-((+)-2-methyl-4-fluoro-2,3-dihydroindol-1-yl)-2-oxoethyl]-6-morpholin-4-yl-3H-pyrimidin-4-one

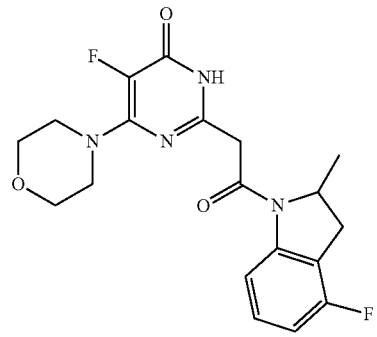 [SMILES: CC1Cc2c(F)cccc2N1C(=O)Cc1nc(N2CCOCC2)c(F)c(=O)[nH]1]

The product is prepared by following the procedure described in example 1a (step 5a) using 124 mg of sodium (5-fluoro-4-morpholin-4-yl-6-oxo-1,6-dihydropyrimidin-2-yl)acetate obtained in step 2a of example 6a and 73 mg of (−)-2-methyl-4-fluoro-2,3-dihydro-1H-indole (reference example 5a). After silica column purification: eluent 98/02 dichloromethane/methanol, 70 mg of 5-fluoro-2-[2-((+)-2-methyl-4-fluoro-2,3-dihydroindol-1-yl)-2-oxoethyl]-6-morpholin-4-yl-3H-pyrimidin-4-one are obtained in the form of a solid, the characteristics of which are the following:

$^1$H NMR spectrum (400 MHz, d in ppm, DMSO-d6) for this batch, all the signals are broad with: 1.28 (d, J=6.6 Hz, 3H); 2.76 (d, J=16.3 Hz, 1H); 3.36 (partially masked m, 1H); 3.52 to 3.64 (m, 8H); 3.74 (d, J=16.9 Hz, 1H); 3.93 (d, J=16.9 Hz, 1H); 4.78 (m, 1H); 6.90 (t, J=8.6 Hz, 1H); 7.23 (m, 1H); 7.78 (d, J=8.6 Hz, 1H); 12.33 (broad m, 1H)

Mass spectrometry: method A

Retention time Tr (min)=0.77; [M+H]+: m/z 391; [M−H]−: m/z 389

Optical rotation: $\alpha_D$=+75.1+/−1.3. C=1.998 mg/0.5 ml DMSO

Example 11a

Synthesis of 5-fluoro-2-[2-((−)-2-methyl-4-fluoro-2,3-dihydroindol-1-yl)-2-oxoethyl]-6-morpholin-4-yl-3H-pyrimidin-4-one

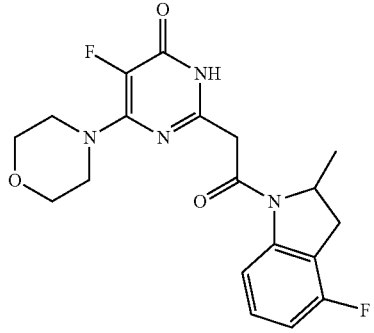 [SMILES: CC1Cc2c(F)cccc2N1C(=O)Cc1nc(N2CCOCC2)c(F)c(=O)[nH]1]

The product is prepared by following the procedure described in example 1a (step 5a) using 125 mg of sodium (5-fluoro-4-morpholin-4-yl-6-oxo-1,6-dihydropyrimidin-2-yl)acetate obtained in step 2a of example 6a and 74 mg of (+)-2-methyl-4-fluoro-2,3-dihydro-1H-indole (reference example 5a). After silica column purification: eluent 98/02 dichloromethane/methanol, 105 mg of 5-fluoro-2-[2-((−)-2-methyl-4-fluoro-2,3-dihydroindol-1-yl)-2-oxoethyl]-6-morpholin-4-yl-3H-pyrimidin-4-one are obtained in the form of a solid, the characteristics of which are the following:

$^1$H NMR spectrum (400 MHz, d in ppm, DMSO-d6): 1.28 (broad d, J=6.6 Hz, 3H); 2.76 (d, J=16.3 Hz, 1H); 3.37 (partially masked m, 1H); 3.51 to 3.66 (m, 8H); 3.74 (d, J=16.1 Hz, 1H); 3.94 (d, J=16.1 Hz, 1H); 4.78 (m, 1H); 6.90 (t, J=8.6 Hz, 1H); 7.23 (m, 1H); 7.78 (broad d, J=8.6 Hz, 1H); 12.30 (broad m, 1H)

Mass spectrometry: method A

Retention time Tr (min)=0.77; [M+H]+: m/z 391; [M−H]−: m/z 389

Optical rotation: $\alpha_D$=−83.4+1/−1.5. C=1.719 mg/0.5 ml DMSO

Example 12a

Synthesis of 2-[2-((+)-5,6-difluoro-2-methyl-2,3-dihydroindol-1-yl)-2-oxoethyl]-5-fluoro-6-morpholin-4-yl-3H-pyrimidin-4-one

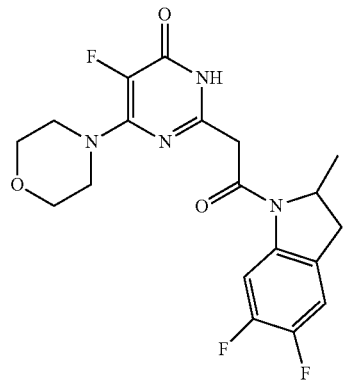 [SMILES: CC1Cc2cc(F)c(F)cc2N1C(=O)Cc1nc(N2CCOCC2)c(F)c(=O)[nH]1]

The product is prepared by following the procedure described in example 1a (step 5a) using 131 mg of sodium (5-fluoro-4-morpholin-4-yl-6-oxo-1,6-dihydropyrimidin-2-yl)acetate obtained in step 2a of example 6a and 87 mg of (−)-2-methyl-5,6-fluoro-2,3-dihydro-1H-indole (reference example 3a). After silica column purification: eluent 98/02 dichloromethane/methanol, 119 mg of 2-[2-((+)-5,6-difluoro-2-methyl-2,3-dihydroindol-1-yl)-2-oxoethyl]-5-fluoro-6-morpholin-4-yl-3H-pyrimidin-4-one are obtained in the form of a solid, the characteristics of which are the following:

$^1$H NMR spectrum (400 MHz, d in ppm, DMSO-d6): 1.26 (d, J=6.4 Hz, 3H); 2.68 (d, J=16.3 Hz, 1H); 3.35 (partially masked m, 1H); 3.55 (m, 4H); 3.62 (m, 4H); 3.73 (d, J=16.1 Hz, 1H); 3.92 (d, J=16.1 Hz, 1H); 4.73 (m, 1H); 7.39 (dd, J=8.5 and 10.5 Hz, 1H); 7.89 (dd, J=7.2 and 12.3 Hz, 1H); 12.34 (broad m, 1H)

Mass spectrometry: method A

Retention time Tr (min)=0.79; [M+H]+: m/z 409; [M−H]−: m/z 407

Optical rotation: $\alpha_D$=+65.9+/−1.2. C=1.931 mg/0.5 ml DMSO

Example 13a

Synthesis of 2-[2-((−)-5,6-difluoro-2-methyl-2,3-dihydroindol-1-yl)-2-oxoethyl]-5-fluoro-6-morpholin-4-yl-3H-pyrimidin-4-one

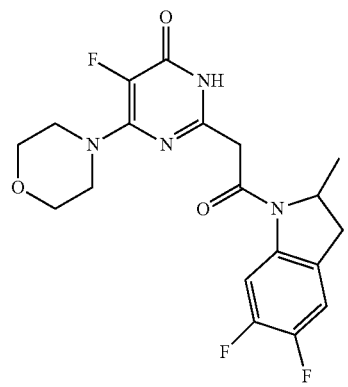 [SMILES: CC1Cc2cc(F)c(F)cc2N1C(=O)Cc1nc(N2CCOCC2)c(F)c(=O)[nH]1]

The product is prepared by following the procedure described in example 1a (step 5a) using 131 mg of sodium (5-fluoro-4-morpholin-4-yl-6-oxo-1,6-dihydropyrimidin-2-yl)acetate obtained in step 2a of example 6a and 93 mg of (+)-2-methyl-5,6-difluoro-2,3-dihydro-1H-indole (reference example 3a). After silica column purification: eluent 98/02 dichloromethane/methanol, 64 mg of 2-[2-((−)-5,6-difluoro-2-methyl-2,3-dihydroindol-1-yl)-2-oxoethyl]-5-fluoro-6-morpholin-4-yl-3H-pyrimidin-4-one are obtained in the form of a solid, the characteristics of which are the following:

$^1$H NMR spectrum (400 MHz, d in ppm, DMSO-d6): 1.26 (d, J=6.4 Hz, 3H); 2.68 (d, J=16.3 Hz, 1H); 3.35 (partially masked m, 1H); 3.55 (m, 4H); 3.62 (m, 4H); 3.73 (d, J=16.1 Hz, 1H); 3.92 (d, J=16.1 Hz, 1H); 4.73 (m, 1H); 7.39 (dd, J=8.5 and 10.5 Hz, 1H); 7.89 (dd, J=7.2 and 12.3 Hz, 1H); 12.34 (broad m, 1H)

Mass spectrometry: method A

Retention time Tr (min)=0.79; [M+H]+: m/z 409; [M−H]−: m/z 407

Optical rotation: $\alpha_D$=−60.0+/−1.2. C=1.748 mg/0.5 ml DMSO

Example 14a

Synthesis of 5-fluoro-2-[2-((−)-5-fluoro-2-methyl-2,3-dihydroindol-1-yl)-2-oxoethyl]-3-methyl-6-morpholin-4-yl-3H-pyrimidin-4-one

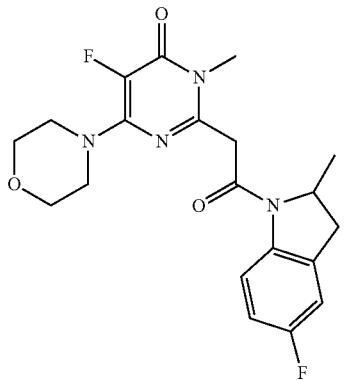 [SMILES: CC1Cc2cc(F)ccc2N1C(=O)Cc1nc(N2CCOCC2)c(F)c(=O)n1C]

The product is prepared by following the procedure described in example 1a (step 5a) using 126 mg of sodium (5-fluoro-1-methyl-4-morpholin-4-yl-6-oxo-1,6-dihydropyrimidin-2-yl)acetate obtained in step 2a of example 8a and 64 mg of (+)-2-methyl-5-fluoro-2,3-dihydro-1H-indole (reference example 1a). After silica column purification: eluent 98/02 dichloromethane/methanol, 80 mg of 5-fluoro-2-[2-((−)-5-fluoro-2-methyl-2,3-dihydroindol-1-yl)-2-oxoethyl]-3-methyl-6-morpholin-4-yl-3H-pyrimidin-4-one are obtained in the form of a solid, the characteristics of which are the following:

$^1$H NMR spectrum (400 MHz, d in ppm, DMSO-d6): 1.27 (d, J=6.6 Hz, 3H); 2.70 (d, J=16.3 Hz, 1H); 3.38 (s, 3H); 3.40 (partially masked m, 1H); 3.53 to 3.62 (m, 8H); 4.01 (d, J=16.6 Hz, 1H); 4.26 (d, J=16.6 Hz, 1H); 4.72 (m, 1H); 7.00 (broad t, J=9.1 Hz, 1H); 7.16 (broad d, J=7.8 Hz, 1H); 7.93 (dd, J=5.2 and 9.1 Hz, 1H)

Mass spectrometry: method A

Retention time Tr (min)=0.80; [M+H]+: m/z 405; [M−H]−: m/z 403

Optical rotation: $\alpha_D$=−44.4+/−1.0. C=1.822 mg/0.5 ml DMSO

Example 15a

Synthesis of 5-fluoro-2-[2-((+)-5-fluoro-2-methyl-2,3-dihydroindol-1-yl)-2-oxoethyl]-3-methyl-6-morpholin-4-yl-3H-pyrimidin-4-one

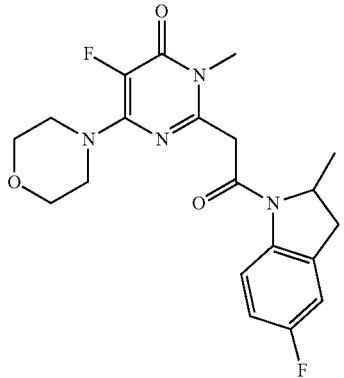 [SMILES: CC1Cc2cc(F)ccc2N1C(=O)Cc1nc(N2CCOCC2)c(F)c(=O)n1C]

The product is prepared by following the procedure described in example 1a (step 5a) using 118 mg of sodium (5-fluoro-1-methyl-4-morpholin-4-yl-6-oxo-1,6-dihydropyrimidin-2-yl)acetate obtained in step 2a of example 8a and 60 mg of (−)-2-methyl-5-fluoro-2,3-dihydro-1H-indole (reference example 1a). After silica column purification: eluent 98/02 dichloromethane/methanol, 89 mg of 5-fluoro-2-[2-((+)-5-fluoro-2-methyl-2,3-dihydroindol-1-yl)-2-oxoethyl]-3-methyl-6-morpholin-4-yl-3H-pyrimidin-4-one are obtained in the form of a solid, the characteristics of which are the following:

$^1$H NMR spectrum (400 MHz, d in ppm, DMSO-d6): 1.27 (d, J=6.4 Hz, 3H); 2.70 (d, J=16.3 Hz, 1H); 3.38 (s, 3H); 3.40 (partially masked m, 1H); 3.52 to 3.62 (m, 8H); 4.01 (d, J=16.6 Hz, 1H); 4.26 (d, J=16.6 Hz, 1H); 4.72 (m, 1H); 7.00 (dt, J=2.0 and 9.1 Hz, 1H); 7.16 (broad d, J=9.1 Hz, 1H); 7.93 (dd, J=5.2 and 9.1 Hz, 1H)

Mass spectrometry: method A

Retention time Tr (min)=0.80; [M+H]+: m/z 405; [M−H]−: m/z 403

Optical rotation: $\alpha_D$=+ 57.8+/−1.2. C=1.840 mg/0.5 ml DMSO

Example 16a and Example 17a

Synthesis of (+)-2-{2-[4-bromo-2-methyl-2,3-dihydro-1H-indol-1-yl]-2-oxoethyl}-5-fluoro-6-(morpholin-4-yl)pyrimidin-4(3H)-one and (−)-2-{2-[4-bromo-2-methyl-2,3-dihydro-1H-indol-1-yl]-2-oxoethyl}-5-fluoro-6-(morpholin-4-yl)pyrimidin-4(3H)-one

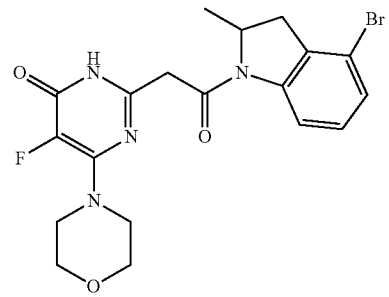

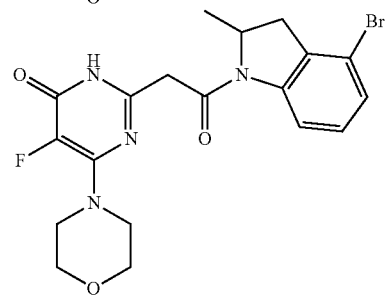

150 mg of 4-bromo-2-methyl-2,3-dihydro-1H-indole [reference example 4a] and 197 mg of N-[3-(dimethylamino)propyl]-N'-ethylcarbodiimide hydrochloride are added to a solution of 217 mg of sodium (5-fluoro-4-morpholin-4-yl-6-oxo-1,6-dihydropyrimidin-2-yl)acetate (obtained in step 2a of example 6a) in 7 ml of N,N-dimethylformamide and 7 ml of pyridine. The reaction mixture is stirred at ambient temperature for 72 hours, then 50 ml of water are added and the mixture is extracted with ethyl acetate. The organic phase is washed successively with a 0.1N hydrochloric acid solution, water and a saturated sodium chloride solution, dried over magnesium sulfate, filtered and concentrated under reduced pressure. The residue is triturated from dichloromethane, filtered and washed with diethyl ether so as to give 163 mg of 2-{2-[4-bromo-2-methyl-2,3-dihydro-1H-indol-1-yl]-2-oxoethyl}-5-fluoro-6-(morpholin-4-yl)pyrimidin-4(3H)-one.

The enantiomers are separated by chiral column chromatography:

Chiral column: Whelk 01 SS phase, 10 μm (10 μm, 77×350 mm), elution being carried out with a mixture of: heptane/dichloromethane/ethanol/methanol: 69/20/5/6; flow rate: 250 ml/min.

71 mg of (+)-2-{2-[4-bromo-2-methyl-2,3-dihydro-1H-indol-1-yl]-2-oxoethyl}-5-fluoro-6-(morpholin-4-yl)pyrimidin-4(3H)-one are obtained, as first enantiomer, in the form of a white solid, the characteristics of which are the following:

¹H NMR spectrum (400 MHz): 1.29 (d, J=6.4 Hz, 3H); 2.67 (s, 1H); 3.31 to 3.40 (m, 1H); 3.51 to 3.64 (m, 8H); 3.73 (d, J=16.1 Hz, 1H); 3.93 (d, J=16.1 Hz, 1H); 4.68 to 4.80 (m, 1H); 7.16 (t, J=8.2 Hz, 1H); 7.26 (d, J=8.2 Hz, 1H); 7.95 (d, J=8.2 Hz, 1H); 12.30 (d, J=3.2 Hz, 1H)

Mass spectrometry: method B
Retention time Tr (min)=3.50;
[M+H]+: m/z 452; [M−H]−: m/z 450;
Optical rotation: $\alpha_D$=+134° (c=1.784 mg/0.5 ml DMSO)

Then 74 mg of (−)-2-{2-[4-bromo-2-methyl-2,3-dihydro-1H-indol-1-yl]-2-oxoethyl}-5-fluoro-6-(morpholin-4-yl)pyrimidin-4(3H)-one are obtained, as second enantiomer, in the form of a white solid, the characteristics of which are the following:

¹H NMR spectrum (400 MHz): 1.29 (d, J=6.4 Hz, 3H); 2.67 (m, 1H); 3.32 (m, 1H); 3.50 to 3.65 (m, 8H); 3.73 (d, J=15.9 Hz, 1H); 3.92 (d, J=15.9 Hz, 1H); 4.74 (m, 1H); 7.16 (t, J=8.1 Hz, 1H); 7.26 (d, J=8.1 Hz, 1H); 7.95 (broad d, J=8.1 Hz, 1H); 12.32 (broad m, 1H)

Mass spectrometry: method B
Retention time Tr (min)=3.50;
[M+H]+: m/z 452; [M−H]−: m/z 450;
Optical rotation: $\alpha_D$=−109° (c=1.861 mg/0.5 ml DMSO)

Example 18a and Example 19a

Synthesis of 5-fluoro-2-[2-((+)-4-chloro-2-methyl-2,3-dihydroindol-1-yl)-2-oxoethyl]-6-morpholin-4-yl-3H-pyrimidin-4-one and 5-fluoro-2-[2-((−)-4-chloro-2-methyl-2,3-dihydroindol-1-yl)-2-oxoethyl]-6-morpholin-4-yl)-3H-pyrimidin-4-one

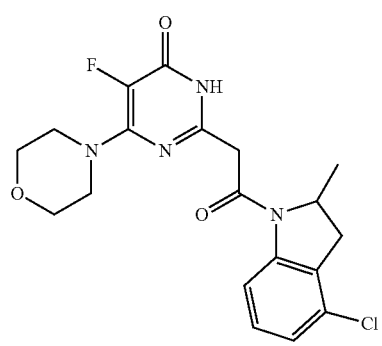

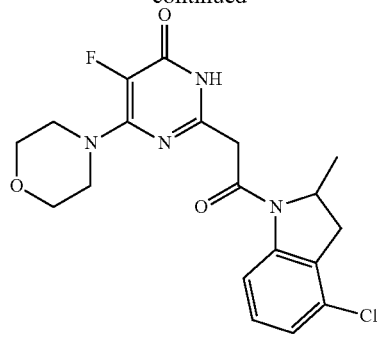

5-Fluoro-2-[2-(5-fluoro-2-methyl-2,3-dihydroindol-1-yl)-2-oxoethyl]-6-morpholin-4-yl-3H-pyrimidin-4-one is prepared by following the procedure described in example 1a (step 5a) using 206 mg of sodium (5-fluoro-4-morpholin-4-yl-6-oxo-1,6-dihydropyrimidin-2-yl)acetate obtained in step 2a of example 6a and 197 mg of 4-chloro-2-methyl-2,3-dihydro-1H-indole [which can be prepared according to U.S. Pat. No. 4,416,884 (1983)]. After purification, 151 mg of 5-fluoro-2-[2-(4-chloro-2-methyl-2,3-dihydroindol-1-yl)-2-oxoethyl]-6-morpholin-4-yl-3H-pyrimidin-4-one are obtained in the form of a solid which will be separated, on a chiral column, into its two enantiomers.

The enantiomers are separated by chiral column chromatography:

Stationary phase: Chiralpak AY 20 μm (T304); mobile phase: acetonitrile (95%)/isopropanol (05%); flow rate: 250 ml/min.

The dextrorotatory enantiomer is concentrated so as to obtain 58 mg of 5-fluoro-2-[2-((+)-4-chloro-2-methyl-2,3-dihydroindol-1-yl)-2-oxoethyl]-6-morpholin-4-yl-3H-pyrimidin-4-one in the form of a white solid, the characteristics of which are the following:

¹H NMR spectrum (400 MHz, d in ppm, DMSO-d6): 1.28 (d, J=6.4 Hz, 3H); 2.72 (d, J=16.3 Hz, 1H); 3.37 (dd, J=8.6 and 16.3 Hz, 1H); 3.51 to 3.65 (m, 8H); 3.73 (d, J=16.4 Hz, 1H); 3.93 (d, J=16.4 Hz, 1H); 4.76 (m, 1H); 7.12 (d, J=8.3 Hz, 1H); 7.24 (t, J=8.3 Hz, 1H); 7.91 (broad d, J=8.3 Hz, 1H); 12.24 (broad m, 1H)

Mass spectrometry: method A

Retention time Tr (min)=0.85; [M+H]+: m/z 407; [M−H]−: m/z 405

Optical rotation: $\alpha_D$=+143. C=0.569 mg/0.5 ml DMSO

The levorotatory enantiomer is concentrated so as to obtain 64 mg of 5-fluoro-2-[2-((−)-4-chloro-2-methyl-2,3-dihydroindol-1-yl)-2-oxoethyl]-6-morpholin-4-yl-3H-pyrimidin-4-one in the form of a white solid, the characteristics of which are the following:

¹H NMR spectrum (400 MHz, d in ppm, DMSO-d6): 1.29 (broad d, J=6.4 Hz, 3H); 2.72 (d, J=16.3 Hz, 1H); 3.37 (dd, J=8.6 and 16.3 Hz, 1H); 3.50 to 3.66 (m, 8H); 3.73 (d, J=15.9 Hz, 1H); 3.93 (d, J=15.9 Hz, 1H); 4.75 (m, 1H); 7.12 (d, J=8.6 Hz, 1H); 7.24 (t, J=8.6 Hz, 1H); 7.91 (broad d, J=8.6 Hz, 1H); 12.32 (broad m, 1H)

Mass spectrometry: method A

Retention time Tr (min)=0.85; [M+H]+: m/z 407; [M−H]−: m/z 405

Optical rotation: αD=−171. C=0.764 mg/0.5 ml DMSO

Example 20a

Synthesis of 2-[2-((−)-4,5-difluoro-2-methyl-2,3-dihydroindol-1-yl)-2-oxoethyl]-5-fluoro-6-morpholin-4-yl-3H-pyrimidin-4-one

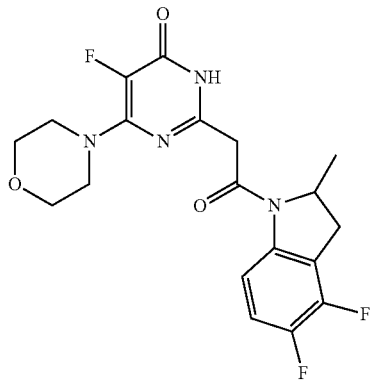 [SMILES: CC1Cc2c(ccc(F)c2F)N1C(=O)Cc1nc(N2CCOCC2)c(F)c(=O)[nH]1]

The product is prepared by following the procedure described in example 1a (step 5a) using 144 mg of sodium (5-fluoro-4-morpholin-4-yl-6-oxo-1,6-dihydropyrimidin-2-yl)acetate obtained in step 2a of example 6a and 87 mg of (+)-2-methyl-4,5-fluoro-2,3-dihydro-1H-indole (reference example 2a). After silica column purification: eluent 98/02 dichloromethane/methanol, 102 mg of 2-[2-((−)-4,5-difluoro-2-methyl-2,3-dihydroindol-1-yl)-2-oxoethyl]-5-fluoro-6-morpholin-4-yl-3H-pyrimidin-4-one are obtained in the form of a solid, the characteristics of which are the following:

$^1$H NMR spectrum (400 MHz, d in ppm, DMSO-d6): 1.29 (d, J=6.4 Hz, 3H); 2.81 (d, J=16.6 Hz, 1H); 3.40 (dd, J=8.6 and 16.6 Hz, 1H); 3.52 to 3.66 (m, 8H); 3.73 (d, J=16.1 Hz, 1H); 3.92 (d, J=16.1 Hz, 1H); 4.794 (m, 1H); 7.24 (m, 1H); 7.74 (broad d, J=9.0 Hz, 1H); 12.29 (broad m, 1H)

Mass spectrometry: method A
Retention time Tr (min)=0.81; [M+H]+: m/z 409; [M−H]−: m/z 407
Optical rotation: $\alpha_D$=−72.4+/−1.4. C=1.731 mg/0.5 ml DMSO

Example 21a

Synthesis of 2-[2-((+)-4,5-difluoro-2-methyl-2,3-dihydroindol-1-yl)-2-oxoethyl]-5-fluoro-6-morpholin-4-yl-3H-pyrimidin-4-one

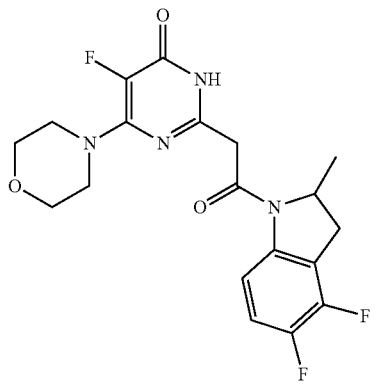 [SMILES: CC1Cc2c(ccc(F)c2F)N1C(=O)Cc1nc(N2CCOCC2)c(F)c(=O)[nH]1]

The product is prepared by following the procedure described in example 1a (step 5a) using 140 mg of sodium (5-fluoro-4-morpholin-4-yl-6-oxo-1,6-dihydropyrimidin-2-yl)acetate obtained in step 2a of example 6a and 93 mg of (−)-2-methyl-4,5-difluoro-2,3-dihydro-1H-indole (reference example 2a). After silica column purification: eluent 98/02 dichloromethane/methanol, 117 mg of 2-[2-((+)-4,5-difluoro-2-methyl-2,3-dihydroindol-1-yl)-2-oxoethyl]-5-fluoro-6-morpholin-4-yl-3H-pyrimidin-4-one are obtained in the form of a solid, the characteristics of which are the following:

$^1$H NMR spectrum (400 MHz, d in ppm, DMSO-d6): 1.29 (d, J=6.4 Hz, 3H); 2.82 (d, J=16.6 Hz, 1H); 3.40 (dd, J=8.6 and 16.6 Hz, 1H); 3.53 to 3.64 (m, 8H); 3.73 (d, J=16.1 Hz, 1H); 3.92 (d, J=16.1 Hz, 1H); 4.79 (m, 1H); 7.24 (m, 1H); 7.74 (d, J=9.0 Hz, 1H); 12.31 (broad m, 1H)

Mass spectrometry: method A
Retention time Tr (min)=0.81; [M+H]+: m/z 409; [M−H]−: m/z 407
Optical rotation: $\alpha_D$=+76.3+/−1.3. C=2.144 mg/0.5 ml DMSO

Example 22a

Synthesis of 5-fluoro-2-[2-((+)-4-fluoro-2-methyl-2,3-dihydroindol-1-yl)-2-oxoethyl]-3-methyl-6-morpholin-4-yl-3H-pyrimidin-4-one

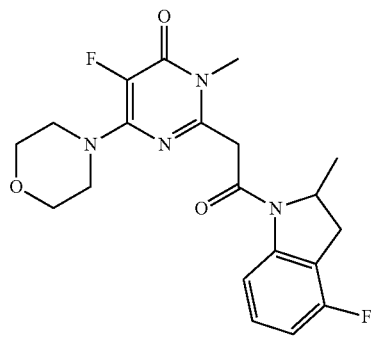 [SMILES: CC1Cc2c(F)cccc2N1C(=O)Cc1nc(N2CCOCC2)c(F)c(=O)n1C]

The product is prepared by following the procedure described in example 1a (step 5a) using 133 mg of sodium (5-fluoro-1-methyl-4-morpholin-4-yl-6-oxo-1,6-dihydropyrimidin-2-yl)acetate obtained in step 2a of example 8a and 75 mg of (−)-2-methyl-4-fluoro-2,3-dihydro-1H-indole (reference example 5a). After silica column purification: eluent 98/02 dichloromethane/methanol, 78 mg of 5-fluoro-2-[2-((+)-4-fluoro-2-methyl-2,3-dihydroindol-1-yl)-2-oxoethyl]-3-methyl-6-morpholin-4-yl-3H-pyrimidin-4-one are obtained in the form of a solid, the characteristics of which are the following:

$^1$H NMR spectrum (400 MHz, d in ppm, DMSO-d6): 1.30 (d, J=6.3 Hz, 3H); 2.77 (d, J=16.1 Hz, 1H); 3.38 (m, 4H); 3.50 to 3.67 (m, 8H); 4.03 (d, J=16.9 Hz, 1H); 4.28 (d, J=16.9 Hz, 1H); 4.79 (m, 1H); 6.91 (t, J=8.6 Hz, 1H); 7.25 (m, 1H); 7.78 (d, J=8.6 Hz, 1H)

Mass spectrometry: method A
Retention time Tr (min)=0.82; [M+H]+: m/z 405; [M−H]−: m/z 403
Optical rotation: $\alpha_D$=+71.3+/−1.3. C=1.947 mg/0.5 ml DMSO

Example 23a

Synthesis of 5-fluoro-2-[2-((−)-4-fluoro-2-methyl-2,3-dihydroindol-1-yl)-2-oxoethyl]-3-methyl-6-morpholin-4-yl-3H-pyrimidin-4-one

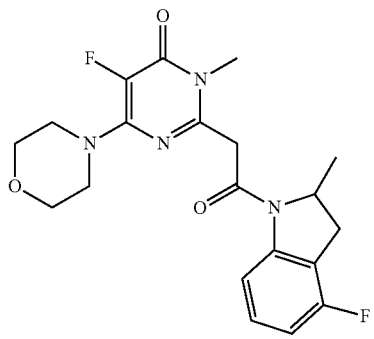 [SMILES: CC1Cc2c(F)cccc2N1C(=O)Cc1nc(N2CCOCC2)c(F)c(=O)n1C]

The product is prepared by following the procedure described in example 1a (step 5a) using 133 mg of sodium (5-fluoro-1-methyl-4-morpholin-4-yl-6-oxo-1,6-dihydropyrimidin-2-yl)acetate obtained in step 2a of example 8a and 75 mg of (+)-2-methyl-4-fluoro-2,3-dihydro-1H-indole (reference example 5a). After silica column purification: eluent 98/02 dichloromethane/methanol, 90 mg of 5-fluoro-2-[2-((−)-4-fluoro-2-methyl-2,3-dihydroindol-1-yl)-2-oxoethyl]-3-methyl-6-morpholin-4-yl-3H-pyrimidin-4-one are obtained in the form of a solid, the characteristics of which are the following:

$^1$H NMR spectrum (400 MHz, d in ppm, DMSO-d6): 1.30 (d, J=6.6 Hz, 3H); 2.77 (d, J=16.3 Hz, 1H); 3.38 (m, 4H); 3.51 to 3.63 (m, 8H); 4.03 (d, J=16.6 Hz, 1H); 4.28 (d, J=16.6 Hz, 1H); 4.78 (m, 1H); 6.91 (t, J=8.6 Hz, 1H); 7.24 (m, 1H); 7.78 (d, J=8.6 Hz, 1H)

Mass spectrometry: method A

Retention time Tr (min)=0.82; [M+H]+: m/z 405; [2M+Na]+: m/z 831

(base peak); [M−H]−: m/z 403

Optical rotation $\alpha_D$=−54.6+/−1.1. C=2.168 mg/0.5 ml DMSO

Example 24a

Synthesis of 5-fluoro-2-[2-((−)-4,5-difluoro-2-methyl-2,3-dihydroindol-1-yl)-2-oxoethyl]-3-methyl-6-morpholin-4-yl-3H-pyrimidin-4-one

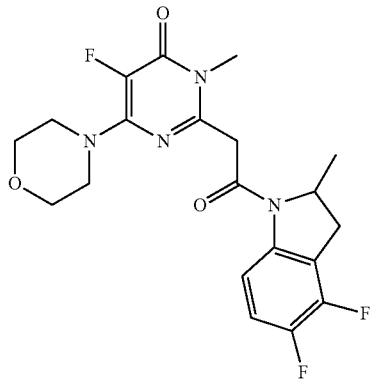 [SMILES: CC1Cc2c(ccc(F)c2F)N1C(=O)Cc1nc(N2CCOCC2)c(F)c(=O)n1C]

The product is prepared by following the procedure described in example 1a (step 5a) using 80 mg of sodium (5-fluoro-1-methyl-4-morpholin-4-yl-6-oxo-1,6-dihydropyrimidin-2-yl)acetate obtained in step 2a of example 8a and 51 mg of (+)-2-methyl-4,5-difluoro-2,3-dihydro-1H-indole (reference example 2a). After silica column purification: eluent 98/02 dichloromethane/methanol, 54 mg of 5-fluoro-2-[2-((−)-4,5-difluoro-2-methyl-2,3-dihydroindol-1-yl)-2-oxoethyl]-3-methyl-6-morpholin-4-yl-3H-pyrimidin-4-one are obtained in the form of a solid, the characteristics of which are the following:

$^1$H NMR spectrum (400 MHz, d in ppm, DMSO-d6): 1.31 (d, J=6.4 Hz, 3H); 2.83 (d, J=16.3 Hz, 1H); 3.37 (s, 3H); 3.42 (dd, J=8.6 and 16.3 Hz, 1H); 3.51 to 3.66 (m, 8H); 4.02 (d, J=16.9 Hz, 1H); 4.27 (d, J=16.9 Hz, 1H); 4.80 (m, 1H); 7.25 (m, 1H); 7.73 (dd, J=4.1 and 9.1 Hz, 1H)

Mass spectrometry: method A

Retention time Tr (min)=0.86; [M+H]+: m/z 423; [M−H]−: m/z 421

Optical rotation: $\alpha_D$=−56.0+/−1.1. C=2.060 mg/0.5 ml DMSO

Example 25a

Synthesis of 5-fluoro-2-[2-((+)-4,5-difluoro-2-methyl-2,3-dihydroindol-1-yl)-2-oxoethyl]-3-methyl-6-morpholin-4-yl-3H-pyrimidin-4-one

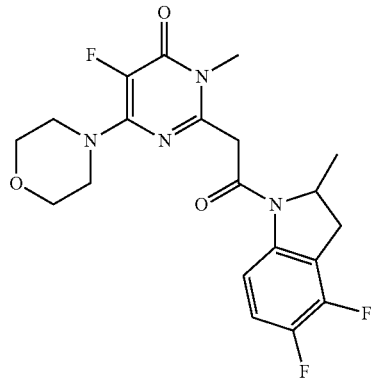 [SMILES: CC1Cc2c(ccc(F)c2F)N1C(=O)Cc1nc(N2CCOCC2)c(F)c(=O)n1C]

The product is prepared by following the procedure described in example 1a (step 5a) using 80 mg of sodium (5-fluoro-1-methyl-4-morpholin-4-yl-6-oxo-1,6-dihydropyrimidin-2-yl)acetate obtained in step 2a of example 8a and 46 mg of (−)-2-methyl-4,5-difluoro-2,3-dihydro-1H-indole (reference example 2a). After silica column purification: eluent 98/02 dichloromethane/methanol, 53 mg of 5-fluoro-2-[2-((+)-4,5-difluoro-2-methyl-2,3-dihydroindol-1-yl)-2-oxoethyl]-3-methyl-6-morpholin-4-yl-3H-pyrimidin-4-one are obtained in the form of a solid, the characteristics of which are the following:

$^1$H NMR spectrum (400 MHz, d in ppm, DMSO-d6): 1.31 (d, J=6.4 Hz, 3H); 2.83 (d, J=16.3 Hz, 1H); 3.37 (s, 3H); 3.42 (dd, J=8.6 and 16.3 Hz, 1H); 3.52 to 3.65 (m, 8H); 4.02 (d, J=16.9 Hz, 1H); 4.27 (d, J=16.9 Hz, 1H); 4.75 to 4.85 (m, 1H); 7.25 (m, 1H); 7.73 (dd, J=4.0 and 9.0 Hz, 1H)

Mass spectrometry: method A

Retention time Tr (min)=0.86; [M+H]+: m/z 423; [M−H]−: m/z 421

Optical rotation: $\alpha_D$=+62.4+/−1.2. C=2.051 mg/0.5 ml DMSO

Example 26a

Synthesis of 5-fluoro-2-[2-((+)-5,6-difluoro-2-methyl-2,3-dihydroindol-1-yl)-2-oxoethyl]-3-methyl-6-morpholin-4-yl-3H-pyrimidin-4-one

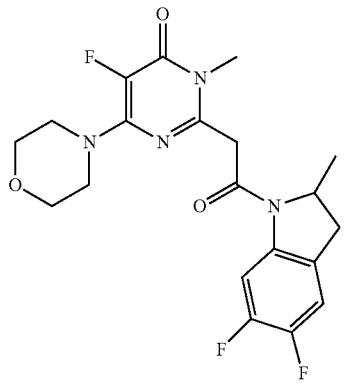 [SMILES: CC1Cc2cc(F)c(F)cc2N1C(=O)Cc1nc(N2CCOCC2)c(F)c(=O)n1C]

The product is prepared by following the procedure described in example 1a (step 5a) using 80 mg of sodium (5-fluoro-1-methyl-4-morpholin-4-yl-6-oxo-1,6-dihydropyrimidin-2-yl)acetate obtained in step 2a of example 8a and 46 mg of (−)-2-methyl-5,6-difluoro-2,3-dihydro-1H-indole (reference example 3a). After silica column purification: eluent 98/02 dichloromethane/methanol, 47 mg of 5-fluoro-2-[2-((+)-5,6-difluoro-2-methyl-2,3-dihydroindol-1-yl)-2-oxoethyl]-3-methyl-6-morpholin-4-yl-3H-pyrimidin-4-one are obtained in the form of a solid, the characteristics of which are the following:

$^1$H NMR spectrum (400 MHz, d in ppm, DMSO-d6): 1.28 (d, J=6.4 Hz, 3H); 2.68 (d, J=16.3 Hz, 1H); 3.38 (m, 4H); 3.51 to 3.67 (m, 8H); 4.02 (d, J=16.9 Hz, 1H); 4.27 (d, J=16.9 Hz, 1H); 4.74 (m, 1H); 7.40 (t, J=8.5 Hz, 1H); 7.89 (dd, J=7.5 and 12.1 Hz, 1H)

Mass spectrometry: method A
Retention time Tr (min)=0.85; [M+H]+: m/z 423; [M−H]−: m/z 421
Optical rotation: α$_D$=+51.5+/−0.9. C=2.396 mg/0.5 ml DMSO

Example 27a

Synthesis of 5-fluoro-2-[2-((−)-5,6-difluoro-2-methyl-2,3-dihydroindol-1-yl)-2-oxoethyl]-3-methyl-6-morpholin-4-yl-3H-pyrimidin-4-one

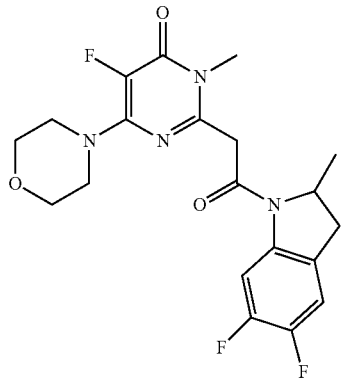 [SMILES: CC1Cc2cc(F)c(F)cc2N1C(=O)Cc1nc(N2CCOCC2)c(F)c(=O)n1C]

The product is prepared by following the procedure described in example 1a (step 5a) using 80 mg of sodium (5-fluoro-1-methyl-4-morpholin-4-yl-6-oxo-1,6-dihydropyrimidin-2-yl)acetate obtained in step 2a of example 8a and 51 mg of (+)-2-methyl-5,6-difluoro-2,3-dihydro-1H-indole (reference example 3a). After silica column purification: eluent 98/02 dichloromethane/methanol, 55 mg of 5-fluoro-2-[2-((−)-5,6-difluoro-2-methyl-2,3-dihydroindol-1-yl)-2-oxoethyl]-3-methyl-6-morpholin-4-yl-3H-pyrimidin-4-one are obtained in the form of a solid, the characteristics of which are the following:

$^1$H NMR spectrum (400 MHz, d in ppm, DMSO-d6): 1.28 (d, J=6.6 Hz, 3H); 2.69 (d, J=16.3 Hz, 1H); 3.38 (m, 4H); 3.52 to 3.66 (m, 8H); 4.02 (d, J=16.9 Hz, 1H); 4.27 (d, J=16.9 Hz, 1H); 4.74 (m, 1H); 7.40 (t, J=8.5 Hz, 1H); 7.89 (dd, J=7.6 and 12.2 Hz, 1H)

Mass spectrometry: method A
Retention time Tr (min)=0.85; [M+H]+: m/z 423; [M−H]−: m/z 421
Optical rotation: α$_D$=−44.9+/−0.9. C=2.387 mg/0.5 ml DMSO

Example 28a and Example 29a

Synthesis, of 5-fluoro-2-[2-((+)-4-chloro-2-methyl-2,3-dihydroindol-1-yl)-2-oxoethyl]-3-methyl-6-morpholin-4-yl-3H-pyrimidin-4-one and 5-fluoro-2-[2-((−)-4-chloro-2-methyl-2,3-dihydroindol-1-yl)-2-oxoethyl]-3-methyl-6-morpholin-4-yl-3H-pyrimidin-4-one

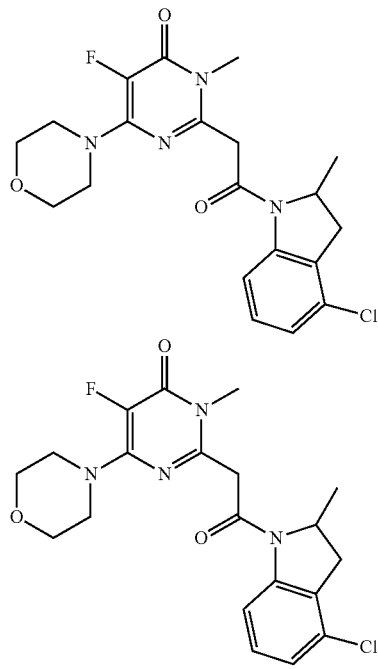

5-Fluoro-2-[2-(4-chloro-2-methyl-2,3-dihydroindol-1-yl)-2-oxoethyl]-3-methyl-6-morpholin-4-yl-3H-pyrimidin-4-one is prepared by following the procedure described in example 1a (step 5a) using 220 mg of sodium (5-fluoro-1-methyl-4-morpholin-4-yl-6-oxo-1,6-dihydropyrimidin-2-yl)acetate obtained in step 2a of example 8a and 120 mg of 4-chloro-2-methyl-2,3-dihydro-1H-indole [which can be prepared according to U.S. Pat. No. 4,416,884 (1983)]. After purification, 151 mg of 5-fluoro-2-[2-(4-chloro-2-methyl-2,3-dihydroindol-1-yl)-2-oxoethyl]-3-methyl-6-morpholin-4-yl-3H-pyrimidin-4-one are obtained in the form of a solid which will be separated, on a chiral column, into its two enantiomers.

¹H NMR spectrum (400 MHz, d in ppm, DMSO-d6): 1.31 (d, J=6.4 Hz, 3H); 2.74 (d, J=16.3 Hz, 1H); 3.37 (m, 4H); 3.50 to 3.62 (m, 8H); 4.03 (d, J=16.9 Hz, 1H); 4.28 (d, J=16.9 Hz, 1H); 4.75 (m, 1H); 7.13 (d, J=8.3 Hz, 1H); 7.24 (t, J=8.3 Hz, 1H); 7.90 (d, J=8.3 Hz, 1H)

The enantiomers are separated by chiral column chromatography:

Stationary phase: Whelk 01 SS phase, 5 μm; mobile phase: heptane (50%)/dichloromethane (35%)/methanol (15%); flow rate: 43 ml/min.

The dextrorotatory enantiomer is concentrated so as to obtain 81 mg of 5-fluoro-2-[2-((+)-4-chloro-2-methyl-2,3-dihydroindol-1-yl)-2-oxoethyl]-3-methyl-6-morpholin-4-yl-3H-pyrimidin-4-one in the form of a white solid, the characteristics of which are the following:

¹H NMR spectrum (400 MHz, d in ppm, DMSO-d6): 1.31 (d, J=6.4 Hz, 3H); 2.74 (d, J=16.3 Hz, 1H); 3.39 (m, 4H); 3.51 to 3.62 (m, 8H); 4.03 (d, J=17.1 Hz, 1H); 4.28 (d, J=17.1 Hz, 1H); 4.76 (m, 1H); 7.13 (d, J=8.1 Hz, 1H); 7.24 (t, J=8.1 Hz, 1H); 7.90 (broad d, J=8.1 Hz, 1H)

Mass spectrometry: method A

Retention time Tr (min)=0.90; [M+H]+: m/z 421; [M−H]−: m/z 419

Optical rotation: $\alpha_D$=+85. C=0.806 mg/0.5 ml DMSO

The levorotatory enantiomer is concentrated so as to obtain 81 mg of 5-fluoro-2-[2-((−)-4-chloro-2-methyl-2,3-dihydroindol-1-yl)-2-oxoethyl]-6-morpholin-4-yl-3H-pyrimidin-4-one in the form of a white solid, the characteristics of which are the following:

¹H NMR spectrum (400 MHz, d in ppm, DMSO-d6): 1.31 (d, J=6.4 Hz, 3H); 2.73 (d, J=16.3 Hz, 1H); 3.39 (m, 4H); 3.51 to 3.62 (m, 8H); 4.03 (d, J=17.1 Hz, 1H); 4.28 (d, J=17.1 Hz, 1H); 4.76 (m, 1H); 7.13 (d, J=8.1 Hz, 1H); 7.24 (t, J=8.1 Hz, 1H); 7.90 (broad d, J=8.1 Hz, 1H)

Mass spectrometry: method A

Retention time Tr (min)=0.90; [M+H]+: m/z 421; [M−H]−: m/z 419

Optical rotation: $\alpha_D$=−83. C=1.340 mg/0.5 ml DMSO

Example 30a and Example 31a

Synthesis of 5-fluoro-2-[2-((+)-4-bromo-2-methyl-2,3-dihydroindol-1-yl)-2-oxoethyl]-3-methyl-6-morpholin-4-yl-3H-pyrimidin-4-one and 5-fluoro-2-[2-((−)-4-bromo-2-methyl-2,3-dihydroindol-1-yl)-2-oxoethyl]-3-methyl-6-morpholin-4-yl-3H-pyrimidin-4-one

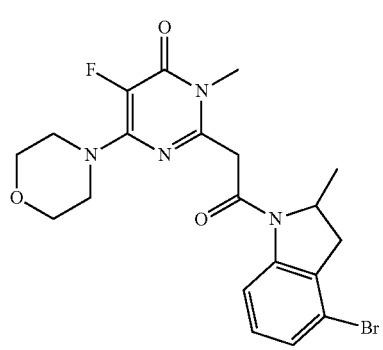

-continued

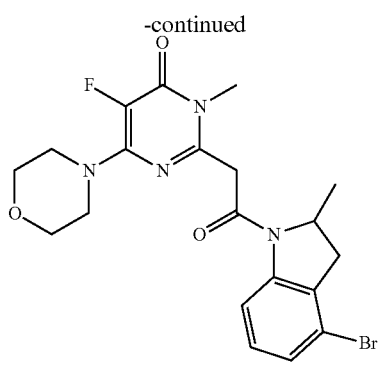

5-Fluoro-2-[2-(4-bromo-2-methyl-2,3-dihydroindol-1-yl)-2-oxoethyl]-3-methyl-6-morpholin-4-yl-3H-pyrimidin-4-one is prepared by following the procedure described in example 1a (step 5a) using 200 mg of sodium (5-fluoro-1-methyl-4-morpholin-4-yl-6-oxo-1,6-dihydropyrimidin-2-yl)acetate obtained in step 2a of example 8a and 104 mg of 4-bromo-2-methyl-2,3-dihydro-1H-indole (reference example 4a). After purification, 154 mg of 5-fluoro-2-[2-(4-bromo-2-methyl-2,3-dihydroindol-1-yl)-2-oxoethyl]-3-methyl-6-morpholin-4-yl-3H-pyrimidin-4-one are obtained in the form of a solid which will be separated, on a chiral column, into its two enantiomers.

Mass spectrometry: method A

Retention time Tr (min)=0.93; [M+H]+: m/z 465; [M−H]−: m/z 463

The enantiomers are separated by chiral column chromatography:

Stationary phase: 5 μm Kromasil-grafted Whelk; mobile phase: heptane (50%)/dichloromethane (30%)/methanol (10%)/ethanol (10%); flow rate: 43 ml/min.

The dextrorotatory enantiomer is concentrated so as to obtain 45 mg of 5-fluoro-2-[2-((+)-4-bromo-2-methyl-2,3-dihydroindol-1-yl)-2-oxoethyl]-3-methyl-6-morpholin-4-yl-3H-pyrimidin-4-one in the form of a white solid, the characteristics of which are the following:

¹H NMR spectrum (500 MHz, d in ppm, DMSO-d6): 1.31 (t, J=6.4 Hz, 3H); 2.68 (d, J=16.3 Hz, 1H); 3.38 (m, 4H); 3.50 to 3.62 (m, 8H); 4.03 (d, J=16.6 Hz, 1H); 4.28 (d, J=16.6 Hz, 1H); 4.74 (m, 1H); 7.17 (t, J=8.3 Hz, 1H); 7.27 (d, J=8.3 Hz, 1H); 7.94 (d, J=8.3 Hz, 1H)

Mass spectrometry: method A

Retention time Tr (min)=0.93; [M+H]+: m/z 465; [M−H]−: m/z 463

The levorotatory enantiomer is concentrated so as to obtain 54 mg of 5-fluoro-2-[2-((−)-4-bromo-2-methyl-2,3-dihydroindol-1-yl)-2-oxoethyl]-6-morpholin-4-yl-3H-pyrimidin-4-one in the form of a white solid, the characteristics of which are the following:

¹H NMR spectrum (500 MHz, d in ppm, DMSO-d6): 1.31 (d, J=6.3 Hz, 3H); 2.68 (d, J=16.3 Hz, 1H); 3.37 (m, 4H); 3.50 to 3.63 (m, 8H); 4.03 (d, J=16.6 Hz, 1H); 4.28 (d, J=16.6 Hz, 1H); 4.74 (m, 1H); 7.17 (t, J=8.3 Hz, 1H); 7.27 (d, J=8.3 Hz, 1H); 7.94 (d, J=8.3 Hz, 1H)

Mass spectrometry: method A

Retention time Tr (min)=0.93; [M+H]+: m/z 465; [M−H]−: m/z 463

Example 32a 5-fluoro-2-[2-((−)-6-fluoro-2-methyl-2,3-dihydroindol-1-yl)-2-oxoethyl]-6-morpholin-4-yl-3H-pyrimidin-4-one

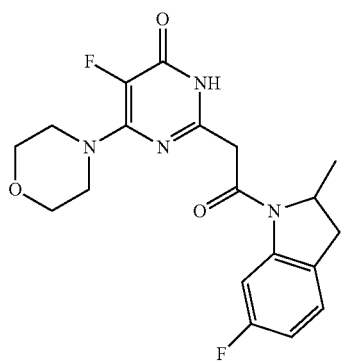 [SMILES: CC1Cc2ccc(F)cc2N1C(=O)Cc1nc(N2CCOCC2)c(F)c(=O)[nH]1]

The product is prepared by following the procedure described in example 1a (step 5a) using 123 mg of sodium (5-fluoro-4-morpholin-4-yl-6-oxo-1,6-dihydropyrimidin-2-yl)acetate obtained in step 2a of example 6a and 62 mg of (+)-2-methyl-6-fluoro-2,3-dihydro-1H-indole (reference example 6a). After silica column purification: eluent 98/02 dichloromethane/methanol, 84 mg of 5-fluoro-2-[2-((−)-6-fluoro-2-methyl-2,3-dihydroindol-1-yl)-2-oxoethyl]-6-morpholin-4-yl-3H-pyrimidin-4-one are obtained in the form of a solid, the characteristics of which are the following:

$^1$H NMR spectrum (400 MHz, d in ppm, DMSO-d6): 126 (d, J=6.4 Hz, 3H); 2.67 (d, J=16.3 Hz, 1H); 327 to 3.38 (partially masked m, 1H); 3.53 to 3.65 (m, 8H); 3.74 (d, J=15.9 Hz, 1H); 3.94 (d, J=15.9 Hz, 1H); 4.74 (m, 1H); 6.87 (ddd, J=2.6 and 8.3 and 9.2 Hz, 1H); 7.29 (dd, J=5.7 and 8.3 Hz, 1H); 7.71 (broad d, J=11.0 Hz, 1H); 12.31 (broad m, 1H)

Mass spectrometry: method A

Retention time Tr (min)=0.76; [M+H]+: m/z 391; [M−H]−: m/z 389

Optical rotation $\alpha_D$=−65.5+/−1.3. C=1.798 mg/0.5 ml DMSO

Example 33a

5-Fluoro-2-[2-((+)-6-fluoro-2-methyl-2,3-dihydroindol-1-yl)-2-oxoethyl]-6-morpholin-4-yl-3H-pyrimidin-4-one

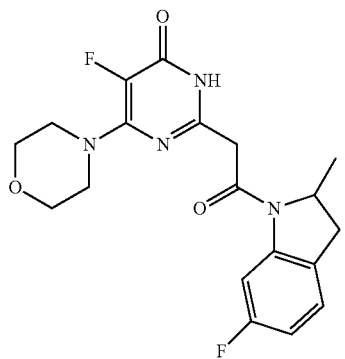 [SMILES: CC1Cc2ccc(F)cc2N1C(=O)Cc1nc(N2CCOCC2)c(F)c(=O)[nH]1]

The product is prepared by following the procedure described in example 1a (step 5a) using 123 mg of sodium (5-fluoro-4-morpholin-4-yl-6-oxo-1,6-dihydropyrimidin-2-yl)acetate obtained in step 2a of example 6a and 62 mg of (−)-2-methyl-6-fluoro-2,3-dihydro-1H-indole (reference example 6a). After silica column purification: eluent 98/02 dichloromethane/methanol, 74 mg of 5-fluoro-2-[2-((+)-6-fluoro-2-methyl-2,3-dihydroindol-1-yl)-2-oxoethyl]-6-morpholin-4-yl-3H-pyrimidin-4-one are obtained in the form of a solid, the characteristics of which are the following:

$^1$H NMR spectrum (400 MHz, d in ppm, DMSO-d6): 1.26 (d, J=6.6 Hz, 3H); 2.67 (d, J=16.3 Hz, 1H); 3.25 to 3.38 (partially masked m, 1H); 3.52 to 3.66 (m, 8H); 3.73 (d, J=16.4 Hz, 1H); 3.94 (d, J=16.4 Hz, 1H); 4.74 (m, 1H); 6.87 (ddd, J=2.6 and 8.3 and 9.2 Hz, 1H); 7.29 (dd, J=5.7 and 8.3 Hz, 1H); 7.71 (broad d, J=11.0 Hz, 1H); 12.30 (broad m, 1H)

Mass spectrometry: method A

Retention time Tr (min)=0.76; [M+H]+: m/z 391; [M−H]−: m/z 389

Optical rotation: $\alpha_D$=+72.1+/−1.3. C=2.018 mg/0.5 ml DMSO

Example 34a

5-Fluoro-2-[2-(4-chloro-5-fluoro-2-methyl-2,3-dihydroindol-1-yl)-2-oxoethyl]-6-morpholin-4-yl-3H-pyrimidin-4-one

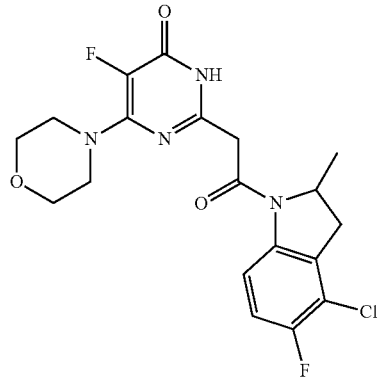 [SMILES: CC1Cc2c(ccc(F)c2Cl)N1C(=O)Cc1nc(N2CCOCC2)c(F)c(=O)[nH]1]

The product is prepared by following the procedure described in example 1a (step 5a) using 91 mg of sodium (5-fluoro-4-morpholin-4-yl-6-oxo-1,6-dihydropyrimidin-2-yl)acetate and 55 mg of 4-chloro-5-fluoro-2-methyl-2,3-dihydro-1H-indole. After purification, 44 mg of 2-[2-(4-chloro-5-fluoro-2-methyl-2,3-dihydroindol-1-yl)-2-oxoethyl]-3-methyl-6-morpholin-4-yl-3H-pyrimidin-4-one are obtained in the form of a solid, the characteristics of which are the following:

$^1$H NMR spectrum (400 MHz, d in ppm, DMSO-d6): 1.30 (d, J=6.4 Hz, 3H); 2.76 (d, J=17.4 Hz, 1H); 3.41 (dd, J=8.6 and 17.4 Hz, 1H); 3.52 to 3.65 (m, 8H); 3.73 (d, J=16.1 Hz, 1H); 3.92 (d, J=16.1 Hz, 1H); 4.78 (m, 1H); 7.24 (t, J=9.4 Hz, 1H); 7.90 (broad m, 1H); 12.31 (broad m, 1H)

Mass spectrometry: method A

Retention time Tr (min)=0.87; [M+H]+: m/z 425; [M−H]−: m/z 423

Example 35a

Synthesis of 5-chloro-2-[2-((S)-2-methyl-2,3-dihydroindol-1-yl)-2-oxoethyl]-6-morpholin-4-yl-3H-pyrimidin-4-one

Step 1a 4,5-Dichloro-6-methoxy-2-methylpyrimidine

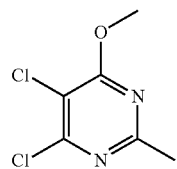

1.37 g of sodium methoxide are added to a solution of 5 g of 2-methyl-4,5,6-trichloropyrimidine in 41 ml of THF cooled to 5° C. in an ice bath. The ice bath is removed. The suspension is stirred at ambient temperature for 18 hours. The reaction medium is cooled to 5° C. in an ice bath. 20 ml of water and 100 ml of ethyl acetate are added. After settling out, the organic phase is dried over magnesium sulfate, filtered, and concentrated under reduced pressure so as to give 4.73 g of 4,5-dichloro-6-methoxy-2-methylpyrimidine in the form of a colorless oil which crystallizes, the characteristics of which are the following:

Mass spectrometry: method B
CI: [M+H]+: m/z 193

Step 2a (4,5-Dichloro-6-methoxypyrimidin-2-yl)acetic acid methyl ester

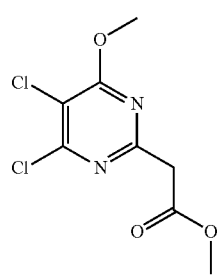

61 ml of 2M LDA (THF) are added dropwise to a solution of 4.7 g of 4,5-dichloro-6-methoxy-2-methylpyrimidine and 3.1 ml of methyl chloroformate in 65 ml of anhydrous THF cooled to −60° C. in a dry ice/MeOH bath.

The reaction medium is stirred at −60° C. for one hour.

The cooling bath is lowered so as to allow the temperature to rise to 22° C. The reaction medium is stirred at 22° C. for two hours.

20 ml of water and 150 ml of ethyl acetate are added. After settling out, the organic phase is dried over magnesium sulfate, filtered, and then concentrated under reduced pressure. The residue obtained is purified on a silica cartridge: eluent: DCM, so as to give 4.08 g of (4,5-dichloro-6-methoxypyrimidin-2-yl)acetic acid methyl ester in the form of a bright yellow oil, the characteristics of which are the following:

Mass spectrometry: method A
Retention time Tr (min)=0.88; [M+H]+: m/z 251; [M−H]−: m/z 249

Step 3a (5-Chloro-4-methoxy-6-morpholin-4-ylpyrimidin-2-yl)acetic acid methyl ester

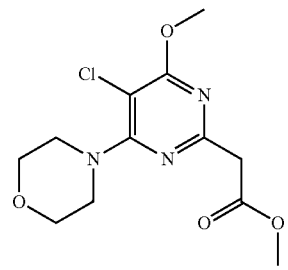 [SMILES: COC(=O)Cc1nc(OC)c(Cl)c(N2CCOCC2)n1]

A solution of 4.08 g of (4,5-dichloro-6-methoxypyrimidin-2-yl)acetic acid methyl ester in 35 ml of morpholine is stirred at ambient temperature for one and a half hours. The reaction medium is concentrated under reduced pressure. The residue obtained is taken up with 50 ml of water and 200 ml of ethyl acetate. After settling out, the organic phase is dried over magnesium sulfate, filtered, and then concentrated under reduced pressure so as to give 4.61 g of (5-chloro-4-methoxy-6-morpholin-4-ylpyrimidin-2-yl)acetic acid methyl ester in the form of a beige solid, the characteristics of which are the following:

Mass spectrometry: method A
Retention time Tr (min)=0.87; [M+H]+: m/z 302

Step 4a (5-Chloro-4-morpholin-4-yl-6-oxo-1,6-dihydropyrimidin-2-yl)acetic acid methyl ester

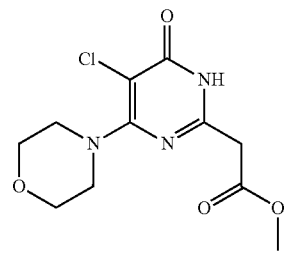 [SMILES: COC(=O)Cc1nc(N2CCOCC2)c(Cl)c(=O)[nH]1]

500 mg of (5-chloro-4-methoxy-6-morpholin-4-ylpyrimidin-2-yl)acetic acid methyl ester and 5 ml of 4N hydrochloric dioxane are placed in a microwave tube. After microwave irradiation for 30 minutes at a temperature of 110° C., the reaction medium is concentrated under reduced pressure. The residue obtained is taken up in ethyl ether. The solid formed is filtered off so as to give 414 mg of (5-chloro-4-morpholin-4-yl-6-oxo-1,6-dihydropyrimidin-2-yl)acetic acid methyl ester, the characteristics of which are the following:

Mass spectrometry: method A
Retention time Tr (min)=0.47; [M+H]+: m/z 288; [M−H]−: m/z 286; base peak: m/z 254

Step 5a

Sodium (5-chloro-4-morpholin-4-yl-6-oxo-1,6-dihydropyrimidin-2-yl)acetate

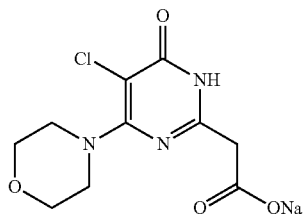

1.4 ml of 2N sodium hydroxide are added to a solution of 410 mg of (5-chloro-4-morpholin-4-yl-6-oxo-1,6-dihydropyrimidin-2-yl)acetic acid methyl ester in 3.6 ml of THF. The reaction medium is stirred at ambient temperature for 24 hours. The reaction medium is concentrated under reduced pressure. The residue obtained is oven-dried under vacuum in the presence of $P_2O_5$, so as to give 400 mg of sodium (5-chloro-4-morpholin-4-yl-6-oxo-1,6-dihydropyrimidin-2-yl)acetate, the characteristics of which are the following:

Mass spectrometry: method A
Retention time Tr (min)=0.37; [M+H]+: m/z 274; [2M+H]+: m/z 547 (base peak) [M–H]–: m/z 272; base peak: m/z 228

Alternatively, the sodium (5-chloro-4-morpholin-4-yl-6-oxo-1,6-dihydropyrimidin-2-yl)acetate compound can be obtained in two steps:

Step (5'a)a (5-Chloro-4-morpholin-4-yl-6-oxo-1,6-dihydropyrimidin-2-yl)acetic acid ethyl ester

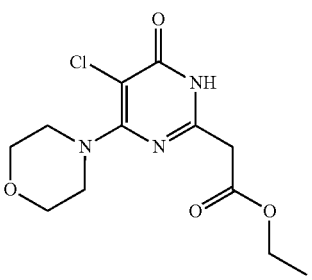 [SMILES: CCOC(=O)Cc1nc(N2CCOCC2)c(Cl)c(=O)[nH]1]

1.87 g of N-chlorosuccinimide are added to a solution of 3.75 g of ethyl [4-(morpholin-4-yl)-6-oxo-1,6-dihydropyrimidin-2-yl]acetate described in example 6a (step (2'a)a) in 50 ml of chloroform. The reaction medium is stirred at ambient temperature for 2 hours. 20 ml of water and 50 ml of dichloromethane are added. After settling out, the organic phase is dried over magnesium sulfate, filtered, and then concentrated under reduced pressure. The residue obtained is purified on a silica column, eluent: 99/01 then 98/02 then 97/03 dichloromethane/methanol, so as to give 2.81 g of (5-chloro-4-morpholin-4-yl-6-oxo-1,6-dihydropyrimidin-2-yl)acetic acid ethyl ester, the characteristics of which are the following:

Mass spectrometry: method A
Retention time Tr (min)=0.56; [M+H]+: m/z 302; [M–H]–: m/z 300; base peak: m/z 254

Step (5'b)a

Sodium (5-chloro-4-morpholin-4-yl-6-oxo-1,6-dihydropyrimidin-2-yl)acetate

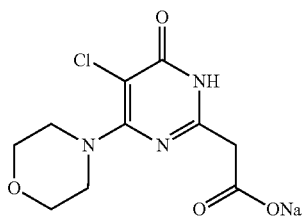

2.8 ml of 2N sodium hydroxide are added to a solution of 800 mg of (5-chloro-4-morpholin-4-yl-6-oxo-1,6-dihydropyrimidin-2-yl)acetic acid ethyl ester in 7.2 ml of THF. The reaction medium is stirred at ambient temperature for 24 hours. The reaction medium is concentrated under reduced pressure. The residue obtained is oven-dried under vacuum in the presence of $P_2O_5$, so as to give 750 mg of sodium (5-chloro-4-morpholin-4-yl-6-oxo-1,6-dihydropyrimidin-2-yl)acetate, the characteristics of which are the following:

Mass spectrometry: method A
Retention time Tr (min)=0.37; [M+H]+: m/z 274; [2M+H]+: m/z 547 (base peak) [M–H]–: m/z 272; base peak: m/z 228

Step 6a

5-Chloro-2-[2-((S)-2-methyl-2,3-dihydroindol-1-yl)-2-oxoethyl]-6-morpholin-4-yl-3H-pyrimidin-4-one

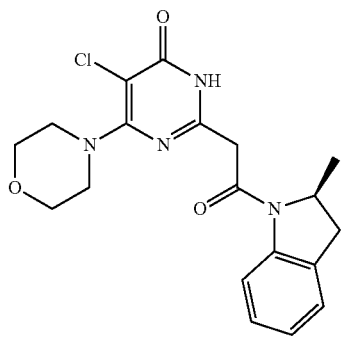 [SMILES: C[C@H]1Cc2ccccc2N1C(=O)Cc1nc(N2CCOCC2)c(Cl)c(=O)[nH]1]

The product is prepared by following the procedure described in example 1a (step 5a) using 220 mg of sodium (5-chloro-4-morpholin-4-yl-6-oxo-1,6-dihydropyrimidin-2-yl)acetate and 110 mg of (S)-2-methyl-4-fluoro-2,3-dihydro-1H-indole (which can be prepared according to Krasnov, V. P. et al. (Mendeleev Commun. 2002, 12(1), 27-28)). After silica column purification: eluent 99/01 then 98/02 then 97/03 dichloromethane/methanol, 99 mg of 5-chloro-2-[2-((S)-2-methyl-4-fluoro-2,3-dihydroindol-1-yl)-2-oxoethyl]-6-morpholin-4-yl-3H-pyrimidin-4-one are obtained in the form of a solid, the characteristics of which are the following:

$^1$H NMR spectrum (400 MHz): 1.26 (broad d, J=6.4 Hz, 3H); 2.69 (d, J=16.3 Hz, 1H); 3.38 (m, 1H); 3.50 to 3.65 (m, 8H); 3.76 (d, J=15.9 Hz, 1H); 3.97 (d, J=15.9 Hz, 1H); 4.70 (m, 1H); 7.05 (t, J=8.1 Hz, 1H); 7.18 (t, J=8.1 Hz, 1H); 7.29 (d, J=8.1 Hz, 1H); 7.95 (d, J=8.1 Hz, 1H); 12.42 (broad m, 1H)

Mass spectrometry: method A

Retention time Tr (min)=0.77; [M+H]+: m/z 389; [M−H]−: m/z 387

Optical rotation: α_D=+74.1+/−1.4. C=1.696 mg/0.5 ml DMSO

Alternatively, the 5-chloro-2-[2-((S)-2-methyl-2,3-dihydroindol-1-yl)-2-oxoethyl]-6-morpholin-4-yl-3H-pyrimidin-4-one compound can be obtained in three steps:

Step (6'a)a

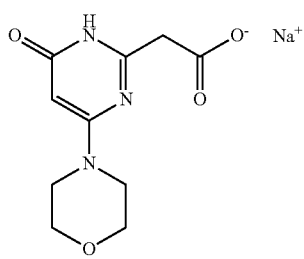 [SMILES: O=C([O-])Cc1nc(N2CCOCC2)cc(=O)[nH]1 ; [Na+]]

18.7 ml of 2M sodium hydroxide are added to a solution of 10 g of ethyl [4-(morpholin-4-yl)-6-oxo-1,6-dihydropyrimidin-2-yl]acetate described in example 6a (step (2'a)a) in 300 ml of tetrahydrofuran. The reaction mixture is stirred for 48 hours at ambient temperature. The precipitate formed is filtered off through sintered glass, washed with ethyl acetate and rinsed several times with ethyl ether. The solid obtained is then dried in a rotary evaporator so as to give 8.7 g of sodium [4-(morpholin-4-yl)-6-oxo-1,6-dihydropyrimidin-2-yl]acetate in the form of a white solid, the characteristics of which are the following:

¹H NMR spectrum (400 MHz, d in ppm, DMSO-d6): 3.08 (s, 2H); 3.38 (t, J=4.6 Hz, 4H); 3.61 (t, J=4.6 Hz, 4H); 5.08 (s, 1H); 13.16 (broad s, 1H)

Mass spectrometry: method A

Retention time Tr (min)=0.29;

[M+H]+: m/z 240; [M−H]−: m/z 238

Step (6'b)a

Synthesis of 2-{2-[(2S)-2-methyl-2,3-dihydro-1H-indol-1-yl]-2-oxoethyl}-6-(morpholin-4-yl)pyrimidin-4(3H)-one and of 2-{2-[(2R)-2-methyl-2,3-dihydro-1H-indol-1-yl]-2-oxoethyl}-6-(morpholin-4-yl)pyrimidin-4(3H)-one

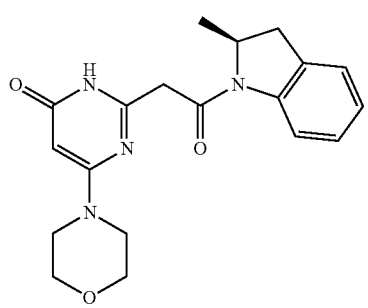

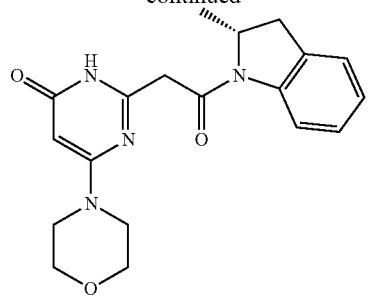

2-[2-(2-Methyl-2,3-dihydro-1H-indol-1-yl)-2-oxoethyl]-6-(morpholin-4-yl)pyrimidin-4(3H)-one is prepared by following the procedure described in example 1a (step 5a) using 500 mg of sodium [4-(morpholin-4-yl)-6-oxo-1,6-dihydropyrimidin-2-yl]acetate, 510 mg of 2-methyl-2,3-dihydro-1H-indole and 487 mg of N-[3-(dimethylamino)propyl]-N'-ethylcarbodiimide hydrochloride in a mixture of 0.308 ml of pyridine and 8 ml of N,N-dimethylformamide. 400 mg of 2-[2-(2-methyl-2,3-dihydro-1H-indol-1-yl)-2-oxoethyl]-6-(morpholin-4-yl)pyrimidin-4(3H)-one are obtained in the form of a white powder, the characteristics of which are the following:

¹H NMR spectrum (400 MHz):

1.26 (d, J=6.1 Hz, 3H); 2.65 to 2.72 (m, 1H); 3.18 to 3.44 (partially masked m, 5H); 3.54 to 3.63 (m, 4H); 3.72 (d, J=15.7 Hz, 1H); 3.92 (d, J=15.7 Hz, 1H); 4.71 (m, 1H); 5.20 (s, 1H); 7.04 (t, J=7.8 Hz, 1H); 7.18 (t, J=7.8 Hz, 1H); 7.29 (d, J=7.8 Hz, 1H); 7.96 (d, J=7.8 Hz, 1H); 11.69 (broad m, 1H)

Mass spectrometry: method A

Retention time Tr (min)=0.70;

[M+H]+: m/z 355; [M−H]−: m/z 353

Melting point (Kofler): 172° C.

The enantiomers are separated by chiral column chromatography: Chiralpak T304 20 μm chiral column (1080 g, 20 μm, 8/35 cm), eluent: acetonitrile/isopropanol: 90/10; flow rate: 185 ml/min. After purification, 160 mg of (+)-2-{2-[(2-methyl-2,3-dihydro-1H-indol-1-yl]-2-oxoethyl}-6-(morpholin-4-yl)pyrimidin-4(3H)-one are obtained, as first enantiomer, in the form of a pink amorphous solid, the characteristics of which are the following:

¹H NMR spectrum (400 MHz): for this batch, the signals are broad with: 1.26 (d, J=6.8 Hz, 3H); 2.44 (partially masked m, 1H); 2.69 (d, J=15.2 Hz, 1H); 3.42 (m, 4H); 3.60 (m, 4H); 3.72 (d, J=15.7 Hz, 1H); 3.92 (d, J=15.7 Hz, 1H); 4.72 (m, 1H); 5.20 (s, 1H); 7.04 (t, J=7.8 Hz, 1H); 7.18 (t, J=7.8 Hz, 1H); 7.28 (d, J=7.8 Hz, 1H); 7.96 (d, J=7.8 Hz, 1H); 11.67 (broad m, 1H)

Mass spectrometry: method A

Retention time Tr (min)=0.70;

[M+H]+: m/z 355; [M−H]−: m/z 353;

Optical rotation: α_D=+65.0°+/−1.3 (c=1.736 mg in 0.5 ml of methanol)

Then the second enantiomer is obtained, i.e.: 143 mg of (−)-2-{2-[(2-methyl-2,3-dihydro-1H-indol-1-yl]-2-oxoethyl}-6-(morpholin-4-yl)pyrimidin-4(3H)-one in the form of a white amorphous solid, the characteristics of which are the following:

¹H NMR spectrum (400 MHz): for this batch, the signals are broad with: 1.26 (d, J=6.8 Hz, 3H); 2.45 (partially masked m, 1H); 2.69 (m, 1H); 3.41 (m, 4H); 3.61 (m, 4H); 3.72 (d, J=15.7 Hz, 1H); 3.92 (d, J=15.7 Hz, 1H); 4.70 (m, 1H); 5.20 (s, 1H); 7.04 (t, J=7.8 Hz, 1H); 7.18 (t, J=7.8 Hz, 1H); 7.28 (d, J=7.8 Hz, 1H); 7.96 (d, J=7.8 Hz, 1H); 11.64 (broad m, 1H)

Mass spectrometry: method A

Retention time Tr (min)=0.70;

[M+H]+: m/z 355; [M−H]−: m/z 353;

Optical rotation: α_D=−72.8°+/−1.2 (c=2.338 mg in 0.5 ml of methanol)

Step (6'c)a

5-Chloro-2-[2-((S)-2-methyl-2,3-dihydroindol-1-yl)-2-oxoethyl]-6-morpholin-4-yl-3H-pyrimidin-4-one

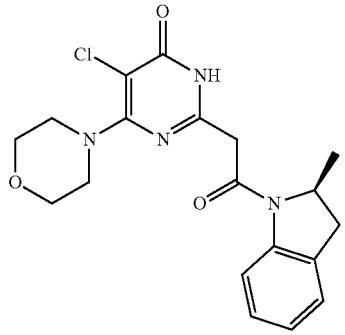 [SMILES: C[C@H]1Cc2ccccc2N1C(=O)Cc1nc(N2CCOCC2)c(Cl)c(=O)[nH]1]

37.6 mg of N-chlorosuccinimide are added to a solution of 100 mg of 2-{2-[(2S)-2-methyl-2,3-dihydro-1H-indol-1-yl]-2-oxoethyl}-6-(morpholin-4-yl)pyrimidin-4(3H)-one in 4 ml of chloroform. The reaction medium is stirred at ambient temperature for 2 hours. 5 ml of water and 20 ml of dichloromethane are added. After settling out, the organic phase is dried over magnesium sulfate, filtered, and then concentrated under reduced pressure. The residue obtained is purified on a silica column, eluent: 99/01 then 98/02 then 97/03 dichloromethane/methanol, so as to give 69 mg of 5-chloro-2-[2-((S)-2-methyl-2,3-dihydroindol-1-yl)-2-oxoethyl]-6-morpholin-4-yl-3H-pyrimidin-4-one, the characteristics of which are the following:

$^1$H NMR spectrum (400 MHz): 1.26 (broad d, J=6.4 Hz, 3H); 2.69 (d, J=16.3 Hz, 1H); 3.38 (m, 1H); 3.50 to 3.65 (m, 8H); 3.76 (d, J=15.9 Hz, 1H); 3.97 (d, J=15.9 Hz, 1H); 4.70 (m, 1H); 7.05 (t, J=8.1 Hz, 1H); 7.18 (t, J=8.1 Hz, 1H); 7.29 (d, J=8.1 Hz, 1H); 7.95 (d, J=8.1 Hz, 1H); 12.42 (broad m, 1H)

Mass spectrometry: method A

Retention time Tr (min)=0.77; [M+H]+: m/z 389; [M−H]−: m/z 387

Optical rotation: α_D=+74.1+/−1.4. C=1.696 mg/0.5 ml DMSO

Example 36a

Synthesis of 5-chloro-2-[2-((R)-2-methyl-2,3-dihydroindol-1-yl)-2-oxoethyl]-6-morpholin-4-yl-3H-pyrimidin-4-one

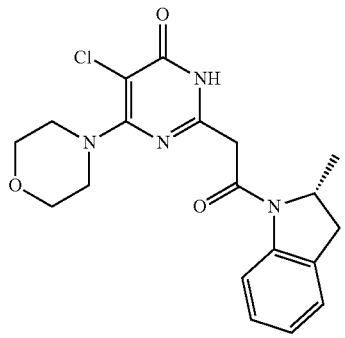 [SMILES: C[C@@H]1Cc2ccccc2N1C(=O)Cc1nc(N2CCOCC2)c(Cl)c(=O)[nH]1]

The product is prepared by following the procedure described in example 1a (step 5a) using 220 mg of sodium (5-chloro-4-morpholin-4-yl-6-oxo-1,6-dihydropyrimidin-2-yl)acetate and 110 mg of (R)-2-methyl-4-fluoro-2,3-dihydro-1H-indole (which can be prepared according to Krasnov, V. P. et al. (Mendeleev Commun. 2002, 12(1), 27-28)). After silica column purification: eluent 99/01 then 98/02 then 97/03 dichloromethane/methanol, 100 mg of 5-chloro-2-[2-((R)-2-methyl-4-fluoro-2,3-dihydroindol-1-yl)-2-oxoethyl]-6-morpholin-4-yl-3H-pyrimidin-4-one are obtained in the form of a solid, the characteristics of which are the following:

$^1$H NMR spectrum (400 MHz): 1.26 (broad d, J=6.4 Hz, 3H); 2.69 (d, J=16.3 Hz, 1H); 3.38 (m, 1H); 3.50 to 3.65 (m, 8H); 3.76 (d, J=15.9 Hz, 1H); 3.97 (d, J=15.9 Hz, 1H); 4.70 (m, 1H); 7.05 (t, J=8.1 Hz, 1H); 7.18 (t, J=8.1 Hz, 1H); 7.29 (d, J=8.1 Hz, 1H); 7.95 (d, J=8.1 Hz, 1H); 12.43 (broad m, 1H)

Mass spectrometry: method A

Retention time Tr (min)=0.77; [M+H]+: m/z 389; [M−H]−: m/z 387

Optical rotation: α_D=−79.4+/−1.4. C=1.858 mg/0.5 ml DMSO

Example 37a

Synthesis of 5-bromo-2-[2-((S)-2-methyl-2,3-dihydroindol-1-yl)-2-oxoethyl]-6-morpholin-4-yl-3H-pyrimidin-4-one

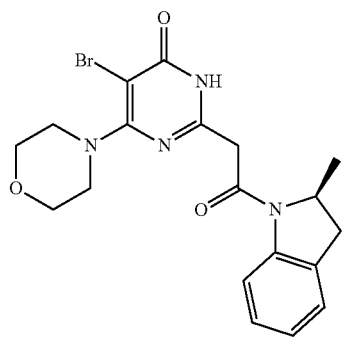 [SMILES: C[C@H]1Cc2ccccc2N1C(=O)Cc1nc(N2CCOCC2)c(Br)c(=O)[nH]1]

100 mg of N-bromosuccinimide are added to a solution of 200 mg of 2-{2-[(2S)-2-methyl-2,3-dihydro-1H-indol-1-yl]-2-oxoethyl}-6-(morpholin-4-yl)pyrimidin-4(3H)-one in 4 ml of chloroform. The reaction medium is stirred at ambient temperature for 2 hours. 5 ml of water and 30 ml of dichloromethane are added. After settling out, the organic phase is dried over magnesium sulfate, filtered, and then concentrated under reduced pressure. The residue obtained is purified on a silica column, eluent: 99/01 to 96/04 dichloromethane/methanol gradient, so as to give 93 mg of 5-bromo-2-[2-((S)-2-methyl-2,3-dihydroindol-1-yl)-2-oxoethyl]-6-morpholin-4-yl-3H-pyrimidin-4-one, the characteristics of which are the following:

$^1$H NMR spectrum (400 MHz, d in ppm, DMSO-d6): 1.27 (d, J=5.9 Hz, 3H); 2.63 to 2.75 (m, 2H); 3.53 (m, 4H); 3.61 (m, 4H); 3.77 (d, J=16.1 Hz, 1H); 3.97 (d, J=15.7 Hz, 1H); 4.71 (m, 1H); 7.05 (t, J=7.3 Hz, 1H); 7.18 (t, J=7.5 Hz, 1H); 7.29 (d, J=7.6 Hz, 1H); 7.95 (d, J=7.8 Hz, 1H); 12.42 (broad s, 1H)

Mass spectrometry: method A

Retention time Tr (min)=0.78;

[M+H]+: m/z 433; [M−H]−: m/z 431

Example 38a

5-Fluoro-2-[2-((+)-2-hydroxymethyl-2,3-dihydroindol-1-yl)-2-oxoethyl]-6-morpholin-4-yl-3H-pyrimidin-4-one

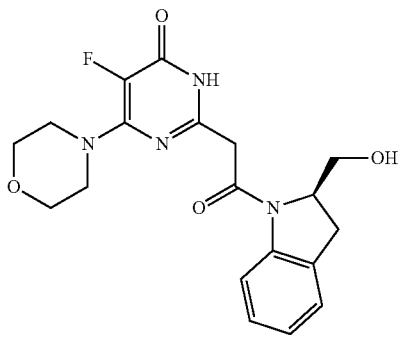 [SMILES: O=C(Cc1nc(N2CCOCC2)c(F)c(=O)[nH]1)N1c2ccccc2C[C@@H]1CO]

198 mg of N-[3-(dimethylamino)propyl]-N'-ethylcarbodiimide hydrochloride and 105 mg of (−)-(2,3-dihydro-1H-indol-2-yl)methanol (reference example 8a) are added to a solution of 207 mg of sodium (5-fluoro-4-morpholin-4-yl-6-oxo-1,6-dihydropyrimidin-2-yl)acetate in 6 ml of DMF and 6 ml of pyridine. The reaction medium is stirred at ambient temperature for 18 hours and then a mixture of water and dichloromethane is added. After settling out, the organic phase is dried over magnesium sulfate, filtered, and then concentrated under reduced pressure. The residue obtained is purified on a silica column, eluent: 95/05 dichloromethane/methanol, so as to give 77 mg of 5-fluoro-2-[2-((+)-2-hydroxymethyl-2,3-dihydroindol-1-yl)-2-oxoethyl]-6-morpholin-4-yl-3H-pyrimidin-4-one, the characteristics of which are the following:

$^1$H NMR spectrum (400 MHz, d in ppm, DMSO-d6): 2.86 (d, J=16.4 Hz, 1H); 3.23 (m, 1H); 3.38 (m, 1H); 3.45 to 3.57 (m, 5H); 3.63 (m, 4H); 3.82 (d, J=16.1 Hz, 1H); 4.01 (d, J=16.1 Hz, 1H); 4.61 (m, 1H); 5.13 (broad s, 1H); 7.03 (t, J=6.4 Hz, 1H); 7.16 (t, J=7.7 Hz, 1H); 7.26 (d, J=7.1 Hz, 1H); 7.93 (d, J=7.6 Hz, 1H); 12.25 (broad s, 1H)

Mass spectrometry: method A
Retention time Tr (min)=0.58;
[M+H]+: m/z 389; [M−H]−: m/z 387
Optical rotation: α$_D$=PR=+79.1+/−1.4. C=1.925 mg/0.5 ml DMSO

Example 39a

5-Fluoro-2-[2-((−)-2-hydroxymethyl-2,3-dihydroindol-1-yl)-2-oxoethyl]-6-morpholin-4-yl-3H-pyrimidin-4-one

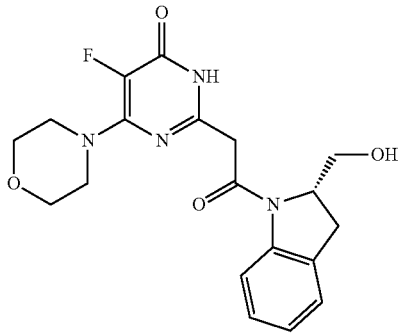 [SMILES: O=C(Cc1nc(N2CCOCC2)c(F)c(=O)[nH]1)N1c2ccccc2C[C@H]1CO]

471 mg of N-[3-(dimethylamino)propyl]-N'-ethylcarbodiimide hydrochloride and 258 mg of (+)-(2,3-dihydro-1H-indol-2-yl)methanol (reference example 8a) are added to a solution of 470 mg of sodium (5-fluoro-4-morpholin-4-yl-6-oxo-1,6-dihydropyrimidin-2-yl)acetate in 14 ml of DMF and 14 ml of pyridine. The reaction medium is stirred at ambient temperature for 18 hours then a mixture of water and dichloromethane is added. After settling out, the organic phase is dried over magnesium sulfate, filtered, and then concentrated under reduced pressure. The residue obtained is purified on a silica column, eluent: 95/05 dichloromethane/methanol, so as to give 280 mg of 5-fluoro-2-[2-((−)-2-hydroxymethyl-2,3-dihydroindol-1-yl)-2-oxoethyl]-6-morpholin-4-yl-3H-pyrimidin-4-one, the characteristics of which are the following:

$^1$H NMR spectrum (400 MHz, d in ppm, DMSO-d6): 2.86 (d, J=15.9 Hz, 1H); 3.23 (m, 1H); 3.36 (m, 1H); 3.50 (dd, J=6.8 and 11.0 Hz, 1H); 3.55 (m, 4H); 3.61 (m, 4H); 3.82 (d, J=15.9 Hz, 1H); 4.01 (d, J=16.1 Hz, 1H); 4.60 (m, 1H); 5.13 (broad s, 1H); 7.02 (m, 1H); 7.16 (t, J=7.6 Hz, 1H); 7.26 (d, J=7.1 Hz, 1H); 7.93 (d, J=8.1 Hz, 1H); 12.25 (broad s, 1H)

Mass spectrometry: method A
Retention time Tr (min)=0.58;
[M+H]+: m/z 389; [M−H]−: m/z 387

Reference Examples for Preparing the Compounds of Formula (Ia)

Reference Example 1a 5-fluoro-2-methyl-2,3-dihydro-1H-indole

Step 1a

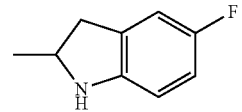

6.22 g of sodium cyanoborohydride are added, in four steps, to a solution of 5 g of 5-fluoro-2-methylindole in 60 ml of trifluoroacetic acid cooled to 5° C. The reaction medium is stirred at 0° C. for 30 minutes and then at ambient temperature for five hours.

The reaction medium is again cooled to 5° C. 700 ml of ice-cold water, 150 ml of 31% sodium hydroxide and then 300 ml of ethyl acetate are added. The reaction mixture is stirred at ambient temperature for one hour. After settling out, the organic phase is dried over magnesium sulfate, filtered, and then concentrated under reduced pressure. The residue obtained is purified on a silica column, eluent: 90/10 heptane/ethyl acetate, so as to give 2.14 g of 5-fluoro-2-methyl-2,3-dihydro-1H-indole, the characteristics of which are the following:

Mass spectrometry: method A
Retention time Tr (min)=0.24; [M+H]+: m/z 152;

Step 2a (R)-1-(5-Fluoro-2-methyl-2,3-dihydroindol-1-yl)-2-phenoxypropan-1-one: diastereoisomer A

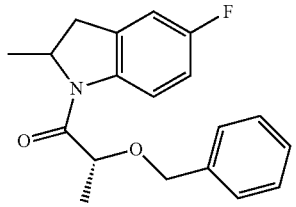 [SMILES: CC1Cc2cc(F)ccc2N1C(=O)[C@@H](C)OCc1ccccc1]

And (R)-1-(5-Fluoro-2-methyl-2,3-dihydroindol-1-yl)-2-phenoxypropan-1-one: diastereoisomer B

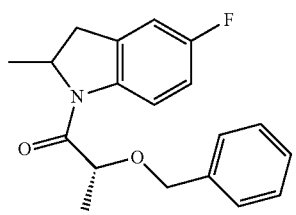 [SMILES: CC1Cc2cc(F)ccc2N1C(=O)[C@@H](C)OCc1ccccc1]

2.9 g of 5-Fluoro-2-methyl-2,3-dihydro-1H-indole and 5.3 g of N-[3-(dimethylamino)propyl]-N'-ethylcarbodiimide hydrochloride are added to a solution of 4.17 g of o-benzyl-D-lactic acid in 17 ml of DMF and 3.43 ml of pyridine.

The reaction medium is stirred at ambient temperature for 18 hours.

500 ml of ethyl acetate and 500 ml of water are added. After settling out, the organic phase is dried over magnesium sulfate, filtered, and then concentrated under reduced pressure. The residue obtained is purified on a silica cartridge: eluent: heptane, then 95/05 heptane/ethyl acetate, then 90/10 heptane/ethyl acetate, so as to give 2.8 g of (R)-1-(5-fluoro-2-methyl-2,3-dihydroindol-1-yl)-2-phenoxypropan-1-one: diastereoisomer A in the form of a yellow oil, the characteristics of which are the following:

Mass spectrometry: method A
Retention time Tr (min)=1.08;
[M+H]+: m/z 314

And 2.63 g of (R)-1-(5-fluoro-2-methyl-2,3-dihydroindol-1-yl)-2-phenoxpropan-1-one: diastereoisomer B in the form of a white solid, the characteristics of which are the following:
Mass spectrometry: method A
Retention time Tr (min)=1.06;
[M+H]+: m/z 314; base peak: m/z 242

Step (3a)a (+)-5-Fluoro-2-methyl-2,3-dihydro-1H-indole

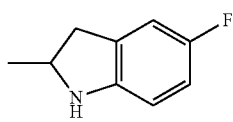

28 ml of 37% hydrochloric acid are added to a solution of 2.8 g of (R)-1-(5-fluoro-2-methyl-2,3-dihydroindol-1-yl)-2-phenoxypropan-1-one: diastereoisomer A.

The reaction medium is refluxed for 5 hours.

The reaction medium is concentrated under reduced pressure. The residue obtained is taken up with 260 ml of water. 2N sodium hydroxide is added until the pH=10. The medium is extracted with 200 ml of dichloromethane. After settling out, the organic phase is dried over magnesium sulfate, filtered, and then concentrated under reduced pressure. The residue obtained is purified on a silica cartridge: eluent: 90/10 heptane/ethyl acetate, so as to give 1.29 g of (+)-5-fluoro-2-methyl-2,3-dihydro-1H-indole in the form of a yellow oil, the characteristics of which are the following:

Mass spectrometry: method A
Retention time Tr (min)=0.25; [M+H]+: m/z 152
Optical rotation: $\alpha_D$=+8.2+/−0.7. C=1.801 mg/0.5 ml DMSO Step (3b)a (−)-5-Fluoro-2-methyl-2,3-dihydro-1H-indole

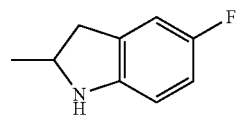

26.5 ml of 37% hydrochloric acid are added to a solution of 2.63 g of (R)-1-(5-fluoro-2-methyl-2,3-dihydroindol-1-yl)-2-phenoxypropan-1-one: diastereoisomer B.

The reaction medium is refluxed for 4 hours.

The reaction medium is concentrated under reduced pressure. The residue obtained is taken up with 250 ml of water. 2N sodium hydroxide is added until the pH=10. The medium is extracted with 200 ml of dichloromethane. After settling out, the organic phase is dried over magnesium sulfate, filtered, and then concentrated under reduced pressure. The residue obtained is purified on a silica cartridge: eluent: 90/10 heptane/ethyl acetate, so as to give 1.11 g of (−)-5-fluoro-2-methyl-2,3-dihydro-1H-indole in the form of a yellow oil, the characteristics of which are the following:

Mass spectrometry: method A
Retention time Tr (min)=0.24; [M+H]+: m/z 152;
Optical rotation: $\alpha_D$=−7.9+/−0.4. C=3.023 mg/0.5 ml DMSO Reference Example 2a 4,5-difluoro-2-methyl-2,3-dihydro-1H-indole Step 1a 4,5-Difluoro-2-methyl-2,3-dihydro-1H-indole

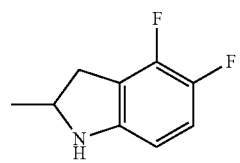

5.07 g of sodium cyanoborohydride are added, in 3 steps, to a solution of 4.5 g of 4,5-difluoro-2-methylindole in 180 ml of acetic acid cooled to 15° C. The reaction medium is stirred at 15° C. for 30 minutes and then at ambient temperature for 4 hours.

The reaction medium is again cooled to 5° C. Ice-cold water is added. 30% aqueous ammonia is added until the pH=9. The resulting mixture is extracted 3 times with dichloromethane. The organic phases are combined, dried over magnesium sulfate, filtered and then concentrated under reduced pressure. The residue obtained is purified on a silica column, eluent: 90/10 cyclohexane/ethyl acetate, so as to give 4.4 g of 4,5-difluoro-2-methyl-2,3-dihydro-1H-indole, the characteristics of which are the following:

Mass spectrometry: method A
Retention time Tr (min)=0.60; [M+H]+: m/z 170

Step 2a (R)-1-(4,5-Difluoro-2-methyl-2,3-dihydroindol-1-yl)-2-phenoxpropan-1-one: diastereoisomer A

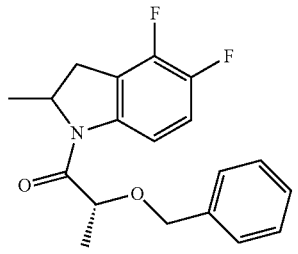 [SMILES: CC1Cc2c(ccc(F)c2F)N1C(=O)[C@@H](C)OCc1ccccc1]

And (R)-1-(4,5-Difluoro-2-methyl-2,3-dihydroindol-1-yl)-2-phenoxypropan-1-one: diastereoisomer B

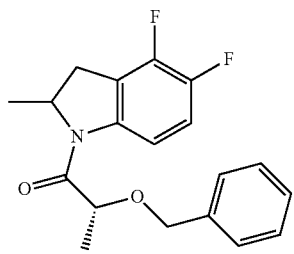 [SMILES: CC1Cc2c(ccc(F)c2F)N1C(=O)[C@@H](C)OCc1ccccc1]

The products are prepared by following the procedure described in reference example 1a (step 2a) using 4.4 g of 4,5-difluoro-2-methyl-2,3-dihydro-1H-indole and 5.62 g of o-benzyl-D-lactic acid. After silica column purification, eluent: 90/10 then 80/20 cyclohexane/ethyl acetate, 4.2 g of (R)-1-(4,5-difluoro-2-methyl-2,3-dihydroindol-1-yl)-2-phenoxypropan-1-one: diastereoisomer A are obtained in the form of a yellow oil, the characteristics of which are the following:

Mass spectrometry: method A
Retention time Tr (min)=1.11; [M+H]+: m/z 332; base peak: m/z 260
Optical rotation: $\alpha_D$=+41.6+/−0.9. C=2.266 mg/0.5 ml DMSO And 4.1 g of (R)-1-(4,5-difluoro-2-methyl-2,3-dihydroindol-1-yl)-2-phenoxypropan-1-one: diastereoisomer B are obtained in the form of a white solid, the characteristics of which are the following:

Mass spectrometry: method A
Retention time Tr (min)=1.10; [M+H]+: m/z 332; base peak: m/z 260
Optical rotation: $\alpha_D$=+120.1+/−1.8. C=2.252 mg/0.5 ml DMSO Step 3a (+)-4,5-Difluoro-2-methyl-2,3-dihydro-1H-indole

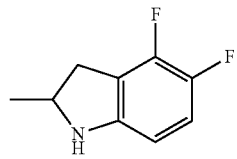

The product is prepared by following the procedure described in reference example 1a (step 3a) using 4.2 g of (R)-1-(4,5-difluoro-2-methyl-2,3-dihydroindol-1-yl)-2-phenoxypropan-1-one: diastereoisomer A and 40 ml of 37% hydrochloric acid.

After silica column purification, eluent: 90/10 cyclohexane/ethyl acetate, 1.6 g of (+)-4,5-difluoro-2-methyl-2,3-dihydro-1H-indole are obtained, the characteristics of which are the following:

Mass spectrometry: method A
Retention time Tr (min)=0.58; [M+H]+: m/z 170

Step 3a (−)-4,5-Difluoro-2-methyl-2,3-dihydro-1H-indole

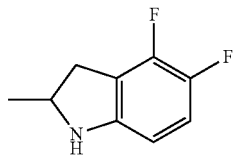

The product is prepared by following the procedure described in reference example 1a (step 3a) using 4.1 g of (R)-1-(4,5-difluoro-2-methyl-2,3-dihydroindol-1-yl)-2-phenoxypropan-1-one: diastereoisomer B and 41 ml of 37% hydrochloric acid.

After silica column purification, eluent: 90/10 heptane/ethyl acetate, 1.5 g of (−)-4,5-difluoro-2-methyl-2,3-dihydro-1H-indole are obtained, the characteristics of which are the following:

Mass spectrometry: method A
Retention time Tr (min)=0.60; [M+H]+: m/z 170

Reference Example 3a 2-methyl-5,6-fluoro-2,3-dihydro-1H-indole

Step 1a 4,5-Difluoro-2-iodoaniline

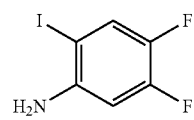

16.5 g of iodine and 6.3 g of sodium bicarbonate are added, at ambient temperature, to a suspension of 6.45 g of 3,4-difluoroaniline in 250 ml of water. The reaction medium is stirred at ambient temperature for 1 hour.

A saturated sodium thiosulfate solution is added and then the resulting mixture is extracted 3 times with ethyl acetate. The organic phases are combined, dried over magnesium sulfate, filtered, and then concentrated under reduced pressure, so as to give 12 g of 4,5-difluoro-2-iodoainiline, the characteristics of which are the following:

Mass spectrometry: method A
Retention time Tr (min)=0.90; [M+H]+: m/z 256; base peak: m/z 297

Step 2a 4,5-Difluoro-2-prop-1-ynylphenylamine

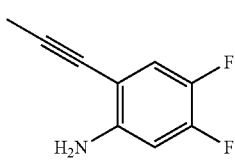

426 mg of copper(I) iodide and 523 mg of bis(triphenylphosphine)palladium(II)dichloride are added, at ambient temperature, to a solution of 19 g of 4,5-difluoro-2-iodoaniline in 150 ml of triethylamine. The suspension is cooled to −30° C. in a dry ice/ethanol bath. Furthermore, 20 ml of propyne are condensed by sparging in a trap cooled to −70° C. using a dry ice/methanol mixture. The propyne is added to the suspension cooled to −30° C. The cooling bath is kept. The temperature is allowed to rise to ambient temperature overnight.

The reaction medium is filtered. The filtrate is concentrated to dryness under reduced pressure. The residue obtained is taken up with water and with ethyl acetate. After settling out, the organic phase is dried over magnesium sulfate, filtered, and then concentrated under reduced pressure. The residue obtained is purified on a silica column, eluent: 80/20 cyclohexane/dichloromethane, so as to give 10.8 g of 4,5-difluoro-2-prop-1-ynylphenylamine, the characteristics of which are the following:

Mass spectrometry: method A
Retention time Tr (min)=0.90; [M+H]+: m/z 168

Step 3a 5,6-Difluoro-2-methylindole

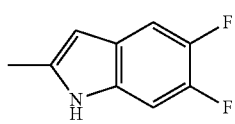

246 mg of copper(I) iodide are added to a solution of 10.8 g of 4,5-difluoro-2-prop-1-ynylphenylamine in 100 ml of DMF. The reaction medium is refluxed for one hour.

After cooling, the reaction medium is filtered. The filtrate is concentrated under reduced pressure. The crude residue obtained is purified on a silica column, eluent: 90/10 cyclohexane/dichloromethane, so as to give 7.2 g of 5,6-difluoro-2-methylindole, the characteristics of which are the following:

Mass spectrometry: method A
Retention time Tr (min)=0.94; [M−H]−: m/z 166

Step 4a 5,6-Difluoro-2-methyl-2,3-dihydro-1H-indole

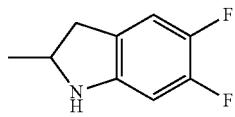

8.11 g of sodium cyanoborohydride are added, in 3 steps, to a solution of 7.2 g of 5,6-difluoro-2-methylindole in 220 ml of acetic acid cooled to 15° C. The reaction medium is stirred at 15° C. for 30 minutes and then at ambient temperature for 4 hours.

The reaction medium is again cooled to 5° C. 900 ml of ice-cold water are added. 30% aqueous ammonia is added until the pH=9. The resulting mixture is extracted 3 times with dichloromethane. The organic phases are combined, dried over magnesium sulfate, filtered, and then concentrated under reduced pressure. The residue obtained is purified on a silica column, eluent: 90/10 heptane/ethyl acetate, so as to give 6.3 g of 5,6-difluoro-2-methyl-2,3-dihydro-1H-indole, the characteristics of which are the following:

Mass spectrometry: method A
Retention time Tr (min)=0.53; [M+H]+: m/z 170

Step 5a (R)-1-(5,6-Difluoro-2-methyl-2,3-dihydroindol-1-yl)-2-phenoxypropan-1-one: diastereoisomer A

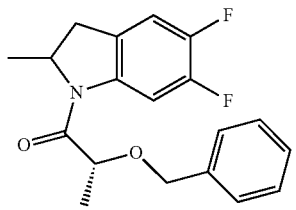

And (R)-1-(5,6-Difluoro-2-methyl-2,3-dihydroindol-1-yl)-2-phenoxypropan-1-one: diastereoisomer B

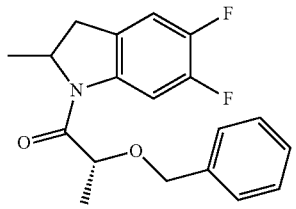

The products are prepared by following the procedure described in reference example 1a (step 2a) using 6.3 g of 5,6-difluoro-2-methyl-2,3-dihydro-1H-indole and 6.8 g of o-benzyl-D-lactic acid. After silica column purification, 6.45 g of (R)-1-(5,6-difluoro-2-methyl-2,3-dihydroindol-1-yl)-2- phenoxypropan-1-one: diastereoisomer A are obtained in the form of a yellow oil, the characteristics of which are the following:

Mass spectrometry: method A

Retention time Tr (min)=1.11; [M+H]+: m/z 332; base peak: m/z 260

And 6.29 g of (R)-1-(5,6-difluoro-2-methyl-2,3-dihydroindol-1-yl)-2-phenoxypropan-1-one: diastereoisomer B are obtained in the form of a white solid, the characteristics of which are the following:

Mass spectrometry: method A

Retention time Tr (min)=1.10; [M+H]+: m/z 332; base peak: m/z 260

Step (6a)a (+)-5,6-Difluoro-2-methyl-2,3-dihydro-1H-indole

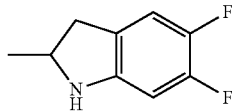

The product is prepared by following the procedure described in reference example 1a (step 3a) using 6.45 g of (R)-1-(5,6-difluoro-2-methyl-2,3-dihydroindol-1-yl)-2-phenoxypropan-1-one: diastereoisomer A and 64.5 ml of 37% hydrochloric acid.

After silica column purification, eluent: 90/10 heptane/ethyl acetate, 2.7 g of (+)-5,6-difluoro-2-methyl-2,3-dihydro-1H-indole are obtained, the characteristics of which are the following:

Mass spectrometry: method A

Retention time Tr (min)=0.53; [M+H]+: m/z 170;

Optical rotation: $\alpha_D$=+17.6+/−0.7. C=1.834 mg/0.5 ml DMSO

Step (6b)a (−)-5,6-Difluoro-2-methyl-2,3-dihydro-1H-indole

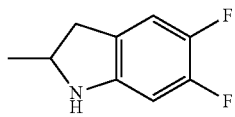

The product is prepared by following the procedure described in reference example 1a (step 3a) using 6.29 g of (R)-1-(5,6-difluoro-2-methyl-2,3-dihydroindol-1-yl)-2-phenoxypropan-1-one: diastereoisomer B and 63 ml of 37% hydrochloric acid.

After silica column purification, eluent: 90/10 heptane/ethyl acetate, 2.76 g of (−)-5,6-difluoro-2-methyl-2,3-dihydro-1H-indole are obtained, the characteristics of which are the following:

Mass spectrometry: method A

Retention time Tr (min)=0.55; [M+H]+: m/z 170;

Optical rotation: $\alpha_D$=−6.7+/−0.6. C=1.832 mg/0.5 ml DMSO

Reference Example 4a

4-Bromo-2-methyl-2,3-dihydro-1H-indole

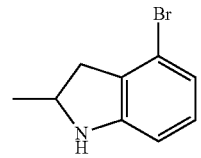

7.99 g of sodium cyanoborohydride are gradually added to a solution of 8.90 g of 4-bromo-2-methylindole (which can be prepared according to patent US2010/160647 A1, 2010) in 310 ml of acetic acid under argon cooled to a temperature of about 14° C. The reaction mixture is stirred at a temperature of about 14° C. for 15 minutes, and is then left to warm back up to ambient temperature. After 2 hours, the reaction mixture is poured into an Erlenmayer flask containing ice-cold water (200 ml) and the pH is then brought to 9 with an aqueous ammonia solution. The reaction medium is extracted with dichloromethane (2×200 ml) and then the organic phases are combined, washed with water, dried over magnesium sulfate, filtered, and then concentrated to dryness under reduced pressure. After purification of the residue by silica column chromatography, elution being carried out with a mixture of heptane and ethyl acetate (90/10), 5.92 g of 4-bromo-2-methylindoline are obtained.

Reference Example 5a

4-Fluoro-2-methyl-2,3-dihydro-1H-indole

Step 1a tert-Butyl (3-fluoro-2-methylphenyl)carbamate

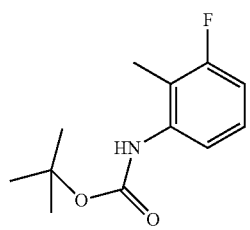 [SMILES: Cc1c(F)cccc1NC(=O)OC(C)(C)C]

9.9 g of di-tert-Butyl dicarbonate are added to a solution of 5 g of 3-fluoro-2-methylaniline in 25 ml of tetrahydrofuran. The reaction mixture is refluxed with stirring for 16 hours, then it is cooled to ambient temperature and concentrated to dryness under reduced pressure. The residue is triturated from 20 ml of cyclohexane and the precipitate obtained is filtered off through sintered glass, dried with suction and then dried under reduced pressure at 40° C. 7.1 g of tert-butyl (3-fluoro-2-methylphenyl)carbamate are thus obtained in the form of a shiny white solid, the characteristics of which are the following:

Mass spectrometry: EI: [M]+.m/z=225

Method A

Retention time Tr (min)=1.04;

m/z 170; base peak m/z: 211

Melting point (Kofler): 72° C.

Step 2a tert-Butyl
[3-fluoro-2-(2-oxopropyl)phenyl]carbamate

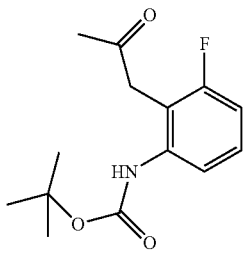 [SMILES: CC(=O)Cc1c(F)cccc1NC(=O)OC(C)(C)C]

4.3 ml of a 1.3 M solution of sec-butyllithium in 98/2 v/v cyclohexane/hexane are added dropwise, while maintaining the temperature between −40° C. and −30° C., to a solution of 0.5 g of tert-butyl (3-fluoro-2-methylphenyl)carbamate in 10 ml of tetrahydrofuran under argon and cooled to −40° C. The reaction mixture is then cooled to −50° C., and then a solution of 0.27 ml of N-methoxy-N-methylacetamide in 4 ml of tetrahydrofuran is added dropwise while maintaining the temperature between −50° C. and −40° C. The mixture is then left to warm up to approximately −10° C., and then stirred at this temperature for 0.5 hour. It is then treated with 5.6 ml of a 1N hydrochloric acid solution and then diluted with 20 ml of diethyl ether and left to warm up to ambient temperature with stirring for 1 hour. After settling out, the organic phase is separated and the aqueous phase is extracted with 40 ml of diethyl ether. The organic phases are combined, washed with 3×40 ml of water, dried over magnesium sulfate, filtered, and then concentrated to dryness under reduced pressure. The residue is purified by chromatography on a 30 g cartridge of 15-40 µm silica, elution being carried out with a 90/10 v/v cyclohexane/ethyl acetate mixture, at a flow rate of 30 ml/min, and then on a 30 g cartridge of 15-40 µm silica, elution being carried out with pure dichloromethane, at a flow rate of 30 ml/min. 0.38 g of tert-butyl [3-fluoro-2-(2-oxopropyl)phenyl]carbamate is thus obtained, in the form of a white solid, the characteristics of which are the following:

Mass spectrometry: EI: [M]+. m/z=267
Method A
Retention time Tr (min)=0.93;
[M+Na]+: m/z 290

Step 3a

4-Fluoro-2-methylindole

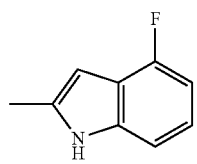

1.43 ml of trifluoroacetic acid are added to a solution of 0.35 g of tert-butyl [3-fluoro-2-(2-oxopropyl)phenyl]carbamate in 13 ml of anhydrous dichloromethane at ambient temperature. The reaction mixture is then stirred at ambient temperature for 24 h, and is then diluted with 27 ml of dichloromethane and treated with 25 ml of a 5% sodium hydrogen carbonate solution. After stirring at ambient temperature for 1 hour and then settling out, the organic phase is separated and the aqueous phase is extracted with 25 ml of dichloromethane. The organic phases are combined, washed with saturated brine, dried over magnesium sulfate, filtered, and then concentrated to dryness under reduced pressure. 0.19 g of 4-fluoro-2-methylindole is thus obtained in the form of a dark red-colored oil, the characteristics of which are the following:

$^1$H NMR spectrum (400 MHz, CDCl$_3$): 2.46 (s, 3H); 6.30 (broad m, 1H); 6.74 (dd, J=7.9 and 10.6 Hz, 1H); 7.02 (dt, J=4.9 and 7.9 Hz, 1H); 7.08 (d, J=7.9 Hz, 1H); 7.95 (broad m, 1H)

Mass spectrometry: EI: [M]+. m/z=149

Step 4a

4-Fluoro-2-methyl-2,3-dihydro-1H-indole

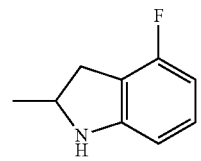

3.63 g of sodium cyanoborohydride are gradually added to a solution of 2.87 g of 4-fluoro-2-methylindole in 98 ml of acetic acid under argon cooled to a temperature of about 14° C. The reaction mixture is left to warm up to ambient temperature. After 2 hours, the reaction mixture is poured into a mixture of water and ice, and is then treated with a 28% aqueous ammonia solution until the pH is 9. The mixture is then extracted twice with dichloromethane. The organic phases are combined, dried over anhydrous magnesium sulfate, filtered, and then concentrated to dryness under reduced pressure. The residue is purified on a 300 g silica column, elution being carried out with a 100/0 to 90/10 v/v heptane/ethyl acetate gradient. 2.19 g of 4-fluoro-2-methyl-2,3-dihydro-1H-indole are thus obtained in the form of a colorless oil, the characteristics of which are the following:

$^1$H NMR spectrum (400 MHz): 1.18 (d, J=6.3 Hz, 3H); 2.49 (partially masked dd, J=7.6 and 15.7 Hz, 1H); 3.08 (dd, J=9.0 and 15.7 Hz, 1H); 3.92 (m, 1H); 5.87 (broad s, 1H); 6.20 to 6.31 (m, 2H); 6.90 (td, J=5.9 and 8.1 Hz, 1H)

Mass spectrometry: method A
Retention time Tr (min)=0.50;
[M+H]+: m/z 152

Step 5a (R)-2-benzyloxy-1-(4-fluoro-2-methyl-2,3-dihydroindol-1-yl)propan-1-one: diastereoisomer (A)

(R)-2-benzyloxy-1-(4-fluoro-2-methyl-2,3-dihydroindol-1-yl)propan-1-one: diastereoisomer (B)

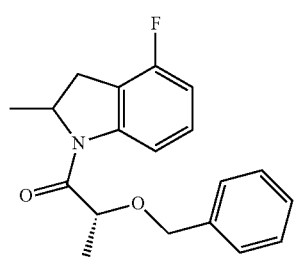

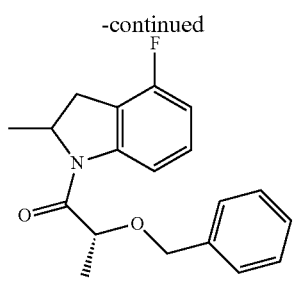

0.69 ml of pyridine and 1.05 g of N-[3-(dimethylamino)propyl]-N'-ethylcarbodiimide hydrochloride are added to a solution of 0.76 g of o-benzyl-D-lactic acid in 3.5 ml of dimethylformamide under argon. The reaction mixture is stirred at ambient temperature for 10 minutes and then 0.64 g of 4-fluoro-2-methylindoline is added. The reaction mixture is stirred at ambient temperature for 20 hours and is then treated with 20 ml of water and extracted with 3×15 ml of ethyl acetate. The organic phases are combined, washed with 15 ml of water, dried over magnesium sulfate, filtered, and then concentrated to dryness under reduced pressure. The residue is purified by chromatography on a 90 g cartridge of 15-40 μm silica, elution being carried out with pure dichloromethane, and then on a 100 g cartridge of 15-40 μm silica, elution being carried out with pure heptane and then with 95/5 then 90/10 v/v heptane/ethyl acetate mixtures, at a flow rate of 85 ml/min. 0.33 g of (R)-2-benzyloxy-1-(4-fluoro-2-methyl-2,3-dihydroindol-1-yl)propan-1-one diastereoisomer (A) is thus obtained in the form of a colorless oil and 0.38 g of (R)-2-benzyloxy-1-(4-fluoro-2-methyl-2,3-dihydroindol-1-yl)propan-1-one diastereoisomer (B) is thus obtained in the form of a white solid. A second trial under identical conditions using 1.85 g of o-benzyl-D-lactic acid and 1.55 g of 4-fluoro-2-methylindoline makes it possible to obtain 1.39 g of (R)-2-benzyloxy-1-(4-fluoro-2-methyl-2,3-dihydroindol-1-yl)propan-1-one diastereoisomer (A) in the form of a colorless oil and 1.34 g of (R)-2-benzyloxy-1-(4-fluoro-2-methyl-2,3-dihydroindol-1-yl)propan-1-one diastereoisomer (B) in the form of a white solid.

The two batches of (R)-2-benzyloxy-1-(4-fluoro-2-methyl-2,3-dihydroindol-1-yl)propan-1-one diastereoisomer (A) are combined and dissolved in 75 ml of ethyl acetate. The mixture is filtered through paper and then concentrated to dryness under reduced pressure. 1.66 g of (R)-2-benzyloxy-1-(4-fluoro-2-methyl-2,3-dihydroindol-1-yl)propan-1-one diastereoisomer (A) are thus obtained in the form of a very pale yellow viscous oil, the characteristics of which are the following:

$^1$H NMR spectrum (400 MHz): 1.18 (d, J=6.4 Hz, 3H); 1.39 (d, J=6.4 Hz, 3H); 2.71 (d, J=16.3 Hz, 1H); 3.29 (partially masked dd, J=8.8 and 16.3 Hz, 1H); 4.46 to 4.56 (m, 3H); 4.75 (m, 1H); 6.91 (t, J=8.7 Hz, 1H); 7.19 to 7.37 (m, 6H); 7.87 (broad m, 1H)

Mass spectrometry: method A
Retention time Tr (min)=1.09;
[M+H]+: m/z 314; [M+Na]+: m/z 336; base peak—: m/z 242

The two batches of (R)-2-benzyloxy-1-(4-fluoro-2-methyl-2,3-dihydroindol-1-yl)propan-1-one diastereoisomer (B) are combined and dissolved in 75 ml of ethyl acetate. The mixture is filtered through paper and then concentrated to dryness under reduced pressure. 1.70 g of (R)-2-benzyloxy-1-(4-fluoro-2-methyl-2,3-dihydroindol-1-yl)propan-1-one diastereoisomer (B) are thus obtained in the form of a white solid, the characteristics of which are the following:

$^1$H NMR spectrum (400 MHz): 1.18 (d, J=6.4 Hz, 3H); 1.40 (d, J=6.5 Hz, 3H); 2.72 (d, J=16.4 Hz, 1H); 3.28 to 3.37 (partially masked m, 1H); 4.40 to 4.57 (m, 3H); 4.66 (m, 1H); 6.90 (dt, J=0.8 and 8.8 Hz, 1H); 7.20 to 7.39 (m, 6H); 7.91 (broad m, 1H)

Mass spectrometry: method A
Retention time Tr (min)=1.08;
[M+H]+: m/z 314; [M+Na]+: m/z 336; base peak: m/z 242

Step (6a)a (+)-4-Fluoro-2-methylindoline

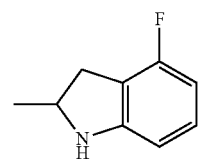

8 ml of concentrated hydrochloric acid are added to a solution of 1.66 g of (R)-2-benzyloxy-1-(4-fluoro-2-methyl-2,3-dihydroindol-1-yl)propan-1-one diastereoisomer (A) in 200 ml of absolute ethanol. The reaction mixture is refluxed with stirring for 40 hours and is then cooled to ambient temperature and concentrated to dryness under reduced pressure. The residue is taken up in 250 ml of water, alkalinized with concentrated sodium hydroxide to pH 14, and then the mixture is extracted with 3×200 ml of dichloromethane. The organic phases are combined, washed with water, dried over magnesium sulfate, filtered, and then concentrated to dryness under reduced pressure. The residue is purified by chromatography on a 70 g cartridge of 15-40 μm silica, elution being carried out with pure heptane and then with a 95/5 heptane/ethyl acetate mixture at a flow rate of 50 ml/min, and then on a 70 g cartridge of 15-40 μm silica, elution being carried out with pure cyclohexane and then with a 70/30 cyclohexane/dichloromethane mixture, at a flow rate of 50 ml/min. 0.50 g of (+)-4-fluoro-2-methylindoline is thus obtained in the form of a colorless oil, the characteristics of which are the following:

$^1$H NMR spectrum (400 MHz): 1.18 (d, J=6.4 Hz, 3H); 2.49 (partially masked dd, J=7.6 and 15.7 Hz, 1H); 3.08 (dd, J=8.8 and 15.7 Hz, 1H); 3.92 (m, 1H); 5.87 (broad s, 1H); 6.21 to 6.28 (m, 2H); 6.90 (dt, J=5.9 and 8.1 Hz, 1H)

Mass spectrometry: method A
Retention time Tr (min)=0.48;
[M+H]+: m/z 152
Optical rotation: $\alpha_D$=+40.8°+/−0.9 (c=2.223 mg in 0.5 ml of DMSO)

Step (6b)a (−)-4-Fluoro-2-methylindoline 8.2 ml of concentrated hydrochloric acid are added to a solution of 1.69 g of (R)-2-benzyloxy-1-(4-fluoro-2-methyl-2,3-dihydroindol-1-yl)propan-1-one diastereoisomer (B) in 200 ml of absolute ethanol. The reaction mixture is refluxed with stirring for 40 hours and is then cooled to ambient temperature and concentrated to dryness under reduced pressure. The residue is taken up in 200 ml of water, alkalinized with concentrated sodium hydroxide to pH 14, and the mixture is then extracted with 3×200 ml of dichloromethane. The organic phases are combined, washed with water, dried over magnesium sulfate, filtered, and then concentrated to dryness under reduced pressure. The residue is purified by chromatography on a 70 g cartridge of 15-40 μm silica, elution being carried out with pure cyclohexane and then with a 70/30 cyclohexane/dichloromethane mixture, at a flow rate of 50 ml/min. 0.56 g of (−)-4-fluoro-2-methylindoline is thus obtained in the form of a very pale yellow oil, the characteristics of which are the following:

$^1$H NMR spectrum (400 MHz): 1.18 (d, J=6.2 Hz, 3H); 2.49 (partially masked dd, J=7.6 and 15.7 Hz, 1H); 3.08 (dd, J=9.0 and 15.7 Hz, 1H); 3.92 (m, 1H); 5.87 (broad s, 1H); 6.20 to 6.29 (m, 2H); 6.90 (dt, J=5.9 and 8.1 Hz, 1H)

Mass spectrometry: method A
Retention time Tr (min)=0.49;
[M+H]+: m/z 152
Optical rotation: $\alpha_D$=−33.7°+/−0.7 (c=2.741 mg in 0.5 ml of DMSO)

Reference Example 6a

6-Fluoro-2-methyl-2,3-dihydro-1H-indole

Step 1a

5-Fluoro-2-prop-1-ynylphenylamine

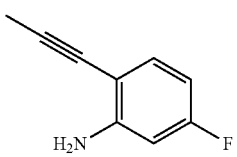

121 mg of copper(1) iodide and 148 mg of bis(triphenylphosphine)palladium(II)dichloride are added, at ambient temperature, to a solution of 5 g of 5-fluoro-2-iodoaniline in 150 ml of triethylamine. The suspension is cooled to −30° C. in a dry ice/ethanol bath. Furthermore, 10 ml of propyne are condensed by sparging in a trap cooled to −70° C. using a dry ice/methanol mixture. The propyne is added to the suspension cooled to −30° C. The cooling bath is kept. The temperature is allowed to rise to ambient temperature overnight.

The reaction medium is filtered. The filtrate is concentrated to dryness under reduced pressure. The residue obtained is taken up with water and with ethyl acetate. After settling out, the organic phase is dried over magnesium sulfate, filtered, and then concentrated under reduced pressure. The residue obtained is purified on a silica column, eluent: 95/05 cyclohexane/ethyl acetate, so as to give 1.7 g of 5-difluoro-2-prop-1-ynylphenylamine, the characteristics of which are the following:

Mass spectrometry: method A
Retention time Tr (min)=0.84; [M+H]+: m/z 150

Step 2a

6-Difluoro-2-methylindole

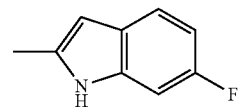

43 mg of copper(I) iodide are added to a solution of 1.7 g of 5-difluoro-2-prop-1-ynylphenylamine in 50 ml of DMF. The reaction medium is refluxed for one hour.

After cooling, the reaction medium is filtered. The filtrate is concentrated under reduced pressure. The crude residue obtained is purified on a silica column, eluent: 90/10 cyclohexane/ethyl acetate, so as to give 1.1 g of 6-fluoro-2-methylindole, the characteristics of which are the following:

Mass spectrometry: method A
Retention time Tr (min)=0.89; [M+H]+: m/z 150

Step 3a

6-Fluoro-2-methyl-2,3-dihydro-1H-indole

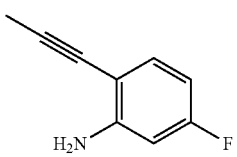

The product is prepared by following the procedure described in reference example 2a (step 1a) using 1.4 g of 6-fluoro-2-methylindole, 51 ml of acetic acid and 1.9 g of sodium cyanoborohydride. After silica column purification, eluent: 90/10 heptane/ethyl acetate, 1.33 g of 6-fluoro-2-methyl-2,3-dihydro-1H-indole are obtained, which is used as it is in the next step.

Step 4a (R)-1-(6-fluoro-2-methyl-2,3-dihydroindol-1-yl)-2-phenoxypropan-1-one: diastereoisomer A

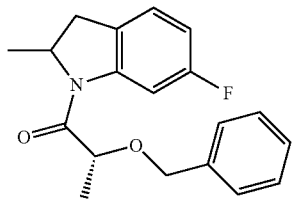 [SMILES: CC1Cc2ccc(F)cc2N1C(=O)[C@@H](C)OCc1ccccc1]

And (R)-1-(6-fluoro-2-methyl-2,3-dihydroindol-1-yl)-2-phenoxypropan-1-one: diastereoisomer B

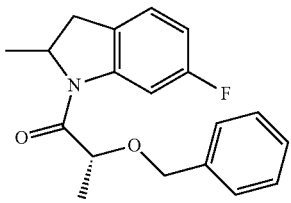 [SMILES: CC1Cc2ccc(F)cc2N1C(=O)[C@@H](C)OCc1ccccc1]

The products are prepared by following the procedure described in reference example 1a (step 2a) using 1.33 g of 6-fluoro-2-methyl-2,3-dihydro-1H-indole and 2.1 g of o-benzyl-D-lactic acid. After silica column purification, 1.3 g of (R)-1-(6-fluoro-2-methyl-2,3-dihydroindol-1-yl)-2-phenoxypropan-1-one: diastereoisomer A are obtained, the characteristics of which are the following:

Mass spectrometry: method A
Retention time Tr (min)=1.09;
[M+H]+: m/z 314; base peak: m/z 242

And 1.13 g of (R)-1-(6-fluoro-2-methyl-2,3-dihydroindol-1-yl)-2-phenoxpropan-1-one: diastereoisomer B are obtained in the form of a white solid, the characteristics of which are the following:

Mass spectrometry: method A
Retention time Tr (min)=1.08;
[M+H]+: m/z 314; [M+Na]+: m/z 336;
base peak: m/z 242

Step (5a)a (+)-6-Fluoro-2-methyl-2,3-dihydro-1H-indole

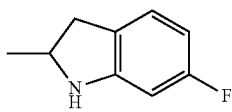

The product is prepared by following the procedure described in reference example 1a (step 3a) using 1.3 g of (R)-1-(6-fluoro-2-methyl-2,3-dihydroindol-1-yl)-2-phenoxypropan-1-one: diastereoisomer A and 13 ml of 37% hydrochloric acid.

After treatment, 547 mg of (+)-6-fluoro-2-methyl-2,3-dihydro-1H-indole are obtained, the characteristics of which are the following:

Mass spectrometry: method A
Retention time Tr (min)=0.48; [M+H]+: m/z 152;
Optical rotation: $\alpha_D$=+35.0+/−0.7. C=2.899 mg/0.5 ml DMSO Step (5b)a (−)-6-Fluoro-2-methyl-2,3-dihydro-1H-indole

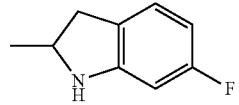

The product is prepared by following the procedure described in reference example 1a (step 3a) using 1.13 g of (R)-1-(6-fluoro-2-methyl-2,3-dihydroindol-1-yl)-2-phenoxypropan-1-one: diastereoisomer B and 12 ml of 37% hydrochloric acid.

After treatment, 540 mg of (R)-6-fluoro-2-methyl-2,3-dihydroindol-1-yl)-2-phenoxypropan-1-one are obtained, the characteristics of which are the following:

Mass spectrometry: method A
Retention time Tr (min)=0.48; [M+H]+: m/z 152;
Optical rotation: $\alpha_D$=−32.6+/−1.0. C=1.506 mg/0.5 ml DMSO Reference Example 7a 4-Chloro-5-fluoro-2-methyl-2,3-dihydro-1H-indole Step 1a 3-Chloro-4-fluoro-2-iodoaniline

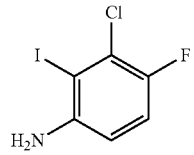

113.3 g of iodine and 43.3 g of sodium bicarbonate are added, at ambient temperature, to a suspension of 50 g of 3-chloro-4-fluoroaniline in 800 ml of water. The reaction medium is stirred at ambient temperature for 18 hours.

A saturated sodium thiosulfate solution is added and then the resulting mixture is extracted 3 times with ethyl acetate. The organic phases are combined, dried over magnesium sulfate, filtered, and then concentrated under reduced pressure. The residue obtained is purified on a silica column, eluent: 95/05 then 85/15 cyclohexane/ethyl acetate, so as to give 40.9 g of 5-chloro-4-fluoro-2-iodoaniline, the characteristics of which are the following:

$^1$H NMR spectrum (400 MHz): 5.29 (broad s, 2H); 6.87 (d, J=6.9 Hz, 1H); 7.61 (d, J=8.8 Hz, 1H)
Mass spectrometry: method A
Retention time Tr (min)=0.99;
[M+H]+: m/z 272; base peak: m/z 313
and 12.5 g of 3-chloro-4-fluoro-2-iodoaniline, the characteristics of which are the following:
$^1$H NMR spectrum (400 MHz): 5.38 (broad s, 2H); 6.76 (dd, J=4.8 and 8.9 Hz, 1H); 7.16 (t, J=8.9 Hz, 1H)
Mass spectrometry: method A
Retention time Tr (min)=0.95;
[M+H]+: m/z 271

Step 2a

3-Chloro-4-fluoro-2-prop-1-ynylphenylamine

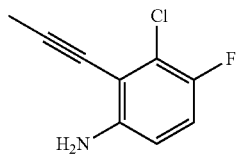

364 mg of copper(I) iodide and 470 mg of bis(triphenylphosphine)palladium(II)dichloride are added, at ambient temperature, to a solution of 9 g of 3-chloro-4-fluoro-2-iodoaniline in 160 ml of triethylamine. The suspension is cooled to −30° C. in a dry ice/ethanol bath. Furthermore, approximately 20 ml of propyne are condensed by sparging in a trap cooled to −70° C. using a dry ice/methanol mixture. The propyne is added to the suspension cooled to −30° C. The cooling bath is kept. The temperature is allowed to rise to ambient temperature overnight.

The reaction medium is filtered. The filtrate is concentrated to dryness under reduced pressure. The residue obtained is purified on a silica column, eluent: 90/10 heptane/ethyl acetate, so as to give 1.76 g of 3-chloro-4-fluoro-2-prop-1-ynylphenylamine, the characteristics of which are the following:

Mass spectrometry: method A
Retention time Tr (min)=0.92; [M+H]+: m/z 184; base peak: m/z 149

Step 3a

4-Chloro-5-fluoro-2-methylindole

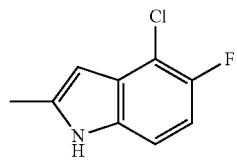

32 mg of copper(1) iodide are added to a solution of 1.56 g of 3-chloro-4-fluoro-2-prop-1-ynylphenylamine in 17 ml of DMF. The reaction medium is refluxed for 45 minutes.

After cooling, the reaction medium is filtered. The filtrate is concentrated under reduced pressure. The crude residue obtained is purified on a silica column, eluent: 70/30 heptane/toluene, so as to give 0.5 g of 4-chloro-5-fluoro-2-methylindole, the characteristics of which are the following:

Mass spectrometry: method A
Retention time Tr (min)=1.01; [M−H]−: m/z 182

Step 4a

4-Chloro-5-fluoro-2-methyl-2,3-dihydro-1H-indole

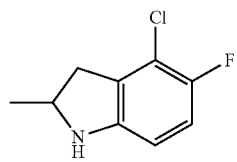

719 mg of sodium cyanoborohydride are added, in one step, to a solution of 700 mg of 4-chloro-5-fluoro-2-methylindole in 16 ml of acetic acid cooled to 15° C. The reaction medium is stirred at 15° C. for 10 minutes and then at ambient temperature for 90 minutes.

The reaction medium is again cooled to 5° C. Ice-cold water is added. 30% aqueous ammonia is added until the pH=9. The resulting mixture is extracted with ethyl acetate. The organic phase is dried over magnesium sulfate, filtered, and then concentrated under reduced pressure so as to give 683 mg of 4-chloro-5-fluoro-2-methyl-2,3-dihydro-1H-indole, the characteristics of which are the following:

Mass spectrometry: method A
Retention time Tr (min)=0.75;
[M+H]+: m/z 186

Reference Example 8a

2-Hydroxymethyl-2,3-dihydro-1H-indole

Step 1a 1-((R)-2-Benzyloxypropionyl)-2,3-dihydro-1H-indole-2-carboxylic acid ethyl ester: diastereoisomer A

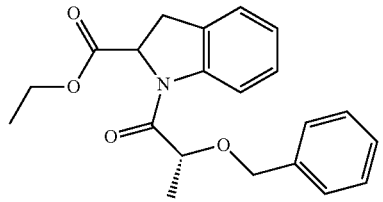 [SMILES: CCOC(=O)C1Cc2ccccc2N1C(=O)[C@@H](C)OCc1ccccc1]

And 1-((R)-2-Benzyloxypropionyl)-2,3-dihydro-1H-indole-2-carboxylic acid ethyl ester diastereoisomer B

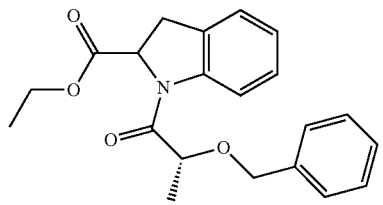 [SMILES: CCOC(=O)C1Cc2ccccc2N1C(=O)[C@@H](C)OCc1ccccc1]

16.6 g of N-[3-(dimethylamino)propyl]-N'-ethylcarbodiimide hydrochloride and then 10 g of ethyl indoline-2-carboxylate are added to a solution of 12.6 g of o-benzyl-D-lactic acid in 30 ml of DMF and 10.6 ml of pyridine. The reaction medium is stirred at ambient temperature for 18 hours. The reaction medium is concentrated under reduced pressure to ⅔ of the volume of the reaction medium. Ethyl acetate and water are added. After settling out, the organic phase is dried over magnesium sulfate, filtered, and then concentrated under reduced pressure. The residue obtained is purified on a silica cartridge: eluent: gradient: heptane/ethyl acetate from 100/0 to 80/20, so as to give 7.24 g of 1-((R)-2-benzyloxypropionyl)-2,3-dihydro-1H-indole-2-carboxylic acid ethyl ester: diastereoisomer A, the characteristics of which are the following:

Mass spectrometry: method A
Retention time Tr (min)=1.08;
[M+H]+: m/z 354; [M+Na]+: m/z 376 (base peak)

And 7.5 g of 1-((R)-2-benzyloxypropionyl)-2,3-dihydro-1H-indole-2-carboxylic acid ethyl ester: diastereoisomer B in the form of a white solid, the characteristics of which are the following:

Mass spectrometry: method A
Retention time Tr (min)=1.06;
[M+H]+: m/z 354; [M+Na]+: m/z 376; base peak: m/z 282

Step 2a (R)-2-Benzyloxy-1-(2-hydroxymethyl-2,3-dihydroindol-1-yl)propan-1-one: diastereoisomer A

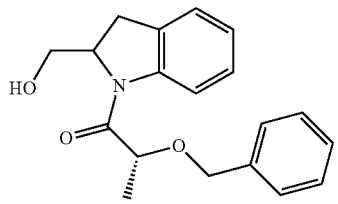 [SMILES: C[C@@H](OCc1ccccc1)C(=O)N1c2ccccc2CC1CO]

And (+)-(2,3-Dihydro-1H-indol-2-yl)methanol

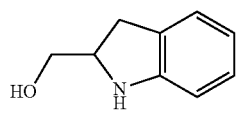 [SMILES: OCC1Cc2ccccc2N1]

1.04 g of sodium borohydride are added to a solution of 3.31 g of 1-((R)-2-benzyloxypropionyl)-2,3-dihydro-1H-indole-2-carboxylic acid ethyl ester: diastereoisomer A in 7.5 ml of THF and 7.5 ml of ethanol.

The reaction medium is stirred at ambient temperature for 5 hours.

Dichloromethane and water are added. After settling out, the organic phase is dried over magnesium sulfate, filtered, and then concentrated under reduced pressure. The residue obtained is purified on a silica cartridge: eluent: 50/50 heptane/ethyl acetate, so as to give 0.98 g of (R)-2-benzyloxy-1-(2-hydroxymethyl-2,3-dihydroindol-1-yl)propan-1-one: diastereoisomer A, the characteristics of which are the following:
Mass spectrometry: method A
Retention time Tr (min)=0.85;
[M+H]+: m/z 312
And 1.65 g of (+)-(2,3-dihydro-1H-indol-2-yl)methanol in the form of a white solid, the characteristics of which are the following:
Mass spectrometry: method A
Retention time Tr (min)=0.19;
[M+H]+: m/z 150

Step 3a (+)-(2,3-Dihydro-1H-indol-2-yl)methanol

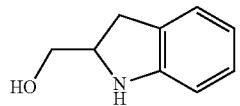 [SMILES: OCC1Cc2ccccc2N1]

To a solution of 0.9 g of (R)-2-benzyloxy-1-(2-hydroxymethyl-2,3-dihydroindol-1-yl)propan-1-one: diastereoisomer A in 9 ml of ethanol and 9 ml of 37% hydrochloric acid are refluxed for two hours.

The reaction medium is concentrated under reduced pressure. The residue obtained is taken up with water. 2N sodium hydroxide is added until the pH=10. The medium is extracted with dichloromethane. After settling out, the organic phase is dried over magnesium sulfate, filtered, and then concentrated under reduced pressure, so as to give 0.4 g of (+)-(2,3-dihydro-1H-indol-2-yl)methanol, the characteristics of which are the following:
Mass spectrometry: method A
Retention time Tr (min)=0.19;
[M+H]+: m/z 150
OR=+38.5+/−0.9. C=1.974 mg/0.5 ml DMSO Step 4a (R)-2-Benzyloxy-1-(2-hydroxymethyl-2,3-dihydroindol-1-yl)propan-1-one: diastereoisomer B

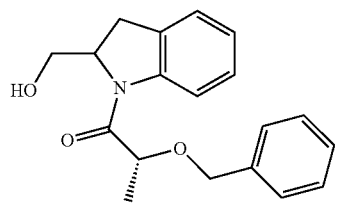 [SMILES: C[C@@H](OCc1ccccc1)C(=O)N1c2ccccc2CC1CO]

And (−)-(2,3-Dihydro-1H-indol-2-yl)methanol

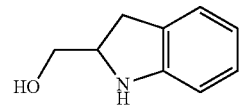

1.36 g of sodium borohydride are added to a solution of 5.75 g of 1-((R)-2-benzyloxypropionyl)-2,3-dihydro-1H-indole-2-carboxylic acid ethyl ester: diastereoisomer B in 20 ml of THF.

The reaction medium is stirred at ambient temperature for 18 hours.

10 ml of ethanol and 0.4 g of sodium borohydride are added. After two hours of stirring at ambient temperature, dichloromethane and water are added.

After settling out, the organic phase is dried over magnesium sulfate, filtered, and then concentrated under reduced pressure. The residue obtained is purified on a silica cartridge: eluent: gradient: dichloromethane/methanol from 100/0 to 98/02, so as to give 0.51 g of (R)-2-benzyloxy-1-(2-hydroxymethyl-2,3-dihydroindol-1-yl)propan-1-one: diastereoisomer B, the characteristics of which are the following:
Mass spectrometry: method A
Retention time Tr (min)=0.82; [M+H]+: m/z 312
And 0.96 g of (−)-(2,3-dihydro-1H-indol-2-yl)methanol in the form of a white solid, the characteristics of which are the following:
Mass spectrometry: method A
Retention time Tr (min)=0.19; [M+H]+: m/z 150
OR=−38.9+/−0.8. C=2.255 mg/0.5 ml DMSO

Step 3a (−)-(2,3-Dihydro-1H-indol-2-yl)methanol

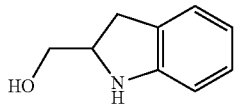 [SMILES: OCC1Cc2ccccc2N1]

To a solution of 117 mg of (R)-2-benzyloxy-1-(2-hydroxymethyl-2,3-dihydroindol-1-yl)propan-1-one: diastereoisomer B in 1.2 ml of ethanol and 1.2 ml of 37% hydrochloric acid are refluxed for two hours.

The reaction medium is concentrated under reduced pressure. The residue obtained is taken up with water. 2N sodium hydroxide is added until the pH=10. The medium is extracted with dichloromethane. After settling out, the organic phase is dried over magnesium sulfate, filtered, and then concentrated under reduced pressure, so as to give 50 mg of (−)-(2,3-dihydro-1H-indol-2-yl)methanol, the characteristics of which are the following:
Mass spectrometry: method A
Retention time Tr (min)=0.19;
[M+H]+: m/z 150
OR=−38.9+/−0.8. C=2.255 mg/0.5 ml DMSO

Synthesis of the Compounds of Formula (Ib)

Example 1b

Synthesis of N-(4-fluorophenyl)-2-[4-(2-methylmorpholin-4-yl)-6-oxo-1,6-dihydropyrimidin-2-yl]acetamide

Step 1b: Synthesis of [4-(2-methylmorpholin-4-yl)-6-oxo-1,6-dihydropyrimidin-2-yl]acetic acid ethyl ester

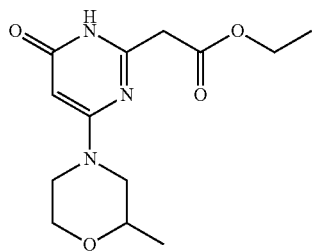 [SMILES: CCOC(=O)Cc1nc(N2CCOC(C)C2)cc(=O)[nH]1]

20 ml of ethanol, 1.5 g of 2-methylmorpholine, 8.7 g of ethyl 3-ethoxy-3-iminopropanoate hydrochloride and 7.75 ml of N,N-diisopropylethylamine are placed in a microwave tube. After one hour of microwave irradiation at a temperature of 130° C., the reaction medium is concentrated under reduced pressure. The residue obtained is purified on a silica column, eluent: dichloromethane/methanol: 97/03, so as to give 0.8 g of [4-(2-methylmorpholin-4-yl)-6-oxo-1,6-dihydropyrimidin-2-yl]acetic acid ethyl ester in the form of a beige solid, the characteristics of which are the following:
Mass spectrometry: method A
Retention time Tr (min)=0.56;
[M+H]+: m/z 282; [M−H]−: m/z 280

Step 2b: Synthesis of the sodium salt of [4-(2-methylmorpholin-4-yl)-6-oxo-1,6-dihydropyrimidin-2-yl]acetic acid

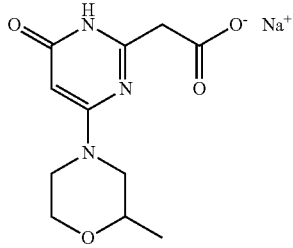

1.8 ml of 2M sodium hydroxide are added to a solution of 0.8 g of [4-(2-methylmorpholin-4-yl)-6-oxo-1,6-dihydropyrimidin-2-yl]acetic acid ethyl ester in 8 ml of tetrahydrofuran. The reaction mixture is stirred for 24 hours at ambient temperature. The reaction medium is concentrated under reduced pressure. The solid obtained is then dried in a rotary evaporator, so as to give 0.7 g of the sodium salt of [4-(2-methylmorpholin-4-yl)-6-oxo-1,6-dihydropyrimidin-2-yl]acetic acid in the form of a beige solid, the characteristics of which are the following:
Mass spectrometry: method A
[M+H]+: m/z 254; [M−H]−: m/z 252; base peak: m/z 208

Step 3b: Synthesis of N-(4-fluorophenyl)-2-[4-(2-methylmorpholin-4-yl)-6-oxo-1,6-dihydropyrimidin-2-yl]acetamide

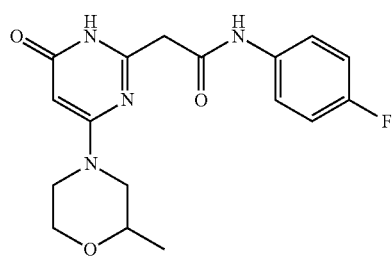 [SMILES: CC1CN(c2cc(=O)[nH]c(CC(=O)Nc3ccc(F)cc3)n2)CCO1]

1.46 g of N-[3-(dimethylamino)propyl]-N'-ethylcarbodiimide hydrochloride, 6.7 ml of pyridine and 0.7 ml of 4-fluoroaniline are added to a solution of 700 mg of sodium salt of [4-(2-methylmorpholin-4-yl)-6-oxo-1,6-dihydropyrimidin-2-yl]acetic acid in 6.7 ml of N,N-dimethylformamide. The reaction mixture is stirred at ambient temperature for 24 hours and then concentrated under reduced pressure. Water and ethyl acetate are added and the resulting mixture is stirred for 30 minutes. The precipitate formed is filtered off and washed with dichloromethane and with ethyl ether, so as to give 300 mg of N-(4-fluorophenyl)-2-[4-(2-methylmorpholin-4-yl)-6-oxo-1,6-dihydropyrimidin-2-yl]acetamide in the form of a white solid, the characteristics of which are the following:
$^1$H NMR spectrum (400 MHz): 1.07 (d, J=6.1 Hz, 3H); 2.47 (dd, J=10.9 and 13.0 Hz, 1H); 2.80 (m, 1H); 3.39 to 3.50 (m, 2H); 3.58 (s, 2H); 3.82 (dd, J=3.0 and 10.9 Hz, 1H); 3.95 (m, 1H); 4.04 (m, 1H); 5.21 (s, 1H); 7.15 (t, J=8.9 Hz, 2H);

7.58 (dd, J=5.4 and 8.9 Hz, 2H); 10.19 (broad s, 1H); 11.62 (broad m, 1H)

Mass spectrometry: method A

Retention time Tr (min)=0.66;

[M+H]+: m/z 347; [M−H]−: m/z 345

Example 2b

Synthesis of (+)-N-(4-fluorophenyl)-2-[4-(2-methyl-morpholin-4-yl)-6-oxo-1,6-dihydropyrimidin-2-yl]acetamide

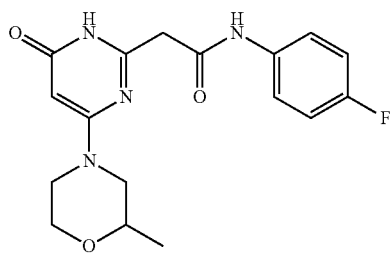 [SMILES: CC1CN(c2cc(=O)[nH]c(CC(=O)Nc3ccc(F)cc3)n2)CCO1]

The separation of the two enantiomers of N-(4-fluorophenyl)-2-[4-(2-methylmorpholin-4-yl)-6-oxo-1,6-dihydropyrimidin-2-yl]acetamide (example 1b) (250 mg) was carried out by chiral chromatography: stationary phase: Chiralpak AS 20 μm; mobile phase: heptane (80%)/EtOH (10%)/MeOH (10%); flow rate: 140 ml/min.

The levorotatory enantiomer is concentrated so as to obtain 112 mg of N-(4-fluorophenyl)-2-[4-((−)-2-methylmorpholin-4-yl)-6-oxo-1,6-dihydropyrimidin-2-yl]acetamide in the form of a white solid, the characteristics of which are the following:

Mass spectrometry: method A

Retention time Tr (min)=0.66; [M+H]+: m/z 347; [M−H]−: m/z 345

Optical rotation: $\alpha_D$=−15.0+/−0.6. C=2.243 mg/0.5 ml DMSO

The dextrorotatory enantiomer is concentrated so as to obtain 117 mg of N-(4-fluorophenyl)-2-[4-((+)-2-methylmorpholin-4-yl)-6-oxo-1,6-dihydropyrimidin-2-yl]acetamide in the form of a white solid, the characteristics of which are the following:

$^1$H NMR spectrum (400 MHz): 1.07 (d, J=6.4 Hz, 3H); 2.47 (dd, J=10.9 and 13.0 Hz, 1H); 2.80 (m, 1H); 3.39 to 3.50 (m, 2H); 3.58 (s, 2H); 3.82 (dd, J=3.5 and 10.9 Hz, 1H); 3.95 (m, 1H); 4.04 (m, 1H); 5.21 (s, 1H); 7.15 (t, J=8.9 Hz, 2H); 7.58 (dd, J=5.4 and 8.9 Hz, 2H); 10.21 (broad s, 1H); 11.62 (broad m, 1H)

Mass spectrometry: method A

Retention time Tr (min)=0.66; [M+H]+: m/z 347; [M−H]−: m/z 345

Optical rotation: $\alpha_D$=+16.2+/−0.7. C=1.824 mg/0.5 ml DMSO

Example 3b

Synthesis of 2-[4-(2-fluoromethylmorpholin-4-yl)-6-oxo-1,6-dihydropyrimidin-2-yl]-N-(4-fluorophenyl)acetamide Step 1b: Synthesis of [4-(2-fluoromethylmorpholin-4-yl)-6-oxo-1,6-dihydropyrimidin-2-yl]acetic acid ethyl ester

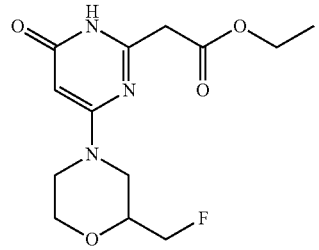 [SMILES: CCOC(=O)Cc1nc(N2CCOC(CF)C2)cc(=O)[nH]1]

The product is prepared by following the procedure described in step 1b of example 1b using 1.5 g of 2-fluoromethylmorpholine hydrochloride (which can be prepared according to Yoshikazu J. et al. (J. Med. Chem. (1994), 37(17), 2791-2796; 1994) instead of 2-methylmorpholine and 5.6 g of ethyl 3-ethoxy-3-iminopropanoate hydrochloride. 700 mg of [4-(2-fluoromethylmorpholin-4-yl)-6-oxo-1,6-dihydropyrimidin-2-yl]acetic acid ethyl ester are obtained in the form of a white solid, the characteristics of which are the following:

Mass spectrometry: method A

Retention time Tr (min)=0.55;

[M+H]+: m/z 300; [M−H]−: m/z 298

Step 2b: Synthesis of the sodium salt of [4-(2-fluoromethylmorpholin-4-yl)-6-oxo-1,6-dihydropyrimidin-2-yl]acetic acid

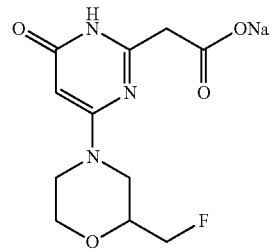

The product is prepared by following the procedure described in step 2b of example 1b using 700 mg of [4-(2-fluoromethylmorpholin-4-yl)-6-oxo-1,6-dihydropyrimidin-2-yl]acetic acid ethyl ester and 1.4 ml of 2M sodium hydroxide. 670 mg of the sodium salt of [4-(2-fluoromethylmorpholin-4-yl)-6-oxo-1,6-dihydropyrimidin-2-yl]acetic acid are obtained, the characteristics of which are the following:

Mass spectrometry: method A

[M+H]+: m/z 272; [M−H]−: m/z 270; base peak: m/z 226

Step 3b: Synthesis of 2-[4-(2-fluoromethylmorpholin-4-yl)-6-oxo-1,6-dihydropyrimidin-2-yl]-N-(4-fluorophenyl)acetamide

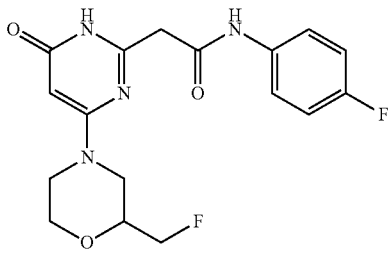 [SMILES: O=C(Cc1nc(N2CCOC(CF)C2)cc(=O)[nH]1)Nc1ccc(F)cc1]

The product is prepared by following the procedure described in step 3b of example 1b, but using 670 mg of the sodium salt of [4-(2-fluoromethylmorpholin-4-yl)-6-oxo-1,6-dihydropyrimidin-2-yl]acetic acid and 762 mg of 4-fluoroaniline. 300 mg of 2-[4-(2-fluoromethylmorpholin-4-yl)-6-oxo-1,6-dihydropyrimidin-2-yl]-N-(4-fluorophenyl)acetamide are obtained in the form of a white solid, the characteristics of which are the following:

$^1$H NMR spectrum (400 MHz): 2.69 (dd, J=10.9 and 13.0 Hz, 1H); 2.85 (m, 1H); 3.49 (m, 1H); 3.59 (s, 2H); 3.64 (m, 1H); 3.90 (dd, J=3.0 and 10.9 Hz, 1H); 3.98 (m, 1H); 4.09 (m, 1H); 4.44 (dm, J=47.5 Hz, 2H); 5.24 (s, 1H); 7.15 (t, J=8.9 Hz, 2H); 7.58 (dd, J=5.4 and 8.9 Hz, 2H); 10.21 (broad s, 1H); 11.68 (broad m, 1H)

Mass spectrometry: method A
Retention time Tr (min)=0.65;
[M+H]+: m/z 365; [M−H]−: m/z 363

Example 4b

Synthesis of (+)-N-(4-fluorophenyl)-2-[4-(2-fluoromethyl-morpholin-4-yl)-6-oxo-1,6-dihydropyrimidin-2-yl]acetamide

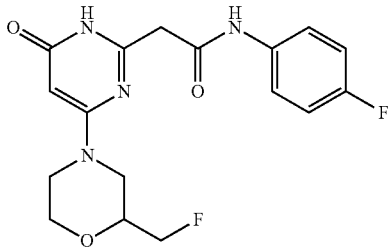 [SMILES: O=C(Cc1nc(N2CCOC(CF)C2)cc(=O)[nH]1)Nc1ccc(F)cc1]

The separation of the two enantiomers of N-(4-fluorophenyl)-2-[4-(2-fluoromethylmorpholin-4-yl)-6-oxo-1,6-dihydropyrimidin-2-yl]acetamide (215 mg) was carried out by chiral chromatography:
stationary phase: Chiralpak AS 20 μm; mobile phase: heptane (70%)/EtOH (20%)/MeOH (10%); flow rate: 180 ml/min.

The levorotatory enantiomer is concentrated so as to obtain 74 mg of (−)-N-(4-fluorophenyl)-2-[4-(2-fluoromethylmorpholin-4-yl)-6-oxo-1,6-dihydropyrimidin-2-yl]acetamide in the form of a white solid, the characteristics of which are the following:

Mass spectrometry: method A
Retention time Tr (min)=3.05;
[M+H]+: m/z 365; [M−H]−: m/z 363
Optical rotation: $\alpha_D$=−14.3+/−0.6 C=2.173 mg/0.5 ml/DMSO The dextrorotatory enantiomer is concentrated so as to obtain 97 mg of (+)-N-(4-fluorophenyl)-2-[4-(2-fluoromethylmorpholin-4-yl)-6-oxo-1,6-dihydropyrimidin-2-yl]acetamide in the form of a white solid, the characteristics of which are the following:

$^1$H NMR spectrum (400 MHz): 2.69 (dd, J=10.9 and 13.0 Hz, 1H); 2.85 (m, 1H); 3.49 (m, 1H); 3.59 (s, 2H); 3.66 (m, 1H); 3.90 (dd, J=3.5 and 10.9 Hz, 1H); 3.98 (m, 1H); 4.09 (m, 1H); 4.44 (dm, J=47.5 Hz, 2H); 5.24 (s, 1H); 7.15 (t, J=8.9 Hz, 2H); 7.58 (dd, J=5.4 and 8.9 Hz, 2H); 10.22 (broad s, 1H); 11.68 (broad m, 1H)

Mass spectrometry: method B
Retention time Tr (min)=3.05;
[M+H]+: m/z 365; [M−H]−: m/z 363
Optical rotation: $\alpha_D$=+16.1+/−0.5. C=3.046 mg/0.5 ml DMSO Example 5b Synthesis of (+)-N-(3-chloro-4-fluorophenyl)-2-[4-(2-fluoro-methylmorpholin-4-yl)-1-methyl-6-oxo-1,6-dihydropyrimidin-2-yl]acetamide Step 1b: Synthesis of [4-(2-fluoromethylmorpholin-4-yl)-1-methyl-6-oxo-1,6-dihydropyrimidin-2-yl]acetic acid ethyl ester

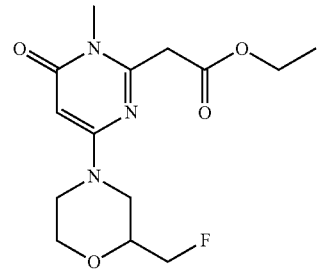 [SMILES: CCOC(=O)Cc1nc(N2CCOC(CF)C2)cc(=O)n1C]

2.1 g of cesium carbonate and 0.8 ml of iodomethane are added to a mixture of 1.5 g of [4-(2-fluoromethylmorpholin-4-yl)-6-oxo-1,6-dihydropyrimidin-2-yl]acetic acid ethyl ester in 35 ml of dioxane. The suspension is stirred at ambient temperature for 24 hours.

The reaction medium is filtered. The filtrate is concentrated under reduced pressure. The residue obtained is purified on a silica column: eluent 98/02 dichloromethane/methanol, so as to give 253 mg of [4-(2-fluoromethylmorpholin-4-yl)-1-methyl-6-oxo-1,6-dihydropyrimidin-2-yl]acetic acid ethyl ester, the characteristics of which are the following:

Mass spectrometry: method A
Retention time Tr (min)=0.60;
[M+H]+: m/z 314; [M−H]−: m/z 312

Step 2b: Synthesis of the sodium salt of [4-(2-fluoromethylmorpholin-4-yl)-1-methyl-6-oxo-1,6-dihydropyrimidin-2-yl]acetic acid

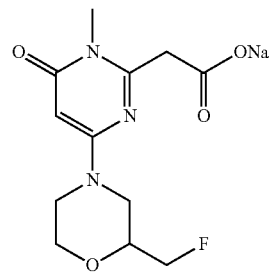

The product is prepared by following the procedure described in step 2b of example 1b using 250 mg of [4-(2- fluoromethylmorpholin-4-yl)-1-methyl-6-oxo-1,6-dihydropyrimidin-2-yl]acetic acid ethyl ester and 0.6 ml of 2M sodium hydroxide. 250 mg of the sodium salt of [4-(2-fluoromethylmorpholin-4-yl)-1-methyl-6-oxo-1,6-dihydropyrimidin-2-yl]acetic acid are obtained, the characteristics of which are the following:

Mass spectrometry: method A

Retention time Tr (min)=0.38;

[M+H]+: m/z 286; [M–H]–: m/z 284; base peak: m/z 240

Step 3b: Synthesis of (+)-N-(3-chloro-4-fluorophenyl)-2-[4-(2-fluoromethyl-morpholin-4-yl)-1-methyl-6-oxo-1,6-dihydropyrimidin-2-yl]acetamide

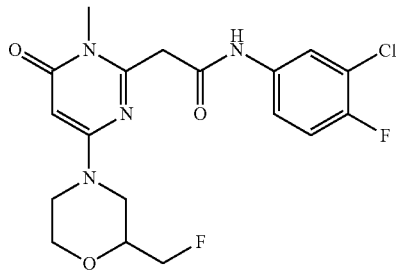 [SMILES: Cn1c(CC(=O)Nc2ccc(F)c(Cl)c2)nc(N2CCOC(CF)C2)cc1=O]

The product is prepared by following the procedure described in step 3b of example 1b, but using 250 mg of the sodium salt of [4-(2-fluoromethylmorpholin-4-yl)-1-methyl-6-oxo-1,6-dihydropyrimidin-2-yl]acetic acid and 237 mg of 3-chloro-4-fluoroaniline. 97 mg of 2-[4-(2-fluoromethylmorpholin-4-yl)-1-methyl-6-oxo-1,6-dihydropyrimidin-2-yl]-N-(3-chloro-4-fluorophenyl)acetamide are obtained in the form of a white solid, the characteristics of which are the following:

Mass spectrometry: method A

Retention time Tr (min)=3.58;

[M+H]+: m/z 413; [M–H]–: m/z 411

The separation of the two enantiomers of N-(3-chloro-4-fluorophenyl)-2-[4-(2-fluoromethylmorpholin-4-yl)-1-methyl-6-oxo-1,6-dihydropyrimidin-2-yl]acetamide (80 mg) was carried out by chiral chromatography: stationary phase: Chiralpak AS 20 μm; mobile phase: heptane (70%)/EtOH (20%)/MeOH (10%); flow rate: 120 ml/min.

The first enantiomer is concentrated so as to obtain 36 mg of (−)-N-(3-chloro-4-fluorophenyl)-2-[4-(2-fluoromethyl-morpholin-4-yl)-1-methyl-6-oxo-1,6-dihydropyrimidin-2-yl]acetamide in the form of a white solid, the characteristics of which are the following:

Mass spectrometry: method A

Retention time Tr (min)=0.79; [M+H]+: m/z 413; [M–H]–: m/z 411

The second enantiomer is concentrated so as to obtain 36 mg of (+)-N-(3-chloro-4-fluorophenyl)-2-[4-(2-fluoromethylmorpholin-4-yl)-1-methyl-6-oxo-1,6-dihydropyrimidin-2-yl]acetamide in the form of a white solid, the characteristics of which are the following:

$^1$H NMR spectrum (500 MHz): 2.67 (m, 1H); 2.83 (m, 1H); 3.34 (partially masked m, 3H); 3.47 (m, 1H); 3.62 (m, 1H); 3.85 to 3.98 (m, 4H); 4.07 (m, 1H); 4.40 (dm, J=47.5 Hz, 2H); 5.40 (s, 1H); 7.38 (t, J=9.1 Hz, 1H); 7.44 (m, 1H); 7.89 (dd, J=2.2 and 6.6 Hz, 1H); 10.44 (broad s, 1H)

Mass spectrometry: method

Retention time Tr (min)=0.79;

[M+H]+: m/z 413; [M–H]–: m/z 411

Example 6b

Synthesis of 2-[2-(4-fluoro-2,3-dihydroindol-1-yl)-2-oxoethyl]-6-(2-fluoromethylmorpholin-4-yl)-3H-pyrimidin-4-one

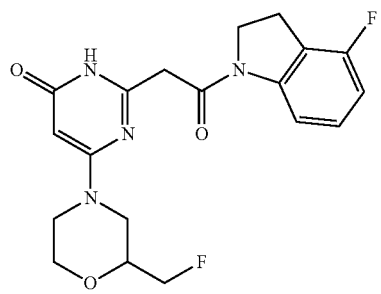 [SMILES: O=C(Cc1nc(N2CCOC(CF)C2)cc(=O)[nH]1)N1CCc2c(F)cccc21]

The product is prepared by following the procedure described in step 3b of example 1b, but using 670 mg of the sodium salt of [4-(2-fluoromethylmorpholin-4-yl)-6-oxo-1,6-dihydropyrimidin-2-yl]acetic acid and 345 mg of 4-fluoro-2,3-dihydro-1H-indole. 161 mg of 2-[2-(4-fluoro-2,3-dihydroindol-1-yl)-2-oxoethyl]-6-(2-fluoromethylmorpholin-4-yl)-3H-pyrimidin-4-one are obtained in the form of a white solid, the characteristics of which are the following:

$^1$H NMR spectrum (400 MHz): 2.70 (dd, J=10.6 and 12.8 Hz, 1H); 2.87 (m, 1H); 3.20 (t, J=8.4 Hz, 2H); 3.50 (m, 1H); 3.67 (m, 1H); 3.77 (s, 2H); 3.90 (dd, J=3.5 and 10.6 Hz, 1H); 3.96 (m, 1H); 4.09 (m, 1H); 4.21 (t, J=8.4 Hz, 2H); 4.43 (dm, J=47.5 Hz, 2H); 5.25 (s, 1H); 6.86 (t, J=8.7 Hz, 1H); 7.22 (m, 1H); 7.84 (d, J=8.1 Hz, 1H); 11.63 (broad m, 1H)

Mass spectrometry: method A

Retention time Tr (min)=0.74;

[M+H]+: m/z 391; [M–H]–: m/z 389

Example 7b

Synthesis of (+)-2-[2-(4-fluoro-2,3-dihydroindol-1-yl)-2-oxoethyl]-6-(2-fluoromethylmorpholin-4-yl)-3H-pyrimidin-4-one

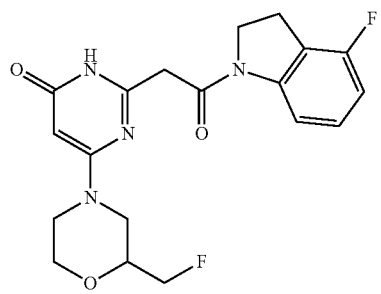 [SMILES: O=C(Cc1nc(N2CCOC(CF)C2)cc(=O)[nH]1)N1CCc2c(F)cccc21]

The separation of the two enantiomers of 2-[2-(4-fluoro-2,3-dihydroindol-1-yl)-2-oxoethyl]-6-(2-fluoromethylmorpholin-4-yl)-3H-pyrimidin-4-one (157 mg) was carried out by chiral chromatography in SFC mode: stationary phase: Chiralpak AS-V 20 μm; mobile phase: $CO_2$ (80%)/MeOH (20%)/TEA (0.1%); flow rate: 300 ml/min.

The levorotatory enantiomer is concentrated so as to obtain 77 mg of (−)-2-[2-(4-fluoro-2,3-dihydroindol-1-yl)-2-oxoethyl]-6-(2-fluoromethylmorpholin-4-yl)-3H-pyrimidin-4-one in the form of a white solid, the characteristics of which are the following:

¹H NMR spectrum (400 MHz): 2.69 (dd, J=10.6 and 12.8 Hz, 1H); 2.85 (m, 1H); 3.20 (t, J=8.7 Hz, 2H); 3.50 (m, 1H); 3.64 (m, 1H); 3.77 (s, 2H); 3.90 (dd, J=3.5 and 10.6 Hz, 1H); 3.97 (m, 1H); 4.09 (m, 1H); 4.21 (t, J=8.7 Hz, 2H); 4.43 (dm, J=47.5 Hz, 2H); 5.25 (s, 1H); 6.86 (t, J=8.7 Hz, 1H); 7.22 (m, 1H); 7.84 (d, J=8.1 Hz, 1H); 11.65 (broad m, 1H)

Mass spectrometry: method A

Retention time Tr (min)=0.77; [M+H]+: m/z 391; [M−H]−: m/z 389

The dextrorotatory enantiomer is concentrated so as to obtain 97 mg of (+)-N-(4-fluorophenyl)-2-[4-(2-fluoromethylmorpholin-4-yl)-6-oxo-1,6-dihydropyrimidin-2-yl]acetamide in the form of a white solid, the characteristics of which are the following:

¹H NMR spectrum (400 MHz): 2.69 (m, 1H); 2.86 (m, 1H); 3.19 (t, J=8.4 Hz, 2H); 3.51 (m, 1H); 3.65 (m, 1H); 3.77 (s, 2H); 3.90 (dd, J=3.5 and 10.6 Hz, 1H); 3.96 (m, 1H); 4.09 (m, 1H); 4.21 (t, J=8.4 Hz, 2H); 4.43 (dm, =47.5 Hz, 2H); 5.25 (s, 1H); 6.86 (t, J=8.7 Hz, 1H); 7.21 (m, 1H); 7.84 (d, J=8.1 Hz, 1H); 11.65 (broad m, 1H)

Mass spectrometry: method A

Retention time Tr (min)=0.77;

[M+H]+: m/z 391; [M−H]−: m/z 389

Example 8b

Synthesis of 2-[2-(4-fluoro-2,3-dihydroindol-1-yl)-2-oxoethyl]-6-(2-methylmorpholin-4-yl)-3H-pyrimidin-4-one Step 1b: Synthesis of 2,4-dichloro-6-methoxypyrimidine

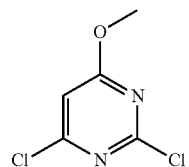

3.24 g of sodium methoxide dissolved beforehand in 13 ml of methanol are added dropwise to a solution of 11 g of 2,4,6-trichloropyrimidine in 140 ml of methanol cooled to 0° C. in an ice bath. The ice bath is removed. The reaction medium is stirred at 0° C. for 45 minutes and then the cooling bath is removed so as to allow the temperature to rise to ambient temperature. The reaction medium is concentrated under reduced pressure. The residue obtained is taken up with 30 ml of water and 100 ml of ethyl acetate. After settling out, the organic phase is dried over magnesium sulfate, filtered, and concentrated under reduced pressure so as to give an oil which is left to crystallize for 24 hours at ambient temperature. The product crystallizes in the form of needles in the middle of an oil. The needles are separated, so as to give 3.94 g of 2,4-dichloro-6-methoxypyrimidine, the characteristics of which are the following:

Mass spectrometry: method A

EI: [M]+. m/z=178; base peak: m/z=148

Step 2b: Synthesis of (4-chloro-6-methoxypyrimidin-2-yl)acetic acid ethyl ester

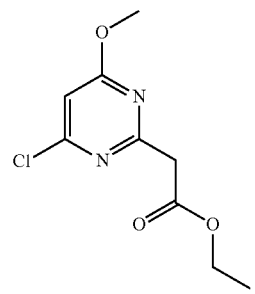

91.4 ml of 1M lithium bis(trimethylsilyl)amide (THF) are added dropwise to a solution of 7.4 g of 2,4-dichloro-6-methoxypyrimidine and 4.5 ml of ethyl acetate in 100 ml of anhydrous THF cooled to −75° C. in a dry ice/acetone bath.

The reaction medium is stirred at −75° C. for one hour.

The cooling bath is removed so as to allow the temperature to rise to 22° C. The reaction medium is stirred at 22° C. for one hour.

100 ml of water and 400 ml of ethyl acetate are added. After settling out, the organic phase is dried over magnesium sulfate, filtered, and then concentrated under reduced pressure so as to give 9.5 g of (4-chloro-6-methoxypyrimidin-2-yl)acetic acid ethyl ester in the form of an orange oil, the characteristics of which are the following:

Mass spectrometry: method A

Retention time Tr (min)=0.80;

[M+H]+: m/z 231

Step 3b: Synthesis of the sodium salt of (4-methoxy-6-chloropyrimidin-2-yl)acetic acid

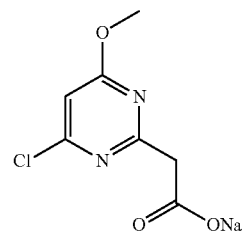

12.1 ml of 2N sodium hydroxide are added to a solution of 5.58 g of (4-chloro-6-methoxypyrimidin-2-yl)acetic acid ethyl ester in 56 ml of THF. The reaction medium is stirred at ambient temperature for 48 hours. The reaction medium is concentrated under reduced pressure. The residue obtained is oven-dried under vacuum in the presence of P₂O₅, so as to give 5.4 g of the sodium salt of (4-methoxy-6-chloropyrimidin-2-yl)acetic acid which will be used as it is in the next step.

Step 4b: Synthesis of 1-(4-fluoro-2,3-dihydroindol-1-yl)-2-(4-methoxy-6-chloropyrimidin-2-yl)ethanone

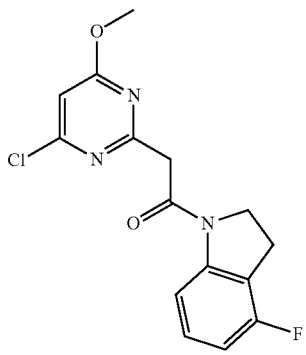 [SMILES: COc1cc(Cl)nc(CC(=O)N2CCc3c(F)cccc32)n1]

3.32 g of 4-fluoro-2,3-dihydro-1H-indole and 5.56 g of N-[3-(dimethylamino)propyl]-N'-ethylcarbodiimide hydrochloride are added to a solution of 5.4 g of the sodium salt of (4-methoxy-6-chloropyrimidin-2-yl)acetic acid in 50 ml of DMF and 4.3 ml of pyridine. The reaction medium is stirred at ambient temperature for one hour. 200 ml of ethyl acetate and 100 ml of water are added, and also 1N hydrochloric acid to pH=5-6. After settling out, the organic phase is dried over magnesium sulfate, filtered, and then concentrated under reduced pressure. The oil obtained is taken up with ethyl ether. The solid formed is filtered off so as to give 2.2 g of 1-(4-fluoro-2,3-dihydroindol-1-yl)-2-(4-methoxy-6-chloropyrimidin-2-yl)ethanone in the form of an orangey-colored solid, the characteristics of which are the following:

Mass spectrometry: method A
Retention time Tr (min)=0.97;
[M+H]+: m/z 322; [M−H]−: m/z 320

Step 5b: Synthesis of 2-[2-(4-fluoro-2,3-dihydroindol-1-yl)-2-oxoethyl]-6-chloro-3H-pyrimidin-4-one

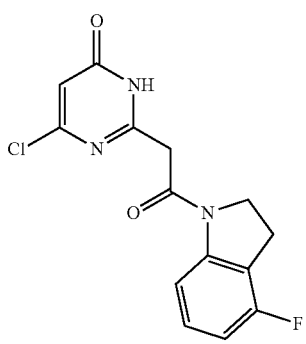 [SMILES: O=C(Cc1nc(Cl)cc(=O)[nH]1)N1CCc2c(F)cccc21]

2 g of 1-(4-fluoro-2,3-dihydroindol-1-yl)-2-(4-methoxy-6-chloropyrimidin-2-yl)ethanone are added to a microwave tube with 30 ml of acetonitrile. 3.1 g of KI and 2.4 ml of trimethylchlorosilane are added. After microwave irradiation for one hour at a temperature of 100° C., the reaction medium is diluted with 100 ml of ethyl acetate and 20 ml of water. After settling out, the organic phase is dried over magnesium sulfate, filtered, and then concentrated under reduced pressure. The residue obtained is purified on a silica column, eluent: 95/05 dichloromethane/methanol, so as to give 1.13 of 2-[2-(4-fluoro-2,3-dihydroindol-1-yl)-2-oxoethyl]-6-chloro-3H-pyrimidin-4-one in the form of a white solid.

Mass spectrometry: method A
Retention time Tr (min)=0.73;
[M+H]+: m/z 308; [M−H]−: m/z 306

Step 6b: Synthesis of 2-[2-(4-fluoro-2,3-dihydroindol-1-yl)-2-oxoethyl]-6-(2-methylmorpholin-4-yl)-3H-pyrimidin-4-one

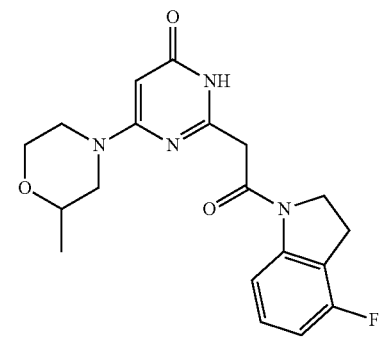 [SMILES: CC1CN(c2cc(=O)[nH]c(CC(=O)N3CCc4c(F)cccc43)n2)CCO1]

A solution of 200 mg of 2-[2-(4-fluoro-2,3-dihydroindol-1-yl)-2-oxoethyl]-6-chloro-3H-pyrimidin-4-one in 2 ml of 2-methylmorpholine is heated at 100° C. for 15 minutes. The reaction medium is taken up with 10 ml of water. The solid formed is filtered off and washed with water and then dried so as to give 216 mg of 2-[2-(4-fluoro-2,3-dihydroindol-1-yl)-2-oxoethyl]-6-(2-methylmorpholin-4-yl)-3H-pyrimidin-4-one in the form of a beige solid, the characteristics of which are the following:

$^1$H NMR spectrum (400 MHz): 1.06 (d, J=6.1 Hz, 3H); 2.47 (partially masked m, 1H); 2.80 (m, 1H); 3.19 (t, J=8.4 Hz, 2H); 3.39 to 3.50 (m, 2H); 3.76 (s, 2H); 3.81 (m, 1H); 3.93 (m, 1H); 4.04 (m, 1H); 4.21 (t, J=8.4 Hz, 2H); 5.22 (s, 1H); 6.86 (t, J=8.6 Hz, 1H); 7.22 (m, 1H); 7.84 (d, J=8.3 Hz, 1H); 11.60 (broad m, 1H)

Mass spectrometry: method A
Retention time Tr (min)=0.74;
[M+H]+: m/z 373; [M−H]−: m/z 371

Example 9b

Synthesis of (−)-2-[2-(4-fluoro-2,3-dihydroindol-1-yl)-2-oxoethyl]-6-(2-methylmorpholin-4-yl)-3H-pyrimidin-4-one and example 10b: Synthesis of (+)-2-[2-(4-fluoro-2,3-dihydroindol-1-yl)-2-oxoethyl]-6-(2-methylmorpholin-4-yl)-3H-pyrimidin-4-one

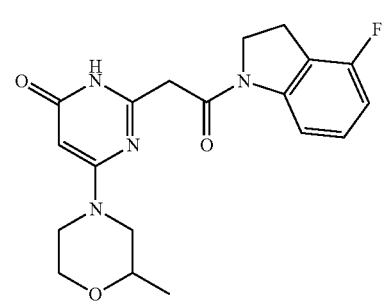

163
-continued

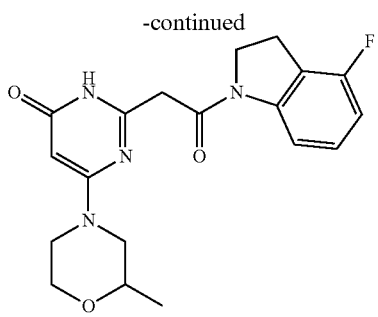

The separation of the two enantiomers of 2-[2-(4-fluoro-2,3-dihydroindol-1-yl)-2-oxoethyl]-6-(2-methylmorpholin-4-yl)-3H-pyrimidin-4-one (211 mg) was carried out by chiral chromatography: stationary phase: Chiralpak AS-V 20 μm; mobile phase: heptane (50%)/EtOH (50%)/TEA (0.1%); flow rate: 300 nil/min.

The levorotatory enantiomer is concentrated so as to obtain 100 mg of (−)-2-[2-(4-fluoro-2,3-dihydroindol-1-yl)-2-oxoethyl]-6-(2-methylmorpholin-4-yl)-3H-pyrimidin-4-one in the form of a white solid, the characteristics of which are the following:

$^1$H NMR spectrum (400 MHz): 1.06 (d, J=6.3 Hz, 3H); 2.48 (partially masked m, 1H); 2.80 (m, 1H); 3.20 (t, J=8.7 Hz, 2H); 3.37 to 3.51 (m, 2H); 3.77 (s, 2H); 3.82 (m, 1H); 3.94 (m, 1H); 4.05 (m, 1H); 4.21 (t, J=8.6 Hz, 2H); 5.23 (s, 1H); 6.87 (t, J=8.8 Hz, 1H); 7.23 (m, 1H); 7.84 (d, J=8.1 Hz, 1H); 11.64 (broad m, 1H)

Mass spectrometry: method A
Retention time Tr (min)=0.75;
[M+H]+: m/z 373; [M−H]−: m/z 371;
Optical rotation: $\alpha_D$=−10 C=0.477 mg/0.5 ml DMSO The dextrorotatory enantiomer is concentrated so as to obtain 85 mg of (+)-N-(4-fluorophenyl)-2-[4-(2-methylmorpholin-4-yl)-6-oxo-1,6-dihydropyrimidin-2-yl]acetamide in the form of a white solid, the characteristics of which are the following:

$^1$H NMR spectrum (400 MHz): 1.06 (d, J=6.3 Hz, 3H); 2.47 (m, 1H); 2.80 (m, 1H); 3.19 (t, J=8.7 Hz, 2H); 3.39 to 3.49 (m, 2H); 3.77 (s, 2H); 3.82 (m, 1H); 3.94 (m, 1H); 4.05 (m, 1H); 4.21 (t, J=8.7 Hz, 2H); 5.23 (s, 1H); 6.87 (t, J=8.8 Hz, 1H); 7.22 (m, 1H); 7.84 (d, J=8.1 Hz, 1H); 11.64 (broad m, 1H)

Mass spectrometry: method A
Retention time Tr (min)=0.74;
[M−H]−: m/z 371;
Optical rotation: $\alpha_D$=+15 ds DMSO at 589 nm C=0.388 mg/0.5 ml Example 11b Synthesis of 2-[2-(4-fluoro-2,3-dihydroindol-1-yl)-2-oxoethyl]-6-(hexahydrocyclopenta[1,4]oxazin-4-yl)-3H-pyrimidin-4-one

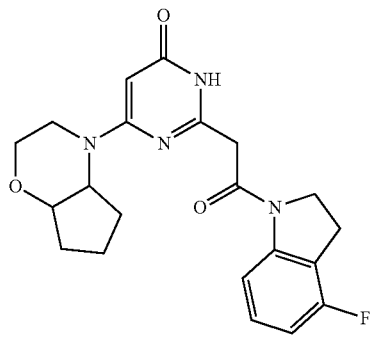 [SMILES: O=C(Cc1nc(N2CCOC3CCCC32)cc(=O)[nH]1)N1CCc2c(F)cccc21]

164

532 mg of hexahydrocyclopenta[1,4]oxazine hydrochloride are added to a solution of 100 mg of 2-[2-(4-fluoro-2,3-dihydroindol-1-yl)-2-oxoethyl]-6-chloro-3H-pyrimidin-4-one in 5 ml of diisopropylethylamine. The reaction medium is heated at 100° C. for 2 hours. The reaction medium is taken up with 10 ml of water. The solid formed is filtered off and washed with water and then dried so as to give 30 mg of 2-[2-(4-fluoro-2,3-dihydroindol-1-yl)-2-oxoethyl]-6-(hexahydrocyclopenta[1,4]oxazin-4-yl)-3H-pyrimidin-4-one in the form of a beige solid, the characteristics of which are the following:

$^1$H NMR spectrum (400 MHz): 1.29 to 1.55 (m, 4H); 1.75 (m, 1H); 2.45 (m, 1H); 2.78 (m, 1H); 2.88 (m, 1H); 3.19 (t, J=8.1 Hz, 2H); 3.37 (m, 1H); 3.62 (dt, J=3.4 and 11.5 Hz, 1H); 3.76 (m, 3H); 3.92 (td, J=3.4 and 11.5 Hz, 1H); 4.19 (m, 2H); 5.30 (s, 1H); 6.86 (t, J=8.7 Hz, 1H); 7.22 (m, 1H); 7.85 (d, J=8.1 Hz, 1H); 11.77 (broad m, 1H)

Mass spectrometry: method A
Retention time Tr (min)=0.79;
[M+H]+: m/z 399; [M−H]−: m/z 397

Example 12b

Synthesis of 2-[2-(4-fluoro-2,3-dihydroindol-1-yl)-2-oxoethyl]-6-pyridin-4-yl-3H-pyrimidin-4-one

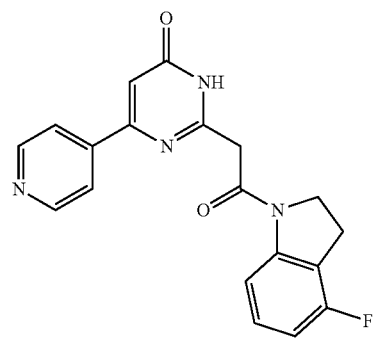 [SMILES: O=C(Cc1nc(-c2ccncc2)cc(=O)[nH]1)N1CCc2c(F)cccc21]

In a microwave tube, a mixture of 59 mg of 2-[2-(4-fluoro-2,3-dihydroindol-1-yl)-2-oxoethyl]-6-chloro-3H-pyrimidin-4-one, 88 mg of pyridine-4-boronic acid pinacol ester, 32 mg of tetrakis(triphenylphosphine)palladium and 0.26 ml of a 1.5M cesium carbonate solution in 1.25 ml of dioxane is microwave-irradiated for one and a half hours at 100° C. The reaction medium is taken up with a mixture of methanol, ethyl acetate and a few drops of water. The solid formed is filtered off and washed with water and then dried so as to give 20 mg of 2-[2-(4-fluoro-2,3-dihydroindol-1-yl)-2-oxoethyl]-6-pyridin-4-yl-3H-pyrimidin-4-one in the form of a beige solid, the characteristics of which are the following:

$^1$H NMR spectrum (400 MHz): 3.23 (t, J=8.5 Hz, 2H); 3.99 (s, 2H); 4.28 (t, J=8.5 Hz, 2H); 6.88 (t, J=8.9 Hz, 1H); 7.01 (s, 1H); 7.22 (m, 1H); 7.85 (d, J=8.1 Hz, 1H); 7.96 (d, J=6.0 Hz, 2H); 8.69 (d, J=6.0 Hz, 2H); 12.69 (broad m, 1H)

Mass spectrometry: method A
Retention time Tr (min)=0.52;
[M+H]+: m/z 351; [M−H]−: m/z 349

Example 13b

Synthesis of 2-[2-(4-fluoro-2,3-dihydroindol-1-yl)-2-oxoethyl]-6-(2-methoxypyridin-4-yl)-3H-pyrimidin-4-one

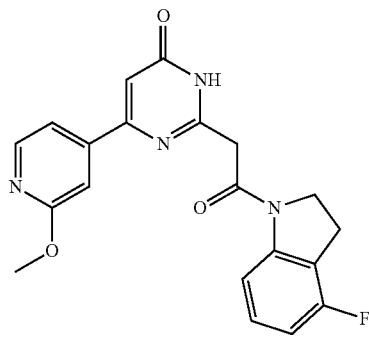 [SMILES: COc1cc(-c2cc(=O)[nH]c(CC(=O)N3CCc4c(F)cccc43)n2)ccn1]

The product is prepared by following the procedure described in example 12b using 100 mg of 2-[2-(4-fluoro-2,3-dihydroindol-1-yl)-2-oxoethyl]-6-chloro-3H-pyrimidin-4-one and 160 mg of 2-methoxypyridine-4-boronic acid pinacol ester. 75 mg of 2-[2-(4-fluoro-2,3-dihydroindol-1-yl)-2-oxoethyl]-6-(2-methoxypyridin-4-yl)-3H-pyrimidin-4-one are obtained in the form of a beige solid, the characteristics of which are the following:

¹H NMR spectrum (400 MHz): 3.23 (t, J=8.6 Hz, 2H); 3.88 (s, 3H); 3.98 (s, 2H); 4.27 (t, J=8.6 Hz, 2H); 6.88 (t, J=8.6 Hz, 1H); 7.00 (s, 1H); 7.23 (m, 1H); 7.39 (broad s, 1H); 7.56 (broad d, J=5.4 Hz, 1H); 7.85 (d, J=8.3 Hz, 1H); 8.26 (d, J=5.4 Hz, 1H); 12.66 (broad m, 1H)

Mass spectrometry: method A
Retention time Tr (min)=0.82;
[M+H]+: m/z 381; [M−H]−: m/z 379

Example 14b

Synthesis of (±)-2-[4-(2-ethylmorpholin-4-yl)-6-oxo-1,6-dihydropyrimidin-2-yl]-N-(4-fluorophenyl)acetamide Step 1b: Synthesis of [4-(2-ethylmorpholin-4-yl)-6-oxo-1,6-dihydropyrimidin-2-yl]acetic acid ethyl ester

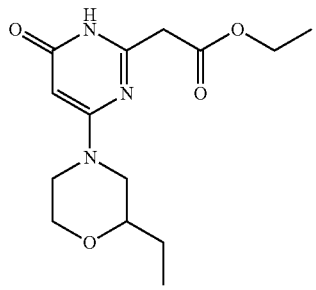 [SMILES: CCOC(=O)Cc1nc(N2CCOC(CC)C2)cc(=O)[nH]1]

In a microwave tube, 0.45 g of 2-ethylmorpholine is placed in 10 ml of ethanol, 2.11 ml of N,N-diisopropylethylamine and 2.29 g of ethyl 3-ethoxy-3-iminopropanoate hydrochloride. The tube is then microwave-heated at 130° C. for 1 hour and then allowed to return to ambient temperature. The reaction mixture is concentrated under reduced pressure. After purification by silica column chromatography, eluent: 90/05 dichloromethane/methanol, 550 mg of [4-(2-ethylmorpholin-4-yl)-6-oxo-1,6-dihydropyrimidin-2-yl]acetic acid ethyl ester are obtained in the form of a beige powder, the characteristics of which are the following:

Mass spectrometry: method A;
Retention time Tr (min)=0.66;
[M+H]+: m/z 296; [M−H]−: m/z 294

Step 2b: Synthesis of the sodium salt of [4-(2-ethylmorpholin-4-yl)-6-oxo-1,6-dihydropyrimidin-2-yl]acetic acid

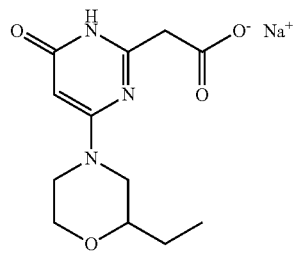 [SMILES: CCC1CN(c2cc(=O)[nH]c(CC(=O)[O-])n2)CCO1 ; [Na+]]

0.93 ml of 2M sodium hydroxide is added to a solution of 520 mg of [4-(2-ethylmorpholin-4-yl)-6-oxo-1,6-dihydropyrimidin-2-yl]acetic acid ethyl ester in 14 ml of tetrahydrofuran. The reaction mixture is stirred for 48 hours at ambient temperature and then evaporated under vacuum. 420 mg of the sodium salt of [4-(2-ethylmorpholin-4-yl)-6-oxo-1,6-dihydropyrimidin-2-yl]acetic acid are obtained in the form of a yellow powder which is used as it is for the next step.

Step 3b: (±)-2-[4-(2-Ethylmorpholin-4-yl)-6-oxo-1,6-dihydropyrimidin-2-yl]-N-(4-fluorophenyl)acetamide

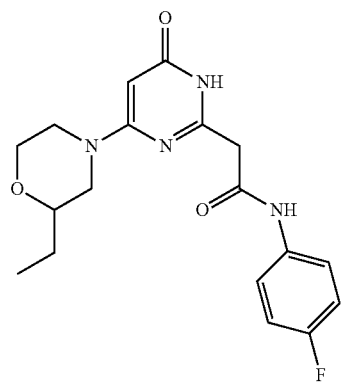 [SMILES: CCC1CN(c2cc(=O)[nH]c(CC(=O)Nc3ccc(F)cc3)n2)CCO1]

4 ml of pyridine, 472 mg of 4-fluoroaniline and 815 mg of N-[3-(dimethylamino)propyl]-N'-ethylcarbodiimide hydrochloride are successively added to a solution of 410 mg of the sodium salt of [4-(2-ethylmorpholin-4-yl)-6-oxo-1,6-dihydropyrimidin-2-yl]acetic acid in 4 ml of N,N-dimethylformamide. The reaction mixture is stirred at ambient temperature for 16 hours, and then concentrated under reduced pressure. The residue is taken up in 25 ml of water and then the pH is brought back to about 7 with a 2M hydrochloric acid solution. 30 ml of ethyl acetate are added and then the resulting mixture is allowed to stir at ambient temperature for 1 hour. The precipitate formed is filtered off, and then rinsed successively with water and diethyl ether. 300 mg of (±)-2-[4-(2-ethylmorpholin-4-yl)-6-oxo-1,6-dihydropyrimidin-2-yl]-N-(4-fluorophenyl)-acetamide are thus obtained in the form of an off-white powder, the characteristics of which are the following:

Mass spectrometry: method C*
Retention time Tr (min)=3.37;
[M+H]+: m/z 361; [M−H]−: m/z 359

C*=ZQ XBridge C18 2.5 μm 3×50 mm 900 μl/min 5 to 100% B(CH₃CN) with 0.1% HCO₂H in 5 min Example 15b (+)-2-[4-(2-Ethylmorpholin-4-yl)-6-oxo-1,6-dihydropyrimidin-2-yl]-N-(4-fluorophenyl)acetamide

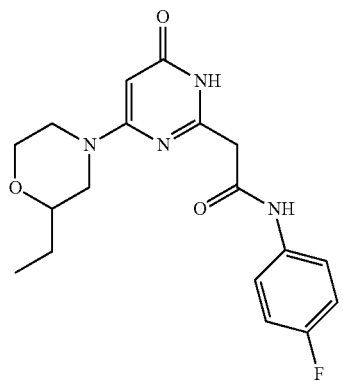 [SMILES: CCC1CN(c2cc(=O)[nH]c(CC(=O)Nc3ccc(F)cc3)n2)CCO1]

(±)-2-[4-(2-ethylmorpholin-4-yl)-6-oxo-1,6-dihydropyrimidin-2-yl]-N-(4-fluorophenyl)acetamide (example 14, step 3, 268 mg) is resolved into its two enantiomers by chiral chromatography on Chiralpak AS-V phase (20 μm, 6×35 cm), eluent: heptane/ethanol: 60/40; flow rate: 150 ml/min. After elution, the fractions containing the second enantiomer are combined and evaporated under reduced pressure.

The dextrorotatory enantiomer, 93.6 mg: (+)-2-[4-(2-ethylmorpholin-4-yl)-6-oxo-1,6-dihydropyrimidin-2-yl]-N-(4-fluorophenyl)acetamide, is isolated in the form of a white powder, the characteristics of which are the following:

Mass spectrometry: method A
Retention time Tr (min)=0.74;
[M+H]+: m/z 361; [M−H]−: m/z 359
Optical rotation: α$_D$=+12° (c=1.330 mg in 1 ml of methanol, 589 nm)

Example 16b

Synthesis of 2-[2-(4-fluoro-2,3-dihydroindol-1-yl)-2-oxoethyl]-6-(2,2,3,3,5,5,6,6-D8-morpholin)-4-yl-3H-pyrimidin-4-one Step 1b: Synthesis of (4-chloro-6-oxo-1,6-dihydropyrimidin-2-yl)acetic acid ethyl ester

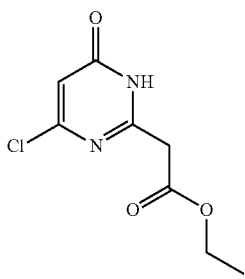

33 g of (4-chloro-6-methoxypyrimidin-2-yl)acetic acid ethyl ester (example 8b, step 2b) and 750 ml of acetonitrile are placed in a 1000 ml autoclave and then 71.2 g of potassium iodide and 55.85 ml of trimethylchlorosilane are added; an orangey-colored heterogeneous solution is obtained, which is stirred while heating under an argon pressure of 10 bar at 100° C. for 2 hours. The reaction medium is drawn off and then the insoluble material is filtered off and washed with 3 times approximately 100 ml of EtOAc, and the filtrate is concentrated until a pasty residue is obtained, which is taken up in 500 ml of water. After stirring and extraction with 3 times approximately 350 ml of ethyl acetate, the combined organic extracts are washed with 500 ml of saturated NaCl solution, dried over MgSO₄, filtered through a VF filter, and concentrated under vacuum. The compound obtained is purified by chromatography on silica gel (40-63 μm), elution being carried out with a mixture of 2/8 v/v EtOAc/n-heptane. The fractions containing the expected compound are combined and evaporated. A solid is isolated, which is triturated from diisopropyl ether, filtered through sintered glass and dried. (4-Chloro-6-oxo-1,6-dihydropyrimidin-2-yl)acetic acid ethyl ester is isolated in the form of a beige solid: 25.2 g; yield 81%

LCMS ES+DMSO Tr 0.71 min;
[MH+] m/z=217

Step 2b: Synthesis of (4-(2,2,3,3,5,5,6,6-D8-morpholin)-4-yl-6-oxo-1,6-dihydropyrimidin-2-yl)acetic acid ethyl ester

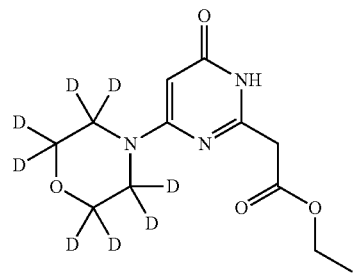 [SMILES: [2H]C1([2H])OC([2H])([2H])C([2H])([2H])N(c2cc(=O)[nH]c(CC(=O)OCC)n2)C1([2H])[2H]]

In a three-necked flask, 1.8 g of (4-chloro-6-oxo-1,6-dihydropyrimidin-2-yl)acetic acid ethyl ester and 1 g of morpholine D8 (CAS, 342611-02-3) are placed in 35 ml of dioxane. 1.4 ml of TEA are added at ambient temperature, and the resulting mixture is stirred while heating at 85° C. for 20 hours. The mixture is concentrated under vacuum and the residue is taken up in 200 ml of CH₂Cl₂, and the resulting product is washed with 100 ml of saturated NaCl solution, dried over MgSO₄, filtered through a VF filter, and concentrated under vacuum. The solid obtained is triturated from 25 ml of water in the presence of 1 ml of ethyl acetate, filtered through a VF filter, rinsed with diisopropyl ether and air-dried. (4-(2,2,3,3,5,5,6,6-D8-Morpholin)-4-yl-6-oxo-1,6-dihydropyrimidin-2-yl)acetic acid ethyl ester is isolated: 1.7 g; yield 74%, and is used as it is in the next step.

Step 3b: Synthesis of the sodium salt of (4-(2,2,3,3,5,5,6,6-D8-morpholin)-4-yl-6-oxo-1,6-dihydropyrimidin-2-yl)acetic acid

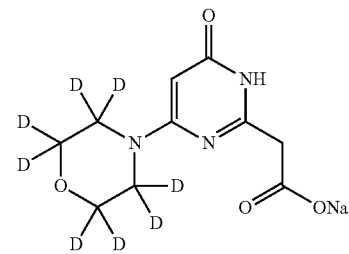

In a round-bottomed flask, 2.75 g of (4-(2,2,3,3,5,5,6,6-D8-morpholin)-4-yl-6-oxo-1,6-dihydropyrimidin-2-yl)acetic acid ethyl ester are placed in 80 ml of THF and then 5 ml of 2M sodium hydroxide are added. The reaction medium is stirred at ambient temperature (20° C.) for 6 days. The solid formed is filtered off and the filtrate is evaporated under reduced pressure. The resulting two solids are combined and washed with petroleum ether and dried under vacuum. The sodium salt of (4-(2,2,3,3,5,5,6,6-D8-morpholin)-4-yl-6-oxo-1,6-dihydropyrimidin-2-yl)acetic acid is isolated: 1.45 g, and is used as it is in the next step (LCMS ES+ retention time Tr (min)=2.08; [M+H]+: m/z 248 (corresponding acid)).

Step 4b: Synthesis of 2-[2-(4-fluoro-2,3-dihydroindol-1-yl)-2-oxoethyl]-6-(2,2,3,3,5,5,6,6-D8-morpholin)-4-yl-3H-pyrimidin-4-one

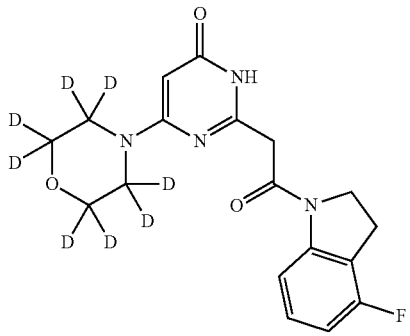 [SMILES: [2H]C1([2H])OC([2H])([2H])C([2H])([2H])N(c2cc(=O)[nH]c(CC(=O)N3CCc4c(F)cccc43)n2)C1([2H])[2H]]

In a round-bottomed flask, 300 mg of the sodium salt of (4-(2,2,3,3,5,5,6,6-D8-morpholin)-4-yl-6-oxo-1,6-dihydropyrimidin-2-yl)acetic acid are suspended in 3 ml of dimethylformamide and 2 ml of pyridine, and then 277 mg of N-[3-(dimethylamino)propyl]-N'-ethylcarbodiimide and 168 mg of 4-fluoro-2,3-dihydro-1H-indole are added. The reaction mixture is stirred at ambient temperature (20° C.) overnight and then evaporated under reduced pressure. The residue is taken up in 40 ml of water and 5 ml of ethyl acetate and stirred for 10 minutes. The solid formed is filtered off, dried with suction and dried under reduced pressure at ambient temperature (20° C.). 250 mg of 2-[2-(4-fluoro-2,3-dihydroindol-1-yl)-2-oxoethyl]-6-(2,2,3,3,5,5,6,6-D8-morpholin)-4-yl-3H-pyrimidin-4-one are isolated, the characteristics of which are the following:

$^1$H NMR spectrum (400 MHz): 3.20 (t, J=8.7 Hz, 2H); 3.76 (broad s, 2H); 4.21 (t, J=8.7 Hz, 2H); 5.20 (s, 1H); 6.86 (t, J=8.6 Hz, 1H); 7.22 (m, 1H); 7.84 (d, J=8.6 Hz, 1H); 11.60 (broad m, 1H)

Example 17b

Synthesis of 2-[2-(4-fluoro-2,3-dihydroindol-1-yl)-2-oxoethyl]-6-(3,3,5,5-D4-morpholin)-4-yl-3H-pyrimidin-4-one Step 1b: Synthesis of 2-(4-chloro-6-methoxypyrimidin-2-yl)-1-(4-fluoro-2,3-dihydroindol-1-yl)ethanone

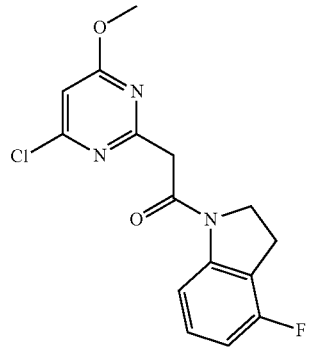 [SMILES: COc1cc(Cl)nc(CC(=O)N2CCc3c(F)cccc32)n1]

50 ml of dimethylformamide, 4.3 ml of pyridine and 5.6 g of N-[3-(dimethylamino)propyl]-N'-ethylcarbodiimide hydrochloride are added to a 100 ml round-bottomed flask containing 5.44 g of the sodium salt of (4-methoxy-6-chloropyrimidin-2-yl)acetic acid (example 8b, step 3b). The mixture is stirred for 10 minutes at ambient temperature (20° C.) and then 3.3 g of 4-fluorodihydroindole are added. The mixture is stirred overnight at ambient temperature. Ethyl acetate is added to the reaction medium and the resulting mixture is washed with a water/2N HCl mixture. Extraction is carried out with ethyl acetate, and washing is carried out 3 times with a water/2N HCl mixture and then with water. The organic phases are combined, dried over magnesium sulfate, filtered and evaporated. The solid obtained is triturated with ethyl ether and then filtered and dried. 2-(4-Chloro-6-methoxypyrimidin-2-yl)-1-(4-fluoro-2,3-dihydroindol-1-yl)ethanone is isolated (2.2 g); yield 28% (LCMS ES+ retention time Tr (min)=1.35; [M+H]+: m/z 322).

Step 2b: Synthesis of 2-(4-chloro-6-oxopyrimidin-2-yl)-1-(4-fluoro-2,3-dihydroindol-1-yl)ethanone

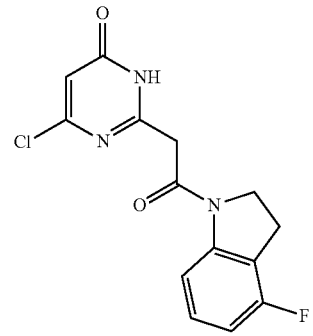 [SMILES: O=C(Cc1nc(Cl)cc(=O)[nH]1)N1CCc2c(F)cccc21]

2 g of 2-(4-chloro-6-methoxypyrimidin-2-yl)-1-(4-fluoro-2,3-dihydroindol-1-yl)ethanone (example 17b, step 1b), potassium iodide (3.1 g), 30 ml of acetonitrile and 2.03 g of trimethylchlorosilane are placed in a reactor suitable for microwave-heating. The reactor is closed and irradiated for 30 minutes at 100° C. and then left overnight at A.T. The reaction medium is diluted with EtOAc and then washed twice with water and then with brine. The organic phases are combined, dried over magnesium sulfate, filtered and evaporated. The product obtained is chromatographed on silica. Elution is then carried out with dichloromethane/methanol (from 100/0 to 95/5). The fractions containing the expected product are evaporated under reduced pressure. The compound obtained is triturated from methanol, filtered and dried. 2-(4-Chloro-6-oxopyrimidin-2-yl)-1-(4-fluoro-2,3-dihydroindol-1-yl) ethanone is isolated (1.13 g); yield=59% (LCMS ES+ retention time Tr (min)=1.04; [M+H]+: m/z 308).

Step 3b: Synthesis of 2-[2-(4-fluoro-2,3-dihydroindol-1-yl)-2-oxoethyl]-6-(3,3,5,5-D4-morpholin)-4-yl-3H-pyrimidin-4-one

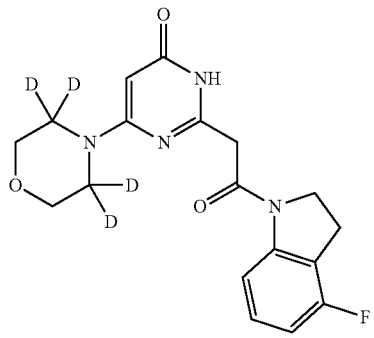 [SMILES: [2H]C1([2H])COCC([2H])([2H])N1c1cc(=O)[nH]c(CC(=O)N2CCc3c(F)cccc32)n1]

100 mg of 2-(4-chloro-6-oxopyrimidin-2-yl)-1-(4-fluoro-2,3-dihydroindol-1-yl)ethanone, 62 mg of 3,3,5,5-D4-morpholine (prepared according to WO2009/23233), 2 ml of DMSO and then 113 μl of TEA are introduced into a three-necked flask under argon, at ambient temperature, and stirring is carried out while heating at 85° C. for 20 hours. The reaction mixture is poured into 20 ml of saturated NaCl solution, extraction is carried out with 3 times approximately 20 ml of $CH_2Cl_2$, dried over $MgSO_4$, and the resulting product is filtered through a VF filter. The compound obtained is chromatographed on silica gel (40-63 μm), elution being carried out with a mixture of dichloromethane and ammoniacal methanol, 7M (95/5, v/v). The fractions containing the expected compound are combined and evaporated. The compound obtained is triturated from EtOAc, filtered, and dried at ambient temperature (20° C.). 2-[2-(4-Fluoro-2,3-dihydroindol-1-yl)-2-oxoethyl]-6-(3,3,5,5-D4-morpholin)-4-yl-3H-pyrimidin-4-one is isolated (25 mg).

$^1$H NMR spectrum (400 MHz): 3.20 (t, J=8.6 Hz, 2H); 3.59 (s, 4H); 3.76 (s, 2H); 4.21 (t, J=8.6 Hz, 2H); 5.20 (s, 1H); 6.86 (t, J=8.7 Hz, 1H); 7.22 (dt, J=6.0 and 8.7 Hz, 1H); 7.84 (d, J=8.7 Hz, 1H); 11.61 (broad s, 1H)

LCMS: The spectra were obtained on a Waters UPLC-SQD apparatus

Ionization: positive and/or negative mode electrospray (ES+/−)

Chromatographic Conditions:

column: Acquity BEH C18—1.7 μm-2.1×50 mm solvents: A: $H_2O$ (0.1% formic acid) B: $CH_3CN$ (0.1% formic acid)

column temperature: 50° C.

flow rate: 1 ml/min gradient (2 min): from 5 to 50% of B in 0.8 min; 1.2 min: 100% of B; 1.85 min: 100% of B; 1.95: 5% of B Analytical Results:

Retention time Tr (min)=0.68; [M+H]+: m/z 363; [M−H]−: m/z 361

Example 18b

Synthesis of 2-[2-(3,3-dimethyl-2,3-dihydroindol-1-yl)-2-oxoethyl]-6-morpholin(D4)-4-yl-3H-pyrimidin-4-one

Step 1b: Synthesis of 2-(4-chloro-6-methoxypyrimidin-2-yl)-1-(3,3-dimethyl-2,3-dihydroindol-1-yl)ethanone

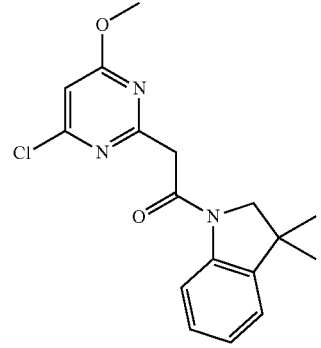 [SMILES: COc1cc(Cl)nc(CC(=O)N2CC(C)(C)c3ccccc32)n1]

0.5 g of the sodium salt of (4-methoxy-6-chloropyrimidin-2-yl)acetic acid (example 8b, step 3b), 0.33 g of 3,3-dimethyl-2,3-dihydro-1H-indole (CAS 1914-02-9), 0.4 ml of pyridine and 5 ml of dimethylformamide are placed in a three-necked flask so as to obtain a homogeneous brown solution. 512 mg of N-[3-(dimethylamino)propyl]-N'-ethylcarbodiimide are added at ambient temperature and the mixture is stirred at ambient temperature for 20 hours. The resulting product is concentrated in a rotary evaporator under vacuum, 40 ml of water are added, extraction is carried out with 3 times approximately 25 ml of dichloromethane, washing is carried out with 50 ml of saturated NaCl solution, drying is carried out over $MgSO_4$, and the resulting product is filtered through a VF filter. The compound obtained is purified by chromatography on silica gel (40-63 μm), elution being carried out with a 98/2 dichloromethane/methanol mixture. The fractions containing the expected compound are combined and evaporated under reduced pressure. 2-(4-Chloro-6-methoxypyrimidin-2-yl)-1-(3,3-dimethyl-2,3-dihydroindol-1-yl)ethanone is isolated: 0.3 g of a yellow oil; yield 41%, which is used as it is in the next step.

Step 2b: Synthesis of 6-chloro-2-[2-(3,3-dimethyl-2,3-dihydroindol-1-yl)-2-oxoethyl]-3H-pyrimidin-4-one

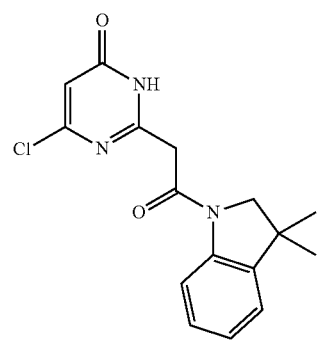 [SMILES: CC1(C)CN(C(=O)Cc2nc(Cl)cc(=O)[nH]2)c2ccccc21]

106 mg of 2-(4-chloro-6-methoxypyrimidin-2-yl)-1-(3,3-dimethyl-2,3-dihydroindol-1-yl)ethanone and 4 ml of acetonitrile are placed in a reactor suitable for microwave irradiation and then 0.45 g of potassium iodide and 347 μl of trimethylchlorosilane are added. The orangey-colored heterogeneous solution is stirred and irradiated at 100° C. for 1 hour. The resulting product is taken up in 25 ml of water and stirred, extraction is carried out with 3 times approximately 25 ml of EtOAc, washing is carried out with 25 ml of saturated NaCl solution, drying is carried out over MgSO$_4$, filtered through a VF filter and the resulting product is concentrated under vacuum. The compound obtained is chromatographed on silica gel, elution being carried out with methanol/dichloromethane (2.5/97.5). The fractions containing the expected compound are combined and evaporated under reduced pressure. 6-Chloro-2-[2-(3,3-dimethyl-2,3-dihydroindol-1-yl)-2-oxoethyl]-3H-pyrimidin-4-one is isolated and characterized: 0.20 g in the form of a yellow solid; yield 70% (LCMS ES+ retention time Tr (min)=1.19; [M+H]+: m/z 318).

Step 3b: Synthesis of 2-[2-(3,3-dimethyl-2,3-dihydroindol-1-yl)-2-oxoethyl]-6-morpholin(D4)-4-yl-3H-pyrimidin-4-one

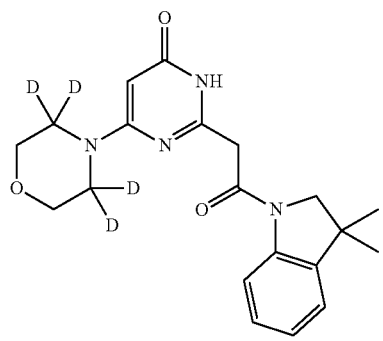 [SMILES: [2H]C1([2H])COCC([2H])([2H])N1c1cc(=O)[nH]c(CC(=O)N2CC(C)(C)c3ccccc32)n1]

280 mg of 6-chloro-2-[2-(3,3-dimethyl-2,3-dihydroindol-1-yl)-2-oxoethyl]-3H-pyrimidin-4-one, 169 mg of 3,3,5,5-D4-morpholine (prepared according to WO2009/23233), 5 ml of DMSO and then 307 µl of TEA are placed in a three-necked flask under argon, at ambient temperature; the reaction medium is stirred while heating at 85° C. for 20 hours. The reaction medium is poured into 20 ml of saturated NaCl solution, extraction is carried out with 3 times approximately 20 ml of dichloromethane, drying is carried out over MgSO$_4$, filtration is carried out through a VF filter, and the resulting product is concentrated under vacuum. The compound obtained is chromatographed on silica gel (40-63 µm), elution being carried out with a 2.5/97.5 mixture of MeOH/dichloromethane. The fractions containing the expected compound are combined and evaporated under reduced pressure. 2-[2-(3,3-Dimethyl-2,3-dihydroindol-1-yl)-2-oxoethyl]-6-morpholin(D4)-4-yl-3H-pyrimidin-4-one is isolated and characterized (45 mg) in the form of a pinkish solid; yield 14%.

Chromatographic Conditions:
column: Acquity BEH C18—1.7 µm-2.1×50 mm
solvents: A: H$_2$O (0.1% formic acid) B: CH$_3$CN (0.1% formic acid)
column temperature: 50° C.
flow rate: 1 ml/min
gradient (2 min): from 5 to 50% of B in 0.8 min; 1.2 min: 100% of B; 1.85 min: 100% of B; 1.95: 5% of B Analytical Results:
Retention time Tr (min)=0.77;
[M+H]+: m/z 373; [M–H]–: m/z 371
$^1$H NMR spectrum (400 MHz): 1.31 (s, 6H); 3.58 (s, 4H); 3.75 (s, 2H); 3.91 (s, 2H); 5.20 (s, 1H); 7.05 (t, J=7.8 Hz, 1H); 7.18 (t, J=7.8 Hz, 1H); 7.27 (d, J=7.8 Hz, 1H); 8.00 (d, J=7.8 Hz, 1H); 11.61 (broad s, 1H)

Example 19b

Synthesis of (+)-2-[2-(2-methyl-2,3-dihydroindol-1-yl)-2-oxoethyl]-6-morpholin(D4)-4-yl-3H-pyrimidin-4-one and example 20b: (–)-2-[2-(2-methyl-2,3-dihydroindol-1-yl)-2-oxoethyl]-6-(2,2,6,6-morpholin-D4)-4-yl-3H-pyrimidin-4-one Step 1b: Synthesis of 2-(4-chloro-6-methoxpyrimidin-2-yl)-1-(2-methyl-2,3-dihydroindol-1-yl)ethanone

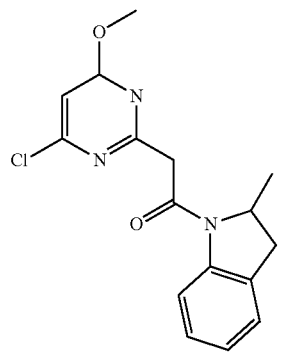 [SMILES: COC1C=C(Cl)N=C(CC(=O)N2c3ccccc3CC2C)N1]

In a three-necked flask, under argon, 4 g of the sodium salt of (4-chloro-6-methoxypyrimidin-2-yl)acetic acid (example 8b, step 3b) and 2.6 g of 2-methylindoline (6872-06-6, Aldrich) are placed in 3 ml of pyridine and 60 ml of DMF. The heterogeneous solution obtained is stirred at ambient temperature (20° C.), then N-[3-(dimethylamino)propyl]-N'-ethylcarbodiimide hydrochloride is added and stirring is maintained for 20 hours. The reaction mixture is concentrated in a rotary evaporator under vacuum, 100 ml of water are added, extraction is carried out with 3 times approximately 50 ml of dichloromethane, washing is carried out with 50 ml of saturated NaCl solution, drying is carried out over MgSO$_4$ and filtration is carried out through a VF filter. The compound obtained is chromatographed on silica gel (40-63 µm), elution being carried out with dichloromethane. The fractions containing the expected compound are combined and evaporated. The compound obtained is triturated from diisopropyl ether, filtration is carried out, and drying is carried out at 20° C. 2-(4-Chloro-6-methoxypyrimidin-2-yl)-1-(2-methyl-2,3-dihydroindol-1-yl)ethanone is isolated (2.6 g) in the form of a solid (yield 46%) which is used as it is in the next step.

Step 2b: Synthesis of 6-chloro-2-[2-(2-methyl-2,3-dihydroindol-1-yl)-2-oxoethyl]-5H-pyrimidin-4-one

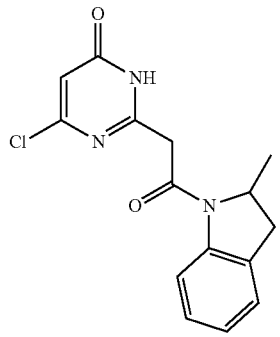 [SMILES: CC1Cc2ccccc2N1C(=O)Cc1nc(Cl)cc(=O)[nH]1]

In a reactor suitable for microwave irradiation, 1.3 g of 2-(4-chloro-6-methoxypyrimidin-2-yl)-1-(2-methyl-2,3-dihydroindol-1-yl)ethanone are placed in 20 ml of acetonitrile, 2 g of potassium iodide and 1.7 ml of trimethylchlorosilane. The heterogeneous solution is stirred while microwave-heating at 100° C. for 90 minutes. The resulting product is taken up in 25 ml of water, extraction is carried out with ethyl acetate, washing is carried out with 25 ml of saturated NaCl solution, drying is carried out over MgSO₄, filtration is carried out through a VF filter and the resulting product is concentrated under vacuum. The compound obtained is chromatographed on silica gel (40-63 µm), elution being carried out with a mixture of dichloromethane and methanol (90/10, v/v). The fractions containing the expected compound are combined and evaporated. The compound obtained is triturated from a mixture of ethyl acetate and diisopropyl ether, filtered and dried at ambient temperature (20° C.). 6-Chloro-2-[2-(2-methyl-2,3-dihydroindol-1-yl)-2-oxoethyl]-5H-pyrimidin-4-one is isolated in the form of a beige solid (2.2 g), yield 89%.

Step 3b: Synthesis of (±)-2-[2-(2-methyl-2,3-dihydroindol-1-yl)-2-oxoethyl]-6-(2,2,6,6-morpholin-D4)-4-yl-3H-pyrimidin-4-one

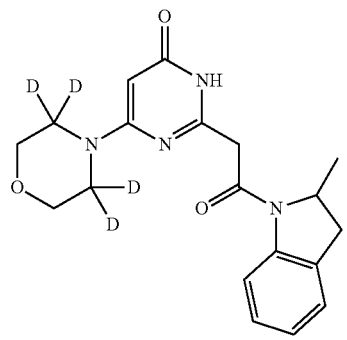 [SMILES: [2H]C1([2H])COCC([2H])([2H])N1c1cc(=O)[nH]c(CC(=O)N2c3ccccc3CC2C)n1]

In a three-necked flask, 304 mg of 6-chloro-2-[2-(2-methyl-2,3-dihydroindol-1-yl)-2-oxoethyl]-5H-pyrimidin-4-one and 191 mg of 3,3,5,5-D4-morpholine (prepared according to WO2009/23233) are placed in 10 ml of dioxane. 350 µl of TEA are added at ambient temperature and the mixture is stirred while heating at 85° C. for 20 hours. The reaction mixture is concentrated under vacuum, the resulting product is taken up in 20 ml of dichloromethane, 10 ml of saturated NaCl solution are added, separation is carried out by settling out, drying is carried out over MgSO₄, filtration is carried out on a VF filter and the resulting product is concentrated under vacuum. The compound obtained is chromatographed on silica gel (40-63 µm), elution being carried out with a mixture of dichloromethane and methanol (95/5, v/v). The fractions containing the expected compound are combined and evaporated. The compound obtained, (±)-2-[2-(2-methyl-2,3-dihydroindol-1-yl)-2-oxoethyl]-6-(2,2,6,6-morpholin-D4)-4-yl-3H-pyrimidin-4-one (0.22 g), is resolved into its two enantiomers in the next step.

The racemic compound (±)-2-[2-(2-methyl-2,3-dihydroindol-1-yl)-2-oxoethyl]-6-morpholin(D4)-4-yl-3H-pyrimidin-4-one obtained above is separated into its two enantiomers by chiral chromatography on a column containing 1.08 kg of Chiralpak AY 20 µm, 7.7×35 cm, stationary phase, batch KLB001, elution being carried out with a mixture of acetonitrile and isopropanol (90/10 v/v) at 200 ml/min. The fractions containing the enantiomers are combined and evaporated.

The first enantiomer (+)-2-[2-(2-methyl-2,3-dihydroindol-1-yl)-2-oxoethyl]-6-morpholin(D4)-4-yl-3H-pyrimidin-4-one is isolated (70.6 mg) and characterized (+81°, c=1.422 mg/0.5 ml DMSO, 589 nm).

Mass spectrometry: the spectra were obtained on a Waters UPLC-SQD apparatus

Ionization: positive and/or negative mode electrospray (ES+/−)

Chromatographic Conditions:
column: Acquity BEH C18—1.7 µm-2.1×50 mm
solvents: A: H₂O (0.1% formic acid) B: CH₃CN (0.1% formic acid)
column temperature: 50° C.
flow rate: 1 ml/min
gradient (2 min): from 5 to 50% of B in 0.8 min; 1.2 min: 100% of B; 1.85 min: 100% of B; 1.95: 5% of B
Analytical Results:
Retention time Tr (min)=0.69; [M+H]+: m/z 359; [M−H]−: m/z 357

¹H NMR spectrum (400 MHz): 1.26 (broad d, J=6.4 Hz, 3H); 2.69 (d, J=16.5 Hz, 1H); 3.28 to 3.44 (partially masked m, 1H); 3.59 (s, 4H); 3.72 (d, J=15.9 Hz, 1H); 3.92 (d, J=15.9 Hz, 1H); 4.71 (m, 1H); 5.20 (s, 1H); 7.05 (t, J=7.8 Hz, 1H); 7.18 (t, J=7.8 Hz, 1H); 7.28 (d, J=7.8 Hz, 1H); 7.96 (d, J=7.8 Hz, 1H); 11.67 (broad s, 1H)

The second enantiomer (−)-2-[2-(2-methyl-2,3-dihydroindol-1-yl)-2-oxoethyl]-6-morpholin(D4)-4-yl-3H-pyrimidin-4-one is isolated (78.4 mg) (−67.9°, c=1.609 mg/0.5 ml DMSO, 589 nm)

Mass Spectrometry:
The spectra were obtained on a Waters UPLC-SQD apparatus

Ionization: positive and/or negative mode electrospray (ES+/−)

Chromatographic Conditions:
column: Acquity BEH C18—1.7 µm-2.1×50 mm
solvents: A: H₂O (0.1% formic acid) B: CH₃CN (0.1% formic acid)
column temperature: 50° C.
flow rate: 1 ml/min
gradient (2 min): from 5 to 50% of B in 0.8 min; 1.2 min: 100% of B; 1.85 min: 100% of B; 1.95: 5% of B
Analytical Results:
Retention time Tr (min)=0.69;
[M+H]+: m/z 359; [M−H]−: m/z 357

¹H NMR spectrum (400 MHz): 1.26 (d, J=6.4 Hz, 3H); 2.69 (d, J=16.3 Hz, 1H); 3.25 to 3.46 (partially masked m, 1H); 3.59 (s, 4H); 3.72 (d, J=15.9 Hz, 1H); 3.92 (d, J=15.9 Hz, 1H); 4.70 (m, 1H); 5.20 (s, 1H); 7.04 (t, J=7.9 Hz, 1H); 7.18 (t, J=7.9 Hz, 1H); 7.29 (d, J=7.9 Hz, 1H); 7.96 (d, J=7.9 Hz, 1H); 11.71 (broad s, 1H)

The enantiomeric purity of the two compounds obtained above is characterized by analytical chiral chromatography carried out on a Chiralpak AY-5 μm, 250×4.6 mm column, elution being carried out with a mixture of acetonitrile and isopropanol (90/10 v/v) at the flow rate of 1 ml/min. The enantiomeric excesses are respectively 99% and 99% for the levorotatory and dextrorotatory enantiomers.

Example 21b

Synthesis of (+)-2-[2-(2-methyl-2,3-dihydroindol-1-yl)-2-oxoethyl]-6-morpholin(D8)-4-yl-3H-pyrimidin-4-one & example 22b: (−)-2-[2-(2-methyl-2,3-dihydroindol-1-yl)-2-oxoethyl]-6-morpholin(D8)-4-yl-3H-pyrimidin-4-one

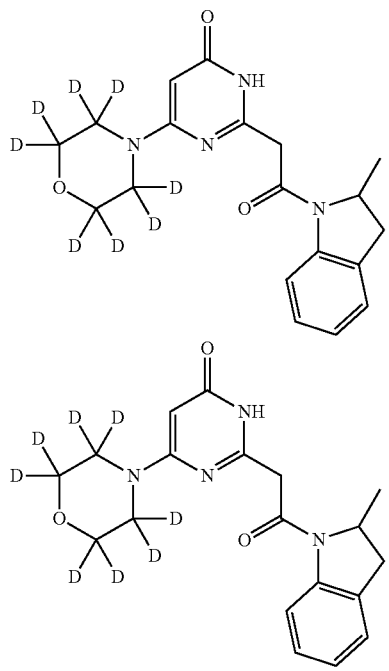

In a three-necked flask, under argon, 304 mg of 6-chloro-2-[2-(2-methyl-2,3-dihydroindol-1-yl)-2-oxoethyl]-5H-pyrimidin-4-one (example 19b, step 2b) and 0.5 g of morpholine-2,2,3,3,5,5,6,6-D8 (342611-02-3) are placed in 40 ml of dioxane, then 700 μl of TEA are added at ambient temperature, and stirring is carried out while heating at 85° C. for 20 hours. The reaction mixture is concentrated under vacuum, the resulting product is taken up in 50 ml of EtOAc, 20 ml of saturated NaCl solution are added, separation is carried out by settling out, drying is carried out over MgSO₄, and filtration is carried out through a VF filter. The compound obtained is chromatographed on silica gel (40-63 μm), elution being carried out with a 97/3 v/v mixture of dichloromethane and methanol. The fractions containing the expected compound are combined and evaporated. (±)-2-[2-(2-Methyl-2,3-dihydroindol-1-yl)-2-oxoethyl]-6-morpholin(D8)-4-yl-3H-pyrimidin-4-one is obtained in the form of a solid (1.2 g), and resolved into its two enantiomers in the next step.

The racemic compound (±)-2-[2-(2-methyl-2,3-dihydroindol-1-yl)-2-oxoethyl]-6-morpholin(D8)-4-yl-3H-pyrimidin-4-one obtained above is resolved into its two enantiomers by chiral chromatography on a column containing 1.08 kg of Chiralpak AY 20 μm stationary phase (7.7×35 cm), elution being carried out with a mixture of acetonitrile and isopropanol (90/10 v/v) at 250 ml/min. The fractions containing each enantiomer are evaporated. Example 21b and example 22b below are isolated.

The first enantiomer, (+)-2-[2-(2-methyl-2,3-dihydroindol-1-yl)-2-oxoethyl]-6-morpholin(D8)-4-yl-3H-pyrimidin-4-one, is isolated (502 mg) and characterized (+83.3°, c=2.003 mg/0.5 ml DMSO, 589 nm).

Mass Spectrometry:
The spectra were obtained on a Waters UPLC-SQD apparatus
Ionization: positive and/or negative mode electrospray (ES+/−)
Chromatographic Conditions:
column: Acquity BEH C18—1.7 μm-2.1×50 mm
solvents: A: H₂O (0.1% formic acid) B: CH₃CN (0.1% formic acid)
column temperature: 50° C.
flow rate: 1 ml/min
gradient (2 min): from 5 to 50% of B in 0.8 min; 1.2 min: 100% of B; 1.85 min: 100% of B; 1.95: 5% of B
Analytical Results:
Retention time Tr (min)=0.69;
[M+H]+: m/z 363; [M−H]−: m/z 361
Nuclear Magnetic Resonance:
¹H NMR spectrum (400 MHz): 1.26 (d, J=6.4 Hz, 3H); 2.68 (d, J=16.3 Hz, 1H); 3.37 (dd, J=8.6 and 16.3 Hz, 1H); 3.72 (d, J=15.9 Hz, 1H); 3.92 (d, J=15.9 Hz, 1H); 4.71 (m, 1H); 5.19 (s, 1H); 7.04 (t, J=7.9 Hz, 1H); 7.18 (t, J=7.9 Hz, 1H); 7.28 (d, J=7.9 Hz, 1H); 7.96 (d, J=7.9 Hz, 1H); 11.68 (broad s, 1H)

The second enantiomer, (−)-2-[2-(2-methyl-2,3-dihydroindol-1-yl)-2-oxoethyl]-6-morpholin(D4)-4-yl-3H-pyrimidin-4-one, is isolated (505 mg) (−82°, c=1.670 mg/0.5 ml DMSO, 589 nm)

Mass Spectrometry:
The spectra were obtained on a Waters UPLC-SQD apparatus
Ionization: positive and/or negative mode electrospray (ES+/−)
Chromatographic Conditions:
column: Acquity BEH C18—1.7 μm-2.1×50 mm
solvents: A: H₂O (0.1% formic acid) B: CH₃CN (0.1% formic acid)
column temperature: 50° C.
flow rate: 1 ml/min
gradient (2 min): from 5 to 50% of B in 0.8 min; 1.2 min: 100% of B; 1.85 min: 100% of B; 1.95: 5% of B
Analytical Results:
Retention time Tr (min)=0.69; [M+H]+: m/z 363; [M−H]−: m/z 361
¹H NMR spectrum (400 MHz): 1.26 (d, J=6.3 Hz, 3H); 2.68 (d, J=16.3 Hz, 1H); 3.37 (dd, J=8.6 and 16.3 Hz, 1H); 3.72 (d, J=15.9 Hz, 1H); 3.92 (d, J=15.9 Hz, 1H); 4.71 (m, 1H); 5.19 (s, 1H); 7.04 (t, J=7.9 Hz, 1H); 7.18 (t, J=7.9 Hz, 1H); 7.28 (d, J=7.9 Hz, 1H); 7.96 (d, J=7.9 Hz, 1H); 11.66 (broad s, 1H)

The enantiomeric purity of the two compounds obtained above is characterized by analytical chiral chromatography carried out on a Chiralpak AY-5 μm, 250×4.6 mm column,

Example 23b

Synthesis of 2-[2-(4-fluoro-2,3-dihydroindol-1-yl)-2-oxoethyl]-6-(2-methylpyridin-4-yl)-3H-pyrimidin-4-one

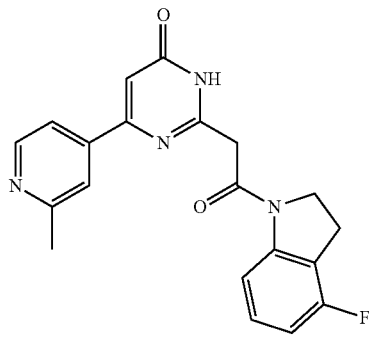

120 mg of 6-chloro-2-[2-(4-fluoro-2,3-dihydroindol-1-yl)-2-oxoethyl]-3H-pyrimidin-4-one, 96 mg of 2-methylpyridine-4-boronic acid pinacol ester, 45 mg of tetrakis(triphenylphosphine)palladium(0), 2.5 ml of 1,4-dioxane and 0.52 ml of an aqueous 1.5 M cesium carbonate solution are successively placed in a 5 ml microwave tube. The resulting suspension is stirred under microwave irradiation at a temperature of 100° C. for 2×1 hour. After cooling to ambient temperature, the reaction mixture is diluted with 6 ml of ethyl acetate and then filtered through Clarcel®. The solid is washed with 3 ml of ethyl acetate, and then the filtrate is treated with 12 ml of water and stirred at ambient temperature for 1.5 hours. After settling out, the organic phase is separated and the aqueous phase is extracted with 3×10 ml of ethyl acetate. The organic extracts are combined, washed with 10 ml of saturated brine, dried over magnesium sulfate, filtered, and then concentrated to dryness under reduced pressure. The residue is purified by chromatography on a 25 g cartridge of 15-40 µm silica, by making a solid deposit and eluting with a 95/5 v/v dichloromethane/methanol mixture at a flow rate of 25 ml/min. The fractions containing the desired product are combined and concentrated to dryness under reduced pressure. The residue is taken up twice in diethyl ether, triturated, and then concentrated to dryness under reduced pressure. 46 mg of 2-[2-(4-fluoro-2,3-dihydroindol-1-yl)-2-oxoethyl]-6-(2-methylpyridin-4-yl)-3H-pyrimidin-4-one are thus obtained in the form of a white crystalline powder, the characteristics of which are the following:

$^1$H NMR spectrum (400 MHz): 2.54 (s, 3H); 3.23 (t, J=8.7 Hz, 2H); 3.99 (s, 2H); 4.27 (t, J=8.7 Hz, 2H); 6.88 (t, J=8.7 Hz, 1H); 6.99 (s, 1H); 7.24 (m, 1H); 7.75 (broad d, J=5.1 Hz, 1H); 7.82 to 7.88 (m, 2H); 8.54 (d, J=5.1 Hz, 1H); 12.65 (broad s, 1H)

Mass spectrometry: method A
Retention time Tr (min)=0.50;
[M+H]+: m/z 365; [M−H]−: m/z 363
Melting point (Kofler): 229° C.

Example 24b

2-[2-(4-Fluoro-2,3-dihydroindol-1-yl)-2-oxoethyl]-6-(2-fluoropyridin-4-yl)-3H-pyrimidin-4-one

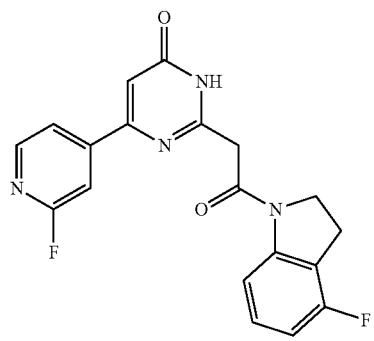

130 mg of 6-chloro-2-[2-(4-fluoro-2,3-dihydroindol-1-yl)-2-oxoethyl]-3H-pyrimidin-4-one, 3 ml of 1,4-dioxane, 104 mg of 2-fluoropyridine-4-boronic acid pinacol ester, 50 mg of tetrakis(triphenylphosphine)palladium(0), and 0.58 ml of an aqueous 1.5 M cesium carbonate solution are successively placed in a three-necked round-bottomed flask under argon and with stirring. The mixture is heated at a temperature of 100° C. for 20 hours, and then filtered while hot. After cooling to ambient temperature, the filtrate is concentrated to dryness under reduced pressure. The residue is taken up in a mixture of 20 ml of dichloromethane and 30 ml of water. After settling out, the organic phase is separated and the aqueous phase is extracted with dichloromethane. The aqueous phase is concentrated to dryness under reduced pressure. The residue is taken up in a mixture of 30 ml of ethyl acetate and a few drops of ethanol, and then washed with 5 ml of water. After settling out, the organic phase is separated and the aqueous phase is extracted with 2×20 ml of ethyl acetate. The organic extracts are combined, dried over magnesium sulfate, filtered, and then concentrated to dryness under reduced pressure. The residue is taken up in 1 ml of dioxane and the mixture is refluxed, and then filtered through sintered glass. After drying of the isolated solid, 44 mg of 2-[2-(4-fluoro-2,3-dihydroindol-1-yl)-2-oxoethyl]-6-(2-fluoropyridin-4-yl)-3H-pyrimidin-4-one are obtained in the form of a beige solid, the characteristics of which are the following:

$^1$H NMR spectrum (400 MHz): 3.20 to 3.38 (partially masked m, 2H); 4.00 (s, 2H); 4.27 (t, J=8.2 Hz, 2H); 6.87 (t, J=8.1 Hz, 1H); 7.11 (s, 1H); 7.23 (m, 1H); 7.74 (s, 1H); 7.85 (d, J=8.1 Hz, 1H); 7.95 (d, J=5.4 Hz, 1H); 8.36 (d, J=5.4 Hz, 1H); 12.86 (broad m, 1H)

Mass spectrometry: method A
Retention time Tr (min)=0.80;
[M+H]+: m/z 369; [M−H]−: m/z 367
Melting point (Kofler): above 260° C.

Example 25b

Synthesis of 2-[2-(4-chloro-2,3-dihydroindol-1-yl)-2-oxoethyl]-6-((−)-2-hydroxymethylmorpholin-4-yl)-3H-pyrimidin-4-one and

Example 26b

Synthesis of 2-[2-(4-chloro-2,3-dihydroindol-1-yl)-2-oxoethyl]-6-((+)-2-hydroxymethylmorpholin-4-yl)-3H-pyrimidin-4-one

Step 1b: Synthesis of 2-[2-(4-chloro-2,3-dihydroindol-1-yl)-2-oxoethyl-2-(2-benzylaminoethoxy)-3-chloropropan-1-ol

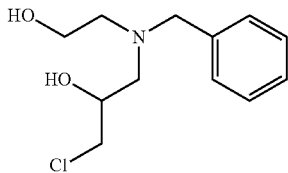 [SMILES: OCCN(Cc1ccccc1)CC(O)CCl]

23.6 ml of N-benzylethanolamine (104-63-2) are placed in a 250 ml round-bottomed flask with a condenser, under argon, and then 26 ml of epichlorohydrin (106-89-8) are added dropwise. The reaction medium is heated at 45° C. for 3 h. After returning to ambient temperature (20° C.), the reaction medium is evaporated under reduced pressure (bath at 40° C., pressure at 20 mbar then at 2 mbar), for one hour. 2-[2-(4-Chloro-2,3-dihydroindol-1-yl)-2-oxoethyl-2-(2-benzylaminoethoxy)-3-chloropropan-1-ol is isolated (41.25 g) in the form of an oil which is used in the next step.

Step 2b: Synthesis of 4-benzyl-2-chloromethylmorpholine

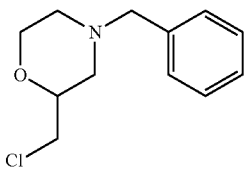 [SMILES: ClCC1CN(Cc2ccccc2)CCO1]

41.25 g of 2-[2-(4-chloro-2,3-dihydroindol-1-yl)-2-oxoethyl-2-(2-benzylaminoethoxy)-3-chloropropan-1-ol previously obtained are placed in a 250 ml round-bottomed flask equipped with a condenser, and then 50 ml of concentrated sulfuric acid (d=1.84) are added dropwise. The temperature increases, and the water formed condenses in the condenser. The reaction medium is then heated for one hour at 150° C., then cooled to ambient temperature (20° C.), before being poured slowly onto ice; the reaction medium is brought to pH=10 with 40% NaOH, and then extracted with toluene (2×150 ml), and the organic phases are combined, dried over magnesium sulfate, filtered and evaporated under reduced pressure. 4-Benzyl-2-chloromethylmorpholine is isolated (20.30 g, light brown oil, yield=54%) and is used in the next step.

Step 3b: Synthesis of (4-benzylmorpholin-2-yl)methanol

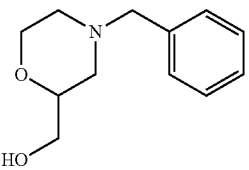

20.3 g of 4-benzyl-2-chloromethylmorpholine, previously obtained, 3.5 ml of water and then 45 ml of formamide (75-12-7) are placed in a 250 ml round-bottomed flask with a condenser and a thermometer and under argon. The reaction medium is heated at 215° C. at the reflux of formamide for 3 h and then cooled to 50° C. with a bath of ice-cold water. A further 3.5 ml of water are added and the refluxing is resumed for a further 2 h. After returning to ambient temperature (20° C.), the medium is poured into ice-cold water (150 ml), the resulting mixture is basified with 10M sodium hydroxide (50 ml) at pH=12, extraction is carried out twice with toluene, and the organic phases are combined and washed with a saturated NaCl solution (50 ml), dried over magnesium sulfate and brought to dryness under a vacuum of 3 mbar for 1 h. (4-Benzylmorpholin-2-yl)methanol (13.4 g) is isolated in the form of an amber oil (yield=72%).

Step 4b: Synthesis of morpholin-2-yl-methanol hydrochloride

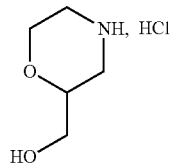

In an autoclave under an argon atmosphere at ambient temperature (20° C.), 215 ml of methanol, 1.7 g of palladium hydroxide (12135-22-7), 12.4 g of (4-benzylmorpholin-2-yl)methanol and 15 ml of 4M HCl are successively placed in dioxane. After the autoclave has been closed, the reaction medium is placed under 6 bar of hydrogen at 25° C. for 24 h. The reaction medium is filtered through Clarcel, rinsed several times with methanol; the filtrate is concentrated under reduced pressure. Morpholin-2-ylmethanol hydrochloride (9.65 g) is isolated in the form of a yellow oil.

Step 5b: Synthesis of (4-chloro-6-oxo-1,6-dihydropyrimidin-2-yl)acetic acid ethyl ester

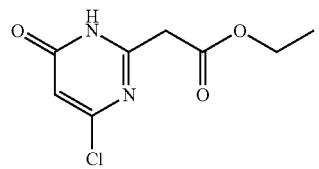

33 g of (4-chloro-6-methoxypyrimidin-2-yl)acetic acid ethyl ester (example 8b, step 2b) and 750 ml of acetonitrile are placed in a 1000 ml autoclave and then 71.2 g of potassium iodide and 55.85 ml of trimethylchlorosilane are added; an orangey-colored heterogeneous solution is obtained, which is stirred while heating under an argon pressure of 10 bar at 100° C. for 2 hours. The reaction medium is drawn off, then insoluble material is filtered off, washing is carried out with 3 times approximately 100 ml of EtOAc, and the filtrate is concentrated until a pasty residue is obtained, which is taken up in 500 ml of water. After stirring, extraction is carried out with 3 times approximately 350 ml of ethyl acetate, the combined organic extracts are washed with 500 ml of saturated NaCl solution, drying is carried out over MgSO$_4$, filtration is carried out through a VF filter, and the resulting product is concentrated under vacuum. The compound obtained is purified by chromatography on silica gel (40-63 μm), elution being carried out with a mixture of EtOAc/n-heptane (2/8 v/v). The fractions containing the expected compound are combined and evaporated. A solid is isolated, which is triturated from diisopropyl ether, filtered through sintered glass and dried. (4-Chloro-6-oxo-1,6-dihydropyrimidin-2-yl)acetic acid ethyl ester is isolated in the form of a beige solid: 25.2 g; yield 81%.

LCMS ES+DMSO Tr 0.71 min; MH+nm/z=217

Step 6b: Synthesis of [4-(2-hydroxymethylmorpholin-4-yl)-6-oxo-1,6-dihydropyrimidin-2-yl]acetic acid ethyl ester

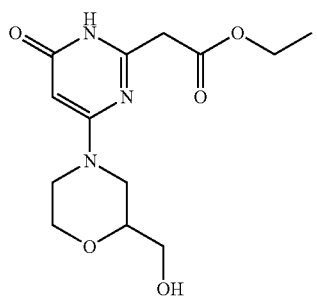

Under argon, in a 500 ml round-bottomed flask equipped with a thermometer and a condenser, 10 g of (4-chloro-6-oxo-1,6-dihydropyrimidin-2-yl)acetic acid ethyl ester (example 25b, step 5b) and 9.6 g of morpholin-2-yl-methanol hydrochloride obtained previously are successively placed in 200 ml of DMSO and 16.1 ml of triethylamine. The reaction medium is heated for 22 h at 85° C. After returning to ambient temperature (20° C.), the reaction medium is poured into a saturated NaCl solution, and the mixture is extracted with 8×250 ml of ethyl acetate. The organic extracts are combined, dried over magnesium sulfate, filtered, and evaporated under reduced pressure. A solid is obtained which is slurried in diisopropyl ether containing 10% of methylene chloride. The solid is filtered off, and rinsed twice and then once with pentane. [4-(2-Hydroxymethylmorpholin-4-yl)-6-oxo-1,6-dihydropyrimidin-2-yl]acetic acid ethyl ester is isolated (1.9 g; yield=14%) in the form of a beige solid.

Step 7b: Synthesis of the sodium salt of [4-(2-hydroxymethylmorpholin-4-yl)-6-oxo-1,6-dihydropyrimidin-2-yl]acetic acid

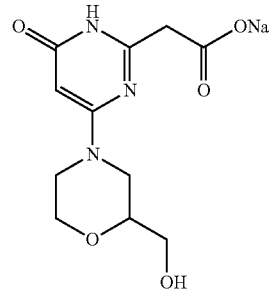

A solution of 2 g of [4-(2-hydroxymethylmorpholin-4-yl)-6-oxo-1,6-dihydropyrimidin-2-yl]acetic acid ethyl ester in 15 ml of THF is placed in a round-bottomed flask and then a stoichiometric amount of sodium hydroxide in a 2M solution is run in dropwise. The medium is stirred for 72 hours at ambient temperature and then concentrated under reduced pressure. 2.5 g of solid are obtained which are taken up in 20 ml of THF, and which are triturated; the solid obtained is filtered off through sintered glass, rinsed with ethyl ether and oven-dried under vacuum. The sodium salt of [4-(2-hydroxymethylmorpholin-4-yl)-6-oxo-1,6-dihydropyrimidin-2-yl]acetic acid is isolated: 1.6 g of yellow solid which is used in the next step.

Step 8b: Chiral separation: Synthesis of (+)-[4-(2-hydroxymethylmorpholin-4-yl)-6-oxo-1,6-dihydropyrimidin-2-yl]acetic acid ethyl ester and (−)-[4-(2-hydroxymethylmorpholin-4-yl)-6-oxo-1,6-dihydropyrimidin-2-yl]acetic acid ethyl ester

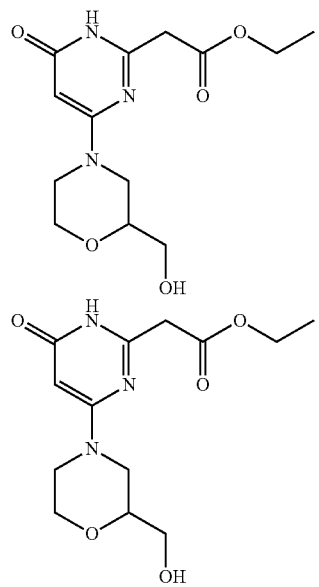

The (±)-[4-(2-hydroxymethylmorpholin-4-yl)-6-oxo-1,6-dihydropyrimidin-2-yl]acetic acid ethyl ester obtained previously (example 25b, step 6b) is resolved into its two enantiomers by chiral chromatography on Chiralpak T304 20 μm, 7.5 cm×35 cm phase, elution being carried out at 300 ml/min using a mixture of heptane/ethyl acetate/triethylamine: 70/30/0.1. The fractions containing the enantiomers are evaporated.

The following are successively isolated:

The intermediate 25-A: first enantiomer of [4-(2-hydroxymethylmorpholin-4-yl)-6-oxo-1,6-dihydropyrimidin-2-yl]acetic acid ethyl ester, 92 mg.

The intermediate 25-B: second enantiomer of [4-(2-hydroxymethylmorpholin-4-yl)-6-oxo-1,6-dihydropyrimidin-2-yl]acetic acid ethyl ester, 72 mg.

The enantiomeric purity of these compounds is characterized by chiral analysis on Chiralpak T304 5 μm 250 mm×4.6 mm, 1 ml/min, 70% heptane 30% EtOH 0.1% TEA.

Step 9b: Synthesis of the sodium salt of (+)-[4-(2-hydroxymethylmorpholin-4-yl)-6-oxo-1,6-dihydropyrimidin-2-yl]acetic acid

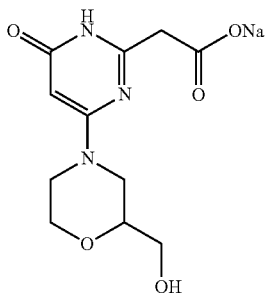

In a 10 ml round-bottomed flask under argon, 92 mg of [4-(2-hydroxymethylmorpholin-4-yl)-6-oxo-1,6-dihydropyrimidin-2-yl]acetic acid ethyl ester (intermediate 25-A, example 25b, step 8b) are placed in 1 ml of THF and 155 μl of 2N sodium hydroxide are added thereto. The reaction medium is stirred at ambient temperature (20° C.) for 96 h. The THF is evaporated off at ambient temperature (20° C.), then 2 ml of water are added and extraction is carried out with ethyl ether. The water is evaporated off at ambient temperature (20° C.) under 4 mbar for 2 h. The sodium salt of [4-(2-hydroxymethylmorpholin-4-yl)-6-oxo-1,6-dihydropyrimidin-2-yl]acetic acid is isolated: 71 mg of an off-white solid; yield 83%, used as it is in the next step.

Step 10b, Example 25b: (−)-2-[2-(4-Chloro-2,3-dihydroindol-1-yl)-2-oxoethyl]-6-(2-hydroxymethyl-morpholin-4-yl)-3H-pyrimidin-4-one

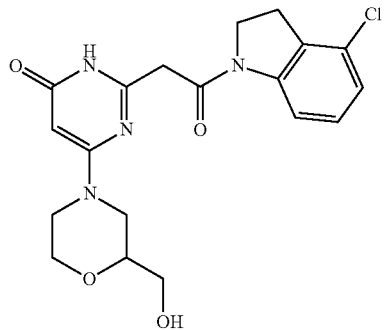 [SMILES: O=C(Cc1nc(N2CCOC(CO)C2)cc(=O)[nH]1)N1CCc2c(Cl)cccc21]

In a 25 ml round-bottomed flask, 71 mg of the sodium salt of [4-(2-hydroxymethylmorpholin-4-yl)-6-oxo-1,6-dihydropyrimidin-2-yl]acetic acid (example 25b, step 9b) and 38 mg of 4-chloro-2,3-dihydro-1H-indole are placed in 1 ml of dimethylformamide and 0.24 ml of pyridine, and then 57 mg of N-[3-(dimethylamino)propyl]-N'-ethylcarbodiimide hydrochloride are added. The reaction medium is stirred at ambient temperature for 20 h, then evaporated, water is added, and the resulting mixture is triturated. The solid formed is filtered off, and rinsed successively with water then with diisopropyl ether, with methylene chloride and then with pentane. The resulting solid is dried under vacuum for 2 h. (−)-2-[2-(4-Chloro-2,3-dihydroindol-1-yl)-2-oxoethyl]-6-(2-hydroxymethylmorpholin-4-yl)-3H-pyrimidin-4-one (62 mg) is isolated in the form of a pulverulent solid (yield=63%).

Mass Spectrometry:

The spectra were obtained on a Waters UPLC-SQD apparatus

Ionization: positive and/or negative mode electrospray (ES+/−)

Chromatographic Conditions:

Column: Acquity BEH C18—1.7 μm-2.1×50 mm

Solvents: A: $H_2O$ (0.1% formic acid) B: $CH_3CN$ (0.1% formic acid)

Column temperature: 50° C.

Flow rate: 1 ml/min

Gradient (2 min): from 5 to 50% of B in 0.8 min; 1.2 min: 100% of B; 1.85 min: 100% of B; 1.95: 5% of B Analytical Results:

Retention time Tr (min)=0.66; [M+H]+: m/z 405; [M−H]−: m/z 403

$^1$H NMR spectrum (400 MHz): 2.58 (partially masked m, 1H); 2.83 (m, 1H); 3.19 (t, J=8.7 Hz, 2H); 3.27 to 3.52 (partially masked m, 4H); 3.77 (s, 2H); 3.82 to 3.96 (m, 2H); 4.12 (m, 1H); 4.21 (t, J=8.7 Hz, 2H); 4.71 (t, J=6.1 Hz, 1H); 5.20 (s, 1H); 7.09 (d, J=7.9 Hz, 1H); 7.22 (t, J=7.9 Hz, 1H); 7.97 (d, J=7.9 Hz, 1H); 11.61 (broad s, 1H)

Optical rotation: $\alpha_D$=−22° C.=0.351 mg/0.5 ml in DMSO

Step 11b, Example 26b: (+)-2-[2-(4-Chloro-2,3-dihydroindol-1-yl)-2-oxoethyl]-6-(2-hydroxymethyl-morpholin-4-yl)-3H-pyrimidin-4-one

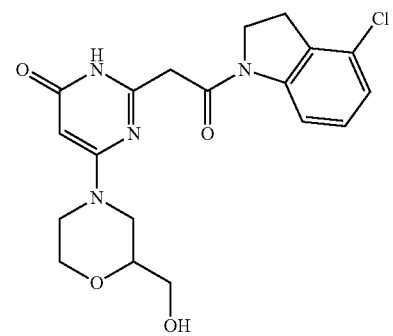 [SMILES: O=C(Cc1nc(N2CCOC(CO)C2)cc(=O)[nH]1)N1CCc2c(Cl)cccc21]

In a 25 ml round-bottomed flask, 42 mg of the sodium salt of [4-(2-hydroxymethylmorpholin-4-yl)-6-oxo-1,6-dihydropyrimidin-2-yl]acetic acid (example 25b, step 9b) and 22 mg of 4-chloro-2,3-dihydro-1H-indole are placed in 1 ml of dimethylformamide and 0.2 ml of pyridine, and then 33 mg of N-[3-(dimethylamino)propyl]-N'-ethylcarbodiimide hydrochloride are added. The reaction medium is stirred at ambient temperature for 20 h, then evaporated, water is added, and the resulting mixture is triturated. The solid formed is filtered off, and rinsed successively with water, then with diisopropyl ether, with methylene chloride and then with pentane. The resulting solid is dried under vacuum for 2 h. (+)-2-[2-(4-

Chloro-2,3-dihydroindol-1-yl)-2-oxoethyl]-6-(2-hydroxymethylmorpholin-4-yl)-3H-pyrimidin-4-one is isolated (18 mg) in the form of a pulverulent solid (yield=31%).

Mass Spectrometry:

The spectra were obtained on a Waters UPLC-SQD apparatus

Ionization: positive and/or negative mode electrospray (ES+/−)

Chromatographic Conditions:

Column: Acquity BEH C18—1.7 μm-2.1×50 mm

Solvents: A: $H_2O$ (0.1% formic acid) B: $CH_3CN$ (0.1% formic acid)

Column temperature: 50° C.

Flow rate: 1 ml/min

Gradient (2 min): from 5 to 50% of B in 0.8 min; 1.2 min: 100% of B; 1.85 min: 100% of B; 1.95: 5% of B Analytical Results:

Retention time Tr (min)=0.66; [M+H]+: m/z 405; [M−H]−: m/z 403

$^1$H NMR spectrum (400 MHz): 2.58 (partially masked m, 1H); 2.83 (m, 1H); 3.19 (t, J=8.7 Hz, 2H); 3.27 to 3.52 (partially masked m, 4H); 3.77 (s, 2H); 3.82 to 3.96 (m, 2H); 4.12 (m, 1H); 4.21 (t, J=8.7 Hz, 2H); 4.71 (t, J=6.1 Hz, 1H); 5.20 (s, 1H); 7.09 (d, J=7.9 Hz, 1H); 7.22 (t, J=7.9 Hz, 1H); 7.97 (d, J=7.9 Hz, 1H); 11.61 (broad s, 1H)

Optical rotation: $\alpha_D$=+19° C.=0.950 mg/0.5 ml in DMSO

Example 27b

Synthesis of (±)-2-[2-(4-fluoro-2,3-dihydroindol-1-yl)-2-oxoethyl]-6-(2-hydroxymethylmorpholin-4-yl)-3H-pyrimidin-4-one

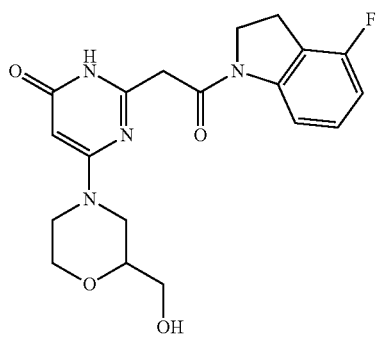 [SMILES: O=C(Cc1nc(N2CCOC(CO)C2)cc(=O)[nH]1)N1CCc2c(F)cccc21]

0.975 g of the sodium salt of (±)-[4-(2-hydroxymethylmorpholin-4-yl)-6-oxo-1,6-dihydropyrimidin-2-yl]acetic acid (example 25b, step 6b), 0.534 g of 4-fluoroindoline, 0.57 ml of pyridine and 15 ml of DMF are placed in a three-necked flask. 0.9 g of N-[3-(dimethylamino)propyl]-N'-ethylcarbodiimide hydrochloride is added and the mixture is stirred at ambient temperature (20° C.) for 72 hours. The reaction mixture is poured into 50 ml of water, with stirring, and then the insoluble material is filtered off through a VF filter, and washed 3 times with approximately 15 ml of water and then with 10 ml of ethyl acetate and twice approximately 5 ml of diisopropyl ether. The solid is air-dried under a hood. 2-[2-(4-Fluoro-2,3-dihydroindol-1-yl)-2-oxoethyl]-6-(2-hydroxymethylmorpholin-4-yl)-3H-pyrimidin-4-one is isolated (0.82 g) and characterized in the form of a pinkish solid, yield 60%.

Mass Spectrometry:

The spectra were obtained on a Waters UPLC-SQD apparatus

Ionization: positive and/or negative mode electrospray (ES+/−)

Chromatographic Conditions:

Column: Acquity BEH C18—1.7 μm-2.1×50 mm

Solvents: A: $H_2O$ (0.1% formic acid) B: $CH_3CN$ (0.1% formic acid)

Column temperature: 50° C.

Flow rate: 1 ml/min

Gradient (2 min): from 5 to 50% of B in 0.8 min; 1.2 min: 100% of B; 1.85 min: 100% of B; 1.95: 5% of B Analytical Results:

Retention time Tr (min)=0.59; [M+H]+: m/z 389; [M−H]−: m/z 387

$^1$H NMR spectrum (400 MHz): 2.58 (m, 1H); 2.83 (m, 1H); 3.20 (t, J=8.6 Hz, 2H); 3.32 to 3.50 (m, 4H); 3.77 (s, 2H); 3.83 to 3.96 (m, 2H); 4.12 (m, 1H); 4.22 (t, J=8.6 Hz, 2H); 4.73 (t, J=5.5 Hz, 1H); 5.20 (s, 1H); 6.86 (t, J=8.7 Hz, 1H); 7.21 (m, 1H); 7.84 (d, J=8.7 Hz, 1H); 11.62 (broad s, 1H)

Example 28b

Synthesis of 2-[2-(4-chloro-2,3-dihydroindol-1-yl)-2-oxoethyl]-6-(2-methylmorpholin-4-yl)-3H-pyrimidin-4-one

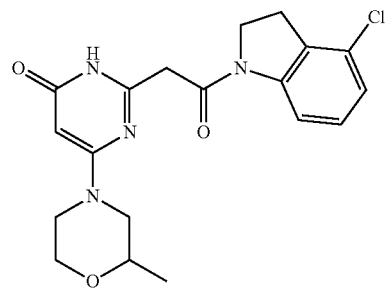 [SMILES: CC1CN(c2cc(=O)[nH]c(CC(=O)N3CCc4c(Cl)cccc43)n2)CCO1]

0.975 g of the sodium salt of [4-(2-methylmorpholin-4-yl)-6-oxo-1,6-dihydropyrimidin-2-yl]acetic acid (example 1b, step 2b), 0.534 g of 4-chloroindoline, 0.57 ml of pyridine and 15 ml of DMF are placed in a round-bottomed flask, and then 0.9 g of N-[3-(dimethylamino)propyl]-N'-ethylcarbodiimide hydrochloride is added. The reaction mixture is stirred at ambient temperature for 72 hours. The reaction mixture is poured into 50 ml of water, with stirring, and then the solid formed is filtered off through sintered glass and washed 3 times with approximately 15 ml of water, washed with 10 ml of EtOAc and rinsed with twice approximately 5 ml of diisopropyl ether, and the resulting product is left to air-dry under a hood. 2-[2-(4-Chloro-2,3-dihydroindol-1-yl)-2-oxoethyl]-6-(2-methylmorpholin-4-yl)-3H-pyrimidin-4-one is isolated (0.98 g) and characterized in the form of an off-white solid (yield 71%).

LCMS ES+DMSO Tr 1.15; MH+m/z=389

Mass Spectrometry:

The spectra were obtained on a Waters UPLC-SQD apparatus

Ionization: positive and/or negative mode electrospray (ES+/−)

Chromatographic Conditions:

Column: Acquity BEH C18—1.7 μm-2.1×50 mm

Solvents: A: $H_2O$ (0.1% formic acid) B: $CH_3CN$ (0.1% formic acid)

Column temperature: 50° C.

Flow rate: 1 ml/min

Gradient (2 min): from 5 to 50% of B in 0.8 min; 1.2 min: 100% of B; 1.85 min: 100% of B; 1.95: 5% of B Analytical Results:

Retention time Tr (min)=0.82; [M+H]+: m/z 389; [M−H]−: m/z 387

¹H NMR spectrum (400 MHz): 1.06 (d, J=6.4 Hz, 3H); 2.48 (partially masked m, 1H); 2.80 (m, 1H); 3.19 (t, J=8.7 Hz, 2H); 3.40 to 3.50 (m, 2H); 3.76 (s, 2H); 3.81 (dd, J=3.0 and 11.5 Hz, 1H); 3.93 (m, 1H); 4.03 (m, 1H); 4.20 (t, J=8.7 Hz, 2H); 5.22 (s, 1H); 7.09 (d, J=8.1 Hz, 1H); 7.22 (t, J=8.1 Hz, 1H); 7.97 (d, J=8.1 Hz, 1H); 11.61 (broad s, 1H)

Example 29b

Synthesis of (+)-2-[2-[(S)-2-methyl-2,3-dihydroindol-1-yl)-2-oxoethyl]-6-(2-methylmorpholin-4-yl)-3H-pyrimidin-4-one Step 1b: chiral chromatography of (±)-[4-(2-methylmorpholin-4-yl)-6-oxo-1,6-dihydropyrimidin-2-yl] acetic acid

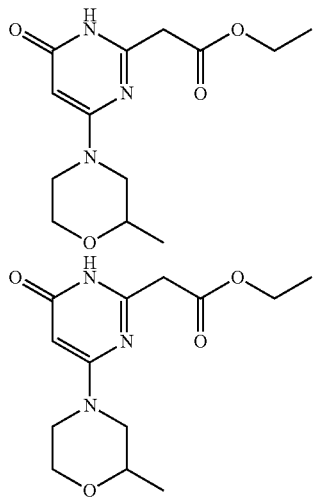

(±)-[4-(2-Methylmorpholin-4-yl)-6-oxo-1,6-dihydropyrimidin-2-yl]acetic acid ethyl ester (example 1b, step 1b) is resolved into its two enantiomers by chiral chromatography on a column containing 1.2 kg of Chiralpak AS 20 µm stationary phase (7.7×35 cm), elution being carried out with a mixture of 80% heptane, 20% ethanol and 0.05% triethylamine at 300 ml/min. The fractions containing the enantiomers are combined and evaporated. The solids obtained are dried and characterized by their optical rotation. The following intermediate esters are isolated:

Intermediate 29-A: A first enantiomer (1.1 g), [4-(2-methylmorpholin-4-yl)-6-oxo-1,6-dihydropyrimidin-2-yl]acetic acid ethyl ester −12°, c=2.047 mg/0.5 ml DMSO, 589 nm, the characteristics of which are:

Waters UPLC-SQD: Ionization: positive and/or negative mode electrospray (ES+/−)

Chromatographic Conditions:

Column: Acquity BEH C18—1.7 µm-2.1×50 mm

Solvents: A: H₂O (0.1% formic acid) B: CH₃CN (0.1% formic acid)

Column temperature: 50° C.

Flow rate: 1 ml/min

Gradient (2 min): from 5 to 50% of B in 0.8 min; 1.2 min: 100% of B; 1.85 min: 100% of B; 1.95: 5% of B Analytical Results:

Retention time Tr (min)=0.55; [M+H]+: m/z 282; [M−H]−: m/z 280

¹H NMR spectrum (400 MHz): 1.11 (d, J=6.3 Hz, 3H); 1.19 (t, J=7.1 Hz, 3H); 2.48 (partially masked m, 1H); 2.81 (m, 1H); 3.36 to 3.51 (m, 2H); 3.56 (s, 2H); 3.83 (m, 1H); 3.95 (m, 1H); 4.03 (m, 1H); 4.12 (q, J=7.1 Hz, 2H); 5.21 (s, 1H); 11.65 (broad m, 1H)

Intermediate 29-B: A second enantiomer (1 g), [4-(2-methylmorpholin-4-yl)-6-oxo-1,6-dihydropyrimidin-2-yl]acetic acid ethyl ester (1 g)+19°, c=1.799 mg/0.5 ml DMSO, 589 nm, the characteristics of which are:

Waters UPLC-SQD: Ionization: positive and/or negative mode electrospray (ES+/−)

Chromatographic Conditions:

Column: Acquity BEH C18—1.7 µm-2.1×50 mm

Solvents: A: H₂O (0.1% formic acid) B: CH₃CN (0.1% formic acid)

Column temperature: 50° C.

Flow rate: 1 ml/min

Gradient (2 min): from 5 to 50% of B in 0.8 min; 1.2 min: 100% of B; 1.85 min: 100% of B; 1.95: 5% of B Analytical Results:

Retention time Tr (min)=0.55; [M+H]+: m/z 282; [M−H]−: m/z 280; base peak: m/z 234

¹H NMR spectrum (400 MHz): 1.11 (d, J=6.3 Hz, 3H); 1.19 (t, J=7.1 Hz, 3H); 2.48 (partially masked m, 1H); 2.81 (m, 1H); 3.36 to 3.51 (m, 2H); 3.56 (s, 2H); 3.83 (m, 1H); 3.95 (m, 1H); 4.03 (m, 1H); 4.12 (q, J=7.1 Hz, 2H); 5.21 (s, 1H); 11.65 (broad m, 1H)

The enantiomeric purity of the two compounds obtained above is characterized by analytical chiral chromatography carried out on a Chiralpak AS-H-5 µm, 250×4.6 mm column, elution being carried out with an 80% heptane/20% EtOH/ 0.05% TEA mixture at the flow rate of 1 ml/min. The enantiomeric ratios are respectively 98.5/1.5% and 1.3/98.7% for the levorotatory and dextrorotatory enantiomers.

Step 2b: Synthesis of the sodium salt of [4-(2-methylmorpholin-4-yl)-6-oxo-1,6-dihydropyrimidin-2-yl] acetic acid

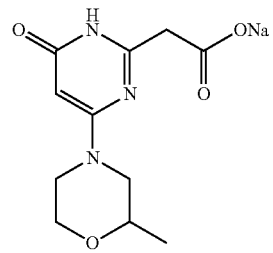

The dextrorotatory ethyl ester of [4-(2-methylmorpholin-4-yl)-6-oxo-1,6-dihydropyrimidin-2-yl]acetic acid (intermediate 29-B, example 29b, step 1b), 1 g in 10 ml of THF, is treated under the conditions described in step 2b of example 1b, in the presence of 1 equivalent of sodium hydroxide, so as to give 1.1 g of the sodium salt of [4-(2-methylmorpholin-4-yl)-6-oxo-1,6-dihydropyrimidin-2-yl]acetic acid, which is used in the next step.

Step 3b: Synthesis of 2-[2-((S)-2-methyl-2,3-dihydroindol-1-yl)-2-oxoethyl]-6-(2-methylmorpholin-4-yl)-3H-pyrimidin-4-one

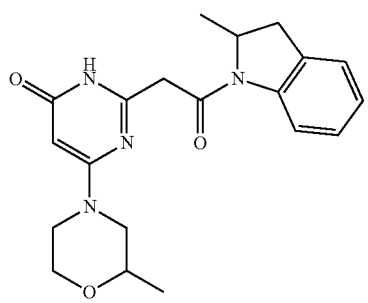 [SMILES: CC1CN(c2cc(=O)[nH]c(CC(=O)N3c4ccccc4CC3C)n2)CCO1]

A solution of 500 mg of the sodium salt of [4-(2-methylmorpholin-4-yl)-6-oxo-1,6-dihydropyrimidin-2-yl]acetic acid obtained above in 7.5 ml of DMF and 7.5 ml of pyridine is placed in a round-bottomed flask, and then 420 mg of N-[3-(dimethylamino)propyl]-N'-ethylcarbodiimide hydrochloride and 0.27 g of (S)-2-methyl-1H-indoline (CAS 22160-09-4) are added. The reaction mixture is stirred at ambient temperature for 48 h. 50 ml of water are added and the mixture is extracted with 3 times approximately 30 ml of ethyl acetate. The organic extracts are combined and successively washed with 30 ml of water, twice 30 ml of 1M hydrochloric acid solution and then 30 ml of saturated NaCl solution, dried over MgSO$_4$ and concentrated under vacuum. The compound obtained is purified by chromatography on a 30 g Merck column (15-40 μm) at the flow rate of 30 ml/min, elution being carried out with dichloromethane/methanol from 98/2 to 95/5. The fractions containing the expected compound are combined and evaporated. (+)-2-[2-((S)-2-Methyl-2,3-dihydroindol-1-yl)-2-oxoethyl]-6-(2-methylmorpholin-4-yl)-3H-pyrimidin-4-one is isolated (237 mg), the characteristics of which are the following:

Optical rotation: +91°, c=0.135 mg/0.5 ml DMSO

Waters UPLC-SQD: Ionization: positive and/or negative mode electrospray (ES+/−)

Chromatographic Conditions:

Column: Acquity BEH C18—1.7 μm-2.1×50 mm

Solvents: A: H$_2$O (0.1% formic acid) B: CH$_3$CN (0.1% formic acid))

Column temperature: 50° C.

Flow rate: 1 ml/min

Gradient (2 min): from 5 to 50% of B in 0.8 min; 1.2 min: 100% of B; 1.85 min: 100% of B; 1.95: 5% of B Analytical Results: Retention time Tr (min)=0.75; [M+H]+: m/z 369; [M−H]−: m/z 367

$^1$H NMR spectrum (400 MHz): 1.07 (d, J=6.4 Hz, 3H); 1.26 (broad d, J=6.6 Hz, 3H); 2.47 (partially masked m, 1H); 2.69 (d, J=16.3 Hz, 1H); 2.81 (m, 1H); 3.31 to 3.51 (m, 3H); 3.66 to 4.10 (m, 5H); 4.70 (m, 1H); 5.21 (s, 1H); 7.04 (t, J=8.0 Hz, 1H); 7.18 (t, J=8.0 Hz, 1H); 7.28 (d, J=8.0 Hz, 1H); 7.96 (broad d, J=8.0 Hz, 1H); 11.67 (broad m, 1H)

Example 30b

Synthesis of 6-(2-fluoromethylmorpholin-4-yl)-2-[2-((S)-2-methyl-2,3-dihydroindol-1-yl)-2-oxoethyl]-3H-pyrimidin-4-one Step 1b: Synthesis of (±)-[4-(2-fluoromethylmorpholin-4-yl)-6-oxo-1,6-dihydropyrimidin-2-yl]acetic acid ethyl ester

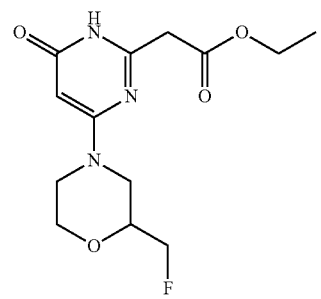

In a 50 ml round-bottomed flask, 680 mg of 2-fluoromethylmorpholine (Yoshikazu Jinho et al.; J. Med. Chem., 37(17), 2791-2796; 1994) and 0.63 g of (4-chloro-6-methoxypyrimidin-2-yl)acetic acid ethyl ester (example 8b, step 2b) are placed in 15 ml of DMSO and 1,013 ml of triethylamine. The reaction medium is heated for 18 h at 85° C. The reaction medium is poured into a saturated NaCl solution and the mixture is extracted with 3 times 25 ml of ethyl acetate. The organic extracts are combined and washed with a saturated NaCl solution, dried over magnesium sulfate and evaporated. The compound obtained is chromatographed on silica gel (15-40 μm, Merck), elution being carried out with a gradient of dichloromethane and methanol (98/2 to 95/5 v/v). The fractions containing the expected compound are combined and evaporated, so as to give (±)-[4-(2-fluoromethylmorpholin-4-yl)-6-oxo-1,6-dihydropyrimidin-2-yl]acetic acid ethyl ester (412 mg).

LC/MS, ES+, Tr=0.78 min, m/z=299

Step 2b: Chiral chromatography of (±)-[4-(2-fluoromethylmorpholin-4-yl)-6-oxo-1,6-dihydropyrimidin-2-yl]acetic acid ethyl ester

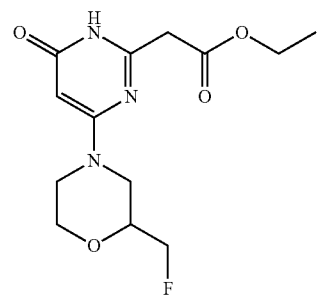 [SMILES: CCOC(=O)Cc1nc(N2CCOC(CF)C2)cc(=O)[nH]1]

193

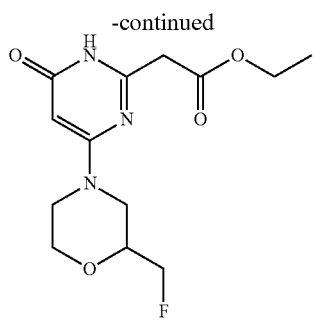

The racemic (±)-[4-(2-fluoromethylmorpholin-4-yl)-6-oxo-1,6-dihydropyrimidin-2-yl]acetic acid ethyl ester compound (example 30b, step 1b) is separated into its two enantiomers by chiral chromatography on Chiralpak AS 20 μm, 7.7×35 cm stationary phase, elution being carried out with a mixture of 70% heptane, 30% isopropanol and triethylamine at 250 ml/min. After evaporation of the fractions of interest, the following intermediates are isolated:

Intermediate 30-A: The first enantiomer, (−)-[4-(2-fluoromethylmorpholin-4-yl)-6-oxo-1,6-dihydropyrimidin-2-yl]acetic acid ethyl ester (1.17 g) (−19.6°, c=1.946 mg/0.5 ml DMSO, 589 nm), the characteristics of which are the following:

Waters UPLC-SQD: Ionization: positive and/or negative mode electrospray (ES+/−)
Chromatographic Conditions:
Column: Acquity BEH C18—1.7 μm-2.1×50 mm
Solvents: A: $H_2O$ (0.1% formic acid) B: $CH_3CN$ (0.1% formic acid)
Column temperature: 50° C.
Flow rate: 1 ml/min
Gradient (2 min): from 5 to 50% of B in 0.8 min; 1.2 min: 100% of B; 1.85 min: 100% of B; 1.95: 5% of B
Analytical Results:
Retention time Tr (min)=0.53; [M+H]+: m/z 300; [M−H]−: m/z 298; base peak: m/z 252
$^1$H NMR spectrum (400 MHz): 1.19 (t, J=7.1 Hz, 3H); 2.70 (m, 1H); 2.86 (m, 1H); 3.50 (m, 1H); 3.57 (s, 2H); 3.66 (m, 1H); 3.87 to 4.00 (m, 2H); 4.05 to 4.16 (m, 3H); 4.47 (dm, J=47.2 Hz, 2H); 5.25 (s, 1H); 11.64 (broad m, 1H)

Intermediate 30-B: The second enantiomer, (+)-[4-(2-fluoromethylmorpholin-4-yl)-6-oxo-1,6-dihydropyrimidin-2-yl]acetic acid ethyl ester (1.01 g) (+18.2°, c=1.75 mg/0.5 ml DMSO, 589 nm), the characteristics of which are the following:

Waters UPLC-SQD: Ionization: positive and/or negative mode electrospray (ES+/−)
Chromatographic Conditions:
Column: Acquity BEH C18—1.7 μm-2.1×50 mm
Solvents: A: $H_2O$ (0.1% formic acid) B: $CH_3CN$ (0.1% formic acid)
Column temperature: 50° C.
Flow rate: 1 ml/min
Gradient (2 min): from 5 to 50% of B in 0.8 min; 1.2 min: 100% of B; 1.85 min: 100% of B; 1.95: 5% of B
Analytical Results:
Retention time Tr (min)=0.53; [M+H]+: m/z 300; [M−H]−: m/z 298; base peak: m/z 252
$^1$H NMR spectrum (400 MHz): 1.19 (t, J=7.1 Hz, 3H); 2.70 (m, 1H); 2.86 (m, 1H); 3.50 (m, 1H); 3.57 (s, 2H); 3.66 (m, 1H); 3.87 to 4.00 (m, 2H); 4.05 to 4.16 (m, 3H); 4.47 (dm, J=47.2 Hz, 2H); 5.25 (s, 1H); 11.64 (broad m, 1H)

The enantiomeric purity of the two compounds obtained above is characterized by analytical chiral chromatography carried out on a Chiralpak AS 10 μm, 250×4.6 mm column, elution being carried out with a mixture of 70% Heptane, 30%

194

EtOH and 0.1% TEA at the flow rate of 1 ml/min. The enantiomeric excesses are respectively 99.5% and 99.1%.

Step 3b: Synthesis of the sodium salt of [4-(2-fluoromethylmorpholin-4-yl)-6-oxo-1,6-dihydropyrimidin-2-yl]acetic acid

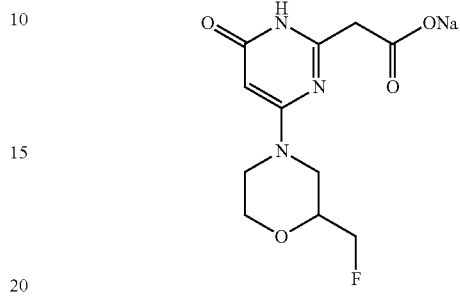

In a round-bottomed flask, 2.8 g of (+)-[4-(2-fluoromethylmorpholin-4-yl)-6-oxo-1,6-dihydropyrimidin-2-yl]acetic acid ethyl ester (intermediate 30-B, example 30b, step 2b) are placed in 10 ml of THF, and then a stoichiometric amount of 2M sodium hydroxide is run in dropwise. The mixture is left to stir for 5 days at ambient temperature (20° C.). The resulting product is concentrated to dryness under vacuum in a rotary evaporator at ambient temperature. 1 g of a semi-oily orange solid is obtained, which is taken up in 20 ml of THF, triturated, and filtered through a VF filter. The solid is rinsed with ethyl ether and oven-dried under vacuum. 1 g of the sodium salt of [4-(2-fluoromethylmorpholin-4-yl)-6-oxo-1,6-dihydropyrimidin-2-yl]acetic acid is isolated in the form of a beige solid, which is used as it is in the next step.

LCMS ES+Retention time Tr (min)=0.56; [M+H]+: m/z 271 (corresponding acid)

Step 4b: Synthesis of (+)-6-(2-fluoromethylmorpholin-4-yl)-2-[2-((S)-2-methyl-2,3-dihydroindol-1-yl)-2-oxoethyl]-3H-pyrimidin-4-one

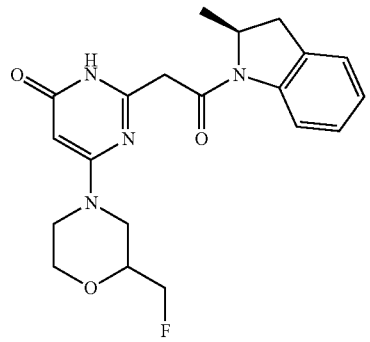 [SMILES: C[C@H]1Cc2ccccc2N1C(=O)Cc1nc(N2CCOC(CF)C2)cc(=O)[nH]1]

In a three-necked flask under argon, 0.5 g of the sodium salt of [4-(2-fluoromethylmorpholin-4-yl)-6-oxo-1,6-dihydropyrimidin-2-yl]acetic acid previously obtained (example 30b, step 3b) is placed in 7 ml of pyridine and 7 ml of dimethylformamide, and then N-[3-(dimethylamino)propyl]-N'-ethylcarbodiimide hydrochloride is added at ambient temperature, followed by 0.25 g of (S)-2-methylindoline (CAS 22160-09-4). The reaction medium is stirred at ambient temperature (20° C.) for 72 hours. 25 ml of water are added, extraction is carried out with 3 times approximately 25 ml of dichloromethane, washing is carried out with 25 ml of water, washing is carried out with twice approximately 15 ml of 1M hydrochloric acid solution, washing is carried out with 25 ml of water, washing is carried out with 25 ml of saturated NaCl solution, drying is carried out over MgSO₄, filtration is carried out through a VF filter, and the resulting product is concentrated under vacuum. The compound obtained is chromatographed on silica gel (40-63 µm), elution being carried out with a mixture of dichloromethane and ethanol (95/5, v/v). The fractions containing the expected compound are combined and evaporated. The compound obtained is triturated from 1 ml of dichloromethane and 10 ml of diisopropyl ether, filtered, and dried at ambient temperature (20° C.). (+)-6-(2-Fluoromethylmorpholin-4-yl)-2-[2-((S)-2-methyl-2,3-dihydroindol-1-yl)-2-oxoethyl]-3H-pyrimidin-4-one is isolated (0.315 g).

Waters UPLC-SQD: Ionization: positive and/or negative mode electrospray (ES+/−)

Chromatographic Conditions:

Column: Acquity BEH C18—1.7 µm-2.1×50 mm

Solvents: A: H₂O (0.1% formic acid) B: CH₃CN (0.1% formic acid)

Column temperature: 50° C.

Flow rate: 1 ml/min

Gradient (2 min): from 5 to 50% of B in 0.8 min; 1.2 min: 100% of B; 1.85 min: 100% of B; 1.95: 5% of B Analytical Results: Retention time Tr (min)=0.74; [M+H]+: M/z 387; [M−H]−: m/z 385

¹H NMR spectrum (400 MHz): 1.26 (broad d, J=6.3 Hz, 3H); 2.63 to 2.74 (m, 2H); 2.86 (m, 1H); 3.37 (m, 1H); 3.49 (m, 1H); 3.56 to 3.77 (m, 2H); 3.86 to 4.00 (m, 3H); 4.09 (m, 1H); 4.44 (dm, J=47.2 Hz, 2H); 4.71 (m, 1H); 5.25 (s, 1H); 7.04 (t, J=8.0 Hz, 1H); 7.18 (t, J=8.0 Hz, 1H); 7.29 (d, J=8.0 Hz, 1H); 7.96 (broad d, J=8.0 Hz, 1H); 11.72 (broad m, 1H)

Optical rotation OR=+76.4+/−1.3 ds DMSO at 589 nm C=0.4%

Diastereoisomeric excess: 99.2% (Chiralpak AS-5 µm, 250×4.6 mm; 60% heptane, 20% methanol, 20% ethanol, 1 ml/min)

Example 31b

Synthesis of (+)-6-(2-hydroxymethylmorpholin-4-yl)-2-[2-((S)-2-methyl-2,3-dihydroindol-1-yl)-2-oxoethyl]-3H-pyrimidin-4-one Step 1b: (−)-[4-(2-Hydroxymethylmorpholin-4-yl)-6-oxo-1,6-dihydropyrimidin-2-yl]acetic acid ethyl ester

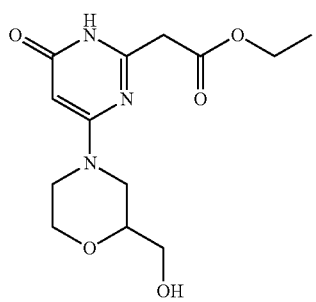 [SMILES: CCOC(=O)Cc1nc(N2CCOC(CO)C2)cc(=O)[nH]1]

The (±)-[4-(2-hydroxymethylmorpholin-4-yl)-6-oxo-1,6-dihydropyrimidin-2-yl]acetic acid ethyl ester previously obtained (Ex 25b, step 6b) is separated into its two enantiomers by chiral chromatography on a column containing 1.080 kg of Chiralpak AY 20 µm stationary phase, elution being carried out with a mixture of 30/70/0.1(%) ethanol/heptane/TEA at 300 ml/min.

After evaporation of the fractions of interest, the following are isolated:

The intermediate 31-A, first enantiomer, (−)-[4-(2-hydroxymethylmorpholin-4-yl)-6-oxo-1,6-dihydropyrimidin-2-yl]acetic acid ethyl ester, 730 mg (OR=−0.6°, c=1.587 mg/0.5 ml DMSO, 589 nm), which is used in the next step.

The intermediate 31-B, second enantiomer, (+)-[4-(2-hydroxymethylmorpholin-4-yl)-6-oxo-1,6-dihydropyrimidin-2-yl]acetic acid ethyl ester, 880 mg (OR=+4°, c=1.904 mg/0.5 ml DMSO, 589 nm).

The enantiomeric purity of the two compounds obtained above is characterized by analytical chiral chromatography carried out on a Chiralpak AY-H, 5µ, 250×4.6 mm column, elution being carried out with a 70/30/01(%) heptane/ethanol/TEA mixture at the flow rate of 1 ml/min. The enantiomeric excesses are respectively >99% and >98%.

Step 2b: Synthesis of the sodium salt of (−)-[4-(2-hydroxymethylmorpholin-4-yl)-6-oxo-1,6-dihydropyrimidin-2-yl]acetic acid

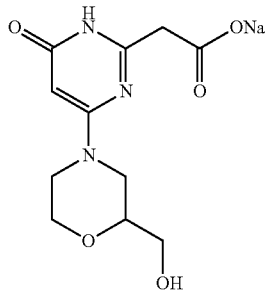

In a round-bottomed flask under argon, 0.73 g of (−)-[4-(2-hydroxymethylmorpholin-4-yl)-6-oxo-1,6-dihydropyrimidin-2-yl]acetic acid ethyl ester (intermediate 31-A, example 31b, step 1b) is placed in 10 ml of THF; a stoichiometric amount of 2M sodium hydroxide solution is rapidly dropwise run into the homogeneous solution obtained, and the mixture is left to stir for 5 days at ambient temperature. The mixture is concentrated to dryness under vacuum in a rotary evaporator at ambient temperature (20° C.). A semi-oily orange solid is obtained, which is taken up in 20 ml of THF, triturated, and filtered through a VF filter. The solid is rinsed with ethyl ether, and oven-dried under vacuum. The sodium salt of (−)-[4-(2-hydroxymethylmorpholin-4-yl)-6-oxo-1,6-dihydropyrimidin-2-yl]acetic acid (0.69 g) is isolated in the form of a pale yellow solid, which is used as it is in the next steps.

Step 3b: Synthesis of (+)-6-(2-hydroxymethylmorpholin-4-yl)-2-[2-((S)-2-methyl-2,3-dihydroindol-1-yl)-2-oxoethyl]-3H-pyrimidin-4-one

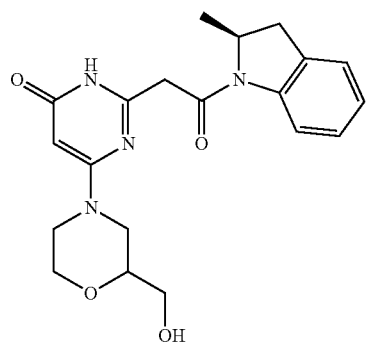 [SMILES: C[C@H]1Cc2ccccc2N1C(=O)Cc1nc(N2CCOC(CO)C2)cc(=O)[nH]1]

In a three-necked flask under argon, 0.35 g of the sodium salt of (−)-[4-(2-hydroxymethylmorpholin-4-yl)-6-oxo-1,6-dihydropyrimidin-2-yl]acetic acid (example 31b, step 2b) is placed in 5 ml of pyridine and 5 ml of DMF whitish heterogeneous solution. N-[3-(dimethylamino)propyl]-N'-ethylcarbodiimide hydrochloride is added at ambient temperature, 0.18 g of (S)-2-methylindoline (CAS 22160-09-4) is added, and the mixture is stirred at ambient temperature for 72 hours. 25 ml of water are added, extraction is carried out with 3 times approximately 25 ml of dichloromethane, washing is carried out with 25 ml of water, washing is carried out with twice approximately 15 ml of 1M hydrochloric acid solution, washing is carried out with 25 ml of water, washing is carried out with 25 ml of saturated NaCl solution, drying is carried out over MgSO$_4$, filtration is carried out through a VF filter, and the resulting product is concentrated under vacuum. The compound obtained is chromatographed on silica gel (40-63 μm), elution being carried out with a mixture of dichloromethane and ethanol (95/5, v/v). The fractions containing the expected compound are combined and evaporated. The compound obtained is triturated from dichloromethane and diisopropyl ether, filtered, and dried at ambient temperature (20° C.). (+)-6-(2-Hydroxymethylmorpholin-4-yl)-2-[2-((S)-2-methyl-2,3-dihydroindol-1-yl)-2-oxoethyl]-3H-pyrimidin-4-one is isolated (0.11 g).

Waters UPLC-SQD: Ionization: positive and/or negative mode electrospray (ES+/−)

Chromatographic Conditions:
Column: Acquity BEH C18—1.7 μm-2.1×50 mm
Solvents: A: H$_2$O (0.1% formic acid) B: CH$_3$CN (0.1% formic acid)
Column temperature: 50° C.
Flow rate: 1 ml/min
Gradient (2 min): from 5 to 50% of B in 0.8 min; 1.2 min: 100% of B; 1.85 min: 100% of B; 1.95: 5% of B
Analytical Results: Retention time Tr (min)=0.60;
[M+H]+: m/z 385; [M−H]−: m/z 383
$^1$H NMR spectrum (400 MHz): 1.26 (broad d, J=6.4 Hz, 3H); 2.57 (m, 1H); 2.68 (d, J=16.3 Hz, 1H); 2.84 (m, 1H); 3.33 to 3.49 (m, 5H); 3.72 (m, 1H); 3.81 to 3.98 (m, 3H); 4.12 (m, 1H); 4.72 (m, 2H); 5.19 (s, 1H); 7.04 (t, J=8.0 Hz, 1H); 7.18 (t, J=8.0 Hz, 1H); 7.28 (d, J=8.0 Hz, 1H); 7.96 (d, J=8.0 Hz, 1H); 11.69 (broad m, 1H)
Optical rotation: α$_D$=+72+/−1.5 ds DMSO at 589 nm C=0.27%

Synthesis of the Compounds of Formula (Ic)

Example 1c

Synthesis of 2-[2-(4-chloro-2-methyl-2,3-dihydro-1H-indol-1-yl)-2-oxoethyl]-6-(morpholin-4-yl)pyrimidin-4(3H)-one Step 1c

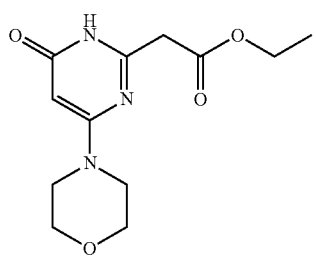 [SMILES: CCOC(=O)Cc1nc(N2CCOCC2)cc(=O)[nH]1]

168.5 ml of ethyl 3-ethoxy-3-iminopropanoate hydrochloride and then 155 ml of N,N-diisopropylethylamine in 200 ml of ethanol are added to a solution of 25 g of morpholine in 400 ml of ethanol; heated to 95° C. The reaction mixture is heated at 95° C. for 30 hours and then allowed to return to ambient temperature. The precipitate formed is filtered off through sintered glass and then washed with 100 ml of ethanol, twice 500 ml of water and, finally, 500 ml of ethyl ether. The solid is dried under vacuum, so as to give 35 g of ethyl [4-(morpholin-4-yl)-6-oxo-1,6-dihydropyrimidin-2-yl]acetate in the form of a white solid, the characteristics of which are the following:

$^1$H NMR spectrum (400 MHz): 1.19 (t, J=7.1 Hz, 3H); 3.38 to 3.44 (m, 4H); 3.56 (s, 2H); 3.61 (dd, J=4.0 and 5.7 Hz, 4H); 4.12 (q, J=7.1 Hz, 2H); 5.20 (s, 1H); 11.69 (broad s, 1H)
Mass spectrometry: method A
Retention time Tr (min)=0.48;
[M+H]+: m/z 268; [M−H]−: m/z 266

Step 2c

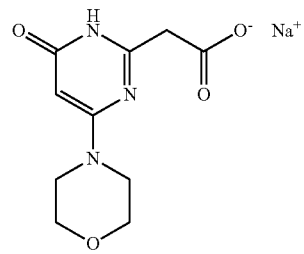 [SMILES: O=C([O-])Cc1nc(N2CCOCC2)cc(=O)[nH]1 ; [Na+]]

18.7 ml of 2M sodium hydroxide are added to a solution of 10 g of ethyl [4-(morpholin-4-yl)-6-oxo-1,6-dihydropyrimidin-2-yl]acetate in 300 ml of tetrahydrofuran. The reaction mixture is stirred for 48 hours at ambient temperature. The precipitate formed is filtered off through sintered glass, washed with ethyl acetate and rinsed several times with ethyl ether. The solid obtained is then dried in a rotary evaporator, so as to give 8.7 g of sodium [4-(morpholin-4-yl)-6-oxo-1,6-dihydropyrimidin-2-yl]acetate in the form of a white solid, the characteristics of which are the following:

$^1$H NMR spectrum (400 MHz): 3.08 (s, 2H); 3.38 (t, J=4.6 Hz, 4H); 3.61 (t, J=4.6 Hz, 4H); 5.08 (s, 1H); 13.16 (broad s, 1H)
Mass spectrometry: method A
Retention time Tr (min)=0.29;
[M+H]+: m/z 240; [M−H]−: m/z 238

Step 3c

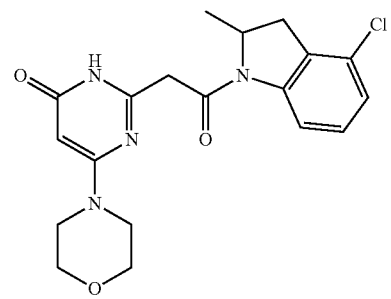 [SMILES: CC1Cc2c(Cl)cccc2N1C(=O)Cc1nc(N2CCOCC2)cc(=O)[nH]1]

549 mg of N-[3-(dimethylamino)propyl]-N'-ethylcarbodiimide hydrochloride and 350 μl of pyridine are added to a solution of 564 mg of sodium [4-(morpholin-4-yl)-6-oxo-1,6-dihydropyrimidin-2-yl]acetate in 5 ml of N,N-dimethylformamide. The resulting suspension is stirred at ambient temperature for 10 minutes, and then a solution of 398 mg of 4-chloro-2-methyl-2,3-dihydro-1H-indoline [which can be prepared according to U.S. Pat. No. 4,416,884 (1983)] in 9 ml of N,N-dimethylformamide is rapidly added. The reaction mixture is stirred at ambient temperature for 16 hours, and then concentrated under reduced pressure. The residue is taken up in a mixture of 32 ml of water and 15 ml of ethyl acetate, and then the resulting product is stirred at ambient temperature for 3 hours. The precipitate formed is filtered off, and then rinsed successively with water, diisopropyl ether and diethyl ether. The solid obtained is dried with suction, and then dried under reduced pressure at 40° C. 485 mg of 2-[2-(4-chloro-2-methyl-2,3-dihydro-1H-indol-1-yl)-2-oxoethyl]-6-(morpholin-4-yl)pyrimidin-4(3H)-one are thus obtained in the form of a white crystalline powder, the characteristics of which are the following:

$^1$H NMR spectrum (400 MHz): 1.30 (d, J=6.4 Hz, 3H); 2.73 (d, J=16.6 Hz, 1H); 3.34 to 3.44 (m, 5H); 3.60 (m, 4H); 3.75 (d, J=16.1 Hz, 1H); 3.93 (d, J=16.1 Hz, 1H); 4.77 (m, 1H); 5.21 (s, 1H); 7.12 (d, J=7.8 Hz, 1H); 7.24 (t, J=7.8 Hz, 1H); 7.92 (broad d, J=7.8 Hz, 1H); 11.69 (broad m, 1H)

Mass spectrometry: method A
Retention time Tr (min)=0.82;
[M+H]+: m/z 389; [M−H]−: m/z 387
Melting point (Kofler): 232° C.

Example 2c and Example 3c

Separation of (+)-2-{2-[4-chloro-2-methyl-2,3-dihydro-1H-indol-1-yl]-2-oxoethyl}-6-(morpholin-4-yl)pyrimidin-4(3H)-one and of (−)-2-{2-[4-chloro-2-methyl-2,3-dihydro-1H-indol-1-yl]-2-oxoethyl}-6-(morpholin-4-yl)pyrimidin-4(3H)-one

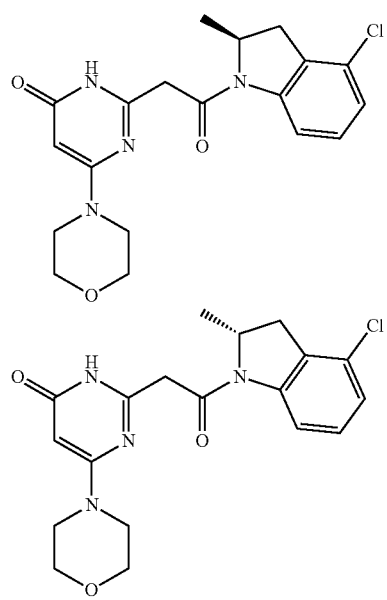

The products were obtained by chiral chromatographic separation of 428 mg of 2-[2-(4-chloro-2-methyl-2,3-dihydro-1H-indol-1-yl)-2-oxoethyl]-6-(morpholin-4-yl)pyrimidin-4(3H)-one (example 1c) on a Whelk 01 SS column (10 μm mixed batch, 7.5/40 cm), eluent: heptane/methanol/ethanol/triethylamine: 75/20/5/0.1; flow rate: 300 ml/min. After purification, 186 mg of (+)-2-[2-(4-chloro-2-methyl-2,3-dihydro-1H-indol-1-yl)-2-oxoethyl]-6-(morpholin-4-yl)pyrimidin-4(3H)-one are obtained, as first enantiomer, in the form of a white powder, the characteristics of which are the following:

$^1$H NMR spectrum (400 MHz): 1.30 (broad d, J=6.4 Hz, 3H); 2.72 (d, J=16.3 Hz, 1H); 3.33 to 3.44 (m, 5H); 3.60 (m, 4H); 3.74 (d, J=15.9 Hz, 1H); 3.93 (d, J=15.9 Hz, 1H); 4.78 (m, 1H); 5.20 (s, 1H); 7.12 (d, J=8.1 Hz, 1H); 7.24 (t, J=8.1 Hz, 1H); 7.92 (broad d, J=8.1 Hz, 1H); 11.68 (broad m, 1H)

Mass spectrometry: method A
Retention time Tr (min)=0.82;
[M+H]+: m/z 389; [M−H]−: m/z 387
Optical rotation: $\alpha_D$=+98°+/−2 (c=0.24% in DMSO)

Then the second enantiomer is obtained, i.e.: 206 mg of (−)-2-[2-(4-chloro-2-methyl-2,3-dihydro-1H-indol-1-yl)-2-oxoethyl]-6-(morpholin-4-yl)pyrimidin-4(3H)-one in the form of a white solid, the characteristics of which are the following:

$^1$H NMR spectrum (400 MHz): 1.30 (broad d, J=6.4 Hz, 3H); 2.73 (d, J=16.4 Hz, 1H); 3.33 to 3.44 (m, 5H); 3.60 (m, 4H); 3.74 (d, J=16.1 Hz, 1H); 3.93 (d, J=16.1 Hz, 1H); 4.78 (m, 1H); 5.20 (s, 1H); 7.12 (d, J=8.2 Hz, 1H); 7.24 (t, J=8.2 Hz, 1H); 7.92 (broad d, J=8.2 Hz, 1H); 11.69 (broad m, 1H)

Mass spectrometry: method A
Retention time Tr (min)=0.82;
[M+H]+: m/z 389; [M−H]−: m/z 387
Optical rotation: $\alpha_D$=−85°+/−2 (c=0.18% in DMSO)

Example 4c

Synthesis of 2-[2-(4-chloro-3,3-dimethyl-2,3-dihydro-1H-indol-1-yl)-2-oxoethyl]-3-methyl-6-(morpholin-4-yl)pyrimidin-4(3H)-one Step 1c

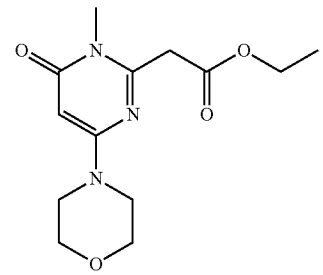 [SMILES: CCOC(=O)Cc1nc(N2CCOCC2)cc(=O)n1C]

330 mg of potassium carbonate and 150 ml of methyl iodide are added to a solution of 500 mg of ethyl [4-(morpholin-4-yl)-6-oxo-1,6-dihydropyrimidin-2-yl]acetate (prepared in step 1c of example 1c) in 1.5 ml of dioxane. The reaction mixture is heated at 40° C. for 16 and then cooled to ambient temperature. The suspension is filtered through sintered glass and then rinsed with dioxane, and the filtrate is concentrated under reduced pressure. The residue is purified by silica column chromatography, elution being carried out with a mixture of dichloromethane, acetonitrile and methanol (98/01/01, 96/02/02, then 90/05/05 V/V/V). 200 mg of ethyl [1-methyl-4-(morpholin-4-yl)-6-oxo-1,6-dihydropyrimidin-2-yl]acetate are obtained in the form of a white solid, the characteristics of which are the following:

¹H NMR spectrum (400 MHz): 1.21 (t, J=7.1 Hz, 3H); 3.29 (partially masked m, 3H); 3.40 (m, 4H); 3.61 (m, 4H); 3.92 (s, 2H); 4.15 (q, J=7.1 Hz, 2H); 5.35 (s, 1H)

Mass spectrometry: method A
Retention time Tr (min)=0.53;
[M+H]+: m/z 282; [M–H]–: m/z 280;

Step 2c

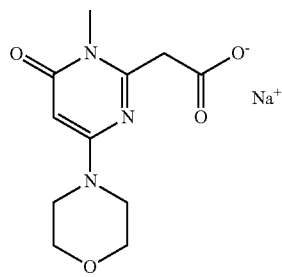 [SMILES: Cn1c(CC(=O)[O-])nc(N2CCOCC2)cc1=O ; [Na+]]

2.88 ml of 2M sodium hydroxide are added to a solution of 1.62 g of ethyl [1-methyl-4-(morpholin-4-yl)-6-oxo-1,6-dihydropyrimidin-2-yl]acetate in 20 ml of tetrahydrofuran. The reaction mixture is stirred for 48 hours at ambient temperature. The precipitate formed is filtered off through sintered glass, washed with ethyl acetate and rinsed several times with ethyl ether. The solid obtained is then dried in a rotary evaporator. 730 mg of sodium [1-methyl-4-(morpholin-4-yl)-6-oxo-1,6-dihydropyrimidin-2-yl]acetate are obtained in the form of a white solid, the characteristics of which are the following:

¹H NMR spectrum (400 MHz): 3.27 to 3.43 (partially masked m, 9H); 3.61 (m, 4H); 5.23 (s, 1H)

Mass spectrometry: method A
Retention time Tr (min)=0.31;
[M+H]+: m/z 254; [M–H]–: m/z 252;

Step 3c

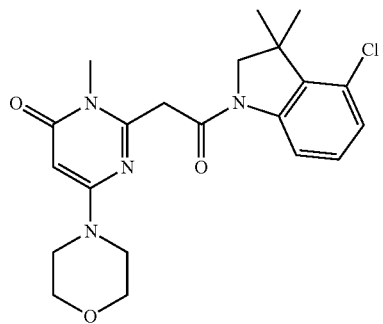 [SMILES: Cn1c(CC(=O)N2CC(C)(C)c3c(Cl)cccc32)nc(N2CCOCC2)cc1=O]

20 mg of 4-chloro-3,3-dimethyl-2,3-dihydro-1H-indole [which can be prepared according to Tet. Let. (1987) (28), 5291-5294] and 34 mg of N-[3-(dimethylamino)propyl]-N'-ethylcarbodiimide hydrochloride are added to a solution of 30 mg of sodium [1-methyl-4-(morpholin-4-yl)-6-oxo-1,6-dihydropyrimidin-2-yl]acetate in 0.5 ml of N,N-dimethylformamide and 0.5 ml of pyridine. The reaction mixture is stirred at ambient temperature for 16 hours, and then 10 ml of water are added and the mixture is extracted with ethyl acetate. The organic phase is washed successively with water and a saturated sodium chloride solution, dried over magnesium sulfate, filtered, and concentrated under reduced pressure. The residue is purified by silica column chromatography, elution being carried out with ethyl acetate, so as to give 12 mg of 2-[2-(4-chloro-3,3-dimethyl-2,3-dihydro-1H-indol-1-yl)-2-oxoethyl]-3-methyl-6-(morpholin-4-yl)pyrimidin-4(3H)-one, the characteristics of which are the following:

¹H NMR spectrum (400 MHz): 1.46 (s, 6H); 3.26 to 3.45 (partially masked m, 7H); 3.56 (m, 4H); 3.97 (s, 2H); 4.12 (s, 2H); 5.37 (s, 1H); 7.06 (d, J=7.9 Hz, 1H); 7.22 (t, J=7.9 Hz, 1H); 8.06 (d, J=7.9 Hz, 1H)

Mass spectrometry: method A
Retention time Tr (min)=0.95;
[M+H]+: m/z 417; [M–H]–: m/z 415

Example 5c

Synthesis of 2-[2-(4-chloro-3,3-dimethyl-2,3-dihydro-1H-indol-1-yl)-2-oxoethyl]-6-(morpholin-4-yl)pyrimidin-4(3H)-one

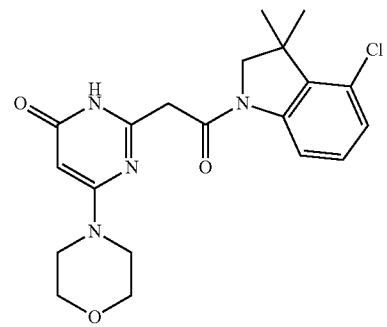 [SMILES: CC1(C)CN(C(=O)Cc2nc(N3CCOCC3)cc(=O)[nH]2)c2cccc(Cl)c21]

130 mg of 4-chloro-3,3-dimethyl-2,3-dihydro-1H-indole [which can be prepared according to Tet. Let. (1987) (28), 5291-5294] and 220 mg of N-[3-(dimethylamino)propyl]-N'-ethylcarbodiimide hydrochloride are added to a solution of 187 mg of sodium [4-(morpholin-4-yl)-6-oxo-1,6-dihydropyrimidin-2-yl]acetate (obtained in step 2c of example 1c) in 3 ml of N,N-dimethylformamide and 3 ml of pyridine. The reaction mixture is stirred at ambient temperature for 16 hours and then 15 ml of water are added and the mixture is extracted with ethyl acetate. The organic phase is washed successively with water and a saturated sodium chloride solution, dried over magnesium sulfate, filtered, and concentrated under reduced pressure. The residue is purified by silica column chromatography, elution being carried out with a mixture of dichloromethane and methanol (95/05: v/v), so as to give 24 mg of 2-[2-(4-chloro-3,3-dimethyl-2,3-dihydro-1H-indol-1-yl)-2-oxoethyl]-6-(morpholin-4-yl)pyrimidin-4(3H)-one, the characteristics of which are the following:

¹H NMR spectrum (400 MHz): 1.48 (s, 6H); 3.43 (m, 4H); 3.62 (m, 4H); 3.79 (s, 2H); 3.97 (s, 2H); 5.23 (s, 1H); 7.07 (d, J=8.0 Hz, 1H); 7.24 (t, J=8.0 Hz, 1H); 8.07 (d, J=8.0 Hz, 1H); 11.65 (s, 1H)

Mass spectrometry: method A
Retention time Tr (min)=0.90;
[M+H]+: m/z 403; [M–H]–: m/z 401

Example 6c

Synthesis of 2-[2-(4-hydroxy-2-methyl-2,3-dihydro-1H-indol-1-yl)-2-oxoethyl]-6-(morpholin-4-yl)pyrimidin-4(3H)-one

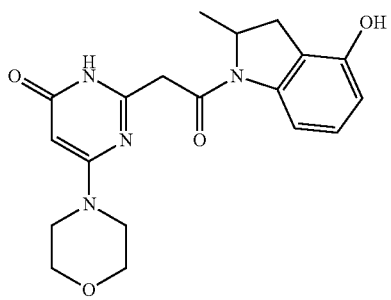 [SMILES: CC1Cc2c(O)cccc2N1C(=O)Cc1nc(N2CCOCC2)cc(=O)[nH]1]

The product is prepared by following the procedure described in example 1c using 1.2 g of sodium [4-(morpholin-4-yl)-6-oxo-1,6-dihydropyrimidin-2-yl]acetate, 0.82 g of 2-methyl-2,3-dihydro-1H-indol-4-ol [reference example 1c] and 1.17 g of N-[3-(dimethylamino)propyl]-N'-ethylcarbodiimide hydrochloride in a mixture of 1.1 ml of pyridine and 25 ml of N,N-dimethylformamide. After purification of the residue by chromatography on a 90 g cartridge of 15-40 μm silica, elution being carried out with pure dichloromethane and then with 98/2 then 95/5 v/v dichloromethane/methanol mixtures at a flow rate of 80 ml/min, 0.84 g of 2-[2-(4-hydroxy-2-methyl-2,3-dihydro-1H-indol-1-yl)-2-oxoethyl]-6-(morpholin-4-yl)pyrimidin-4(3H)-one is obtained in the form of a very pale pink powder, the characteristics of which are the following:

$^1$H NMR spectrum (400 MHz): 1.26 (d, J=6.4 Hz, 3H); 2.60 (d, J=15.4 Hz, 1H); 3.16 (dd, J=8.6 and 15.4 Hz, 1H); 3.41 (m, 4H); 3.60 (m, 4H); 3.69 (d, J=15.7 Hz, 1H); 3.89 (d, J=15.7 Hz, 1H); 4.69 (m, 1H); 5.20 (s, 1H); 6.53 (d, J=8.1 Hz, 1H); 6.99 (t, J=8.1 Hz, 1H); 7.45 (d, J=8.1 Hz, 1H); 9.44 (s, 1H); 11.66 (s, 1H)

Mass spectrometry: method A
Retention time Tr (min)=0.52;
[M+H]+: m/z 371; [M−H]−: m/z 369
Melting point (Kofler): 254° C.

Example 7c

Synthesis of 2-[2-(4-fluoro-3,3-dimethyl-2,3-dihydro-1H-indol-1-yl)-2-oxoethyl]-3-methyl-6-(morpholin-4-yl)pyrimidin-4(3H)-one

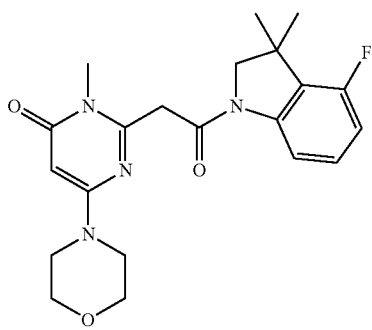 [SMILES: Cn1c(CC(=O)N2CC(C)(C)c3c(F)cccc32)nc(N2CCOCC2)cc1=O]

150 mg of 4-fluoro-3,3-dimethyl-2,3-dihydro-1H-indole [reference example 2c] and 279 mg of N-[3-(dimethylamino)propyl]-N'-ethylcarbodiimide hydrochloride are added to a solution of 300 mg of sodium [1-methyl-4-(morpholin-4-yl)-6-oxo-1,6-dihydropyrimidin-2-yl]acetate (obtained in step 2c of example 4c) in 5 ml of N,N-dimethylformamide and 5 ml of pyridine. The reaction mixture is stirred at ambient temperature for 16 hours and then 30 ml of water are added and the mixture is extracted with ethyl acetate. The organic phase is washed successively with water and a saturated sodium chloride solution, dried over magnesium sulfate, filtered, and concentrated under reduced pressure. The residue is purified by trituration from a mixture of ethyl acetate and diisopropyl ether, so as to give 260 mg of 2-[2-(4-fluoro-3,3-dimethyl-2,3-dihydro-1H-indol-1-yl)-2-oxoethyl]-3-methyl-6-(morpholin-4-yl)pyrimidin-4(3H)-one, the characteristics of which are the following:

$^1$H NMR spectrum (400 MHz): 1.42 (s, 6H); 3.30 (partially masked m, 3H); 3.38 (m, 4H); 3.57 (m, 4H); 3.98 (s, 2H); 4.11 (s, 2H); 5.37 (s, 1H); 6.86 (t, J=8.2 Hz, 1H); 7.23 (dt, J=5.7 and 8.2 Hz, 1H); 7.87 (d, J=8.2 Hz, 1H)

Mass spectrometry: method A
Retention time Tr (min)=0.88;
[M+H]+: m/z 401; [M−H]−: m/z 399

Example 8c

Synthesis of 2-[2-(4-fluoro-3,3-dimethyl-2,3-dihydro-1H-indol-1-yl)-2-oxoethyl]-6-(morpholin-4-yl)pyrimidin-4(3H)-one

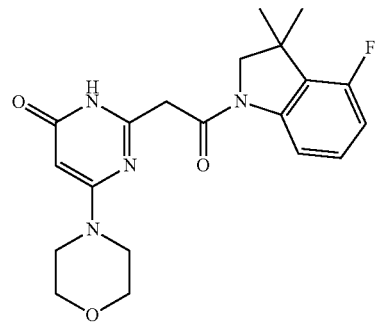 [SMILES: CC1(C)CN(C(=O)Cc2nc(N3CCOCC3)cc(=O)[nH]2)c2cccc(F)c21]

150 mg of 4-fluoro-3,3-dimethyl-2,3-dihydro-1H-indole [reference example 2c] and 279 mg of N-[3-(dimethylamino)propyl]-N'-ethylcarbodiimide hydrochloride are added to a solution of 261 mg of sodium [1-methyl-4-(morpholin-4-yl)-6-oxo-1,6-dihydropyrimidin-2-yl]acetate (obtained in step 2c of example 1c) in 5 ml of N,N-dimethylformamide and 5 ml of pyridine. The reaction mixture is stirred at ambient temperature for 16 hours and then 30 ml of water are added and the mixture is extracted with ethyl acetate. The organic phase is washed successively with water and a saturated sodium chloride solution, dried over magnesium sulfate, filtered, and concentrated under reduced pressure. The residue is purified by trituration from a mixture of ethyl acetate and diisopropyl ether, so as to give 194 mg of 2-[2-(4-fluoro-3,3-dimethyl-2,3-dihydro-1H-indol-1-yl)-2-oxoethyl]-6-(morpholin-4-yl)pyrimidin-4(3H)-one, the characteristics of which are the following:

$^1$H NMR spectrum (400 MHz): 1.42 (s, 6H); 3.42 (m, 4H); 3.60 (m, 4H); 3.76 (s, 2H); 3.96 (s, 2H); 5.21 (s, 1H); 6.85 (t, J=8.3 Hz, 1H); 7.23 (dt, J=5.7 and 8.3 Hz, 1H); 7.86 (d, J=8.3 Hz, 1H); 11.62 (broad s, 1H)

Mass spectrometry: method A
Retention time Tr (min)=0.83;
[M+H]+: m/z 387; [M−H]−: m/z 385

Example 9c and Example 10c

Separation of (+)-2-{2-[4-hydroxy-2-methyl-2,3-dihydro-1H-indol-1-yl]-2-oxoethyl}-6-(morpholin-4-yl)pyrimidin-4(3H)-one and of (−)-2-{2-[4-hydroxy-2-methyl-2,3-dihydro-1H-indol-1-yl]-2-oxoethyl}-6-(morpholin-4-yl)pyrimidin-4(3H)-one

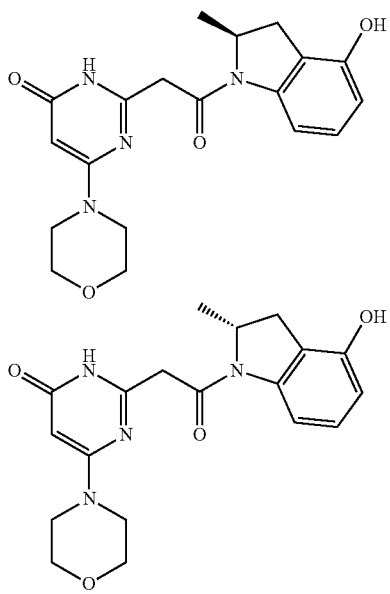

The products were obtained by chiral chromatographic separation of 0.73 g of 2-[2-(4-hydroxy-2-methyl-2,3-dihydro-1H-indol-1-yl)-2-oxoethyl]-6-(morpholin-4-yl)pyrimidin-4(3H)-one (example 4c) on a Whelk 01 SS column (1200 g, 10 µm, 8/35 cm), eluent: heptane/dichloromethane/ethanol/methanol: 65/25/5/5; flow rate: 200 ml/min. After purification, 337 mg of (+)-2-[2-(4-hydroxy-2-methyl-2,3-dihydro-1H-indol-1-yl)-2-oxoethyl]-6-(morpholin-4-yl)pyrimidin-4(3H)-one are obtained, as first enantiomer, in the form of an off-white solid, the characteristics of which are the following:

$^1$H NMR spectrum (400 MHz): 1.25 (d, J=6.4 Hz, 3H); 2.60 (d, J=16.1 Hz, 1H); 3.16 (dd, J=8.3 and 16.1 Hz, 1H); 3.41 (m, 4H); 3.60 (m, 4H); 3.69 (d, J=15.9 Hz, 1H); 3.89 (d, J=15.9 Hz, 1H); 4.69 (m, 1H); 5.21 (s, 1H); 6.52 (d, J=8.1 Hz, 1H); 6.99 (t, J=8.1 Hz, 1H); 7.44 (d, J=8.1 Hz, 1H); 9.51 (s, 1H); 11.71 (broad m, 1H)

Mass spectrometry: method A
Retention time Tr (min)=0.52;
[M+H]+: m/z 371; [M−H]−: m/z 369
Optical rotation: $\alpha_D$=+103.6°+/−1.8 (c=0.32% in DMSO)

Then the second enantiomer is obtained, i.e.: 335 mg of (−)-2-[2-(4-hydroxy-2-methyl-2,3-dihydro-1H-indol-1-yl)-2-oxoethyl]-6-(morpholin-4-yl)pyrimidin-4(3H)-one in the form of an off-white solid, the characteristics of which are the following:

$^1$H NMR spectrum (400 MHz): 1.25 (d, J=6.4 Hz, 3H); 2.60 (d, J=16.3 Hz, 1H); 3.16 (dd, J=8.7 and 16.3 Hz, 1H); 3.40 (m, 4H); 3.60 (m, 4H); 3.69 (d, J=15.7 Hz, 1H); 3.89 (d, J=15.7 Hz, 1H); 4.69 (m, 1H); 5.21 (s, 1H); 6.52 (d, J=8.1 Hz, 1H); 6.99 (t, J=8.1 Hz, 1H); 7.44 (d, J=8.1 Hz, 1H); 9.50 (s, 1H); 11.71 (broad m, 1H)

Mass spectrometry: method A
Retention time Tr (min)=0.52;
[M+H]+: m/z 371; [M−H]−: m/z 369
Optical rotation: $\alpha_D$=−71.8°+/−1.4 (c=0.33% in DMSO)

Example 11c and Example 12c

Synthesis of (+)-2-{2-[4-hydroxy-3-methyl-2,3-dihydro-1H-indol-1-yl]-2-oxoethyl}-6-(morpholin-4-yl)pyrimidin-4(3H)-one and of (−)-2-{2-[4-hydroxy-3-methyl-2,3-dihydro-1H-indol-1-yl]-2-oxoethyl}-6-(morpholin-4-yl)pyrimidin-4(3H)-one

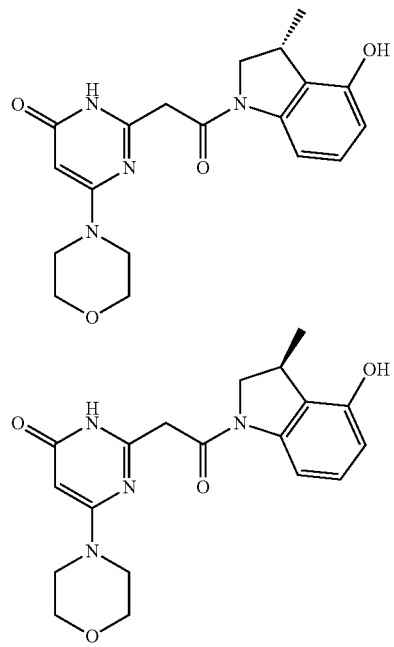

(±)-2-{2-[4-Hydroxy-3-methyl-2,3-dihydro-1H-indol-1-yl]-2-oxoethyl}-6-(morpholin-4-yl)pyrimidin-4(3H)-one is prepared by following the procedure described in example 1c using 0.70 g of sodium [4-(morpholin-4-yl)-6-oxo-1,6-dihydropyrimidin-2-yl]acetate, 0.44 g of 4-hydroxy-3-methylindoline (reference example 3c), and 0.68 g of N-[3-(dimethylamino)propyl]-N'-ethylcarbodiimide hydrochloride in a mixture of 0.65 ml of pyridine and 15 ml of N,N-dimethylformamide. 0.55 g of (±)-2-{2-[4-hydroxy-3-methyl-2,3-dihydro-1H-indol-1-yl]-2-oxoethyl}-6-(morpholin-4-yl)pyrimidin-4(3H)-one is thus obtained in the form of a bright pink powder, the characteristics of which are the following:

Mass spectrometry: method A
Retention time Tr (min)=0.55;
[M+H]+: m/z 371; [M−H]−: m/z 369

The products were obtained by chiral chromatographic separation of 530 mg of (±)-2-{2-[4-hydroxy-3-methyl-2,3-dihydro-1H-indol-1-yl]-2-oxoethyl}-6-(morpholin-4-yl)pyrimidin-4(3H)-one on a Chiralpak AS column (IK001) (1200 g, 20 µm, 8/35 cm), eluent: heptane/ethanol/methanol: 60/20/20; flow rate: 200 ml/min. After purification, 189 mg of (+)-2-{2-[4-hydroxy-3-methyl-2,3-dihydro-1H-indol-1-yl]-2-oxoethyl}-6-(morpholin-4-yl)pyrimidin-4(3H)-one are obtained, as first enantiomer, in the form of a pinkish solid, the characteristics of which are the following:

$^1$H NMR spectrum (400 MHz): 1.25 (d, J=6.8 Hz, 3H); 3.41 (m, 4H); 3.46 (m, 1H); 3.60 (m, 4H); 3.67 (d, J=15.9 Hz, 1H); 3.72 (dd, J=4.3 and 10.3 Hz, 1H); 3.77 (d, J=15.9 Hz, 1H); 4.22 (t, J=10.3 Hz, 1H); 5.20 (s, 1H); 6.50 (d, J=8.3 Hz, 1H); 6.97 (t, J=8.3 Hz, 1H); 7.50 (d, J=8.3 Hz, 1H); 9.45 (broad s, 1H); 11.58 (broad m, 1H)

Mass spectrometry: method A
Retention time Tr (min)=0.54;
[M+H]+: m/z 371; [M−H]−: m/z 369

Optical rotation: $\alpha_D$=+11°+/−0.7 (c=0.34 mg in 0.5 ml of methanol)

Then the second enantiomer is obtained, i.e.: 183 mg of (−)-2-{2-[4-hydroxy-3-methyl-2,3-dihydro-1H-indol-1-yl]-2-oxoethyl}-6-(morpholin-4-yl)pyrimidin-4(3H)-one in the form of a pink solid, the characteristics of which are the following:

$^1$H NMR spectrum (400 MHz): 1.25 (d, J=6.8 Hz, 3H); 3.42 (m, 4H); 3.47 (m, 1H); 3.60 (m, 4H); 3.67 (d, J=15.9 Hz, 1H); 3.72 (dd, J=4.2 and 10.3 Hz, 1H); 3.77 (d, J=15.9 Hz, 1H); 4.22 (t, J=10.3 Hz, 1H); 5.20 (s, 1H); 6.50 (d, J=8.3 Hz, 1H); 6.97 (t, J=8.3 Hz, 1H); 7.50 (d, J=8.3 Hz, 1H); 9.46 (broad s, 1H); 11.58 (broad m, 1H)

Mass spectrometry: method A
Retention time Tr (min)=0.54;
[M+H]+: m/z 371; [M−H]−: m/z 369
Optical rotation: $\alpha_D$=−2.6°+/−0.5 (c=0.38 mg in 0.5 ml of methanol)

Example 13c and Example 14c

Synthesis of (+)-2-{2-[5-fluoro-2-methyl-2,3-dihydro-1H-indol-1-yl]-2-oxoethyl}-6-(morpholin-4-yl)pyrimidin-4(3H)-one and of (−)-2-{2-[5-fluoro-2-methyl-2,3-dihydro-1H-indol-1-yl]-2-oxoethyl}-6-(morpholin-4-yl)pyrimidin-4(3H)-one

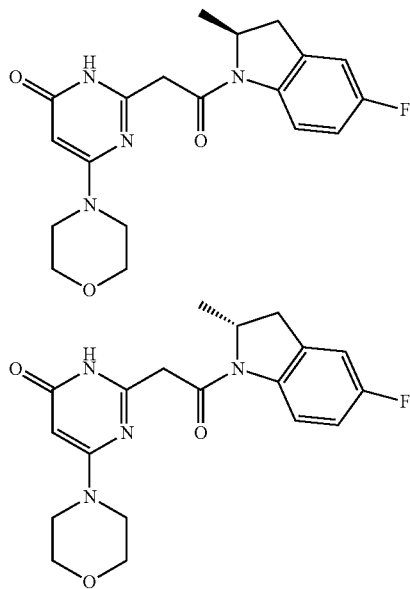

430 mg of 5-fluoro-2-methyl-2,3-dihydro-1H-indole (reference example 4c, step 1c) and 872 mg of N-[3-(dimethylamino)propyl]-N'-ethylcarbodiimide hydrochloride are added to a solution of 743 mg of sodium [4-(morpholin-4-yl)-6-oxo-1,6-dihydropyrimidin-2-yl]acetate (obtained in step 2c of example 1c) in 25 ml of N,N-dimethylformamide and 25 ml of pyridine. The reaction mixture is stirred at ambient temperature for 48 hours and then 100 ml of water are added and the mixture is extracted with ethyl acetate. The organic phase is washed successively with a 0.1N hydrochloric acid solution, water and a saturated sodium chloride solution, dried over magnesium sulfate, filtered, and concentrated under reduced pressure. The residue is purified by silica column chromatography, elution being carried out with a mixture of dichloromethane and methanol (95/05: v/v), so as to give 580 mg of 2-{2-[5-fluoro-2-methyl-2,3-dihydro-1H-indol-1-yl]-2-oxoethyl}-6-(morpholin-4-yl)pyrimidin-4(3H)-one.

The enantiomers are separated by chiral chromatography on a Whelk 01 SS, 10 µm column (10 µm, 80×350 mm), elution being carried out with a mixture of: heptane/dichloromethane/ethanol/methanol: 70/20/5/5; flow rate: 200 ml/min.

252 mg of (+)-2-{2-[5-fluoro-2-methyl-2,3-dihydro-1H-indol-1-yl]-2-oxoethyl}-6-(morpholin-4-yl)pyrimidin-4(3H)-one are obtained, as first enantiomer, in the form of a white solid, the characteristics of which are the following:

$^1$H NMR spectrum (400 MHz): 1.26 (d, J=6.4 Hz, 3H); 2.70 (m, 1H); 3.34 to 3.48 (m, 5H); 3.60 (m, 4H); 3.71 (d, J=15.9 Hz, 1H); 3.91 (d, J=15.9 Hz, 1H); 4.73 (m, 1H); 5.20 (s, 1H); 7.00 (dt, J=3.0 and 9.1 Hz, 1H); 7.15 (dd, J=3.0 and 9.1 Hz, 1H); 7.95 (dd, J=5.0 and 9.1 Hz, 1H); 11.65 (broad m, 1H)

Mass spectrometry: method A
Retention time Tr (min)=0.72;
[M+H]+: m/z 373; [M−H]−: m/z 371;
Optical rotation: $\alpha_D$=+60.4° (c=1.939 mg/0.5 ml CH$_3$OH)

Then the second enantiomer, 246 mg of (−)-2-{2-[5-fluoro-2-methyl-2,3-dihydro-1H-indol-1-yl]-2-oxoethyl}-6-(morpholin-4-yl)pyrimidin-4(3H)-one, is obtained in the form of a white solid, the characteristics of which are the following:

$^1$H NMR spectrum (400 MHz): 1.26 (d, J=6.5 Hz, 3H); 2.69 (m, 1H); 3.35 to 3.47 (m, 5H); 3.60 (m, 4H); 3.71 (d, J=15.9 Hz, 1H); 3.91 (d, J=15.9 Hz, 1H); 4.72 (m, 1H); 5.20 (s, 1H); 7.00 (td, J=3.0 and 9.1 Hz, 1H); 7.15 (dd, J=3.0 and 9.1 Hz, 1H); 7.95 (dd, J=5.0 and 9.1 Hz, 1H); 11.66 (broad m, 1H)

Mass spectrometry: method A
Retention time Tr (min)=0.72;
[M+H]+: m/z 373; [M−H]−: m/z 371;
Optical rotation: $\alpha_D$=−57.9°+/−1.1 (c=1.833 mg/0.5 ml CH$_3$OH)

Example 15c and Example 16c

Synthesis of (+)-2-{2-[5-fluoro-2-methyl-2,3-dihydro-1H-indol-1-yl]-2-oxoethyl}-3-methyl-6-(morpholin-4-yl)pyrimidin-4(3H)-one and of (−)-2-{2-[5-fluoro-2-methyl-2,3-dihydro-1H-indol-1-yl]-2-oxoethyl}-3-methyl-6-(morpholin-4-yl)pyrimidin-4(3H)-one

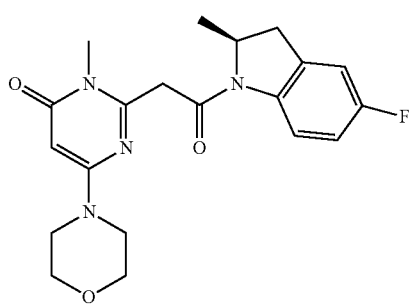

-continued

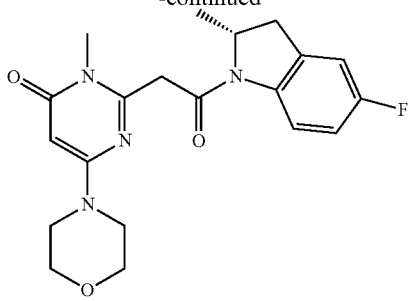

430 mg of 5-fluoro-2-methyl-2,3-dihydro-1H-indole (reference example 4c) and 872 mg of N-[3-(dimethylamino)propyl]-N'-ethylcarbodiimide hydrochloride are added to a solution of 1.1 g of sodium [1-methyl-4-(morpholin-4-yl)-6-oxo-1,6-dihydropyrimidin-2-yl]acetate in 25 ml of N,N-dimethylformamide and 25 ml of pyridine. The reaction mixture is stirred at ambient temperature for 48 hours and then 100 ml of water are added and the mixture is extracted with ethyl acetate. The organic phase is washed successively with a 0.1N hydrochloric acid solution, water and a saturated sodium chloride solution, dried over magnesium sulfate, filtered, and concentrated under reduced pressure. The residue is purified by silica column chromatography, elution being carried out with a mixture of dichloromethane and methanol (95/05: v/v), so as to give 538 mg of 2-{2-[(5-fluoro-2-methyl-2,3-dihydro-1H-indol-1-yl]-2-oxoethyl}-3-methyl-6-(morpholin-4-yl)pyrimidin-4(3H)-one.

The enantiomers are separated by chiral chromatography on a Whelk 01 SS, 10 μm column (10 μm, 80×350 mm), elution being carried out with a mixture of: heptane/dichloromethane/ethanol/methanol: 60/20/10/10; flow rate: 240 ml/min.

212 mg of (+)-2-{2-[(5-fluoro-2-methyl-2,3-dihydro-1H-indol-1-yl]-2-oxoethyl}-3-methyl-6-(morpholin-4-yl)pyrimidin-4(3H)-one are obtained, as first enantiomer, in the form of a white solid, the characteristics of which are the following:

$^1$H NMR spectrum (400 MHz): 1.28 (d, J=6.6 Hz, 3H); 2.70 (d, J=16.2 Hz, 1H); 3.33 (s, 3H); 3.36 to 3.44 (m, 5H); 3.58 (m, 4H); 4.02 (d, J=16.6 Hz, 1H); 4.27 (d, J=16.6 Hz, 1H); 4.73 (m, 1H); 5.36 (s, 1H); 7.00 (td, J=2.9 and 8.9 Hz, 1H); 7.16 (dd, J=2.9 and 8.9 Hz, 1H); 7.94 (dd, J=5.0 and 8.9 Hz, 1H)

Mass spectrometry: method A
Retention time Tr (min)=0.76;
[M+H]+: m/z 387; [M−H]−: m/z 385;
Optical rotation: $\alpha_D$=+72.0° (c=1.704 mg/0.5 ml CH$_3$OH)

Then the second enantiomer (Tr=17.61 min), 210 mg of (−)-2-{2-[(5-fluoro-2-methyl-2,3-dihydro-1H-indol-1-yl]-2-oxoethyl}-3-methyl-6-(morpholin-4-yl)pyrimidin-4(3H)-one, is obtained in the form of a white solid, the characteristics of which are the following:

$^1$H NMR spectrum (400 MHz): 1.28 (d, J=6.4 Hz, 3H); 2.70 (d, J=16.2 Hz, 1H); 3.33 (s, 3H); 3.37 to 3.44 (m, 5H); 3.59 (m, 4H); 4.02 (d, J=16.6 Hz, 1H); 4.27 (d, J=16.6 Hz, 1H); 4.72 (m, 1H); 5.36 (s, 1H); 7.00 (td, J=3.0 and 8.8 Hz, 1H); 7.16 (dd, J=3.0 and 8.8 Hz, 1H); 7.93 (dd, J=5.1 and 8.8 Hz, 1H)

Mass spectrometry: method A
Retention time Tr (min)=0.76;
[M+H]+: m/z 387; [M−H]−: m/z 385;
Optical rotation: $\alpha_D$=−59.5° (c=2.182 mg/0.5 ml CH$_3$OH)

Example 17c and Example 18c

Synthesis of (+)-2-{2-[4,5-difluoro-2-methyl-2,3-dihydro-1H-indol-1-yl]-2-oxoethyl}-6-(morpholin-4-yl)pyrimidin-4(3H)-one and of (−)-2-{2-[4,5-difluoro-2-methyl-2,3-dihydro-1H-indol-1-yl]-2-oxoethyl}-6-(morpholin-4-yl)pyrimidin-4(3H)-one

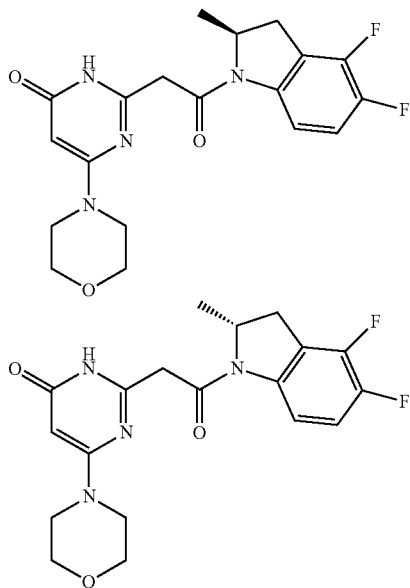

180 mg of 4,5-difluoro-2-methyl-2,3-dihydro-1H-indole (reference example 5c) and 326 mg of N-[3-(dimethylamino)propyl]-N'-ethylcarbodiimide hydrochloride are added to a solution of 278 mg of sodium [4-(morpholin-4-yl)-6-oxo-1,6-dihydropyrimidin-2-yl]acetate (obtained in step 2c of example 1c) in 10 ml of N,N-dimethylformamide and 10 ml of pyridine. The reaction mixture is stirred at ambient temperature for 16 hours and then 50 ml of water are added and the mixture is extracted with ethyl acetate. The organic phase is washed successively with a 0.1N hydrochloric acid solution, water and a saturated sodium chloride solution, dried over magnesium sulfate, filtered, and concentrated under reduced pressure. The residue is purified by silica column chromatography, elution being carried out with a mixture of dichloromethane and methanol (95/05: v/v), so as to give 230 mg of 2-{2-[4,5-difluoro-2-methyl-2,3-dihydro-1H-indol-1-yl]-2-oxoethyl}-6-(morpholin-4-yl)pyrimidin-4(3H)-one.

The enantiomers are separated by chiral chromatography on a Whelk 01 SS, 10 μm column (10 μm, 75×350 mm), elution being carried out with a mixture of: heptane/dichloromethane/ethanol/methanol: 70/20/5/5; flow rate: 220 ml/min.

100 mg of (+)-2-{2-[4,5-difluoro-2-methyl-2,3-dihydro-1H-indol-1-yl]-2-oxoethyl}-6-(morpholin-4-yl)pyrimidin-4(3H)-one are obtained, as first enantiomer, in the form of a white solid, the characteristics of which are the following:

$^1$H NMR spectrum (400 MHz): 1.30 (d, J=6.1 Hz, 3H); 2.82 (d, J=16.1 Hz, 1H); 3.36 to 3.46 (m, 5H); 3.60 (m, 4H); 3.73 (d, J=16.1 Hz, 1H); 3.92 (d, J=16.1 Hz, 1H); 4.81 (m, 1H); 5.21 (s, 1H); 7.25 (td, J=8.6 and 11.2 Hz, 1H); 7.74 (d, J=8.6 Hz, 1H); 11.71 (broad s, 1H)

Mass spectrometry: method A
Retention time Tr (min)=0.77;

[M+H]+: m/z 391; [M−H]−: m/z 389;
Optical rotation: 1α_D=+81° (c=2.066 mg/1 ml DMSO)
Then the second enantiomer, 101 mg of (−)-2-{2-[4,5-difluoro-2-methyl-2,3-dihydro-1H-indol-1-yl]-2-oxoethyl}-6-(morpholin-4-yl)pyrimidin-4(3H)-one, is obtained in the form of a white solid, the characteristics of which are the following:
$^1$H NMR spectrum (400 MHz): 1.30 (d, J=6.4 Hz, 3H); 2.82 (d, J=16.9 Hz, 1H); 3.37 to 3.47 (m, 5H); 3.57 to 3.63 (m, 4H); 3.73 (d, J=15.7 Hz, 1H); 3.92 (d, J=15.7 Hz, 1H); 4.81 (m, 1H); 5.21 (s, 1H); 7.26 (td, J=8.6 and 11.2 Hz, 1H); 7.74 (dd, J=3.6 and 8.6 Hz, 1H); 11.71 (broad s, 1H)
Mass spectrometry: method A
Retention time Tr (min)=0.77;
[M+H]+: m/z 391; [M−H]−: m/z 389;
Optical rotation: α_D=−80° (c=2.438 mg/1 ml DMSO)

Example 19c and Example 20c

Synthesis of (+)-2-{2-[4,5-difluoro-2-methyl-2,3-dihydro-1H-indol-1-yl]-2-oxoethyl}-3-methyl-6-(morpholin-4-yl)pyrimidin-4(3H)-one and of (−)-2-{2-[4,5-difluoro-2-methyl-2,3-dihydro-1H-indol-1-yl]-2-oxoethyl}-3-methyl-6-(morpholin-4-yl)pyrimidin-4(3H)-one

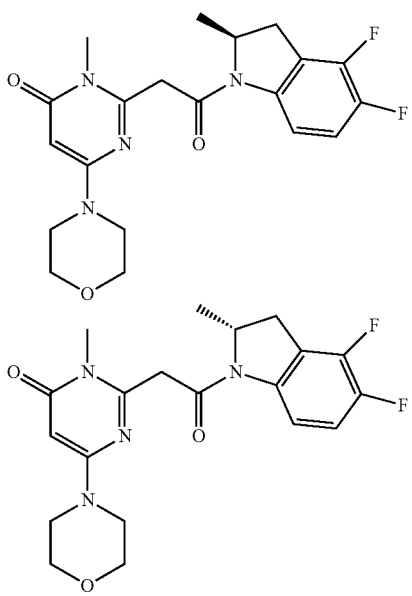

180 mg of 4,5-difluoro-2-methyl-2,3-dihydro-1H-indole [reference example 5c] and 326 mg of N-[3-(dimethylamino)propyl]-N'-ethylcarbodiimide hydrochloride are added to a solution of 278 mg of sodium [1-methyl-4-(morpholin-4-yl)-6-oxo-1,6-dihydropyrimidin-2-yl]acetate (obtained in step 2c of example 9c) in 10 ml of N,N-dimethylformamide and 10 ml of pyridine. The reaction mixture is stirred at ambient temperature for 16 hours and then 50 ml of water are added and the mixture is extracted with ethyl acetate. The organic phase is washed successively with a 0.1N hydrochloric acid solution, water and a saturated sodium chloride solution, dried over magnesium sulfate, filtered, and concentrated under reduced pressure. The residue is purified by silica column chromatography, elution being carried out with a mixture of dichloromethane and methanol (95/05: v/v), so as to give 230 mg of 2-{2-[4,5-difluoro-2-methyl-2,3-dihydro-1H-indol-1-yl]-2-oxoethyl}-3-methyl-6-(morpholin-4-yl)pyrimidin-4(3H)-one.

The enantiomers are separated by chiral chromatography on a Whelk 01 SS, 10 μm column (10 μm, 75×350 mm), elution being carried out with a mixture of: heptane/dichloromethane/ethanol/methanol: 70/20/5/5; flow rate: 220 ml/min.

100 mg of (+)-2-{2-[4,5-difluoro-2-methyl-2,3-dihydro-1H-indol-1-yl]-2-oxoethyl}-3-methyl-6-(morpholin-4-yl)pyrimidin-4(3H)-one are obtained, as first enantiomer, in the form of a white solid, the characteristics of which are the following:
$^1$H NMR spectrum (400 MHz): 1.30 (d, J=6.1 Hz, 3H); 2.82 (d, J=16.1 Hz, 1H); 3.36 to 3.46 (m, 5H); 3.60 (m, 4H); 3.73 (d, J=16.1 Hz, 1H); 3.92 (d, J=16.1 Hz, 1H); 4.81 (m, 1H); 5.21 (s, 1H); 7.25 (td, J=8.6 and 11.2 Hz, 1H); 7.74 (d, J=8.6 Hz, 1H); 11.71 (broad s, 1H)
Mass spectrometry: method A
Retention time Tr (min)=0.77;
[M+H]+: m/z 391; [M−H]−: m/z 389;
Optical rotation: α_D=+81° (c=2.066 mg/1 ml of DMSO)
Then the second enantiomer, 101 mg of (−)-2-{2-[4,5-difluoro-2-methyl-2,3-dihydro-1H-indol-1-yl]-2-oxoethyl}-3-methyl-6-(morpholin-4-yl)pyrimidin-4(3H)-one, is obtained in the form of a white solid, the characteristics of which are the following:
$^1$H NMR spectrum (400 MHz): 1.30 (d, J=6.4 Hz, 3H); 2.82 (d, J=16.9 Hz, 1H); 3.37 to 3.47 (m, 5H); 3.57 to 3.63 (m, 4H); 3.73 (d, J=15.7 Hz, 1H); 3.92 (d, J=15.7 Hz, 1H); 4.81 (m, 1H); 5.21 (s, 1H); 7.26 (td, J=8.6 and 11.2 Hz, 1H); 7.74 (dd, J=3.6 and 8.6 Hz, 1H); 11.71 (broad s, 1H)
Mass spectrometry: method A
Retention time Tr (min)=0.77;
[M+H]+: m/z 391; [M−H]−: m/z 389;
Optical rotation: α_D=−80° (c=2.438 mg/1 ml DMSO)

Example 21c

Synthesis of 2-{2-[(+)-5,6-difluoro-2-methyl-2,3-dihydro-1H-indol-1-yl]-2-oxoethyl}-6-(morpholin-4-yl)pyrimidin-4(3H)-one

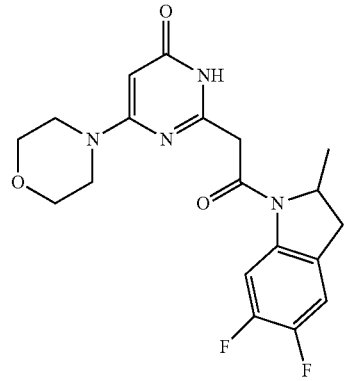 [SMILES: CC1Cc2cc(F)c(F)cc2N1C(=O)Cc1nc(N2CCOCC2)cc(=O)[nH]1]

150 mg of (−)-2-methyl-5,6-fluoro-2,3-dihydro-1H-indole [reference example 6c, step 6c] and 272 mg of N-[3-(dimethylamino)propyl]-N'-ethylcarbodiimide hydrochloride are added to a solution of 231 mg of sodium (4-morpholin-4-yl-6-oxo-1,6-dihydropyrimidin-2-yl)acetate (obtained in step 2c of example 1c) in 8 ml of DMF and 8 ml of pyridine.

The reaction mixture is stirred at ambient temperature for 18 hours.

50 ml of ethyl acetate and 20 ml of water are added. Hydrochloric acid is added until the pH=5-6. After settling out, the organic phase is dried over magnesium sulfate, filtered, and then concentrated under reduced pressure. The residue obtained is purified on a silica column, eluent: 98/02 then 95/05 dichloromethane/methanol, so as to give 170 mg of 2-[2-((+)-5,6-difluoro-2-methyl-2,3-dihydroindol-1-yl)-2-oxoethyl]-6-morpholin-4-yl-3H-pyrimidin-4-one, the characteristics of which are the following:

$^1$H NMR spectrum (400 MHz): 1.27 (d, J=6.4 Hz, 3H); 2.68 (d, J=17.1 Hz, 1H); 3.36 (partially masked m, 1H); 3.40 (m, 4H); 3.60 (m, 4H); 3.73 (d, J=16.1 Hz, 1H); 3.92 (d, J=16.1 Hz, 1H); 4.76 (m, 1H); 5.21 (s, 1H); 7.39 (dd, J=8.7 and 9.8 Hz, 1H); 7.90 (dd, J=7.5 and 12.1 Hz, 1H); 11.70 (broad m, 1H)

Mass spectrometry: method A

Retention time Tr (min)=0.76;

[M+H]+: m/z 391; [M−H]−: m/z 389

Optical rotation: $\alpha_D$=+62.8+/−1.3 (C=1.771 mg/0.5 ml DMSO)

Example 22c

Synthesis of 2-{(2-[(−)-5,6-difluoro-2-methyl-2,3-dihydro-1H-indol-1-yl]-2-oxoethyl}-6-(morpholin-4-yl)pyrimidin-4(3H)-one

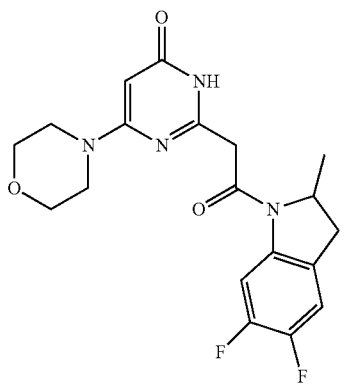 [SMILES: CC1Cc2cc(F)c(F)cc2N1C(=O)Cc1nc(N2CCOCC2)cc(=O)[nH]1]

The product is prepared by following the procedure described in example 21c using 231 mg of sodium (4-morpholin-4-yl-6-oxo-1,6-dihydropyrimidin-2-yl)acetate (obtained in step 2c of example 1c) and 160 mg of (+)-2-methyl-5,6-fluoro-2,3-dihydro-1H-indole (reference example 6c, step 6c]. After silica column purification: eluent 98/02 then 95/05 dichloromethane/methanol, 247 mg of 2-[2-((−)-5,6-difluoro-2-methyl-2,3-dihydroindol-1-yl)-2-oxoethyl]-6-morpholin-4-yl-3H-pyrimidin-4-one are obtained in the form of a solid, the characteristics of which are the following:

$^1$H NMR spectrum (400 MHz): 127 (d, J=6.4 Hz, 3H); 2.68 (d, J=17.1 Hz, 1H); 3.35 (partially masked m, 1H); 3.41 (m, 4H); 3.61 (m, 4H); 3.73 (d, J=16.1 Hz, 1H); 3.92 (d, J=16.1 Hz, 1H); 4.77 (m, 1H); 5.21 (s, 1H); 7.39 (dd, J=8.7 and 9.8 Hz, 1H); 7.90 (dd, J=7.5 and 12.1 Hz, 1H); 11.68 (broad m, 1H)

Mass spectrometry: method A

Retention time Tr (min)=0.76;

[M+H]+: m/z 391; [M−H]−: m/z 389

Optical rotation: $\alpha_D$=−49.1+/−0.9 (C=2.157 mg/0.5 ml DMSO)

Example 23c

Synthesis of 2-{2-[(−)-5,6-difluoro-2-methyl-2,3-dihydro-1H-indol-1-yl]-2-oxoethyl}-3-methyl-6-(morpholin-4-yl)pyrimidin-4(3H)-one

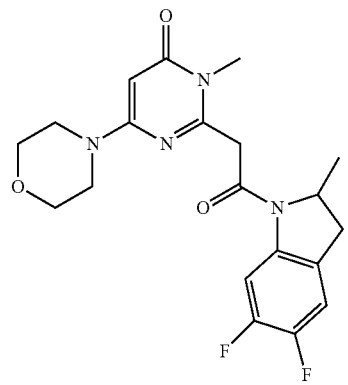 [SMILES: CC1Cc2cc(F)c(F)cc2N1C(=O)Cc1nc(N2CCOCC2)cc(=O)n1C]

The product is prepared by following the procedure described in example 21c using 304 mg of sodium (1-methyl-4-morpholin-4-yl-6-oxo-1,6-dihydropyrimidin-2-yl)acetate (obtained in step 2c of example 4c) and 159 mg of (+)-2-methyl-5,6-fluoro-2,3-dihydro-1H-indole [reference example 6c, step 6c]. After silica column purification: eluent 98/02 dichloromethane/methanol, 86 mg of 2-[2-((−)-5,6-difluoro-2-methyl-2,3-dihydroindol-1-yl)-2-oxoethyl]-3-methyl-6-morpholin-4-yl-3H-pyrimidin-4-one are obtained in the form of a solid, the characteristics of which are the following:

$^1$H NMR spectrum (400 MHz): 1.29 (d, J=6.4 Hz, 3H); 2.69 (d, J=16.3 Hz, 1H); 3.33 (s, 3H); 3.39 (m, 5H); 3.60 (m, 4H); 4.03 (d, J=16.9 Hz, 1H); 4.28 (d, J=16.9 Hz, 1H); 4.77 (m, 1H); 5.36 (s, 1H); 7.40 (dd, J=8.7 and 9.8 Hz, 1H); 7.89 (dd, J=7.6 and 12.0 Hz, 1H)

Retention time Tr (min)=0.81;

[M+H]+: m/z 405; [M−H]−: m/z 403

Optical rotation: $\alpha_D$=−47.6+/−0.9 (C=2.131 mg/0.5 ml DMSO)

Example 24c

Synthesis of 2-{2-[(+)-5,6-difluoro-2-methyl-2,3-dihydro-1H-indol-1-yl]-2-oxoethyl}-3-methyl-6-(morpholin-4-yl)pyrimidin-4(3H)-one

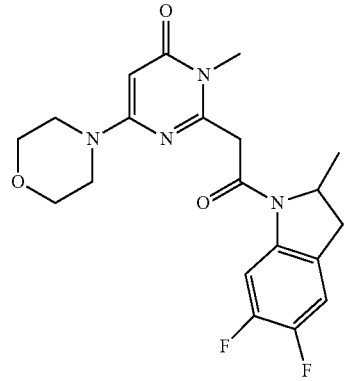 [SMILES: CC1Cc2cc(F)c(F)cc2N1C(=O)Cc1nc(N2CCOCC2)cc(=O)n1C]

The product is prepared by following the procedure described in example 21c using 315 mg of sodium (1-methyl-4-morpholin-4-yl-6-oxo-1,6-dihydropyrimidin-2-yl)acetate (obtained in step 2c of example 4c) and 164 mg of (−)-2- methyl-5,6-fluoro-2,3-dihydro-1H-indole (reference example 6c, step 6c]. After silica column purification: eluent 98/02 dichloromethane/methanol, 88 mg of 2-[2-((+)-5,6-difluoro-2-methyl-2,3-dihydroindol-1-yl)-2-oxoethyl]-3-methyl-6-morpholin-4-yl-3H-pyrimidin-4-one are obtained in the form of a solid, the characteristics of which are the following:

$^1$H NMR spectrum (400 MHz): 1.29 (d, J=6.6 Hz, 3H); 2.69 (d, J=16.3 Hz, 1H); 3.33 (s, 3H); 3.39 (m, 5H); 3.60 (m, 4H); 4.03 (d, J=16.9 Hz, 1H); 4.28 (d, J=16.9 Hz, 1H); 4.77 (m, 1H); 5.36 (s, 1H); 7.40 (dd, J=8.7 and 9.8 Hz, 1H); 7.89 (dd, J=7.5 and 12.1 Hz, 1H)

Retention time Tr (min)=0.81;
[M+H]+: m/z 405; [M–H]–: m/z 403
Optical rotation: $\alpha_D$=+25.9+/–0.8 (C=2.011 mg/0.5 ml DMSO)

Example 25c and Example 26c

Synthesis of (+)-2-{2-[4-bromo-2-methyl-2,3-dihydro-1H-indol-1-yl]-2-oxoethyl}-6-(morpholin-4-yl)pyrimidin-4(3H)-one and of (–)-2-{2-[4-bromo-2-methyl-2,3-dihydro-1H-indol-1-yl]-2-oxoethyl}-6-(morpholin-4-yl)pyrimidin-4(3H)-one

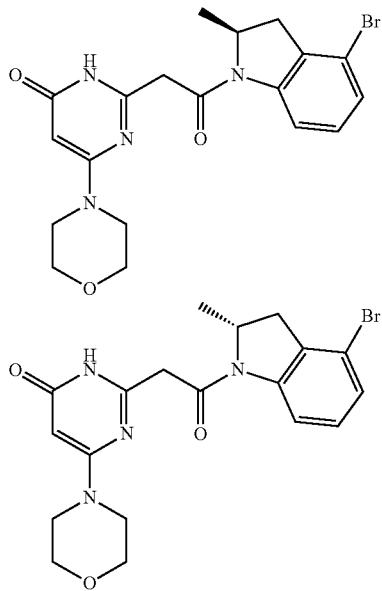

150 mg of 4-bromo-2-methyl-2,3-dihydro-1H-indole [reference example 7c] and 217 mg of N-[3-(dimethylamino)propyl]-N'-ethylcarbodiimide hydrochloride are added to a solution of 221 mg of sodium [4-(morpholin-4-yl)-6-oxo-1,6-dihydropyrimidin-2-yl]acetate (obtained in step 2c of example 1c) in 7 ml of N,N-dimethylformamide and 7 ml of pyridine. The reaction mixture is stirred at ambient temperature for 72 hours and then 50 ml of water are added and the mixture is extracted with ethyl acetate. The organic phase is washed successively with a 0.1N hydrochloric acid solution, water and a saturated sodium chloride solution, dried over magnesium sulfate, filtered, and concentrated under reduced pressure. The residue is purified by silica column chromatography, elution being carried out with a mixture of dichloromethane and methanol (95/05: v/v), so as to give 220 mg of 2-{2-[4-bromo-2-methyl-2,3-dihydro-1H-indol-1-yl]-2-oxoethyl}-6-(morpholin-4-yl)pyrimidin-4(3H)-one.

The enantiomers are separated by chiral chromatography on a Chiralpak T304 20 μm column (20 μm, 77×350 mm), elution being carried out with a mixture of: acetonitrile/isopropanol: 90/10; flow rate: 250 ml/min.

94 mg of (+)-2-{2-[4-bromo-2-methyl-2,3-dihydro-1H-indol-1-yl]-2-oxoethyl}-6-(morpholin-4-yl)pyrimidin-4(3H)-one are obtained, as first enantiomer, in the form of a white solid, the characteristics of which are the following:

$^1$H NMR spectrum (400 MHz): 1.30 (d, J=6.1 Hz, 3H); 2.68 (m, 1H); 3.27 to 3.45 (partially masked m, 5H); 3.61 (m, 4H); 3.74 (d, J=15.2 Hz, 1H); 3.93 (d, J=15.2 Hz, 1H); 4.77 (m, 1H); 5.20 (s, 1H); 7.16 (t, J=7.8 Hz, 1H); 7.27 (d, J=7.8 Hz, 1H); 7.96 (broad d, J=7.8 Hz, 1H); 11.68 (broad m, 1H)

Mass spectrometry: method A
Retention time Tr (min)=0.84;
[M+H]+: m/z 433; [M–H]–: m/z 431;
Optical rotation: $\alpha_D$=+93.9° (c=1.536 mg/0.5 ml DMSO)

Then the second enantiomer, 95.5 mg of (–)-2-{2-[4-bromo-2-methyl-2,3-dihydro-1H-indol-1-yl]-2-oxoethyl}-6-(morpholin-4-yl)pyrimidin-4(3H)-one, is obtained in the form of a white solid, the characteristics of which are the following:

$^1$H NMR spectrum (400 MHz): 1.30 (d, J=6.7 Hz, 3H); 2.68 (m, 1H); 3.25 to 3.45 (partially masked m, 5H); 3.60 (m, 4H); 3.74 (d, J=16.2 Hz, 1H); 3.93 (d, J=16.2 Hz, 1H); 4.75 (m, 1H); 5.20 (s, 1H); 7.16 (t, J=7.8 Hz, 1H); 7.26 (d, J=7.8 Hz, 1H); 7.96 (broad d, J=7.8 Hz, 1H); 11.67 (broad m, 1H)

Mass spectrometry: method A
Retention time Tr (min)=0.84;
[M+H]+: m/z 433; [M–H]–: m/z 431;
Optical rotation: $\alpha_D$=–98° (c=0.714 mg/0.5 ml DMSO)

Example 27c

Synthesis of (–)-2-{2-[4-fluoro-2-methyl-2,3-dihydro-1H-indol-1-yl]-2-oxoethyl}-6-(morpholin-4-yl)pyrimidin-4(3H)-one

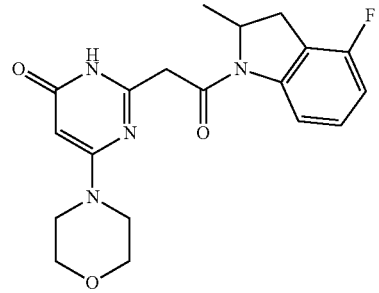 [SMILES: CC1Cc2c(F)cccc2N1C(=O)Cc1nc(N2CCOCC2)cc(=O)[nH]1]

The product is prepared by following the procedure described in example 1c using 0.2 g of sodium [4-(morpholin-4-yl)-6-oxo-1,6-dihydropyrimidin-2-yl]acetate, 127 mg of (+)-4-fluoro-2-methyl-2,3-dihydro-1H-indole [reference example 8c, step 6c] and 0.20 g of N-[3-(dimethylamino)propyl]-N'-ethylcarbodiimide hydrochloride in a mixture of 123 μl of pyridine and 3.5 ml of N,N-dimethylformamide. 0.15 g of (–)-2-{2-[4-fluoro-2-methyl-2,3-dihydro-1H-indol-1-yl]-2-oxoethyl}-6-(morpholin-4-yl)pyrimidin-4(3H)-one is thus obtained in the form of a white solid, the characteristics of which are the following:

$^1$H NMR spectrum (400 MHz): 1.29 (broad d, J=6.4 Hz, 3H); 2.75 (d, J=16.3 Hz, 1H); 3.19 to 3.35 (partially masked m, 1H); 3.41 (m, 4H); 3.60 (m, 4H); 3.74 (d, J=16.1 Hz, 1H); 3.93 (d, J=16.1 Hz, 1H); 4.79 (m, 1H); 5.21 (s, 1H); 6.90 (t, J=8.6 Hz, 1H); 7.24 (m, 1H); 7.79 (broad d, J=8.6 Hz, 1H); 11.66 (broad m, 1H)

Mass spectrometry: method A
Retention time Tr (min)=0.74;
[M+H]+: m/z 373; [M–H]–: m/z 371
Melting point (Kofler): above 260° C.
Optical rotation: $\alpha_D$=–73.2°+/–1.4 (c=1.834 mg in 0.5 ml of methanol)

Example 28c

Synthesis of (+)-2-{2-[4-fluoro-2-methyl-2,3-dihydro-1H-indol-1-yl]-2-oxoethyl}-6-(morpholin-4-yl)pyrimidin-4(3H)-one

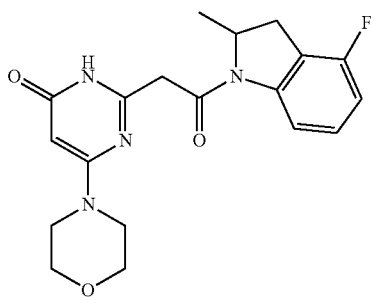 [SMILES: CC1Cc2c(F)cccc2N1C(=O)Cc1nc(N2CCOCC2)cc(=O)[nH]1]

The product is prepared by following the procedure described in example 1c using 0.22 g of sodium [4-(morpholin-4-yl)-6-oxo-1,6-dihydropyrimidin-2-yl]acetate, 116 mg of (−)-4-fluoro-2-methyl-2,3-dihydro-1H-indole [reference example 8c, step 6c] and 0.19 g of N-[3-(dimethylamino)propyl]-N'-ethylcarbodiimide hydrochloride in a mixture of 123 μl of pyridine and 3.5 ml of N,N-dimethylformamide. 0.15 g of (+)-2-{2-[4-fluoro-2-methyl-2,3-dihydro-1H-indol-1-yl]-2-oxoethyl}-6-(morpholin-4-yl)pyrimidin-4(3H)-one is thus obtained in the form of a white solid, the characteristics of which are the following:

$^1$H NMR spectrum (400 MHz): 1.29 (broad d, J=6.5 Hz, 3H); 2.76 (d, J=17.1 Hz, 1H); 3.20 to 3.37 (partially masked m, 1H); 3.41 (m, 4H); 3.60 (m, 4H); 3.74 (d, J=15.9 Hz, 1H); 3.93 (d, J=15.9 Hz, 1H); 4.80 (m, 1H); 5.21 (s, 1H); 6.90 (t, J=8.3 Hz, 1H); 7.24 (m, 1H); 7.79 (broad m, 1H); 11.67 (broad m, 1H)

Mass spectrometry: method B
Retention time Tr (min)=0.74;
[M+H]+: m/z 373; [M−H]−: m/z 371
Melting point (Kofler): above 260° C.
Optical rotation: $α_D$=+77.0°+/−1.2 (c=2.55 mg in 0.5 ml of methanol)

Example 29c

Synthesis of (−)-2-{2-[4-fluoro-2-methyl-2,3-dihydro-1H-indol-1-yl]-2-oxoethyl}-3-methyl-6-(morpholin-4-yl)pyrimidin-4(3H)-one

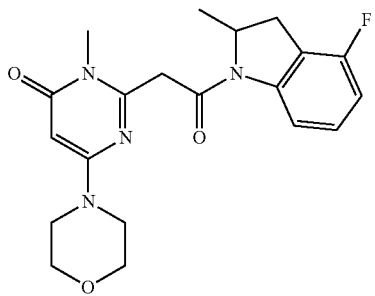 [SMILES: CC1Cc2c(F)cccc2N1C(=O)Cc1nc(N2CCOCC2)cc(=O)n1C]

0.19 g of N-[3-(dimethylamino)propyl]-N'-ethylcarbodiimide hydrochloride and 120 μl of pyridine are added to a solution of 0.22 g of sodium [1-methyl-4-(morpholin-4-yl)-6-oxo-1,6-dihydropyrimidin-2-yl]acetate (prepared in step 2c of example 4c) in 3 ml of N,N-dimethylformamide. The resulting suspension is stirred at ambient temperature for 15 minutes and then 0.11 g of (+)-4-fluoro-2-methyl-2,3-dihydro-1H-indole [reference example 8c, step 6c] is rapidly added. The reaction mixture is stirred at ambient temperature for 64 hours and is then treated with a mixture of 20 ml of water and 2 ml of ethyl acetate, and then stirred at ambient temperature for 2 hours. The precipitate formed is filtered off, and then rinsed successively with 3 ml of water and 3×6 ml of diethyl ether. The solid obtained is dried with suction, then dried under reduced pressure at 40° C. 82 mg of (−)-2-{2-[4-fluoro-2-methyl-2,3-dihydro-1H-indol-1-yl]-2-oxoethyl}-3-methyl-6-(morpholin-4-yl)pyrimidin-4(3H)-one are thus obtained in the form of a white solid, the characteristics of which are the following:

$^1$H NMR spectrum (400 MHz): 1.31 (d, J=6.1 Hz, 3H); 2.77 (d, J=15.4 Hz, 1H); 3.15 to 3.47 (partially masked m, 8H); 3.58 (m, 4H); 4.04 (d, J=18.3 Hz, 1H); 4.29 (d, J=18.3 Hz, 1H); 4.80 (m, 1H); 5.36 (s, 1H); 6.91 (t, J=8.8 Hz, 1H); 7.25 (m, 1H); 7.78 (d, J=8.8 Hz, 1H)

Mass spectrometry: method A
Retention time Tr (min)=0.78;
[M+H]+: m/z 387; [M−H]−: m/z 385
Melting point (Kofler): 244° C.
Optical rotation: $α_D$=−33.0° (c=0.64 mg in 0.5 ml of methanol)

Example 30c

Synthesis of (+)-2-{2-[4-fluoro-2-methyl-2,3-dihydro-1H-indol-1-yl]-2-oxoethyl}-3-methyl-6-(morpholin-4-yl)pyrimidin-4(3H)-one

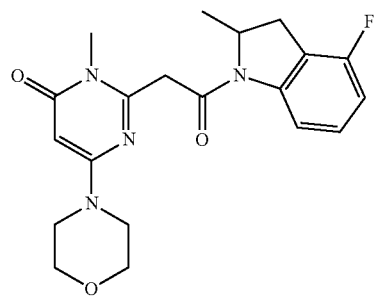 [SMILES: CC1Cc2c(F)cccc2N1C(=O)Cc1nc(N2CCOCC2)cc(=O)n1C]

The product is prepared by following the procedure described in example 29c using 0.22 g of sodium [1-methyl-4-(morpholin-4-yl)-6-oxo-1,6-dihydropyrimidin-2-yl]acetate (prepared in step 2c of example 4c), 0.11 g of (−)-4-fluoro-2-methyl-2,3-dihydro-1H-indole [reference example 8c, step 6c], and 0.19 g of N-[3-(dimethylamino)propyl]-N'-ethylcarbodiimide hydrochloride in a mixture of 120 μl of pyridine and 3.0 ml of N,N-dimethylformamide. 79 mg of (+)-2-{2-[4-fluoro-2-methyl-2,3-dihydro-1H-indol-1-yl]-2-oxoethyl}-6-(morpholin-4-yl)pyrimidin-4(3H)-one are thus obtained in the form of a white solid, the characteristics of which are the following:

$^1$H NMR spectrum (400 MHz): 1.31 (d, J=6.5 Hz, 3H); 2.77 (d, J=15.9 Hz, 1H); 3.18 to 3.41 (partially masked m, 8H); 3.59 (m, 4H); 4.04 (d, J=16.3 Hz, 1H); 4.29 (d, J=16.3 Hz, 1H); 4.79 (m, 1H); 5.36 (s, 1H); 6.91 (t, J=8.6 Hz, 1H); 7.24 (m, 1H); 7.78 (d, J=8.8 Hz, 1H)

Mass spectrometry: method A
Retention time Tr (min)=0.78;
[M+H]+: m/z 387; [M−H]−: m/z 385
Melting point (Kofler): 252° C.
Optical rotation: α_D=+90.0° (c=1.044 mg in 0.5 ml of methanol)

Example 31c and Example 32c

Synthesis of (+)-2-{2-[4-bromo-2-methyl-2,3-dihydro-1H-indol-1-yl]-2-oxoethyl}-3-methyl-6-(morpholin-4-yl)pyrimidin-4(3H)-one and of (−)-2-{2-[4-bromo-2-methyl-2,3-dihydro-1H-indol-1-yl]-2-oxoethyl}-3-methyl-6-(morpholin-4-yl)pyrimidin-4(3H)-one

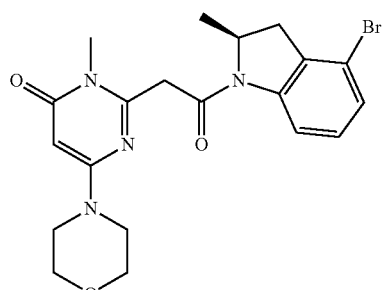

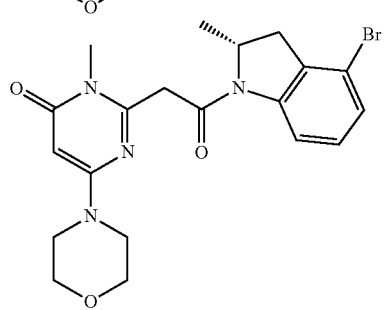

150 mg of 4-bromo-2-methyl-2,3-dihydro-1H-indole [reference example 7c] and 217 mg of N-[3-(dimethylamino)propyl]-N'-ethylcarbodiimide hydrochloride are added to a solution of 272 mg of sodium [1-methyl-4-(morpholin-4-yl)-6-oxo-1,6-dihydropyrimidin-2-yl]acetate (obtained in step 2c of example 4c) in 6.5 ml of N,N-dimethylformamide and 6.5 ml of pyridine. The reaction mixture is stirred at ambient temperature for 72 hours and then 50 ml of water are added and the mixture is extracted with ethyl acetate. The organic phase is washed successively with a 0.1N hydrochloric acid solution, water and a saturated sodium chloride solution, dried over magnesium sulfate, filtered, and concentrated under reduced pressure. The residue is purified by silica column chromatography, elution being carried out with a mixture of dichloromethane and methanol (95/05: v/v), so as to give 236 mg of 2-{2-[4-bromo-2-methyl-2,3-dihydro-1H-indol-1-yl]-2-oxoethyl}-3-methyl-6-(morpholin-4-yl)pyrimidin-4(3H)-one.

The enantiomers are separated by chiral chromatography on a Whelk 01 SS, 10 μm column (10 μm, 46×250 mm), elution being carried out with a mixture of: heptane/ethanol/methanol/TEA: 60/20/20/0.1; flow rate: 250 ml/min.

The first enantiomer, 60 mg of (+)-2-{2-[4-bromo-2-methyl-2,3-dihydro-1H-indol-1-yl]-2-oxoethyl}-3-methyl-6-(morpholin-4-yl)pyrimidin-4(3H)-one, is obtained in the form of a white solid, the characteristics of which are the following:

¹H NMR spectrum (400 MHz): 1.31 (d, J=6.4 Hz, 3H); 2.68 (m, 1H); 3.32 (s, 3H); 3.35 to 3.41 (m, 5H); 3.58 (m, 4H); 4.03 (d, J=16.8 Hz, 1H); 4.29 (d, J=16.8 Hz, 1H); 4.73 (m, 1H); 5.36 (s, 1H); 7.16 (t, J=7.8 Hz, 1H); 7.27 (d, J=7.8 Hz, 1H); 7.95 (broad d, J=7.8 Hz, 1H)
Mass spectrometry: method A
Retention time Tr (min)=0.89;
[M+H]+: m/z 447; [M−H]−: m/z 445;
Optical rotation: α_D=+116.2° (c=1.984 mg/0.5 ml of DMSO)

Then the second enantiomer, 61 mg of (−)-2-{2-[4-bromo-2-methyl-2,3-dihydro-1H-indol-1-yl]-2-oxoethyl}-3-methyl-6-(morpholin-4-yl)pyrimidin-4(3H)-one, is obtained in the form of a white solid, the characteristics of which are the following:

¹H NMR spectrum (400 MHz): 1.31 (d, J=6.6 Hz, 3H); 2.68 (d, J=15.9 Hz, 1H); 3.32 (s, 3H); 3.36 to 3.40 (m, 5H); 3.58 (m, 4H); 4.03 (d, J=16.9 Hz, 1H); 4.29 (d, J=16.9 Hz, 1H); 4.74 (m, 1H); 5.36 (s, 1H); 7.16 (t, J=8.1 Hz, 1H); 7.27 (d, J=8.1 Hz, 1H); 7.95 (broad d, J=8.1 Hz, 1H)
Mass spectrometry: method A
Retention time Tr (min)=0.89;
[M+H]+: m/z 447; [M−H]−: m/z 445;
Optical rotation: α_D=−91.2° (c=1.706 mg/0.5 ml DMSO)

Example 33c and Example 34c

Synthesis of (+)-2-{2-[4-chloro-2-methyl-2,3-dihydro-1H-indol-1-yl]-2-oxoethyl}-3-methyl-6-(morpholin-4-yl)pyrimidin-4(3H)-one and of (−)-2-{2-[4-chloro-2-methyl-2,3-dihydro-1H-indol-1-yl]-2-oxoethyl}-3-methyl-6-(morpholin-4-yl)pyrimidin-4(3H)-one Step 1c

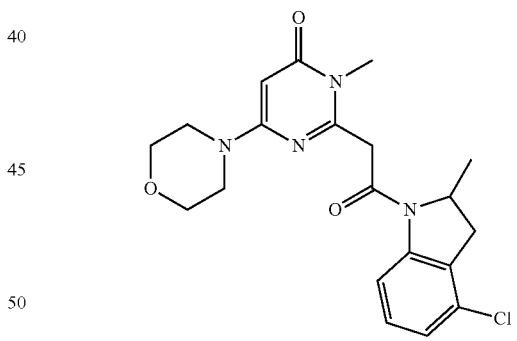

The product is prepared by following the procedure described in example 21c using 252 mg of sodium (1-methyl-4-morpholin-4-yl-6-oxo-1,6-dihydropyrimidin-2-yl)acetate (obtained in step 2c of example 4c) and 152 mg of 4-chloro-2-methyl-2,3-dihydro-1H-indoline [which can be prepared according to U.S. Pat. No. 4,416,884 (1983)]. After purification, 122 mg of 2-[2-(4-chloro-2-methyl-2,3-dihydroindol-1-yl)-2-oxoethyl]-3-methyl-6-morpholin-4-yl-3H-pyrimidin-4-one are obtained in the form of a solid which will be separated into its two enantiomers on a chiral column.

¹H NMR spectrum (400 MHz): 1.31 (d, J=6.4 Hz, 3H); 2.73 (d, J=16.3 Hz, 1H); 3.36 to 3.44 (m, 8H); 3.58 (m, 4H); 4.04 (d, J=16.9 Hz, 1H); 4.29 (d, J=16.9 Hz, 1H); 4.77 (m, 1H); 5.36 (s, 1H); 7.13 (d, J=8.4 Hz, 1H); 7.24 (t, J=8.4 Hz, 1H); 7.91 (d, J=8.4 Hz, 1H)

Step 2c

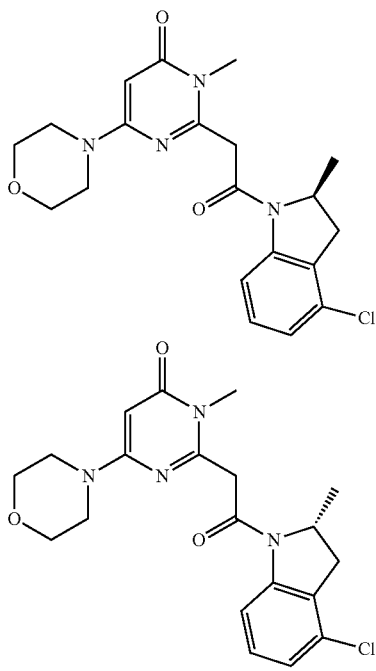

The separation of the two enantiomers of 2-[2-(4-chloro-2-methyl-2,3-dihydroindol-1-yl)-2-oxoethyl]-3-methyl-6-morpholin-4-yl-3H-pyrimidin-4-one (195 mg) was carried out by chiral chromatography:

Stationary phase: Whelk 01 SS, 5 μm phase; mobile phase: heptane (60%)/dichloromethane (20%)/methanol (20%); flow rate 42 ml/min.

The dextrorotatory enantiomer is concentrated so as to obtain 81 mg of 2-[2-((+)-4-chloro-2-methyl-2,3-dihydroindol-1-yl)-2-oxoethyl]-3-methyl-6-morpholin-4-yl-3H-pyrimidin-4-one in the form of a white solid, the characteristics of which are the following:

$^1$H NMR spectrum (400 MHz): 1.31 (d, J=6.4 Hz, 3H); 2.74 (d, J=16.3 Hz, 1H); 3.33 (s, 3H); 3.39 (m, 5H); 3.59 (m, 4H); 4.04 (d, J=16.9 Hz, 1H); 4.29 (d, J=16.9 Hz, 1H); 4.78 (m, 1H); 5.36 (s, 1H); 7.13 (d, J=7.9 Hz, 1H); 7.24 (t, J=7.9 Hz, 1H); 7.91 (broad d, J=7.9 Hz, 1H)

Mass spectrometry: method A
Retention time Tr (min)=0.87;
[M+H]+: m/z 403; [M−H]−: m/z 401
Optical rotation: $α_D$=+86.2+/−1.6 (C=1.504 mg/0.5 ml DMSO)

The levorotatory enantiomer is concentrated so as to obtain 81 mg of 2-[2-((−)-4-chloro-2-methyl-2,3-dihydroindol-1-yl)-2-oxoethyl]-3-methyl-6-morpholin-4-yl-3H-pyrimidin-4-one in the form of a white solid, the characteristics of which are the following:

$^1$H NMR spectrum (400 MHz): 1.31 (d, J=6.6 Hz, 3H); 2.73 (d, J=16.3 Hz, 1H); 3.33 (s, 3H); 3.38 (m, 5H); 3.57 (m, 4H); 4.04 (d, J=17.1 Hz, 1H); 4.29 (d, J=17.1 Hz, 1H); 4.78 (m, 1H); 5.36 (s, 1H); 7.13 (d, J=7.9 Hz, 1H); 7.24 (t, J=7.9 Hz, 1H); 7.91 (broad d, J=7.9 Hz, 1H)

Mass spectrometry: method A
Retention time Tr (min)=0.87;
[M+H]+: m/z 403; [M−H]−: m/z 401
Optical rotation: $α_D$=−79.3+/−1.5 (C=1.708 mg/0.5 ml DMSO)

Example 35c

Synthesis of 2-{2-[(+)-6-fluoro-2-methyl-2,3-dihydro-1H-indol-1-yl]-2-oxoethyl}-6-(morpholin-4-yl)pyrimidin-4(3H)-one

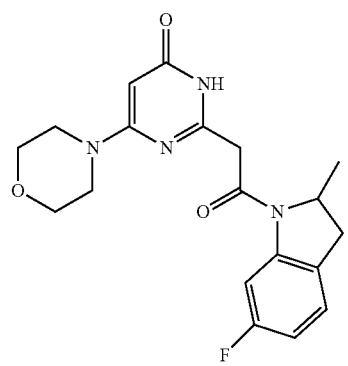 [SMILES: CC1Cc2ccc(F)cc2N1C(=O)Cc1nc(N2CCOCC2)cc(=O)[nH]1]

The product is prepared by following the procedure described in example 21c using 115 mg of sodium (4-morpholin-4-yl-6-oxo-1,6-dihydropyrimidin-2-yl)acetate (obtained in step 2c of example 1c) and 62 mg of (−)-2-methyl-6-fluoro-2,3-dihydro-1H-indole [reference example 9c, step 5c]. After silica column purification: eluent 98/02 then 95/05 dichloromethane/methanol, 113 mg of 2-[2-((+)-6-fluoro-2-methyl-2,3-dihydroindol-1-yl)-2-oxoethyl]-6-morpholin-4-yl-3H-pyrimidin-4-one are obtained in the form of a solid, the characteristics of which are the following:

$^1$H NMR spectrum (400 MHz): 1.27 (d, J=6.4 Hz, 3H); 2.67 (d, J=16.3 Hz, 1H); 3.33 (partially masked m, 1H); 3.41 (m, 4H); 3.60 (m, 4H); 3.74 (d, J=16.1 Hz, 1H); 3.94 (d, J=16.1 Hz, 1H); 4.76 (m, 1H); 5.21 (s, 1H); 6.86 (ddd, J=2.6 and 8.3 and 9.2 Hz, 1H); 7.29 (dd, J=5.7 and 8.3 Hz, 1H); 7.72 (broad d, J=11.0 Hz, 1H); 11.68 (broad m, 1H)

Mass spectrometry: method A
Retention time Tr (min)=0.73;
[M+H]+: m/z 373; [M−H]−: m/z 371
Optical rotation: $α_D$=+60.0+/−1.0 (C=2.778 mg/0.5 ml DMSO)

Example 36c

Synthesis of 2-{2-[(−)-6-fluoro-2-methyl-2,3-dihydro-1H-indol-1-yl]-2-oxoethyl}-6-(morpholin-4-yl)pyrimidin-4(3H)-one

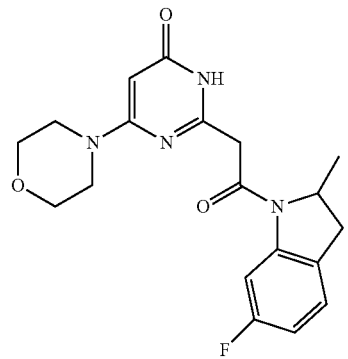 [SMILES: CC1Cc2ccc(F)cc2N1C(=O)Cc1nc(N2CCOCC2)cc(=O)[nH]1]

The product is prepared by following the procedure described in example 15c using 115 mg of sodium (4-morpholin-4-yl-6-oxo-1,6-dihydropyrimidin-2-yl)acetate and 62 mg of (+)-2-methyl-6-fluoro-2,3-dihydro-1H-indole [reference example 9c, step 5c]. After silica column purification: eluent 98/02 then 95/05 dichloromethane/methanol, 84 mg of -[2-((−)-6-fluoro-2-methyl-2,3-dihydroindol-1-yl)-2-oxoethyl]-6-morpholin-4-yl-3H-pyrimidin-4-one are obtained in the form of a solid, the characteristics of which are the following:

$^1$H NMR spectrum (400 MHz): 1.27 (d, J=6.4 Hz, 3H); 2.67 (d, J=16.3 Hz, 1H); 3.27 to 3.38 (partially masked m, 1H); 3.41 (m, 4H); 3.60 (m, 4H); 3.73 (d, J=15.9 Hz, 1H); 3.94 (d, J=15.9 Hz, 1H); 4.76 (m, 1H); 5.21 (s, 1H); 6.86 (ddd, J=2.6 and 8.3 and 9.2 Hz, 1H); 7.29 (dd, J=5.7 and 8.3 Hz, 1H); 7.72 (broad d, J=11.0 Hz, 1H); 11.68 (broad m, 1H)

Mass spectrometry: method A
Retention time Tr (min)=0.73;
[M+H]+: m/z 371; [M−H]−: m/z 373
Optical rotation: $\alpha_D$=−54.6+/−0.9 (C=2.702 mg/0.5 ml DMSO)

Example 37c and Example 38c

Synthesis of (+)-2-{2-[4-chloro-5-fluoro-2-methyl-2,3-dihydro-1H-indol-1-yl]-2-oxoethyl}-6-(morpholin-4-yl)pyrimidin-4(3H)-one and of (−)-2-{2-[4-chloro-5-fluoro-2-methyl-2,3-dihydro-1H-indol-1-yl]-2-oxoethyl}-6-(morpholin-4-yl)pyrimidin-4(3H)-one Step 1c 2-[2-(4-Chloro-5-fluoro-2-methyl-2,3-dihydroindol-1-yl)-2-oxoethyl 6-morpholin-4-yl-3H-pyrimidin-4-one

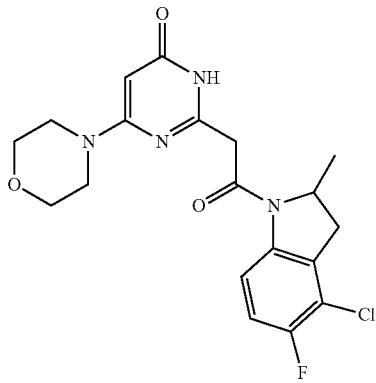 [SMILES: CC1Cc2c(ccc(F)c2Cl)N1C(=O)Cc1nc(N2CCOCC2)cc(=O)[nH]1]

The product is prepared according to the procedure described in example 1c, step 3c, using 248 mg of sodium (4-morpholin-4-yl-6-oxo-1,6-dihydropyrimidin-2-yl)acetate and 160 mg of 4-chloro-5-fluoro-2-methyl-2,3-dihydro-1H-indole (reference example 10c). After silica column purification: eluent 99/01 then 98/02 dichloromethane/methanol, 157 mg of 2-[2-(4-chloro-5-fluoro-2-methyl-2,3-dihydroindol-1-yl)-2-oxoethyl]-6-morpholin-4-yl-3H-pyrimidin-4-one are obtained in the form of a solid which will be separated into its two enantiomers on a chiral column.

Mass spectrometry: method A
Retention time Tr (min)=0.84;
[M+H]+: m/z 407; [M−H]−: m/z 405

Step 2c

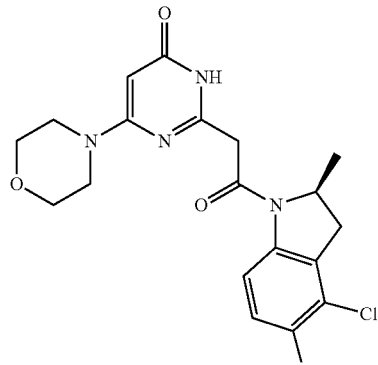

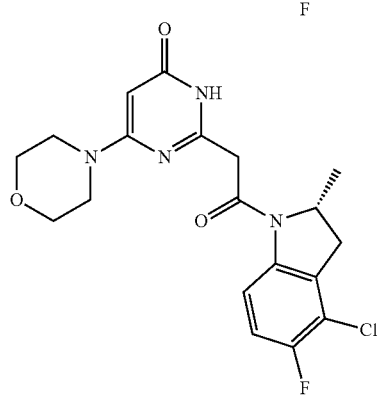

The separation of the two enantiomers of 2-[2-(4-chloro-5-fluoro-2-methyl-2,3-dihydroindol-1-yl)-2-oxoethyl]-6-morpholin-4-yl-3H-pyrimidin-4-one (157 mg) was carried out by chiral chromatography:

Stationary phase: Whelk 01 SS, 5 μm phase; mobile phase: heptane (65%)/dichloromethane (20%)/methanol (10%)/ethanol (5%); flow rate 43 ml/min.

The dextrorotatory enantiomer is concentrated so as to obtain 58 mg of 2-[2-((+)-4-chloro-5-fluoro-2-methyl-2,3-dihydroindol-1-yl)-2-oxoethyl]-6-morpholin-4-yl-3H-pyrimidin-4-one in the form of a white solid, the characteristics of which are the following:

$^1$H NMR spectrum (400 MHz): 1.31 (d, J=6.4 Hz, 3H); 2.76 (d, J=17.4 Hz, 1H); 3.41 (m, 5H); 3.60 (m, 4H); 3.73 (d, J=15.9 Hz, 1H); 3.92 (d, J=15.9 Hz, 1H); 4.80 (m, 1H); 5.20 (s, 1H); 7.24 (t, J=9.2 Hz, 1H); 7.90 (broad m, 1H); 11.68 (broad m, 1H)

Retention time Tr (min)=0.84;
[M+H]+: m/z 407; [M−H]−: m/z 405
Optical rotation: $\alpha_D$=+25.8+/−1.0 (C=1.506 mg/0.5 ml DMSO)

The levorotatory enantiomer is concentrated so as to obtain 52 mg of 2-[2-((−)-4-chloro-5-fluoro-2-methyl-2,3-dihydroindol-1-yl)-2-oxoethyl]-6-morpholin-4-yl-3H-pyrimidin-4-one in the form of a white solid, the characteristics of which are the following:

$^1$H NMR spectrum (400 MHz): 1.31 (d, J=6.4 Hz, 3H); 2.76 (d, J=17.4 Hz, 1H); 3.41 (m, 5H); 3.60 (m, 4H); 3.73 (d, J=15.9 Hz, 1H); 3.92 (d, J=15.9 Hz, 1H); 4.80 (m, 1H); 5.20 (s, 1H); 7.24 (t, J=9.2 Hz, 1H); 7.90 (broad m, 1H); 11.68 (broad m, 1H)

Mass spectrometry: method A
Retention time Tr (min)=0.84;
[M+H]+: m/z 407; [M−H]−: m/z 405
Optical rotation: $\alpha_D$=−24.9+/−0.9 (C=1.704 mg/0.5 ml DMSO)

Example 39c

Synthesis of (−)-2-[2-(2-isopropyl-2,3-dihydroindol-1-yl)-2-oxoethyl]-6-morpholin-4-yl-3H-pyrimidin-4-one

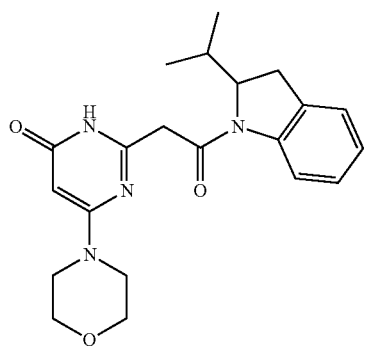 [SMILES: CC(C)C1Cc2ccccc2N1C(=O)Cc1nc(N2CCOCC2)cc(=O)[nH]1]

The product is prepared by following the procedure described in example 1c using 0.30 g of sodium [4-(morpholin-4-yl)-6-oxo-1,6-dihydropyrimidin-2-yl]acetate, 0.17 g of (−)-2-isopropylindoline and 0.27 g of N-[3-(dimethylamino)propyl]-N'-ethylcarbodiimide hydrochloride in a mixture of 0.26 ml of pyridine and 4.4 ml of N,N-dimethylformamide. 0.25 g of (−)-2-[2-(2-isopropyl-2,3-dihydroindol-1-yl)-2-oxoethyl]-6-morpholin-4-yl-3H-pyrimidin-4-one (reference example 11c) is thus obtained in the form of a very pale pink solid, the characteristics of which are the following:

$^1$H NMR spectrum (400 MHz): for this batch, all the signals are broad with: 0.58 (d, J=6.8 Hz, 3H); 0.94 (d, J=6.8 Hz, 3H); 2.19 (m, 1H); 2.92 (d, J=16.4 Hz, 1H); 3.18 (dd, J=9.8 and 16.4 Hz, 1H); 3.40 (m, 4H); 3.59 (m, 4H); 3.75 (d, J=15.7 Hz, 1H); 3.92 (d, J=15.7 Hz, 1H); 4.54 (m, 1H); 5.19 (s, 1H); 7.01 (t, J=7.9 Hz, 1H); 7.14 (t, J=7.9 Hz, 1H); 7.24 (d, J=7.9 Hz, 1H); 7.93 (d, J=7.9 Hz, 1H); 11.66 (m, 1H)

Mass spectrometry: method A
Retention time Tr (min)=0.82;
[M+H]+: m/z 383; [M−H]−: m/z 381
Melting point (Kofler): 172° C.
Optical rotation: $\alpha_D$=−110.8°+/−1.8 (c=0.35% in DMSO)

Example 40c

Synthesis of (+)-2-[2-(2-isopropyl-2,3-dihydroindol-1-yl)-2-oxoethyl]-6-morpholin-4-yl-3H-pyrimidin-4-one

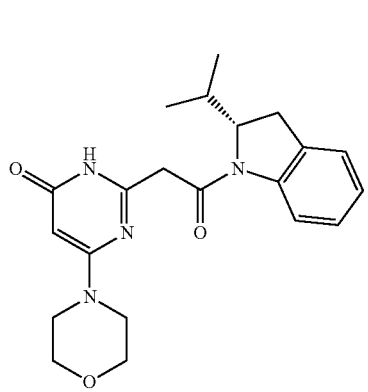

The product is prepared by following the procedure described in example 1c using 0.27 g of sodium [4-(morpholin-4-yl)-6-oxo-1,6-dihydropyrimidin-2-yl]acetate, 0.15 g of (+)-2-isopropylindoline and 0.24 g of N-[3-(dimethylamino)propyl]-N'-ethylcarbodiimide hydrochloride in a mixture of 0.23 ml of pyridine and 3.8 ml of N,N-dimethylformamide. 0.24 g of (+)-2-[2-(2-isopropyl-2,3-dihydroindol-1-yl)-2-oxoethyl]-6-morpholin-4-yl-3H-pyrimidin-4-one (reference example 12c) is thus obtained in the form of a white solid, the characteristics of which are the following:

$^1$H NMR spectrum (400 MHz): for this batch, all the signals are broad with: 0.58 (d, J=6.1 Hz, 3H); 0.94 (d, J=6.1 Hz, 3H); 2.20 (m, 1H); 2.93 (d, J=16.3 Hz, 1H); 3.18 (dd, J=9.7 and 16.3 Hz, 1H); 3.40 (m, 4H); 3.59 (m, 4H); 3.75 (d, J=15.4 Hz, 1H); 3.92 (d, J=15.4 Hz, 1H); 4.54 (m, 1H); 5.20 (s, 1H); 7.01 (t, J=7.9 Hz, 1H); 7.14 (t, J=7.9 Hz, 1H); 7.24 (d, J=7.9 Hz, 1H); 7.93 (d, J=7.9 Hz, 1H); 11.67 (s, 1H)

Mass spectrometry: method A
Retention time Tr (min)=0.82;
[M+H]+: m/z 383; [M−H]−: m/z 381
Melting point (Kofler): 174° C.
Optical rotation: $\alpha_D$=+117.3°+/−1.6 (c=2.857 mg in 0.5 ml of methanol)

Example 41c

Synthesis of 2-[1-(4-fluoro-2,3-dihydro-1H-indol-1-yl)-1-oxopropan-2-yl]-6-(morpholin-4-yl)pyrimidin-4(3H)-one

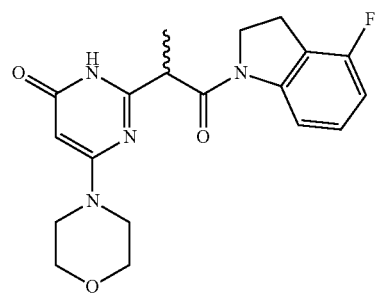 [SMILES: CC(C(=O)N1CCc2c(F)cccc21)c1nc(N2CCOCC2)cc(=O)[nH]1]

Step 1c 2,4-Dichloro-6-methoxypyrimidine

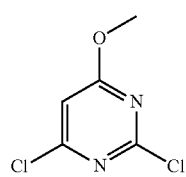

3.24 g of sodium methoxide dissolved beforehand in 13 ml of methanol are added dropwise to a solution of 11 g of 2,4,6-trichloropyrimidine in 140 ml of methanol cooled to 0° C. in an ice bath. The ice bath is withdrawn. The reaction medium is stirred at 0° C. for 45 minutes, and then the cooling bath is removed so as to allow the temperature to rise to ambient temperature. The reaction medium is concentrated under reduced pressure. The residue obtained is taken up with 30 ml of water and 100 ml of ethyl acetate. After settling out, the organic phase is dried over magnesium sulfate, filtered, and concentrated under reduced pressure so as to give an oil which is left to crystallize for 24 hours at ambient temperature. The product crystallizes in the form of needles in the middle of an oil. The needles are separated so as to give 3.94 g of 2,4-dichloro-6-methoxypyrimidine, the characteristics of which are the following:

Mass spectrometry: method A
EI: [M]+. m/z=178; base peak: m/z=148

Step 2c (4-Chloro-6-methoxypyrimidin-2-yl)acetic acid ethyl ester

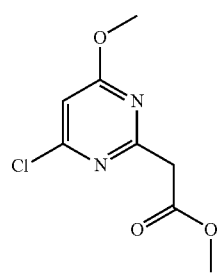

91.4 ml of 1M lithium bis(trimethylsilyl)amide (THF) are added dropwise to a solution of 7.4 g of 2,4-dichloro-6-methoxypyrimidine and 4.5 ml of ethyl acetate in 100 ml of anhydrous THF cooled to −75° C. in a dry ice/acetone bath. The reaction medium is stirred at −75° C. for one hour. The cooling bath is removed so as to allow the temperature to rise to 22° C. The reaction medium is stirred at 22° C. for one hour. 100 ml of water and 400 ml of ethyl acetate are added. After settling out, the organic phase is dried over magnesium sulfate, filtered, and then concentrated under reduced pressure so as to give 9.5 g of (4-chloro-6-methoxypyrimidin-2-yl)acetic acid ethyl ester in the form of an orange oil, the characteristics of which are the following:

Mass spectrometry: method A
Retention time Tr (min)=0.80; [M+H]+: m/z 231;

Step 3c (4-Methoxy-6-morpholin-4-ylpyrimidin-2-yl)acetic acid ethyl ester

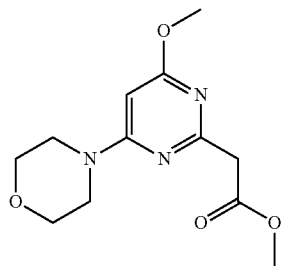 [SMILES: COC(=O)Cc1nc(OC)cc(N2CCOCC2)n1]

1.5 g of (4-chloro-6-methoxypyrimidin-2-yl)acetic acid ethyl ester and 20 ml of morpholine are mixed together in a microwave tube. After microwave irradiation for 1 h at 90° C., the reaction mixture is concentrated under reduced pressure and then diluted with 300 ml of ethyl acetate and 300 ml of water. After settling out, the organic phase is dried over magnesium sulfate, filtered, and then concentrated under reduced pressure. 1.9 g of (4-methoxy-6-morpholin-4-ylpyrimidin-2-yl)acetic acid ethyl ester are thus obtained in the form of a viscous oil which crystallizes and which is used as it is in the next step.

Step 4c

Sodium (4-methoxy-6-morpholin-4-ylpyrimidin-2-yl)acetate

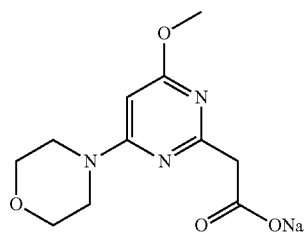

8.8 ml of 1N sodium hydroxide are added to a solution of 2.5 g of (4-methoxy-6-morpholin-4-ylpyrimidin-2-yl)acetic acid ethyl ester in 15 ml of THF. The reaction medium is stirred at ambient temperature for 48 hours and then concentrated under reduced pressure. After oven-drying under vacuum, 2.4 g of sodium (4-methoxy-6-morpholin-4-yl-pyrimidin-2-yl)acetate are obtained, which will be used as it is in the next step.

Step 5c 1-(4-Fluoro-2,3-dihydroindol-1-yl)-2-(4-methoxy-6-morpholin-4-ylpyrimidin-2-yl)ethanone

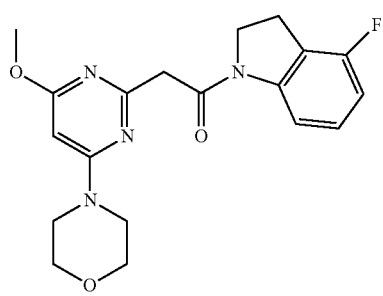 [SMILES: COc1cc(N2CCOCC2)nc(CC(=O)N2CCc3c(F)cccc32)n1]

1.2 g of 4-fluoro-2,3-dihydro-1H-indole and 1.9 g of N-[3-(dimethylamino)propyl]-N'-ethylcarbodiimide hydrochloride are added to a solution of 1.7 g of sodium (4-methoxy-6-morpholin-4-ylpyrimidin-2-yl)acetate in 15 ml of DMF and 5 ml of pyridine. The reaction medium is stirred at ambient temperature for 3 hours. The reaction mixture is concentrated under reduced pressure and then diluted in 80 ml of water and 15 ml of ethyl acetate. The precipitate formed is washed with 15 ml of ethyl ether and then with 15 ml of petroleum ether. After drying under reduced pressure, 1.53 g of 1-(4-fluoro-2,3-dihydroindol-1-yl)-2-(4-methoxy-6-morpholin-4-ylpyrimidin-2-yl)ethanone are obtained in the form of a pink solid used as it is in the next step.

Step 6c 1-(4-Fluoro-2,3-dihydroindol-1-yl)-2-(4-methoxy-6-morpholin-4-ylpyrimidin-2-yl)-propan-1-one

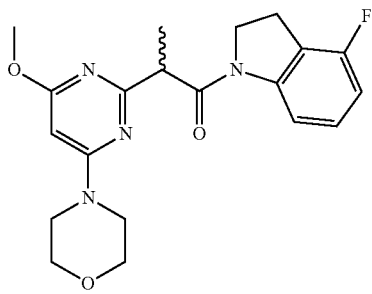 [SMILES: COc1cc(N2CCOCC2)nc(C(C)C(=O)N2CCc3c(F)cccc32)n1]

300 mg of 1-(4-fluoro-2,3-dihydroindol-1-yl)-2-(4-methoxy-6-morpholin-4-yl-pyrimidin-2-yl)ethanone dissolved in 10 ml of tetrahydrofuran are cooled to −78° C. using a dry ice bath. 2.65 ml of 1N potassium bis(trimethylsilyl)amide in THF are slowly added while maintaining the temperature at −75° C. After 30 minutes of stirring, 0.125 ml of methyl iodide is added and the stirring is continued for 2 h 15. The reaction mixture is diluted with 50 ml of a saturated ammonium chloride solution and 30 ml of ethyl acetate. After settling out, the organic phase is washed with 5 times 15 ml of water, dried over magnesium sulfate, filtered, and then concentrated under reduced pressure. The residue is purified by silica column chromatography, elution being carried out with a 99/01 mixture of dichloromethane and methanol, so as to give 215 mg of 1-(4-fluoro-2,3-dihydroindol-1-yl)-2-(4-methoxy-6-morpholin-4-ylpyrimidin-2-yl)propan-1-one in the form of a white solid, the characteristics of which are the following:

$^1$H NMR spectrum (400 MHz): 1.42 (d, J=6.8 Hz, 3H); 3.11 (t, J=8.4 Hz, 2H); 3.48 (m, 4H); 3.59 (m, 4H); 3.77 (s, 3H); 3.95 to 4.09 (m, 2H); 4.30 (m, 1H); 5.94 (s, 1H); 6.81 (t, J=8.7 Hz, 1H); 7.19 (m, 1H); 7.92 (broad d, J=8.1 Hz, 1H)

Mass spectrometry: method A
Retention time Tr (min)=0.96;
[M+H]+: m/z 387;

Step 7c

2-[1-(4-Fluoro-2,3-dihydro-1H-indol-1-yl)-1-oxopropan-2-yl]-6-(morpholin-4-yl)pyrimidin-4(3H)-one

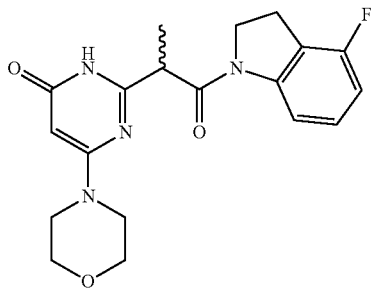 [SMILES: CC(C(=O)N1CCc2c(F)cccc21)c1nc(N2CCOCC2)cc(=O)[nH]1]

210 mg of 1-(4-fluoro-2,3-dihydroindol-1-yl)-2-(4-methoxy-6-morpholin-4-yl-pyrimidin-2-yl)propan-1-one, 270 mg of potassium iodide, 7 ml of acetonitrile and 208 ml of trimethylchlorosilane are added to a microwave tube. After microwave irradiation for one hour at a temperature of 100° C., the reaction medium is diluted with 20 ml of ethyl acetate and 20 ml of water. After settling out, the organic phase is dried over magnesium sulfate, filtered, and then concentrated under reduced pressure. The residue obtained is stirred in the presence of 5 ml of ethyl acetate and 20 ml of petroleum ether. The solid obtained is filtered off and then dried under reduced pressure. 163 mg of 2-[1-(4-fluoro-2,3-dihydro-1H-indol-1-yl)-1-oxopropan-2-yl]-6-(morpholin-4-yl)pyrimidin-4(3H)-one are thus obtained in the form of a pale yellow solid, the characteristics of which are the following:

$^1$H NMR spectrum (400 MHz): 1.42 (d, J=6.8 Hz, 3H); 3.16 (t, J=8.4 Hz, 2H); 3.39 (m, 4H); 3.58 (m, 4H); 3.94 to 4.10 (m, 2H); 4.24 (m, 1H); 5.20 (broad s, 1H); 6.85 (t, J=8.7 Hz, 1H); 7.21 (m, 1H); 7.88 (broad d, J=8.1 Hz, 1H); 11.73 (broad m, 1H)

Mass spectrometry: method A
Retention time Tr (min)=0.71;
[M+H]+: m/z 373; [M−H]−: m/z 371

Example 42c and Example 43c

Synthesis of (+)-2-[2-(2-ethyl-2,3-dihydroindol-1-yl)-2-oxoethyl]-6-morpholin-4-yl-3H-pyrimidin-4-one and of (−)-2-[2-(2-ethyl-2,3-dihydroindol-1-yl)-2-oxoethyl]-6-morpholin-4-yl-3H-pyrimidin-4-one

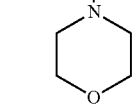

(±)-2-[2-(2-Ethyl-2,3-dihydroindol-1-yl)-2-oxoethyl]-6-morpholin-4-yl-3H-pyrimidin-4-one is prepared by following the procedure described in example 1c using 0.40 g of sodium [4-(morpholin-4-yl)-6-oxo-1,6-dihydropyrimidin-2-yl]acetate, 0.25 g of 2-ethylindoline [which can be prepared according to patent WO2009065920] and 0.39 g of N-[3-(dimethylamino)propyl]-N'-ethylcarbodiimide hydrochloride in a mixture of 250 ml of pyridine and 6.5 ml of N,N-dimethylformamide. After purification by chromatography on a 25 g cartridge of 15-40 μm silica, elution being carried out successively with 99/1 then 98/2 and 97/3 v/v dichloromethane/methanol mixtures, at a flow rate of 30 ml/min, 0.35 g of (±)-2-[2-(2-ethyl-2,3-dihydroindol-1-yl)-2-oxoethyl]-6-morpholin-4-yl-3H-pyrimidin-4-one is obtained in the form of a white foam, the characteristics of which are the following:

Mass spectrometry: method A
Retention time Tr (min)=0.76;
[M+H]+: m/z 369; [M–H]–: m/z 367
Melting point (Kofler): 155° C.

The products were obtained by chiral chromatographic separation of 350 mg of (±)-2-[2-(2-ethyl-2,3-dihydroindol-1-yl)-2-oxoethyl]-6-morpholin-4-yl-3H-pyrimidin-4-one on a Chiralpak AY column (1080 g, 20 μm, 10/23 cm), eluent: acetonitrile/isopropanol: 90/10; flow rate: 400 ml/min. After purification, 138 mg of (+)-2-[2-(2-ethyl-2,3-dihydroindol-1-yl)-2-oxoethyl]-6-morpholin-4-yl-3H-pyrimidin-4-one are obtained, as first enantiomer, in the form of a white foam, the characteristics of which are the following:

$^1$H NMR spectrum (400 MHz): 0.85 (t, J=7.5 Hz, 3H); 1.55 (m, 1H); 1.71 (m, 1H); 2.84 (d, J=16.3 Hz, 1H); 3.31 (partially masked m, 1H); 3.41 (m, 4H); 3.60 (m, 4H); 3.71 (d, J=16.0 Hz, 1H); 3.92 (d, J=16.0 Hz, 1H); 4.52 (m, 1H); 5.20 (s, 1H); 7.03 (t, J=7.9 Hz, 1H); 7.16 (t, J=7.9 Hz, 1H); 7.26 (d, J=7.9 Hz, 1H); 7.94 (broad d, J=7.9 Hz, 1H); 11.67 (broad m, 1H)

Mass spectrometry: method A
Retention time Tr (min)=0.77;
[M+H]+: m/z 369; [M–H]–: m/z 367
Optical rotation: $α_D$=+109° (c=1.438 mg in 0.5 ml of DMSO)

Then the second enantiomer, i.e.: 142 mg of (–)-2-[2-(2-ethyl-2,3-dihydroindol-1-yl)-2-oxoethyl]-6-morpholin-4-yl-3H-pyrimidin-4-one, is obtained in the form of a white foam, the characteristics of which are the following:

$^1$H NMR spectrum (400 MHz): 0.85 (t, J=7.5 Hz, 3H); 1.55 (m, 1H); 1.73 (m, 1H); 2.84 (d, J=16.3 Hz, 1H); 3.30 (partially masked m, 1H); 3.41 (m, 4H); 3.60 (m, 4H); 3.71 (d, J=16.0 Hz, 1H); 3.92 (d, J=16.0 Hz, 1H); 4.53 (m, 1H); 5.20 (s, 1H); 7.03 (t, J=7.9 Hz, 1H); 7.16 (t, J=7.9 Hz, 1H); 7.27 (d, J=7.9 Hz, 1H); 7.94 (broad d, J=7.9 Hz, 1H); 11.67 (broad m, 1H)

Mass spectrometry: method A
Retention time Tr (min)=0.77;
[M+H]+: m/z 369; [M–H]–: m/z 367
Optical rotation: $α_D$=–89° (c=0.883 mg in 0.5 ml of DMSO)

Example 44c and Example 45c

Synthesis of (–)-2-[2-fluoro-1-(4-fluoro-2,3-dihydro-1H-indol-1-yl)-1-oxopropan-2-yl]-6-(morpholin-4-yl)pyrimidin-4(3H)-one and of (+)-2-[2-fluoro-1-(4-fluoro-2,3-dihydro-1H-indol-1-yl)-1-oxopropan-2-yl]-6-(morpholin-4-yl)pyrimidin-4(3H)-one

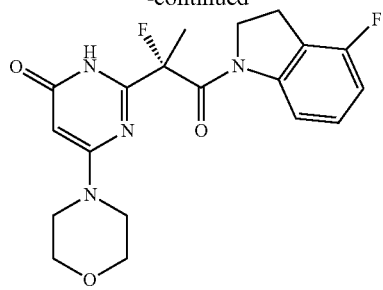

Step 1c

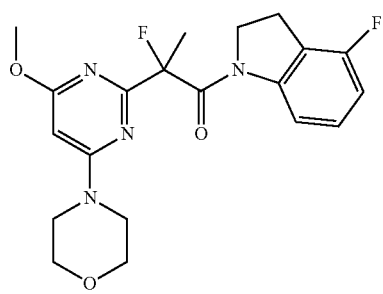 [SMILES: COc1cc(N2CCOCC2)nc(C(C)(F)C(=O)N2CCc3c(F)cccc32)n1]

2.4 ml of 0.91M potassium bis(trimethylsilyl)amide in THF are added slowly, while maintaining the temperature at –70° C., to a solution of 386 mg of 1-(4-fluoro-2,3-dihydroindol-1-yl)-2-(4-methoxy-6-morpholin-4-ylpyrimidin-2-yl)propan-1-one, which can be obtained according to example 41c, step 6c, dissolved in 10 ml of tetrahydrofuran and cooled to –78° C. in a dry ice bath. After 30 minutes of stirring, a solution of 694 mg of N-fluorobenzenesulfonimide in 5 ml of tetrahydrofuran is added and the stirring is continued at –70° C. for 2 hours. The reaction mixture is diluted with 20 ml of water and 20 ml of ethyl acetate. After settling out, the organic phase is washed with a saturated sodium chloride solution, dried over magnesium sulfate, filtered, and then concentrated under reduced pressure. The residue is purified by silica column chromatography, elution being carried out with dichloromethane, so as to give 340 mg of 2-fluoro-1-(4-fluoro-2,3-dihydro-1H-indol-1-yl)-2-[4-methoxy-6-(morpholin-4-yl)pyrimidin-2-yl]propan-1-one in the form of a pale yellow solid which will be used as it is in the next step.

Step 2c

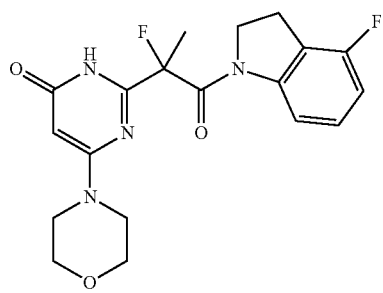 [SMILES: CC(F)(C(=O)N1CCc2c(F)cccc21)c1nc(N2CCOCC2)cc(=O)[nH]1]

17 ml of hydrochloric acid (4M in dioxane) are added to 340 mg of 2-fluoro-1-(4-fluoro-2,3-dihydro-1H-indol-1-yl)-2-[4-methoxy-6-(morpholin-4-yl)pyrimidin-2-yl]propan-1-one, obtained according to the previous step. The reaction medium is stirred at reflux for 5 hours, allowed to return to ambient temperature, and then concentrated under reduced pressure. The residue obtained is purified on a silica column, eluent: 98/02 dichloromethane/methanol, so as to give 236 mg of racemic 2-[2-fluoro-1-(4-fluoro-2,3-dihydro-1H-indol-1-yl)-1-oxopropan-2-yl]-6-(morpholin-4-yl)pyrimidin-4(3H)-one in the form of a white solid which will be used as it is in the next step.

$^1$H NMR spectrum (400 MHz): 1.86 (d, J=23.2 Hz, 3H); 3.10 (m, 2H); 3.42 (m, 4H); 3.58 (m, 4H); 3.84 (m, 1H); 4.21 (m, 1H); 5.61 (broad m, 1H); 6.91 (t, J=8.4 Hz, 1H); 7.25 (dt, J=5.9 and 8.4 Hz, 1H); 7.92 (d, J=8.4 Hz, 1H); 11.81 (broad m, 1H)

Mass spectrometry: method A
Retention time Tr (min)=0.79;
[M+H]+: m/z 391;
[M−H]−: m/z 389; [2M−H]−: m/z 779 (base peak)

Step 3c

The products were obtained by chiral chromatographic separation of 200 mg of (±)-2-[2-fluoro-1-(4-fluoro-2,3-dihydro-1H-indol-1-yl)-1-oxopropan-2-yl]-6-(morpholin-4-yl)pyrimidin-4(3H)-one on a Chiralpak AY-H column (5 μm, 30×250 mm), eluent: heptane/ethanol/methanol/triethylamine: 75/20/5/0.1; flow rate: 43 ml/min. After purification, 65 mg of (−)-2-[2-fluoro-1-(4-fluoro-2,3-dihydro-1H-indol-1-yl)-1-oxopropan-2-yl]-6-(morpholin-4-yl)pyrimidin-4(3H)-one are obtained, as first enantiomer, in the form of a white lyophilisate, the characteristics of which are the following:

$^1$H NMR spectrum (400 MHz): 1.85 (d, J=23.2 Hz, 3H); 3.10 (m, 2H); 3.42 (m, 4H); 3.59 (m, 4H); 3.84 (m, 1H); 4.21 (m, 1H); 5.62 (broad m, 1H); 6.91 (t, J=8.4 Hz, 1H); 7.25 (dt, J=5.9 and 8.4 Hz, 1H); 7.92 (d, J=8.4 Hz, 1H); 11.79 (broad m, 1H)

Mass spectrometry: method A
Retention time Tr (min)=0.77;
[M+H]+: m/z 391; [M−H]−: m/z 389
Optical rotation: $\alpha_D$=−68.6°+/−1.3 (c=1.767 mg in 0.5 ml of DMSO)

Then the second enantiomer, i.e.: 71 mg of (+)-2-[2-fluoro-1-(4-fluoro-2,3-dihydro-1H-indol-1-yl)-1-oxopropan-2-yl]-6-(morpholin-4-yl)pyrimidin-4(3H)-one, is obtained in the form of a white lyophilisate, the characteristics of which are the following:

$^1$H NMR spectrum (400 MHz): 1.85 (d, J=23.2 Hz, 3H); 3.11 (m, 2H); 3.42 (m, 4H); 3.58 (m, 4H); 3.84 (m, 1H); 4.21 (m, 1H); 5.61 (broad m, 1H); 6.91 (t, J=8.3 Hz, 1H); 7.25 (dt, J=6.1 and 8.3 Hz, 1H); 7.92 (d, J=8.3 Hz, 1H); 11.79 (broad m, 1H)

Mass spectrometry: method A
Retention time Tr (min)=0.77;
[M+H]+: m/z 391; [M−H]−: m/z 389
Optical rotation: $\alpha_D$=+75.2+/−1.5 (c=1.532 mg in 0.5 ml of DMSO)

Example 46c

Synthesis of 1-{[4-(morpholin-4-yl)-6-oxo-1,6-dihydropyrimidin-2-yl]acetyl}-2,3-dihydro-1H-indole-4-carbonitrile

VAC.SON5.167.1

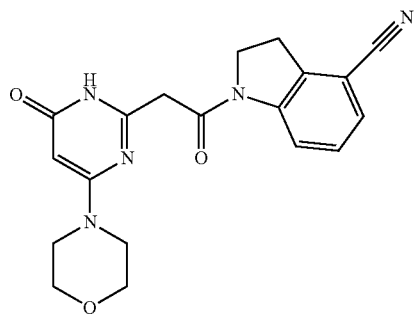 [SMILES: N#Cc1cccc2c1CCN2C(=O)Cc1nc(N2CCOCC2)cc(=O)[nH]1]

242 mg of N-[3-(dimethylamino)propyl]-N'-ethylcarbodiimide hydrochloride, 371 mg of N,N-diisopropylamine and 210 mg of 2,3-dihydro-1H-indole-4-carbonitrile hydrochloride are added to a solution of 300 mg of sodium [4-(morpholin-4-yl)-6-oxo-1,6-dihydropyrimidin-2-yl]acetate, obtained according to example 1c, step 2c, in 3 ml of N,N-dimethylformamide. The reaction mixture is stirred at ambient temperature for 72 hours and then concentrated under reduced pressure. The residue is taken up with 100 ml of water and 20 ml of ethyl acetate, and then stirred at ambient temperature for 1 hour. The precipitate formed is filtered off, and then rinsed successively with water and petroleum ether. The solid obtained is dried with suction, and then dried under reduced pressure at 40° C. 190 mg of 1-{[4-(morpholin-4-yl)-6-oxo-1,6-dihydropyrimidin-2-yl]acetyl}-2,3-dihydro-1H-indole-4-carbonitrile are thus obtained in the form of a white solid, the characteristics of which are the following:

$^1$H NMR spectrum (400 MHz): 3.36 (t, J=8.5 Hz, 2H); 3.41 (m, 4H); 3.60 (m, 4H); 3.79 (s, 2H); 4.23 (t, J=8.5 Hz, 2H); 5.21 (s, 1H); 7.38 (t, J=8.0 Hz, 1H); 7.45 (d, J=8.0 Hz, 1H); 8.27 (d, J=8.0 Hz, 1H); 11.62 (broad s, 1H)

Mass spectrometry: method A
Retention time Tr (min)=0.61;
[M+H]+: m/z 366; [M−H]−: m/z 361

Reference Examples for Preparing the Compounds of Formula (Ic)

Reference Example 1c 4-hydroxy-2-methylindoline

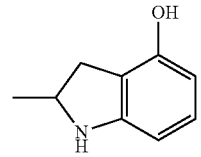

1.35 g of sodium cyanoborohydride are gradually added to a solution of 1 g of 4-hydroxy-2-methylindole in 35 ml of acetic acid under argon cooled to a temperature of about 14° C. The reaction mixture is stirred at a temperature of about 14° C. for 15 minutes, and is then allowed to warm up to ambient temperature. After 1.5 hours, the reaction mixture is treated with 15 ml of water, stirred at ambient temperature for 1 hour, and then concentrated to dryness under reduced pressure. The residue is taken up in 75 ml of ethyl acetate and then treated with 60 ml of a saturated sodium hydrogen carbonate solution. After stirring for 1 hour and then settling out, the organic phase is separated and the aqueous phase is extracted with 50 ml of ethyl acetate. The organic phases are combined, washed with saturated brine, dried over anhydrous magnesium sulfate, filtered, and then concentrated to dryness under reduced pressure. The residue is purified on a 70 g cartridge of 15-40 µm silica, elution being carried out with an 80/20 v/v cyclohexane/ethyl acetate mixture, with a flow rate of 80 ml/min. 0.87 g of 4-hydroxy-2-methylindoline is thus obtained in the form of a yellow oil, the characteristics of which are the following:

$^1$H NMR spectrum (400 MHz, CDCl$_3$): 2.46 (s, 3H); 6.30 (d, J=0.7 Hz, 1H); 6.74 (dd, J=7.9 and 10.6 Hz, 1H); 7.02 (dt, J=4.9 and 7.9 Hz, 1H); 7.08 (d, J=7.9 Hz, 1H); 7.95 (broad s, 1H)

Reference Example 2c 4-fluoro-3,3-dimethyl-2,3-dihydro-1H-indole

Step 1c

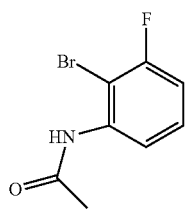

2.7 ml of triethylamine and then 1.2 ml of acetyl chloride are added to a solution of 3 g of 2-bromo-3-fluoroaniline in 30 ml of dichloromethane. The reaction mixture is stirred for 72 hours and then treated with a mixture of water and dichloromethane. The phases are separated and the organic phase is concentrated so as to give 3.75 g of N-(2-bromo-3-fluorophenyl)acetamide.

Step 2c

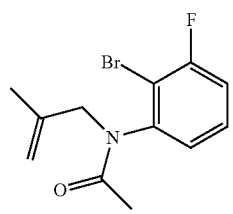 [SMILES: C=C(C)CN(C(C)=O)c1cccc(F)c1Br]

2 g of 3-bromo-2-methylpropene, 1.9 g of potassium carbonate and 570 mg of sodium hydride (dispersion in oil at 60%) are added to a solution of 3 g of N-(2-bromo-3-fluorophenyl)acetamide in 25 ml of toluene. The reaction mixture is placed under an argon atmosphere and heated at 75° C. for 16 hours. The reaction mixture is treated with a mixture of water and ethyl acetate, and the organic phase is then washed with water and a saturated sodium chloride solution, dried over magnesium sulfate, filtered, and concentrated under reduced pressure, so as to give 3.8 g of N-(2-bromo-3-fluorophenyl)-N-(2-methylallyl)acetamide.

Step 3c

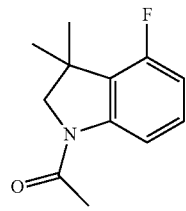

59 mg of palladium acetate, 1.5 g of tetrabutylammonium hydrochloride and 1.8 ml of triethylamine are added to a solution of 1.5 g of N-(2-bromo-3-fluorophenyl)-N-(2-methylallyl)acetamide in 10 ml of N,N-dimethylformamide. The reaction mixture is heated at 100° C. under an argon atmosphere for 16 hours. After cooling, 50 ml of water are added and the mixture is extracted with ethyl acetate. The organic phase is then washed with water and a saturated sodium chloride solution, dried over magnesium sulfate, filtered, and concentrated under reduced pressure. The residue is purified by silica column chromatography, elution being carried out with a mixture of heptane and ethyl acetate (50/50: v/v), so as to give 520 mg of 1-(4-fluoro-3,3-dimethyl-2,3-dihydroindol-1-yl)ethanone in the form of a yellow oil.

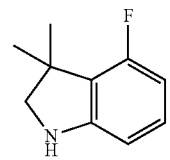

Step 4c

A solution of 520 mg of 1-(4-fluoro-3,3-dimethyl-2,3-dihydroindol-1-yl)ethanone in 10 ml of concentrated hydrochloric acid is heated at 90° C. for 2 hours. The solution is then treated with sodium bicarbonate until the pH is 7, and extracted with dichloromethane. The organic phase is filtered on a phase-separation column and concentrated under reduced pressure, so as to give 300 mg of 4-fluoro-3,3-dimethyl-2,3-dihydro-1H-indole in the form of a brown oil, the characteristics of which are the following:

$^1$H NMR spectrum (400 MHz): 1.31 (s, 6H); 3.17 to 3.22 (m, 2H); 5.76 (broad m, 1H); 6.19 to 6.31 (m, 2H); 6.91 (m, 1H)

Reference Example 3c 4-hydroxy-3-methylindoline

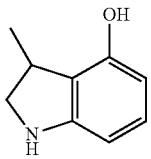

1.35 g of sodium cyanoborohydride are gradually added to a solution of 1.0 g of 3-methyl-1H-indol-4-ol in 35 ml of acetic acid under argon cooled to a temperature of about 15° C. The reaction mixture is allowed to warm up to ambient temperature. After 16.5 hours, the reaction mixture is treated with 15 ml of water, and then concentrated to dryness under reduced pressure. The residue is taken up in 75 ml of ethyl acetate, and then treated with 60 ml of a saturated sodium hydrogen carbonate solution. After stirring for 1 hour and then settling out, the organic phase is separated and the aqueous phase is extracted with 50 ml of ethyl acetate. The organic phases are combined, washed with saturated brine, dried over anhydrous magnesium sulfate, filtered, and then concentrated to dryness under reduced pressure. The residue is purified by chromatography on a 70 g cartridge of 15-40 μm silica, elution being carried out with an 80/20 v/v cyclohexane/ethyl acetate mixture, with a flow rate of 80 ml/min. 0.45 g of 4-hydroxy-3-methylindoline is thus obtained in the form of a pale yellow solid, the characteristics of which are the following:

Mass spectrometry: method A
Retention time Tr (min)=0.14;
[M+H]+: m/z 150
Melting point (Kofler): 115° C.

Reference Example 4c 5-fluoro-2-methyl-2,3-dihydro-1H-indole

Step 1c

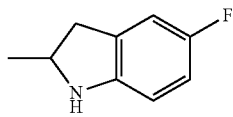

6.22 g of sodium cyanoborohydride are added, in four steps, to a solution of 5 g of 5-fluoro-2-methylindole in 60 ml of trifluoroacetic acid cooled to 5° C. The reaction medium is stirred at 0° C. for 30 minutes and then at ambient temperature for five hours.

The reaction medium is again cooled to 5° C. 700 ml of ice-cold water, 150 ml of 31% sodium hydroxide and then 300 ml of ethyl acetate are added. The mixture is stirred at ambient temperature for one hour. After settling out, the organic phase is dried over magnesium sulfate, filtered, and then concentrated under reduced pressure. The residue obtained is purified on a silica column, eluent: 90/10 heptane/ethyl acetate, so as to give 2.14 g of 5-fluoro-2-methyl-2,3-dihydro-1H-indole, the characteristics of which are the following:

Mass spectrometry: method A
Retention time Tr (min)=0.24; [M+H]+: m/z 152;

Step 2c (R)-1-(5-Fluoro-2-methyl-2,3-dihydroindol-1-yl)-2-phenoxypropan-1-one: diastereoisomer A

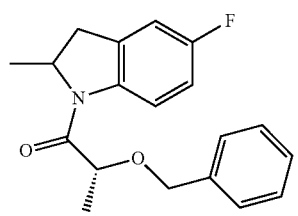 [SMILES: CC1Cc2cc(F)ccc2N1C(=O)[C@@H](C)OCc1ccccc1]

And (R)-1-(5-Fluoro-2-methyl-2,3-dihydroindol-1-yl)-2-phenoxypropan-1-one: diastereoisomer B

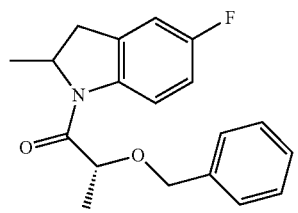 [SMILES: CC1Cc2cc(F)ccc2N1C(=O)[C@@H](C)OCc1ccccc1]

2.9 g of 5-fluoro-2-methyl-2,3-dihydro-1H-indole and 5.3 g of N-[3-(dimethylamino)propyl]-N'-ethylcarbodiimide hydrochloride are added to a solution of 4.17 g of o-benzyl-D-lactic acid in 17 ml of DMF and 3.43 ml of pyridine.

The reaction medium is stirred at ambient temperature for 18 hours.

500 ml of ethyl acetate and 500 ml of water are added. After settling out, the organic phase is dried over magnesium sulfate, filtered, and then concentrated under reduced pressure. The residue obtained is purified on a silica cartridge: eluent: heptane, then 95/05 heptane/ethyl acetate, then 90/10 heptane/ethyl acetate, so as to give 2.8 g of (R)-1-(5-fluoro-2-methyl-2,3-dihydroindol-1-yl)-2-phenoxypropan-1-one: diastereoisomer A in the form of a yellow oil, the characteristics of which are the following:

Mass spectrometry: method A
Retention time Tr (min)=1.08;
[M+H]+: m/z 314

And 2.63 g of (R)-1-(5-fluoro-2-methyl-2,3-dihydroindol-1-yl)-2-phenoxypropan-1-one: diastereoisomer B in the form of a white solid, the characteristics of which are the following:

Mass spectrometry: method A
Retention time Tr (min)=1.06;
[M+H]+: m/z 314; base peak: m/z 242

Step (3a)c (+)-5-Fluoro-2-methyl-2,3-dihydro-1H-indole

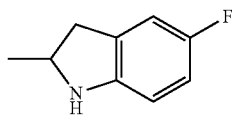

28 ml of 37% hydrochloric acid are added to a solution of 2.8 g of (R)-1-(5-fluoro-2-methyl-2,3-dihydroindol-1-yl)-2-phenoxypropan-1-one: diastereoisomer A in 28 ml of ethanol.

The reaction medium is refluxed for 5 hours.

The reaction medium is concentrated under reduced pressure. The residue obtained is taken up with 260 ml of water. 2N sodium hydroxide is added until the pH=10. The medium is extracted with 200 ml of dichloromethane. After settling out, the organic phase is dried over magnesium sulfate, filtered, and then concentrated under reduced pressure. The residue obtained is purified on a silica cartridge, eluent: 90/10 heptane/ethyl acetate, so as to give 1.29 g of (+)-5-fluoro-2-methyl-2,3-dihydro-1H-indole in the form of a yellow oil, the characteristics of which are the following:

Mass spectrometry: method A

Retention time Tr (min)=0.25; [M+H]+: m/z 152

Optical rotation: αD=+8.2+/−0.7. C=1.801 mg/0.5 ml DMSO

Step (3b)c (−)-5-Fluoro-2-methyl-2,3-dihydro-1H-indole

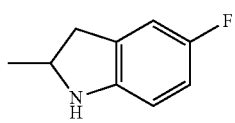

26.5 ml of 37% hydrochloric acid are added to a solution of 2.63 g of (R)-1-(5-fluoro-2-methyl-2,3-dihydroindol-1-yl)-2-phenoxypropan-1-one: diastereoisomer B in 26.5 ml of ethanol.

The reaction medium is refluxed for 4 hours.

The reaction medium is concentrated under reduced pressure. The residue obtained is taken up with 250 ml of water. 2N sodium hydroxide is added until the pH=10. The medium is extracted with 200 ml of dichloromethane. After settling out, the organic phase is dried over magnesium sulfate, filtered, and then concentrated under reduced pressure. The residue obtained is purified on a silica cartridge: eluent: 90/10 heptane/ethyl acetate, so as to give 1.11 g of (−)-5-fluoro-2-methyl-2,3-dihydro-1H-indole in the form of a yellow oil, the characteristics of which are the following:

Mass spectrometry: method A

Retention time Tr (min)=0.24; [M+H]+: m/z 152;

OR=−7.9+/−0.4. C=3.023 mg/0.5 ml DMSO

Reference Example 5c 4,5-difluoro-2-methyl-2,3-dihydro-1H-indole

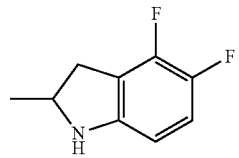

750 mg of sodium cyanoborohydride are gradually added to a solution of 1 g of 4,5-difluoro-2-methylindole in 20 ml of acetic acid under argon cooled to a temperature of about 5° C. The reaction mixture is stirred at ambient temperature for 3 hours and 5 ml of water are added. The mixture is then concentrated under reduced pressure and the residue is taken up in ethyl acetate, then treated with 60 ml of a saturated sodium hydrogen carbonate solution. After stirring for 1 hour and then settling out, the organic phase is separated and the aqueous phase is extracted with 50 ml of ethyl acetate. The organic phases are combined, washed with saturated brine, dried over anhydrous magnesium sulfate, filtered, and then concentrated to dryness under reduced pressure. The residue is purified by silica gel chromatography, elution being carried out with an 80/20 v/v heptane/ethyl acetate mixture. 0.37 g of 4-hydroxy-2-methylindoline is thus obtained in the form of a yellow oil, the characteristics of which are the following:

$^1$H NMR spectrum (400 MHz, CDCl$_3$): 1.17 (d, J=6.2 Hz, 3H); 2.54 (dd, J=7.7 and 16.0 Hz, 1H); 3.13 (dd, J=8.8 and 16.0 Hz, 1H); 3.94 (m, 1H); 5.75 (broad m, 1H); 6.17 (dd, J=3.5 and 8.6 Hz, 1H); 6.89 (td J=8.6 and 11.4 Hz, 1H)

Reference Example 6c 2-methyl-5,6-fluoro-2,3-dihydro-1H-indole

Step 1c 4,5-Difluoro-2-iodoaniline

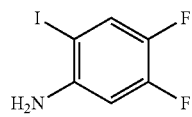

16.5 g of iodine and 6.3 g of sodium bicarbonate are added, at ambient temperature, to a suspension of 6.45 g of 3,4-difluoroaniline in 250 ml of water. The reaction medium is stirred at ambient temperature for 1 hour.

A saturated sodium thiosulfate solution is added and the mixture is then extracted 3 times with ethyl acetate. The organic phases are combined, dried over magnesium sulfate, filtered, and then concentrated under reduced pressure, so as to give 12 g of 4,5-difluoro-2-iodoaniline, the characteristics of which are the following:

Mass spectrometry: method A

Retention time Tr (min)=0.90;

[M+H]+: m/z 256; base peak: m/z 297

Step 2c 4,5-Difluoro-2-prop-1-ynylphenylamine

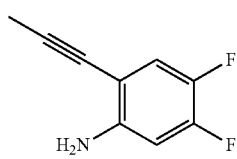

426 mg of copper(I) iodide and 523 mg of bis(triphenylphosphine)palladium(II)dichloride are added, at ambient temperature, to a solution of 19 g of 4,5-difluoro-2-iodoaniline in 150 ml of triethylamine. The suspension is cooled to −30° C. in a dry ice/ethanol bath. Furthermore, 20 ml of propyne are condensed by sparging in a trap cooled to −70° C. using a dry ice/methanol mixture. The propyne is added to the suspension cooled to −30° C. The cooling bath is kept. The temperature is allowed to rise to ambient temperature overnight.

The reaction medium is filtered. The filtrate is concentrated to dryness under reduced pressure. The residue obtained is taken up with water and with ethyl acetate. After settling out, the organic phase is dried over magnesium sulfate, filtered, and then concentrated under reduced pressure. The residue obtained is purified on a silica column, eluent: 80/20 cyclohexane/dichloromethane, so as to give 10.8 g of 4,5-difluoro-2-prop-1-ynylphenylamine, the characteristics of which are the following:

Mass spectrometry: method A
Retention time Tr (min)=0.90; [M+H]+: m/z 168

Step 3c 5,6-Difluoro-2-methylindole

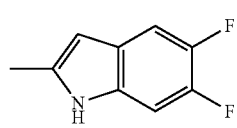

246 mg of copper(I) iodide are added to a solution of 10.8 g of 4,5-difluoro-2-prop-1-ynylphenylamine in 100 ml of DMF. The reaction medium is refluxed for one hour.

After cooling, the reaction medium is filtered. The filtrate is concentrated under reduced pressure. The crude residue obtained is purified on a silica column, eluent: 90/10 cyclohexane/dichloromethane, so as to give 7.2 g of 5,6-difluoro-2-methylindole, the characteristics of which are the following:

Mass spectrometry: method A
Retention time Tr (min)=0.94;
[M−H]−: m/z 166

Step 4c 5,6-Difluoro-2-methyl-2,3-dihydro-1H-indole

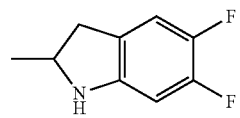

8.11 g of sodium cyanoborohydride are added, in 3 steps, to a solution of 7.2 g of 5,6-difluoro-2-methylindole in 220 ml of acetic acid cooled to 15° C. The reaction medium is stirred at 15° C. for 30 minutes and then at ambient temperature for 4 hours.

The reaction medium is again cooled to 5° C. 900 ml of ice-cold water are added. 30% aqueous ammonia is added until the pH=9. The mixture is extracted 3 times with dichloromethane. The organic phases are combined, dried over magnesium sulfate, filtered, and then concentrated under reduced pressure. The residue obtained is purified on a silica column, eluent: 90/10 heptane/ethyl acetate, so as to give 6.3 g of 5,6-difluoro-2-methyl-2,3-dihydro-1H-indole, the characteristics of which are the following:

Mass spectrometry: method A
Retention time Tr (min)=0.53;
[M+H]+: m/z 170;

Step 5c (R)-1-(5,6-Difluoro-2-methyl-2,3-dihydroindol-1-yl)-2-phenoxypropan-1-one: diastereoisomer A

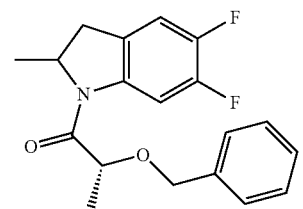 [SMILES: CC1Cc2cc(F)c(F)cc2N1C(=O)[C@@H](C)OCc1ccccc1]

And (R)-1-(5,6-Difluoro-2-methyl-2,3-dihydroindol-1-yl)-2-phenoxypropan-1-one: diastereoisomer B

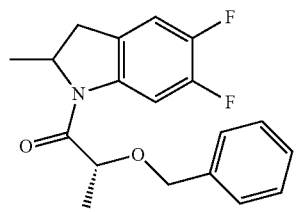 [SMILES: CC1Cc2cc(F)c(F)cc2N1C(=O)[C@@H](C)OCc1ccccc1]

The products are prepared by following the procedure described in reference example 1c (step 2c) using 6.3 g of 5,6-difluoro-2-methyl-2,3-dihydro-1H-indole and 6.8 g of o-benzyl-D-lactic acid. After silica column purification, 6.45 g of (R)-1-(5,6-difluoro-2-methyl-2,3-dihydroindol-1-yl)-2- phenoxypropan-1-one: diastereoisomer A are obtained in the form of a yellow oil, the characteristics of which are the following:
Mass spectrometry: method A
Retention time Tr (min)=1.11;
[M+H]+: m/z 332; base peak: m/z 260
And 6.29 g of (R)-1-(5,6-difluoro-2-methyl-2,3-dihydroindol-1-yl)-2-phenoxypropan-1-one: diastereoisomer B are obtained in the form of a white solid, the characteristics of which are the following:
Mass spectrometry: method A
Retention time Tr (min)=1.10;
[M+H]+: m/z 332; base peak: m/z 260

Step (6a)c (+)-5,6-Difluoro-2-methyl-2,3-dihydro-1H-indole

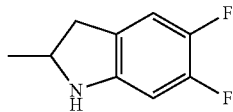

The product is prepared by following the procedure described in reference example 4c (step 3c) using 6.45 g of (R)-1-(5,6-difluoro-2-methyl-2,3-dihydroindol-1-yl)-2-phenoxypropan-1-one: diastereoisomer A and 64.5 ml of 37% hydrochloric acid.

After silica column purification, eluent: 90/10 heptane/ethyl acetate, 2.7 g of (+)-5,6-difluoro-2-methyl-2,3-dihydro-1H-indole are obtained, the characteristics of which are the following:
Mass spectrometry: method A
Retention time Tr (min)=0.53; [M+H]+: m/z 170;
Optical rotation: $\alpha_D$=+17.6+/−0.7. C=1.834 mg/0.5 ml DMSO Step (6b)c (−)-5,6-Difluoro-2-methyl-2,3-dihydro-1H-indole

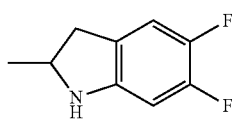

The product is prepared by following the procedure described in reference example 4c (step 3c) using 6.29 g of (R)-1-(5,6-difluoro-2-methyl-2,3-dihydroindol-1-yl)-2-phenoxypropan-1-one: diastereoisomer B and 63 ml of 37% hydrochloric acid.

After silica column purification, eluent: 90/10 heptane/ethyl acetate, 2.76 g of (−)-5,6-difluoro-2-methyl-2,3-dihydro-1H-indole are obtained, the characteristics of which are the following:
Mass spectrometry: method A
Retention time Tr (min)=0.55; [M+H]+: m/z 170;
Optical rotation: $\alpha_D$=−6.7+/−0.6. C=1.832 mg/0.5 ml DMSO Reference Example 7c 4-Bromo-2-methyl-2,3-dihydro-1H-indole

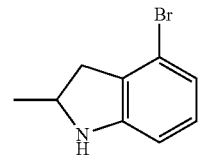

7.99 g of sodium cyanoborohydride are gradually added to a solution of 8.90 g of 4-bromo-2-methylindole (which can be prepared according to patent US2010/160647 A1, 2010) in 310 ml of acetic acid under argon cooled to a temperature of about 14° C. The reaction mixture is stirred at a temperature of about 14° C. for 15 minutes, and it is then allowed to warm up to ambient temperature. After 2 hours, the reaction mixture is poured into an Erlenmeyer flask containing ice-cold water (200 ml) and then the pH is brought to 9 with an aqueous ammonia solution. The reaction medium is extracted with dichloromethane (2×200 ml) and then the organic phases are combined, washed with water, dried over magnesium sulfate, filtered, and then concentrated to dryness under reduced pressure. After purification of the residue by silica column chromatography, elution being carried out with a mixture of heptane and ethyl acetate (90/10), 5.92 g of 4-bromo-2-methylindoline are obtained, the characteristics of which are the following:
$^1$H NMR spectrum (400 MHz): 1.18 (d, J=6.1 Hz, 3H); 2.47 (dd, J=7.9 and 16.0 Hz, 1H); 3.05 (dd, J=8.9 and 16.1 Hz, 1H); 3.84 to 3.97 (m, 1H); 5.98 (broad s, 1H); 6.39 (d, J=7.7 Hz, 1H); 6.62 (dd, J=0.8 and 8.0 Hz, 1H); 6.82 (t, J=7.9 Hz, 1H)

Reference Example 8c (+)-4-Fluoro-2-methyl-2,3-dihydro-1H-indole and (−)-4-fluoro-2-methyl-2,3-dihydro-1H-indole

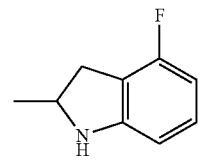

Step 1c 9.9 g of di-tert-butyl dicarbonate are added to a solution of 5 g of 3-fluoro-2-methylaniline in 25 ml of tetrahydrofuran. The reaction mixture is refluxed with stirring for 16 hours, and then is cooled to ambient temperature and concentrated to dryness under reduced pressure. The residue is triturated from 20 ml of cyclohexane and the precipitate obtained is filtered off through sintered glass, dried with suction and then dried under reduced pressure at 40° C. 7.1 g of tert-butyl (3-fluoro-2-methylphenyl)carbamate are thus obtained in the form of a shiny white solid, the characteristics of which are the following:
Mass spectrometry: EI: [M]+. m/z=225
method A
Retention time Tr (min)=1.04;
[M+H-tBu]+: m/z 170; base peak m/z: 211
Melting point (Kofler): 72° C.

Step 2c 4.3 ml of a 1.3M solution of sec-butyllithium in 98/2 v/v cyclohexane/hexane are added, dropwise, while maintaining the temperature between −40° C. and −30° C., to a solution of 0.5 g of tert-butyl (3-fluoro-2-methylphenyl)carbamate in 10 ml of tetrahydrofuran under argon and cooled to −40° C. The reaction mixture is then cooled to −50° C., and then a solution of 0.27 ml of N-methoxy-N-methylacetamide in 4 ml of tetrahydrofuran is added dropwise while maintaining the temperature between −50° C. and −40° C. The mixture is then allowed to warm up to approximately −10° C., and then stirred at this temperature for 0.5 hour. It is then treated with 5.6 ml of a 1N hydrochloric acid solution and then diluted with 20 ml of diethyl ether and allowed to warm up to ambient temperature with stirring for 1 hour. After settling out, the organic phase is separated and the aqueous phase is extracted with 40 ml of diethyl ether. The organic phases are combined, washed with 3×40 ml of water, dried over magnesium sulfate, filtered, and then concentrated to dryness under reduced pressure. The residue is purified by chromatography on a 30 g cartridge of 15-40 μm silica, elution being carried out with a 90/10 v/v cyclohexane/ethyl acetate mixture, at a flow rate of 30 ml/min, and then on a 30 g cartridge of 15-40 μm silica, elution being carried out with pure dichloromethane, at a flow rate of 30 ml/min. 0.38 g of tert-butyl [3-fluoro-2-(2-oxopropyl)phenyl]carbamate is thus obtained in the form of a white solid, the characteristics of which are the following:
Mass spectrometry: EI: [M]+. m/z=267
method A
Retention time Tr (min)=0.93;
[M+Na]+: m/z 290;

Step 3c 1.43 ml of trifluoroacetic acid are added to a solution of 0.35 g of tert-butyl [3-fluoro-2-(2-oxopropyl)phenyl]carbamate in 13 ml of anhydrous dichloromethane at ambient temperature. The reaction mixture is then stirred at ambient temperature for 24 h, and is then diluted with 27 ml of dichloromethane and treated with 25 ml of a 5% sodium hydrogen carbonate solution. After stirring at ambient temperature for 1 hour and then settling out, the organic phase is separated and the aqueous phase is extracted with 25 ml of dichloromethane. The organic phases are combined, washed with saturated brine, dried over magnesium sulfate, filtered, and then concentrated to dryness under reduced pressure. 0.19 g of 4-fluoro-2-methylindole is thus obtained in the form of a dark red-colored oil, the characteristics of which are the following:
$^1$H NMR spectrum (400 MHz, CDCl$_3$): 2.46 (s, 3H); 6.30 (broad m, 1H); 6.74 (dd, J=7.9 and 10.6 Hz, 1H); 7.02 (dt, J=4.9 and 7.9 Hz, 1H); 7.08 (d, J=7.9 Hz, 1H); 7.95 (broad m, 1H)
Mass spectrometry: EI: [M]+. m/z=149

Step 4c 3.63 g of sodium cyanoborohydride are gradually added to a solution of 2.87 g of 4-fluoro-2-methylindole in 98 ml of acetic acid under argon cooled to a temperature of about 14° C. The reaction mixture is allowed to warm up to ambient temperature. After 2 hours, the reaction mixture is poured into a mixture of water and ice, and is then treated with a 28% aqueous ammonia solution until the pH is 9. The mixture is then extracted twice with dichloromethane. The organic phases are combined, dried over anhydrous magnesium sulfate, filtered, and then concentrated to dryness under reduced pressure. The residue is purified on a 300 g silica column, elution being carried out with a 100/0 to 90/10 v/v heptane/ethyl acetate gradient. 2.19 g of 4-fluoro-2-methyl-2,3-dihydro-1H-indole are thus obtained in the form of a colorless oil, the characteristics of which are the following:
$^1$H NMR spectrum (400 MHz): 1.18 (d, J=6.3 Hz, 3H); 2.49 (partially masked dd, J=7.6 and 15.7 Hz, 1H); 3.08 (dd, J=9.0 and 15.7 Hz, 1H); 3.92 (m, 1H); 5.87 (broad s, 1H); 6.20 to 6.31 (m, 2H); 6.90 (td, J=5.9 and 8.1 Hz, 1H)
Mass spectrometry: method A
Retention time Tr (min)=0.50;
[M+H]+: m/z 152

Step 5c 0.69 ml of pyridine and 1.05 g of N-[3-(dimethylamino)propyl]-N'-ethylcarbodiimide hydrochloride are added to a solution of 0.76 g of o-benzyl-D-lactic acid in 3.5 ml of dimethylformamide under argon. The reaction mixture is stirred at ambient temperature for 10 minutes and then 0.64 g of 4-fluoro-2-methyl-2,3-dihydro-1H-indole is added. The reaction mixture is stirred at ambient temperature for 20 hours and is then treated with 20 ml of water and extracted with 3×15 ml of ethyl acetate. The organic phases are combined, washed with 15 ml of water, dried over magnesium sulfate, filtered, and then concentrated to dryness under reduced pressure. The residue is purified by chromatography on a 90 g cartridge of 15-40 μm silica, elution being carried out with pure dichloromethane, and then on a 100 g cartridge of 15-40 μm silica, elution being carried out with pure heptane and then with 95/5 then 90/10 v/v heptane/ethyl acetate mixtures, at a flow rate of 85 ml/min. 0.33 g of (R)-2-benzyloxy-1-(4-fluoro-2-methyl-2,3-dihydroindol-1-yl)propan-1-one diastereoisomer (1), in the form of a colorless oil, and 0.38 g of (R)-2-benzyloxy-1-(4-fluoro-2-methyl-2,3-dihydroindol-1-yl)propan-1-one diastereoisomer (2), in the form of a white solid, are thus obtained. A second trial under identical conditions using 1.85 g of o-benzyl-D-lactic acid and 1.55 g of 4-fluoro-2-methylindoline makes it possible to obtain 1.39 g of (R)-2-benzyloxy-1-(4-fluoro-2-methyl-2,3-dihydroindol-1-yl)propan-1-one diastereoisomer (1) in the form of a colorless oil and 1.34 g of (R)-2-benzyloxy-1-(4-fluoro-2-methyl-2,3-dihydroindol-1-yl)propan-1-one diastereoisomer (2) in the form of a white solid.

The two batches of (R)-2-benzyloxy-1-(4-fluoro-2-methyl-2,3-dihydroindol-1-yl)propan-1-one diastereoisomer (1) are combined and dissolved in 75 ml of ethyl acetate. The mixture is filtered through paper and then concentrated to dryness under reduced pressure. 1.66 g of (R)-2-benzyloxy-1-(4-fluoro-2-methyl-2,3-dihydroindol-1-yl)propan-1-one diastereoisomer (1) are thus obtained in the form of a very pale yellow viscous oil, the characteristics of which are the following:
$^1$H NMR spectrum (400 MHz): 1.18 (d, J=6.4 Hz, 3H); 1.39 (d, J=6.4 Hz, 3H); 2.71 (d, J=16.3 Hz, 1H); 3.29 (partially masked dd, J=8.8 and 16.3 Hz, 1H); 4.46 to 4.56 (m, 3H); 4.75 (m, 1H); 6.91 (t, J=8.7 Hz, 1H); 7.19 to 7.37 (m, 6H); 7.87 (broad m, 1H)
Mass spectrometry: method A
Retention time Tr (min)=1.09;
[M+H]+: m/z 314; [M+Na]+: m/z 336; base peak: m/z 242

The two batches of (R)-2-benzyloxy-1-(4-fluoro-2-methyl-2,3-dihydroindol-1-yl)propan-1-one diastereoisomer (2) are combined and dissolved in 75 ml of ethyl acetate. The mixture is filtered through paper and then concentrated to dryness under reduced pressure. 1.70 g of (R)-2-benzyloxy- 1-(4-fluoro-2-methyl-2,3-dihydroindol-1-yl)propan-1-one diastereoisomer (2) are thus obtained in the form of a white solid, the characteristics of which are the following:

¹H NMR spectrum (400 MHz): 1.18 (d, J=6.4 Hz, 3H); 1.40 (d, J=6.5 Hz, 3H); 2.72 (d, J=16.4 Hz, 1H); 3.28 to 3.37 (partially masked m, 1H); 4.40 to 4.57 (m, 3H); 4.66 (m, 1H); 6.90 (dt, J=0.8 and 8.8 Hz, 1H); 7.20 to 7.39 (m, 6H); 7.91 (broad m, 1H)

Mass spectrometry: method A
Retention time Tr (min)=1.08;
[M+H]+: m/z 314; [M+Na]+: m/z 336; base peak: m/z 242

Step 6c 8 ml of concentrated hydrochloric acid are added to a solution of 1.66 g of (R)-2-benzyloxy-1-(4-fluoro-2-methyl-2,3-dihydroindol-1-yl)propan-1-one diastereoisomer (1) in 200 ml of absolute ethanol. The reaction mixture is refluxed with stirring for 40 hours and is then cooled to ambient temperature and concentrated to dryness under reduced pressure. The residue is taken up in 250 ml of water, alkalinized with concentrated sodium hydroxide until the pH is 14, and then the mixture is extracted with 3×200 ml of dichloromethane. The organic phases are combined, washed with water, dried over magnesium sulfate, filtered, and then concentrated to dryness under reduced pressure. The residue is purified by chromatography on a 70 g cartridge of 15-40 μm silica, elution being carried out with pure heptane and then with a 95/5 heptane/ethyl acetate mixture at a flow rate of 50 ml/min, and then on a 70 g cartridge of 15-40 μm silica, elution being carried out with pure cyclohexane and then with a 70/30 cyclochexane/dichloromethane mixture, at a flow rate of 50 ml/min. 0.50 g of (+)-4-fluoro-2-methylindoline is thus obtained in the form of a colorless oil, the characteristics of which are the following:

¹H NMR spectrum (400 MHz): 1.18 (d, J=6.4 Hz, 3H); 2.49 (partially masked dd, J=7.6 and 15.7 Hz, 1H); 3.08 (dd, J=8.8 and 15.7 Hz, 1H); 3.92 (m, 1H); 5.87 (broad s, 1H); 6.21 to 6.28 (m, 2H); 6.90 (dt, J=5.9 and 8.1 Hz, 1H)

Mass spectrometry: method A
Retention time Tr (min)=0.48;
[M+H]+: m/z 152
Optical rotation: $\alpha_D$=+40.8°+/−0.9 (c=2.223 mg in 0.5 ml of DMSO)

Step 6c 8.2 ml of concentrated hydrochloric acid are added to a solution of 1.69 g of (R)-2-benzyloxy-1-(4-fluoro-2-methyl-2,3-dihydroindol-1-yl)propan-1-one diastereoisomer (2) in 200 ml of absolute ethanol. The reaction mixture is refluxed with stirring for 40 hours and is then cooled to ambient temperature and concentrated to dryness under reduced pressure. The residue is taken up in 200 ml of water, alkalinized with concentrated sodium hydroxide until the pH is 14, and then the mixture is extracted with 3×200 ml of dichloromethane. The organic phases are combined, washed with water, dried over magnesium sulfate, filtered, and then concentrated to dryness under reduced pressure. The residue is purified by chromatography on a 70 g cartridge of 15-40 μm silica, elution being carried out with pure cyclohexane and then with a 70/30 cyclochexane/dichloromethane mixture, at a flow rate of 50 ml/min. 0.56 g of (−)-4-fluoro-2-methylindoline is thus obtained in the form of a very pale yellow oil, the characteristics of which are the following:

¹H NMR spectrum (400 MHz): 1.18 (d, J=6.2 Hz, 3H); 2.49 (partially masked dd, J=7.6 and 15.7 Hz, 1H); 3.08 (dd, J=9.0 and 15.7 Hz, 1H); 3.92 (m, 1H); 5.87 (broad s, 1H); 6.20 to 6.29 (m, 2H); 6.90 (dt, J=5.9 and 8.1 Hz, 1H)

Mass spectrometry: method A
Retention time Tr (min)=0.49;
[M+H]+: m/z 152
Optical rotation: $\alpha_D$=−33.7°+/−0.7 (c=2.741 mg in 0.5 ml of DMSO)

Reference Example 9c

6-Fluoro-2-methyl-2,3-dihydro-1H-indole

Step 1c

5-Fluoro-2-prop-1-ynylphenylamine

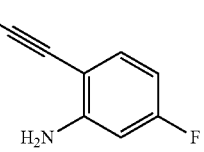

121 mg of copper(1) iodide and 148 mg of bis(triphenylphosphine)palladium(II)dichloride are added, at ambient temperature, to a solution of 5 g of 5-fluoro-2-iodoaniline in 150 ml of triethylamine. The suspension is cooled to −30° C. in a dry ice/ethanol bath. Furthermore, 10 ml of propyne are condensed by sparging in a trap cooled to −70° C. using a dry ice/methanol mixture. The propyne is added to the suspension cooled to −30° C. The cooling bath is kept. The temperature is allowed to rise to ambient temperature overnight.

The reaction medium is filtered. The filtrate is concentrated to dryness under reduced pressure. The residue obtained is taken up with water and with ethyl acetate. After settling out, the organic phase is dried over magnesium sulfate, filtered, and then concentrated under reduced pressure. The residue obtained is purified on a silica column, eluent: 95/05 cyclohexane/ethyl acetate, so as to give 1.7 g of 5-difluoro-2-prop-1-ynylphenylamine, the characteristics of which are the following:

Mass spectrometry: method A
Retention time Tr (min)=0.84;
[M+H]+: m/z 150;

Step 2c

6-Difluoro-2-methylindole

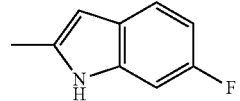

43 mg of copper(I) iodide are added to a solution of 1.7 g of 5-difluoro-2-prop-1-ynylphenylamine in 50 ml of DMF. The reaction medium is refluxed for one hour.

After cooling, the reaction medium is filtered. The filtrate is concentrated under reduced pressure. The crude residue obtained is purified on a silica column, eluent: 90/10 cyclohexane/ethyl acetate, so as to give 1.1 g of 6-fluoro-2-methylindole, the characteristics of which are the following:

Mass spectrometry: method A
Retention time Tr (min)=0.89; [M+H]+: m/z 150;

Step 3c

6-Fluoro-2-methyl-2,3-dihydro-1H-indole

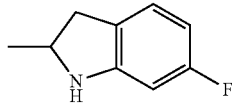

The product is prepared by following the procedure described in reference example 2c (step 1c) using 1.4 g of 6-fluoro-2-methylindole, 51 ml of acetic acid and 1.9 g of sodium cyanoborohydride. After silica column purification, eluent: 90/10 heptane/ethyl acetate, 1.33 g of 6-fluoro-2-methyl-2,3-dihydro-1H-indole are obtained, which is used as it is in the next step.

Step 4c (R)-1-(6-Fluoro-2-methyl-2,3-dihydroindol-1-yl)-2-phenoxypropan-1-one: diastereoisomer A

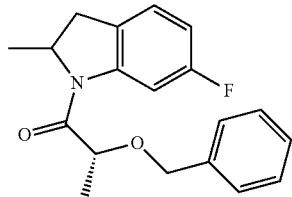

And (R)-1-(6-Fluoro-2-methyl-2,3-dihydroindol-1-yl)-2-phenoxypropan-1-one: diastereoisomer B

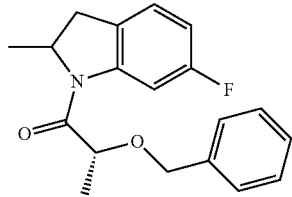 [SMILES: CC1Cc2ccc(F)cc2N1C(=O)[C@@H](C)OCc1ccccc1]

The products are prepared by following the procedure described in reference example 1c (step 2c) using 1.33 g of 6-fluoro-2-methyl-2,3-dihydro-1H-indole and 2.1 g of o-benzyl-D-lactic acid. After silica column purification, 1.3 g of (R)-1-(6-fluoro-2-methyl-2,3-dihydroindol-1-yl)-2-phenoxypropan-1-one: diastereoisomer A are obtained, the characteristics of which are the following:
Mass spectrometry: method A
Retention time Tr (min)=1.09;
[M+H]+: m/z 314; base peak: m/z 242
And 1.13 g of (R)-1-(6-fluoro-2-methyl-2,3-dihydroindol-1-yl)-2-phenoxypropan-1-one: diastereoisomer B are obtained in the form of a white solid, the characteristics of which are the following:
Mass spectrometry: method A
Retention time Tr (min)=1.08;
[M+H]+: m/z 314; [M+Na]+: m/z 336; base peak: m/z 242

Step (5a)c (+)-6-Fluoro-2-methyl-2,3-dihydro-1H-indole

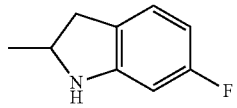

The product is prepared by following the procedure described in reference example 1c (step 3c) using 1.3 g of (R)-1-(6-fluoro-2-methyl-2,3-dihydroindol-1-yl)-2-phenoxypropan-1-one: diastereoisomer A and 13 ml of 37% hydrochloric acid.
After treatment, 547 mg of (+)-6-fluoro-2-methyl-2,3-dihydro-1H-indole are obtained, the characteristics of which are the following:
Mass spectrometry: method A
Retention time Tr (min)=0.48; [M+H]+: m/z 152;
Optical rotation: $\alpha_D$=+35.0+/−0.7. C=2.899 mg/0.5 ml DMSO Step (5b)c (−)-6-Fluoro-2-methyl-2,3-dihydro-1H-indole

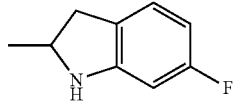

The product is prepared by following the procedure described in reference example 1c (step 3c) using 1.13 g of (R)-1-(6-fluoro-2-methyl-2,3-dihydroindol-1-yl)-2-phenoxypropan-1-one: diastereoisomer B and 12 ml of 37% hydrochloric acid.
After treatment, 540 mg of (R)-6-fluoro-2-methyl-2,3-dihydroindol-1-yl)-2-phenoxypropan-1-one are obtained, the characteristics of which are the following:
Mass spectrometry: method A
Retention time Tr (min)=0.48; [M+H]+: m/z 152;
Optical rotation: $\alpha_D$=−32.6+/−1.0. C=1.506 mg/0.5 ml DMSO Reference Example 10c 4-chloro-5-fluoro-2-methyl-2,3-dihydro-1H-indole Step 1c 3-Chloro-4-fluoro-2-iodoaniline

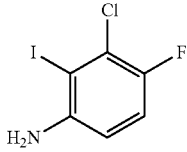

113.3 g of iodine and 43.3 g of sodium bicarbonate are added, at ambient temperature, to a suspension of 50 g of 3-chloro-4-fluoroaniline in 800 ml of water. The reaction medium is stirred at ambient temperature for 18 hours.
A saturated sodium thiosulfate solution is added and then the mixture is extracted 3 times with ethyl acetate. The organic phases are combined, dried over magnesium sulfate, filtered, and then concentrated under reduced pressure. The residue obtained is purified on a silica column, eluent: 95/05 then 85/15 cyclohexane/ethyl acetate, so as to give 40.9 g of 5-chloro-4-fluoro-2-iodoaniline, the characteristics of which are the following:

$^1$H NMR spectrum (400 MHz): 5.29 (broad s, 2H); 6.87 (d, J=6.9 Hz, 1H); 7.61 (d, J=8.8 Hz, 1H)
Mass spectrometry: method A
Retention time Tr (min)=0.99;
[M+H]+: m/z 272; base peak: m/z 313
and 12.5 g of 3-chloro-4-fluoro-2-iodoaniline, the characteristics of which are the following:
$^1$H NMR spectrum (400 MHz): 5.38 (broad s, 2H); 6.76 (dd, J=4.8 and 8.9 Hz, 1H); 7.16 (t, J=8.9 Hz, 1H)
Mass spectrometry: method A
Retention time Tr (min)=0.95;
[M+H]+: m/z 271

Step 2c

3-Chloro-4-fluoro-2-prop-1-ynylphenylamine

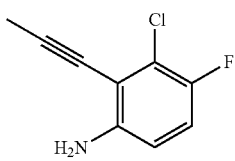

364 mg of copper(I) iodide and 470 mg of bis(triphenylphosphine)palladium(II)dichloride are added, at ambient temperature, to a solution of 9 g of 3-chloro-4-fluoro-2-iodoaniline in 160 ml of triethylamine. The suspension is cooled to −30° C. in a dry ice/ethanol bath. Furthermore, approximately 20 ml of propyne are condensed by sparging in a trap cooled to −70° C. using a dry ice/methanol mixture. The propyne is added to the suspension cooled to −30° C. The cooling bath is kept. The temperature is allowed to rise to ambient temperature overnight.

The reaction medium is filtered. The filtrate is concentrated to dryness under reduced pressure. The residue obtained is purified on a silica column, eluent: 90/10 heptane/ethyl acetate, so as to give 1.76 g of 3-chloro-4-fluoro-2-prop-1-ynylphenylamine, the characteristics of which are the following:

Mass spectrometry: method A
Retention time Tr (min)=0.92;
[M+H]+: m/z 184; base peak: m/z 149

Step 3c

4-Chloro-5-fluoro-2-methylindole

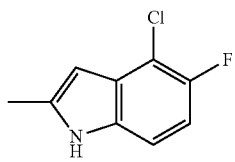

32 mg of copper(I) iodide are added to a solution of 1.56 g of 3-chloro-4-fluoro-2-prop-1-ynylphenylamine in 17 ml of DMF. The reaction medium is refluxed for 45 minutes.

After cooling, the reaction medium is filtered. The filtrate is concentrated under reduced pressure. The crude residue obtained is purified on a silica column, eluent: 70/30 heptane/toluene, so as to give 0.5 g of 4-chloro-5-fluoro-2-methylindole, the characteristics of which are the following:

Mass spectrometry: method A
Retention time Tr (min)=1.01;
[M−H]−: m/z 182

Step 4c

4-Chloro-5-fluoro-2-methyl-2,3-dihydro-1H-indole

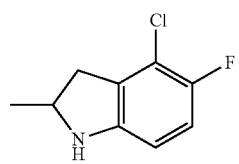

719 mg of sodium cyanoborohydride are added, in one step, to a solution of 700 mg of 4-chloro-5-fluoro-2-methylindole in 16 ml of acetic acid cooled to 15° C. The reaction medium is stirred at 15° C. for 10 minutes and then at ambient temperature for 90 minutes.

The reaction medium is again cooled to 5° C. Ice-cold water is added. 30% aqueous ammonia is added until the pH=9. The mixture is extracted with ethyl acetate. The organic phase is dried over magnesium sulfate, filtered, and then concentrated under reduced pressure, so as to give 683 mg of 4-chloro-5-fluoro-2-methyl-2,3-dihydro-1H-indole, the characteristics of which are the following:

Mass spectrometry: method A
Retention time Tr (min)=0.75;
[M+H]+: m/z 186;

Reference Example 11c

Synthesis of (−)-2-isopropylindoline

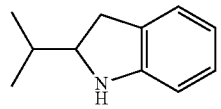

Step 1c 4.65 g of sodium cyanoborohydride are gradually added to a solution of 5.0 g of 2-isopropylindole in 50 ml of acetic acid under argon cooled to a temperature of about 15° C. The reaction mixture is stirred at a temperature of about 15° C. for 2 hours and is then treated with 25 ml of water. It is then cooled to a temperature of about 5° C. and alkalinized by gradual addition of powdered sodium hydroxide. The reaction mixture is allowed to warm up to ambient temperature and is then stirred for 16 hours. The precipitate is filtered off through sintered glass and washed with 50 ml of water and then 50 ml of ethyl acetate. The filtrate is diluted with 50 ml of water and 70 ml of ethyl acetate and then separated by settling out. The organic phase is separated and the aqueous phase is extracted with 2×100 ml of ethyl acetate. The organic phases are combined, washed with saturated brine, dried over anhydrous magnesium sulfate, filtered, and then concentrated to dryness under reduced pressure. The residue is purified by chromatography on a 90 g cartridge of 15-40 μm silica, elution being carried out with a 95/5 v/v cyclohexane/ethyl acetate mixture, at a flow rate of 50 ml/min. 4.0 g of (±)-2-isopropylindoline are thus obtained in the form of a colorless oil which crystallizes into a white solid, the characteristics of which are the following:

Mass spectrometry: method A
Retention time Tr (min)=0.41;
[M+H]+: m/z 162

Step 2c 3.9 ml of pyridine and 6.15 g of N-[3-(dimethylamino)propyl]-N'-ethylcarbodiimide hydrochloride are added to a solution of 4.36 g of o-benzyl-D-lactic acid in 17 ml of N,N-dimethylformamide under argon. The reaction mixture is stirred at ambient temperature for 15 minutes, and then a solution of 3.9 g of (±)-2-isopropylindoline in 3 ml of N,N-dimethylformamide is added. The reaction mixture is stirred at ambient temperature for 16 hours and is then poured into a mixture of 100 ml of water and 80 ml of ethyl acetate and separated by settling out. The organic phase is separated and the aqueous phase is extracted with 2×80 ml of ethyl acetate. The organic phases are combined, washed with 60 ml of water, dried over magnesium sulfate, filtered, and then concentrated to dryness under reduced pressure. The residue is purified by chromatography on a 400 g cartridge of 15-40 μm silica, elution being carried out with pure heptane, and then with a 95/5 v/v heptane/ethyl acetate mixture, at a flow rate of 100 ml/min. 3.20 g of (R)-2-benzyloxy-1-(2-isopropyl-2,3-dihydroindol-1-yl)propan-1-one diastereoisomer (1) are thus obtained in the form of a very pale yellow oil, the characteristics of which are the following:

$^1$H NMR spectrum (400 MHz): 0.52 (broad d, J=6.8 Hz, 3H); 0.81 (d, J=6.8 Hz, 3H); 1.37 (d, J=6.4 Hz, 3H); 1.84 (broad m, 1H); 2.84 (d, J=16.6 Hz, 1H); 3.10 (dd, J=9.7 and 16.6 Hz, 1H); 4.27 to 4.57 (m, 4H); 7.01 (dt, J=1.3 and 7.8 Hz, 1H); 7.15 (t, J=7.8 Hz, 1H); 7.22 (d, J=7.8 Hz, 1H); 7.25 to 7.38 (m, 5H); 8.01 (broad m, 1H)
Mass spectrometry: method A
Retention time Tr (min)=1.15;
[M+H]+: m/z 324; [M+Na]+: m/z 346 and 3.55 g of (R)-2-benzyloxy-1-(2-isopropyl-2,3-dihydroindol-1-yl)propan-1-one diastereoisomer (2) are thus obtained in the form of a colorless oil, the characteristics of which are the following:

$^1$H NMR spectrum (400 MHz): for this batch, all the signals are broad with: 0.53 (d, J=6.8 Hz, 3H); 0.83 (d, J=6.8 Hz, 3H); 1.40 (d, J=6.4 Hz, 3H); 1.86 (m, 1H); 2.87 (d, J=16.6 Hz, 1H); 3.19 (dd, J=9.7 and 16.6 Hz, 1H); 4.24 to 4.62 (m, 4H); 7.01 (t, J=7.8 Hz, 1H); 7.15 (t, J=7.8 Hz, 1H); 7.22 (d, J=7.8 Hz, 1H); 7.25 to 7.42 (m, 5H); 8.06 (d, J=7.8 Hz, 1H)
Mass spectrometry: method A
Retention time Tr (min)=1.13;
[M+H]+: m/z 324; [M+Na]+: m/z 346

Step 3c 5.6 ml of concentrated hydrochloric acid are added to a solution of 1.2 g of (R)-2-benzyloxy-1-(2-isopropyl-2,3-dihydroindol-1-yl)propan-1-one in 34 ml of absolute ethanol. The reaction mixture is microwave-heated at 120° C. for 1 hour, and is then cooled to ambient temperature and concentrated to dryness under reduced pressure. The residue is cooled in an ice bath and taken up in 200 ml of water, and then alkalinized with concentrated sodium hydroxide. The mixture is extracted with 2×150 ml of dichloromethane. The organic phases are combined, washed with 150 ml of water, dried over magnesium sulfate, filtered, and then concentrated to dryness under reduced pressure. The residue is purified by chromatography on a 70 g cartridge of 15-40 μm silica, elution being carried out with a 95/5 v/v cyclohexane/ethyl acetate mixture at a flow rate of 50 ml/min, and then on a 30 g cartridge of 15-40 μm silica, elution being carried out with pure cyclohexane and then with a 98/2 cyclohexane/ethyl acetate mixture, at a flow rate of 30 ml/min. 0.40 g of (−)-2-isopropylindoline is thus obtained in the form of a colorless oil, the characteristics of which are the following:

$^1$H NMR spectrum (400 MHz): 0.87 (d, J=6.8 Hz, 3H); 0.92 (d, J=6.8 Hz, 3H); 1.64 (m, 1H); 2.58 (dd, J=9.6 and 15.8 Hz, 1H); 2.95 (dd, J=9.0 and 15.8 Hz, 1H); 3.46 (m, 1H); 5.62 (broad d, J=3.3 Hz, 1H); 6.35 to 6.49 (m, 2H); 6.85 (t, J=7.5 Hz, 1H); 6.94 (d, J=7.5 Hz, 1H)
Mass spectrometry: method A
Retention time Tr (min)=0.41;
[M+H]+: m/z 162
Optical rotation: $\alpha_D$=−17.7°+/−0.6 (c=0.5% in DMSO)

Reference Example 12c

Synthesis of (+)-2-isopropylindoline

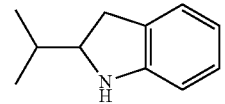

Step 1c 5.6 ml of concentrated hydrochloric acid are added to a solution of 1.2 g of (R)-2-benzyloxy-1-(2-isopropyl-2,3-dihydroindol-1-yl)propan-1-one diastereoisomer (2) in 34 ml of absolute ethanol. The reaction mixture is microwave-heated at 120° C. for 1 hour, and is then cooled to ambient temperature and concentrated to dryness under reduced pressure. The residue is taken up in 100 ml of water and is then alkalinized with concentrated sodium hydroxide. The mixture is extracted with 2×120 ml of dichloromethane. The organic phases are combined, washed with water, dried over magnesium sulfate, filtered, and then concentrated to dryness under reduced pressure. The residue is purified by chromatography on a 70 g cartridge of 15-40 μm silica, elution being carried out with pure cyclohexane and then with a 95/5 v/v cyclohexane/ethyl acetate mixture at a flow rate of 50 ml/min, and then on a 30 g cartridge of 15-40 μm silica, elution being carried out with a 98/2 cyclohexane/ethyl acetate mixture, at a flow rate of 30 ml/min. 0.26 g of (+)-2-isopropylindoline is thus obtained in the form of a colorless oil, the characteristics of which are the following:

$^1$H NMR spectrum (400 MHz): 0.87 (d, J=6.8 Hz, 3H); 0.92 (d, J=6.8 Hz, 3H); 1.63 (m, 1H); 2.57 (dd, J=9.6 and 15.8 Hz, 1H); 2.95 (dd, J=9.0 and 15.8 Hz, 1H); 3.47 (m, 1H); 5.65 (broad d, J=3.3 Hz, 1H); 6.39 to 6.51 (m, 2H); 6.86 (t, J=7.5 Hz, 1H); 6.94 (d, J=7.5 Hz, 1H)
Mass spectrometry: method A
Retention time Tr (min)=0.41;
[M+H]+: m/z 162
Optical rotation: $\alpha_D$=+26.9°+/−0.9 (c=0.5% in DMSO)

Synthesis of the Compounds of Formula (Id)

Example 1d

Synthesis of 6-(morpholin-4-yl)-2-[2-oxo-2-(spiro[cyclopropan-1,3'-indol]-1'(2'H)-yl)ethyl]pyrimidin-4(3H)-one

Step 1d

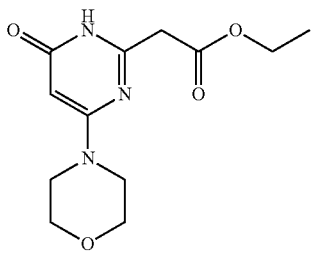 [SMILES: CCOC(=O)Cc1nc(N2CCOCC2)cc(=O)[nH]1]

168.5 ml of ethyl 3-ethoxy-3-iminopropanoate hydrochloride and then 155 ml of N,N-diisopropylamine in 200 ml of ethanol are added to a solution of 25 g of morpholine in 400 ml of ethanol, heated to 95° C. The reaction mixture is heated at 95° C. for 30 hours and then allowed to return to ambient temperature. The precipitate formed is filtered off through sintered glass and then washed with 100 ml of ethanol, twice 500 ml of water and, finally, 500 ml of ethyl ether. The solid is dried under vacuum so as to give 35 g of ethyl [4-(morpholin-4-yl)-6-oxo-1,6-dihydropyrimidin-2-yl]acetate in the form of a white solid, the characteristics of which are the following:

$^1$H NMR spectrum (400 MHz, δ in ppm, DMSO-d6): 1.19 (t, J=7.1 Hz, 3H); 3.38 to 3.44 (m, 4H); 3.56 (s, 2H); 3.61 (dd, J=4.0 and 5.7 Hz, 4H); 4.12 (q, J=7.1 Hz, 2H); 5.20 (s, 1H); 11.69 (broad s, 1H)

Mass spectrometry: method A
Retention time Tr (min)=0.48;
[M+H]+: m/z 268; [M−H]−: m/z 266

Step 2d

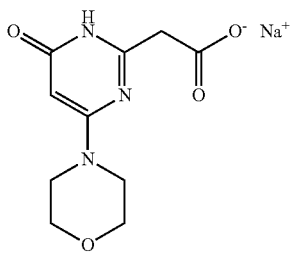 [SMILES: O=C([O-])Cc1nc(N2CCOCC2)cc(=O)[nH]1 ; [Na+]]

18.7 ml of 2M sodium hydroxide are added to a solution of 10 g of ethyl [4-(morpholin-4-yl)-6-oxo-1,6-dihydropyrimidin-2-yl]acetate in 300 ml of tetrahydrofuran. The reaction mixture is stirred for 48 hours at ambient temperature. The precipitate formed is filtered off through sintered glass, washed with ethyl acetate and rinsed several times with ethyl ether. The solid obtained is then dried in a rotary evaporator so as to give 8.7 g of sodium [4-(morpholin-4-yl)-6-oxo-1,6-dihydropyrimidin-2-yl]acetate in the form of a white solid, the characteristics of which are the following:

$^1$H NMR spectrum (400 MHz, δ in ppm, DMSO-d6): 3.08 (s, 2H); 3.38 (t, J=4.6 Hz, 4H); 3.61 (t, J=4.6 Hz, 4H); 5.08 (s, 1H); 13.16 (broad s, 1H)

Mass spectrometry: method A
Retention time Tr (min)=0.29;
[M+H]+: m/z 240; [M−H]−: m/z 238

Step 3d

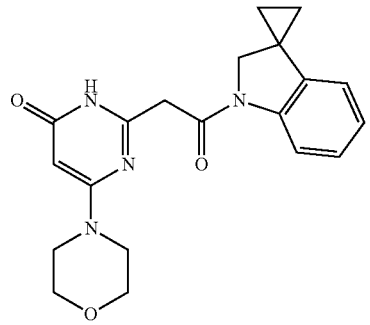 [SMILES: O=C(Cc1nc(N2CCOCC2)cc(=O)[nH]1)N1CC2(CC2)c2ccccc21]

0.14 ml of pyridine and 216 mg of N-[3-(dimethylamino)propyl]-N'-ethylcarbodiimide hydrochloride are successively added to a suspension of 222 mg of sodium [4-(morpholin-4-yl)-6-oxo-1,6-dihydropyrimidin-2-yl]acetate obtained in the previous step (example 1d, step 2d) in 1 ml of N,N-dimethylformamide. After stirring at ambient temperature for 10 minutes, a solution of 136 mg of 1,2-dihydro-3-spiro-1'-cyclopropyl-1H-indole (which can be prepared according to U.S. Pat. No. 7,507,748 B2 (2009)) in 4 ml of N,N-dimethylformamide is added. The reaction mixture is stirred at ambient temperature for 65 hours, and then 13 ml of water and 26 ml of ethyl acetate are added. After stirring for 1 hour, the precipitate formed is filtered off, and then rinsed successively with water (2×8 ml) and diethyl ether (3×12 ml). After drying under reduced pressure at 40° C., 208 mg of 6-(morpholin-4-yl)-2-[2-oxo-2-(spiro[cyclopropan-1,3'-indol]-1'(2'H)-yl)ethyl]pyrimidin-4(3H)-one are obtained in the form of a pink-colored crystalline powder, the characteristics of which are the following:

$^1$H NMR spectrum (400 MHz): 1.02 to 1.14 (m, 4H); 3.42 (m, 4H); 3.60 (m, 4H); 3.71 (s, 2H); 4.17 (s, 2H); 5.21 (s, 1H); 6.82 (d, J=7.8 Hz, 1H); 6.99 (t, J=7.8 Hz, 1H); 7.13 (t, J=7.8 Hz, 1H); 8.01 (d, J=7.8 Hz, 1H); 11.60 (broad s, 1H)

Mass spectrometry: method A
Retention time Tr (min)=0.74;
[M+H]+: m/z 367; [M−H]−: m/z 365
Melting point (Kofler): above 260° C.

Example 2d

Synthesis of 6-(morpholin-4-yl)-2-[2-oxo-2-(4-phenyl-2,3-dihydro-1H-indol-1-yl)ethyl]pyrimidin-4(3H)-one

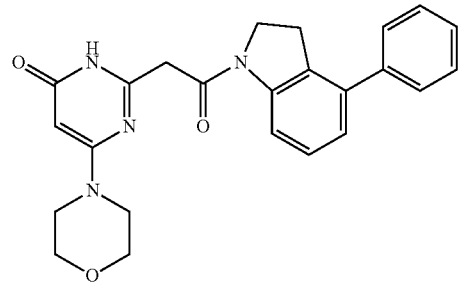 [SMILES: O=C(Cc1nc(N2CCOCC2)cc(=O)[nH]1)N1CCc2c(-c3ccccc3)cccc21]

0.16 ml of pyridine, 240 mg of N-[3-(dimethylamino)propyl]-N'-ethylcarbodiimide hydrochloride and 210 mg of 4-phenyl-2,3-dihydro-1H-indole (reference example 1d) are successively added to a suspension of 250 mg of sodium [4-(morpholin-4-yl)-6-oxo-1,6-dihydropyrimidin-2-yl]acetate (example 1d, step 2d) in 5 ml of N,N-dimethylformamide. The reaction mixture is stirred at ambient temperature for 15 hours, and is then concentrated to dryness under reduced pressure. The residue is taken up in and triturated from 30 ml of water, and then the precipitate formed is filtered off and then solubilized in a 90/10 dichloromethane/methanol mixture and, finally, concentrated to dryness under reduced pressure. The residue is purified by chromatography on a 30 g column of 20-45 µm silica, elution being carried out with a mixture of dichloromethane and methanol (90/10: v/v). The fractions containing the expected product are concentrated to dryness under reduced pressure and the residue is triturated from 20 ml of diisopropyl ether. The solid obtained is filtered off and then dried under reduced pressure at 40° C. 232 mg of 6-(morpholin-4-yl)-2-[2-oxo-2-(4-phenyl-2,3-dihydro-1H-indol-1-yl)ethyl]pyrimidin-4(3H)-one are thus obtained in the form of a pink solid, the characteristics of which are the following:

$^1$H NMR spectrum (400 MHz): 3.22 (t, J=8.7 Hz, 2H); 3.42 (m, 4H); 3.61 (m, 4H); 3.78 (s, 2H); 4.14 (t, J=8.7 Hz, 2H); 5.21 (s, 1H); 7.07 (d, J=7.8 Hz, 1H); 7.28 (t, J=7.8 Hz, 1H); 7.36 to 7.51 (m, 5H); 8.08 (d, J=7.8 Hz, 1H); 11.62 (broad s, 1H)

Mass spectrometry: method A
Retention time Tr (min)=0.89;
[M+H]+: m/z 417; [M−H]−: m/z 415
Melting point (Kofler): 266° C.

Example 3d

Synthesis of 6-(morpholin-4-yl)-2-{2-oxo-2-[4-(trifluoromethoxy)-2,3-dihydro-1H-indol-1-yl]ethyl}pyrimidin-4(3H)-one

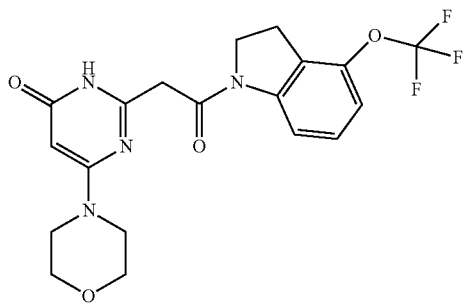 [SMILES: O=C(Cc1nc(N2CCOCC2)cc(=O)[nH]1)N1CCc2c(OC(F)(F)F)cccc21]

70 µl of pyridine and 107 mg of N-[3-(dimethylamino)propyl]-N'-ethylcarbodiimide hydrochloride are successively added to a solution of 110 mg of sodium [4-(morpholin-4-yl)-6-oxo-1,6-dihydropyrimidin-2-yl]acetate (example 1d, step 2d) in 1 ml of N,N-dimethylformamide. After stirring at ambient temperature for 10 minutes, a solution of 178 mg of 4-(trifluoromethoxy)indoline (reference example 2d) in 1 ml of N,N-dimethylformamide is added. The reaction mixture is stirred at ambient temperature for 23 hours, and then 13 ml of water and 6 ml of ethyl acetate are added. After stirring at ambient temperature for 2 hours, the precipitate formed is filtered off, and then rinsed successively with water (2×4 ml) and with diethyl ether (3×6 ml). After drying under reduced pressure at 40° C., 97 mg of 6-(morpholin-4-yl)-2-{2-oxo-2-[4-(trifluoromethoxy)-2,3-dihydro-1H-indol-1-yl]ethyl}pyrimidin-4(3H)-one are obtained in the form of a white crystalline powder, the characteristics of which are the following:

$^1$H NMR spectrum (400 MHz): 3.21 (t, J=8.6 Hz, 2H); 3.41 (m, 4H); 3.60 (m, 4H); 3.77 (s, 2H); 4.22 (t, J=8.6 Hz, 2H); 5.21 (s, 1H); 7.02 (d, J=8.1 Hz, 1H); 7.32 (t, J=8.1 Hz, 1H); 8.02 (d, J=8.1 Hz, 1H); 11.62 (broad s, 1H)

Mass spectrometry: method A
Retention time Tr (min)=0.85;
[M+H]+: m/z 425; [M−H]−: m/z 423
Melting point (Kofler): above 260° C.

Example 4d

Synthesis of 3-methyl-6-(morpholin-4-yl)-2-{2-oxo-2-[4-(trifluoromethyl)-2,3-dihydro-1H-indol-1-yl]ethyl}pyrimidin-4(3H)-one Step 1d

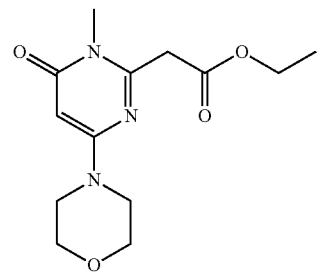 [SMILES: CCOC(=O)Cc1nc(N2CCOCC2)cc(=O)n1C]

330 mg of potassium carbonate and 0.15 ml of methyl iodide are added to a solution of 500 mg of ethyl [4-(morpholin-4-yl)-6-oxo-1,6-dihydropyrimidin-2-yl]acetate (prepared in step 1d of example 1d) in 1.5 ml of dioxane. The reaction mixture is heated at 40° C. for 16 hours and then cooled to ambient temperature. The suspension is filtered through sintered glass and then rinsed with dioxane, and the filtrate is concentrated under reduced pressure. The residue is purified by chromatography on a silica column, elution being carried out with a mixture of dichloromethane, acetonitrile and methanol (98/01/01, 96/02/02, then 90/05/05 V/V/V). 200 mg of ethyl [1-methyl-4-(morpholin-4-yl)-6-oxo-1,6-dihydropyrimidin-2-yl]acetate are obtained in the form of a white solid, the characteristics of which are the following:

$^1$H NMR spectrum (400 MHz): 1.21 (t, J=7.1 Hz, 3H); 3.29 (partially masked m, 3H); 3.40 (m, 4H); 3.61 (m, 4H); 3.92 (s, 2H); 4.15 (q, J=7.1 Hz, 2H); 5.35 (s, 1H)

Mass spectrometry: method A
Retention time Tr (min)=0.53;
[M+H]+: m/z 282; [M−H]−: m/z 280;

Step 2d

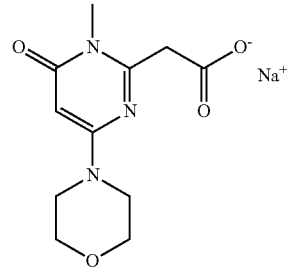 [SMILES: Cn1c(CC(=O)[O-])nc(N2CCOCC2)cc1=O ; [Na+]]

2.88 ml of 2M sodium hydroxide are added to a solution of 1.62 g of ethyl [1-methyl-4-(morpholin-4-yl)-6-oxo-1,6-dihydropyrimidin-2-yl]acetate in 20 ml of tetrahydrofuran. The reaction mixture is stirred for 48 hours at ambient temperature. The precipitate formed is filtered off through sintered glass, washed with ethyl acetate, rinsed with diethyl ether and dried, so as to give 730 mg of sodium [1-methyl-4-(morpholin-4-yl)-6-oxo-1,6-dihydropyrimidin-2-yl]acetate in the form of a white solid, the characteristics of which are the following:

$^1$H NMR spectrum (400 MHz): 3.27 to 3.43 (partially masked m, 9H); 3.61 (m, 4H); 5.23 (s, 1H)

Mass spectrometry: method A
Retention time Tr (min)=0.31;
[M+H]+: m/z 254; [M−H]−: m/z 252;

Step 3d

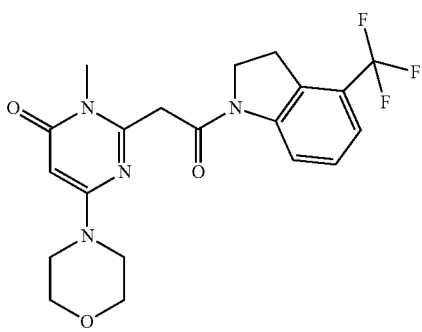 [SMILES: Cn1c(CC(=O)N2CCc3c2cccc3C(F)(F)F)nc(N2CCOCC2)cc1=O]

3 ml of pyridine, 94 mg of 4-trifluoromethyl-2,3-dihydro-1H-indole and 153 mg of N-[3-(dimethylamino)propyl]-N'-ethylcarbodiimide hydrochloride are successively added to a solution of 138 mg of sodium [1-methyl-4-(morpholin-4-yl)-6-oxo-1,6-dihydropyrimidin-2-yl]acetate in 3 ml of N,N-dimethylformamide. The reaction mixture is stirred at ambient temperature for 16 hours. After the addition of 50 ml of water and extraction with ethyl acetate (3×15 ml), the organic phases are combined and then washed with water (2×15 ml), and a saturated aqueous sodium chloride solution (15 ml), and then dried over magnesium sulfate, filtered through sintered glass, and concentrated under reduced pressure. The solid obtained is washed with diethyl ether (5 ml) and then dried, so as to give 64 mg of 3-methyl-6-(morpholin-4-yl)-2-{2-oxo-2-[4-(trifluoromethyl)-2,3-dihydro-1H-indol-1-yl]ethyl}pyrimidin-4(3H)-one in the form of a pink solid, the characteristics of which are the following:

¹H NMR spectrum (400 MHz): 3.24 to 3.42 (partially masked m, 9H); 3.57 (m, 4H); 4.14 (s, 2H); 4.26 (t, J=8.6 Hz, 2H); 5.37 (s, 1H); 7.35 (d, J=8.1 Hz, 1H); 7.41 (t, J=8.1 Hz, 1H); 8.30 (d, J=8.1 Hz, 1H)
Mass spectrometry: method A
Retention time Tr (min)=0.87;
[M+H]+: m/z 423; [M−H]−: m/z 421

Example 5d

Synthesis of 6-(morpholin-4-yl)-2-{2-oxo-2-[4-(trifluoromethyl)-2,3-dihydro-1H-indol-1-yl]ethyl}pyrimidin-4(3H)-one

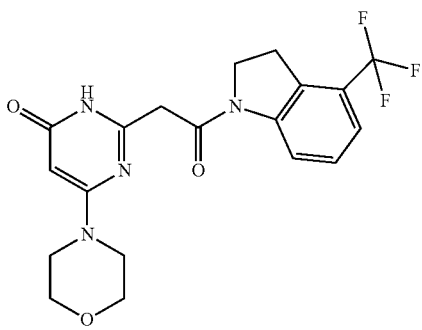 [SMILES: O=C(Cc1nc(N2CCOCC2)cc(=O)[nH]1)N1CCc2c1cccc2C(F)(F)F]

700 mg of 4-trifluoromethyl-2,3-dihydro-1H-indole and 1.15 g of N-[3-(dimethylamino)propyl]-N'-ethylcarbodiimide hydrochloride are added to a solution of 977 mg of sodium [4-(morpholin-4-yl)-6-oxo-1,6-dihydropyrimidin-2-yl]acetate (obtained in step 2d of example 1d) in 25 ml of N,N-dimethylformamide and 25 ml of pyridine. The reaction mixture is stirred at ambient temperature for 16 hours, and then water is added and the mixture is extracted with ethyl acetate. The organic phase is washed successively with water and a saturated sodium chloride solution, dried over magnesium sulfate, filtered, and concentrated under reduced pressure. The residue is purified by silica column chromatography, elution being carried out with a mixture of dichloromethane and methanol (95/05: v/v), so as to give 220 mg of 6-(morpholin-4-yl)-2-{2-oxo-2-[4-(trifluoromethyl)-2,3-dihydro-1H-indol-1-yl]ethyl}pyrimidin-4(3H)-one in the form of a white solid, the characteristics of which are the following:

¹H NMR spectrum (400 MHz): 3.27 to 3.45 (partially masked m, 6H); 3.60 (m, 4H); 3.79 (s, 2H); 4.22 (t, J=8.6 Hz, 2H); 5.22 (s, 1H); 7.34 (d, J=8.1 Hz, 1H); 7.41 (t, J=8.1 Hz, 1H); 8.30 (d, J=8.1 Hz, 1H); 11.64 (broad m, 1H)
Mass spectrometry: method A
Retention time Tr (min)=0.82;
[M+H]+: m/z 409; [M−H]−: m/z 407

Example 6d

Synthesis of 2-{2-[4-(2-methoxyphenyl)-2,3-dihydro-1H-indol-1-yl]-2-oxoethyl}-6-(morpholin-4-yl)pyrimidin-4(3H)-one

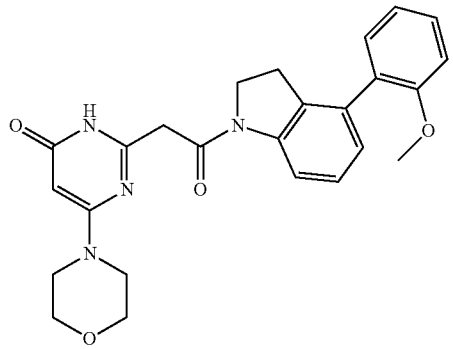 [SMILES: COc1ccccc1-c1cccc2c1CCN2C(=O)Cc1nc(N2CCOCC2)cc(=O)[nH]1]

0.105 ml of pyridine and 165 mg of N-[3-(dimethylamino)propyl]-N'-ethylcarbodiimide hydrochloride are successively added to a solution of 170 mg of sodium [4-(morpholin-4-yl)-6-oxo-1,6-dihydropyrimidin-2-yl]acetate (example 1d, step 2d) in 3 ml of N,N-dimethylformamide. After stirring at ambient temperature for 15 minutes, 140 mg of 4-(2-methoxyphenyl)-2,3-dihydro-1H-indole (reference example 3d) are added. The reaction mixture is stirred at ambient temperature for 16 hours, and then 20 ml of water and 3 ml of ethyl acetate are added. After stirring at ambient temperature for 1 hour, the precipitate formed is filtered off, and then rinsed successively with water and diethyl ether. After drying under reduced pressure at 40° C., 202 mg of 2-{2-[4-(2-methoxyphenyl)-2,3-dihydro-1H-indol-1-yl]-2-oxoethyl}-6-(morpholin-4-yl)pyrimidin-4(3H)-one are obtained in the form of a pale pink solid, the characteristics of which are the following:

¹H NMR spectrum (400 MHz): 2.93 (t, J=8.7 Hz, 2H); 3.42 (m, 4H); 3.61 (m, 4H); 3.74 (s, 3H); 3.76 (s, 2H); 4.11 (t, J=8.7 Hz, 2H); 5.21 (s, 1H); 6.91 (d, J=7.9 Hz, 1H); 7.02 (t, J=7.9 Hz, 1H); 7.11 (d, J=7.9 Hz, 1H); 7.15 to 7.26 (m, 2H); 7.38 (broad t, J=7.9 Hz, 1H); 8.03 (d, J=7.9 Hz, 1H); 11.63 (broad s, 1H)
Mass spectrometry: method A
Retention time Tr (min)=0.88;
[M+H]+: m/z 447; [M−H]−: m/z 445
Melting point (Kofler): above 260° C.

Example 7d

Synthesis of 6-(morpholin-4-yl)-2-{2-oxo-2-[4-(1-propylpiperidin-3-yl)-2,3-dihydro-4H-indol-1-yl]ethyl}pyrimidin-4(3H)-one

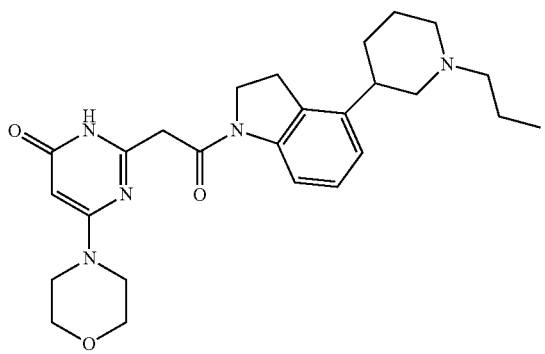 [SMILES: CCCN1CCCC(c2cccc3c2CCN3C(=O)Cc2nc(N3CCOCC3)cc(=O)[nH]2)C1]

0.2 ml of pyridine, 25.7 mg of 4-(1-propylpiperidin-3-yl)-2,3-dihydro-1H-indole (reference example 4d) and 17.8 mg of N-[3-(dimethylamino)propyl]-N'-ethylcarbodiimide hydrochloride are successively added to a solution of 20.5 mg of sodium [4-(morpholin-4-yl)-6-oxo-1,6-dihydropyrimidin-2-yl]acetate (example 1d, step 2d) in 0.8 ml of N,N-dimethylformamide. The reaction mixture is stirred at ambient temperature for 24 hours, and then concentrated under reduced pressure. The residue is taken up in 10 ml of water and then extracted with dichloromethane (4×20 ml). The organic phases are combined and then washed with water and concentrated under reduced pressure. After oven-drying, 16.1 mg of 6-(morpholin-4-yl)-2-{2-oxo-2-[4-(1-propylpiperidin-3-yl)-2,3-dihydro-1H-indol-1-yl]ethyl}pyrimidin-4(3H)-one are obtained in the form of a pink solid, the characteristics of which are the following:

Example 8d

Synthesis of 2-{2-[4-(difluoromethoxy)-2,3-dihydro-1H-indol-1-yl]-2-oxoethyl}-3-methyl-6-(morpholin-4-yl)pyrimidin-4(3H)-one

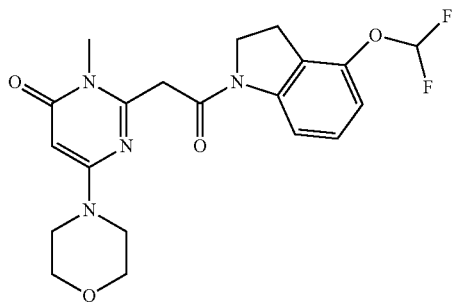 [SMILES: Cn1c(CC(=O)N2CCc3c(OC(F)F)cccc32)nc(N2CCOCC2)cc1=O]

220 mg of 4-difluoromethoxy-2,3-dihydro-1H-indole (reference example 5d) and 364 mg of N-[3-(dimethylamino)propyl]-N'-ethylcarbodiimide hydrochloride are added to a solution of 237 mg of sodium [1-methyl-4-(morpholin-4-yl)-6-oxo-1,6-dihydropyrimidin-2-yl]acetate (obtained in step 2d of example 4d) in 7 ml of N,N-dimethylformamide and 7 ml of pyridine. The reaction mixture is stirred at ambient temperature for 16 hours, and then 20 ml of water are added and the mixture is extracted with ethyl acetate. The organic phase is washed successively with a 0.1N hydrochloric acid solution, water and a saturated sodium chloride solution, dried over magnesium sulfate, filtered, and concentrated under reduced pressure. The residue is purified by silica column chromatography, elution being carried out with a mixture of dichloromethane and methanol (95/05: v/v), so as to give 110 mg of 2-[2-(4-difluoromethoxy-2,3-dihydroindol-1-yl)-2-oxoethyl]-3-methyl-6-morpholin-4-yl-3H-pyrimidin-4-one in the form of a pale pink solid, the characteristics of which are the following:

$^1$H NMR spectrum (400 MHz): 3.15 (t, J=8.6 Hz, 2H); 3.30 (partially masked s, 3H); 3.39 (m, 4H); 3.58 (m, 4H); 4.12 (s, 2H); 4.23 (t, J=8.6 Hz, 2H); 5.37 (s, 1H); 6.88 (d, J=8.1 Hz, 1H); 7.24 (t, J=74.2 Hz, 1H); 7.24 (t, J=8.1 Hz, 1H); 7.89 (d, J=8.1 Hz, 1H)

Mass spectrometry: method A
Retention time Tr (min)=0.77;
[M+H]+: m/z 421; [M−H]−: m/z 419

Example 9d

Synthesis of 2-{2-[4-(difluoromethoxy)-2,3-dihydro-1H-indol-1-yl]-2-oxoethyl}-6-(morpholin-4-yl)pyrimidin-4(3H)-one

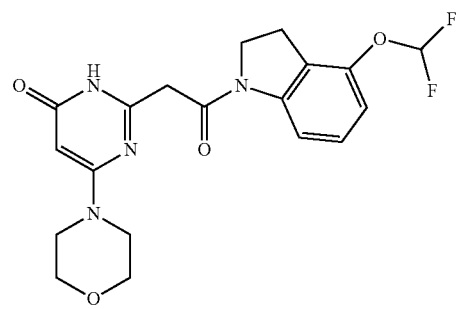 [SMILES: O=C(Cc1nc(N2CCOCC2)cc(=O)[nH]1)N1CCc2c(OC(F)F)cccc21]

220 mg of 4-difluoromethoxy-2,3-dihydro-1H-indole (reference example 5d) and 364 mg of N-[3-(dimethylamino)propyl]-N'-ethylcarbodiimide hydrochloride are added to a solution of 327 mg of sodium [4-(morpholin-4-yl)-6-oxo-1,6-dihydropyrimidin-2-yl]acetate (obtained in step 2d of example 1d) in 7 ml of N,N-dimethylformamide and 7 ml of pyridine. The reaction mixture is stirred at ambient temperature for 16 hours, and then 15 ml of water are added and the mixture is extracted with ethyl acetate. The organic phase is washed successively with water and a saturated sodium chloride solution, dried over magnesium sulfate, filtered, and concentrated under reduced pressure. The residue is purified by silica column chromatography, elution being carried out with a mixture of dichloromethane and methanol (95/05: v/v), so as to give 24 mg of 2-{2-[4-(difluoromethoxy)-2,3-dihydro-1H-indol-1-yl]-2-oxoethyl}-6-(morpholin-4-yl)pyrimidin-4(3H)-one, the characteristics of which are the following:

$^1$H NMR spectrum (400 MHz): 3.15 (t, J=8.6 Hz, 2H); 3.42 (m, 4H); 3.60 (m, 4H); 3.76 (s, 2H); 4.19 (t, J=8.6 Hz, 2H); 5.21 (s, 1H); 6.87 (d, J=8.1 Hz, 1H); 7.24 (t, J=74.2 Hz, 1H); 7.25 (t, J=8.1 Hz, 1H); 7.89 (d, J=8.1 Hz, 1H); 11.63 (broad m, 1H)

Mass spectrometry: method A
Retention time Tr (min)=0.73;
[M+H]+: m/z 407; [M−H]−: m/z 405

Example 10d

Synthesis of 6-(morpholin-4-yl)-2-{2-oxo-2-[4-(pyridin-4-yl)-2,3-dihydro-1H-indol-1-yl]ethyl}pyrimidin-4(3H)-one

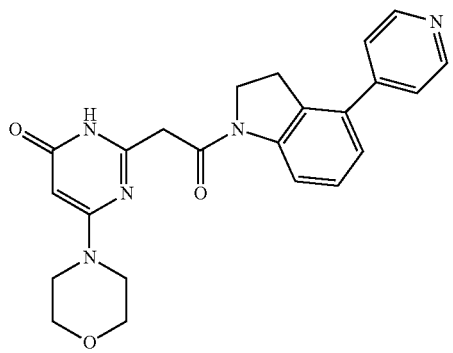 [SMILES: O=C(Cc1nc(N2CCOCC2)cc(=O)[nH]1)N1CCc2c(-c3ccncc3)cccc21]

0.2 ml of pyridine, 25 mg of 4-pyridin-4-yl-2,3-dihydro-1H-indole and 23 mg of N-[3-(dimethylamino)propyl]-N'-ethylcarbodiimide hydrochloride are successively added to a solution of 26.7 mg of sodium [4-(morpholin-4-yl)-6-oxo-1,6-dihydropyrimidin-2-yl]acetate (example 1d, step 2d) in 0.8 ml of N,N-dimethylformamide. The reaction mixture is stirred at ambient temperature for 24 hours, and then concentrated under reduced pressure. The residue is taken up in 10 ml of water and then filtered through sintered glass, and the precipitate is washed with water (2×1 ml) and oven-dried. 27.6 mg of 6-(morpholin-4-yl)-2-{2-oxo-2-[4-(pyridin-4-yl)-2,3-dihydro-1H-indol-1-yl]ethyl}pyrimidin-4(3H)-one are obtained in the form of a pink solid, the characteristics of which are the following:

$^1$H NMR spectrum (400 MHz): 3.27 (masked m, 2H); 3.41 (m, 4H); 3.61 (m, 4H); 3.79 (s, 2H); 4.16 (t, J=8.4 Hz, 2H); 5.22 (s, 1H); 7.18 (d, J=7.6 Hz, 1H); 7.35 (t, J=7.9 Hz, 1H); 7.61 (d, J=6.4 Hz, 2H); 8.16 (d, J=8.3 Hz, 1H); 8.69 (d, J=6.1 Hz, 2H); 11.66 (broad s, 1H)

Mass spectrometry: method A
Retention time Tr (min)=0.40;
[M+H]+: m/z 418; [M−H]−: m/z 416

Example 11d

Synthesis of 2-[2-(1'-methylspiro[indole-3,4'-piperidin]-1(2H)-yl)-2-oxoethyl]-6-(morpholin-4-yl)pyrimidin-4(3H)-one

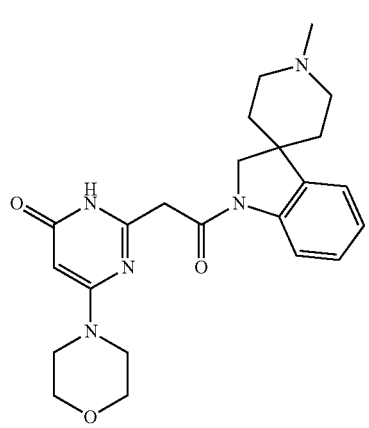 [SMILES: CN1CCC2(CC1)CN(C(=O)Cc1nc(N3CCOCC3)cc(=O)[nH]1)c1ccccc12]

The product is prepared by following the procedure described in example 10d using 35.5 mg of sodium [4-(morpholin-4-yl)-6-oxo-1,6-dihydropyrimidin-2-yl]acetate (example 1d, step 2d) and 25 mg of 1'-methylspiro[indoline-3,4'-piperidine] in place of 4-pyridin-4-yl-2,3-dihydro-1H-indole. 13.8 mg of 2[2-r-methylspiro[indole-3,4'-piperidin]-1(2H)-yl)-2-oxoethyl]-6-(morpholin-4-yl)pyrimidin-4(3H)-one are obtained in the form of a pale pink powder, the characteristics of which are the following:

$^1$H NMR spectrum (400 MHz): 1.56 (d, J=13.0 Hz, 2H); 1.88 (td, J=3.3 and 12.8 Hz, 2H); 2.03 (t, J=11.0 Hz, 2H); 2.21 (s, 3H); 2.75 (d, J=12.0 Hz, 2H); 3.41 (t, J=4.8 Hz, 4H); 3.60 (t, J=5.0 Hz, 4H); 3.82 (s, 2H); 4.00 (s, 2H); 5.21 (s, 1H); 7.05 (t, J=7.3 Hz, 1H); 7.19 (t, J=7.5 Hz, 1H); 7.27 (d, J=8.1 Hz, 1H); 8.02 (d, J=8.1 Hz, 1H); 11.61 (broad s, 1H)

Mass spectrometry: method A
Retention time Tr (min)=0.40;
[M+H]+: m/z 424; [M−H]−: m/z 422

Example 12d

Synthesis of 6-(morpholin-4-yl)-2-{2-oxo-2-[4-(pyridin-2-yl)-2,3-dihydro-1H-indol-1-yl]ethyl}pyrimidin-4(3H)-one

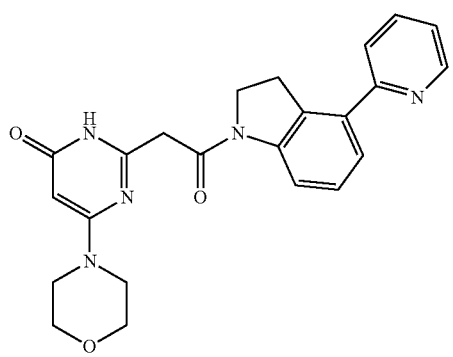 [SMILES: O=C(Cc1nc(N2CCOCC2)cc(=O)[nH]1)N1CCc2c(-c3ccccn3)cccc21]

The product is prepared by following the procedure described in example 10d using 26.7 mg of sodium [4-(morpholin-4-yl)-6-oxo-1,6-dihydropyrimidin-2-yl]acetate (example 1d, step 2d) and 25 mg of 4-pyridin-2-yl-2,3-dihydro-1H-indole in place of 4-pyridin-4-yl-2,3-dihydro-1H-indole. 26.8 mg of 6-(morpholin-4-yl)-2-{2-oxo-2-[4-(pyridin-2-yl)-2,3-dihydro-1H-indol-1-yl]ethyl}pyrimidin-4(3H)-one are obtained in the form of a purple solid, the characteristics of which are the following:

$^1$H NMR spectrum (400 MHz): 3.37 to 3.46 (m, J=5.9 Hz, 6H); 3.61 (m, 4H); 3.79 (broad s, 2H); 4.16 (t, J=8.6 Hz, 2H); 5.23 (s, 1H); 7.26 to 7.47 (m, 3H); 7.77 (d, J=8.3 Hz, 1H); 7.93 (t, J=8.1 Hz, 1H); 8.16 (d, J=8.1 Hz, 1H); 8.69 (d, J=5.6 Hz, 1H); 11.69 (broad s, 1H)

Mass spectrometry: method A
Retention time Tr (min)=0.53;
[M+H]+: m/z 418; [M−H]−: m/z 416

Example 13d

Synthesis of 6-(morpholin-4-yl)-2-{2-oxo-2-[4-(pyridin-3-yl)-2,3-dihydro-1H-indol-1-yl]ethyl}pyrimidin-4(3H)-one

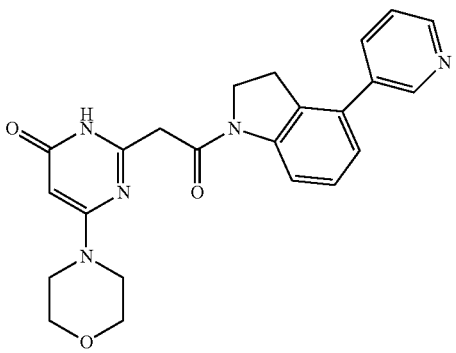 [SMILES: O=C(Cc1nc(N2CCOCC2)cc(=O)[nH]1)N1CCc2c(-c3cccnc3)cccc21]

The product is prepared by following the procedure described in example 10d using 26.7 mg of sodium [4-(morpholin-4-yl)-6-oxo-1,6-dihydropyrimidin-2-yl]acetate (example 1d, step 2d) and 25 mg of 4-pyridin-3-yl-2,3-dihydro-1H-indole in place of 4-pyridin-4-yl-2,3-dihydro-1H-indole. 30.7 mg of 6-(morpholin-4-yl)-2-{2-oxo-2-[4-(pyridin-3-yl)-2,3-dihydro-1H-indol-1-yl]ethyl}pyrimidin-4(3H)-one are obtained in the form of a pink powder, the characteristics of which are the following:

$^1$H NMR spectrum (400 MHz): 3.25 (t, J=8.1 Hz, 2H); 3.43 (m, 4H); 3.61 (m, 4H); 3.79 (s, 2H); 4.16 (t, J=8.4 Hz, 2H); 5.22 (s, 1H); 7.14 (d, J=7.8 Hz, 1H); 7.33 (t, J=7.9 Hz, 1H); 7.57 (dd, J=4.9 and 7.8 Hz, 1H); 8.02 (d, J=8.1 Hz, 1H); 8.13 (d, J=8.1 Hz, 1H); 8.63 (dd, J=1.7 and 4.9 Hz, 1H); 8.76 (dd, J=0.6 and 1.8 Hz, 1H); 11.65 (broad s, 1H)

Mass spectrometry: method A
Retention time Tr (min)=0.45;
[M+H]+: m/z 418; [M-H]-: m/z 416

Example 14d

Synthesis of 2-{2-[4-(2-chlorophenyl)-2,3-dihydro-1H-indol-1-yl]-2-oxoethyl}-6-(morpholin-4-yl)pyrimidin-4(3H)-one

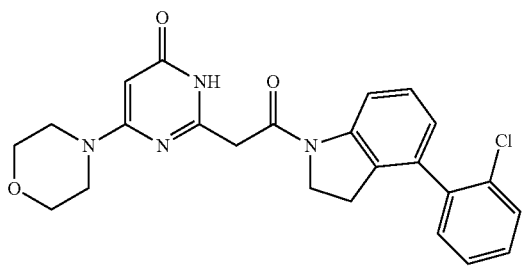 [SMILES: O=C(Cc1nc(N2CCOCC2)cc(=O)[nH]1)N1CCc2c(-c3ccccc3Cl)cccc21]

300 mg of sodium [4-(morpholin-4-yl)-6-oxo-1,6-dihydropyrimidin-2-yl]acetate (example 1d, step 2d), 330 mg of N-[3-(dimethylamino)propyl]-N'-ethylcarbodiimide hydrochloride and 6 ml of pyridine are successively added to a solution of 264 mg of 4-(2-chlorophenyl)-2,3-dihydro-1H-indole (reference example 6d) in 5 ml of pyridine. The reaction mixture is stirred at ambient temperature for 4 days. The reaction medium is diluted with ethyl acetate (60 ml) and then successively washed with an aqueous 1M hydrochloric acid solution, an aqueous 1M sodium hydroxide solution, and a saturated aqueous sodium chloride solution. The organic phase is then dried over magnesium sulfate and filtered through sintered glass. A precipitate appears after a few hours, which is then filtered off through sintered glass and washed with diethyl ether. 294 mg of 2-{2-[4-(2-chlorophenyl)-2,3-dihydro-1H-indol-1-yl]-2-oxoethyl}-6-(morpholin-4-yl)pyrimidin-4(3H)-one are obtained in the form of a beige solid, the characteristics of which are the following:

$^1$H NMR spectrum (400 MHz): 2.93 (t, J=8.6 Hz, 2H); 3.41 (m, 4H); 3.60 (m, 4H); 3.77 (s, 2H); 4.14 (t, J=8.4 Hz, 2H); 5.22 (s, 1H); 6.92 (d, J=7.6 Hz, 1H); 7.28 (t, J=7.8 Hz, 1H); 7.37 (m, 1H); 7.44 (m, 2H); 7.59 (m, 1H); 8.08 (d, J=7.6 Hz, 1H); 11.65 (broad s, 1H)

Mass spectrometry: method A
Retention time Tr (min)=0.93;
[M+H]+: m/z 451; [M-H]-: m/z 449

Example 15d

Synthesis of 2-[2-(4-chloro-2,3-dihydro-1H-indol-1-yl)-2-oxoethyl]-3-cyclopropyl-6-(morpholin-4-yl)pyrimidin-4(3H)-one

Step 1d

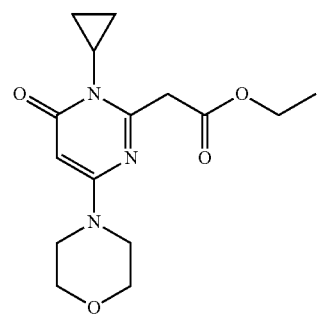 [SMILES: CCOC(=O)Cc1nc(N2CCOCC2)cc(=O)n1C1CC1]

643 mg of cyclopropylboronic acid, 680 g of copper(II) acetate, 1.37 g of dimethylaminopyridine and, finally, 6.23 ml of a solution of sodium bis(trimethylsilyl)amide (0.6M in toluene) are added, using a dropping funnel, to a solution of 1 g of ethyl [4-(morpholin-4-yl)-6-oxo-1,6-dihydropyrimidin-2-yl]acetate, prepared in step 1d of example 1d, in 12 ml of toluene. The reaction mixture is heated at 95° C. for 16 and then cooled to ambient temperature. After the addition of 20 ml of an aqueous 1N hydrochloric acid solution and extraction with dichloromethane (3×50 ml), the organic phases are combined and then dried over magnesium sulfate, filtered through sintered glass, and concentrated under reduced pressure. The residue is purified by silica column chromatography, elution being carried out with a mixture of dichloromethane and methanol (98/02 then 95/05 V/V). 90 mg of ethyl (1-cyclopropyl-4-morpholin-4-yl-6-oxo-1,6-dihydropyrimidin-2-yl)acetate are obtained in the form of a yellow oil, used as it is in the next step.

Step 2d

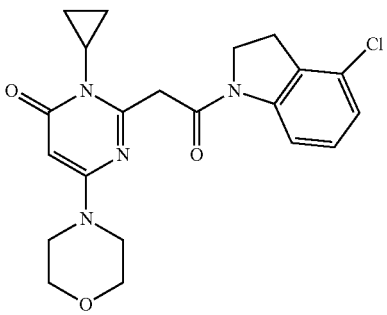 [SMILES: O=C(Cc1nc(N2CCOCC2)cc(=O)n1C1CC1)N1CCc2c(Cl)cccc21]

2 ml of toluene, 90 mg of ethyl (1-cyclopropyl-4-morpholin-4-yl-6-oxo-1,6-dihydropyrimidin-2-yl)acetate and, finally, dropwise, 0.55 ml of a 2M solution of trimethylaluminum in toluene are successively added to a solution of 113 mg of 4-chloroindoline in 4 ml of tetrahydrofuran. The reaction mixture is heated at 90° C. for 4 hours, and then cooled to ambient temperature, and 5 ml of methanol are added. After the addition of 10 g of silica, the reaction mixture is concentrated under reduced pressure. After purification by silica column chromatography (solid deposit), elution being carried out with a mixture of dichloromethane and methanol (100/0 then 98/02 V/V), 39 mg of 2-[2-(4-chloro-2,3-dihydro-1H-indol-1-yl)-2-oxoethyl]-3-cyclopropyl-6-(morpholin-4-yl)pyrimidin-4(3H)-one are obtained in the form of a white solid, the characteristics of which are the following:

$^1$H NMR spectrum (400 MHz): 0.83 (m, 2H); 1.07 (m, 2H); 2.69 (m, 1H); 3.18 (t, J=8.6 Hz, 2H); 3.36 (m, 4H); 3.55 (m, 4H); 4.18 (s, 2H); 4.23 (t, J=8.6 Hz, 2H); 5.27 (s, 1H); 7.09 (d, J=8.1 Hz, 1H); 7.21 (t, J=8.1 Hz, 1H); 7.98 (d, J=7.9 Hz, 1H)

Mass spectrometry: method A
Retention time Tr (min)=0.85;
[M+H]+: m/z 415; [M−H]−: m/z 413

Example 16d

Synthesis of 6-(morpholin-4-yl)-2-[2-oxo-2-(2,3,3a,8b-tetrahydrocyclopenta[b]indol-4(1H)-yl)ethyl]pyrimidin-4(3H)-one

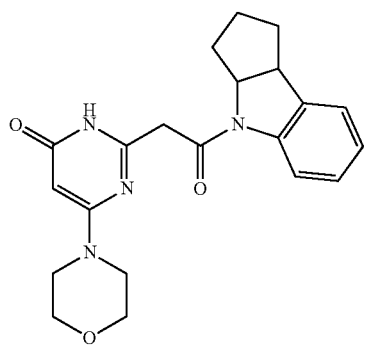 [SMILES: O=C(Cc1nc(N2CCOCC2)cc(=O)[nH]1)N1c2ccccc2C2CCCC21]

320 mg of 1,2,3,3a,4,8b-hexahydrocyclopenta[b]indole [reference example 7d] and 424 mg of N-[3-(dimethylamino)propyl]-N'-ethylcarbodiimide hydrochloride are added to a solution of 525 mg of sodium [4-(morpholin-4-yl)-6-oxo-1,6-dihydropyrimidin-2-yl]acetate (obtained in step 2d of example 1d) in 4 ml of N,N-dimethylformamide and 4 ml of pyridine. The reaction mixture is stirred at ambient temperature for 72 hours and then concentrated under reduced pressure. The residue is taken up in a mixture of water and ethyl acetate and the organic phase is washed successively with water, a 1M hydrochloric acid solution and water, dried over magnesium sulfate, filtered, and concentrated under reduced pressure. The residue is triturated from methanol, filtered and washed with diisopropyl ether, so as to give 375 mg of 6-(morpholin-4-yl)-2-[2-oxo-2-(2,3,3a,8b-tetrahydrocyclopenta[b]indol-4(1H)-yl)ethyl]pyrimidin-4(3H)-one, the characteristics of which are the following:

$^1$HNMR spectrum (400 MHz): 1.27 (m, 1H); 1.61 (m, 1H); 1.80 to 2.14 (m, 4H); 3.41 (m, 4H); 3.60 (m, 4H); 3.73 (d, J=16.0 Hz, 1H); 3.91 (m, 2H); 4.89 (m, 1H); 5.20 (s, 1H); 7.05 (t, J=7.9 Hz, 1H); 7.16 (t, J=7.9 Hz, 1H); 7.24 (d, J=7.9 Hz, 1H); 7.99 (d, J=7.9 Hz, 1H); 11.67 (broad m, 1H)

Mass spectrometry: method A
Retention time Tr (min)=0.79;
[M+H]+: m/z 381; [M−H]−: m/z 379

Example 17d

Synthesis of 2-[2-(4-{[4-(methylsulfonyl)piperazin-1-yl]methyl}-2,3-dihydro-1H-indol-1-yl)-2-oxoethyl]-6-(morpholin-4-yl)pyrimidin-4(3H)-one

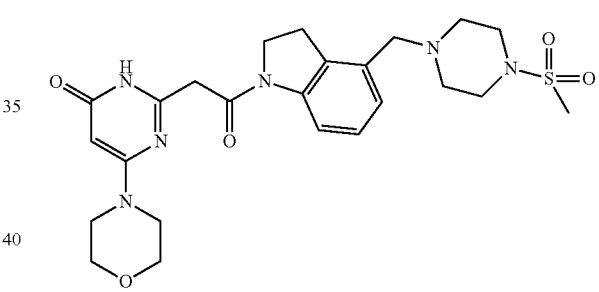

5 ml of pyridine, 299 mg of 4-(4-methanesulfonylpiperazin-1-ylmethyl)-2,3-dihydro-1H-indole (reference example 8d) and 264 mg of N-[3-(dimethylamino)propyl]-N'-ethylcarbodiimide hydrochloride are successively added to a solution of 240 mg of sodium [4-(morpholin-4-yl)-6-oxo-1,6-dihydropyrimidin-2-yl]acetate (example 1d, step 2d) in 5 ml of N,N-dimethylformamide. The reaction mixture is stirred at ambient temperature for 16 hours, and then concentrated under reduced pressure. The residue is taken up in 30 ml of water and then extracted with dichloromethane (3×30 ml). The organic phases are combined, then washed with a saturated aqueous sodium chloride solution, then dried over magnesium sulfate, filtered through sintered glass and concentrated under reduced pressure. After purification of the residue by silica column chromatography, elution being carried out with a mixture of dichloromethane and 7N ammoniacal methanol (90/10), 190 mg of 2-[2-(4-{[4-(methylsulfonyl)piperazin-1-yl]methyl}-2,3-dihydro-1H-indol-1-yl)-2-oxoethyl]-6-(morpholin-4-yl)pyrimidin-4(3H)-one are obtained in the form of a white solid, the characteristics of which are the following:

$^1$H NMR spectrum (300 MHz): 2.45 (m, 4H); 2.86 (s, 3H); 3.10 (m, 4H); 3.19 (m, 2H); 3.42 (m, 4H); 3.48 (s, 2H); 3.61

(m, 4H); 3.76 (s, 2H); 4.15 (t, J=8.6 Hz, 2H); 5.21 (s, 1H); 6.97 (d, J=7.0 Hz, 1H); 7.15 (t, J=7.8 Hz, 1H); 7.95 (d, J=8.1 Hz, 1H); 11.60 (broad s, 1H)

Mass spectrometry: method A
Retention time Tr (min)=0.37;
[M+H]+: m/z 517; [M−H]−: m/z 515

Example 18d

Synthesis of 2-(2-{4-[(4-methylpiperazin-1-yl)methyl]-2,3-dihydro-1H-indol-1-yl}-2-oxoethyl)-6-(morpholin-4-yl)pyrimidin-4(3H)-one

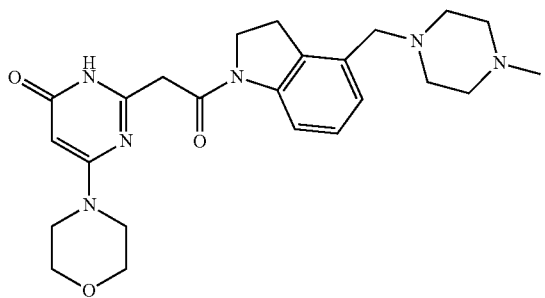 [SMILES: CN1CCN(Cc2cccc3c2CCN3C(=O)Cc2nc(N3CCOCC3)cc(=O)[nH]2)CC1]

The product is prepared by following the procedure described in example 17d using 410 mg of sodium [4-(morpholin-4-yl)-6-oxo-1,6-dihydropyrimidin-2-yl]acetate (example 1d, step 2d) and 400 mg of 4-(4-methylpiperazin-1-ylmethyl)-2,3-dihydro-1H-indole (reference example 9d) in place of 4-(4-methanesulfonylpiperazin-1-ylmethyl)-2,3-dihydro-1H-indole. 120 mg of 2-(2-{4-[(4-methylpiperazin-1-yl)methyl]-2,3-dihydro-1H-indol-1-yl}-2-oxoethyl)-6-(morpholin-4-yl)pyrimidin-4(3H)-one are obtained in the form of a white solid, the characteristics of which are the following:

$^1$H NMR spectrum (300 MHz): 2.14 (s, 3H); 2.24 to 2.41 (m, 8H); 3.17 (t, J=8.4 Hz, 2H); 3.38 to 3.47 (m, 6H); 3.60 (m, 4H); 3.75 (s, 2H); 4.15 (t, J=8.1 Hz, 2H); 5.21 (s, 1H); 6.95 (d, J=7.6 Hz, 1H); 7.12 (t, J=7.8 Hz, 1H); 7.93 (d, J=7.8 Hz, 1H); 11.61 (broad s, 1H)

Mass spectrometry: method A
Retention time Tr (min)=0.36;
[M+H]+: m/z 453; [M−H]−: m/z 451

Example 19d

Synthesis of 2-{2-[4-(2-fluorophenyl)-2,3-dihydro-1H-indol-1-yl]-2-oxoethyl}-6-(morpholin-4-yl)pyrimidin-4(3H)-one

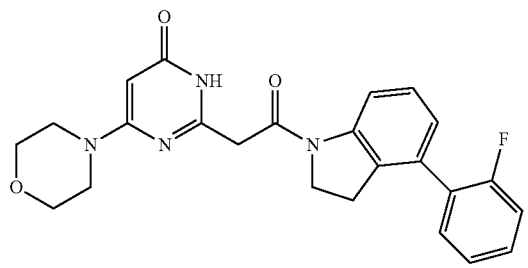 [SMILES: O=C(Cc1nc(N2CCOCC2)cc(=O)[nH]1)N1CCc2c(-c3ccccc3F)cccc21]

115 mg of 4-(2-fluorophenyl)-2,3-dihydro-1H-indole (diluted in 3 ml of pyridine) and 125 mg of N-[3-(dimethylamino)propyl]-N'-ethylcarbodiimide hydrochloride are successively added to a solution of 211 mg of sodium [4-(morpholin-4-yl)-6-oxo-1,6-dihydropyrimidin-2-yl]acetate (example 1d, step 2d) in 3 ml of pyridine. The reaction mixture is stirred at ambient temperature for 3 days. The reaction medium is diluted in ethyl acetate (100 ml) and then successively washed with an aqueous 1N hydrochloric acid solution, an aqueous 1N sodium hydroxide solution and a saturated aqueous sodium chloride solution. The organic phase is then dried over magnesium sulfate, filtered through sintered glass, and concentrated under reduced pressure. 187 mg of 2-{2-[4-(2-fluorophenyl)-2,3-dihydro-1H-indol-1-yl]-2-oxoethyl}-6-(morpholin-4-yl)pyrimidin-4(3H)-one are obtained in the form of a beige solid, the characteristics of which are the following:

$^1$H NMR spectrum (400 MHz): 3.03 (t, J=8.4 Hz, 2H); 3.42 (m, 4H); 3.61 (m, 4H); 3.77 (s, 2H); 4.15 (t, J=8.4 Hz, 2H); 5.21 (s, 1H); 7.01 (d, J=7.7 Hz, 1H); 7.22 to 7.37 (m, 3H); 7.38 to 7.52 (m, 2H); 8.10 (d, J=8.1 Hz, 1H); 11.64 (broad s, 1H)

Mass spectrometry: method A
Retention time Tr (min)=0.88;
[M+H]+: m/z 435; [M−H]−: m/z 433

Example 20d

Synthesis of 3-methyl-2-(2-{4[(4-methylpiperazin-1-yl)methyl]-2,3-dihydro-1H-indol-1-yl}-2-oxoethyl)-6-(morpholin-4-yl)pyrimidin-4(3H)-one

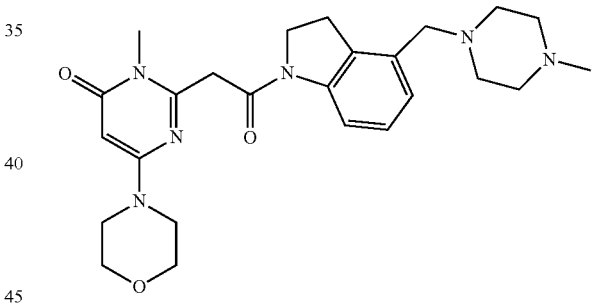

5 ml of pyridine, 404 mg of 4-(4-methylpiperazin-1-ylmethyl)-2,3-dihydro-1H-indole (reference example 9d) and 390 mg of N-[3-(dimethylamino)propyl]-N'-ethylcarbodiimide hydrochloride are successively added to a solution of 500 mg of sodium [1-methyl-4-(morpholin-4-yl)-6-oxo-1,6-dihydropyrimidin-2-yl]acetate (example 4d, step 2d) in 5 ml of N,N-dimethylformamide. The reaction mixture is stirred at ambient temperature for 16 hours, and then concentrated under reduced pressure. The residue is taken up in 30 ml of saturated aqueous sodium chloride solution and then extracted with dichloromethane (3×30 ml). The organic phases are combined and then dried over magnesium sulfate, filtered through sintered glass and concentrated under reduced pressure. After purification of the residue by silica column chromatography, elution being carried out with a mixture of dichloromethane and 7N ammoniacal methanol (95/05), 40 mg of 3-methyl-2-(2-{4-[(4-methylpiperazin-1-yl)methyl]-2,3-dihydro-1H-indol-1-yl}-2-oxoethyl)-6-(morpholin-4-yl)pyrimidin-4(3H)-one are obtained in the form of a white solid, the characteristics of which are the following:

¹H NMR spectrum (400 MHz): 2.14 (s, 3H); 2.20 to 2.44 (m, 8H); 3.17 (t, J=8.6 Hz, 2H); 3.31 (s, 3H); 3.39 (m, 6H); 3.58 (m, 4H); 4.10 (s, 2H); 4.18 (t, J=8.4 Hz, 2H); 5.37 (s, 1H); 6.95 (d, J=7.0 Hz, 1H); 7.12 (t, J=7.9 Hz, 1H); 7.93 (d, J=7.5 Hz, 1H)

Mass spectrometry: method A
Retention time Tr (min)=0.37;
[M+H]+: m/z 467; [M−H]−: m/z 465

Example 21d

Synthesis of 6-(morpholin-4-yl)-2-[2-oxo-2-(2',3',5',6'-tetrahydrospiro[indole-3,4'-pyran]-1(2H)-yl)ethyl]pyrimidin-4(3H)-one

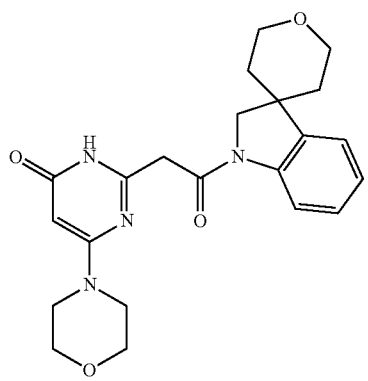 [SMILES: O=C(Cc1nc(N2CCOCC2)cc(=O)[nH]1)N1CC2(CCOCC2)c2ccccc21]

3.8 ml of pyridine, 378 mg of 1,2,2',3',5',6'-hexahydrospiro[3H-indole-3,4'-[4H]pyran] and 575 mg of N-[3-(dimethylamino)propyl]-N'-ethylcarbodiimide hydrochloride are successively added to a solution of 679 mg of sodium [4-(morpholin-4-yl)-6-oxo-1,6-dihydropyrimidin-2-yl]acetate (example 1d, step 2d) in 11.3 ml of N,N-dimethylformamide. The reaction mixture is stirred at ambient temperature for 16 hours, and then concentrated under reduced pressure. The residue is taken up in 25 ml of water and 20 ml of ethyl acetate, and then left to stir at ambient temperature for 1 hour. The precipitate formed is filtered off, and then rinsed successively with water and diethyl ether. 640 mg of 6-(morpholin-4-yl)-2-[2-oxo-2-(2',3',5',6'-tetrahydrospiro[indole-3,4'-pyran]-1(2H)-yl)ethyl]pyrimidin-4(3H)-one are thus obtained in the form of an off-white powder, the characteristics of which are the following:

¹H NMR spectrum (300 MHz): 1.53 (d, J=13.0 Hz, 2H); 1.91 (td, J=4.8 and 12.9 Hz, 2H); 3.41 (dd, J=4.7 and 5.0 Hz, 4H); 3.51 (t, J=10.4 Hz, 2H); 3.60 (m, 4H); 3.86 (m, 4H); 4.14 (s, 2H); 5.21 (s, 1H); 7.07 (t, J=7.3 Hz, 1H); 7.20 (t, J=8.2 Hz, 1H); 7.33 (d, J=6.7 Hz, 1H); 8.03 (dd, J=0.3 and 7.6 Hz, 1H); 11.63 (broad s, 1H)

Mass spectrometry: method A
Retention time Tr (min)=0.65;
[M+H]+: m/z 411; [M−H]−: m/z 409

Example 22d

Synthesis of 3-methyl-6-(morpholin-4-yl)-2-[2-oxo-2-(2',3',5',6'-tetrahydrospiro[indole-3,4'-pyran]-1(2H)-yl)ethyl]pyrimidin-4(3H)-one

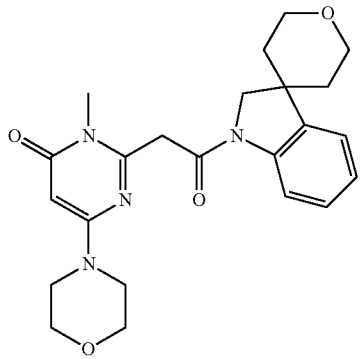 [SMILES: Cn1c(CC(=O)N2CC3(CCOCC3)c3ccccc32)nc(N2CCOCC2)cc1=O]

3.8 ml of pyridine, 378 mg of 1,2,2',3',5',6'-hexahydrospiro[3H-indole-3,4'-[4H]pyran] and 575 mg of N-[3-(dimethylamino)propyl]-N'-ethylcarbodiimide hydrochloride are successively added to a solution of 770 mg of sodium [1-methyl-4-(morpholin-4-yl)-6-oxo-1,6-dihydropyrimidin-2-yl]acetate (example 4d, step 2d) in 11.3 ml of N,N-dimethylformamide. The reaction mixture is stirred at ambient temperature for 16 hours, and then concentrated under reduced pressure. The residue is taken up in 15 ml of water and 20 ml of ethyl acetate, and then left to stir at ambient temperature for 1 hour. The precipitate formed is filtered off, and then rinsed successively with water and diethyl ether. 45 mg of 3-methyl-6-(morpholin-4-yl)-2-[2-oxo-2-(2',3',5',6'-tetrahydrospiro[indole-3,4'-pyran]-1(2H)-yl)ethyl]pyrimidin-4(3H)-one are thus obtained in the form of an off-white powder, the characteristics of which are the following:

¹H NMR spectrum (400 MHz): 1.55 (d, J=12.9 Hz, 2H); 1.91 (t, J=11.4 Hz, 2H); 3.37 (masked m, 8H); 3.54 (m, 6H); 3.88 (d, J=10.3 Hz, 2H); 4.17 (broad s, 3H); 5.37 (broad s, 1H); 7.08 (t, J=7.9 Hz, 1H); 7.20 (t, J=8.1 Hz, 1H); 7.33 (d, J=8.1 Hz, 1H); 8.03 (d, J=8.1 Hz, 1H)

Mass spectrometry: method A
Retention time Tr (min)=0.69;
[M+H]+: m/z 425; [M−H]−: m/z 423

Example 23d

Synthesis of 3-methyl-6-(morpholin-4-yl)-2-[2-oxo-2-(spiro[indole-3,4'-piperidin]-1(2H)-yl)ethyl]pyrimidin-4(3H)-one Step 1d

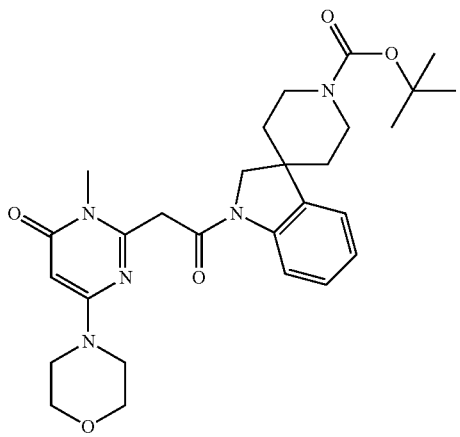 [SMILES: Cn1c(CC(=O)N2CC3(CCN(C(=O)OC(C)(C)C)CC3)c3ccccc32)nc(N2CCOCC2)cc1=O]

1.5 ml of pyridine, 231 mg of 2-methylpropan-2-yl 1,2-dihydro-1'H-spiro[indole-3,4'-piperidine]-1'-carboxylate (which can be prepared according to Tetrahedron (2010), 66, 573-577) and 230 mg of N-[3-(dimethylamino)propyl]-N'-ethylcarbodiimide hydrochloride are successively added to a solution of 308 mg of sodium [1-methyl-4-(morpholin-4-yl)-6-oxo-1,6-dihydropyrimidin-2-yl]acetate (example 4d, step 2d) in 4.5 ml of N,N-dimethylformamide. The reaction mixture is stirred at ambient temperature for 16 hours, and then concentrated under reduced pressure. The residue is taken up in 15 ml of water and 5 ml of diethyl ether, and then left to stir at ambient temperature for 1 hour. The precipitate formed is filtered off, and then rinsed successively with water and diisopropyl ether. 230 mg of 2-methylpropan-2-yl 1-{[1-methyl-4-(morpholin-4-yl)-6-oxo-1,6-dihydropyrimidin-2-yl]acetyl}-1,2-dihydro-1'H-spiro[indole-3,4'-piperidine]-1-carboxylate are thus obtained in the form of a white solid which is used as it is in the next step:

Step 2d

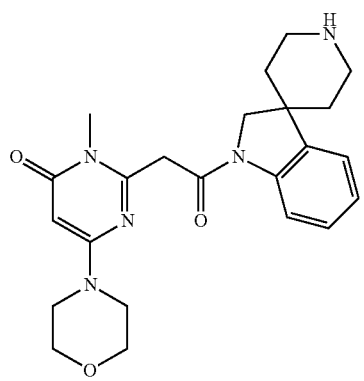 [SMILES: Cn1c(CC(=O)N2CC3(CCNCC3)c3ccccc32)nc(N2CCOCC2)cc1=O]

In a microwave tube, 225 mg of 2-methylpropan-2-yl 1-{[1-methyl-4-(morpholin-4-yl)-6-oxo-1,6-dihydropyrimidin-2-yl]acetyl}-1,2-dihydro-1'H-spiro[indole-3,4'-piperidine]-1'-carboxylate are placed in 10 ml of dioxane and 2 ml of an aqueous 2N hydrochloric acid solution. The tube is then microwave-heated at 110° C. for 10 minutes, and then allowed to return to ambient temperature. The reaction mixture is concentrated under reduced pressure. The residue is taken up in 10 ml of a saturated aqueous sodium hydrogen carbonate solution. After 10 minutes of stirring, the precipitate formed is filtered off, and then rinsed successively with water and diisopropyl ether. 140 mg of 3-methyl-6-(morpholin-4-yl)-2-[2-oxo-2-(spiro[indole-3,4'-piperidin]-1(2H)-yl)ethyl]pyrimidin-4(3H)-one are thus obtained in the form of a white powder, the characteristics of which are the following:

¹H NMR spectrum (400 MHz): 1.52 (d, J=12.0 Hz, 2H); 1.70 (m, 2H); 2.60 (t, J=12.3 Hz, 2H); 2.90 (d, J=13.4 Hz, 2H); 3.30 (masked s, 3H); 3.40 (m, 4H); 3.57 (m, 4H); 4.06 (s, 2H); 4.17 (s, 2H); 5.37 (s, 1H); 7.06 (t, J=7.3 Hz, 1H); 7.18 (t, J=7.8 Hz, 1H); 7.25 (d, J=8.8 Hz, 1H); 8.02 (d, J=7.8 Hz, 1H)

Mass spectrometry: method A

Retention time Tr (min)=0.42

[M+H]+: m/z 424; [M–H]–: m/z 422

Example 24d and Example 25d

Synthesis of (+)-6-(morpholin-4-yl)-2-{2-oxo-2-[2-phenyl-2,3-dihydro-1H-indol-1-yl]ethyl}pyrimidin-4(3H)-one and of (–)-6-(morpholin-4-yl)-2-{2-oxo-2-[2-phenyl-2,3-dihydro-1H-indol-1-yl]ethyl}pyrimidin-4(3H)-one

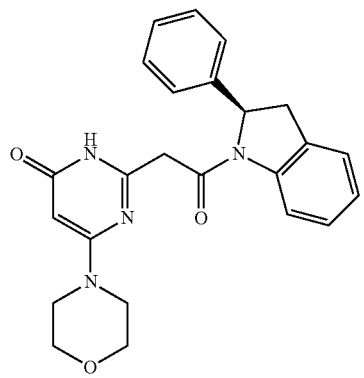

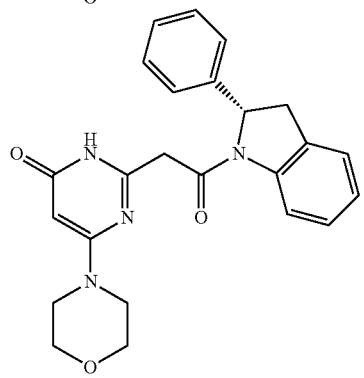

(±)-6-(Morpholin-4-yl)-2-{2-oxo-2-[2-phenyl-2,3-dihydro-1H-indol-1-yl]ethyl}pyrimidin-4(3H)-one is prepared by following the procedure described in example 1d, step 3d, using 0.50 g of sodium [4-(morpholin-4-yl)-6-oxo-1,6-dihydropyrimidin-2-yl]acetate, 0.42 g of 2-phenylindoline (which can be prepared according to Santangelo, E. M. et al. *Eur. J. Org. Chem.* 2008, 5915), and 0.48 g of N-[3-(dimethylamino)propyl]-N'-ethylcarbodiimide hydrochloride in a mixture of 0.31 ml of pyridine and 10 ml of N,N-dimethylformamide. After purification by chromatography on a 50 g column of 20-45 μm silica, elution being carried out with a 90/10 v/v dichloromethane/methanol mixture, 0.43 g of (±)-6-(morpholin-4-yl)-2-{2-oxo-2-[2-phenyl-2,3-dihydro-1H-indol-1-yl]ethyl}pyrimidin-4(3H)-one is obtained in the form of a cream-colored solid, the characteristics of which are the following:

Mass spectrometry: method A

Retention time Tr (min)=0.85;

[M+H]+: m/z 417; [M–H]–: m/z 415

The products were obtained by chiral chromatographic separation of 420 mg of (±)-6-(morpholin-4-yl)-2-{2-oxo-2-[2-phenyl-2,3-dihydro-1H-indol-1-yl]ethyl}pyrimidin-4(3H)-one on a Chiralpak AY (T304) column (1080 mg, 20 μm, 7.7/35 cm), eluent: acetonitrile/isopropanol: 90/10; flow rate: 250 ml/min. After purification, 208 mg of (+)-6-(morpholin-4-yl)-2-{2-oxo-2-[2-phenyl-2,3-dihydro-1H-indol-1-yl]ethyl}pyrimidin-4(3H)-one are obtained, as first enantiomer, in the form of a pale pink powder, the characteristics of which are the following:

$^1$H NMR spectrum (400 MHz): 2.89 (d, J=16.3 Hz, 1H); 3.13 (d, J=15.7 Hz, 1H); 3.25 to 3.40 (partially masked m, 4H); 3.57 (m, 4H); 3.81 (dd, J=9.5 and 16.3 Hz, 1H); 3.86 (d, J=15.7 Hz, 1H); 5.15 (s, 1H); 5.77 (d, J=9.5 Hz, 1H); 7.07 (t, J=7.5 Hz, 1H); 7.16 to 7.40 (m, 7H); 8.12 (d, J=8.3 Hz, 1H); 11.60 (broad m, 1H)

Mass spectrometry: method A
Retention time Tr (min)=0.84;
[M+H]+: m/z 417; [M−H]−: m/z 415
Optical rotation: $\alpha_D$=+170° (c=1.389 mg in 0.5 ml of DMSO)

Then the second enantiomer, i.e.: 202 mg of (−)-6-(morpholin-4-yl)-2-{2-oxo-2-[2-phenyl-2,3-dihydro-1H-indol-1-yl]ethyl}pyrimidin-4(3H)-one, is obtained in the form of an off-white powder, the characteristics of which are the following:

$^1$H NMR spectrum (400 MHz): 2.89 (d, J=16.3 Hz, 1H); 3.13 (d, J=15.7 Hz, 1H); 3.25 to 3.38 (partially masked m, 4H); 3.57 (m, 4H); 3.81 (dd, J=9.5 and 16.3 Hz, 1H); 3.86 (d, J=15.7 Hz, 1H); 5.15 (s, 1H); 5.77 (d, J=9.5 Hz, 1H); 7.07 (t, J=7.5 Hz, 1H); 7.17 to 7.40 (m, 7H); 8.12 (d, J=8.3 Hz, 1H); 11.60 (broad m, 1H)

Mass spectrometry: method A
Retention time Tr (min)=0.84;
[M+H]+: m/z 417; [M−H]−: m/z 415
Optical rotation: $\alpha_D$=−172° (c=0.681 mg in 0.5 ml of DMSO)

Example 26d

Synthesis of 2-{2-[4-(4-methylpiperazin-1-yl)-2,3-dihydro-1H-indol-1-yl]-2-oxoethyl}-6-(morpholin-4-yl)pyrimidin-4(3H)-one

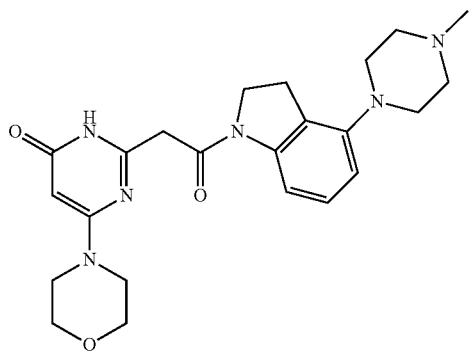 [SMILES: CN1CCN(c2cccc3c2CCN3C(=O)Cc2nc(N3CCOCC3)cc(=O)[nH]2)CC1]

8 ml of pyridine, 160 mg of 4-(4-methylpiperazin-1-yl)-2,3-dihydro-1H-indole (reference example 10d) and 212 mg of N-[3-(dimethylamino)propyl]-N'-ethylcarbodiimide hydrochloride are successively added to a solution of 288 mg of sodium [4-(morpholin-4-yl)-6-oxo-1,6-dihydropyrimidin-2-yl]acetate (example 1d, step 2d) in 8 ml of N,N-dimethylformamide. The reaction mixture is stirred at ambient temperature for 48 hours. After the addition of 50 ml of water and extraction with ethyl acetate, the organic phases are combined and then dried over magnesium sulfate, filtered through sintered glass, and concentrated under reduced pressure. After purification of the residue by silica column chromatography, elution being carried out with a mixture of dichloromethane and 7N ammoniacal methanol (90/10), 29 mg of 2-{2-[4-(4-methylpiperazin-1-yl)-2,3-dihydro-1H-indol-1-yl]-2-oxoethyl}-6-(morpholin-4-yl)pyrimidin-4(3H)-one are obtained in the form of a white-pink powder, the characteristics of which are the following:

$^1$H NMR spectrum (400 MHz): 2.23 (s, 3H); 2.44 (masked m, 4H); 2.93 (m, J=4.2 Hz, 4H); 3.06 (t, J=8.3 Hz, 2H); 3.43 (m, 4H); 3.60 (m, 4H); 3.74 (s, 2H); 4.11 (t, J=8.2 Hz, 2H); 5.20 (s, 1H); 6.67 (d, J=7.6 Hz, 1H); 7.11 (t, J=8.4 Hz, 1H); 7.71 (d, J=8.1 Hz, 1H); 11.60 (s, 1H)

Mass spectrometry: method A
Retention time Tr (min)=0.36;
[M+H]+: m/z 439; [M−H]−: m/z 437

Example 27d and Example 28d

Synthesis of (+)-2-{2-[2-(4-fluorophenyl)-2,3-dihydro-1H-indol-1-yl]-2-oxoethyl}-6-(morpholin-4-yl)pyrimidin-4(3H)-one and of (−)-2-{2-[2-(4-fluorophenyl)-2,3-dihydro-1H-indol-1-yl]-2-oxoethyl}-6-(morpholin-4-yl)pyrimidin-4(3H)-one

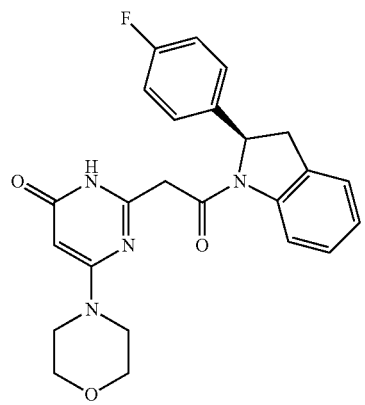

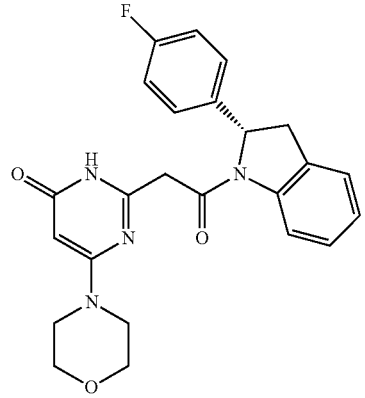

(±)-2-{2-[2-(4-Fluorophenyl)-2,3-dihydro-1H-indol-1-yl]-2-oxoethyl}-6-(morpholin-4-yl)pyrimidin-4(3H)-one is prepared by following the procedure described in example 1d, step 3, using 0.50 g of sodium [4-(morpholin-4-yl)-6-oxo-1,6-dihydropyrimidin-2-yl]acetate, 0.46 g of 2-(4-fluorophenyl)indoline and 0.48 g of N-[3-(dimethylamino)propyl]-N'-ethylcarbodiimide hydrochloride in a mixture of 0.31 ml of pyridine and 10 ml of N,N-dimethylformamide. After purification by chromatography on a 50 g column of 20-45 μm silica, elution being carried out with a 90/10 v/v dichloromethane/methanol mixture, 0.46 g of (±)-2-{2-[2-(4-fluorophenyl)-2,3-dihydro-1H-indol-1-yl]-2-oxoethyl}-6-(morpholin-4-yl)pyrimidin-4(3H)-one are obtained in the form of a cream-colored foam, the characteristics of which are the following:

Mass spectrometry: method A

Retention time Tr (min)=0.86;

[M+H]+: m/z 435; [M−H]−: m/z 433

The products were obtained by chiral chromatographic separation of 460 mg of (±)-2-{2-[2-(4-fluorophenyl)-2,3-dihydro-1H-indol-1-yl]-2-oxoethyl}-6-(morpholin-4-yl)pyrimidin-4(3H)-one on a Chiralpak AY (T304) column (1080 mg, 20 μm, 7.7/35 cm), eluent: acetonitrile/isopropanol: 90/10; flow rate: 250 ml/min. After purification, 190 mg of (+)-2-{2-[2-(4-fluorophenyl)-2,3-dihydro-1H-indol-1-yl]-2-oxoethyl}-6-(morpholin-4-yl)pyrimidin-4(3H)-one are obtained, as first enantiomer, in the form of a white lyophilisate, the characteristics of which are the following:

$^1$H NMR spectrum (400 MHz): 2.88 (d, J=15.8 Hz, 1H); 3.15 (d, J=16.3 Hz, 1H); 3.33 (m, 4H); 3.57 (m, 4H); 3.79 (dd, J=9.5 and 16.3 Hz, 1H); 3.86 (d, J=15.8 Hz, 1H); 5.15 (s, 1H); 5.78 (d, J=9.5 Hz, 1H); 7.04 to 7.29 (m, 7H); 8.11 (d, J=7.8 Hz, 1H); 11.60 (broad m, 1H)

Mass spectrometry: method A

Retention time Tr (min)=0.86;

[M+H]+: m/z 435; [M−H]−: m/z 433

Optical rotation: $\alpha_D$=+114.3°+/−1.9 (c=1.720 mg in 0.5 ml of DMSO)

Then the second enantiomer, i.e.: 225 mg of (−)-2-{2-[2-(4-fluorophenyl)-2,3-dihydro-1H-indol-1-yl]-2-oxoethyl}-6-(morpholin-4-yl)pyrimidin-4(3H)-one, is obtained in the form of a white lyophilisate, the characteristics of which are the following:

$^1$H NMR spectrum (400 MHz): 2.88 (d, J=16.3 Hz, 1H); 3.15 (d, J=15.9 Hz, 1H); 3.33 (m, 4H); 3.57 (m, 4H); 3.79 (dd, J=9.5 and 16.3 Hz, 1H); 3.86 (d, J=15.9 Hz, 1H); 5.15 (s, 1H); 5.78 (d, J=9.5 Hz, 1H); 7.03 to 7.29 (m, 7H); 8.11 (d, J=7.8 Hz, 1H); 11.60 (broad m, 1H)

Mass spectrometry: method A

Retention time Tr (min)=0.86;

[M+H]+: m/z 435; [M−H]−: m/z 433

Optical rotation: $\alpha_D$=−137.1°+/−2.1 (c=1.844 mg in 0.5 ml in DMSO)

Example 29d and Example 30d

Synthesis of (+)-2-{2-[4-(difluoromethoxy)-2-methyl-2,3-dihydro-1H-indol-1-yl]-2-oxoethyl}-6-(morpholin-4-yl)pyrimidin-4(3H)-one and of (−)-2-{2-[4-(difluoromethoxy)-2-methyl-2,3-dihydro-1H-indol-1-yl]-2-oxoethyl}-6-(morpholin-4-yl)pyrimidin-4(3H)-one

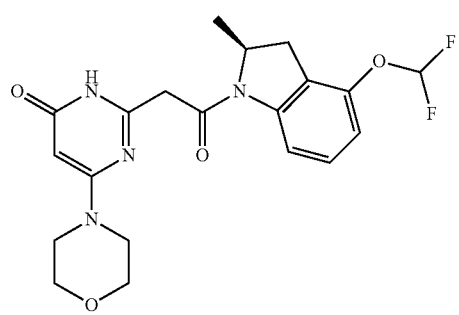

-continued

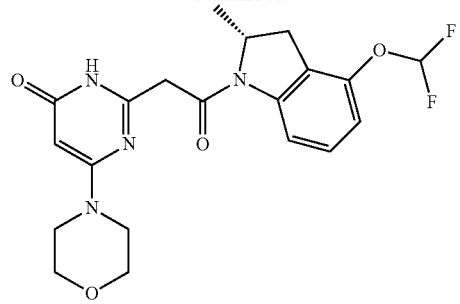

125 mg of 4-difluoromethoxy-2-methyl-2,3-dihydro-1H-indole (reference example 11d) and 192.7 mg of N-[3-(dimethylamino)propyl]-N'-ethylcarbodiimide hydrochloride are added to a solution of 196.8 mg of sodium [4-(morpholin-4-yl)-6-oxo-1,6-dihydropyrimidin-2-yl]acetate (obtained in step 2d of example 1d) in 6 ml of N,N-dimethylformamide and 6 ml of pyridine. The reaction mixture is stirred at ambient temperature for 16 hours, and then 25 ml of water are added and the mixture is extracted with ethyl acetate. The organic phase is washed successively with a 0.1N hydrochloric acid solution, water and a saturated sodium chloride solution, dried over magnesium sulfate, filtered, and concentrated under reduced pressure. The residue is purified by silica column chromatography, elution being carried out with a mixture of dichloromethane and methanol (95/05: v/v), so as to give 220 mg of 2-{2-[4-(difluoromethoxy)-2-methyl-2,3-dihydro-1H-indol-1-yl]-2-oxoethyl}-6-(morpholin-4-yl)pyrimidin-4(3H)-one.

The enantiomers are separated by chiral chromatography on a Whelk 01 SS phase column (5 μm, 30×250 mm), elution being carried out with a mixture of: heptane/dichloromethane/methanol: 60/30/10; flow rate: 43 ml/min.

97 mg of (+)-2-{2-[4-(difluoromethoxy)-2-methyl-2,3-dihydro-1H-indol-1-yl]-2-oxoethyl}-6-(morpholin-4-yl)pyrimidin-4(3H)-one are obtained, as first enantiomer, in the form of a white solid, the characteristics of which are the following:

$^1$H NMR spectrum (400 MHz): 1.28 (broad d, J=6.4 Hz, 3H); 2.71 (d, J=16.3 Hz, 1H); 3.35 (partially masked m, 1H); 3.41 (m, 4H); 3.60 (m, 4H); 3.73 (d, J=15.9 Hz, 1H); 3.93 (d, J=15.9 Hz, 1H); 4.78 (m, 1H); 5.20 (s, 1H); 6.90 (d, J=8.1 Hz, 1H); 7.24 (t, J=74.2 Hz, 1H); 7.26 (t, J=8.1 Hz, 1H); 7.84 (broad d, J=8.1 Hz, 1H); 11.68 (broad m, 1H)

Mass spectrometry: method A

Retention time Tr (min)=0.78;

[M+H]+: m/z 421; [M−H]−: m/z 419;

Optical rotation: $\alpha_D$=+80° (c=0.25%, DMSO)

Then the second enantiomer, 97 mg of (−)-2-{2-[4-(difluoromethoxy)-2-methyl-2,3-dihydro-1H-indol-1-yl]-2-oxoethyl}-6-(morpholin-4-yl)pyrimidin-4(3H)-one, is obtained in the form of a white solid, the characteristics of which are the following:

$^1$H NMR spectrum (400 MHz): 1.28 (d, J=6.4 Hz, 3H); 2.71 (d, J=16.3 Hz, 1H); 3.34 (partially masked m, 1H); 3.41 (m, 4H); 3.59 (m, 4H); 3.74 (d, J=15.9 Hz, 1H); 3.93 (d, J=15.9 Hz, 1H); 4.77 (m, 1H); 5.20 (s, 1H); 6.90 (d, J=8.1 Hz, 1H); 7.24 (t, J=74.2 Hz, 1H); 7.26 (t, J=8.1 Hz, 1H); 7.84 (broad d, J=8.1 Hz, 1H); 11.69 (broad m, 1H)

Mass spectrometry: method A

Retention time Tr (min)=0.78;

[M+H]+: m/z 421; [M−H]−: m/z 419;

Optical rotation: $\alpha_D$=−73° (c=0.25%, DMSO)

Example 31d and Example 32d

Synthesis of (+)-2-{2-[4-(difluoromethoxy)-2-methyl-2,3-dihydro-1H-indol-1-yl]-2-oxoethyl}-3-methyl-6-(morpholin-4-yl)pyrimidin-4(3H)-one and of (−)-2-{2-[4-(difluoromethoxy)-2-methyl-2,3-dihydro-1H-indol-1-yl]-2-oxoethyl}-3-methyl-6-(morpholin-4-yl)pyrimidin-4(3H)-one

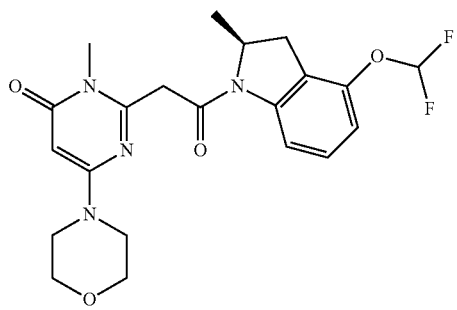

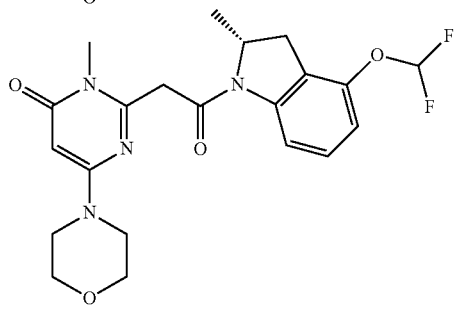

125 mg of 4-difluoromethoxy-2-methyl-2,3-dihydro-1H-indole [reference example 11d] and 193 mg of N-[3-(dimethylamino)propyl]-N'-ethylcarbodiimide hydrochloride are added to a solution of 242 mg of sodium [1-methyl-4-(morpholin-4-yl)-6-oxo-1,6-dihydropyrimidin-2-yl]acetate (obtained in step 2d of example 4d) in 6 ml of N,N-dimethylformamide and 6 ml of pyridine. The reaction mixture is stirred at ambient temperature for 16 hours, and then 25 ml of water are added and the mixture is extracted with ethyl acetate. The organic phase is washed successively with a 0.1N hydrochloric acid solution, water and a saturated sodium chloride solution, dried over magnesium sulfate, filtered, and concentrated under reduced pressure. The residue is purified by silica column chromatography, elution being carried out with a mixture of dichloromethane and methanol (90/10: v/v), so as to give 170 mg of 2-{2-[4-(difluoromethoxy)-2-methyl-2,3-dihydro-1H-indol-1-yl]-2-oxoethyl}-3-methyl-6-(morpholin-4-yl)pyrimidin-4(3H)-one.

The enantiomers are separated by chiral chromatography on a Whelk 01 SS, 5 μm column, (5 μm, 30×250 mm), elution being carried out with a mixture of: heptane/dichloromethane/methanol: 50/35/15; flow rate: 40 ml/min.

The first enantiomer, 40 mg of (+)-2-{2-[4-(difluoromethoxy)-2-methyl-2,3-dihydro-1H-indol-1-yl]-2-oxoethyl}-3-methyl-6-(morpholin-4-yl)pyrimidin-4(3H)-one, is obtained in the form of a white solid, the characteristics of which are the following:

$^1$H NMR spectrum (400 MHz): 1.30 (d, J=6.4 Hz, 3H); 2.72 (d, J=15.9 Hz, 1H); 3.33 (s, 3H); 3.35 to 3.42 (m, 5H); 3.57 (m, 4H); 4.03 (d, J=16.4 Hz, 1H); 4.29 (d, J=16.4 Hz, 1H); 4.78 (m, 1H); 5.36 (s, 1H); 6.91 (d, J=8.1 Hz, 1H); 7.24 (t, J=74.0 Hz, 1H); 7.26 (t, J=8.1 Hz, 1H); 7.83 (d, J=8.1 Hz, 1H)

Mass spectrometry: method A
Retention time Tr (min)=0.82;
[M+H]+: m/z 435; [M−H]−: m/z 433;
Optical rotation: $\alpha_D$=+67° (c=0.3%, DMSO)

Then the second enantiomer, 61 mg of (−)-2-{2-[4-(difluoromethoxy)-2-methyl-2,3-dihydro-1H-indol-1-yl]-2-oxoethyl}-3-methyl-6-(morpholin-4-yl)pyrimidin-4(3H)-one, is obtained in the form of a white solid, the characteristics of which are the following:

$^1$H NMR spectrum (400 MHz): 1.30 (d, J=6.4 Hz, 3H); 2.72 (d, J=15.9 Hz, 1H); 3.33 (s, 3H); 3.35 to 3.42 (m, 5H); 3.53 to 3.60 (m, 4H); 4.03 (d, J=16.4 Hz, 1H); 4.29 (d, J=16.4 Hz, 1H); 4.78 (m, 1H); 5.36 (s, 1H); 6.91 (d, J=8.1 Hz, 1H); 7.24 (t, J=74.0 Hz, 1H); 7.26 (t, J=8.1 Hz, 1H); 7.83 (d, J=8.1 Hz, 1H)

Mass spectrometry: method A
Retention time Tr (min)=0.82;
[M+H]+: m/z 435; [M−H]−: m/z 433;
Optical rotation: $\alpha_D$=−91.2° (c=1.706 mg/0.5 ml DMSO)

Example 33d

Synthesis of 6-(morpholin-4-yl)-2-{2-[4-(morpholin-4-yl)-2,3-dihydro-1H-indol-1-yl]-2-oxoethyl}pyrimidin-4(3H)-one

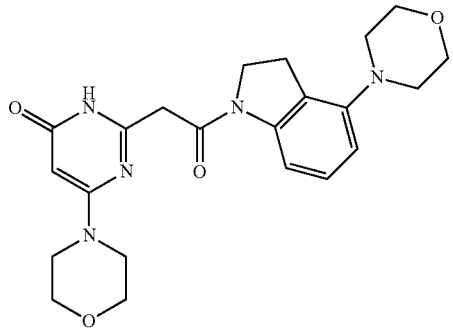 [SMILES: O=C(Cc1nc(N2CCOCC2)cc(=O)[nH]1)N1CCc2c(N3CCOCC3)cccc21]

8 ml of pyridine, 200 mg of 4-morpholin-4-yl-2,3-dihydro-1H-indole (prepared using 4-bromoindoline as described in WO2007103370) and 330 mg of N-[3-(dimethylamino)propyl]-N'-ethylcarbodiimide hydrochloride are successively added to a solution of 300 mg of sodium [4-(morpholin-4-yl)-6-oxo-1,6-dihydropyrimidin-2-yl]acetate (example 1, step 2) in 8 ml of N,N-dimethylformamide. The reaction mixture is stirred at ambient temperature for 48 hours. After the addition of 50 ml of water and extraction with ethyl acetate, the organic phases are combined and then dried over magnesium sulfate, filtered through sintered glass, and concentrated under reduced pressure. After purification of the residue by silica column chromatography, elution being carried out with a mixture of dichloromethane and 7N ammoniacal methanol (90/10), 180 mg of 6-(morpholin-4-yl)-2-{2-[4-(morpholin-4-yl)-2,3-dihydro-1H-indol-1-yl]-2-oxoethyl}pyrimidin-4(3H)-one are obtained in the form of a purple powder, the characteristics of which are the following:

$^1$H NMR spectrum (400 MHz): 2.92 (m, 4H); 3.08 (dd, J=8.1 and 9.3 Hz, 2H); 3.42 (m, 4H); 3.59 (m, 4H); 3.72 (m, 6H); 4.11 (m, 2H); 5.20 (broad s, 1H); 6.68 (d, J=8.6 Hz, 1H); 7.13 (t, J=8.9 Hz, 1H); 7.74 (d, J=7.1 Hz, 1H); 11.61 (broad s, 1H)

Mass spectrometry: method A
Retention time Tr (min)=0.628;
[M+H]+: m/z 426; [M–H]–: m/z 424

Example 34d and Example 35d

Synthesis of (+)-2-[2-(2-cyclopropyl-2,3-dihydroindol-1-yl)-2-oxoethyl]-6-morpholin-4-yl-3H-pyrimidin-4-one and of (−)-2-[2-(2-cyclopropyl-2,3-dihydroindol-1-yl)-2-oxoethyl]-6-morpholin-4-yl-3H-pyrimidin-4-one

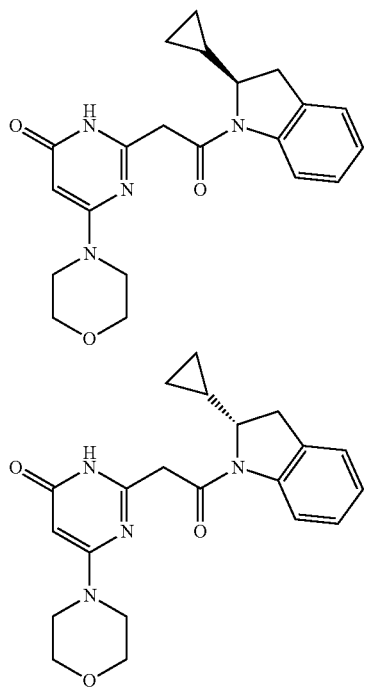

(±)-2-[2-(2-Cyclopropyl-2,3-dihydroindol-1-yl)-2-oxoethyl]-6-morpholin-4-yl-3H-pyrimidin-4-one is prepared by following the procedure described in example 1 using 0.90 g of sodium [4-(morpholin-4-yl)-6-oxo-1,6-dihydropyrimidin-2-yl]acetate, 0.60 g of (±)-2-cyclopropylindoline (reference example 12d) and 0.86 g of N-[3-(dimethylamino)propyl]-N'-ethylcarbodiimide hydrochloride in a mixture of 0.56 ml of pyridine and 10 ml of N,N-dimethylformamide. After purification by chromatography on a 100 g column of 20-45 µm silica, elution being carried out with a 90/10 v/v dichloromethane/methanol mixture, 0.88 g of (±)-2-[2-(2-cyclopropyl-2,3-dihydroindol-1-yl)-2-oxoethyl]-6-morpholin-4-yl-3H-pyrimidin-4-one is obtained in the form of a cream foam, the characteristics of which are the following:

Mass spectrometry: method A
Retention time Tr (min)=0.79;
[M+H]+: m/z 381; [M–H]–: m/z 379

The products were obtained by chiral chromatographic separation of 875 mg of (±)-2-[2-(2-cyclopropyl-2,3-dihydroindol-1-yl)-2-oxoethyl]-6-morpholin-4-yl-3H-pyrimidin-4-one on a Whelk 01 SS column (1200 g, 10 µm, 8/35 cm), eluent: heptane/ethanol/methanol: 70/15/15; flow rate: 250 ml/min, 2 injections. After purification, 407 mg of (+)-2-[2-(2-cyclopropyl-2,3-dihydroindol-1-yl)-2-oxoethyl]-6-morpholin-4-yl-3H-pyrimidin-4-one are obtained, as first enantiomer, in the form of a white powder, the characteristics of which are the following:

$^1$H NMR spectrum (400 MHz): 0.20 to 0.59 (m, 4H); 1.06 (m, 1H); 2.80 (d, J=16.3 Hz, 1H); 3.20 to 3.37 (partially masked m, 1H); 3.40 (m, 4H); 3.60 (m, 4H); 3.78 (d, J=15.7 Hz, 1H); 3.99 (d, J=15.7 Hz, 1H); 4.41 (t, J=7.8 Hz, 1H); 5.20 (s, 1H); 7.04 (t, J=7.9 Hz, 1H); 7.17 (t, J=7.9 Hz, 1H); 7.28 (d, J=7.9 Hz, 1H); 7.94 (broad m, 1H); 11.67 (broad m, 1H)

Mass spectrometry: method A
Retention time Tr (min)=0.78;
[M+H]+: m/z 381; [M–H]–: m/z 379

Optical rotation: $\alpha_D$=+61.3°+/−1.1 (c=2.4 mg in 0.5 ml of DMSO)

Then the second enantiomer, i.e.: 361 mg of impure (−)-2-[2-(2-cyclopropyl-2,3-dihydroindol-1-yl)-2-oxoethyl]-6-morpholin-4-yl-3H-pyrimidin-4-one, is obtained in the form of a white powder. After repurification of 330 mg of this product by chiral chromatography on a Chiralpak IC column (xx g, 5 µm, 2/25 cm), eluent: ethanol; flow rate: 15 ml/min; 16 injections, 223 mg of (−)-2-[2-(2-cyclopropyl-2,3-dihydroindol-1-yl)-2-oxoethyl]-6-morpholin-4-yl-3H-pyrimidin-4-one are obtained in the form of a white powder, the characteristics of which are the following:

$^1$H NMR spectrum (400 MHz): 0.22 to 0.59 (m, 4H); 1.08 (m, 1H); 2.81 (d, J=16.3 Hz, 1H); 3.34 (partially masked m, 1H); 3.40 (m, 4H); 3.60 (m, 4H); 3.78 (d, J=15.9 Hz, 1H); 3.99 (d, J=15.9 Hz, 1H); 4.42 (t, J=7.8 Hz, 1H); 5.20 (s, 1H); 7.04 (t, J=7.9 Hz, 1H); 7.18 (t, J=7.9 Hz, 1H); 7.29 (d, J=7.9 Hz, 1H); 7.94 (broad m, 1H); 11.67 (broad m, 1H)

Mass spectrometry: method A
Retention time Tr (min)=0.78;
[M+H]+: m/z 381; [M–H]–: m/z 379

Optical rotation: $\alpha_D$=−84.7°+/−1.4 (c=2.290 mg in 0.5 ml of DMSO)

Example 36d and Example 37d (+)-2-{2-[2-methyl-4-(trifluoromethyl)-2,3-dihydro-1H-indol-1-yl]-2-oxoethyl}-6-(morpholin-4-yl)pyrimidin-4(3H)-one and (−)-2-{2-[2-methyl-4-(trifluoromethyl)-2,3-dihydro-1H-indol-1-yl]-2-oxoethyl}-6-(morpholin-4-yl)pyrimidin-4(3H)-one

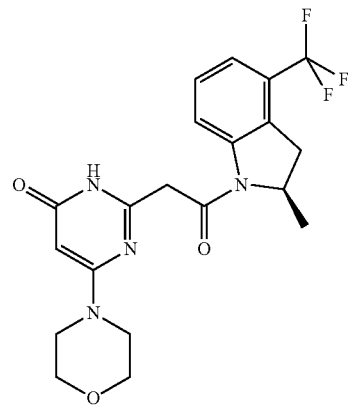

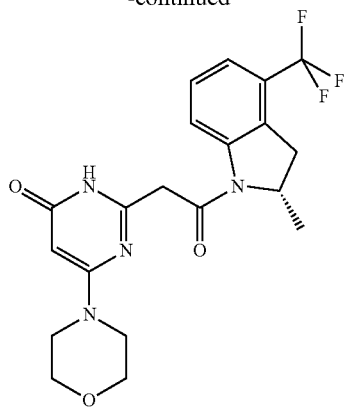

Step 1d: Dimethyl[(E)-2-(2-nitro-6-trifluoromethylphenyl)vinyl]amine

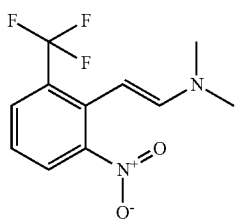 [SMILES: CN(C)/C=C/c1c([N+](=O)[O-])cccc1C(F)(F)F]

3.5 ml of DMF-DMA (N,N-dimethylformamide-dimethyl acetal) are added to a solution of 1 g of 2-methyl-3-nitrobenzotrifluoride in 6 ml of N,N-dimethylformamide. The reaction medium is heated at 110° C. until the starting material has disappeared, then poured into water and extracted with ethyl acetate. The organic phases are washed successively with a 10% sodium bicarbonate solution, a 10% ammonium chloride solution and a saturated sodium chloride solution, dried over magnesium sulfate and filtered. The filtrate is concentrated under reduced pressure so as to give 1.2 g of dimethyl [(E)-2-(2-nitro-6-trifluoromethylphenyl)vinyl]amine in the form of an oil which is used in the next step.

Step 2d: 4-Trifluoromethyl-1H-indole

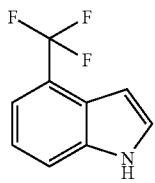

850 mg of powdered iron are added to a solution of 1.2 g of dimethyl[(E)-2-(2-nitro-6-trifluoromethylphenyl)vinyl] amine in 30 ml of acetic acid. The reaction mixture is refluxed for 16 hours and then poured into a solution of hydrochloric acid (HCl, 2N), and extracted with ethyl acetate. The organic phases are washed with a 10% sodium carbonate solution and then with a saturated NaCl solution, dried over magnesium sulfate, filtered, and concentrated under reduced pressure so as to give 959 mg of 4-trifluoromethyl-1H-indole which is used in the next step.

Step 3d: 1-Benzenesulfonyl-4-trifluoromethyl-1H-indole

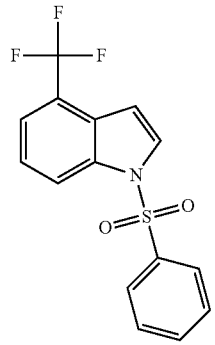 [SMILES: O=S(=O)(c1ccccc1)n1ccc2c(C(F)(F)F)cccc21]

370 mg of NaH at 60% in oil are added to a solution of 0.85 g of 4-trifluoromethyl-1H-indole in 15 ml of tetrahydrofuran, under an inert atmosphere. The reaction mixture is stirred at ambient temperature for one hour and then 0.88 ml of benzenesulfonyl chloride is added dropwise and the stirring is continued for 16 hours. The reaction mixture is then poured into a 10% ammonium chloride solution, extracted with ethyl acetate and dried over magnesium sulfate. After filtration and concentration under reduced pressure, the residue is purified by silica column chromatography, elution being carried out with a mixture of heptane and diisopropyl ether (98/2, then 95/5: v/v), so as to give 1.08 g of 1-benzenesulfonyl-4-trifluoromethyl-1H-indole in the form of a pale yellow oil which is used as it is in the next step.

Step 4d: 1-Benzenesulfonyl-2-methyl-4-trifluoromethyl-1H-indole

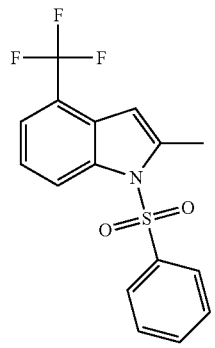 [SMILES: Cc1cc2c(C(F)(F)F)cccc2n1S(=O)(=O)c1ccccc1]

3 ml of n-butyllithium (1.6M in hexane) are added dropwise to a solution of 0.7 ml of diisopropylamine in 10 ml of tetrahydrofuran under argon at −30° C. The solution is stirred for 30 min at ambient temperature, and cooled to −60° C. and a solution of 1.07 g of 1-benzenesulfonyl-4-trifluoromethyl-1H-indole in 10 ml of tetrahydrofuran is added dropwise. The reaction medium is brought back up to ambient temperature and then taken back to −60° C. in order to add, dropwise, 0.31 ml of methyl iodide. After addition, the mixture is allowed to come back up to 0° C. with stirring for 10 minutes, and then to 10° C. for 10 min, before adding a further 0.3 ml of methyl iodide. After returning to ambient temperature, the reaction mixture is stirred for 1 h 30 and then poured into a 10% ammonium chloride solution and extracted with ethyl acetate. The organic phases are washed with a saturated sodium chloride solution, dried over magnesium sulfate, filtered, and concentrated under reduced pressure. The residue is purified by silica column chromatography, elution being carried out with a mixture of heptane and diisopropyl ether (98/2, then 95/5: v/v), so as to give 476 mg of 1-benzenesulfonyl-2-methyl-4-trifluoromethyl-1H-indole, in the form of an oil, which is used in the next step.

Step 5d: 2-Methyl-4-trifluoromethyl-1H-indole

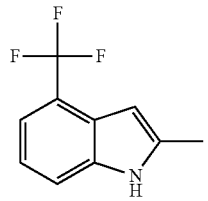

0.271 ml of 5N sodium hydroxide is added to a solution of 460 mg of 1-benzenesulfonyl-2-methyl-4-trifluoromethyl-1H-indole in 1.4 ml of ethanol and 0.44 ml of dimethoxyethane. The reaction mixture is maintained at reflux for 6 hours and poured into water acidified with a hydrochloric acid solution until pH=1 and extracted with ethyl acetate. The organic phases are combined and washed with a 10% sodium bicarbonate solution and a saturated sodium chloride solution, dried over magnesium sulfate, filtered, and concentrated under reduced pressure. The residue is purified by silica column chromatography, elution being carried out with a mixture of heptane and diisopropyl ether (98/2, then 95/5: v/v), so as to give 214 mg of 2-methyl-4-trifluoromethyl-1H-indole, in the form of a pale yellow oil, which is used in the next step.

Step 6d:
2-Methyl-4-trifluoromethyl-2,3-dihydro-1H-indole

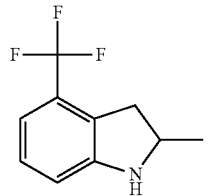

209 mg of 95% sodium cyanoborohydride are added to a solution of 210 mg of 2-methyl-4-trifluoromethyl-1H-indole in 8 ml of acetic acid, cooled to 15° C. The reaction mixture is stirred for 16 hours at ambient temperature and then poured into an aqueous ammonia solution (pH=9). The aqueous phase is extracted with methylene chloride and the combined organic phases are washed with a saturated sodium chloride solution, dried over magnesium sulfate, filtered, and concentrated under reduced pressure, so as to give 196 mg of 2-methyl-4-trifluoromethyl-2,3-dihydro-1H-indole in the form of a pale yellow liquid, which is used in the next step.

Step 7d: 2-[2-(2-Methyl-4-trifluoromethyl-2,3-dihydroindol-1-yl)-2-oxoethyl]-6-morpholin-4-yl-3H-pyrimidin-4-one

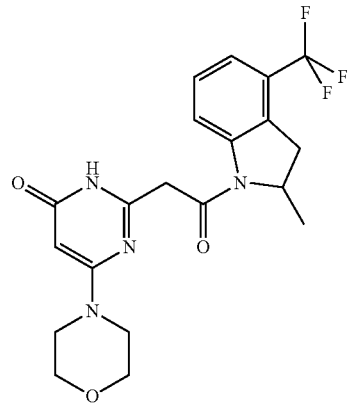 [SMILES: CC1Cc2c(cccc2C(F)(F)F)N1C(=O)Cc1nc(N2CCOCC2)cc(=O)[nH]1]

225 mg of N-[3-(dimethylamino)propyl]-N'-ethylcarbodiimide hydrochloride and 196 mg of 2-methyl-4-trifluoromethyl-2,3-dihydro-1H-indole are added to a solution of 259 mg of sodium [4-(morpholin-4-yl)-6-oxo-1,6-dihydropyrimidin-2-yl]acetate (example 1d, step 2d) in 3 ml of N,N-dimethylformamide and 3 ml of pyridine. The reaction mixture is stirred at ambient temperature for 20 hours and then diluted with water and extracted with ethyl acetate. The extracts are washed successively with water, a hydrochloric acid solution (1M), water and a saturated sodium chloride solution. The organic phase is dried over magnesium sulfate, filtered, and concentrated under reduced pressure, so as to give 144 mg of 2-[2-(2-methyl-4-trifluoromethyl-2,3-dihydroindol-1-yl)-2-oxoethyl]-6-morpholin-4-yl-3H-pyrimidin-4-one in the form of a white solid.

The separation of the two enantiomers of 2-[2-(2-methyl-4-trifluoromethyl-2,3-dihydroindol-1-yl)-2-oxoethyl]-6-morpholin-4-yl-3H-pyrimidin-4-one was carried out by chiral chromatography: stationary phase: Whelk 01 SS 10 μm batch P-130-84-13, 1200 g, 80×350 mm; mobile phase: heptane (70%)/DCM (20%)/EtOH (10%); flow rate: 200 ml/min.

The first enantiomer is concentrated so as to obtain 67.2 mg of (+)-2-[2-(2-methyl-4-trifluoromethyl-2,3-dihydroindol-1-yl)-2-oxoethyl]-6-morpholin-4-yl-3H-pyrimidin-4-one in the form of a white solid, the characteristics of which are the following:

Mass spectrometry: method A
Retention time Tr (min)=0.87;
[M+H]+: m/z 423; [M−H]−: m/z 421;
$^1$H NMR (400 MHz): 1.29 (broad d, J=6.6 Hz, 3H); 2.85 (d, J=16.4 Hz, 1H); 3.41 (m, 4H); 3.51 (dd, J=9.0 and 16.4 Hz, 1H); 3.60 (m, 4H); 3.77 (d, J=16.0 Hz, 1H); 3.96 (d, J=16.0 Hz, 1H); 4.81 (m, 1H); 5.21 (s, 1H); 7.38 (d, J=7.9 Hz, 1H); 7.43 (t, J=7.9 Hz, 1H); 8.24 (broad d, J=7.9 Hz, 1H); 11.68 (broad m, 1H)

Optical rotation: $\alpha_D$=+66.7+/−1.2. C=2.090 mg/0.5 ml MeOH

The second enantiomer is concentrated so as to obtain 60.7 mg of (−)-2-[2-(2-methyl-4-trifluoromethyl-2,3-dihydroindol-1-yl)-2-oxoethyl]-6-morpholin-4-yl-3H-pyrimidin-4-one in the form of a white solid, the characteristics of which are the following:

Mass spectrometry: method A
Retention time Tr (min)=0.87;
[M+H]+: m/z 423; [M−H]−: m/z 421;
$^1$H NMR (400 MHz): 1.29 (broad d, J=6.6 Hz, 3H); 2.85 (d, J=16.4 Hz, 1H); 3.41 (m, 4H); 3.51 (dd, J=9.0 and 16.4 Hz, 1H); 3.60 (m, 4H); 3.77 (d, J=16.0 Hz, 1H); 3.96 (d, J=16.0

Hz, 1H); 4.81 (m, 1H); 5.21 (s, 1H); 7.38 (d, J=7.9 Hz, 1H); 7.43 (t, J=7.9 Hz, 1H); 8.24 (broad d, J=7.9 Hz, 1H); 11.68 (broad m, 1H)

Optical rotation: $\alpha_D$=−43.0+/−0.9. C=2.058 mg/0.5 ml MeOH

Example 38d

2-[2-((+)-2-Fluoromethyl-2,3-dihydroindol-1-yl)-2-oxoethyl]-6-morpholin-4-yl-3H-pyrimidin-4-one Step 1d: 2-[2-((+)-2-hydroxymethyl-2,3-dihydroindol-1-yl)-2-oxoethyl]-6-morpholin-4-yl-3H-pyrimidin-4-one

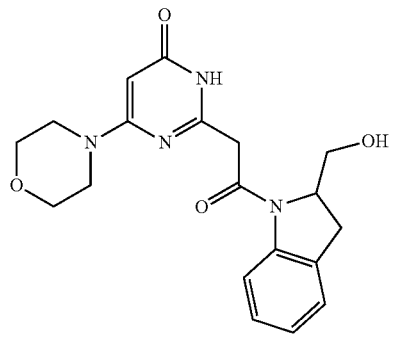 [SMILES: O=C(Cc1nc(N2CCOCC2)cc(=O)[nH]1)N1c2ccccc2CC1CO]

673 mg of N-[3-(dimethylamino)propyl]-N'-ethylcarbodiimide hydrochloride and 378 mg of (−)-(2,3-dihydro-1H-indol-2-yl)methanol (reference example 13d) are added to a solution of 640 mg of sodium (4-morpholin-4-yl-6-oxo-1,6-dihydropyrimidin-2-yl)acetate in 20 ml of DMF and 20 ml of pyridine. The reaction medium is stirred at ambient temperature for 18 hours and then a mixture of water and dichloromethane is added. After settling out, the organic phase is dried over magnesium sulfate, filtered, and then concentrated under reduced pressure. The residue obtained is purified on a silica column, eluent: gradient: dichloromethane/methanol from 100/0 to 95/05, so as to give 456 mg of 2-[2-((+)-2-hydroxymethyl-2,3-dihydroindol-1-yl)-2-oxoethyl]-6-morpholin-4-yl-3H-pyrimidin-4-one, the characteristics of which are the following:

Mass spectrometry: method A
Retention time Tr (min)=0.54;
[M+H]+: m/z 371; [M−H]−: m/z 369
Optical rotation: $\alpha_D$=+80.0+/−1.4. C=2.061 mg/0.5 ml DMSO Step 2d

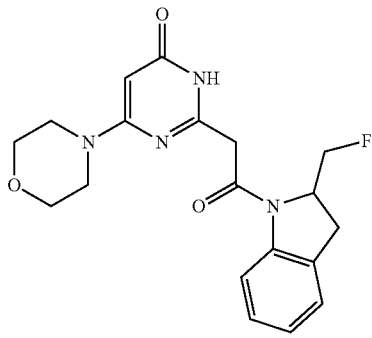 [SMILES: O=C(Cc1nc(N2CCOCC2)cc(=O)[nH]1)N1c2ccccc2CC1CF]

0.07 ml of methanesulfonyl chloride is added to a solution of 200 mg of 2-[2-((+)-2-hydroxymethyl-2,3-dihydroindol-1-yl)-2-oxoethyl]-6-morpholin-4-yl-3H-pyrimidin-4-one in 7 ml of dichloromethane and 0.16 ml of triethylamine at 0° C. The cooling bath is removed so as to allow the temperature to rise to ambient temperature. The mixture is stirred at this temperature for 45 minutes. Cold water and dichloromethane are added. After settling out, the organic phase is washed with a saturated sodium bicarbonate solution. After settling out, the organic phase is dried over magnesium sulfate, filtered, and then concentrated under reduced pressure.

5 ml of a 1M solution of tetrabutylammonium fluoride in THF are added to the residue obtained. The reaction medium is refluxed for one hour. After cooling, dichloromethane and a saturated sodium bicarbonate solution are added.

After settling out, the organic phase is dried over magnesium sulfate, filtered, and then concentrated under reduced pressure. The residue obtained is purified on a silica column, eluent: 97/03 dichloromethane/methanol, so as to give 48 mg of 2-[2-((+)-2-fluoromethyl-2,3-dihydroindol-1-yl)-2-oxoethyl]-6-morpholin-4-yl-3H-pyrimidin-4-one, the characteristics of which are the following:

$^1$H NMR spectrum (300 MHz): 2.91 (d, J=16.3 Hz, 1H); 3.32 to 3.45 (m, 5H); 3.61 (m, 4H); 3.78 (d, J=16.5 Hz, 1H); 3.99 (d, J=16.5 Hz, 1H); 4.35 to 4.68 (m, 2H); 4.97 (m, 1H); 5.18 (s, 1H); 7.04 (t, J=8.0 Hz, 1H); 7.18 (t, J=8.0 Hz, 1H); 7.28 (d, J=8.0 Hz, 1H); 7.83 (broad d, J=8.0 Hz, 1H); 11.40 (broad m, 1H)

Mass spectrometry: method A
Retention time Tr (min)=0.66;
[M+H]+: m/z 373; [M−H]−: m/z 371
Optical rotation: $\alpha_D$=+75.7+/−1.3. C=2.169 mg/0.5 ml DMSO

Example 39d

2-[2-(2,3-Dihydroindol-1-yl)-2-oxoethyl]-6-morpholin-4-yl-3-phenyl-3H-pyrimidin-4-one

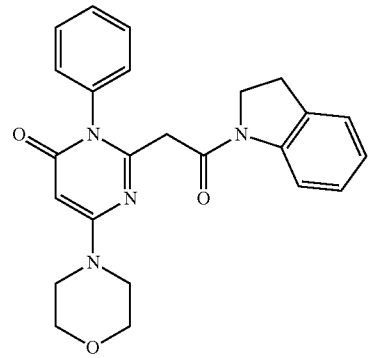 [SMILES: O=C(Cc1nc(N2CCOCC2)cc(=O)n1-c1ccccc1)N1CCc2ccccc21]

Step 1d

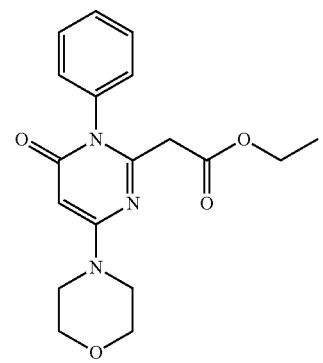 [SMILES: CCOC(=O)Cc1nc(N2CCOCC2)cc(=O)n1-c1ccccc1]

6.24 ml of 0.6 M sodium bis(trimethylsilyl)amide in toluene are added to a suspension of 1 g of ethyl [4-(morpholin-4-yl)-6-oxo-1,6-dihydropyrimidin-2-yl]acetate (obtained in step 1d of example 1d), 912 mg of phenylboronic acid, 680 mg of copper(11) acetate and 1.37 g of 4-dimethylaminopyridine in 12 ml of toluene. The reaction mixture is heated at 95° C. for 16 hours under a stream of dry air, and then filtered through celite. The filtrate is concentrated under reduced pressure and the residue is purified twice by silica column chromatography, elution being carried out with a mixture of dichloromethane and methanol (90/10, V/V) and then with a mixture of diisopropyl ether and methanol (90/10, V/V), so as to give 65 mg of ethyl (4-morpholin-4-yl-6-oxo-1-phenyl-1,6-dihydropyrimidin-2-yl)acetate in the form of a white solid, the characteristics of which are the following:

$^1$H NMR spectrum (400 MHz): 1.06 (t, J=7.0 Hz, 3H); 3.43 (s, 2H); 3.51 (m, 4H); 3.65 (m, 4H); 3.94 (q, J=7.0 Hz, 2H); 5.43 (s, 1H); 7.22 (m, 2H); 7.49 (m, 3H)

Step 2d 56 mg of indoline and 0.36 ml of 2M trimethyl aluminum in toluene are successively added to a solution of 65 mg of ethyl (4-morpholin-4-yl-6-oxo-1-phenyl-1,6-dihydropyrimidin-2-yl)acetate in 3 ml of tetrahydrofuran and 1.5 ml of toluene. The reaction mixture is heated at 90° C. for 4 hours and then concentrated under reduced pressure. The residue is purified twice by silica column chromatography, elution being carried out with a mixture of dichloromethane and methanol (98/2, V/V) and then with ethyl acetate, so as to give 3 mg of 2-[2-(2,3-dihydroindol-1-yl)-2-oxoethyl]-6-morpholin-4-yl-3-phenyl-3H-pyrimidin-4-one in the form of a solid, the characteristics of which are the following:

$^1$H NMR spectrum (400 MHz): 2.97 (t, J=8.4 Hz, 2H); 3.48 (m, 4H); 3.62 (td, J=3.6 and 4.5 Hz, 8H); 5.44 (s, 1H); 6.99 (t, J=7.2 Hz, 1H); 7.14 (t, J=7.7 Hz, 1H); 7.18 (d, J=7.5 Hz, 1H); 7.26 (m, 2H); 7.41 (m, 3H); 7.94 (d, J=7.9 Hz, 1H)

Mass spectrometry: method A
Retention time Tr (min)=0.79;
[M+H]+: m/z 417; [M–H]–: m/z 415

Example 40d

2-[2-((−)-2-Fluoromethyl-2,3-dihydroindol-1-yl)-2-oxoethyl]-6-morpholin-4-yl-3H-pyrimidin-4-one Step 1d: 2-[2-((−)-2-Hydroxymethyl-2,3-dihydroindol-1-yl)-2-oxoethyl]-6-morpholin-4-yl-3H-pyrimidin-4-one

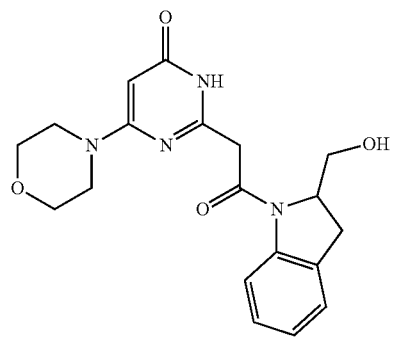 [SMILES: O=C(Cc1nc(N2CCOCC2)cc(=O)[nH]1)N1c2ccccc2CC1CO]

890 mg of N-[3-(dimethylamino)propyl]-N'-ethylcarbodiimide hydrochloride and 500 mg of (+)-(2,3-dihydro-1H-indol-2-yl)methanol (reference example 13d) are added to a solution of 876 mg of sodium (4-morpholin-4-yl-6-oxo-1,6-dihydropyrimidin-2-yl)acetate in 26 ml of DMF and 26 ml of pyridine. The reaction medium is stirred at ambient temperature for 18 hours then a mixture of water and dichloromethane is added. After settling out, the organic phase is dried over magnesium sulfate, filtered, and then concentrated under reduced pressure. The residue obtained is purified on a silica column, eluent: gradient: dichloromethane/methanol from 100/0 to 95/05, so as to give 708 mg of 2-[2-((−)-2-hydroxymethyl-2,3-dihydroindol-1-yl)-2-oxoethyl]-6-morpholin-4-yl-3H-pyrimidin-4-one, the characteristics of which are the following:

Mass spectrometry: method A
Retention time Tr (min)=0.55;
[M+H]+: m/z 371; [M–H]–: m/z 369
Optical rotation: $\alpha_D$=OR=−66.7+/−1.2. C=2.035 mg/0.5 ml DMSO Step 2d

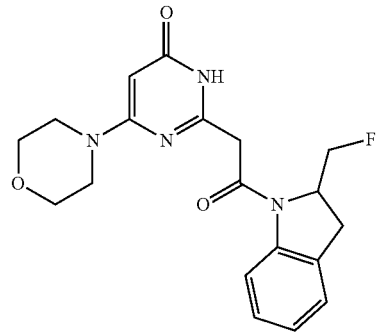 [SMILES: O=C(Cc1nc(N2CCOCC2)cc(=O)[nH]1)N1c2ccccc2CC1CF]

0.07 ml of methanesulfonyl chloride is added to a solution of 200 mg of 2-[2-((−)-2-hydroxymethyl-2,3-dihydroindol-1-yl)-2-oxoethyl]-6-morpholin-4-yl-3H-pyrimidin-4-one in 7 ml of dichloromethane and 0.16 ml of triethylamine, at 0° C. The cooling bath is removed so as to allow the temperature to rise to ambient temperature. The reaction medium is stirred at this same temperature for 45 minutes. Cold water and dichloromethane are added. After settling out, the organic phase is washed with a saturated sodium bicarbonate solution. After settling out, the organic phase is dried over magnesium sulfate, filtered, and then concentrated under reduced pressure.

5 ml of a 1M solution of tetrabutylammonium fluoride in THF are added to the residue obtained. The reaction medium is refluxed for one hour. After cooling, dichloromethane and a saturated sodium bicarbonate solution are added.

After settling out, the organic phase is dried over magnesium sulfate, filtered, and then concentrated under reduced pressure. The residue obtained is purified on a silica column, eluent: 97/03 dichloromethane/methanol, so as to give 42 mg of 2-[2-((−)-2-fluoromethyl-2,3-dihydroindol-1-yl)-2-oxoethyl]-6-morpholin-4-yl-3H-pyrimidin-4-one, the characteristics of which are the following:

$^1$H NMR spectrum (300 MHz): 2.90 (d, J=16.6 Hz, 1H); 3.38 (m, 5H); 3.59 (t, J=4.6 Hz, 4H); 3.75 (d, J=15.4 Hz, 1H); 3.98 (d, J=15.7 Hz, 1H); 4.53 (m, 2H); 4.97 (m, 1H); 5.20 (s, 1H); 7.05 (t, J=7.1 Hz, 1H); 7.18 (t, J=7.7 Hz, 1H); 7.28 (d, J=7.3 Hz, 1H); 7.94 (d, J=5.4 Hz, 1H); 11.67 (broad s, 1H)

Example 41d

Synthesis of 3-amino-2-[2-(2,3-dihydro-1H-indol-1-yl)-2-oxoethyl]-6-(morpholin-4-yl)pyrimidin-4(3H)-one

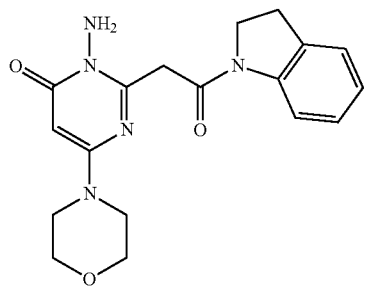 [SMILES: Nn1c(CC(=O)N2CCc3ccccc32)nc(N2CCOCC2)cc1=O]

Step 1d

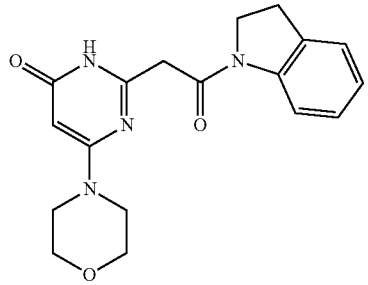 [SMILES: O=C(Cc1nc(N2CCOCC2)cc(=O)[nH]1)N1CCc2ccccc21]

The product is prepared by following the procedure described in example 1d, step 3d, using 260 mg of sodium [4-(morpholin-4-yl)-6-oxo-1,6-dihydropyrimidin-2-yl]acetate and 238 mg of indoline instead of N-[3-(dimethylamino)propyl]-N'-ethylcarbodiimide hydrochloride. 230 mg of 2-[2-(2,3-dihydro-1H-indol-1-yl)-2-oxoethyl]-6-(morpholin-4-yl)pyrimidin-4(3H)-one are obtained in the form of a pale pink solid, the characteristics of which are the following:

$^1$H NMR spectrum: 3.17 (t, J=8.3 Hz, 2H); 3.41 (m, 4H); 3.60 (m, 4H); 3.75 (s, 2H); 4.14 (t, J=8.3 Hz, 2H); 5.21 (s, 1H); 7.01 (t, J=7.6 Hz, 1H); 7.16 (t, J=7.6 Hz, 1H); 7.25 (d, J=7.6 Hz, 1H); 8.02 (d, J=7.6 Hz, 1H); 11.61 (broad s, 1H)

Mass spectrometry: method A
Retention time Tr (min)=0.64
[M+H]+: m/z 341; [M−H]−: m/z 339

Step 2d 957 mg of cesium carbonate and 685 mg of o-diphenylphosphinylhydroxylamine are successively added to a suspension of 500 mg of 2-[2-(2,3-dihydro-1H-indol-1-yl)-2-oxoethyl]-6-(morpholin-4-yl)pyrimidin-4(3H)-one (which can be obtained according to the previous step) in 5 ml of dimethylformamide. The reaction mixture is stirred at ambient temperature for 2 hours and then diluted with 10 ml of water and extracted with dichloromethane (3×25 ml). The organic phases are combined and then dried over anhydrous magnesium sulfate, filtered, and then concentrated to dryness under reduced pressure. The residue is purified by silica column chromatography, elution being carried out with a mixture of dichloromethane and methanol (95/05). The fractions of interest containing the product are combined and then evaporated under reduced pressure, and 154 mg of 3-amino-2-[2-(2,3-dihydro-1H-indol-1-yl)-2-oxoethyl]-6-(morpholin-4-yl)pyrimidin-4(3H)-one are obtained in the form of a pale yellow solid, the characteristics of which are the following:

$^1$H NMR spectrum: 3.17 (t, J=8.5 Hz, 2H); 3.41 (m, 4H); 3.60 (m, 4H); 4.04 (broad s, 2H); 4.16 (t, J=8.5 Hz, 2H); 5.37 (s, 2H); 5.45 (s, 1H); 7.01 (td, J=1.7 and 7.9 Hz, 1H); 7.15 (broad t, J=7.9 Hz, 1H); 7.25 (broad d, J=7.9 Hz, 1H); 8.02 (d, J=7.9 Hz, 1H)

Mass spectrometry: method A
Retention time Tr (min)=0.68;
[M+H]+: m/z 356; [M−H]−: m/z 354

Example 42d

Synthesis of 2-[2-(2,3-dihydro-1H-indol-1-yl)-2-oxoethyl]-4-(morpholin-4-yl)-6-oxopyrimidine-1(6H)-carbonitrile

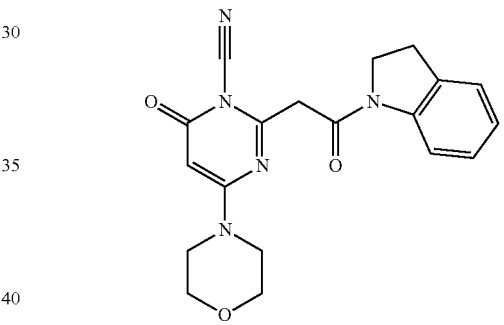

330 mg of cesium carbonate and 404 mg of cyanogen bromide are successively added to a solution of 1 g of 2-[2-(2,3-dihydro-1H-indol-1-yl)-2-oxoethyl]-6-(morpholin-4-yl)pyrimidin-4(3H)-one (which can be obtained according to example 41d, step 1d) in 40 ml of dioxane with 4 Å molecular sieve. The reaction mixture is heated at 40° C. for 2 hours and then cooled to ambient temperature. The suspension is filtered through sintered glass and then rinsed with dioxane, and the filtrate is concentrated under reduced pressure. The residue is purified by silica column chromatography, elution being carried out with a mixture of dichloromethane and methanol (95/05). The fractions of interest containing the product are combined and then evaporated under reduced pressure. The residue is taken up with a mixture of 3 ml of methanol and 10 ml of ethyl ether. After stirring and filtration, the precipitate obtained is rinsed with ethyl ether (3×2 ml) and 22 mg of 2-[2-(2,3-dihydro-1H-indol-1-yl)-2-oxoethyl]-4-(morpholin-4-yl)-6-oxopyrimidine-1(6H)-carbonitrile are obtained in the form of a beige solid, the characteristics of which are the following:

$^1$H NMR spectrum: 3.19 (t, J=8.5 Hz, 2H); 3.55 to 3.69 (m, 8H); 4.17 (t, J=8.5 Hz, 2H); 4.25 (s, 2H); 5.45 (s, 1H); 7.05 (t, J=8.2 Hz, 1H); 7.18 (t, J=8.2 Hz, 1H); 7.28 (d, J=8.2 Hz, 1H); 8.00 (d, J=8.2 Hz, 1H)

Mass spectrometry: method A
Retention time Tr (min)=0.75;
[M+H]+: m/z 366; [M−H]−: m/z 364

Reference Examples for Preparing the Compounds of Formula (Id)

Reference Example 1d

Synthesis of 4-phenyl-2,3-dihydro-1H-indole

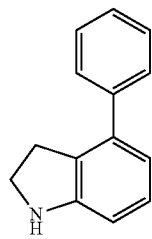 [SMILES: c1ccc(-c2cccc3c2CCN3)cc1]

1.0 g of sodium cyanoborohydride is gradually added to a solution of 1.5 g of 4-phenylindole in 20 ml of trifluoroacetic acid under argon, cooled to a temperature of about −5° C. The reaction mixture is stirred at a temperature of about 0° C. for 2 hours, and is then poured into 50 g of ice and alkalinized with 30 ml of a concentrated sodium hydroxide solution. After the addition of 100 ml of ethyl acetate, the mixture is stirred at ambient temperature and treated with 10 ml of concentrated sodium hydroxide, and then separated by settling out. The organic phase is dried over anhydrous magnesium sulfate, filtered, and then concentrated to dryness under reduced pressure. The residue is treated again with a mixture of 50 ml of water, 50 ml of ethyl acetate and 10 ml of a concentrated sodium hydroxide solution and stirred at ambient temperature for 15 minutes, and then separated by settling out. The organic phase is separated and the aqueous phase is extracted with 2×50 ml of ethyl acetate. The organic phases are combined, dried over anhydrous magnesium sulfate, filtered, and then concentrated to dryness under reduced pressure. The residue is triturated from 20 ml of diisopropyl ether and then concentrated to dryness under reduced pressure. The residue is purified by chromatography on a 50 g column of 20-45 μm silica, elution being carried out with pure dichloromethane. 0.74 g of 4-phenyl-2,3-dihydro-1H-indole is thus obtained in the form of a cream-colored solid, the characteristics of which are the following:
Mass spectrometry: method A
Retention time Tr (min)=0.55;
[M+H]+: m/z 196

Reference Example 2d

4-Trifluoromethoxy-2,3-dihydro-1H-indole

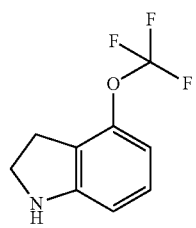 [SMILES: FC(F)(F)Oc1cccc2c1CCN2]

Step 1d 0.18 g of copper(0) is added to a solution of 1.0 g of 4-(trifluoromethoxy)-1H-indole-2-carboxylic acid in 4.5 ml of quinoline under argon. The reaction mixture is heated at 200° C. for 5 hours, and is then cooled to ambient temperature. After dilution with 30 ml of diethyl ether, the mixture is filtered through Clarcel®. The filtrate is washed successively with 6×10 ml of a 6N hydrochloric acid solution, with 10 ml of a saturated sodium hydrogen carbonate solution and then with 10 ml of saturated brine. The organic phase is dried over anhydrous magnesium sulfate, filtered, and then concentrated to dryness under reduced pressure. The residue is purified by chromatography on a 25 g cartridge of 15-40 μm silica, elution being carried out with a 95/5 v/v cyclohexane/ethyl acetate mixture, at a flow rate of 20 ml/min. 0.33 g of 4-(Trifluoromethoxy)indole is thus obtained in the form of an amber oil, the characteristics of which are the following:
$^1$H NMR spectrum (400 MHz): 6.48 (broad s, 1H); 6.96 (d, J=7.9 Hz, 1H); 7.14 (t, J=7.9 Hz, 1H); 7.41 to 7.47 (m, 2H); 11.49 (broad m, 1H)
Mass spectrometry: method A
Retention time Tr (min)=1.01;
[M−H]−: m/z 200

Step 2d 0.57 g of sodium cyanoborohydride is gradually added to a solution of 0.87 g of 4-(trifluoromethoxy)indole in 12 ml of trifluoroacetic acid under argon, cooled to a temperature of about −5° C. The reaction mixture is allowed to warm up to 0° C. for 3 hours, and is then poured into 30 g of ice and alkalinized with 21 ml of a concentrated sodium hydroxide solution. After stirring for 19 hours, the mixture is diluted with 60 ml of ethyl acetate and then stirred at ambient temperature for 30 minutes. After settling out, the organic phase is separated and the aqueous phase is extracted with 3×60 ml of ethyl acetate. The organic phases are combined, dried over anhydrous magnesium sulfate, filtered, and then concentrated to dryness under reduced pressure. The residue is treated again with a mixture of 50 ml of water, 50 ml of ethyl acetate and 10 ml of a concentrated sodium hydroxide solution and stirred at ambient temperature for 30 minutes, and then separated by settling out. The organic phase is separated and the aqueous phase is extracted with 3×50 ml of ethyl acetate. The organic phases are combined, dried over anhydrous magnesium sulfate, filtered, and then concentrated to dryness under reduced pressure. The residue is purified by chromatography on a 25 g cartridge of 15-40 μm silica, elution being carried out with 95/5; 90/10; then 85/15 v/v cyclohexane/ethyl acetate mixtures, at a flow rate of 25 ml/min. 0.18 g of impure 4-(trifluoromethoxy)indoline is thus obtained in the form of a yellow oil which is directly used in the next step.

Reference Example 3d

Synthesis of 4-(2-methoxyphenyl)-2,3-dihydro-1H-indole

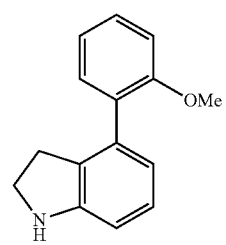 [SMILES: COc1ccccc1-c1cccc2c1CCN2]

Step 1d 0.73 g of 2-methoxyphenylboronic acid and then 1.66 g of potassium carbonate are successively added to a solution of 0.78 g of 4-bromoindole in 15 ml of dioxane and 5 ml of water under argon. The reaction mixture is stirred at ambient temperature for 15 minutes, and then 0.16 g of dichlorobis(tri-o-tolylphosphine)palladium(II) is added. The reaction mixture is stirred at ambient temperature for 16 hours, and then at 60° C. for 18 hours, and, finally, at 110° C. for 3 hours. After returning to ambient temperature, the mixture is concentrated to dryness under reduced pressure. The residue is taken up in a mixture of 15 ml of a 2N sodium hydroxide solution and 30 ml of ethyl acetate. The mixture is filtered through Clarcel®, and then separated by settling out. The organic phase is separated and the aqueous phase is extracted with 2×30 ml of ethyl acetate. The organic phases are combined, dried over anhydrous magnesium sulfate, filtered, and then concentrated to dryness under reduced pressure. The residue is purified on a 30 g cartridge of 15-40 μm silica, elution being carried out with a 60/40 v/v cyclohexane/dichloromethane mixture, at a flow rate of 30 ml/min. 0.44 g of 4-(2-methoxyphenyl)indole is thus obtained in the form of a pale yellow solid, the characteristics of which are the following:

Mass spectrometry: method A
Retention time Tr (min)=1.01;
[M+H]+: m/z 224
Melting point (Kofler): 172° C.

Step 2d 0.26 g of sodium cyanoborohydride is gradually added to a solution of 0.44 g of 4-(2-methoxyphenyl)indole in 5 ml of trifluoroacetic acid under argon, cooled to a temperature of about −5° C. The reaction mixture is stirred at a temperature of about −5° C. for 2 hours, and is then poured into 15 g of ice and alkalinized with 8 ml of a concentrated sodium hydroxide solution. After the addition of 30 ml of ethyl acetate, the mixture is stirred at ambient temperature for 1 hour, and then separated by settling out. The organic phase is separated and the aqueous phase is extracted with 15 ml of ethyl acetate. The organic phases are combined, dried over anhydrous magnesium sulfate, filtered, and then concentrated to dryness under reduced pressure. The residue is treated again with a mixture of 15 ml of water, 15 ml of ethyl acetate and 3 ml of a concentrated sodium hydroxide solution and stirred at ambient temperature for 15 minutes, and then separated by settling out. The organic phase is separated and the aqueous phase is extracted with 2×15 ml of ethyl acetate. The organic phases are combined, dried over anhydrous magnesium sulfate, filtered, and then concentrated to dryness under reduced pressure. The residue is purified by chromatography on a 25 g cartridge of 15-40 μm silica, elution being carried out with pure dichloromethane, at a flow rate of 30 ml/min. 0.14 g of 4-(2-methoxyphenyl)-2,3-dihydro-1H-indole is thus obtained in the form of an off-white solid, the characteristics of which are the following:

Mass spectrometry: method A
Retention time Tr (min)=0.55;
[M+H]+: m/z 226
Melting point (Kofler): 82° C.

Reference Example 4d 4-(1-Propylpiperidin-3-yl)-2,3-dihydro-1H-indole

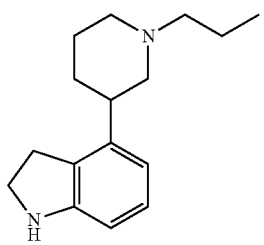 [SMILES: CCCN1CCCC(c2cccc3c2CCN3)C1]

The product can be prepared as described in reference example 1d, step 2d, by reduction of the corresponding indole (which can be prepared according to patent EP21924, example 17d).

Reference Example 5d

4-Difluoromethoxy-2,3-dihydro-1H-indole

Step 1d

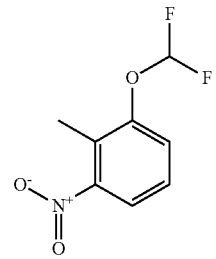

A solution of 10 g of 2-methyl-3-nitrophenol in 20 ml of N,N-dimethylformamide is added to a mixture of 23.4 g of sodium chlorodifluoroacetate and 22 g of potassium carbonate in 30 ml of N,N-dimethylformamide and 6 ml of water. The reaction mixture is then heated at 110° C. for 3 hours and left to stand for 16 hours, and then treated with a mixture of water and ethyl acetate. The organic phase is washed with 1N sodium hydroxide, water and a saturated sodium chloride solution, dried over magnesium sulfate, filtered, and concentrated under reduced pressure, so as to give the expected product in the form of a brown oil, used as it is in the next step.

Step 2d

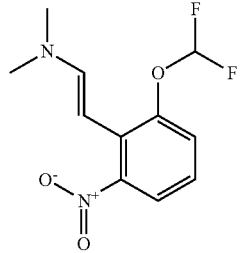 [SMILES: CN(C)/C=C/c1c(OC(F)F)cccc1[N+](=O)[O-]]

17 g of tris(dimethylamino)methane are added to a solution of 6 g of 1-difluoromethoxy-2-methyl-3-nitrobenzene in 60 ml of N,N-dimethylformamide and the reaction mixture is heated at 100° C. for 72 hours. The reaction mixture is then concentrated under reduced pressure so as to give 7.6 g of a crude oil, used as it is in the next step.

Step 3d

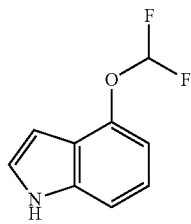 [SMILES: FC(F)Oc1cccc2[nH]ccc12]

7 g of Raney nickel are added to a solution of 7.6 g of [2-(2-difluoromethoxy-6-nitrophenyl)vinyl]dimethylamine in 35 ml of methanol and 35 ml of tetrahydrofuran, under an argon atmosphere. The reaction mixture is heated at 60° C. and 5.6 ml of hydrazine hydrate are added in 4 portions of 1.4 ml every 30 minutes, and the mixture is stirred for 16 hours.

Step 4d

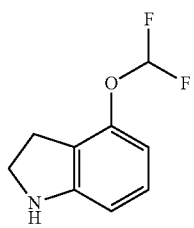 [SMILES: FC(F)Oc1cccc2c1CCN2]

0.722 mg of sodium cyanoborohydride is added to a solution of 1 g of 4-difluoromethoxy-1H-indole in 15 ml of trifluoroacetic acid, cooled to 0° C., and the stirring is continued for 3 hours. The reaction mixture is then concentrated under reduced pressure, treated with a concentrated sodium hydroxide solution, extracted with dichloromethane, dried over magnesium sulfate, filtered, and concentrated under reduced pressure. The residue is purified by silica column chromatography, elution being carried out with a mixture of heptane and ethyl acetate (20/80: v/v), so as to give 300 mg of 4-difluoromethoxy-2,3-dihydro-1H-indole in the form of a yellow oil, the characteristics of which are the following:

$^1$H NMR spectrum (400 MHz): 2.91 (t, J=8.6 Hz, 2H); 3.45 (dt, J=2.0 and 8.6 Hz, 2H); 5.73 (broad m, 1H); 6.30 (d, J=7.9 Hz, 1H); 6.36 (d, J=7.9 Hz, 1H); 6.93 (t, J=7.9 Hz, 1H); 7.10 (t, J=74.8 Hz, 1H)

Reference Example 6d 4-(2-chlorophenyl)-2,3-dihydro-1H-indole

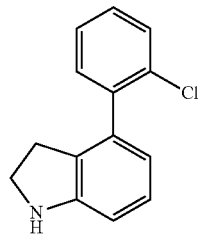 [SMILES: Clc1ccccc1-c1cccc2c1CCN2]

558 g of sodium cyanoborohydride are added in portions to a suspension of 960 mg of 4-(2-chlorophenyl)-1H-indole in 11 ml of trifluoroacetic acid cooled to 0° C. The reaction medium is stirred for 16 hours while allowing it to rise to ambient temperature and then the pH is brought to neutrality with a sodium hydroxide solution. The reaction mixture is diluted with 300 ml of water then extracted with ethyl acetate (2×250 ml). The organic phases are combined and then concentrated to dryness under reduced pressure. After purification of the residue by silica column chromatography, elution being carried out with a mixture of heptane and ethyl acetate (80/20), 395 mg of 4-(2-chlorophenyl)-2,3-dihydro-1H-indole are obtained in the form of a colorless viscous oil.

Reference Example 7d 1,2,3,3a,4,8b-hexahydrocyclopenta[b]indole 1.9 g of sodium cyanoborohydride are added in portions to a solution of 1.5 g of 1,2,3,4-tetrahydrocyclopenta[b]indole in 40 ml of acetic acid cooled to 15° C. The reaction medium is stirred for 20 hours while allowing it to rise to ambient temperature and then the pH is brought to neutrality with a 28% aqueous ammonia solution. The reaction mixture is diluted with water and then extracted with dichloromethane, and the organic phase is washed with a saturated sodium chloride solution, dried over magnesium sulfate, filtered, and concentrated under reduced pressure. The residue is purified by silica column chromatography, elution being carried out with a mixture of heptane and ethyl acetate (95/05), so as to give 1.3 g of 1,2,3,3a,4,8b-hexahydrocyclopenta[b]indole in the form of a colorless oil.

Reference Example 8d 4-(4-methanesulfonylpiperazin-1-ylmethyl)-2,3-dihydro-1H-indole

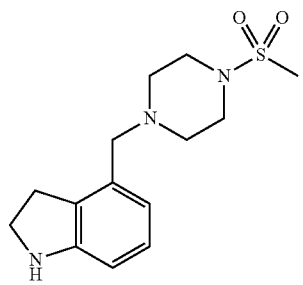 [SMILES: CS(=O)(=O)N1CCN(Cc2cccc3c2CCN3)CC1]

2.92 g of sodium triacetoxyborohydride, 2.26 of 1-methanesulfonylpiperazine hydrochloride and 545 mg of pyridine are successively added to a solution of 1 g of indole-4-carboxaldehyde in 40 ml of tetrahydrofuran under argon. The reaction mixture is stirred at ambient temperature for 15 hours, and then concentrated under reduced pressure. The residue is taken up in 40 ml of acetic acid cooled to 15° C., and then 1.30 g of sodium cyanoborohydride are added in portions. The reaction medium is stirred for 2 hours while allowing it to rise to ambient temperature, poured into a water/ice mixture, treated with 28% aqueous ammonia until the pH is neutral, and extracted with dichloromethane (4×30 ml). The organic phases are combined, dried over magnesium sulfate, filtered, and then concentrated under reduced pressure. The residue obtained is purified on a silica column (eluent: heptane/ethyl acetate, from 0 to 100% of ethyl acetate), so as to give 890 mg of 4-(4-methanesulfonylpiperazin-1-ylmethyl)-2,3-dihydro-1H-indole in the form of a yellow solid.

Reference Example 9d 4-(4-methylpiperazin-1-ylmethyl)-2,3-dihydro-1H-indole

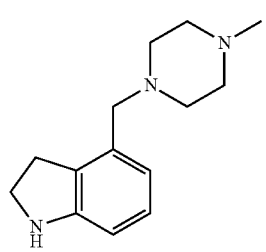 [SMILES: CN1CCN(Cc2cccc3c2CCN3)CC1]

1.38 g of 1-methylpiperazine and 2.92 g of sodium triacetoxyborohydride are successively added to a solution of 1 g of indole-4-carboxaldehyde in 40 ml of tetrahydrofuran under argon. The reaction mixture is stirred at ambient temperature for 15 hours, and then concentrated under reduced pressure. The residue is taken up in 40 ml of acetic acid, cooled to 15° C., and then 1.30 g of sodium cyanoborohydride are added in portions. The reaction medium is stirred for 2 hours while allowing it to rise to ambient temperature, poured into a water/ice mixture, treated with 28% aqueous ammonia until the pH is neutral, and extracted with dichloromethane (4×50 ml). The organic phases are combined, dried over magnesium sulfate, filtered, and then concentrated under reduced pressure. The residue obtained is purified on a silica column, eluent: 95/05 dichloromethane/7N ammoniacal methanol, so as to give 1.22 g of 4-(4-methylpiperazin-1-ylmethyl)-2,3-dihydro-1H-indole in the form of a yellow solid.

Reference Example 10d 4-(4-methylpiperazin-1-yl)-2,3-dihydro-1H-indole

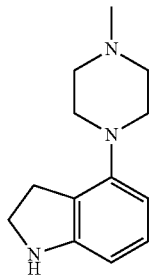 [SMILES: CN1CCN(c2cccc3c2CCN3)CC1]

429 mg of sodium cyanoborohydride are added in portions to a solution of 490 mg of 4-(4-methylpiperazin-1-yl)-1H-indole, in 17 ml of acetic acid cooled to 14° C. The reaction medium is stirred for 2 hours at ambient temperature and then poured into a water/ice mixture and the pH is brought to neutrality with an aqueous ammonia solution. The mixture is then extracted with dichloromethane and the combined organic phases are dried over magnesium sulfate, filtered, and concentrated under reduced pressure. The residue is purified by silica column chromatography, elution being carried out with a mixture of dichloromethane and methanol (95/05), so as to give 395 mg of 4-(4-methylpiperazin-1-yl)-2,3-dihydro-1H-indole in the form of a colorless viscous oil.

Reference Example 11d 4-difluoromethoxy-2-methyl-2,3-dihydro-1H-indole

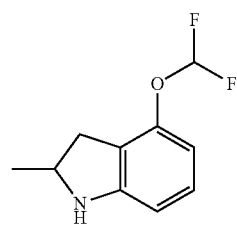

Step 1d

4-Difluoromethoxy-2-methylindole

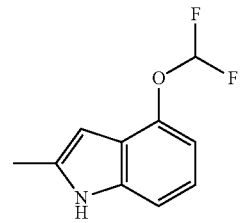

Freon-22 (HCF$_2$Cl) is bubbled into a solution of 3 g of 4-hydroxy-2-methylindole in 90 ml of dichloromethane at 0° C., containing a small amount of tetrabutylammonium bromide (used as a phase-transfer agent). 45 ml of a 10M sodium hydroxide solution are added dropwise to this solution. The reaction mixture is then stirred for 2 hours at 0° C. and is then left to rise to ambient temperature. The phases are separated and the organic phase is concentrated under reduced pressure. The residue obtained is purified on a silica column, elution being carried out with dichloromethane, so as to give 480 mg of 4-difluoromethoxy-2-methylindole in the form of a yellow oil, the characteristics of which are the following:

$^1$H NMR spectrum (400 MHz): 2.38 (s, 3H); 6.15 (s, 1H); 6.71 (d, J=7.2 Hz, 1H); 6.97 (t, J=8.0 Hz, 1H); 7.20 (t, J=75.0 Hz, 1H); 7.16 (d, J=8.1 Hz, 1H); 11.19 (d, J=0.4 Hz, 1H)

Step 2d

4-Difluoromethoxy-2-methyl-2,3-dihydro-1H-indole

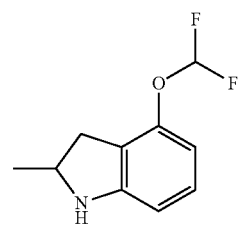

459 mg of sodium cyanoborohydride are added in portions to a solution of 480 mg of 4-difluoromethoxy-2-methylindole in 15 ml of acetic acid cooled to 10° C. The reaction medium is stirred for 16 hours while allowing it to rise to ambient temperature.

The reaction medium is poured into a water/ice mixture and then treated with 28% aqueous ammonia and extracted with ethyl acetate. The organic phase is dried over magnesium sulfate, filtered, and then concentrated under reduced pressure. The residue obtained is purified on a silica column, eluent: 80/20 heptane/ethyl acetate, so as to give 250 mg of 4-difluoromethoxy-2-methyl-2,3-dihydro-1H-indole in the form of an oil, the characteristics of which are the following:

$^1$H NMR spectrum (400 MHz): 1.17 (d, J=6.2 Hz, 3H); 2.47 (dd, J=7.6 and 15.9 Hz, 1H); 3.06 (dd, J=8.9 and 15.9 Hz, 1H); 3.91 (m, 1H); 5.85 (broad m, 1H); 6.25 to 6.35 (m, 2H); 6.93 (t, J=7.9 Hz, 1H); 7.09 (t, J=74.8 Hz, 1H)

Reference Example 12d

Synthesis of (−)-2-isopropylindoline and (+)-2-cyclopropylindoline

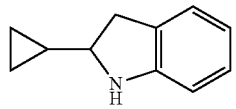 [SMILES: c1ccc2c(c1)CC(C1CC1)N2]

Step 1d 0.26 g of copper(I) iodide, 0.30 g of bis(triphenylphosphine)palladium(II) dichloride and then 0.78 ml of cyclopropylacetylene are successively added to a solution of 1.0 g of 2-iodoaniline in 5 ml of triethylamine under argon. The reaction mixture is stirred at ambient temperature for 30 minutes, and then 1 ml of N,N-dimethylformamide is added. The reaction mixture is stirred at ambient temperature for 30 minutes, then 1 ml of N,N-dimethylformamide is again added. The reaction mixture is stirred at ambient temperature for 15 hours, and is then poured into 100 ml of water. After the addition of 50 ml of ethyl acetate, the mixture is filtered through Celite®, and then separated by settling out. The organic phase is separated and the aqueous phase is extracted with 3×40 ml of ethyl acetate. The organic phases are combined, washed with 2×40 ml of water, dried over anhydrous magnesium sulfate, filtered, and then concentrated to dryness under reduced pressure. The residue is purified on a 50 g column of 20-45 µm silica, elution being carried out with an 80/20 v/v dichloromethane/cyclohexane mixture. 0.42 g of 2-cyclopropylethynylphenylamine is thus obtained in the form of a brown oil which is used directly in the next step.

Step 2d 0.54 g of copper(I) iodide is added to a solution of 0.42 g of 2-cyclopropylethynylphenylamine in 20 ml of N,N-dimethylformamide under argon. The reaction mixture is refluxed for 2 hours, and is then concentrated to dryness under reduced pressure. The residue is taken up in a mixture of 200 ml of water and 100 ml of dichloromethane, filtered through Celite®, and then separated by settling out. The organic phase is separated and the aqueous phase is extracted with 50 ml of dichloromethane. The organic phases are combined, washed with 100 ml of water, dried over anhydrous magnesium sulfate, filtered, and then concentrated to dryness under reduced pressure. The residue is purified on a 50 g column of 20-45 µm silica, elution being carried out with a 50/50 v/v cyclohexane/dichloromethane mixture. 0.18 g of 2-cyclopropylindole is thus obtained in the form of a yellow solid, the characteristics of which are the following:
Mass spectrometry: method A
Retention time Tr (min)=0.96;
[M+H]+: m/z 158

Step 3d 1.0 g of sodium cyanoborohydride is gradually added to a solution of 1.25 g of 2-cyclopropylindole in 80 ml of acetic acid under argon cooled to a temperature of about 15° C. The reaction mixture is stirred at a temperature of about 15° C. for 2 hours, and is then treated with 100 ml of water. It is then cooled to a temperature of about 5° C. and alkalinized by gradual addition of 140 ml of a 30% sodium hydroxide solution. The reaction mixture is diluted with 200 ml of ethyl acetate and is then stirred at ambient temperature for 15 hours. After settling out, the organic phase is separated and the aqueous phase is extracted with 3×200 ml of ethyl acetate. The organic phases are combined, dried over anhydrous magnesium sulfate, filtered, and then concentrated to dryness under reduced pressure. The residue is taken up in a mixture of 60 ml of ethyl acetate, 40 ml of water and 10 ml of concentrated sodium hydroxide, and then the mixture is stirred at ambient temperature for 10 minutes. After settling out, the organic phase is separated and the aqueous phase is extracted with 2×50 ml of ethyl acetate. The organic phases are combined, dried over anhydrous magnesium sulfate, filtered, and then concentrated to dryness under reduced pressure. 1.2 g of (±)-2-cyclopropylindoline are thus obtained in the form of a brown oil which is used as it is.

Reference Example 13d

2-Hydroxymethyl-2,3-dihydro-1H-indole

Step 1d 1-((R)-2-Benzyloxypropionyl)-2,3-dihydro-1H-indole-2-carboxylic acid ethyl ester: diastereoisomer A

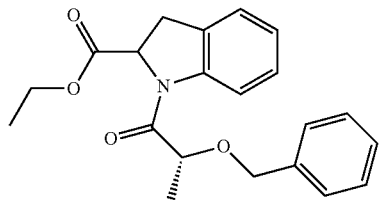 [SMILES: CCOC(=O)C1Cc2ccccc2N1C(=O)[C@@H](C)OCc1ccccc1]

And 1-((R)-2-Benzyloxypropionyl)-2,3-dihydro-1H-indole-2-carboxylic acid ethyl ester: diastereoisomer B

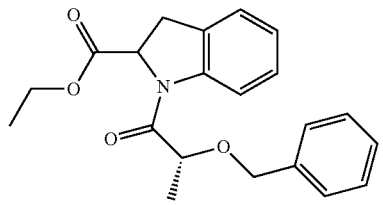 [SMILES: CCOC(=O)C1Cc2ccccc2N1C(=O)[C@@H](C)OCc1ccccc1]

16.6 g of N-[3-(dimethylamino)propyl]-N'-ethylcarbodiimide hydrochloride and then 10 g of ethyl indoline-2-carboxylate are added to a solution of 12.6 g of o-benzyl-D-lactic acid in 30 ml of DMF and 10.6 ml of pyridine. The reaction medium is stirred at ambient temperature for 18 hours. The reaction medium is concentrated under reduced pressure to ⅔ of the volume of the reaction medium. Ethyl acetate and water are added. After settling out, the organic phase is dried over magnesium sulfate, filtered, and then concentrated under reduced pressure. The residue obtained is purified on a silica cartridge: eluent: gradient: heptane/ethyl acetate from 100/0 to 80/20, so as to give 7.24 g of 1-((R)-2-benzyloxypropionyl)-2,3-dihydro-1H-indole-2-carboxylic acid ethyl ester: diastereoisomer A, the characteristics of which are the following:
Mass spectrometry: method A
Retention time Tr (min)=1.08;
[M+H]+: m/z 354; [M+Na]+: m/z 376 (base peak)

And 7.5 g of 1-((R)-2-benzyloxypropionyl)-2,3-dihydro-1H-indole-2-carboxylic acid ethyl ester: diastereoisomer B in the form of a white solid, the characteristics of which are the following:

Mass spectrometry: method A
Retention time Tr (min)=1.06;
[M+H]+: m/z 354; [M+Na]+: m/z 376; base peak: m/z 282

Step 2d (R)-2-Benzyloxy-1-(2-hydroxymethyl-2,3-dihydroindol-1-yl)propan-1-one: diastereoisomer A

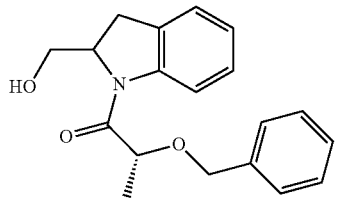 [SMILES: C[C@@H](OCc1ccccc1)C(=O)N1c2ccccc2CC1CO]

and (+)-(2,3-Dihydro-1H-indol-2-yl)methanol

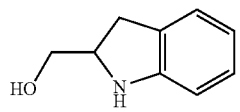 [SMILES: OCC1Cc2ccccc2N1]

1.04 g of sodium borohydride is added to a solution of 3.31 g of 1-((R)-2-benzyloxypropionyl)-2,3-dihydro-1H-indole-2-carboxylic acid ethyl ester: diastereoisomer A in 7.5 ml of THF and 7.5 ml of ethanol.

The reaction medium is stirred at ambient temperature for 5 hours.

Dichloromethane and water are added. After settling out, the organic phase is dried over magnesium sulfate, filtered, and then concentrated under reduced pressure. The residue obtained is purified on a silica cartridge: eluent: 50/50 heptane/ethyl acetate, so as to give 0.98 g of (R)-2-benzyloxy-1-(2-hydroxymethyl-2,3-dihydroindol-1-yl)propan-1-one: diastereoisomer A, the characteristics of which are the following:

Mass spectrometry: method A
Retention time Tr (min)=0.85;
[M+H]+: m/z 312

And 1.65 g of (+)-(2,3-dihydro-1H-indol-2-yl)methanol in the form of a white solid, the characteristics of which are the following:

Mass spectrometry: method A
Retention time Tr (min)=0.19;
[M+H]+: m/z 150

Step 3d (+)-(2,3-Dihydro-1H-indol-2-yl)methanol

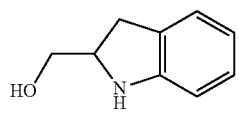 [SMILES: OCC1Cc2ccccc2N1]

To a solution of 0.9 g of (R)-2-benzyloxy-1-(2-hydroxymethyl-2,3-dihydroindol-1-yl)propan-1-one: diastereoisomer A in 9 ml of ethanol and 9 ml of 37% hydrochloric acid are refluxed for two hours.

The reaction medium is concentrated under reduced pressure. The residue obtained is taken up with water. 2N sodium hydroxide is added until the pH=10. The medium is extracted with dichloromethane. After settling out, the organic phase is dried over magnesium sulfate, filtered, and then concentrated under reduced pressure, so as to give 0.4 g of (+)-(2,3-dihydro-1H-indol-2-yl)methanol, the characteristics of which are the following:

Mass spectrometry: method A
Retention time Tr (min)=0.19;
[M+H]+: m/z 150
OR=+38.5+/−0.9. C=1.974 mg/0.5 ml DMSO Step 4d (R)-2-Benzyloxy-1-(2-hydroxymethyl-2,3-dihydroindol-1-yl)propan-1-one: diastereoisomer B

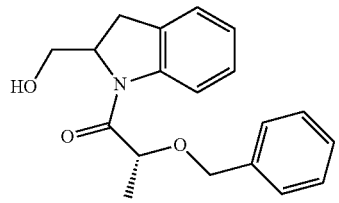 [SMILES: C[C@@H](OCc1ccccc1)C(=O)N1c2ccccc2CC1CO]

And (−)-(2,3-Dihydro-1H-indol-2-yl)methanol

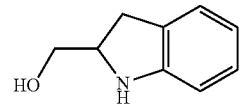

1.36 g of sodium borohydride are added to a solution of 5.75 g of 1-((R)-2-benzyloxypropionyl)-2,3-dihydro-1H-indole-2-carboxylic acid ethyl ester: diastereoisomer B in 20 ml of THF.

The reaction medium is stirred at ambient temperature for 18 hours.

10 ml of ethanol and 0.4 g of sodium borohydride are added. After two hours of stirring at ambient temperature, dichloromethane and water are added.

After settling out, the organic phase is dried over magnesium sulfate, filtered, and then concentrated under reduced pressure. The residue obtained is purified on a silica cartridge: eluent: gradient: dichloromethane/methanol from 100/0 to 98/02, so as to give 0.51 g of (R)-2-benzyloxy-1-(2-hydroxymethyl-2,3-dihydroindol-1-yl)propan-1-one: diastereoisomer B, the characteristics of which are the following:

Mass spectrometry: method A
Retention time Tr (min)=0.82; [M+H]+: m/z 312

And 0.96 g of (−)-(2,3-dihydro-1H-indol-2-yl)methanol in the form of a white solid, the characteristics of which are the following:

Mass spectrometry: method A
Retention time Tr (min)=0.19; [M+H]+: m/z 150
OR=−38.9+/−0.8. C=2.255 mg/0.5 ml DMSO

Step 5d (−)-(2,3-Dihydro-1H-indol-2-yl)methanol

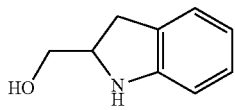 [SMILES: OCC1Cc2ccccc2N1]

To a solution of 117 mg of (R)-2-benzyloxy-1-(2-hydroxymethyl-2,3-dihydroindol-1-yl)propan-1-one: diastereoisomer B in 1.2 ml of ethanol and 1.2 ml of 37% hydrochloric acid are refluxed for two hours.

The reaction medium is concentrated under reduced pressure. The residue obtained is taken up with water. 2N sodium hydroxide is added until the pH=10. The medium is extracted with dichloromethane. After settling out, the organic phase is dried over magnesium sulfate, filtered, and then concentrated under reduced pressure, so as to give 50 mg of (−)-(2,3-dihydro-1H-indol-2-yl)methanol, the characteristics of which are the following:
Mass spectrometry: method A
Retention time Tr (min)=0.19;
[M+H]+: m/z 150
OR=−38.9+/−0.8. C=2.255 mg/0.5 ml DMSO
The optical rotations (ORs) were carried out on a model 341 polarimeter from Perkin Elmer. Wavelength: sodium α line (589 nanometers).

Synthesis of the Compounds of Formula (Ie)

Example 1e

Synthesis of 1-((S)-2-methyl-2,3-dihydroindol-1-yl)-2-(4-morpholin-4-yl-6-thioxo-1,6-dihydropyrimidin-2-yl)ethanone

Step 1e

Ethyl [4-(morpholin-4-yl)-6-oxo-1,6-dihydropyrimidin-2-yl]acetate

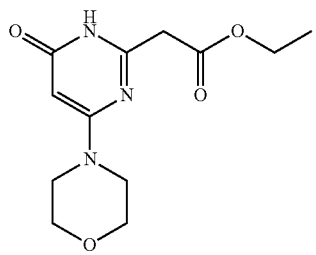 [SMILES: CCOC(=O)Cc1nc(N2CCOCC2)cc(=O)[nH]1]

168.5 ml of ethyl 3-ethoxy-3-iminopropanoate hydrochloride and then 155 ml of N,N-diisopropylethylamine in 200 ml of ethanol are added to a solution of 25 g of morpholine in 400 ml of ethanol heated to 95° C. The reaction mixture is heated at 95° C. for 30 hours and then allowed to return to ambient temperature. The precipitate formed is filtered off through sintered glass and then washed with 100 ml of ethanol, twice 500 ml of water and, finally, 500 ml of ethyl ether. The solid is dried under vacuum, so as to give 35 g of ethyl [4-(morpholin-4-yl)-6-oxo-1,6-dihydropyrimidin-2-yl]acetate in the form of a white solid, the characteristics of which are the following:

$^1$H NMR spectrum (400 MHz): 1.19 (t, J=7.1 Hz, 3H); 3.38 to 3.44 (m, 4H); 3.56 (s, 2H); 3.61 (dd, J=4.0 and 5.7 Hz, 4H); 4.12 (q, J=7.1 Hz, 2H); 5.20 (s, 1H); 11.69 (broad s, 1H)
Mass spectrometry: method A
Retention time Tr (min)=0.48;
[M+H]+: m/z 268; [M−H]−: m/z 266

Step 2e (4-Morpholin-4-yl-6-thioxo-1,6-dihydropyrimidin-2-yl)acetic acid ethyl ester

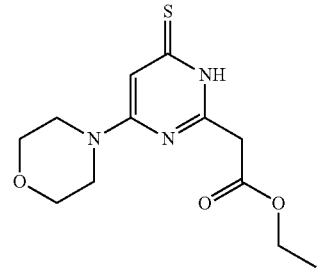 [SMILES: CCOC(=O)Cc1nc(N2CCOCC2)cc(=S)[nH]1]

In a round-bottomed flask, a mixture of 1 g of ethyl [4-(morpholin-4-yl)-6-oxo-1,6-dihydropyrimidin-2-yl]acetate obtained in the previous step with 2.2 g of 2,4-bis(4-methoxyphenyl)-1,3-dithia-2,4-diphosphetane 2,4-disulfide (Lawesson's reagent) in 20 ml of toluene is heated at 60° C. for 18 hours.

After cooling, the solid formed is filtered off. The filtrate is concentrated under reduced pressure. The residue obtained is purified by silica column chromatography (eluent: 85/15 dichloromethane/ethyl acetate), so as to give 0.86 g of (4-morpholin-4-yl-6-thioxo-1,6-dihydropyrimidin-2-yl)acetic acid ethyl ester in the form of a beige solid, the characteristics of which are the following:
Mass spectrometry: method A
Retention time Tr (min)=0.51;
[M+H]+: m/z 284; [M−H]−: m/z 282; base peak: m/z 236

Step 3e

Sodium (4-morpholin-4-yl-6-thioxo-1,6-dihydropyrimidin-2-yl)acetate

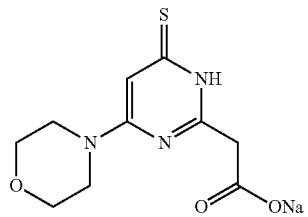

3.05 ml of 2N sodium hydroxide are added to a solution of 865 mg of (4-morpholin-4-yl-6-thioxo-1,6-dihydropyrimidin-2-yl)acetic acid ethyl ester in 15 ml of THF. The reaction medium is stirred at ambient temperature for 24 hours. The reaction medium is concentrated under reduced pressure. The residue obtained is oven-dried under vacuum in the presence of $P_2O_5$, so as to give 0.8 g of sodium (4-morpholin-4-yl-6-thioxo-1,6-dihydropyrimidin-2-yl)acetate, the characteristics of which are the following:
Mass spectrometry: method A
Retention time Tr (min)=0.31;
[M+H]+: m/z 256; [M−H]−: m/z 254; base peak: m/z 210

Step 4e

Synthesis of 1-((S)-2-methyl-2,3-dihydroindol-1-yl)-2-(4-morpholin-4-yl-6-thioxo-1,6-dihydropyrimidin-2-yl)ethanone

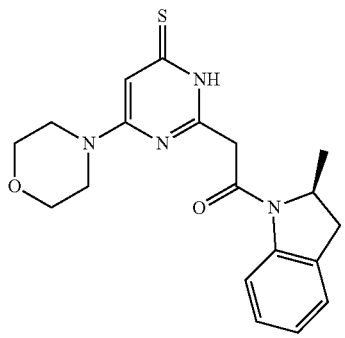 [SMILES: C[C@H]1Cc2ccccc2N1C(=O)Cc1nc(N2CCOCC2)cc(=S)[nH]1]

432 mg of N-[3-(dimethylamino)propyl]-N'-ethylcarbodiimide hydrochloride and 106 mg of (S)-2-methyl-2,3-dihydro-1H-indole (which can be prepared according to Krasnov, V. P. et al. (Mendeleev Commun. 2002, 12(1), 27-28)) are added to a solution of 200 mg of sodium (4-morpholin-4-yl-6-thioxo-1,6-dihydropyrimidin-2-yl)acetate in 5 ml of DMF and 5 ml of pyridine.

The reaction medium is stirred at ambient temperature for 18 hours.

50 ml of dichloromethane and 20 ml of water are added. After settling out, the organic phase is dried over magnesium sulfate, filtered, and then concentrated under reduced pressure. The residue obtained is purified by silica column chromatography (eluent: 99/1 then 98/02 dichloromethane/methanol) so as to give 57 mg of 1-((S)-2-methyl-2,3-dihydroindol-1-yl)-2-(4-morpholin-4-yl-6-thioxo-1,6-dihydropyrimidin-2-yl)ethanone in the form of a beige solid, the characteristics of which are the following:

$^1$H NMR spectrum (400 MHz) for this batch, all the signals are broad with: 1.26 (m, 3H); 2.69 (d, J=15.2 Hz, 1H); 3.38 (dd, J=9.4 and 15.2 Hz, 1H); 3.50 to 3.66 (m, 8H); 3.87 (d, J=15.4 Hz, 1H); 4.06 (d, J=15.4 Hz, 1H); 4.70 (m, 1H); 6.37 (s, 1H); 7.05 (t, J=8.0 Hz, 1H); 7.18 (t, J=8.0 Hz, 1H); 7.29 (d, J=8.0 Hz, 1H); 7.95 (d, J=8.0 Hz, 1H); 12.79 (broad m, 1H)

Mass spectrometry: method A
Retention time Tr (min)=0.75;
[M+H]+: m/z 371; [M−H]−: m/z 369
Optical rotation: $\alpha_D$=+86.0+/−1.6. C=1.606 mg/0.5 ml DMSO

Step 4'e

Alternatively, the compound 1-((S)-2-methyl-2,3-dihydroindol-1-yl)-2-(4-morpholin-4-yl-6-thioxo-1,6-dihydropyrimidin-2-yl)ethanone can also be obtained in three steps:

Step (4'a)e

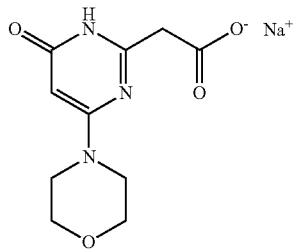 [SMILES: O=C([O-])Cc1nc(N2CCOCC2)cc(=O)[nH]1 ; [Na+]]

18.7 ml of 2M sodium hydroxide are added to a solution of 10 g of ethyl [4-(morpholin-4-yl)-6-oxo-1,6-dihydropyrimidin-2-yl]acetate in 300 ml of tetrahydrofuran. The reaction mixture is stirred for 48 hours at ambient temperature. The precipitate formed is filtered off through sintered glass, washed with ethyl acetate and rinsed several times with ethyl ether. The solid obtained is then dried in a rotary evaporator, so as to give 8.7 g of sodium [4-(morpholin-4-yl)-6-oxo-1,6-dihydropyrimidin-2-yl]acetate in the form of a white solid, the characteristics of which are the following:

$^1$H NMR spectrum (400 MHz): 3.08 (s, 2H); 3.38 (t, J=4.6 Hz, 4H); 3.61 (t, J=4.6 Hz, 4H); 5.08 (s, 1H); 13.16 (broad s, 1H)

Mass spectrometry: method A
Retention time Tr (min)=0.29;
[M+H]+: m/z 240; [M−H]−: m/z 238

Step (4'b)e

Preparation of 2-{2-[(2S)-2-methyl-2,3-dihydro-1H-indol-1-yl]-2-oxoethyl}-6-(morpholin-4-yl)pyrimidin-4(3H)-one and of 2-{2-[(2R)-2-methyl-2,3-dihydro-1H-indol-1-yl]-2-oxoethyl}-6-(morpholin-4-yl)pyrimidin-4(3H)-one

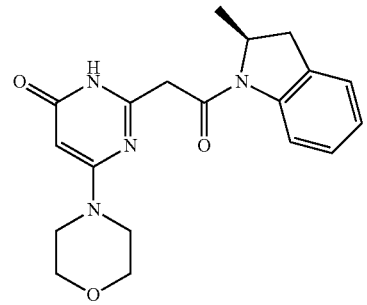

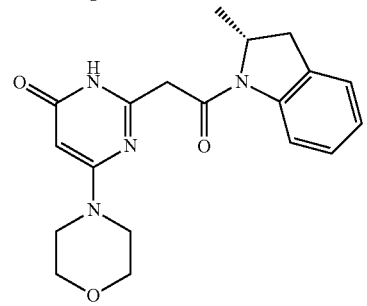

2-[2-(2-Methyl-2,3-dihydro-1H-indol-1-yl)-2-oxoethyl]-6-(morpholin-4-yl)pyrimidin-4(3H)-one is prepared by following the procedure described in example 1e (step 4e) using 500 mg of sodium [4-(morpholin-4-yl)-6-oxo-1,6-dihydropyrimidin-2-yl]acetate and 510 mg of 2-methyl-2,3-dihydro-1H-indole. 400 mg of 2-[2-(2-methyl-2,3-dihydro-1H-indol-1-yl)-2-oxoethyl]-6-(morpholin-4-yl)pyrimidin-4(3H)-one are obtained in the form of a white powder, the characteristics of which are the following:

$^1$H NMR spectrum (400 MHz): 1.26 (d, J=6.1 Hz, 3H); 2.65 to 2.72 (m, 1H); 3.18 to 3.44 (partially masked m, 5H); 3.54 to 3.63 (m, 4H); 3.72 (d, J=15.7 Hz, 1H); 3.92 (d, J=15.7 Hz, 1H); 4.71 (m, 1H); 5.20 (s, 1H); 7.04 (t, J=7.8 Hz, 1H); 7.18 (t, J=7.8 Hz, 1H); 7.29 (d, J=7.8 Hz, 1H); 7.96 (d, J=7.8 Hz, 1H); 11.69 (broad m, 1H)

Mass spectrometry: method A
Retention time Tr (min)=0.70;
[M+H]+: m/z 355; [M−H]−: m/z 353
Melting point (Kofler): 172° C.

The enantiomers are separated by chiral column chromatography: Chiralpak T304 20 μm (1080 g, 20 μm, 8/35 cm), eluent: 90/10 acetonitrile/isopropanol; flow rate: 185 ml/min. After purification, 160 mg of (R)-2-{2-[(2-methyl-2,3-dihydro-1H-indol-1-yl]-2-oxoethyl}-6-(morpholin-4-yl)pyrimidin-4(3H)-one are obtained, as first enantiomer, in the form of a pink amorphous solid, the characteristics of which are the following:

$^1$H NMR spectrum (400 MHz): for this batch, the signals are broad with: 1.26 (d, J=6.8 Hz, 3H); 2.44 (partially masked m, 1H); 2.69 (d, J=15.2 Hz, 1H); 3.42 (m, 4H); 3.60 (m, 4H); 3.72 (d, J=15.7 Hz, 1H); 3.92 (d, J=15.7 Hz, 1H); 4.72 (m, 1H); 5.20 (s, 1H); 7.04 (t, J=7.8 Hz, 1H); 7.18 (t, J=7.8 Hz, 1H); 7.28 (d, J=7.8 Hz, 1H); 7.96 (d, J=7.8 Hz, 1H); 11.67 (broad m, 1H)

Mass spectrometry: method A

Retention time Tr (min)=0.70;

[M+H]+: m/z 355; [M−H]−: m/z 353;

Optical rotation: $\alpha_D$=+65.0°+/−1.3 (c=1.736 mg in 0.5 ml of methanol)

Then the second enantiomer, i.e.: 143 mg of (S)-2-{2-[(2-methyl-2,3-dihydro-1H-indol-1-yl]-2-oxoethyl}-6-(morpholin-4-yl)pyrimidin-4(3H)-one, is obtained in the form of a white amorphous solid, the characteristics of which are the following:

$^1$H NMR spectrum (400 MHz): for this batch, the signals are broad with: 1.26 (d, J=6.8 Hz, 3H); 2.45 (partially masked m, 1H); 2.69 (m, 1H); 3.41 (m, 4H); 3.61 (m, 4H); 3.72 (d, J=15.7 Hz, 1H); 3.92 (d, J=15.7 Hz, 1H); 4.70 (m, 1H); 5.20 (s, 1H); 7.04 (t, J=7.8 Hz, 1H); 7.18 (t, J=7.8 Hz, 1H); 7.28 (d, J=7.8 Hz, 1H); 7.96 (d, J=7.8 Hz, 1H); 11.64 (broad m, 1H)

Mass spectrometry: method A

Retention time Tr (min)=0.70;

[M+H]+: m/z 355; [M−H]−: m/z 353;

Optical rotation: $\alpha_D$=−72.8°+/−1.2 (c=2.338 mg in 0.5 ml of methanol)

Step (4'c)e

Example 1e 1-((S)-2-methyl-2,3-dihydroindol-1-yl)-2-(4-morpholin-4-yl-6-thioxo-1,6-dihydropyrimidin-2-yl)ethanone

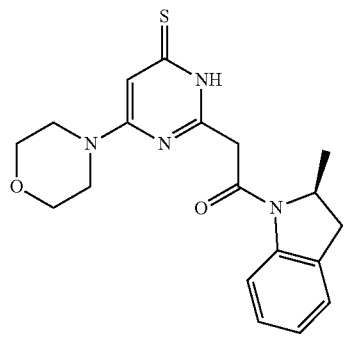 [SMILES: C[C@H]1Cc2ccccc2N1C(=O)Cc1nc(N2CCOCC2)cc(=S)[nH]1]

and

Example 2e

Synthesis of 2-[2-((S)-2-methyl-2,3-dihydroindol-1-yl)-2-thioxoethyl]-6-morpholin-4-yl-3H-pyrimidine-4-thione

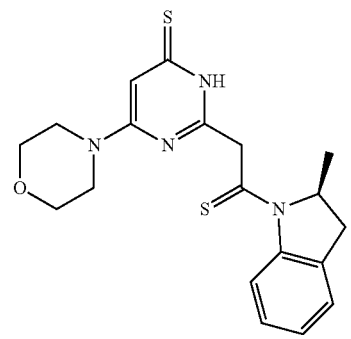 [SMILES: C[C@H]1Cc2ccccc2N1C(=S)Cc1nc(N2CCOCC2)cc(=S)[nH]1]

The product is prepared by following the procedure described in example 1e (step 2e) using 354 mg of 2-{2-[(2S)-2-methyl-2,3-dihydro-1H-indol-1-yl]-2-oxoethyl}-6-(morpholin-4-yl)pyrimidin-4(3H)-one obtained in example 1e (step (4'b)e) and 0.8 g of 2,4-bis(4-methoxyphenyl)-1,3-dithia-2,4-diphosphetane 2,4-disulfide (Lawesson's reagent). After purification by silica column chromatography (eluent: 99/01 then 98/02 dichloromethane/methanol), 135 mg of 2-[2-((S)-2-methyl-2,3-dihydroindol-1-yl)-2-thioxoethyl]-6-morpholin-4-yl-3H-pyrimidine-4-thione are obtained in the form of a light yellow solid, the characteristics of which are the following:

$^1$H NMR spectrum (400 MHz): for this batch, a 2/3-1/3 conformer resolution is observed with: 1.25 (d, J=6.6 Hz, 2H); 1.29 (d, J=6.6 Hz, 1H); 2.65 (d, J=16.3 Hz, 0.65H); 2.73 (d, J=16.3 Hz, 0.35H); 3.34 to 3.42 (m, 1H); 3.45 to 3.66 (m, 8H); 4.15 to 4.55 (m, 2H); 5.18 (m, 0.35H); 5.50 (m, 0.65H); 6.33 (s, 0.65H); 6.36 (s, 0.35H); 7.15 to 7.45 (m, 3H); 7.52 (d, J=8.0 Hz, 0.65H); 9.14 (d, J=8.0 Hz, 0.35H); 12.68 (s, 0.65H); 12.79 (s, 0.35H)

Mass spectrometry: method A

Retention time Tr (min)=0.85;

[M+H]+: m/z 387; [M−H]−: m/z 385 and 134 mg of 1-((S)-2-methyl-2,3-dihydroindol-1-yl)-2-(4-morpholin-4-yl-6-thioxo-1,6-dihydropyrimidin-2-yl)ethanone are obtained in the form of a light yellow solid, the characteristics of which are the following:

$^1$H NMR spectrum (400 MHz): for this batch all the signals are broad with: 1.26 (m, 3H); 2.69 (d, J=15.2 Hz, 1H); 3.38 (dd, J=9.4 and 15.2 Hz, 1H); 3.50 to 3.66 (m, 8H); 3.87 (d, J=15.4 Hz, 1H); 4.06 (d, J=15.4 Hz, 1H); 4.70 (m, 1H); 6.37 (s, 1H); 7.05 (t, J=8.0 Hz, 1H); 7.18 (t, J=8.0 Hz, 1H); 7.29 (d, J=8.0 Hz, 1H); 7.95 (d, J=8.0 Hz, 1H); 12.79 (broad m, 1H)

Mass spectrometry: method A

Retention time Tr (min)=0.75;

[M+H]+: m/z 371; [M−H]−: m/z 369

Example 3e

Synthesis of 1-((R)-2-methyl-2,3-dihydroindol-1-yl)-2-(4-morpholin-4-yl-6-thioxo-1,6-dihydropyrimidin-2-yl)ethanone

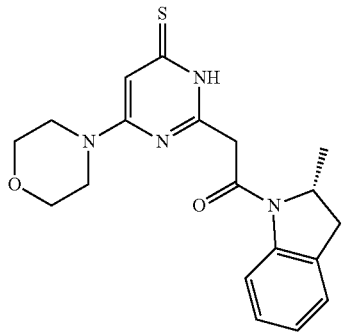 [SMILES: C[C@@H]1Cc2ccccc2N1C(=O)Cc1nc(N2CCOCC2)cc(=S)[nH]1]

The product is prepared by following the procedure described in example 1e (step 4e) using 200 mg of sodium (4-morpholin-4-yl-6-thioxo-1,6-dihydropyrimidin-2-yl)acetate obtained in example 1e (step 2e) and 106 mg of (R)-2-methyl-2,3-dihydro-1H-indole (which can be prepared according to Krasnov, V. P. et al. (Mendeleev Commun. 2002, 12(1), 27-28)). After purification by silica column chromatography (eluent: 98/02 dichloromethane/ethyl dichloromethane), 71 mg of 1-((R)-2-methyl-2,3-dihydroindol-1-yl)-2-(4-morpholin-4-yl-6-thioxo-1,6-dihydropyrimidin-2-yl)ethanone are obtained in the form of a white powder, the characteristics of which are the following:

$^1$H NMR spectrum (400 MHz): 1.27 (broad d, J=6.4 Hz, 3H); 2.69 (d, J=16.3 Hz, 1H); 3.33 to 3.42 (partially masked m, 1H); 3.53 to 3.65 (m, 8H); 3.87 (d, J=15.7 Hz, 1H); 4.06 (d, J=15.7 Hz, 1H); 4.70 (m, 1H); 6.37 (s, 1H); 7.05 (t, J=7.8 Hz, 1H); 7.18 (t, J=7.8 Hz, 1H); 7.29 (d, J=7.8 Hz, 1H); 7.95 (broad d, J=7.8 Hz, 1H); 12.79 (broad m, 1H)

Mass spectrometry: method A
Retention time Tr (min)=0.75;
[M+H]+: m/z 371; [M−H]−: m/z 369

Example 4e

Synthesis of 1-((S)-2-methyl-2,3-dihydroindol-1-yl)-2-(1-methyl-4-morpholin-4-yl-6-thioxo-1,6-dihydropyrimidin-2-yl)ethanone

Step 1e (1-Methyl-4-morpholin-4-yl-6-oxo-1,6-dihydropyrimidin-2-yl)acetic acid ethyl ester

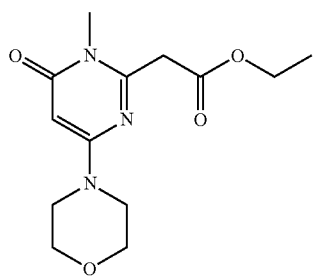 [SMILES: CCOC(=O)Cc1nc(N2CCOCC2)cc(=O)n1C]

7.9 mg of cesium carbonate and 1.5 ml of methyl iodide are added to a solution of 5 g of ethyl [4-(morpholin-4-yl)-6-oxo-1,6-dihydropyrimidin-2-yl]acetate (prepared in step 1e of example 1e) in 100 ml of acetonitrile. The reaction mixture is stirred at ambient temperature for 24 hours. The suspension is filtered through sintered glass and then rinsed with acetonitrile, and the filtrate is concentrated under reduced pressure. The residue is purified by silica column chromatography, elution being carried out with a mixture of dichloromethane and methanol (98.5/1.5 V/V). 2 g of a solid are obtained, which solid is again purified on a silica column, elution being carried out with a mixture of isopropyl ether and methanol (96/4 V/V), so as to give 1.2 g of ethyl [1-methyl-4-(morpholin-4-yl)-6-oxo-1,6-dihydropyrimidin-2-yl]acetate in the form of a white solid, the characteristics of which are the following:

Mass spectrometry: method A
Retention time Tr (min)=0.53;
[M+H]+: m/z 282; [M−H]−: m/z 280

Step 2e (1-Methyl-4-morpholin-4-yl-6-thioxo-1,6-dihydropyrimidin-2-yl)acetic acid ethyl ester

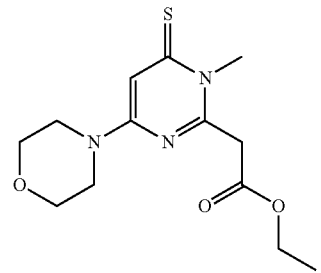 [SMILES: CCOC(=O)Cc1nc(N2CCOCC2)cc(=S)n1C]

In a round-bottomed flask, a mixture of 1.2 g of (1-methyl-4-morpholin-4-yl-6-oxo-1,6-dihydropyrimidin-2-yl)acetic acid ethyl ester with 2.6 g of 2,4-bis(4-methoxyphenyl)-1,3-dithia-2,4-diphosphetane 2,4-disulfide (Lawesson's reagent) in 100 ml of toluene is heated at 100° C. for 2 hours.

After cooling, the solid formed is filtered off. The filtrate is concentrated under reduced pressure. The residue obtained is purified by silica column chromatography (eluent: 99/01 dichloromethane/methanol), so as to give 1.1 g of (1-methyl-4-morpholin-4-yl-6-thioxo-1,6-dihydropyrimidin-2-yl)acetic acid ethyl ester, the characteristics of which are the following:

Mass spectrometry: method A
Retention time Tr (min)=0.88;
[M+H]+: m/z 298; [M−H]−: m/z 296

Step 3e

Sodium (1-methyl-4-morpholin-4-yl-6-thioxo-1,6-dihydropyrimidin-2-yl)acetate

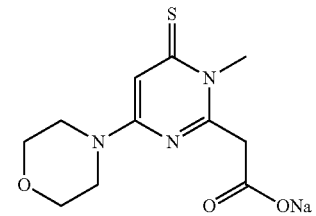

0.85 ml of 2N sodium hydroxide is added to a solution of 255 mg of (5-fluoro-4-morpholin-4-yl-6-thioxo-1,6-dihydropyrimidin-2-yl)acetic acid ethyl ester in 2 ml of THF.

Step 4e

Example 4e

Synthesis of 1-((S)-2-methyl-2,3-dihydroindol-1-yl)-2-(1-methyl-4-morpholin-4-yl-6-thioxo-1,6-dihydropyrimidin-2-yl)ethanone

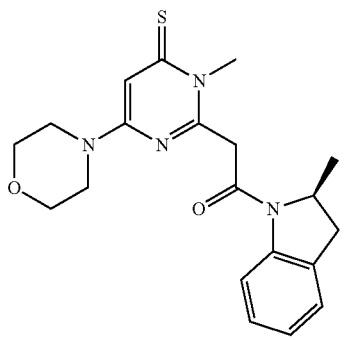 [SMILES: C[C@H]1Cc2ccccc2N1C(=O)Cc1nc(N2CCOCC2)cc(=S)n1C]

512 mg of N-[3-(dimethylamino)propyl]-N'-ethylcarbodiimide hydrochloride and 126 mg of (S)-2-methyl-2,3-dihydro-1H-indole (which can be prepared according to Krasnov, V. P. et al. (Mendeleev Commun. 2002, 12(1), 27-28)) are added to a solution of 250 mg of sodium (1-methyl-4-morpholin-4-yl-6-thioxo-1,6-dihydropyrimidin-2-yl)acetate in 6 ml of DMF and 6 ml of pyridine.

The reaction medium is stirred at ambient temperature for 18 hours.

100 ml of dichloromethane and 40 ml of water are added. After settling out, the organic phase is dried over magnesium sulfate, filtered, and then concentrated under reduced pressure. The residue obtained is purified by silica column chromatography (eluent: isopropyl ether/methanol: 80/20 by volume), so as to give 75 mg of 1-((S)-2-methyl-2,3-dihydroindol-1-yl)-2-(1-methyl-4-morpholin-4-yl-6-thioxo-1,6-dihydropyrimidin-2-yl)ethanone in the form of a white solid, the characteristics of which are the following:

$^1$H NMR spectrum (400 MHz): Spectrum at 80° C.: 1.30 (d, J=6.4 Hz, 3H); 2.70 (d, J=16.2 Hz, 1H); 3.41 (dd, J=8.9 and 16.2 Hz, 1H); 3.48 to 3.68 (m, 8H); 3.87 (s, 3H); 4.19 (d, J=16.8 Hz, 1H); 4.43 (d, J=16.8 Hz, 1H); 4.74 (m, 1H); 6.68 (s, 1H); 7.06 (t, J=7.7 Hz, 1H); 7.19 (t, J=7.7 Hz, 1H); 7.29 (d, J=7.7 Hz, 1H); 7.90 (broad m, 1H)

Mass spectrometry (method A):

Retention time Tr (min)=1.14;

[M+H]+: m/z 385; [M−H]−: m/z 383

Example 5e 1-((R)-2-methyl-2,3-dihydroindol-1-yl)-2-(1-methyl-4-morpholin-4-yl-6-thioxo-1,6-dihydropyrimidin-2-yl)ethanone

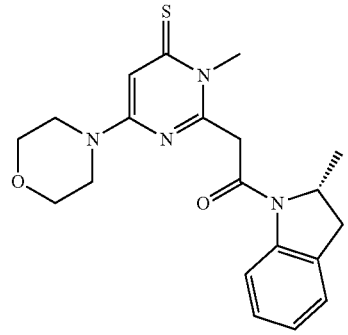 [SMILES: C[C@@H]1Cc2ccccc2N1C(=O)Cc1nc(N2CCOCC2)cc(=S)n1C]

The product is prepared by following the procedure described in example 4e (step 4e) using 250 mg of sodium (1-methyl-4-morpholin-4-yl-6-thioxo-1,6-dihydropyrimidin-2-yl)acetate in 6 ml of DMF and 6 ml of pyridine are added 512 mg of N-[3-(dimethylamino)propyl]-N'-ethylcarbodiimide hydrochloride and 126 mg of (R)-2-methyl-2,3-dihydro-1H-indole (which can be prepared according to Krasnov, V. P. et al. (Mendeleev Commun. 2002, 12(1), 27-28)).

After purification by silica column chromatography (eluent: isopropyl ether/methanol: 80/20 by volume), 23 mg of 1-((R)-2-methyl-2,3-dihydroindol-1-yl)-2-(1-methyl-4-morpholin-4-yl-6-thioxo-1,6-dihydropyrimidin-2-yl)ethanone are obtained in the form of a brown-red solid, the characteristics of which are the following:

$^1$H NMR spectrum (400 MHz): spectrum at 30° C.: 1.28 (d, J=6.4 Hz, 3H); 2.70 (d, J=16.1 Hz, 1H); 3.40 (dd, J=8.9 and 16.1 Hz, 1H); 3.45 to 3.66 (m, 8H); 3.83 (s, 3H); 4.18 (d, J=16.8 Hz, 1H); 4.46 (d, J=16.8 Hz, 1H); 4.71 (s, 1H); 6.69 (s, 1H); 7.06 (t, J=7.7 Hz, 1H); 7.18 (t, J=7.7 Hz, 1H); 7.29 (d, J=7.7 Hz, 1H); 7.94 (d, J=7.7 Hz, 1H)

Mass spectrometry: method A

Retention time Tr (min)=1.16;

[M+H]+: m/z 385; [M−H]−: m/z 383

Example 6e 1-(4-fluoro-2,3-dihydroindol-1-yl)-2-(1-methyl-4-morpholin-4-yl-6-thioxo-1,6-dihydropyrimidin-2-yl)ethanone

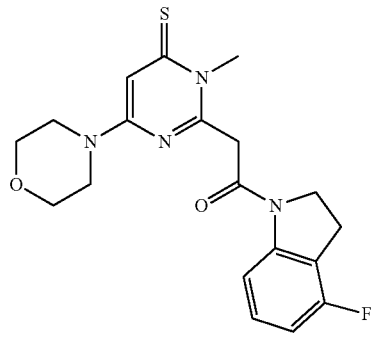 [SMILES: Cn1c(CC(=O)N2CCc3c(F)cccc32)nc(N2CCOCC2)cc1=S]

The product is prepared by following the procedure described in example 4e (step 4e) using 250 mg of sodium (1-methyl-4-morpholin-4-yl-6-thioxo-1,6-dihydropyrimidin-2-yl)acetate in 6 ml of DMF and 6 ml of pyridine are added 512 mg of N-[3-(dimethylamino)propyl]-N'-ethylcarbodiimide hydrochloride and 141 mg of 4-fluoro-2,3-dihydro-1H-indole.

After purification, 65 mg of 1-(4-fluoro-2,3-dihydroindol-1-yl)-2-(1-methyl-4-morpholin-4-yl-6-thioxo-1,6-dihydropyrimidin-2-yl)ethanone are obtained in the form of a brown-red solid, the characteristics of which are the following:

$^1$H NMR spectrum (400 MHz): 3.20 (t, J=8.4 Hz, 2H); 3.47 to 3.63 (m, 8H); 3.81 (s, 3H); 4.26 (t, J=8.4 Hz, 2H); 4.28 (s, 2H); 6.69 (s, 1H); 6.88 (t, J=8.3 Hz, 1H); 7.23 (m, 1H); 7.84 (d, J=8.3 Hz, 1H)

Mass spectrometry: method A

Retention time Tr (min)=1.12;

[M+H]+: m/z 389; [M−H]−: m/z 387

Example 7e 1-(4-chloro-2,3-dihydroindol-1-yl)-2-(1-methyl-4-morpholin-4-yl-6-thioxo-1,6-dihydropyrimidin-2-yl)ethanone

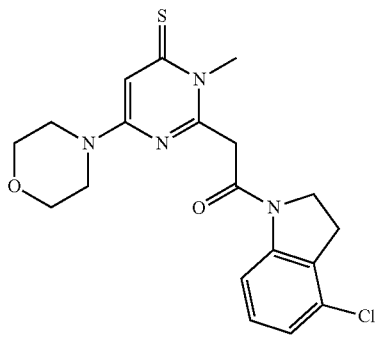 [SMILES: Cn1c(CC(=O)N2CCc3c(Cl)cccc32)nc(N2CCOCC2)cc1=S]

The product is prepared by following the procedure described in example 4e (step 4e) using 250 mg of sodium (1-methyl-4-morpholin-4-yl-6-thioxo-1,6-dihydropyrimidin-2-yl)acetate in 6 ml of DMF and 6 ml of pyridine are added 512 mg of N-[3-(dimethylamino)propyl]-N'-ethylcarbodiimide hydrochloride and 158 mg of 4-chloro-2,3-dihydro-1H-indole.

After purification, 145 mg of 1-(4-chloro-2,3-dihydroindol-1-yl)-2-(1-methyl-4-morpholin-4-yl-6-thioxo-1,6-dihydropyrimidin-2-yl)ethanone are obtained in the form of a brown-red solid, the characteristics of which are the following:

$^1$H NMR spectrum (400 MHz): 3.19 (t, J=8.4 Hz, 2H); 3.46 to 3.66 (m, 8H); 3.80 (s, 3H); 4.24 (t, J=8.4 Hz, 2H); 4.28 (s, 2H); 6.70 (s, 1H); 7.11 (d, J=7.8 Hz, 1H); 7.23 (t, J=7.8 Hz, 1H); 7.96 (d, J=7.8 Hz, 1H)

Mass spectrometry: method A

Retention time Tr (min)=1.24;

[M+H]+: m/z 405; [M−H]−: m/z 403

Example 8e 1-((+)-4,5-difluoro-2-methyl-2,3-dihydroindol-1-yl)-2-(5-fluoro-4-morpholin-4-yl-6-thioxo-1,6-dihydropyrimidin-2-yl)ethanone and

Example 9e

2-[2-((+)-4,5-difluoro-2-methyl-2,3-dihydroindol-1-yl)-2-thioxoethyl]-5-fluoro-6-morpholin-4-yl-3H-pyrimidine-4-thione Step 1e 4-Chloro-5-fluoro-6-methoxy-2-methylpyrimidine

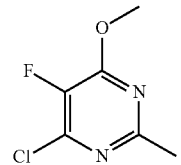

3.21 g of sodium methoxide are added to a solution of 9.8 g of 2-methyl-4,6-dichloro-5-fluoropyrimidine in 80 ml of THF cooled to 5° C. in an ice bath. The ice bath is removed. The suspension is stirred at ambient temperature for 3 hours. The reaction medium is cooled to 5° C. in an ice bath. 20 ml of water and 100 ml of ethyl acetate are added. After settling out, the organic phase is dried over magnesium sulfate, filtered, and concentrated under reduced pressure, so as to give 9 g of 4-chloro-5-fluoro-6-methoxy-2-methylpyrimidine in the form of a colorless oil which crystallizes, the characteristics of which are the following:

Mass spectrometry: method A

Retention time Tr (min)=0.82; [M+H]+: m/z 177

Step 2e (4-Chloro-5-fluoro-6-methoxypyrimidin-2-yl)acetic acid methyl ester

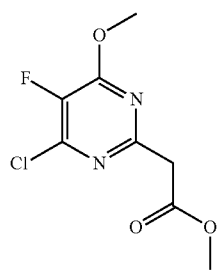

95 ml of 2M LDA (THF) are added dropwise to a solution of 6.7 g of 4-chloro-5-fluoro-6-methoxy-2-methylpyrimidine and 4.83 ml of methyl chloroformate in 100 ml of anhydrous THF cooled to −60° C. in a dry ice/MeOH bath.

The reaction medium is stirred at −60° C. for one hour.

The cooling bath is lowered so as to allow the temperature to rise to 22° C. The reaction medium is stirred at 22° C. for two hours.

20 ml of water and 150 ml of ethyl acetate are added. After settling out, the organic phase is dried over magnesium sulfate, filtered, and then concentrated under reduced pressure. The residue obtained is purified on a silica cartridge: eluent: DCM, so as to give 8.36 g of (4-chloro-5-fluoro-6-methoxypyrimidin-2-yl)acetic acid methyl ester in the form of a bright yellow oil, the characteristics of which are the following:

Mass spectrometry: method A
Retention time Tr (min)=0.84; [M+H]+: m/z 235;

Step 3e (5-Fluoro-4-methoxy-6-morpholin-4-ylpyrimidin-2-yl)acetic acid methyl ester

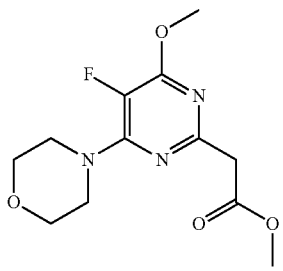 [SMILES: COC(=O)Cc1nc(OC)c(F)c(N2CCOCC2)n1]

A solution of 8.36 g of (4-chloro-5-fluoro-6-methoxypyrimidin-2-yl)acetic acid methyl ester in 76 ml of morpholine is stirred at ambient temperature for one and a half hours. The reaction medium is concentrated under reduced pressure. The residue obtained is taken up with 50 ml of water and 200 ml of ethyl acetate. After settling out, the organic phase is dried over magnesium sulfate, filtered, and then concentrated under reduced pressure, so as to give 8.86 g of (5-fluoro-4-methoxy-6-morpholin-4-ylpyrimidin-2-yl)acetic acid methyl ester in the form of a beige solid, the characteristics of which are the following:

Mass spectrometry: method A
Retention time Tr (min)=0.84; [M+H]+: m/z 286;

Step 4e (5-Fluoro-4-morpholin-4-yl-6-oxo-1,6-dihydropyrimidin-2-yl)acetic acid methyl ester

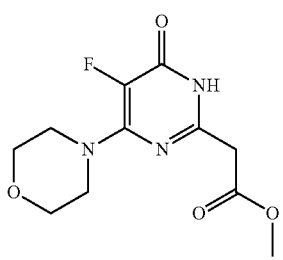 [SMILES: COC(=O)Cc1nc(N2CCOCC2)c(F)c(=O)[nH]1]

In a round-bottomed flask, 722 mg of KI and 0.56 ml of trimethylchlorosilane are added to a solution of 386 mg of (5-fluoro-4-methoxy-6-morpholin-4-ylpyrimidin-2-yl)acetic acid methyl ester obtained in example 1e (step 3e) in 4.7 ml of acetonitrile. The suspension is stirred at ambient temperature for 24 hours.

The reaction medium is concentrated under reduced pressure.

The residue obtained is taken up with water and ethyl acetate. After settling out, the organic phase is dried over magnesium sulfate, filtered, and then concentrated under reduced pressure. The residue obtained is purified by silica column chromatography (eluent: 98/02 dichloromethane/methanol), so as to give 155 mg of (5-fluoro-4-morpholin-4-yl-6-oxo-1,6-dihydropyrimidin-2-yl)acetic acid methyl ester in the form of a beige solid, the characteristics of which are the following:

Mass spectrometry: method A
Retention time Tr (min)=0.43; [M+H]+: m/z 272;
[M−H]−: m/z 270; base peak 238

Step 4'e

Alternatively, the compound (5-fluoro-4-morpholin-4-yl-6-oxo-1,6-dihydropyrimidin-2-yl)acetic acid ethyl ester can be obtained in one step:

Step (4'a)e (5-Fluoro-4-morpholin-4-yl-6-oxo-1,6-dihydropyrimidin-2-yl)acetic acid ethyl ester

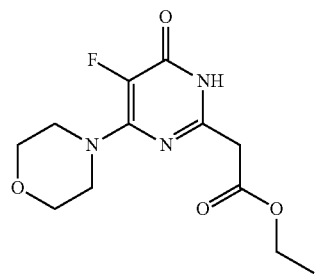 [SMILES: CCOC(=O)Cc1nc(N2CCOCC2)c(F)c(=O)[nH]1]

In a round-bottomed flask, 5 g of ethyl [4-(morpholin-4-yl)-6-oxo-1,6-dihydropyrimidin-2-yl]acetate obtained in example 1e (step 1e) with 50 ml of acetonitrile are heated to 74° C. A solution of 7.67 g of Selectfluor solubilized in a mixture of 25 ml of water and 25 ml of acetonitrile is added dropwise, and at 74° C., to this solution.

The reaction medium is heated at 75° C. for 90 minutes.

After cooling, 200 ml of ethyl acetate and then 100 ml of a saturated sodium bicarbonate solution are added. After settling out, the organic phase is dried over magnesium sulfate, filtered, and then concentrated under reduced pressure. The residue obtained is purified by silica column chromatography (eluent: dichloromethane/methanol gradient of 100/0 to 95/05), so as to give 0.8 g of (5-fluoro-4-morpholin-4-yl-6-oxo-1,6-dihydropyrimidin-2-yl)acetic acid ethyl ester in the form of a beige solid, the characteristics of which are the following:

$^1$H NMR spectrum (400 MHz, d in ppm, DMSO-d6): 1.19 (t, J=7.1 Hz, 3H); 3.56 (m, 6H); 3.63 (m, 4H); 4.12 (q, J=7.1 Hz, 2H); 12.32 (broad m, 1H)

Step 5e

Sodium (5-fluoro-4-morpholin-4-yl-6-oxo-1,6-dihydropyrimidin-2-yl)acetate

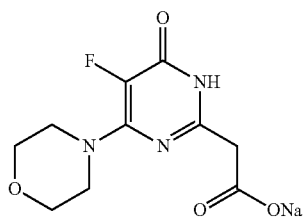

0.43 ml of 2N sodium hydroxide is added to a solution of 116 mg of (5-fluoro-4-morpholin-4-yl-6-oxo-1,6-dihydropyrimidin-2-yl)acetic acid methyl ester in 1.2 ml of THF. The reaction medium is stirred at ambient temperature for 24 hours. The reaction medium is concentrated under reduced pressure. The residue obtained is oven-dried under vacuum in the presence of $P_2O_5$, so as to give 110 mg of sodium (5-fluoro-4-morpholin-4-yl-6-oxo-1,6-dihydropyrimidin-2-yl)acetate, the characteristics of which are the following:

Mass spectrometry: method A
Retention time Tr (min)=0.32; [M+H]+: m/z 258; [M−H]−: m/z 256; base peak: m/z 212

Step 6e

2-[2-((+)-4,5-Difluoro-2-methyl-2,3-dihydroindol-1-yl)-2-oxoethyl]-5-fluoro-6-morpholin-4-yl-3H-pyrimidin-4-one

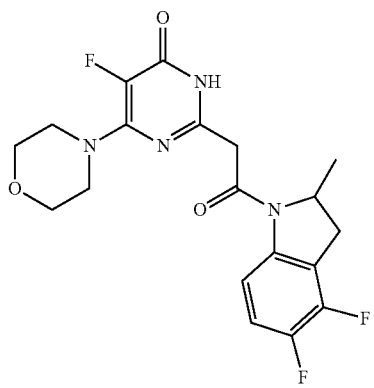 [SMILES: CC1Cc2c(ccc(F)c2F)N1C(=O)Cc1nc(N2CCOCC2)c(F)c(=O)[nH]1]

1.46 g of N-[3-(dimethylamino)propyl]-N'-ethylcarbodiimide hydrochloride and 1 g of (−)-2-methyl-4,5-difluoro-2,3-dihydro-1H-indole (reference example 1e) are added to a solution of 1.3 g of sodium (5-fluoro-4-morpholin-4-yl-6-oxo-1,6-dihydropyrimidin-2-yl)acetate in 40 ml of DMF and 40 ml of pyridine.

The reaction medium is stirred at ambient temperature for 18 hours.

200 ml of dichloromethane and 100 ml of water are added. After settling out, the organic phase is dried over magnesium sulfate, filtered, and then concentrated under reduced pressure. After silica column purification: eluent 98/02 dichloromethane/methanol, 814 mg of 2-[2-((+)-4,5-difluoro-2-methyl-2,3-dihydroindol-1-yl)-2-oxoethyl]-5-fluoro-6-morpholin-4-yl-3H-pyrimidin-4-one are obtained in the form of a solid, the characteristics of which are the following:

$^1$H NMR spectrum (400 MHz): 1.29 (d, J=6.4 Hz, 3H); 2.82 (d, J=16.6 Hz, 1H); 3.40 (dd, J=8.6 and 16.6 Hz, 1H); 3.53 to 3.64 (m, 8H); 3.73 (d, J=16.1 Hz, 1H); 3.92 (d, J=16.1 Hz, 1H); 4.79 (m, 1H); 7.24 (m, 1H); 7.74 (d, J=9.0 Hz, 1H); 12.31 (broad m, 1H)

Mass spectrometry: method A
Retention time Tr (min)=0.81; [M+H]+: m/z 409; [M−H]−: m/z 407

Optical rotation: $α_D$=+76.3+/−1.3. C=2.144 mg/0.5 ml DMSO

Step 7e

Example 8e 1-((+)-4,5-Difluoro-2-methyl-2,3-dihydroindol-1-yl)-2-(5-fluoro-4-morpholin-4-yl-6-thioxo-1,6-dihydropyrimidin-2-yl)ethanone

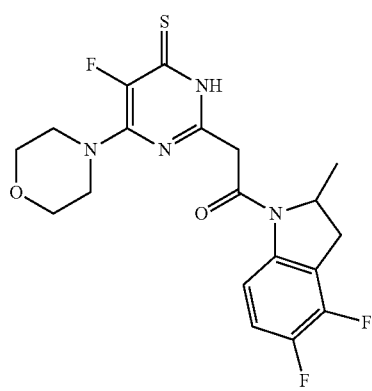

Example 9e

2-[2-((+)-4,5-Difluoro-2-methyl-2,3-dihydroindol-1-yl)-2-thioxoethyl]-5-fluoro-6-morpholin-4-yl-3H-pyrimidine-4-thione

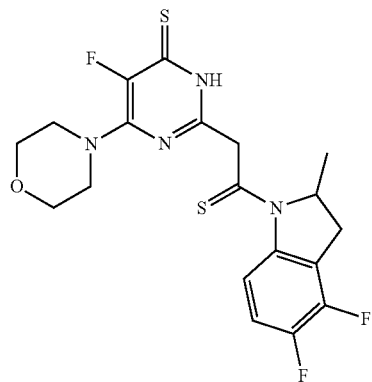 [SMILES: CC1Cc2c(ccc(F)c2F)N1C(=S)Cc1nc(N2CCOCC2)c(F)c(=S)[nH]1]

In a round-bottomed flask, a mixture of 300 mg of 2-[2-((+)-4,5-difluoro-2-methyl-2,3-dihydroindol-1-yl)-2-oxoethyl]-5-fluoro-6-morpholin-4-yl-3H-pyrimidin-4-one obtained in the previous step with 445 mg of 2,4-bis(4-methoxyphenyl)-1,3-dithia-2,4-diphosphetane 2,4-disulfide (Lawesson's reagent) in 8 ml of toluene is heated at 60° C. for 18 hours.

After cooling, the solid formed is filtered off. The filtrate is concentrated under reduced pressure. The residue obtained is purified by silica column chromatography (eluent: 98.33/1.5/0.17 dichloromethane/MeOH/28% NH$_4$OH), so as to give 17 mg of 1-((+)-4,5-difluoro-2-methyl-2,3-dihydroindol-1-yl)-2-(5-fluoro-4-morpholin-4-yl-6-thioxo-1,6-dihydropyrimidin-2-yl)ethanone in the form of a yellow solid, the characteristics of which are the following:

$^1$H NMR spectrum (400 MHz): 1.30 (d, J=6.1 Hz, 3H); 2.82 (d, J=16.4 Hz, 1H); 3.41 (dd, J=8.4 and 16.0 Hz, 1H); 3.67 (m, 8H); 3.86 (m, 1H); 4.05 (d, J=15.9 Hz, 1H); 4.78 (m, 1H); 7.22 (m, 1H); 7.73 (d, J=5.6 Hz, 1H); 13.24 (broad s, 1H)

Retention time Tr (min)=0.87;

[M+H]+: m/z 425; [M−H]−: m/z 423 and 23 mg of 2-[2-((+)-4,5-difluoro-2-methyl-2,3-dihydroindol-1-yl)-2-thioxoethyl]-5-fluoro-6-morpholin-4-yl-3H-pyrimidine-4-thione in the form of a light yellow solid, the characteristics of which are the following:

$^1$H NMR spectrum (400 MHz): 1.29 (d, J=6.4 Hz, 1.5H); 1.33 (d, J=6.6 Hz, 1.5H); 2.83 (m, 1H); 3.39 (m, 1H); 3.61 (m, 8H); 4.11 to 4.58 (m, 2H); 5.25 (m, 0.5H); 5.55 (m, 0.5H); 7.33 (m, 1.5H); 8.96 (m, 0.5H); 13.16 (broad s, 0.5H); 13.27 (broad s, 0.5H)

Retention time Tr (min)=0.96;

[M+H]+: m/z 441; [M−H]−: m/z 439

Example 10e

Synthesis of 2-(5-fluoro-4-morpholin-4-yl-6-thioxo-1,6-dihydropyrimidin-2-yl)-1-((S)-2-methyl-2,3-dihydroindol-1-yl)ethanone Step 1e (5-Fluoro-4-morpholin-4-yl-6-thioxo-1,6-dihydropyrimidin-2-yl)acetic acid ethyl ester

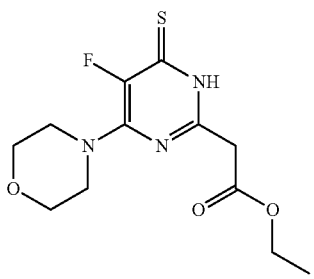 [SMILES: CCOC(=O)Cc1nc(N2CCOCC2)c(F)c(=S)[nH]1]

In a round-bottomed flask, a mixture of 0.53 g of ethyl [4-(morpholin-4-yl)-6-oxo-1,6-dihydropyrimidin-2-yl]acetate obtained in examples 8e and 9e (step 4e) with 1.12 g of 2,4-bis(4-methoxyphenyl)-1,3-dithia-2,4-diphosphetane 2,4-disulfide (Lawesson's reagent) in 20 ml of toluene is heated at 60° C. for 2 hours and then at reflux for 30 minutes.

After cooling, the solid formed is filtered off. The filtrate is concentrated under reduced pressure. The residue obtained is purified by silica column chromatography (eluent: 85/15 dichloromethane/ethyl acetate), so as to give 0.175 g of (5-fluoro-4-morpholin-4-yl-6-thioxo-1,6-dihydropyrimidin-2-yl)acetic acid ethyl ester, the characteristics of which are the following:

Mass spectrometry: method A
Retention time Tr (min)=0.79;
[M+H]+: m/z 302; [M−H]−: m/z 300

And 0.33 g of (4-morpholin-4-yl-6-thioxo-1,6-dihydropyrimidin-2-yl)acetic acid ethyl ester in the form of a beige solid, the characteristics of which are the following:

Mass spectrometry: method A
Retention time Tr (min)=0.74;
[M+H]+: m/z 284; [M−H]−: m/z 282; base peak: m/z 236

Step 2e

Sodium (5-fluoro-4-morpholin-4-yl-6-thioxo-1,6-dihydropyrimidin-2-yl)acetate

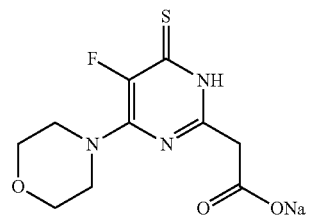

0.85 ml of 2N sodium hydroxide is added to a solution of 255 mg of (5-fluoro-4-morpholin-4-yl-6-thioxo-1,6-dihydropyrimidin-2-yl)acetic acid ethyl ester in 2 ml of THF. The reaction medium is stirred at ambient temperature for 24 hours. The reaction medium is concentrated under reduced pressure. The residue obtained is oven-dried under vacuum in the presence of P$_2$O$_5$, so as to give 0.32 g of sodium (5-fluoro-4-morpholin-4-yl-6-thioxo-1,6-dihydropyrimidin-2-yl)acetate which is used as it is in the next step.

Step 3e

Example 10e

Synthesis of 2-(5-fluoro-4-morpholin-4-yl-6-thioxo-1,6-dihydropyrimidin-2-yl)-1-((S)-2-methyl-2,3-dihydroindol-1-yl)ethanone

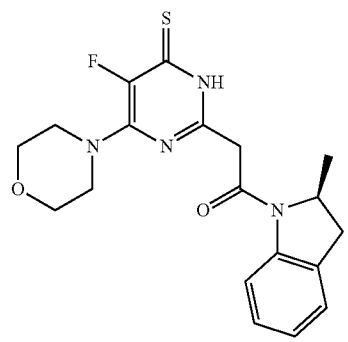 [SMILES: C[C@H]1Cc2ccccc2N1C(=O)Cc1nc(N2CCOCC2)c(F)c(=S)[nH]1]

324 mg of N-[3-(dimethylamino)propyl]-N'-ethylcarbodiimide hydrochloride and 79 mg of (S)-2-methyl-2,3-dihydro-1H-indole (which can be prepared according to Krasnov, V. P. et al. (Mendeleev Commun. 2002, 12(1), 27-28)) are added to a solution of 159 mg of sodium (5-fluoro-4-morpholin-4-yl-6-thioxo-1,6-dihydropyrimidin-2-yl)acetate in 3.7 ml of DMF and 3.7 ml of pyridine.

The reaction medium is stirred at ambient temperature for 18 hours.

50 ml of dichloromethane and 20 ml of water are added. After settling out, the organic phase is dried over magnesium sulfate, filtered, and then concentrated under reduced pressure. The residue obtained is purified by silica column chromatography (eluent: dichloromethane/methanol/28% ammonia gradient from 98.33/1.5/0.17 to 95/4.5/0.5 by volume), so as to give 17 mg of 2-(5-fluoro-4-morpholin-4-yl-6-thioxo-1,6-dihydropyrimidin-2-yl)-1-((S)-2-methyl-2,3-dihydroindol-1-yl)ethanone in the form of a beige solid, the characteristics of which are the following:

$^1$H NMR spectrum (400 MHz): 1.27 (broad d, J=6.3 Hz, 3H); 2.69 (d, J=16.9 Hz, 1H); 3.38 (dd, J=8.8 and 16.9 Hz, 1H); 3.62 to 3.75 (m, 8H); 3.88 (d, J=15.9 Hz, 1H); 4.06 (d, J=15.9 Hz, 1H); 4.68 (m, 1H); 7.05 (t, J=7.6 Hz, 1H); 7.18 (t, J=7.6 Hz, 1H); 7.29 (d, J=7.6 Hz, 1H); 7.95 (d, J=7.6 Hz, 1H); 13.26 (broad s, 1H)

Mass spectrum (method A):
Retention time Tr (min)=1.05;
[M+H]+: m/z 389; [M−H]−: m/z 387

Example 11e

Synthesis of 2-(5-fluoro-4-morpholin-4-yl-6-thioxo-1,6-dihydropyrimidin-2-yl)-1-((R)-2-methyl-2,3-dihydroindol-1-yl)ethanone

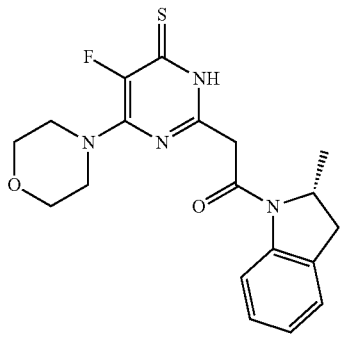 [SMILES: C[C@@H]1Cc2ccccc2N1C(=O)Cc1nc(N2CCOCC2)c(F)c(=S)[nH]1]

324 mg of N-[3-(dimethylamino)propyl]-N'-ethylcarbodiimide hydrochloride and 79 mg of (R)-2-methyl-2,3-dihydro-1H-indole (which can be prepared according to Krasnov, V. P. et al. (Mendeleev Commun. 2002, 12(1), 27-28)) are added to a solution of 159 mg of sodium (5-fluoro-4-morpholin-4-yl-6-thioxo-1,6-dihydropyrimidin-2-yl)acetate in 3.7 ml of DMF and 3.7 ml of pyridine.

The reaction medium is stirred at ambient temperature for 18 hours.

50 ml of dichloromethane and 20 ml of water are added. After settling out, the organic phase is dried over magnesium sulfate, filtered, and then concentrated under reduced pressure. The residue obtained is purified by silica column chromatography (eluent: dichloromethane/methanol/28% ammonia gradient from 98.33/1.5/0.17 to 95/4.5/0.5 by volume), so as to give 45 mg of 2-(5-fluoro-4-morpholin-4-yl-6-thioxo-1,6-dihydropyrimidin-2-yl)-1-((R)-2-methyl-2,3-dihydroindol-1-yl)ethanone in the form of a beige solid, the characteristics of which are the following:

$^1$H NMR spectrum (400 MHz): 1.27 (broad d, J=6.3 Hz, 3H); 2.69 (d, J=15.9 Hz, 1H); 3.38 (dd, J=8.9 and 15.9 Hz, 1H); 3.60 to 3.74 (m, 8H); 3.88 (d, J=15.9 Hz, 1H); 4.06 (d, J=15.9 Hz, 1H); 4.68 (t, J=7.7 Hz, 1H); 7.05 (t, J=7.6 Hz, 1H); 7.18 (t, J=7.6 Hz, 1H); 7.29 (d, J=7.6 Hz, 1H); 7.95 (d, J=7.6 Hz, 1H); 13.26 (broad s, 1H)

Mass spectrum method A):
Retention time Tr (min)=1.05;
[M+H]+: m/z 389; [M−H]−: m/z 387

Reference Examples for Preparing the Compounds of Formula (Ie)

Reference Example 1e 4,5-difluoro-2-methyl-2,3-dihydro-1H-indole

Step 1e 4,5-Difluoro-2-methyl-2,3-dihydro-1H-indole

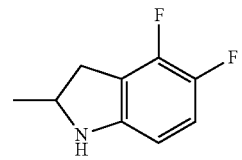

5.07 g of sodium cyanoborohydride are added in 3 steps to a solution of 4.5 g of 4,5-difluoro-2-methylindole in 180 ml of acetic acid cooled to 15° C. The reaction medium is stirred at 15° C. for 30 minutes and then at ambient temperature for 4 hours.

The reaction medium is again cooled to 5° C. Ice-cold water is added. 30% aqueous ammonia is added until the pH=9. The mixture is extracted 3 times with dichloromethane. The organic phases are combined, dried over magnesium sulfate, filtered, and then concentrated under reduced pressure. The residue obtained is purified on a silica column, eluent: 90/10 cyclohexane/ethyl acetate, so as to give 4.4 g of 4,5-difluoro-2-methyl-2,3-dihydro-1H-indole, the characteristics of which are the following:

Mass spectrometry: method A
Retention time Tr (min)=0.60; [M+H]+: m/z 170

Step 2e (R)-1-(4,5-Difluoro-2-methyl-2,3-dihydroindol-1-yl)-2-phenoxypropan-1-one: diastereoisomer A

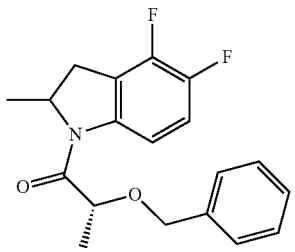 [SMILES: CC1Cc2c(ccc(F)c2F)N1C(=O)[C@@H](C)OCc1ccccc1]

And (R)-1-(4,5-Difluoro-2-methyl-2,3-dihydroindol-1-yl)-2-phenoxypropan-1-one: diastereoisomer B

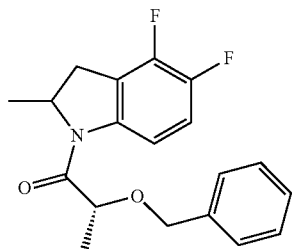 [SMILES: CC1Cc2c(ccc(F)c2F)N1C(=O)[C@@H](C)OCc1ccccc1]

The products are prepared by following the procedure described in reference example 1e (step 2e) using 4.4 g of 4,5-difluoro-2-methyl-2,3-dihydro-1H-indole and 5.62 g of o-benzyl-D-lactic acid. After silica column purification, eluent: 90/10 then 80/20 cyclohexane/ethyl acetate, 4.2 g of (R)-1-(4,5-difluoro-2-methyl-2,3-dihydroindol-1-yl)-2-phenoxypropan-1-one: diastereoisomer A are obtained in the form of a yellow oil, the characteristics of which are the following:

Mass spectrometry: method A
Retention time Tr (min)=1.11; [M+H]+: m/z 332; base peak: m/z 260
Optical rotation: $\alpha_D$=+41.6+/−0.9. C=2.266 mg/0.5 ml DMSO And 4.1 g of (R)-1-(4,5-difluoro-2-methyl-2,3-dihydroindol-1-yl)-2-phenoxypropan-1-one: diastereoisomer B are obtained in the form of a white solid, the characteristics of which are the following:

Mass spectrometry: method A
Retention time Tr (min)=1.10; [M+H]+: m/z 332; base peak: m/z 260
Optical rotation: $\alpha_D$=+120.1+/−1.8. C=2.252 mg/0.5 ml DMSO Step 3e (+)-4,5-Difluoro-2-methyl-2,3-dihydro-1H-indole

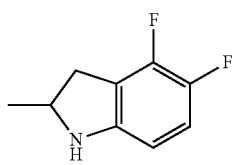

The product is prepared by following the procedure described in reference example 1e (step 3e) using 4.2 g of (R)-1-(4,5-difluoro-2-methyl-2,3-dihydroindol-1-yl)-2-phenoxypropan-1-one: diastereoisomer A and 40 ml of 37% hydrochloric acid.

After silica column purification, eluent: 90/10 cyclohexane/ethyl acetate, 1.6 g of (+)-4,5-difluoro-2-methyl-2,3-dihydro-1H-indole are obtained, the characteristics of which are the following:

Mass spectrometry: method A
Retention time Tr (min)=0.58; [M+H]+: m/z 170;

Step 3e (−)-4,5-Difluoro-2-methyl-2,3-dihydro-1H-indole

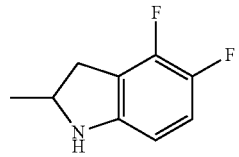

The product is prepared by following the procedure described in reference example 1e (step 3e) using 4.1 g of (R)-1-(4,5-difluoro-2-methyl-2,3-dihydroindol-1-yl)-2-phenoxypropan-1-one: diastereoisomer B and 41 ml of 37% hydrochloric acid.

After silica column purification, eluent: 90/10 heptane/ethyl acetate, 1.5 g of (−)-4,5-difluoro-2-methyl-2,3-dihydro-1H-indole are obtained, the characteristics of which are the following:

Mass spectrometry: method A
Retention time Tr (min)=0.60; [M+H]+: m/z 170

Examples of Pharmaceutical Compositions Comprising Compounds According to the Invention Example a Tablets corresponding to the following formula were prepared:

| | |
|---|---|
| Product of example 1a | 0.2 g |
| Excipient for a tablet having a final weight of | 1 g |

(details of the excipient: lactose, talc, starch, magnesium stearate).

Example b

Tablets corresponding to the following formula were prepared:

| | |
|---|---|
| Product of example 10b | 0.2 g |
| Excipient for a tablet having a final weight of | 1 g |

(details of the excipient: lactose, talc, starch, magnesium stearate).

Example c

Tablets corresponding to the following formula were prepared:

| | |
|---|---|
| Product of example 1c | 0.2 g |
| Excipient for a tablet having a final weight of | 1 g |

(details of the excipient: lactose, talc, starch, magnesium stearate).

Example d

Tablets corresponding to the following formula were prepared:

| | |
|---|---|
| Product of example 1d | 0.2 g |
| Excipient for a tablet having a final weight of | 1 g |

(details of the excipient: lactose, talc, starch, magnesium stearate).

Example e

Tablets corresponding to the following formula were prepared:

| Product of example 1e | 0.2 g |
|---|---|
| Excipient for a tablet having a final weight of | 1 g |

(details of the excipient: lactose, talc, starch, magnesium stearate).

The examples mentioned are taken by way of example of a pharmaceutical preparation, it being possible for this preparation to be carried out, if desired, with other products in examples in the present application.

EXPERIMENTAL DATA

Pharmacological Section:
Experimental Protocols
In Vitro Experimental Procedures The inhibitory activity of the molecules on AKT phosphorylation is measured using the MSD Multi-spot Biomarker detection technique from Meso Scale Discovery also described below.

Study of pAKT Expression in PC3 Human Prostate Carcinoma Cells Measured by the MSD Multi-Spot Biomarker Detection Technique from Meso Scale Discovery (Test A):

This test is based on measuring the expression of the AKT protein phosphorylated on serine 473 (P-AKT-S473), in the PC3 human prostate carcinoma line, by means of the technique based on a sandwich immunoassay using the MSD Multi-spot Biomarker Detection kit from Meso Scale Discovery: phospho-Akt (Ser473) whole cell lysate kit (#K151CAD) or phospho-Akt (Ser473)/Total Akt whole cell lysate kit (#K151OOD). The primary antibody specific for P-AKT-S473 (Kit #K151CAD) is coated on to an electrode in each well of the 96-well plates of the MSD kit: after the addition of a protein lysate to each well, the signal is visualized by adding a secondary detection antibody labeled with an electrochemiluminescent compound. The procedure followed is the one described in the kit.

On day 1, the PC3 cells are seeded into 96-well plates (TPP, #92096) at the concentration of 35 000 cells/well in 200 µl of DMEM medium (DMEM Gibco #11960-044) containing 10% of fetal calf serum (FCS Gibco, #10500-056) and 1% glutamine (L-Glu Gibco #25030-024), and incubated at 37° C., 5% $CO_2$, overnight.

On day 2, the cells are incubated in the presence or absence of the test products for 1 to 2 h at 37° C. in the presence of 5% $CO_2$. The molecules, diluted in dimethyl sulfoxide (DMSO Sigma #D2650), are added from a 20-times concentrated stock solution, the final percentage of DMSO being 0.1%. The molecules are tested either at a single concentration of less than or equal to 10 µM, or at increasing concentrations in a range that can extend from less than 1 nM to 10 µM.

After this incubation, the cells are lysed for the preparation of the proteins. For this, after the culture medium has been drawn off, 50 µl of complete Tris Lysis Buffer of the MSD kit containing the protease and phosphatase inhibitor solutions are added to the wells and the cells are lysed for 1 h at 4° C. with shaking. At this stage, the plates containing the lysates can be frozen at −20° C. or at −80° C.

The wells of the 96 well plates of the MSD kit are saturated for 1 h at ambient temperature with the blocking solution of the MSD kit. Four washes are carried out with 150 µl of Tris Wash Buffer of the MSD kit. The lysates previously prepared are transferred into the 96-well multi-spot plates of the MSD kit and incubated for 1 h at ambient temperature, with shaking. Four washes are carried out with 150 µl of Tris Wash Buffer of the MSD kit. 25 µl of the MSD sulfo-tag detection antibody solution are added to the wells and incubated for 1 h at ambient temperature, with shaking. Four washes are carried out with 150 µl of Tris Wash Buffer of the MSD kit. 150 µl of Read Buffer of the MSD kit are added to the wells and the plates are read immediately on the S12400 instrument from Meso Scale Discovery.

The instrument measures a signal for each well. Wells without cells and containing the lysis buffer serve to determine the background noise that will be subtracted from all the measurements (min). The wells containing cells in the absence of product and in the presence of 0.1% DMSO are considered to be the 100% signal (max). The percentage inhibition is calculated for each concentration of product tested, according to the following formula: $(1-((test-min)/(max-min)))\times 100$.

The activity of the product is translated to $IC_{50}$, obtained from a dose-response curve of various concentrations tested and representing the dose giving 50% specific inhibition (absolute $IC_{50}$). Two independent experiments make it possible to calculate the mean of the $IC_{50}$ values.

The results obtained for the products as examples in the experimental section are given in the pharmacological results tables hereinafter:

Pharmacological Results Tables:

Examples Relating to the Compounds of Formula (Ia):

| Example | Test A $IC_{50}$ (nM) |
|---|---|
| Example 1a | 22 |
| Example 2a | 938 |
| Example 3a | 158 |
| Example 4a | 503 |
| Example 5a | 15 |
| Example 6a | 10 |
| Example 7a | 3 |
| Example 8a | 107 |
| Example 9a | 120 |
| Example 10a | 116 |
| Example 11a | 24 |
| Example 12a | 16 |
| Example 13a | 162 |
| Example 14a | 55 |
| Example 15a | 65 |
| Example 16a | 483 |
| Example 17a | 45 |
| Example 18a | 38 |
| Example 19a | 19 |
| Example 20a | 2 |
| Example 21a | 15 |
| Example 22a | 98 |
| Example 23a | 203 |
| Example 24a | 310 |
| Example 25a | 98 |
| Example 26a | 211 |
| Example 27a | 270 |
| Example 28a | 476 |
| Example 29a | 20 |
| Example 30a | 16 |
| Example 31a | 15 |
| Example 32a | 40 |
| Example 33a | 77 |
| Example 34a | 2 |
| Example 35a | 140 |
| Example 36a | 55 |
| Example 37a | 56 |
| Example 38a | 1138 |
| Example 39a | 568 |

Examples Relating to the Compounds of Formula (Ib):

| Example | Test A IC50 (nM) |
| --- | --- |
| Example 1b | 26 |
| Example 2b | 6 |
| Example 3b | 271 |
| Example 4b | 118 |
| Example 5b | 127 |
| Example 6b | 58 |
| Example 7b | 21 |
| Example 8b | 18 |
| Example 9b | 156 |
| Example 10b | 8 |
| Example 11b | 12 |
| Example 12b | 370 |
| Example 13b | 3000 |
| Example 14b | 280 |
| Example 15b | 105 |
| Example 16b | 18 |
| Example 17b | 12 |
| Example 18b | 91 |
| Example 19b | 16 |
| Example 20b | 5 |
| Example 21b | 27 |
| Example 22b | 9 |
| Example 23b | 244 |
| Example 24b | 2855 |
| Example 25b | 27 |
| Example 26b | 240 |
| Example 27b | 1332 |
| Example 28b | 12 |
| Example 29b | 24 |
| Example 30b | 44 |
| Example 31b | 156 |

Examples Relating to the Compounds of Formula (Ic):

| Example | Test A IC50 (nM) |
| --- | --- |
| Example 1c | 5 |
| Example 2c | 5 |
| Example 3c | 1 |
| Example 4-c | 35 |
| Example 5c | 14 |
| Example 6c | 24 |
| Example 7c | 45 |
| Example 8c | 52 |
| Example 9c | 115 |
| Example 10c | 22 |
| Example 11c | |
| Example 12c | 57 |
| Example 13c | 5 |
| Example 14c | 2 |
| Example 15c | 28 |
| Example 16c | 13 |
| Example 17c | 4 |
| Example 18c | 1 |
| Example 19c | 19 |
| Example 20c | 13 |
| Example 21c | 17 |
| Example 22c | 2 |
| Example 23c | 32 |
| Example 24c | 114 |
| Example 25c | 39 |
| Example 26c | 3 |
| Example 27c | 4 |
| Example 28c | 98 |
| Example 29c | 53 |
| Example 30c | 73 |
| Example 31c | 36 |
| Example 32c | 14 |
| Example 33c | 55 |
| Example 34c | 242 |
| Example 35c | 27 |
| Example 36c | 9 |
| Example 37c | 7 |
| Example 38c | 1 |

-continued

| Example | Test A IC50 (nM) |
| --- | --- |
| Example 39c | 4 |
| Example 40c | 243 |
| Example 41c | 29 |
| Example 42c | 380 |
| Example 43c | 14 |
| Example 44c | 140 |
| Example 45c | 260 |
| Example 46c | 101 |

Examples Relating to the Compounds of Formula (Id):

| Example | Test A IC50 (nM) |
| --- | --- |
| Example 1d | 26 |
| Example 2d | 24 |
| Example 3d | 54 |
| Example 4d | 63 |
| Example 5d | 9 |
| Example 6d | 32 |
| Example 7d | 102 |
| Example 8d | 60 |
| Example 9d | 44 |
| Example 10d | 94 |
| Example 11d | 26 |
| Example 12d | 66 |
| Example 13d | 53 |
| Example 14d | 42 |
| Example 15d | 37 |
| Example 16d | 30 |
| Example 17d | 259 |
| Example 18d | 272 |
| Example 19d | 23 |
| Example 20d | 520 |
| Example 21d | 155 |
| Example 22d | 106 |
| Example 23d | 196 |
| Example 24d | 205 |
| Example 25d | 5 |
| Example 26d | 167 |
| Example 27 | 435 |
| Example 28d | 2 |
| Example 29d | 33 |
| Example 30d | 8 |
| Example 31d | 167 |
| Example 32d | 60 |
| Example 33d | 111 |
| Example 34d | 48 |
| Example 35d | 5 |
| Example 36d | 5 |
| Example 37d | 2 |
| Example 38d | 15 |
| Example 39d | 51 |
| Example 40d | 13 |
| Example 41d | 131 |
| Example 42d | 24 |

Examples Relating to the Compounds of Formula (Ie):

| Example | Test A IC50 (nM) |
| --- | --- |
| Example 1e | 22 |
| Example 2e | 4 |
| Example 3e | 8 |
| Example 4e | 41 |
| Example 5e | 71 |
| Example 6e | 31 |
| Example 7e | 33 |
| Example 8e | 11 |
| Example 9e | 1 |
| Example 10e | 221 |
| Example 11e | 61 |

The invention claimed is:
1. A compound of formula (Ia):

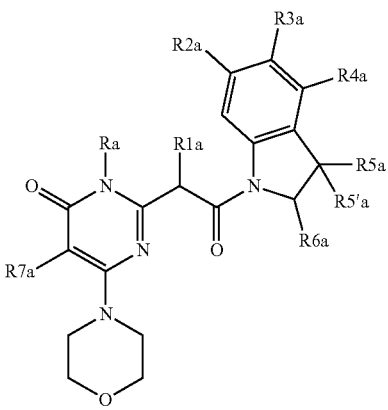

wherein:
Ra is a hydrogen atom or an alkyl radical;
R1a is a hydrogen atom or a methyl radical;
R2a is a hydrogen atom or a fluorine atom;
R3a is a hydrogen atom or a halogen atom;
R4a is a hydrogen atom, a halogen atom or a hydroxyl, alkyl or alkoxy radical, the alkyl radicals being optionally substituted with one or more radicals, which may be identical or different, selected from halogen atoms and the hydroxyl radical, the alkoxy radicals being optionally substituted with one or more halogen atoms;
R5a and R5'a, which may be identical or different, are a hydrogen atom or an alkyl radical;
R6a is a hydrogen atom or an alkyl radical optionally substituted with one or more radicals, which may be identical or different, selected from halogen atoms and the hydroxyl radical;
R7a is a halogen atom;
or a racemic, enantiomeric or diastereoisomeric isomer form, or an addition salt with inorganic and organic acids or with inorganic and organic bases of said compound of formula (Ia).

2. The compound of formula (Ia) as defined in claim 1, selected from the group consisting of:
- 5-fluoro-2-[2-(4-fluoro-2,3-dihydro-1H-indol-1-yl)-2-oxoethyl]-6-(morpholin-4-yl)pyrimidin-4(3H)-one;
- 5-fluoro-2-[2-(4-fluoro-2,3-dihydro-1H-indol-1-yl)-2-oxoethyl]-3-methyl-6-(morpholin-4-yl)pyrimidin-4(3H)-one;
- 5-fluoro-2-[1-(4-fluoro-2,3-dihydro-1H-indol-1-yl)-1-oxopropan-2-yl]-3-methyl-6-(morpholin-4-yl)pyrimidin-4(3H)-one;
- 5-fluoro-2-{2-[(2R)-2-methyl-2,3-dihydro-1H-indol-1-yl]-2-oxoethyl}-6-(morpholin-4-yl)pyrimidin-4(3H)-one;
- 5-fluoro-2-{2-[(2S)-2-methyl-2,3-dihydro-1H-indol-1-yl]-2-oxoethyl}-6-(morpholin-4-yl)pyrimidin-4(3H)-one;
- 5-fluoro-2-{2-[(2R)-5-fluoro-2-methyl-2,3-dihydro-1H-indol-1-yl]-2-oxoethyl}-6-(morpholin-4-yl)pyrimidin-4(3H)-one;
- 5-fluoro-2-{2-[(2S)-5-fluoro-2-methyl-2,3-dihydro-1H-indol-1-yl]-2-oxoethyl}-6-(morpholin-4-yl)pyrimidin-4(3H)-one;
- 5-fluoro-3-methyl-2-{2-[(2S)-2-methyl-2,3-dihydro-1H-indol-1-yl]-2-oxoethyl}-6-(morpholin-4-yl)pyrimidin-4(3H)-one;
- 5-fluoro-3-methyl-2-{2-[(2R)-2-methyl-2,3-dihydro-1H-indol-1-yl]-2-oxoethyl}-6-(morpholin-4-yl)pyrimidin-4(3H)-one;
- 5-fluoro-2-{2-[(2R)-4-fluoro-2-methyl-2,3-dihydro-1H-indol-1-yl]-2-oxoethyl}-6-(morpholin-4-yl)pyrimidin-4(3H)-one;
- 5-fluoro-2-{2-[(2S)-4-fluoro-2-methyl-2,3-dihydro-1H-indol-1-yl]-2-oxoethyl}-6-(morpholin-4-yl)pyrimidin-4(3H)-one;
- 2-{2-[(2S)-5,6-difluoro-2-methyl-2,3-dihydro-1H-indol-1-yl]-2-oxoethyl}-5-fluoro-6-(morpholin-4-yl)pyrimidin-4(3H)-one;
- 2-{2-[(2R)-5,6-difluoro-2-methyl-2,3-dihydro-1H-indol-1-yl]-2-oxoethyl}-5-fluoro-6-(morpholin-4-yl)pyrimidin-4(3H)-one;
- 5-fluoro-2-{2-[(2S)-5-fluoro-2-methyl-2,3-dihydro-1H-indol-1-yl]-2-oxoethyl}-3-methyl-6-(morpholin-4-yl)pyrimidin-4(3H)-one;
- 5-fluoro-2-{2-[(2R)-5-fluoro-2-methyl-2,3-dihydro-1H-indol-1-yl]-2-oxoethyl}-3-methyl-6-(morpholin-4-yl)pyrimidin-4(3H)-one;
- 2-{2-[(2R)-4-bromo-2-methyl-2,3-dihydro-1H-indol-1-yl]-2-oxoethyl}-5-fluoro-6-(morpholin-4-yl)pyrimidin-4(3H)-one;
- 2-{2-[(2S)-4-bromo-2-methyl-2,3-dihydro-1H-indol-1-yl]-2-oxoethyl}-5-fluoro-6-(morpholin-4-yl)pyrimidin-4(3H)-one;
- 2-{2-[(2R)-4-chloro-2-methyl-2,3-dihydro-1H-indol-1-yl]-2-oxoethyl}-5-fluoro-6-(morpholin-4-yl)pyrimidin-4(3H)-one;
- 2-{2-[(2S)-4-chloro-2-methyl-2,3-dihydro-1H-indol-1-yl]-2-oxoethyl}-5-fluoro-6-(morpholin-4-yl)pyrimidin-4(3H)-one;
- 2-{2-[(2R)-4,5-difluoro-2-methyl-2,3-dihydro-1H-indol-1-yl]-2-oxoethyl}-5-fluoro-6-(morpholin-4-yl)pyrimidin-4(3H)-one;
- 2-{2-[(2S)-4,5-difluoro-2-methyl-2,3-dihydro-1H-indol-1-yl]-2-oxoethyl}-5-fluoro-6-(morpholin-4-yl)pyrimidin-4(3H)-one;
- 5-fluoro-2-{2-[(2S)-4-fluoro-2-methyl-2,3-dihydro-1H-indol-1-yl]-2-oxoethyl}-3-methyl-6-(morpholin-4-yl)pyrimidin-4(3H)-one;
- 5-fluoro-2-{2-[(2R)-4-fluoro-2-methyl-2,3-dihydro-1H-indol-1-yl]-2-oxoethyl}-3-methyl-6-(morpholin-4-yl)pyrimidin-4(3H)-one;
- 2-{2-[(2R)-4,5-difluoro-2-methyl-2,3-dihydro-1H-indol-1-yl]-2-oxoethyl}-5-fluoro-3-methyl-6-(morpholin-4-yl)pyrimidin-4(3H)-one;
- 2-{2-[(2S)-4,5-difluoro-2-methyl-2,3-dihydro-1H-indol-1-yl]-2-oxoethyl}-5-fluoro-3-methyl-6-(morpholin-4-yl)pyrimidin-4(3H)-one;
- 2-{2-[(2R)-5,6-difluoro-2-methyl-2,3-dihydro-1H-indol-1-yl]-2-oxoethyl}-5-fluoro-3-methyl-6-(morpholin-4-yl)pyrimidin-4(3H)-one;
- 2-{2-[(2S)-5,6-difluoro-2-methyl-2,3-dihydro-1H-indol-1-yl]-2-oxoethyl}-5-fluoro-3-methyl-6-(morpholin-4-yl)pyrimidin-4(3H)-one;
- 2-{2-[(2R)-4-chloro-2-methyl-2,3-dihydro-1H-indol-1-yl]-2-oxoethyl}-5-fluoro-3-methyl-6-(morpholin-4-yl)pyrimidin-4(3H)-one;
- 2-{2-[(2S)-4-chloro-2-methyl-2,3-dihydro-1H-indol-1-yl]-2-oxoethyl}-5-fluoro-3-methyl-6-(morpholin-4-yl)pyrimidin-4(3H)-one;
- 2-{2-[(2R)-4-bromo-2-methyl-2,3-dihydro-1H-indol-1-yl]-2-oxoethyl}-5-fluoro-3-methyl-6-(morpholin-4-yl)pyrimidin-4(3H)-one;

-2-{2-[(2S)-4-bromo-2-methyl-2,3-dihydro-1H-indol-1-yl]-2-oxoethyl}-5-fluoro-3-methyl-6-(morpholin-4-yl)pyrimidin-4(3H)-one;

-5-fluoro-2-{2-[(2S)-6-fluoro-2-methyl-2,3-dihydro-1H-indol-1-yl]-2-oxoethyl}-6-(morpholin-4-yl)pyrimidin-4(3H)-one;

-5-fluoro-2-{2-[(2R)-6-fluoro-2-methyl-2,3-dihydro-1H-indol-1-yl]-2-oxoethyl}-6-(morpholin-4-yl)pyrimidin-4(3H)-one;

-5-chloro-2-{2-[(2R)-2-methyl-2,3-dihydro-1H-indol-1-yl]-2-oxoethyl}-6-(morpholin-4-yl)pyrimidin-4(3H)-one;

-5-chloro-2-{2-[(2S)-2-methyl-2,3-dihydro-1H-indol-1-yl]-2-oxoethyl}-6-(morpholin-4-yl)pyrimidin-4(3H)-one;

-2-{2-[4-chloro-5-fluoro-2-methyl-2,3-dihydro-1H-indol-1-yl]-2-oxoethyl}-5-fluoro-3-methyl-6-(morpholin-4-yl)pyrimidin-4(3H)-one;

-5-bromo-2-[2-((S)-2-methyl-2,3-dihydroindol-1-yl)-2-oxoethyl]-6-morpholin-4-yl-3H-pyrimidin-4-one;

-5-fluoro-2-[2-((+)-2-hydroxymethyl-2,3-dihydroindol-1-yl)-2-oxoethyl]-6-morpholin-4-yl-3H-pyrimidin-4-one; and -5-fluoro-2-[2-((−)-2-hydroxymethyl-2,3-dihydroindol-1-yl)-2-oxoethyl]-6-morpholin-4-yl-3H-pyrimidin-4-one;

or a racemic, enantiomeric or diastereoisomeric isomer form, or an addition salt with inorganic and organic acids or with inorganic and organic bases of said compound of formula (Ia).

3. A compound of formula (Ie):

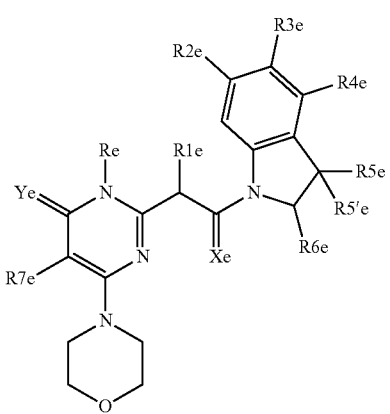

(Ie)

wherein:
Xe and Ye, which may be identical or different, are such that:
Xe is O or S and Ye is S;
Re is a hydrogen atom or an alkyl radical;
R1e is a hydrogen atom or a methyl radical;
R2e is a hydrogen atom or a fluorine atom;
R3e is a hydrogen atom or a halogen atom;
R4e is a hydrogen atom, a halogen atom or a hydroxyl, alkyl or alkoxy radical, the alkyl radicals being optionally substituted with one or more radicals, which may be identical or different, selected from halogen atoms and the hydroxyl radical, the alkoxy radicals being optionally substituted with one or more halogen atoms;
R5e and R5'e, which may be identical or different, are a hydrogen atom or an alkyl radical;
R6e is a hydrogen atom or an alkyl radical optionally substituted with one or more radicals, which may be identical or different, selected from halogen atoms and the hydroxyl radical;
R7e is a hydrogen atom or a halogen atom;
or a racemic, enantiomeric or diastereoisomeric isomer form, or an addition salt with inorganic and organic acids or with inorganic and organic bases of said compound of formula (Ie).

4. The compound of formula (Ie) as defined in claim 3 selected from the group consisting of:
-1-((S)-2-methyl-2,3-dihydroindol-1-yl)-2-(4-morpholin-4-yl-6-thioxo-1,6-dihydropyrimidin-2-yl)ethanone;
-1-((R)-2-methyl-2,3-dihydroindol-1-yl)-2-(4-morpholin-4-yl-6-thioxo-1,6-dihydropyrimidin-2-yl)ethanone;
-2-[2-((S)-2-methyl-2,3-dihydroindol-1-yl)-2-thioxoethyl]-6-morpholin-4-yl-3H-pyrimidine-4-thione;
-1-((S)-2-methyl-2,3-dihydroindol-1-yl)-2-(1-methyl-4-morpholin-4-yl-6-thioxo-1,6-dihydropyrimidin-2-yl)ethanone;
-1-((R)-2-methyl-2,3-dihydroindol-1-yl)-2-(1-methyl-4-morpholin-4-yl-6-thioxo-1,6-dihydropyrimidin-2-yl)ethanone;
-1-(4-fluoro-2,3-dihydroindol-1-yl)-2-(1-methyl-4-morpholin-4-yl-6-thioxo-1,6-dihydropyrimidin-2-yl)ethanone;
-1-(4-chloro-2,3-dihydroindol-1-yl)-2-(1-methyl-4-morpholin-4-yl-6-thioxo-1,6-dihydropyrimidin-2-yl)ethanone;
-1-((+)-4,5-difluoro-2-methyl-2,3-dihydroindol-1-yl)-2-(5-fluoro-4-morpholin-4-yl-6-thioxo-1,6-dihydropyrimidin-2-yl)ethanone;
-2-[2-((+)-4,5-difluoro-2-methyl-2,3-dihydroindol-1-yl)-2-thioxoethyl]-5-fluoro-6-morpholin-4-yl-3H-pyrimidine-4-thione;
-2-(5-fluoro-4-morpholin-4-yl-6-thioxo-1,6-dihydropyrimidin-2-yl)-1-((S)-2-methyl-2,3-dihydroindol-1-yl)ethanone; and
-2-(5-fluoro-4-morpholin-4-yl-6-thioxo-1,6-dihydropyrimidin-2-yl)-1-((R)-2-methyl-2,3-dihydroindol-1-yl)ethanone;
or a racemic, enantiomeric or diastereoisomeric isomer form, or an addition salt with inorganic and organic acids or with inorganic and organic bases of said compound of formula (Ie).

5. A medicament comprising the compound of formula (Ia) as defined in claim 1 or a racemic, enantiomeric or diastereoisomeric isomer form or a pharmaceutically acceptable addition salt with inorganic and organic acids or with inorganic and organic bases of said compound of formula (Ia).

6. A pharmaceutical composition comprising, as active ingredient, the compound of formula (Ia) as defined in claim 1 or a pharmaceutically acceptable addition salt with inorganic and organic acids or with inorganic and organic bases of said compound or a prodrug of said compound and a pharmaceutically acceptable support.

7. A method of treatment of cancer comprising administering to a patient in need of such treatment a therapeutically effective amount of the compound of formula (Ia), or a racemic, enantiomeric and diastereoisomeric isomer form, or an addition salt with inorganic and organic acids or with inorganic and organic bases of said compound of formula (Ia), as defined in claim 1, wherein said cancer is selected from primary prostate tumors and/or metastases of prostate cancer and primary ovarian tumors and/or metastases of ovarian cancer.

8. The method according to claim 7 wherein said cancer is resistant to cytotoxic agents.

9. A medicament comprising the compound of formula (Ie) as defined in claim 3 or a racemic, enantiomeric or diastereoisomeric isomer form or a pharmaceutically acceptable addition salt with inorganic and organic acids or with inorganic and organic bases of said compound of formula (Ie).

10. A pharmaceutical composition comprising, as active ingredient, the compound of formula (Ie) as defined in claim 3 or a pharmaceutically acceptable addition salt of said compound with inorganic and organic acids or with inorganic and organic bases or a prodrug of said compound and a pharmaceutically acceptable support.

11. A method of treatment of cancer comprising administering to a patient in need of such treatment a therapeutically effective amount of the compound of formula (Ie), or a racemic, enantiomeric and diastereoisomeric isomer form, or an addition salt with inorganic and organic acids or with inorganic and organic bases of said compound of formula (Ia), as defined in claim 3, wherein said cancer is selected from primary prostate tumors and/or metastases of prostate cancer and primary ovarian tumors and/or metastases of ovarian cancer.

12. The method according to claim 11 wherein said cancer is resistant to cytotoxic agents.

* * * * *